(12) United States Patent
Thorn et al.

(10) Patent No.: US 11,220,554 B2
(45) Date of Patent: Jan. 11, 2022

(54) PROCOAGULANT ANTIBODIES

(71) Applicant: Novo Nordisk A/S, Bagsvaerd (DK)

(72) Inventors: Karina Thorn, Farum (DK); Bjarne Gram Hansen, Alleroed (DK); Laust Bruun Johnsen, Skodsborg (DK); Mikkel Nors Harndahl, Roskilde (DK); Zhiru Yang, Beijing (CN); Henrik Oestergaard, Oelstykke (DK); Per J. Greisen, Belmont, MA (US); Eva Johansson, Vaerloese (DK); Morten Groenbech Rasch, Smoerum (DK); Jianhe Chen, Beijing (CN); Anders Svensson, Malmoe (SE); Haisun Zhu, Norfolk, MA (US); Rong Zhou, Beijing (CN); Prafull S. Gandhi, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/161,741

(22) Filed: Jan. 29, 2021

(65) Prior Publication Data
US 2021/0238306 A1   Aug. 5, 2021

Related U.S. Application Data

(63) Continuation of application No. PCT/EP2019/070628, filed on Jul. 31, 2018.

(30) Foreign Application Priority Data

Sep. 7, 2018 (EP) .................................. 18193191

(51) Int. Cl.
*C07K 16/36* (2006.01)
*A61P 7/04* (2006.01)
*A61K 39/00* (2006.01)

(52) U.S. Cl.
CPC .............. *C07K 16/36* (2013.01); *A61P 7/04* (2018.01); *A61K 2039/505* (2013.01); *C07K 2317/31* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 6,624,295 B1 | 9/2003 | Adams et al. | |
| 7,279,161 B2 * | 10/2007 | Scheiflinger | C07K 16/40 424/145.1 |
| 8,062,635 B2 * | 11/2011 | Hattori | C07K 16/36 424/136.1 |
| 9,334,331 B2 | 5/2016 | Igawa et al. | |
| 10,450,381 B2 | 10/2019 | Igawa et al. | |
| 10,759,870 B2 | 9/2020 | Teranishi et al. | |
| 2002/0098188 A1 | 7/2002 | Kaibara et al. | |
| 2003/0069700 A1 | 4/2003 | Swairjo | |
| 2004/0110688 A1 | 6/2004 | Bajaj et al. | |
| 2005/0058640 A1 | 3/2005 | Kerschbaumer et al. | |
| 2005/0147618 A1 | 7/2005 | Rivera et al. | |
| 2005/0196397 A1 | 9/2005 | Scheiflinger et al. | |
| 2007/0041978 A1 | 2/2007 | Hattori et al. | |
| 2013/0330345 A1 | 12/2013 | Igawa et al. | |
| 2016/0296602 A1 | 10/2016 | Johansen | |
| 2019/0185578 A1 | 6/2019 | Igawa et al. | |
| 2021/0107994 A1 | 4/2021 | Shima et al. | |

FOREIGN PATENT DOCUMENTS

| | | |
|---|---|---|
| CN | 103396494 A | 11/2013 |
| CN | 103298937 | 5/2016 |
| EP | 1220923 A2 | 7/2002 |
| EP | 1660536 A2 | 5/2006 |
| EP | 2644698 A1 | 10/2013 |
| JP | 2001523971 A | 11/2001 |
| JP | 2003509049 A | 3/2003 |
| JP | WO2006109592 A1 | 11/2008 |
| WO | 94/05692 A1 | 3/1994 |
| WO | 9850431 | 11/1998 |
| WO | 0007626 A1 | 2/2000 |
| WO | 2005025615 | 3/2005 |
| WO | 2009/140598 A1 | 11/2009 |
| WO | 2010020423 A2 | 2/2010 |
| WO | 2010045321 A2 | 4/2010 |
| WO | 11080322 A1 | 7/2011 |
| WO | 2011088267 A1 | 7/2011 |

(Continued)

OTHER PUBLICATIONS

"Anti-Factor IX Antibody, Mouse Monoclonal Clone HIX-1, Purified from Hybridma Cell Culture," Sigma-Aldrich, http://www.sigmaaldrich.com/catalog/product/sigma/f2645?lang=en&region=DK, accessed Jan. 19, 2018.

"Anti-Human Factor IX," Haematologic Technologies, Inc., https://www.haemtech.com/products/antibodies/anti-human-factor-ix, accessed Jan. 19, 2018.

Affinity Biologicals Antibodies to Factor IX http://www.affinitybiologicals.com/factor-ix-polyclonal-antibody/, accessed May 21, 2019.

Anonymous: Assessment report Hemlibra (International nonproprietary name: emicizumab Procedure No. EMEA/H/C/004406/0000), European Medicines Agency, Jan. 25, 2018, pp. 1-126, XP002780260, Retrieved from the Internet: URL:http://www.ema.europa.eu/docs/en_GB/document_library/EPAR_-_public_assessment_report/human/004406/WC500244745.pdf [retrieved on Apr. 19, 2018].

(Continued)

*Primary Examiner* — Michael Szperka
(74) *Attorney, Agent, or Firm* — Jianjie Hu

(57) ABSTRACT

The present invention relates to multispecific procoagulant antibodies capable of binding to coagulation Factor IX (FIX) and/or the activated form thereof Factor IXa (FIXa), and Factor X (FX) and/or the activated form thereof Factor Xa (FXa) and promoting FX activation by FIXa, antibodies binding their epitopes or parts thereof and methods and composition for treating subjects suffering from a coagulopathy such as haemophilia A as well as kits, methods of manufacture and methods of use.

26 Claims, 15 Drawing Sheets

Specification includes a Sequence Listing.

(56) References Cited

FOREIGN PATENT DOCUMENTS

| WO | 2012067176 A1 | 5/2012 |
|---|---|---|
| WO | 2016166014 A1 | 10/2016 |
| WO | 2018098363 | 5/2018 |
| WO | 2018141863 A1 | 8/2018 |
| WO | 2018181870 A1 | 10/2018 |
| WO | 2018234575 A1 | 12/2018 |
| WO | 2019065795 | 4/2019 |
| WO | 2018021450 | 5/2019 |

OTHER PUBLICATIONS

Bajaj et al., "A monoclonal antibody to factor IX that inhibits the factor VIII: CA potentiation of factor X activation," Journal of Biological Chemistry, 1985, vol. 260, No. 1, pp. 11574-11580.
CaptureSelect™ Biotin Anti-FIX Conjugate https://www.thermofisher.com/order/catalog/product/7103002100, accessed May 21, 2019.
Ganesan R. et al., "Structural and mechanistic insight into how antibodies inhibit serine proteases", Biochem. J., 2010, vol. 430, pp. 179-189.
Kolkman et al., "Insertion Loop 256-268 in Coagulation Factor IX Restricts Enzymatic Activity in the Absence but Not in the Presence of Factor VIII," Biochemistry, 2000, vol. 39, No. 25, pp. 7398-7405.
Lin S, et al., "Identification of functionally important residues in the protease domain of Factor IX that are critical for binding factor XIa, TFPI and antibodies", Blood, 2002, vol. 100, Issue 11, pp. 263A-263A.
Norris et al., "Synthetic, switchable enzymes," J Mol Microbiol Biotechnol, 2017, vol. 27, No. 2, pp. 117-127.
Other Anti-FIX Antibody Products http://www.biocompare.com/pfu/110447/soids/35803/Antibodies/FIX, accessed May 21, 2019.
Safari S. et al., "Use of a Bacterially Expressed Human Factor IX Light Chain to Develop Polyclonal Antibody Anti-hFIX", Appl Biochem Biotechnol, 2009, vol. 159, pp. 404-414.
Sampei et al., "Identification and Multidimensional Optimization of an Asymmetric Bispecific IgG Antibody Mimicking the Function of Factor VIII Cofactor Activity," PLoS One, 2013, vol. 8, No. 2, e57479.
Scheiflinger et al., "Enhancement of the enzymatic activity of activated coagulation factor IX by anti-factor IX antibodies," J Thromb Haemost, 2008, vol. 6, pp. 315-322.
Uchida et al., "Plenary paper Clinical Trials and Observations A first-in-human phase 1 study of ACE910, a novel factor VIII-mimetic bispecific antibody, in health subjects," Dec. 1, 2015, vol. 127, pp. 1663-1641, XP055468638, Retrieved from the Internet: URL:http://www.bloodjournal.org/content/bloodjournal/127/13/1633.full.pdf?sso-checked=true (retrieved on Apr. 19, 2018).
Zogg T, "Activation mechanisms of coagulation factor IX," Biol Chem, 2009, vol. 390, Nos. 5-6, pp. 391-400.
F. Scheiflinger et al.,"Enhancement of the enzymatic activity of activated coagulation factor IX by anti-factor IX antibodies" Journal of Thrombosis and Haemostasis, 2008, vol. 6, No. 2, pp. 315-322.
Kerschbaumer et al.,"An Antibody Specific for Coagulation Factor IX Enhances the Activity of the Intrinsic Factor X-activating Complex", Journal of Biological Chemistry, 2004, vol. 279, No. 39, pp. 40445-40450.
Kitazawa et al.,"A bispecific antibody to factors IXa and X restores factor VIII hemostatic activity in a hemophilia A model" Nature Medicine, 2012, vol. 18, No. 10, pp. 1570-1574.
Kitazawa et al.,"Factor VIIIa-mimetic cofactor activity of a bispecific antibody to factors IX/IXa and X/Xa, emicizumab, depends on its ability to bridge the antigens",Thrombosis and Haemostasis, 2017, vol. 117, No. 7, pp. 1348-1357.
Kolkman et al.,"Insertion Loop 256-268 in Coagulation Factor IX Restricts Enzymatic Activity in the Absence but Not in the Presence of Factor VIII" Biochemistry, 2000, vol. 39, pp. 7398-7405.
Sampei et al.,"Identification and Multidimensional Optimization of an Asymmetric Bispecific IgG Antibody Mimicking the Function of Factor VIII Cofactor Activity" PLOS ONE, 2013, vol. 8, No. 2, p. e57479.
Uchida et al., "Plenary Paper Clinical Trials and Observations A first-in human phase 1 study of ACE910, a novel factor VIII-mimetic bispecific antibody, in healthy subjects", 2015, Retrieved from the Internet: URL:http://www.bloodjournal.org/content/bloodjournal/127/13/1633.full.pdf?sso-checked=true, Retrieved on Apr. 19, 2018.
Zogg et al.,"Activation mechanisms of coagulation factor IX" Biol. Chem.,2009, vol. 390, pp. 391-400.
A.V. Filkenshtein et al., Protein Physics: lectures with colour anaglyphies and tasks: 4th edition, M., KDU, 2012, p. 23.
Yarilin A.A., Introduction to immunology, M., Medicine, 1999, pp. 172-174.
Samelson-Jones et al., "Hyperactivity of factor IX Padua (R338L) depends on factor VIIIa cofactor activity," JCI Insight. Jun. 2019, vol. 5, No. 14, e128683, 14 pages.

* cited by examiner

Figure 1:
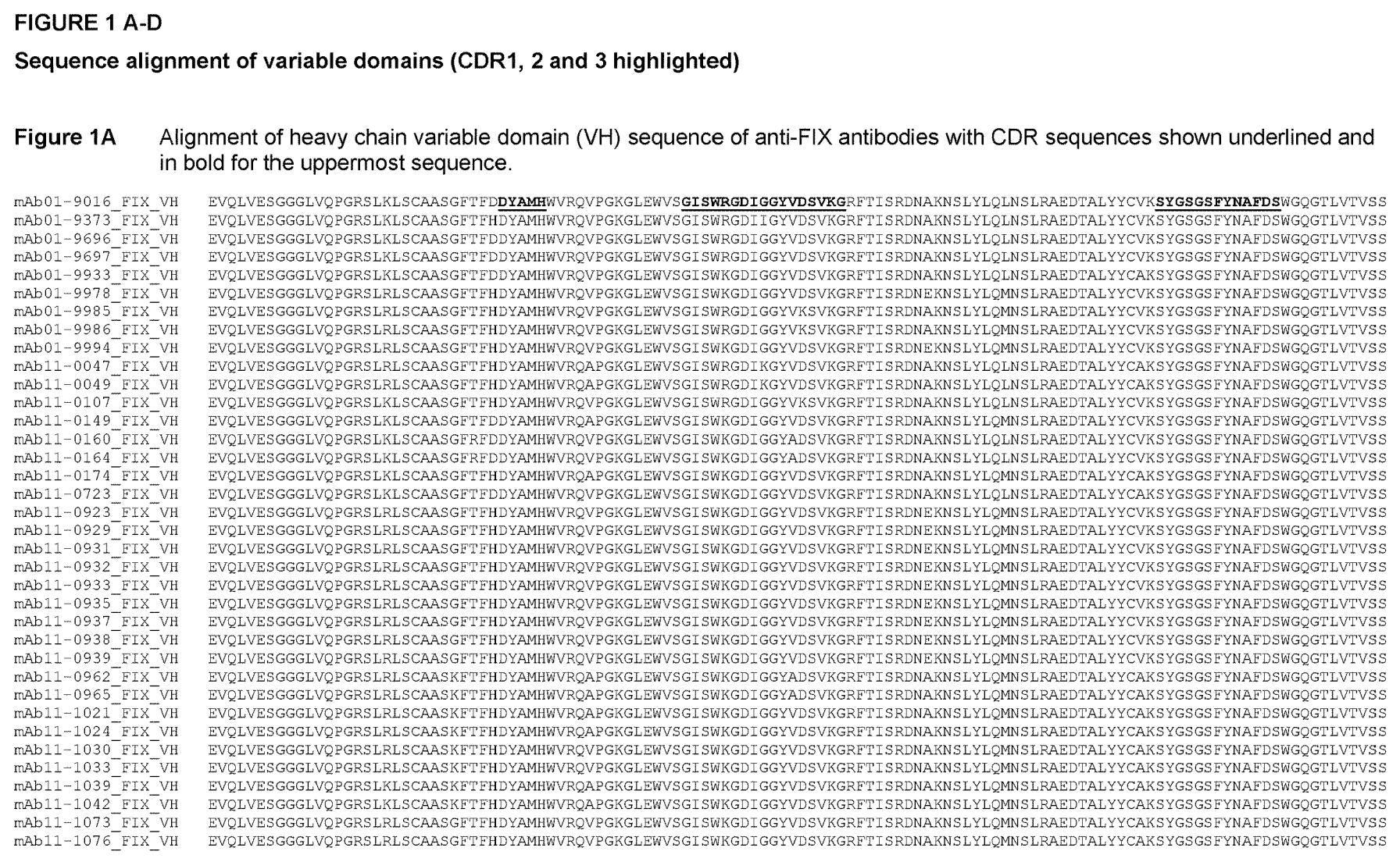

FIGURE 1 A-D

Sequence alignment of variable domains (CDR1, 2 and 3 highlighted)

Figure 1A Alignment of heavy chain variable domain (VH) sequence of anti-FIX antibodies with CDR sequences shown underlined and in bold for the uppermost sequence.

Figure 1A continued

| | |
|---|---|
| mAb11-1091_FIX_VH | EVQLVESGGGLVQPGRSLKLSCAASGFTFHDYAMHWVRQVPGKGLEWVSGISWKGDIGGYVDSVKGRFTISRDNAKNSLYLQMNSLRAEDTALYYCAKSYGSGSFYNAFDSWGQGTLVTVSS |
| mAb11-1094_FIX_VH | EVQLVESGGGLVQPGRSLKLSCAASGFTFHDYAMHWVRQVPGKGLEWVSGISWKGDIGGYVDSVKGRFTISRDNAKNSLYLQMNSLRAEDTALYYCAKSYGSGSFYNAFDSWGQGTLVTVSS |
| mAb11-1233_FIX_VH | EVQLVESGGGLVQPGRSLRLSCAASGFTFHDYAMHWVRQVPGKGLEWVSGISWKGDIGGYVDSVKGRFTISRDNAKNSLYLQMNSLRAEDTALYYCAKSYGSGSFYNAFDSWGQGTLVTVSS |
| mAb11-1254_FIX_VH | EVQLVESGGGLVQPGRSLRLSCAASGFKFHDYAMHWVRQVPGKGLEWVSGISWKGDIGGYVDSVKGRFTISRDNDKNSLYLQMNSLRAEDTALYYCVKSYGSGSFYNAFDSWGQGTLVTVSS |
| mAb11-1259_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1260_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1262_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1266_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1268_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1273_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1275_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1276_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1278_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1279_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1282_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1286_FIX_VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS |
| mAb11-1288_FIX_VH | EVQLVESGGGLVQPGRSLKLSCAASGFTFHDYAMHWVRQVPGKGLEWVSGISWKGDIGGYVDSVKGRFTISRDNEKNSLYLQMNSLRAEDTALYYCAKSYGSGSFYNAFDSWGQGTLVTVSS |
| mAb11-1344_FIX_VH | EVQLVESGGGLVQPGRSLRLSCAASGFTFDDYAMHWVRQVPGKGLEWVSGISWRGDIGGYVDSVKGRFTISRDNAKNSLYLQLNSLRAEDTALYYCVKSYGSGSFYNAFDSWGQGTLVTVSS |
| mAb11-1358_FIX_VH | EVQLVESGGGLVQPGRSLKLSCAASGFTFDDYAMHWVRQVPGKGLEWVSGISWRGDIGGYVDSVKGRFTISRDNAKNSLYLQLNSLRAEDTALYYCVKSYGSGSFYNAFDSWGQGTLVTVSS |
| mAb11-1360_FIX_VH | EVQLVESGGGLVQPGRSLKLSCAASGFTFHDYAMHWVRQVPGKGLEWVSGISWKGDIGGYVDSVKGRFTISRDNAKNSLYLQLNSLRAEDTALYYCVKSYGSGSFYNAFDSWGQGTLVTVSS |
| mAb11-1389_FIX_VH | EVQLVESGGGLVQPGRSLRLSCAASGFTFHDYAMHWVRQAPGKGLEWVSGISWKGDIGGYVDSVKGRFTISRDNAKNSLYLQMNSLRAEDTALYYCVKSYGSGSFYNAFDSWGQGTLVTVSS |
| mAb01-1767_FIX_VH | EVQLVESGGGLVQPGRSLRLSCAASGFTFDDYAMHWVRQVPGKGLEWVSGISWNGDNIGYVDSVKGRFTISRDNAKNSLYLQLNSLRAEDTALYYCAKSYGSGSFYNAFDSWGQGTLVTVSS |
| mAb11-0173_FIX_VH | EVQLVESGGGLVQPGRSLRLSCAASGFTFHDYAMHWVRQAPGKGLEWVSGISWKGDIGGYVDSVKGRFTISRDNAKNSLYLQMNSLRAEDTALYYCAKSYGSGSFYNAFDSWGQGTLVTVSS |
| mAb11-1204_FIX_VH | EVQLVESGGGLVQPGRSLRLSCAASGFTFHDYAMHWVRQVPGKGLEWVSGISWRGDIGGYAKSVKGRFTISRDNAKNSLYLQMNSLRAEDTALYYCVKSYGSGSFYNAFDSWGQGTLVTVSS |
| mAb11-1495_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| mAb11-1501_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| mAb11-1502_FIX_VH | EVQLVESGGGLVQPGRSLRLSCAASGFTFHDYAMHWVRQSVKGRFTISRDNAKNSLYLQMNSLRAEDTALYYCVKSYGSGSFYNAFDSWGQGTLVTVSS |
| mAb11-1499_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |

Figure 1B Alignment of light chain variable domain (VL) sequence of anti-FIX antibodies with CDR sequences shown underlined and in bold for the uppermost sequence.

Figure 1B continued

```
mAb11-1266_FIX_VL  DIQMTQSPSTLSASVGDRVTITCRASQSISSWLAWYQQKPGKAPKFLIYKASRLDKGTPSRFSGSGSGTEFSLTISSLQPDDFATYYCLEYSSYIRTFGQGTKVEIK
mAb11-1268_FIX_VL  DIQMTQSPSTLSASVGDRVTITCRASQSISSWLAWYQQKPGKAPKFLIYKASRLDRGTPKRFSGSGSGTEFSLTISLQPDDFATYYCLEYSSYIRTFGQGTKVEIK
mAb11-1273_FIX_VL  DIQMTQSPSTLSASVGDRVTITCRASQSISSWLAWYQQKPGKAPKFLIYKASRLDRGTPSRFSGSGSGTEFSLTIELQPDDFATYYCLEYSSYIRTFGQGTKVEIK
mAb11-1275_FIX_VL  DIQMTQSPSTLSASVGDRVTITCRASQSISSWLAWYQQKPGKAPKFLIYKASRLDRGTPSRFSGSGSGTEFSLTISLTPDDFATYYCLEYSSYIRTFGQGTKVEIK
mAb11-1276_FIX_VL  DIQMTQSPSTLSASVGDRVTITCRASQSISSWLAWYQQKPGKAPKFLIYKASRLDRGTPSRFSGSGSGTEFSLTISSLSPDDFATYYCLEYSSYIRTFGQGTKVEIK
mAb11-1278_FIX_VL  DIQMTQSPSTLSASVGDRVTITCRASQSISSWLAWYQQKPGKAPKFLIYKASRLDRGTPSRFSGSGSGTEFSLTISSLQPDDFATYYCLEYQSYIRTFGQGTKVEIK
mAb11-1279_FIX_VL  DIQMTQSPSTLSASVGDRVTITCRASQSISSWLAWYQQKPGKAPKFLIYKASRLDRGTPSRFSGSGSGTEFSLTISSLQPDDFATYYCLEYKSYIRTFGQGTKVEIK
mAb11-1282_FIX_VL  DIQMTQSPSTLSASVGDRVTITCRASQSISSWLAWYQQKPGKAPKFLIYKASRLDRGTPSRFSGSGSGTEFSLTISSLQPDDFATYYCLEYRSWIRTFGQGTKVEIK
mAb11-1286_FIX_VL  DIQMTQSPSTLSASVGDRVTITCRASQSISSWLAWYQQKPGKAPKFLIYKASRLDRGTPSRFSGSGSGTEFSLTIYDLQPDDFATYYCLEYRSYIRTFGQGTKVEIK
mAb11-1288_FIX_VL  DIQMTQSPSTLSASVGDRVTITCRASQSISSWLAWYQQKPGKAPKFLIYKASRLDRGTPQRFSGSGSGTEFSLTIYSLQPDDFATYYCLEYNSYIRTFGQGTKVEIK
mAb11-1344_FIX_VL  DIQMTQSPSTLSASAGDRVTITCRASQSISSWLAWYQQKPGKAPKFLIYKASRLDRGTPSRFSGSGSGTEFSLTISSLQPDDFATYYCLEYSSYIRTFGQGTKVEIK
mAb11-1358_FIX_VL  DIQMTQSPSTLSASAGDRVTITCRASQSISSWLAWYQQKPGKAPKFLIYKASKLDRGTPSRLERGTGEFSLTISSLQPDDFATYYCLEYSSYIRTFGQGTKVEIK
mAb11-1360_FIX_VL  DIQMTQSPSTLSASAGDRVTITCRASQSISSWLAWYQQKPGKAPKLLIYKASRLERGTPSRFSGSGSGTEFSLTISSLQPDDFATYYCLEYSSYIRTFGQGTKVEIK
mAb11-1389_FIX_VL  DIQMTQSPSTLSASVGDRVTITCRASQSISSWLAWYQQKPGKAPKFLIYKASSLESGVPSRFSGSGSGTEFSLTISSLQPDDFATYYCLEYSSYIRTFGQGTKVEIK
mAb01-1767_FIX_VL  DIQMTQSPSTLSASVGDRVTITCRASQSISSWLAWYQQKPGKAPKFLIYKASKLDRGTPSRFSGSGSGTEFTLTISSLQPDDFATYYCLEYSSYIRTFGQGTKVEIK
mAb11-0173_FIX_VL  DIQMTQSPSTLSASVGDEVTITCRASQSISSWLAWYQQKPGKAPKFLIYKASKLERGTPSRFSGSGSGTEFSLTISSLQPDDFATYYCLEYSSYIRTFGQGTKVEIK
mAb11-1204_FIX_VL  DIQMTQSPSTLSASVGDRVTITCRASQSISSWLAWYQQKPGKAPKFLIYKASKLDRGTPSRFSGSGSGTEFSLTISSLQPDDFATYYCLEYSSYIRTFGQGTKVEIK
mAb11-1495_FIX_VL  DIQMTQSPSTLSASVGDRVTITCRASQSISSWLAWYQQKPGKAPKFLIYKASKLDRGTPSRFSGSGSGTEFTLTISSLQPDDFATYYCLEYSSYIRTFGQGTKVEIK
mAb11-1501_FIX_VL  DIQMTQSPSTLSASVGDRVTITCRASQSISSWLAWYQQKPGKAPKLLIYKASKLDRGTPSRFSGSGSGTEFTLTISSLQPDDFATYYCLEYSSYIRTFGQGTKVEIK
mAb11-1502_FIX_VL  DIQMTQSPSTLSASVGDRVTITCRASQSISSWLAWYQQKPGKAPKFLIYKASKLDRGTPSRFSGSGSGTEFSLTISSLQPDDFATYYCLEYSSYIRTFGQGTKVEIK
mAb11-1499_FIX_VL  DIQMTQSPSTLSASVGDRVTITCRASQSISSWLAWYQQKPGKAPKFLIYKASKLDRGTPSRFSGSGSGTEFTLTISSLQPDDFATYYCLEYSSYIRTFGQGTKVEIK
```

Figure 1C Alignment of heavy chain variable domain (VH) sequence of anti-FX antibodies with CDR sequences shown underlined and in bold for the uppermost sequence.

| mAb | Sequence |
|---|---|
| mAb01-6723_FX_VH | EVQLVQSGAEVKKPGESLRISCKGSGYSFTTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb01-8174_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb01-8913_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb01-9772_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb01-9778_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1114_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1115_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1116_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1117_FX_VH | EVQLVQSGAEVKKPGESLRISCKGSGYSFSTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1118_FX_VH | EVQLVQSGAEVKKPGESLRISCKGSGYSFSTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1119_FX_VH | EVQLVQSGAEVKKPGESLRISCKGSGYSFSTSWIVWVRQMPGKGLEWMGIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1120_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1121_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1122_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1123_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1124_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1125_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1127_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1128_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1129_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1130_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1131_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1132_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1133_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1416_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1417_FX_VH | EVQLVQSGAEVKKPGESLRISCKGSGYSFSTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1418_FX_VH | EVQLVQSGAEVKKPGESLRISCKGSGYSFSTSWISWVRQMPGKGLEWMGMIDPSDSFTSYSPSFQGHVTISADKSISTAYLQWSSLKASDTAMYYCARLHYYHSEEFDVWGQGTMVTVSS |
| mAb11-1419_FX_VH | EVQLVQSGAEVKKPGESLRISCKGSGYSFSTTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1420_FX_VH | EVQLVQSGAEVKKPGESLRISCKGSGYSFSTSWIVWVRQMPGKGLEWMGIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1421_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1422_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |
| mAb11-1431_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1432_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1433_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1434_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1435_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1436_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1437_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1439_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1440_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1441_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1442_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYHSEEFDVWGQGTMVTVSS |
| mAb11-1443_FX_VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYHSEEFDVWGQGTMVTVSS |

Figure 1C continued

| | |
|---|---|
| mAb11-1444_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1445_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1446_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1447_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1448_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTLVTVSS |
| mAb11-1449_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYHSEEFDVWGQGTMVTVSS |
| mAb11-1450_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYHSEEFDVWGQGTMVTVSS |
| mAb11-1451_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1452_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1453_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1454_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1455_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1456_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1457_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1458_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1459_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1460_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1461_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1463_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1464_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1465_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1466_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1467_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1468_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1470_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1471_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1472_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1473_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1474_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1475_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1476_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1477_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1478_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1479_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1480_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |
| mAb11-1481_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1482_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1483_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1484_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1485_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1486_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1487_FX_VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYNSEEFDVWGQGTMVTVSS |
| mAb11-1488_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |
| mAb11-1489_FX_VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS |

Figure 1C continued

```
mAb11-1490_FX_VH  EVQLVQSGAEVKKPGESLRISCKGSGYSFTTSWISWVRQMPGKGLEWMGMIDPSDSYTSYSPSFQGHVTISADKSISTAYLQWSSLKASDTAMYYCARLHYHSEEFDVWGQGTLVTVSS
mAb11-1491_FX_VH  EVQLVQSGAEVKKPGESLRISCKGSGYSFTTSWISWVRQMPGKGLEWMGMIDPSDSYTSYSPSFQGHVTISADKSISTAYLQWSSLKASDTAMYYCARLHYHSEEFDVWGQGTMVTVSS
mAb11-1492_FX_VH  EVQLVQSGAEVKKPGESLRISCKGSGYSFSTSWIVWVRQMPGKGLEWMGMIDPSDFTSYSPSFQGHVTISADKSISTAYLQWSSLKASDTAMYYCARLHYHSEEFDVWGQGTLVTVSS
mAb11-1493_FX_VH  EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYHSEEFDVWGQGTLVTVSS
mAb11-1494_FX_VH  EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS
```

Figure 1D Alignment of heavy chain variable domain (VL) sequence of anti-FX antibodies with CDR sequences shown underlined and in bold for the uppermost sequence.

```
mAb01-6723_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQFGSSRLFTFGQGTKLEIK
mAb01-8174_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQFGSSRLFTFGQGTKLEIK
mAb01-8913_FX_VL   EIVLTQSPGTLSLSAGERATLSCRASQSVSSSYLAWYQQKPGQAPRLLIYGASSRARGIPDRFSGSGSGTDFTLTISRLEPEDFAVYYCQQFGSSRLFTFGQGTKLEIK
mAb01-9772_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb01-9778_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb11-1114_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1115_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1116_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1117_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1118_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1119_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1120_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb11-1121_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb11-1122_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb11-1123_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb11-1124_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb11-1125_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK
mAb11-1127_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQYGDSRLFTFGQGTKLEIK
mAb11-1128_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQYGDSRLFTFGQGTKLEIK
mAb11-1129_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQYGDSRLFTFGQGTKLEIK
mAb11-1130_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQYGDSRLFTFGQGTKLEIK
mAb11-1131_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQYGDSRLFTFGQGTKLEIK
mAb11-1132_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQYGDSRLFTFGQGTKLEIK
mAb11-1133_FX_VL   EIVLTQSPGTLSLSPGERATLSCRASQSVSSSYLAWYQQKPGQAPRLLIYGASSRARGIPDRFSGSGSGTDFTLTISRLEPEDFAVYYCQQYGDSRLFTFGQGTKLEIK
mAb11-1416_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1417_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1418_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1419_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1420_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1421_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1422_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1431_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGESQLFTFGQGTKLEIK
mAb11-1432_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGNSQLFTFGQGTKLEIK
mAb11-1433_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK
mAb11-1434_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDAQLFTFGQGTKLEIK
mAb11-1435_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDTQLFTFGQGTKLEIK
mAb11-1436_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDNQLFTFGQGTKLEIK
mAb11-1437_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGSSQLFTFGQGTKLEIK
mAb11-1439_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGSSQLFTFGQGTKLEIK
mAb11-1440_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGSSQLFTFGQGTKLEIK
mAb11-1441_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGSSQLFTFGQGTKLEIK
mAb11-1442_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGSSQLFTFGQGTKLEIK
mAb11-1443_FX_VL   EIVLTQSPGTLSLSPGERATLSCRASQSVSSSYLAWYQQKPGQAPRLLIYGQSSRTRGIPDRFSGSGSGTDFTLTISRLEPEDFAVYYCQQFGSSQLFTFGQGTKLEIK
```

```
mAb11-1490_FX_VL  EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDDQLFTFGQGTKLEIK
mAb11-1491_FX_VL  EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDDQLFTFGQGTKLEIK
mAb11-1492_FX_VL  EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDDQLFTFGQGTKLEIK
mAb11-1493_FX_VL  EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDDQLFTFGQGTKLEIK
mAb11-1494_FX_VL  EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDDQLFTFGQGTKLEI
```

FIGURE 4A (C + D)
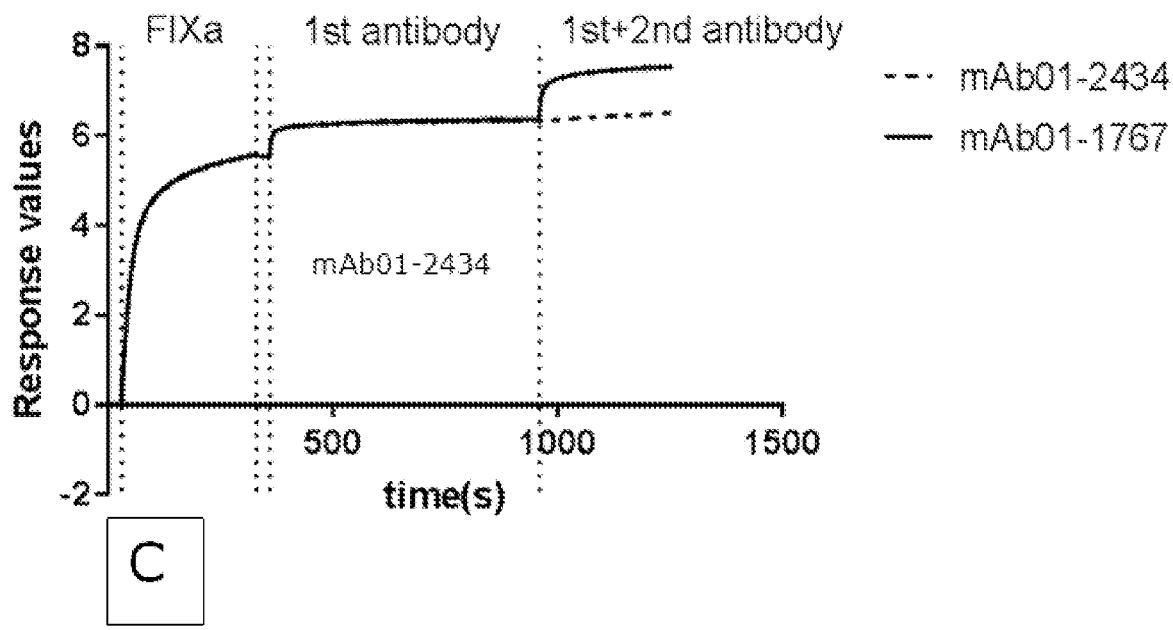
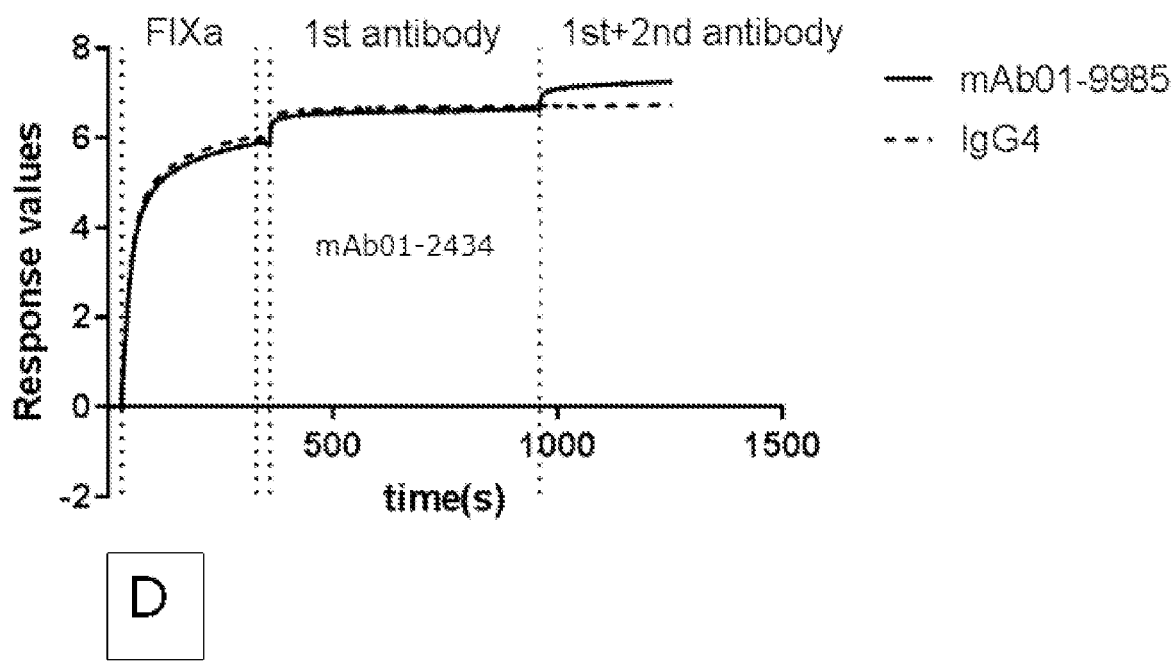

FIGURE 4B (E + F)
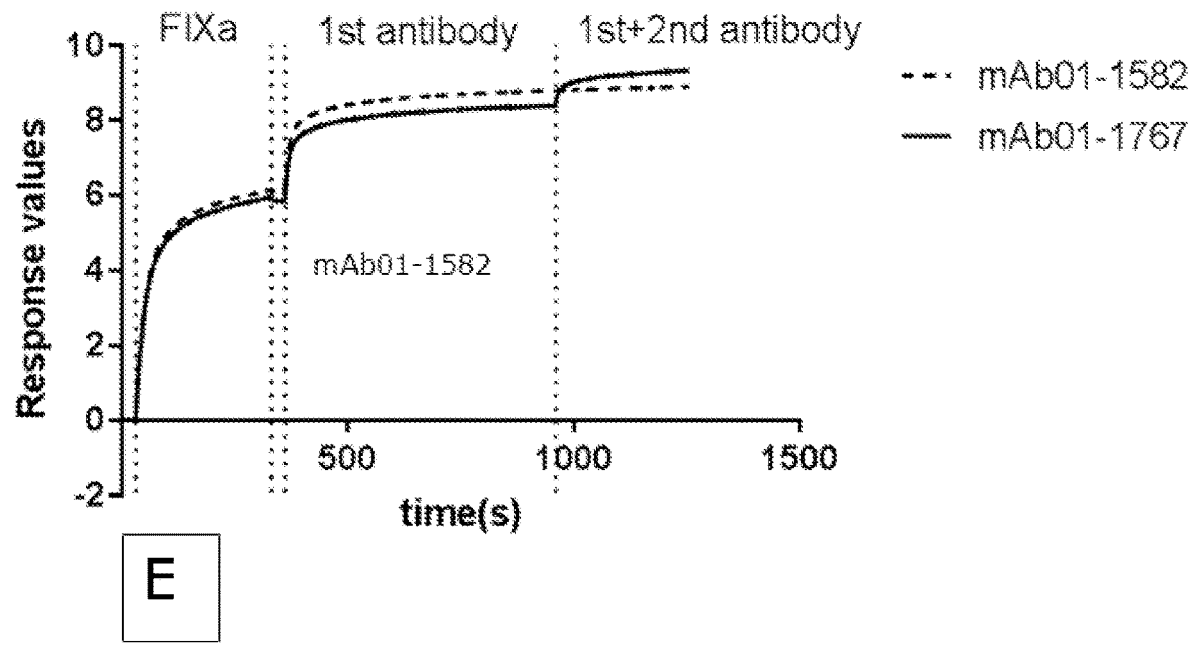
E
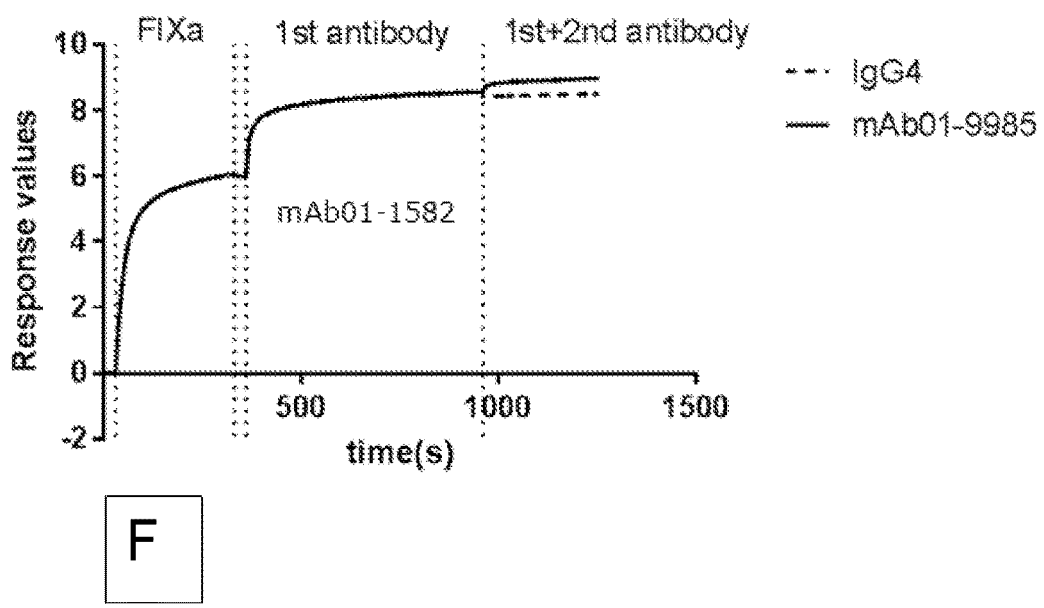
F

FIGURE 5 (A + B)
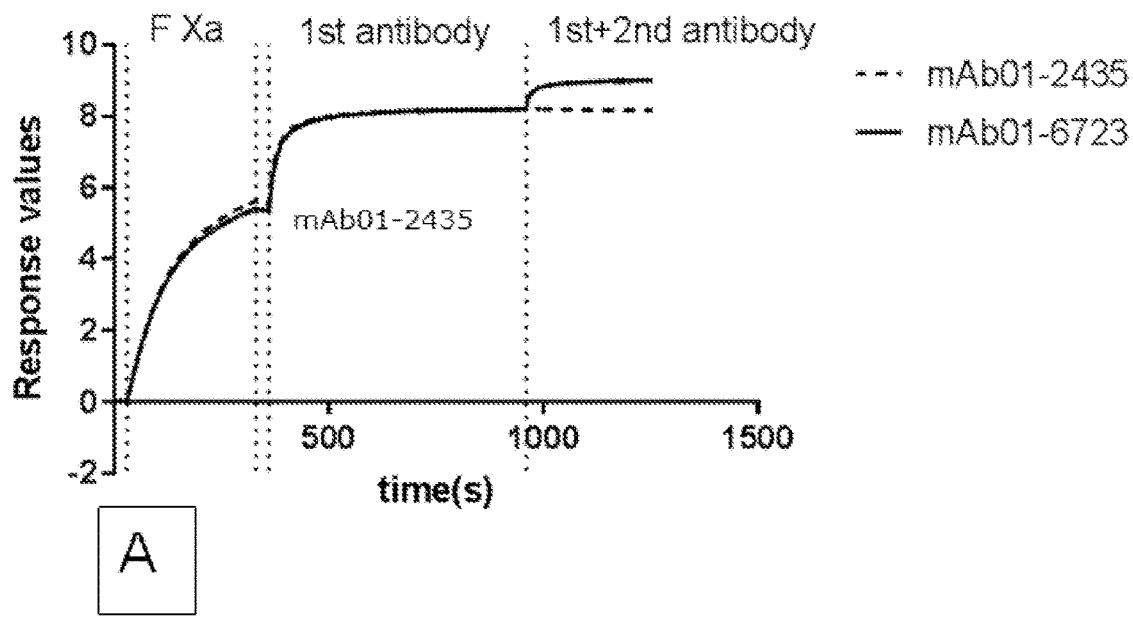
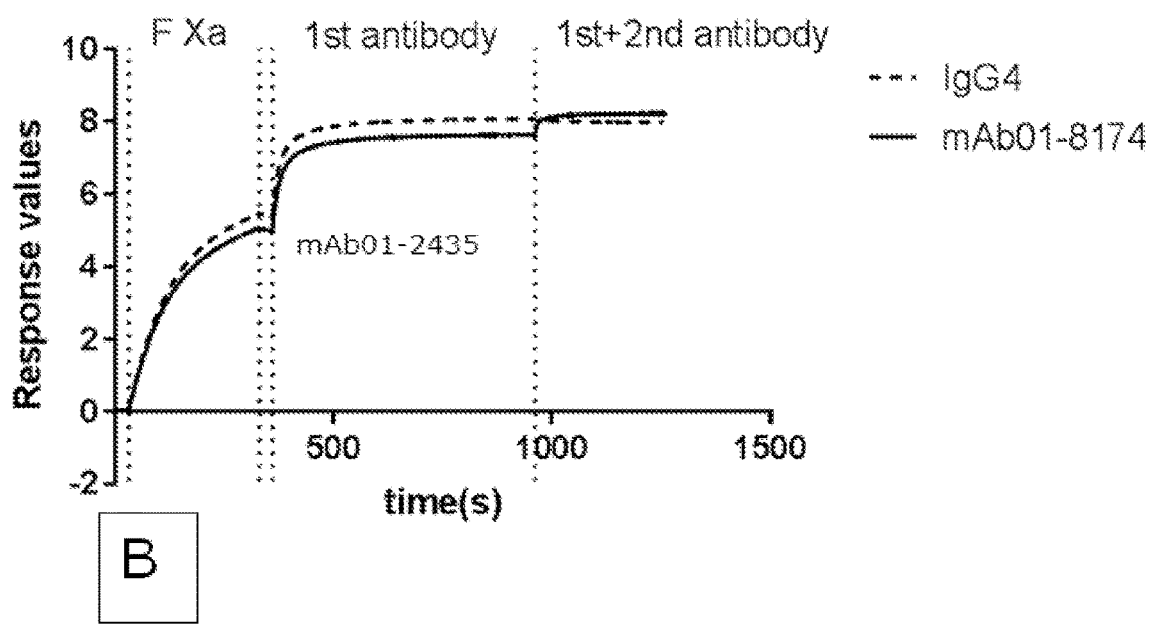

ially life-threatening bleeding, or damage to internal organs, such as the joints.

SEQUENCE LISTING

<160> NUMBER OF SEQ ID NOS: 1249

<210> SEQ ID NO 1
<211> LENGTH: 415
<212> TYPE: PRT
<213> ORGANISM: Homo sapiens

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe

```
                20                  25                  30
Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
        130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
        210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 2
<211> LENGTH: 448
<212> TYPE: PRT
<213> ORGANISM: Homo sapiens
```

<400> SEQUENCE: 2

| | | | | | | | | | | | | | | |
|---|---|---|---|---|---|---|---|---|---|---|---|---|---|---|
|Ala|Asn|Ser|Phe|Leu|Glu|Glu|Met|Lys|Lys|Gly|His|Leu|Glu|Arg|Glu|
|1| | | |5| | | | |10| | | | |15|
|Cys|Met|Glu|Glu|Thr|Cys|Ser|Tyr|Glu|Glu|Ala|Arg|Glu|Val|Phe|Glu|
| | | | |20| | | | |25| | | | |30|
|Asp|Ser|Asp|Lys|Thr|Asn|Glu|Phe|Trp|Asn|Lys|Tyr|Lys|Asp|Gly|Asp|
| | | | |35| | | | |40| | | | |45|
|Gln|Cys|Glu|Thr|Ser|Pro|Cys|Gln|Asn|Gln|Gly|Lys|Cys|Lys|Asp|Gly|
| |50| | | | |55| | | | |60| | | |
|Leu|Gly|Glu|Tyr|Thr|Cys|Thr|Cys|Leu|Glu|Gly|Phe|Glu|Gly|Lys|Asn|
|65| | | | |70| | | | |75| | | | |80|
|Cys|Glu|Leu|Phe|Thr|Arg|Lys|Leu|Cys|Ser|Leu|Asp|Asn|Gly|Asp|Cys|
| | | | |85| | | | |90| | | | |95| |

Ala Asn Ser Phe Leu Glu Glu Met Lys Lys Gly His Leu Glu Arg Glu
1               5                   10                  15
Cys Met Glu Glu Thr Cys Ser Tyr Glu Glu Ala Arg Glu Val Phe Glu
                20                  25                  30
Asp Ser Asp Lys Thr Asn Glu Phe Trp Asn Lys Tyr Lys Asp Gly Asp
                35                  40                  45
Gln Cys Glu Thr Ser Pro Cys Gln Asn Gln Gly Lys Cys Lys Asp Gly
    50                  55                  60
Leu Gly Glu Tyr Thr Cys Thr Cys Leu Glu Gly Phe Glu Gly Lys Asn
65                  70                  75                  80
Cys Glu Leu Phe Thr Arg Lys Leu Cys Ser Leu Asp Asn Gly Asp Cys
                85                  90                  95
Asp Gln Phe Cys His Glu Glu Gln Asn Ser Val Val Cys Ser Cys Ala
                100                 105                 110
Arg Gly Tyr Thr Leu Ala Asp Asn Gly Lys Ala Cys Ile Pro Thr Gly
                115                 120                 125
Pro Tyr Pro Cys Gly Lys Gln Thr Leu Glu Arg Arg Lys Arg Ser Val
                130                 135                 140
Ala Gln Ala Thr Ser Ser Ser Gly Glu Ala Pro Asp Ser Ile Thr Trp
145                 150                 155                 160
Lys Pro Tyr Asp Ala Ala Asp Leu Asp Pro Thr Glu Asn Pro Phe Asp
                165                 170                 175
Leu Leu Asp Phe Asn Gln Thr Gln Pro Glu Arg Gly Asp Asn Asn Leu
                180                 185                 190
Thr Arg Ile Val Gly Gly Gln Glu Cys Lys Asp Gly Glu Cys Pro Trp
                195                 200                 205
Gln Ala Leu Leu Ile Asn Glu Glu Asn Glu Gly Phe Cys Gly Gly Thr
                210                 215                 220
Ile Leu Ser Glu Phe Tyr Ile Leu Thr Ala Ala His Cys Leu Tyr Gln
225                 230                 235                 240
Ala Lys Arg Phe Lys Val Arg Val Gly Asp Arg Asn Thr Glu Gln Glu
                245                 250                 255
Glu Gly Gly Glu Ala Val His Glu Val Glu Val Val Ile Lys His Asn
                260                 265                 270
Arg Phe Thr Lys Glu Thr Tyr Asp Phe Asp Ile Ala Val Leu Arg Leu
                275                 280                 285
Lys Thr Pro Ile Thr Phe Arg Met Asn Val Ala Pro Ala Cys Leu Pro
                290                 295                 300
Glu Arg Asp Trp Ala Glu Ser Thr Leu Met Thr Gln Lys Thr Gly Ile
305                 310                 315                 320
Val Ser Gly Phe Gly Arg Thr His Glu Lys Gly Arg Gln Ser Thr Arg
                325                 330                 335
Leu Lys Met Leu Glu Val Pro Tyr Val Asp Arg Asn Ser Cys Lys Leu
                340                 345                 350
Ser Ser Ser Phe Ile Ile Thr Gln Asn Met Phe Cys Ala Gly Tyr Asp
                355                 360                 365
Thr Lys Gln Glu Asp Ala Cys Gln Gly Asp Ser Gly Gly Pro His Val
                370                 375                 380
Thr Arg Phe Lys Asp Thr Tyr Phe Val Thr Gly Ile Val Ser Trp Gly
385                 390                 395                 400
Glu Gly Cys Ala Arg Lys Gly Lys Tyr Gly Ile Tyr Thr Lys Val Thr

```
                        405                 410                 415
Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

<210> SEQ ID NO 3
<211> LENGTH: 122
<212> TYPE: PRT
<213> ORGANISM: Artificial Sequence
<220> FEATURE:
<223> OTHER INFORMATION: Recombinant protein

<400> SEQUENCE: 3

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 4
<211> LENGTH: 5
<212> TYPE: PRT
<213> ORGANISM: Artificial Sequence
<220> FEATURE:
<223> OTHER INFORMATION: Recombinant protein

<400> SEQUENCE: 4

Asp Tyr Ala Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Recombinant protein

<400> SEQUENCE: 5

Gly Ile Ser Trp Arg Gly Asp Ile Gly Gly Tyr Val Asp Ser Val Lys
1               5                   10                  15

Gly

<210> SEQ ID NO 6
<211> LENGTH: 13
<212> TYPE: PRT
<213> ORGANISM: Artificial Sequence
<220> FEATURE:
<223> OTHER INFORMATION: Recombinant protein

<400> SEQUENCE: 6
```

```
Ser Tyr Gly Ser Gly Ser Phe Tyr Asn Ala Phe Asp Ser
1               5                   10
```

<210> SEQ ID NO 7
<211> LENGTH: 107
<212> TYPE: PRT
<213> ORGANISM: Artificial Sequence
<220> FEATURE:
<223> OTHER INFORMATION: Recombinant protein

<400> SEQUENCE: 7

```
Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Glu Arg Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105
```

<210> SEQ ID NO 8
<211> LENGTH: 11
<212> TYPE: PRT
<213> ORGANISM: Artificial Sequence
<220> FEATURE:
<223> OTHER INFORMATION: Recombinant protein

<400> SEQUENCE: 8

```
Arg Ala Ser Gln Ser Ile Ser Ser Trp Leu Ala
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Recombinant protein

<400> SEQUENCE: 9

```
Lys Ala Ser Arg Leu Glu Arg
1               5
```

<210> SEQ ID NO 10
<211> LENGTH: 9
<212> TYPE: PRT
<213> ORGANISM: Artificial Sequence
<220> FEATURE:
<223> OTHER INFORMATION: Recombinant protein

<400> SEQUENCE: 10

```
Leu Glu Tyr Ser Ser Tyr Ile Arg Thr
1               5
```

<210> SEQ ID NO 11
<211> LENGTH: 122
<212> TYPE: PRT
<213> ORGANISM: Artificial Sequence

```
<220> FEATURE:
<223> OTHER INFORMATION: Recombinant protein

<400> SEQUENCE: 11

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Ile Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 12
<211> LENGTH: 5
<212> TYPE: PRT
<213> ORGANISM: Artificial Sequence
<220> FEATURE:
<223> OTHER INFORMATION: Recombinant protein

<400> SEQUENCE: 12

Asp Tyr Ala Met His
1               5

<210> SEQ ID NO 13
<211> LENGTH: 17
<212> TYPE: PRT
<213> ORGANISM: Artificial Sequence
<220> FEATURE:
<223> OTHER INFORMATION: Recombinant protein

<400> SEQUENCE: 13

Gly Ile Ser Trp Arg Gly Asp Ile Ile Gly Tyr Val Asp Ser Val Lys
1               5                   10                  15

Gly

<210> SEQ ID NO 14
<211> LENGTH: 13
<212> TYPE: PRT
<213> ORGANISM: Artificial Sequence
<220> FEATURE:
<223> OTHER INFORMATION: Recombinant protein

<400> SEQUENCE: 14

Ser Tyr Gly Ser Gly Ser Phe Tyr Asn Ala Phe Asp Ser
1               5                   10

<210> SEQ ID NO 15
<211> LENGTH: 107
<212> TYPE: PRT
<213> ORGANISM: Artificial Sequence
<220> FEATURE:
<223> OTHER INFORMATION: Recombinant protein

<400> SEQUENCE: 15
```

```
Asp Ile Gln Met Thr Gln Ser Pro Ser Thr Leu Ser Ala Ser Ala Gly
1               5                   10                  15

Asp Glu Val Thr Ile Thr Cys Arg Ala Ser Lys Ser Ile Ser Ser Trp
            20                  25                  30

Leu Ala Trp Tyr Gln Gln Lys Pro Gly Lys Ala Pro Arg Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Thr Leu Thr Ile Ser His Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105
```

<210> SEQ ID NO 16
<211> LENGTH: 11
<212> TYPE: PRT
<213> ORGANISM: Artificial Sequence
<220> FEATURE:
<223> OTHER INFORMATION: Recombinant protein

<400> SEQUENCE: 16

```
Arg Ala Ser Lys Ser Ile Ser Ser Trp Leu Ala
1               5                   10
```

<210> SEQ ID NO 17
<211> LENGTH: 7
<212> TYPE: PRT
<213> ORGANISM: Artificial Sequence
<220> FEATURE:
<223> OTHER INFORMATION: Recombinant protein

<400> SEQUENCE: 17

```
Lys Ala Ser Arg Leu Asp Arg
1               5
```

<210> SEQ ID NO 18
<211> LENGTH: 9
<212> TYPE: PRT
<213> ORGANISM: Artificial Sequence
<220> FEATURE:
<223> OTHER INFORMATION: Recombinant protein

<400> SEQUENCE: 18

```
Leu Glu Tyr Ser Ser Tyr Ile Arg Thr
1               5
```

<210> SEQ ID NO 19
<211> LENGTH: 122
<212> TYPE: PRT
<213> ORGANISM: Artificial Sequence
<220> FEATURE:
<223> OTHER INFORMATION: Recombinant protein

<400> SEQUENCE: 19

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45
```

Ser Gly Ile Ser Trp Arg Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120

<210> SEQ ID NO 20
<211> LENGTH: 5
<212> TYPE: PRT
<213> ORGANISM: Artificial Sequence
<220> FEATURE:
<223> OTHER INFORMATION: Recombinant protein

<400> SEQUENCE: 20

Asp Tyr Ala Met His
1               5

<210> SEQ ID NO 21
<211> LENGTH: 17
<212> TYPE: PRT
<213> ORGANISM: Artificial Sequence
<220> FEATURE:
<223> OTHER INFORMATION: Recombinant protein

<400> SEQUENCE: 21

Gly Ile Ser Trp Arg Gly Asp Ile Gly Gly Tyr Val Asp Ser Val Lys
1               5                   10                  15

Gly

<210> SEQ ID NO 22
<211> LENGTH: 13
<212> TYPE: PRT
<213> ORGANISM: Artificial Sequence
<220> FEATURE:
<223> OTHER INFORMATION: Recombinant protein

<400> SEQUENCE: 22

Ser Tyr Gly Ser Gly Ser Phe Tyr Asn Ala Phe Asp Ser
1               5                   10

<210> SEQ ID NO 23
<211> LENGTH: 107
<212> TYPE: PRT
<213> ORGANISM: Artificial Sequence
<220> FEATURE:
<223> OTHER INFORMATION: Recombinant protein

<400> SEQUENCE: 23

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

```
Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
            100                 105

<210> SEQ ID NO 24
<211> LENGTH: 11
<212> TYPE: PRT
<213> ORGANISM: Artificial Sequence
<220> FEATURE:
<223> OTHER INFORMATION: Recombinant protein

<400> SEQUENCE: 24

Arg Ala Ser Gln Ser Ile Ser Ser Trp Leu Ala
1                5                   10

<210> SEQ ID NO 25
<211> LENGTH: 7
<212> TYPE: PRT
<213> ORGANISM: Artificial Sequence
<220> FEATURE:
<223> OTHER INFORMATION: Recombinant protein

<400> SEQUENCE: 25

Lys Ala Ser Arg Leu Asp Arg
1                5

<210> SEQ ID NO 26
<211> LENGTH: 9
<212> TYPE: PRT
<213> ORGANISM: Artificial Sequence
<220> FEATURE:
<223> OTHER INFORMATION: Recombinant protein

<400> SEQUENCE: 26

Leu Glu Tyr Ser Ser Tyr Ile Arg Thr
1                5

<210> SEQ ID NO 27
<211> LENGTH: 122
<212> TYPE: PRT
<213> ORGANISM: Artificial Sequence
<220> FEATURE:
<223> OTHER INFORMATION: Recombinant protein

<400> SEQUENCE: 27

Glu Val Gln Leu Val Glu Ser Gly Gly Gly Leu Val Gln Pro Gly Arg
1                5                   10                  15

Ser Leu Lys Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Arg Gly Asp Ile Gly Gly Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110
```

Gly Gln Gly Thr Leu Val Thr Val Ser Ser
         115                 120

<210> SEQ ID NO 28
<211> LENGTH: 5
<212> TYPE: PRT
<213> ORGANISM: Artificial Sequence
<220> FEATURE:
<223> OTHER INFORMATION: Recombinant protein

<400> SEQUENCE: 28

Asp Tyr Ala Met His
1               5

<210> SEQ ID NO 29
<211> LENGTH: 17
<212> TYPE: PRT
<213> ORGANISM: Artificial Sequence
<220> FEATURE:
<223> OTHER INFORMATION: Recombinant protein

<400> SEQUENCE: 29

Gly Ile Ser Trp Arg Gly Asp Ile Gly Gly Tyr Val Asp Ser Val Lys
1               5                   10                  15

Gly

<210> SEQ ID NO 30
<211> LENGTH: 13
<212> TYPE: PRT
<213> ORGANISM: Artificial Sequence
<220> FEATURE:
<223> OTHER INFORMATION: Recombinant protein

<400> SEQUENCE: 30

Ser Tyr Gly Ser Gly Ser Phe Tyr Asn Ala Phe Asp Ser
1               5                   10

<210> SEQ ID NO 31
<211> LENGTH: 107
<212> TYPE: PRT
<213> ORGANISM: Artificial Sequence
<220> FEATURE:
<223> OTHER INFORMATION: Recombinant protein

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Glu Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 32
<211> LENGTH: 11
<212> TYPE: PRT

```
<213> ORGANISM: Artificial Sequence
<220> FEATURE:
<223> OTHER INFORMATION: Recombinant protein

<400> SEQUENCE: 32

Arg Ala Ser Gln Ser Ile Ser Ser Trp Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Recombinant protein

<400> SEQUENCE: 33

Lys Ala Ser Arg Leu Glu Arg
1               5

<210> SEQ ID NO 34
<211> LENGTH: 9
<212> TYPE: PRT
<213> ORGANISM: Artificial Sequence
<220> FEATURE:
<223> OTHER INFORMATION: Recombinant protein

<400> SEQUENCE: 34

Leu Glu Tyr Ser Ser Tyr Ile Arg Thr
1               5

<210> SEQ ID NO 35
<211> LENGTH: 122
<212> TYPE: PRT
<213> ORGANISM: Artificial Sequence
<220> FEATURE:
<223> OTHER INFORMATION: Recombinant protein

<400> SEQUENCE: 35

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Lys Gly Asp Ile Gly Gly Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 36
<211> LENGTH: 5
<212> TYPE: PRT
<213> ORGANISM: Artificial Sequence
<220> FEATURE:
<223> OTHER INFORMATION: Recombinant protein

<400> SEQUENCE: 36
```

```
Asp Tyr Ala Met His
1               5

<210> SEQ ID NO 37
<211> LENGTH: 17
<212> TYPE: PRT
<213> ORGANISM: Artificial Sequence
<220> FEATURE:
<223> OTHER INFORMATION: Recombinant protein

<400> SEQUENCE: 37

Gly Ile Ser Trp Lys Gly Asp Ile Gly Gly Tyr Val Asp Ser Val Lys
1               5                   10                  15

Gly

<210> SEQ ID NO 38
<211> LENGTH: 13
<212> TYPE: PRT
<213> ORGANISM: Artificial Sequence
<220> FEATURE:
<223> OTHER INFORMATION: Recombinant protein

<400> SEQUENCE: 38

Ser Tyr Gly Ser Gly Ser Phe Tyr Asn Ala Phe Asp Ser
1               5                   10

<210> SEQ ID NO 39
<211> LENGTH: 107
<212> TYPE: PRT
<213> ORGANISM: Artificial Sequence
<220> FEATURE:
<223> OTHER INFORMATION: Recombinant protein

<400> SEQUENCE: 39

Asp Ile Gln Met Thr Gln Ser Pro Ser Thr Leu Ser Ala Ser Ala Gly
1               5                   10                  15

Asp Glu Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Lys Leu Asp Arg Gly Val Pro Ser Arg Phe Ser Gly
    50                  55                  60

Ser Gly Ser Gly Thr Glu Phe Ser Leu Thr Ile Ser Asp Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 40
<211> LENGTH: 11
<212> TYPE: PRT
<213> ORGANISM: Artificial Sequence
<220> FEATURE:
<223> OTHER INFORMATION: Recombinant protein

<400> SEQUENCE: 40

Arg Ala Ser Gln Ser Ile Ser Ser Trp Leu Ala
1               5                   10

<210> SEQ ID NO 41
<211> LENGTH: 7
<212> TYPE: PRT
```

<213> ORGANISM: Artificial Sequence
<220> FEATURE:
<223> OTHER INFORMATION: Recombinant protein

<400> SEQUENCE: 41

Lys Ala Ser Lys Leu Asp Arg
1               5

<210> SEQ ID NO 42
<211> LENGTH: 9
<212> TYPE: PRT
<213> ORGANISM: Artificial Sequence
<220> FEATURE:
<223> OTHER INFORMATION: Recombinant protein

<400> SEQUENCE: 42

Leu Glu Tyr Ser Ser Tyr Ile Arg Thr
1               5

<210> SEQ ID NO 43
<211> LENGTH: 122
<212> TYPE: PRT
<213> ORGANISM: Artificial Sequence
<220> FEATURE:
<223> OTHER INFORMATION: Recombinant protein

<400> SEQUENCE: 43

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 44
<211> LENGTH: 5
<212> TYPE: PRT
<213> ORGANISM: Artificial Sequence
<220> FEATURE:
<223> OTHER INFORMATION: Recombinant protein

<400> SEQUENCE: 44

Asp Tyr Ala Met His
1               5

<210> SEQ ID NO 45
<211> LENGTH: 17
<212> TYPE: PRT
<213> ORGANISM: Artificial Sequence
<220> FEATURE:
<223> OTHER INFORMATION: Recombinant protein

<400> SEQUENCE: 45

```
Gly Ile Ser Trp Lys Gly Asp Ile Gly Gly Tyr Val Asp Ser Val Lys
1               5                   10                  15
Gly
```

<210> SEQ ID NO 46
<211> LENGTH: 13
<212> TYPE: PRT
<213> ORGANISM: Artificial Sequence
<220> FEATURE:
<223> OTHER INFORMATION: Recombinant protein

<400> SEQUENCE: 46

```
Ser Tyr Gly Ser Gly Ser Phe Tyr Asn Ala Phe Asp Ser
1               5                   10
```

<210> SEQ ID NO 47
<211> LENGTH: 107
<212> TYPE: PRT
<213> ORGANISM: Artificial Sequence
<220> FEATURE:
<223> OTHER INFORMATION: Recombinant protein

<400> SEQUENCE: 47

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Arg Leu Glu Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105
```

<210> SEQ ID NO 48
<211> LENGTH: 11
<212> TYPE: PRT
<213> ORGANISM: Artificial Sequence
<220> FEATURE:
<223> OTHER INFORMATION: Recombinant protein

<400> SEQUENCE: 48

```
Arg Ala Ser Gln Ser Ile Ser Ser Trp Leu Ala
1               5                   10
```

<210> SEQ ID NO 49
<211> LENGTH: 7
<212> TYPE: PRT
<213> ORGANISM: Artificial Sequence
<220> FEATURE:
<223> OTHER INFORMATION: Recombinant protein

<400> SEQUENCE: 49

```
Lys Ala Ser Arg Leu Glu Arg
1               5
```

<210> SEQ ID NO 50
<211> LENGTH: 9
<212> TYPE: PRT

<213> ORGANISM: Artificial Sequence
<220> FEATURE:
<223> OTHER INFORMATION: Recombinant protein

<400> SEQUENCE: 50

Leu Glu Tyr Ser Ser Tyr Ile Arg Thr
1               5

<210> SEQ ID NO 51
<211> LENGTH: 122
<212> TYPE: PRT
<213> ORGANISM: Artificial Sequence
<220> FEATURE:
<223> OTHER INFORMATION: Recombinant protein

<400> SEQUENCE: 51

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 52
<211> LENGTH: 5
<212> TYPE: PRT
<213> ORGANISM: Artificial Sequence
<220> FEATURE:
<223> OTHER INFORMATION: Recombinant protein

<400> SEQUENCE: 52

Asp Tyr Ala Met His
1               5

<210> SEQ ID NO 53
<211> LENGTH: 17
<212> TYPE: PRT
<213> ORGANISM: Artificial Sequence
<220> FEATURE:
<223> OTHER INFORMATION: Recombinant protein

<400> SEQUENCE: 53

Gly Ile Ser Trp Arg Gly Asp Ile Gly Gly Tyr Val Lys Ser Val Lys
1               5                   10                  15

Gly

<210> SEQ ID NO 54
<211> LENGTH: 13
<212> TYPE: PRT
<213> ORGANISM: Artificial Sequence
<220> FEATURE:
<223> OTHER INFORMATION: Recombinant protein

```
<400> SEQUENCE: 54

Ser Tyr Gly Ser Gly Ser Phe Tyr Asn Ala Phe Asp Ser
1               5                   10

<210> SEQ ID NO 55
<211> LENGTH: 107
<212> TYPE: PRT
<213> ORGANISM: Artificial Sequence
<220> FEATURE:
<223> OTHER INFORMATION: Recombinant protein

<400> SEQUENCE: 55

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Glu Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 56
<211> LENGTH: 11
<212> TYPE: PRT
<213> ORGANISM: Artificial Sequence
<220> FEATURE:
<223> OTHER INFORMATION: Recombinant protein

<400> SEQUENCE: 56

Arg Ala Ser Gln Ser Ile Ser Ser Trp Leu Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Recombinant protein

<400> SEQUENCE: 57

Lys Ala Ser Lys Leu Glu Arg
1               5

<210> SEQ ID NO 58
<211> LENGTH: 9
<212> TYPE: PRT
<213> ORGANISM: Artificial Sequence
<220> FEATURE:
<223> OTHER INFORMATION: Recombinant protein

<400> SEQUENCE: 58

Leu Glu Tyr Ser Ser Tyr Ile Arg Thr
1               5

<210> SEQ ID NO 59
<211> LENGTH: 122
<212> TYPE: PRT
```

```
<213> ORGANISM: Artificial Sequence
<220> FEATURE:
<223> OTHER INFORMATION: Recombinant protein

<400> SEQUENCE: 59

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 60
<211> LENGTH: 5
<212> TYPE: PRT
<213> ORGANISM: Artificial Sequence
<220> FEATURE:
<223> OTHER INFORMATION: Recombinant protein

<400> SEQUENCE: 60

Asp Tyr Ala Met His
1               5

<210> SEQ ID NO 61
<211> LENGTH: 17
<212> TYPE: PRT
<213> ORGANISM: Artificial Sequence
<220> FEATURE:
<223> OTHER INFORMATION: Recombinant protein

<400> SEQUENCE: 61

Gly Ile Ser Trp Arg Gly Asp Ile Gly Gly Tyr Val Lys Ser Val Lys
1               5                   10                  15

Gly

<210> SEQ ID NO 62
<211> LENGTH: 13
<212> TYPE: PRT
<213> ORGANISM: Artificial Sequence
<220> FEATURE:
<223> OTHER INFORMATION: Recombinant protein

<400> SEQUENCE: 62

Ser Tyr Gly Ser Gly Ser Phe Tyr Asn Ala Phe Asp Ser
1               5                   10

<210> SEQ ID NO 63
<211> LENGTH: 107
<212> TYPE: PRT
<213> ORGANISM: Artificial Sequence
<220> FEATURE:
<223> OTHER INFORMATION: Recombinant protein
```

```
<400> SEQUENCE: 63

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Glu Arg Gly Thr Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 64
<211> LENGTH: 11
<212> TYPE: PRT
<213> ORGANISM: Artificial Sequence
<220> FEATURE:
<223> OTHER INFORMATION: Recombinant protein

<400> SEQUENCE: 64

Arg Ala Ser Gln Ser Ile Ser Ser Trp Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Recombinant protein

<400> SEQUENCE: 65

Lys Ala Ser Arg Leu Glu Arg
1               5

<210> SEQ ID NO 66
<211> LENGTH: 9
<212> TYPE: PRT
<213> ORGANISM: Artificial Sequence
<220> FEATURE:
<223> OTHER INFORMATION: Recombinant protein

<400> SEQUENCE: 66

Leu Glu Tyr Ser Ser Tyr Ile Arg Thr
1               5

<210> SEQ ID NO 67
<211> LENGTH: 122
<212> TYPE: PRT
<213> ORGANISM: Artificial Sequence
<220> FEATURE:
<223> OTHER INFORMATION: Recombinant protein

<400> SEQUENCE: 67

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
```

```
                35                  40                  45
Ser Gly Ile Ser Trp Lys Gly Asp Ile Gly Gly Tyr Val Asp Ser Val
         50                  55                  60

Lys Gly Arg Phe Thr Ile Ser Arg Asp Asn Glu Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 68
<211> LENGTH: 5
<212> TYPE: PRT
<213> ORGANISM: Artificial Sequence
<220> FEATURE:
<223> OTHER INFORMATION: Recombinant protein

<400> SEQUENCE: 68

Asp Tyr Ala Met His
 1               5

<210> SEQ ID NO 69
<211> LENGTH: 17
<212> TYPE: PRT
<213> ORGANISM: Artificial Sequence
<220> FEATURE:
<223> OTHER INFORMATION: Recombinant protein

<400> SEQUENCE: 69

Gly Ile Ser Trp Lys Gly Asp Ile Gly Gly Tyr Val Asp Ser Val Lys
 1               5                  10                  15

Gly

<210> SEQ ID NO 70
<211> LENGTH: 13
<212> TYPE: PRT
<213> ORGANISM: Artificial Sequence
<220> FEATURE:
<223> OTHER INFORMATION: Recombinant protein

<400> SEQUENCE: 70

Ser Tyr Gly Ser Gly Ser Phe Tyr Asn Ala Phe Asp Ser
 1               5                  10

<210> SEQ ID NO 71
<211> LENGTH: 107
<212> TYPE: PRT
<213> ORGANISM: Artificial Sequence
<220> FEATURE:
<223> OTHER INFORMATION: Recombinant protein

<400> SEQUENCE: 71

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Phe Leu Ile
         35                  40                  45

Tyr Lys Ala Ser Arg Leu Asp Arg Gly Thr Pro Ser Arg Phe Ser Gly
     50                  55                  60
```

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 72
<211> LENGTH: 11
<212> TYPE: PRT
<213> ORGANISM: Artificial Sequence
<220> FEATURE:
<223> OTHER INFORMATION: Recombinant protein

<400> SEQUENCE: 72

Arg Ala Ser Gln Ser Ile Ser Ser Trp Leu Ala
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Recombinant protein

<400> SEQUENCE: 73

Lys Ala Ser Arg Leu Asp Arg
1               5

<210> SEQ ID NO 74
<211> LENGTH: 9
<212> TYPE: PRT
<213> ORGANISM: Artificial Sequence
<220> FEATURE:
<223> OTHER INFORMATION: Recombinant protein

<400> SEQUENCE: 74

Leu Glu Tyr Ser Ser Tyr Ile Arg Thr
1               5

<210> SEQ ID NO 75
<211> LENGTH: 122
<212> TYPE: PRT
<213> ORGANISM: Artificial Sequence
<220> FEATURE:
<223> OTHER INFORMATION: Recombinant protein

<400> SEQUENCE: 75

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
                20                  25                  30

Ala Met His Trp Val Arg Gln Ala Pro Gly Lys Gly Leu Glu Trp Val
            35                  40                  45

Ser Gly Ile Ser Trp Arg Gly Asp Ile Lys Gly Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

```
Gly Gln Gly Thr Leu Val Thr Val Ser Ser
        115                 120

<210> SEQ ID NO 76
<211> LENGTH: 5
<212> TYPE: PRT
<213> ORGANISM: Artificial Sequence
<220> FEATURE:
<223> OTHER INFORMATION: Recombinant protein

<400> SEQUENCE: 76

Asp Tyr Ala Met His
1               5

<210> SEQ ID NO 77
<211> LENGTH: 17
<212> TYPE: PRT
<213> ORGANISM: Artificial Sequence
<220> FEATURE:
<223> OTHER INFORMATION: Recombinant protein

<400> SEQUENCE: 77

Gly Ile Ser Trp Arg Gly Asp Ile Lys Gly Tyr Val Asp Ser Val Lys
1               5                   10                  15

Gly

<210> SEQ ID NO 78
<211> LENGTH: 13
<212> TYPE: PRT
<213> ORGANISM: Artificial Sequence
<220> FEATURE:
<223> OTHER INFORMATION: Recombinant protein

<400> SEQUENCE: 78

Ser Tyr Gly Ser Gly Ser Phe Tyr Asn Ala Phe Asp Ser
1               5                   10

<210> SEQ ID NO 79
<211> LENGTH: 107
<212> TYPE: PRT
<213> ORGANISM: Artificial Sequence
<220> FEATURE:
<223> OTHER INFORMATION: Recombinant protein

<400> SEQUENCE: 79

Asp Ile Gln Met Thr Gln Ser Pro Ser Thr Leu Ser Ala Ser Ala Gly
1               5                   10                  15

Asp Arg Val Thr Ile Thr Cys Arg Ala Ser Lys Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Gln Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 80
<211> LENGTH: 11
```

```
<212> TYPE: PRT
<213> ORGANISM: Artificial Sequence
<220> FEATURE:
<223> OTHER INFORMATION: Recombinant protein

<400> SEQUENCE: 80

Arg Ala Ser Lys Ser Ile Ser Ser Trp Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Recombinant protein

<400> SEQUENCE: 81

Lys Ala Ser Arg Leu Asp Arg
1               5

<210> SEQ ID NO 82
<211> LENGTH: 9
<212> TYPE: PRT
<213> ORGANISM: Artificial Sequence
<220> FEATURE:
<223> OTHER INFORMATION: Recombinant protein

<400> SEQUENCE: 82

Leu Glu Tyr Ser Ser Tyr Ile Arg Thr
1               5

<210> SEQ ID NO 83
<211> LENGTH: 122
<212> TYPE: PRT
<213> ORGANISM: Artificial Sequence
<220> FEATURE:
<223> OTHER INFORMATION: Recombinant protein

<400> SEQUENCE: 83

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Gly Ile Ser Trp Arg Gly Asp Ile Lys Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
            85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 84
<211> LENGTH: 5
<212> TYPE: PRT
<213> ORGANISM: Artificial Sequence
<220> FEATURE:
<223> OTHER INFORMATION: Recombinant protein

<400> SEQUENCE: 84
```

```
Asp Tyr Ala Met His
1               5

<210> SEQ ID NO 85
<211> LENGTH: 17
<212> TYPE: PRT
<213> ORGANISM: Artificial Sequence
<220> FEATURE:
<223> OTHER INFORMATION: Recombinant protein

<400> SEQUENCE: 85

Gly Ile Ser Trp Arg Gly Asp Ile Lys Gly Tyr Val Asp Ser Val Lys
1               5                   10                  15

Gly

<210> SEQ ID NO 86
<211> LENGTH: 13
<212> TYPE: PRT
<213> ORGANISM: Artificial Sequence
<220> FEATURE:
<223> OTHER INFORMATION: Recombinant protein

<400> SEQUENCE: 86

Ser Tyr Gly Ser Gly Ser Phe Tyr Asn Ala Phe Asp Ser
1               5                   10

<210> SEQ ID NO 87
<211> LENGTH: 107
<212> TYPE: PRT
<213> ORGANISM: Artificial Sequence
<220> FEATURE:
<223> OTHER INFORMATION: Recombinant protein

<400> SEQUENCE: 87

Asp Ile Gln Met Thr Gln Ser Pro Ser Thr Leu Ser Ala Ser Ala Gly
1               5                   10                  15

Asp Arg Val Thr Ile Ser Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Asn Ser Tyr Ile Arg
                85                  90                  95

Thr Phe Gly Gln Gly Thr Lys Val Glu Ile Lys
            100                 105

<210> SEQ ID NO 88
<211> LENGTH: 11
<212> TYPE: PRT
<213> ORGANISM: Artificial Sequence
<220> FEATURE:
<223> OTHER INFORMATION: Recombinant protein

<400> SEQUENCE: 88

Arg Ala Ser Gln Ser Ile Ser Ser Trp Leu Ala
1               5                   10

<210> SEQ ID NO 89
<211> LENGTH: 7
```

```
<212> TYPE: PRT
<213> ORGANISM: Artificial Sequence
<220> FEATURE:
<223> OTHER INFORMATION: Recombinant protein

<400> SEQUENCE: 89

Lys Ala Ser Arg Leu Asp Arg
1               5

<210> SEQ ID NO 90
<211> LENGTH: 9
<212> TYPE: PRT
<213> ORGANISM: Artificial Sequence
<220> FEATURE:
<223> OTHER INFORMATION: Recombinant protein

<400> SEQUENCE: 90

Leu Glu Tyr Asn Ser Tyr Ile Arg Thr
1               5

<210> SEQ ID NO 91
<211> LENGTH: 122
<212> TYPE: PRT
<213> ORGANISM: Artificial Sequence
<220> FEATURE:
<223> OTHER INFORMATION: Recombinant protein

<400> SEQUENCE: 91

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 92
<211> LENGTH: 5
<212> TYPE: PRT
<213> ORGANISM: Artificial Sequence
<220> FEATURE:
<223> OTHER INFORMATION: Recombinant protein

<400> SEQUENCE: 92

Asp Tyr Ala Met His
1               5

<210> SEQ ID NO 93
<211> LENGTH: 17
<212> TYPE: PRT
<213> ORGANISM: Artificial Sequence
<220> FEATURE:
<223> OTHER INFORMATION: Recombinant protein

<400> SEQUENCE: 93
```

```
Gly Ile Ser Trp Arg Gly Asp Ile Gly Gly Tyr Val Lys Ser Val Lys
1               5                  10                  15

Gly

<210> SEQ ID NO 94
<211> LENGTH: 13
<212> TYPE: PRT
<213> ORGANISM: Artificial Sequence
<220> FEATURE:
<223> OTHER INFORMATION: Recombinant protein

<400> SEQUENCE: 94

Ser Tyr Gly Ser Gly Ser Phe Tyr Asn Ala Phe Asp Ser
1               5                  10

<210> SEQ ID NO 95
<211> LENGTH: 107
<212> TYPE: PRT
<213> ORGANISM: Artificial Sequence
<220> FEATURE:
<223> OTHER INFORMATION: Recombinant protein

<400> SEQUENCE: 95

Asp Ile Gln Met Thr Gln Ser Pro Ser Thr Leu Ser Ala Ser Val Gly
1               5                  10                  15

Asp Glu Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Gln Arg Leu Asp Arg Gly Thr Pro Gln Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 96
<211> LENGTH: 11
<212> TYPE: PRT
<213> ORGANISM: Artificial Sequence
<220> FEATURE:
<223> OTHER INFORMATION: Recombinant protein

<400> SEQUENCE: 96

Arg Ala Ser Gln Ser Ile Ser Ser Trp Leu Ala
1               5                  10

<210> SEQ ID NO 97
<211> LENGTH: 7
<212> TYPE: PRT
<213> ORGANISM: Artificial Sequence
<220> FEATURE:
<223> OTHER INFORMATION: Recombinant protein

<400> SEQUENCE: 97

Lys Ala Gln Arg Leu Asp Arg
1               5

<210> SEQ ID NO 98
<211> LENGTH: 9
```

```
<212> TYPE: PRT
<213> ORGANISM: Artificial Sequence
<220> FEATURE:
<223> OTHER INFORMATION: Recombinant protein

<400> SEQUENCE: 98

Leu Glu Tyr Ser Ser Tyr Ile Arg Thr
1               5

<210> SEQ ID NO 99
<211> LENGTH: 122
<212> TYPE: PRT
<213> ORGANISM: Artificial Sequence
<220> FEATURE:
<223> OTHER INFORMATION: Recombinant protein

<400> SEQUENCE: 99

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 100
<211> LENGTH: 5
<212> TYPE: PRT
<213> ORGANISM: Artificial Sequence
<220> FEATURE:
<223> OTHER INFORMATION: Recombinant protein

<400> SEQUENCE: 100

Asp Tyr Ala Met His
1               5

<210> SEQ ID NO 101
<211> LENGTH: 17
<212> TYPE: PRT
<213> ORGANISM: Artificial Sequence
<220> FEATURE:
<223> OTHER INFORMATION: Recombinant protein

<400> SEQUENCE: 101

Gly Ile Ser Trp Lys Gly Asp Ile Gly Gly Tyr Val Asp Ser Val Lys
1               5                   10                  15

Gly

<210> SEQ ID NO 102
<211> LENGTH: 13
<212> TYPE: PRT
<213> ORGANISM: Artificial Sequence
<220> FEATURE:
<223> OTHER INFORMATION: Recombinant protein
```

```
<400> SEQUENCE: 102

Ser Tyr Gly Ser Gly Ser Phe Tyr Asn Ala Phe Asp Ser
1               5                   10

<210> SEQ ID NO 103
<211> LENGTH: 107
<212> TYPE: PRT
<213> ORGANISM: Artificial Sequence
<220> FEATURE:
<223> OTHER INFORMATION: Recombinant protein

<400> SEQUENCE: 103

Asp Ile Gln Met Thr Gln Ser Pro Ser Thr Leu Ser Ala Ser Ala Gly
1               5                   10                  15

Asp Glu Val Thr Ile Thr Cys Arg Ala Ser Gln Ser Ile Lys Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Gln Arg Phe Ser Gly
    50                  55                  60

Ser Gly Ser Gly Thr Glu Phe Ser Leu Thr Ile Ser Arg Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 104
<211> LENGTH: 11
<212> TYPE: PRT
<213> ORGANISM: Artificial Sequence
<220> FEATURE:
<223> OTHER INFORMATION: Recombinant protein

<400> SEQUENCE: 104

Arg Ala Ser Gln Ser Ile Lys Ser Trp Leu Ala
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Recombinant protein

<400> SEQUENCE: 105

Lys Ala Ser Arg Leu Asp Arg
1               5

<210> SEQ ID NO 106
<211> LENGTH: 9
<212> TYPE: PRT
<213> ORGANISM: Artificial Sequence
<220> FEATURE:
<223> OTHER INFORMATION: Recombinant protein

<400> SEQUENCE: 106

Leu Glu Tyr Ser Ser Tyr Ile Arg Thr
1               5

<210> SEQ ID NO 107
<211> LENGTH: 122
```

```
<212> TYPE: PRT
<213> ORGANISM: Artificial Sequence
<220> FEATURE:
<223> OTHER INFORMATION: Recombinant protein

<400> SEQUENCE: 107

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Arg Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 108
<211> LENGTH: 5
<212> TYPE: PRT
<213> ORGANISM: Artificial Sequence
<220> FEATURE:
<223> OTHER INFORMATION: Recombinant protein

<400> SEQUENCE: 108

Asp Tyr Ala Met His
1               5

<210> SEQ ID NO 109
<211> LENGTH: 17
<212> TYPE: PRT
<213> ORGANISM: Artificial Sequence
<220> FEATURE:
<223> OTHER INFORMATION: Recombinant protein

<400> SEQUENCE: 109

Gly Ile Ser Trp Lys Gly Asp Ile Gly Gly Tyr Ala Asp Ser Val Lys
1               5                   10                  15

Gly

<210> SEQ ID NO 110
<211> LENGTH: 13
<212> TYPE: PRT
<213> ORGANISM: Artificial Sequence
<220> FEATURE:
<223> OTHER INFORMATION: Recombinant protein

<400> SEQUENCE: 110

Ser Tyr Gly Ser Gly Ser Phe Tyr Asn Ala Phe Asp Ser
1               5                   10

<210> SEQ ID NO 111
<211> LENGTH: 107
<212> TYPE: PRT
<213> ORGANISM: Artificial Sequence
<220> FEATURE:
<223> OTHER INFORMATION: Recombinant protein
```

<400> SEQUENCE: 111

Asp Ile Gln Met Thr Gln Ser Pro Ser Thr Leu Ser Ala Ser Val Gly
1               5                   10                  15

Asp Glu Val Thr Ile Thr Cys Arg Ala Ser Lys Ser Ile Ser Ser Trp
            20                  25                  30

Leu Ala Trp Tyr Gln Gln Lys Pro Gly Lys Ala Pro Arg Phe Leu Ile
        35                  40                  45

Tyr Lys Ala Ser Arg Leu Glu Arg Gly Thr Pro Gln Arg Phe Ser Gly
50                  55                  60

Ser Gly Ser Gly Thr Glu Phe Thr Leu Thr Ile Tyr Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 112
<211> LENGTH: 11
<212> TYPE: PRT
<213> ORGANISM: Artificial Sequence
<220> FEATURE:
<223> OTHER INFORMATION: Recombinant protein

<400> SEQUENCE: 112

Arg Ala Ser Lys Ser Ile Ser Ser Trp Leu Ala
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Recombinant protein

<400> SEQUENCE: 113

Lys Ala Ser Arg Leu Glu Arg
1               5

<210> SEQ ID NO 114
<211> LENGTH: 9
<212> TYPE: PRT
<213> ORGANISM: Artificial Sequence
<220> FEATURE:
<223> OTHER INFORMATION: Recombinant protein

<400> SEQUENCE: 114

Leu Glu Tyr Ser Ser Tyr Ile Arg Thr
1               5

<210> SEQ ID NO 115
<211> LENGTH: 122
<212> TYPE: PRT
<213> ORGANISM: Artificial Sequence
<220> FEATURE:
<223> OTHER INFORMATION: Recombinant protein

<400> SEQUENCE: 115

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Arg Phe Asp Asp Tyr
            20                  25                  30

Ala Met His Trp Val Arg Gln Val Pro Gly Lys Gly Leu Glu Trp Val
            35                  40                  45

Ser Gly Ile Ser Trp Lys Gly Asp Ile Gly Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
             100                 105                 110

Gly Gln Gly Thr Leu Val Thr Val Ser Ser
         115                 120

<210> SEQ ID NO 116
<211> LENGTH: 5
<212> TYPE: PRT
<213> ORGANISM: Artificial Sequence
<220> FEATURE:
<223> OTHER INFORMATION: Recombinant protein

<400> SEQUENCE: 116

Asp Tyr Ala Met His
1               5

<210> SEQ ID NO 117
<211> LENGTH: 17
<212> TYPE: PRT
<213> ORGANISM: Artificial Sequence
<220> FEATURE:
<223> OTHER INFORMATION: Recombinant protein

<400> SEQUENCE: 117

Gly Ile Ser Trp Lys Gly Asp Ile Gly Gly Tyr Ala Asp Ser Val Lys
1               5                   10                  15

Gly

<210> SEQ ID NO 118
<211> LENGTH: 13
<212> TYPE: PRT
<213> ORGANISM: Artificial Sequence
<220> FEATURE:
<223> OTHER INFORMATION: Recombinant protein

<400> SEQUENCE: 118

Ser Tyr Gly Ser Gly Ser Phe Tyr Asn Ala Phe Asp Ser
1               5                   10

<210> SEQ ID NO 119
<211> LENGTH: 107
<212> TYPE: PRT
<213> ORGANISM: Artificial Sequence
<220> FEATURE:
<223> OTHER INFORMATION: Recombinant protein

<400> SEQUENCE: 119

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
         35                  40                  45

Tyr Lys Ala Ser Arg Leu Glu Arg Gly Thr Pro Ser Arg Phe Ser Gly

```
                    50                  55                  60
Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
            100                 105

<210> SEQ ID NO 120
<211> LENGTH: 11
<212> TYPE: PRT
<213> ORGANISM: Artificial Sequence
<220> FEATURE:
<223> OTHER INFORMATION: Recombinant protein

<400> SEQUENCE: 120

Arg Ala Ser Gln Ser Ile Ser Ser Trp Leu Ala
 1               5                  10

<210> SEQ ID NO 121
<211> LENGTH: 7
<212> TYPE: PRT
<213> ORGANISM: Artificial Sequence
<220> FEATURE:
<223> OTHER INFORMATION: Recombinant protein

<400> SEQUENCE: 121

Lys Ala Ser Arg Leu Glu Arg
 1               5

<210> SEQ ID NO 122
<211> LENGTH: 9
<212> TYPE: PRT
<213> ORGANISM: Artificial Sequence
<220> FEATURE:
<223> OTHER INFORMATION: Recombinant protein

<400> SEQUENCE: 122

Leu Glu Tyr Ser Ser Tyr Ile Arg Thr
 1               5

<210> SEQ ID NO 123
<211> LENGTH: 122
<212> TYPE: PRT
<213> ORGANISM: Artificial Sequence
<220> FEATURE:
<223> OTHER INFORMATION: Recombinant protein

<400> SEQUENCE: 123

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
         35                  40                  45

Ser Gly Ile Ser Trp Lys Gly Asp Ile Gly Gly Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
             85                  90                  95

Ala Lys Ser Tyr Gly Ser Gly Ser Phe Tyr Asn Ala Phe Asp Ser Trp
```

```
                 100                 105                 110
Gly Gln Gly Thr Leu Val Thr Val Ser Ser
            115                 120

<210> SEQ ID NO 124
<211> LENGTH: 5
<212> TYPE: PRT
<213> ORGANISM: Artificial Sequence
<220> FEATURE:
<223> OTHER INFORMATION: Recombinant protein

<400> SEQUENCE: 124

Asp Tyr Ala Met His
1               5

<210> SEQ ID NO 125
<211> LENGTH: 17
<212> TYPE: PRT
<213> ORGANISM: Artificial Sequence
<220> FEATURE:
<223> OTHER INFORMATION: Recombinant protein

<400> SEQUENCE: 125

Gly Ile Ser Trp Lys Gly Asp Ile Gly Gly Tyr Val Asp Ser Val Lys
1               5                   10                  15

Gly

<210> SEQ ID NO 126
<211> LENGTH: 13
<212> TYPE: PRT
<213> ORGANISM: Artificial Sequence
<220> FEATURE:
<223> OTHER INFORMATION: Recombinant protein

<400> SEQUENCE: 126

Ser Tyr Gly Ser Gly Ser Phe Tyr Asn Ala Phe Asp Ser
1               5                   10

<210> SEQ ID NO 127
<211> LENGTH: 107
<212> TYPE: PRT
<213> ORGANISM: Artificial Sequence
<220> FEATURE:
<223> OTHER INFORMATION: Recombinant protein

<400> SEQUENCE: 127

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 128
```

```
<211> LENGTH: 11
<212> TYPE: PRT
<213> ORGANISM: Artificial Sequence
<220> FEATURE:
<223> OTHER INFORMATION: Recombinant protein

<400> SEQUENCE: 128

Arg Ala Ser Gln Ser Ile Ser Ser Trp Leu Ala
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Recombinant protein

<400> SEQUENCE: 129

Lys Ala Ser Lys Leu Asp Arg
1               5

<210> SEQ ID NO 130
<211> LENGTH: 9
<212> TYPE: PRT
<213> ORGANISM: Artificial Sequence
<220> FEATURE:
<223> OTHER INFORMATION: Recombinant protein

<400> SEQUENCE: 130

Leu Glu Tyr Ser Ser Tyr Ile Arg Thr
1               5

<210> SEQ ID NO 131
<211> LENGTH: 122
<212> TYPE: PRT
<213> ORGANISM: Artificial Sequence
<220> FEATURE:
<223> OTHER INFORMATION: Recombinant protein

<400> SEQUENCE: 131

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 132
<211> LENGTH: 5
<212> TYPE: PRT
<213> ORGANISM: Artificial Sequence
<220> FEATURE:
<223> OTHER INFORMATION: Recombinant protein
```

```
<400> SEQUENCE: 132

Asp Tyr Ala Met His
1               5

<210> SEQ ID NO 133
<211> LENGTH: 17
<212> TYPE: PRT
<213> ORGANISM: Artificial Sequence
<220> FEATURE:
<223> OTHER INFORMATION: Recombinant protein

<400> SEQUENCE: 133

Gly Ile Ser Trp Lys Gly Asp Ile Gly Gly Tyr Val Asp Ser Val Lys
1               5                   10                  15

Gly

<210> SEQ ID NO 134
<211> LENGTH: 13
<212> TYPE: PRT
<213> ORGANISM: Artificial Sequence
<220> FEATURE:
<223> OTHER INFORMATION: Recombinant protein

<400> SEQUENCE: 134

Ser Tyr Gly Ser Gly Ser Phe Tyr Asn Ala Phe Asp Ser
1               5                   10

<210> SEQ ID NO 135
<211> LENGTH: 107
<212> TYPE: PRT
<213> ORGANISM: Artificial Sequence
<220> FEATURE:
<223> OTHER INFORMATION: Recombinant protein

<400> SEQUENCE: 135

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 136
<211> LENGTH: 11
<212> TYPE: PRT
<213> ORGANISM: Artificial Sequence
<220> FEATURE:
<223> OTHER INFORMATION: Recombinant protein

<400> SEQUENCE: 136

Arg Ala Ser Gln Ser Ile Ser Ser Trp Leu Ala
1               5                   10

<210> SEQ ID NO 137
```

<211> LENGTH: 7
<212> TYPE: PRT
<213> ORGANISM: Artificial Sequence
<220> FEATURE:
<223> OTHER INFORMATION: Recombinant protein

<400> SEQUENCE: 137

Lys Ala Ser Arg Leu Asp Arg
1               5

<210> SEQ ID NO 138
<211> LENGTH: 9
<212> TYPE: PRT
<213> ORGANISM: Artificial Sequence
<220> FEATURE:
<223> OTHER INFORMATION: Recombinant protein

<400> SEQUENCE: 138

Leu Glu Tyr Ser Ser Tyr Ile Arg Thr
1               5

<210> SEQ ID NO 139
<211> LENGTH: 122
<212> TYPE: PRT
<213> ORGANISM: Artificial Sequence
<220> FEATURE:
<223> OTHER INFORMATION: Recombinant protein

<400> SEQUENCE: 139

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 140
<211> LENGTH: 5
<212> TYPE: PRT
<213> ORGANISM: Artificial Sequence
<220> FEATURE:
<223> OTHER INFORMATION: Recombinant protein

<400> SEQUENCE: 140

Asp Tyr Ala Met His
1               5

<210> SEQ ID NO 141
<211> LENGTH: 17
<212> TYPE: PRT
<213> ORGANISM: Artificial Sequence
<220> FEATURE:
<223> OTHER INFORMATION: Recombinant protein

<400> SEQUENCE: 141

Gly Ile Ser Trp Lys Gly Asp Ile Gly Gly Tyr Val Asp Ser Val Lys
1               5                   10                  15

Gly

<210> SEQ ID NO 142
<211> LENGTH: 13
<212> TYPE: PRT
<213> ORGANISM: Artificial Sequence
<220> FEATURE:
<223> OTHER INFORMATION: Recombinant protein

<400> SEQUENCE: 142

Ser Tyr Gly Ser Gly Ser Phe Tyr Asn Ala Phe Asp Ser
1               5                   10

<210> SEQ ID NO 143
<211> LENGTH: 107
<212> TYPE: PRT
<213> ORGANISM: Artificial Sequence
<220> FEATURE:
<223> OTHER INFORMATION: Recombinant protein

<400> SEQUENCE: 143

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Cys Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 144
<211> LENGTH: 11
<212> TYPE: PRT
<213> ORGANISM: Artificial Sequence
<220> FEATURE:
<223> OTHER INFORMATION: Recombinant protein

<400> SEQUENCE: 144

Arg Ala Ser Gln Ser Ile Ser Ser Trp Leu Ala
1               5                   10

<210> SEQ ID NO 145
<211> LENGTH: 7
<212> TYPE: PRT
<213> ORGANISM: Artificial Sequence
<220> FEATURE:
<223> OTHER INFORMATION: Recombinant protein

<400> SEQUENCE: 145

Lys Ala Ser Arg Leu Asp Arg
1               5

<210> SEQ ID NO 146

```
<211> LENGTH: 9
<212> TYPE: PRT
<213> ORGANISM: Artificial Sequence
<220> FEATURE:
<223> OTHER INFORMATION: Recombinant protein

<400> SEQUENCE: 146

Leu Glu Tyr Ser Ser Tyr Ile Arg Thr
1               5

<210> SEQ ID NO 147
<211> LENGTH: 122
<212> TYPE: PRT
<213> ORGANISM: Artificial Sequence
<220> FEATURE:
<223> OTHER INFORMATION: Recombinant protein

<400> SEQUENCE: 147

Glu Val Gln Leu Val Glu Ser Gly Gly Gly Leu Val Gln Pro Gly Arg
1               5                  10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 148
<211> LENGTH: 5
<212> TYPE: PRT
<213> ORGANISM: Artificial Sequence
<220> FEATURE:
<223> OTHER INFORMATION: Recombinant protein

<400> SEQUENCE: 148

Asp Tyr Ala Met His
1               5

<210> SEQ ID NO 149
<211> LENGTH: 17
<212> TYPE: PRT
<213> ORGANISM: Artificial Sequence
<220> FEATURE:
<223> OTHER INFORMATION: Recombinant protein

<400> SEQUENCE: 149

Gly Ile Ser Trp Lys Gly Asp Ile Gly Gly Tyr Val Asp Ser Val Lys
1               5                  10                  15

Gly

<210> SEQ ID NO 150
<211> LENGTH: 13
<212> TYPE: PRT
<213> ORGANISM: Artificial Sequence
<220> FEATURE:
```

<223> OTHER INFORMATION: Recombinant protein

<400> SEQUENCE: 150

Ser Tyr Gly Ser Gly Ser Phe Tyr Asn Ala Phe Asp Ser
1               5                   10

<210> SEQ ID NO 151
<211> LENGTH: 107
<212> TYPE: PRT
<213> ORGANISM: Artificial Sequence
<220> FEATURE:
<223> OTHER INFORMATION: Recombinant protein

<400> SEQUENCE: 151

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Ile Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 152
<211> LENGTH: 11
<212> TYPE: PRT
<213> ORGANISM: Artificial Sequence
<220> FEATURE:
<223> OTHER INFORMATION: Recombinant protein

<400> SEQUENCE: 152

Arg Ala Ser Gln Ser Ile Ser Ser Trp Leu Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: Recombinant protein

<400> SEQUENCE: 153

Lys Ala Ser Arg Leu Asp Arg
1               5

<210> SEQ ID NO 154
<211> LENGTH: 9
<212> TYPE: PRT
<213> ORGANISM: Artificial Sequence
<220> FEATURE:
<223> OTHER INFORMATION: Recombinant protein

<400> SEQUENCE: 154

Leu Glu Tyr Ser Ser Tyr Ile Arg Thr
1               5

<210> SEQ ID NO 155

<211> LENGTH: 122
<212> TYPE: PRT
<213> ORGANISM: Artificial Sequence
<220> FEATURE:
<223> OTHER INFORMATION: Recombinant protein

<400> SEQUENCE: 155

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 156
<211> LENGTH: 5
<212> TYPE: PRT
<213> ORGANISM: Artificial Sequence
<220> FEATURE:
<223> OTHER INFORMATION: Recombinant protein

<400> SEQUENCE: 156

Asp Tyr Ala Met His
1               5

<210> SEQ ID NO 157
<211> LENGTH: 17
<212> TYPE: PRT
<213> ORGANISM: Artificial Sequence
<220> FEATURE:
<223> OTHER INFORMATION: Recombinant protein

<400> SEQUENCE: 157

Gly Ile Ser Trp Lys Gly Asp Ile Gly Gly Tyr Val Asp Ser Val Lys
1               5                   10                  15

Gly

<210> SEQ ID NO 158
<211> LENGTH: 13
<212> TYPE: PRT
<213> ORGANISM: Artificial Sequence
<220> FEATURE:
<223> OTHER INFORMATION: Recombinant protein

<400> SEQUENCE: 158

Ser Tyr Gly Ser Gly Ser Phe Tyr Asn Ala Phe Asp Ser
1               5                   10

<210> SEQ ID NO 159
<211> LENGTH: 107
<212> TYPE: PRT
<213> ORGANISM: Artificial Sequence
<220> FEATURE:

```
<223> OTHER INFORMATION: Recombinant protein

<400> SEQUENCE: 159

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Leu Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 160
<211> LENGTH: 11
<212> TYPE: PRT
<213> ORGANISM: Artificial Sequence
<220> FEATURE:
<223> OTHER INFORMATION: Recombinant protein

<400> SEQUENCE: 160

Arg Ala Ser Gln Ser Ile Ser Ser Trp Leu Ala
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Recombinant protein

<400> SEQUENCE: 161

Lys Ala Ser Arg Leu Asp Arg
1               5

<210> SEQ ID NO 162
<211> LENGTH: 9
<212> TYPE: PRT
<213> ORGANISM: Artificial Sequence
<220> FEATURE:
<223> OTHER INFORMATION: Recombinant protein

<400> SEQUENCE: 162

Leu Glu Tyr Ser Ser Tyr Ile Arg Thr
1               5

<210> SEQ ID NO 163
<211> LENGTH: 122
<212> TYPE: PRT
<213> ORGANISM: Artificial Sequence
<220> FEATURE:
<223> OTHER INFORMATION: Recombinant protein

<400> SEQUENCE: 163

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30
```

```
Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
 50                  55                  60

Lys Gly Arg Phe Thr Ile Ser Arg Asp Asn Glu Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
        115                 120

<210> SEQ ID NO 164
<211> LENGTH: 5
<212> TYPE: PRT
<213> ORGANISM: Artificial Sequence
<220> FEATURE:
<223> OTHER INFORMATION: Recombinant protein

<400> SEQUENCE: 164

Asp Tyr Ala Met His
1               5

<210> SEQ ID NO 165
<211> LENGTH: 17
<212> TYPE: PRT
<213> ORGANISM: Artificial Sequence
<220> FEATURE:
<223> OTHER INFORMATION: Recombinant protein

<400> SEQUENCE: 165

Gly Ile Ser Trp Lys Gly Asp Ile Gly Gly Tyr Val Asp Ser Val Lys
1               5                   10                  15

Gly

<210> SEQ ID NO 166
<211> LENGTH: 13
<212> TYPE: PRT
<213> ORGANISM: Artificial Sequence
<220> FEATURE:
<223> OTHER INFORMATION: Recombinant protein

<400> SEQUENCE: 166

Ser Tyr Gly Ser Gly Ser Phe Tyr Asn Ala Phe Asp Ser
1               5                   10

<210> SEQ ID NO 167
<211> LENGTH: 107
<212> TYPE: PRT
<213> ORGANISM: Artificial Sequence
<220> FEATURE:
<223> OTHER INFORMATION: Recombinant protein

<400> SEQUENCE: 167

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45
```

```
Tyr Lys Ala Ser Arg Leu Asp Arg Gly Met Pro Ser Arg Phe Ser Gly
     50                  55                  60

Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
             100                 105
```

<210> SEQ ID NO 168
<211> LENGTH: 11
<212> TYPE: PRT
<213> ORGANISM: Artificial Sequence
<220> FEATURE:
<223> OTHER INFORMATION: Recombinant protein

<400> SEQUENCE: 168

```
Arg Ala Ser Gln Ser Ile Ser Ser Trp Leu Ala
 1               5                  10
```

<210> SEQ ID NO 169
<211> LENGTH: 7
<212> TYPE: PRT
<213> ORGANISM: Artificial Sequence
<220> FEATURE:
<223> OTHER INFORMATION: Recombinant protein

<400> SEQUENCE: 169

```
Lys Ala Ser Arg Leu Asp Arg
 1               5
```

<210> SEQ ID NO 170
<211> LENGTH: 9
<212> TYPE: PRT
<213> ORGANISM: Artificial Sequence
<220> FEATURE:
<223> OTHER INFORMATION: Recombinant protein

<400> SEQUENCE: 170

```
Leu Glu Tyr Ser Ser Tyr Ile Arg Thr
 1               5
```

<210> SEQ ID NO 171
<211> LENGTH: 122
<212> TYPE: PRT
<213> ORGANISM: Artificial Sequence
<220> FEATURE:
<223> OTHER INFORMATION: Recombinant protein

<400> SEQUENCE: 171

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe His Asp Tyr
             20                  25                  30

Ala Met His Trp Val Arg Gln Val Pro Gly Lys Gly Leu Glu Trp Val
         35                  40                  45

Ser Gly Ile Ser Trp Lys Gly Asp Ile Gly Tyr Val Asp Ser Val
     50                  55                  60

Lys Gly Arg Phe Thr Ile Ser Arg Asp Asn Glu Lys Asn Ser Leu Tyr
 65                  70                  75                  80

Leu Gln Met Asn Ser Leu Arg Ala Glu Asp Thr Ala Leu Tyr Tyr Cys
                 85                  90                  95
```

```
Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 172
<211> LENGTH: 5
<212> TYPE: PRT
<213> ORGANISM: Artificial Sequence
<220> FEATURE:
<223> OTHER INFORMATION: Recombinant protein

<400> SEQUENCE: 172

```
Asp Tyr Ala Met His
1               5
```

<210> SEQ ID NO 173
<211> LENGTH: 17
<212> TYPE: PRT
<213> ORGANISM: Artificial Sequence
<220> FEATURE:
<223> OTHER INFORMATION: Recombinant protein

<400> SEQUENCE: 173

```
Gly Ile Ser Trp Lys Gly Asp Ile Gly Gly Tyr Val Asp Ser Val Lys
1               5                   10                  15

Gly
```

<210> SEQ ID NO 174
<211> LENGTH: 13
<212> TYPE: PRT
<213> ORGANISM: Artificial Sequence
<220> FEATURE:
<223> OTHER INFORMATION: Recombinant protein

<400> SEQUENCE: 174

```
Ser Tyr Gly Ser Gly Ser Phe Tyr Asn Ala Phe Asp Ser
1               5                   10
```

<210> SEQ ID NO 175
<211> LENGTH: 107
<212> TYPE: PRT
<213> ORGANISM: Artificial Sequence
<220> FEATURE:
<223> OTHER INFORMATION: Recombinant protein

<400> SEQUENCE: 175

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Asn Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105
```

```
<210> SEQ ID NO 176
<211> LENGTH: 11
<212> TYPE: PRT
<213> ORGANISM: Artificial Sequence
<220> FEATURE:
<223> OTHER INFORMATION: Recombinant protein

<400> SEQUENCE: 176

Arg Ala Ser Gln Ser Ile Ser Ser Trp Leu Ala
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Recombinant protein

<400> SEQUENCE: 177

Lys Ala Ser Arg Leu Asp Arg
1               5

<210> SEQ ID NO 178
<211> LENGTH: 9
<212> TYPE: PRT
<213> ORGANISM: Artificial Sequence
<220> FEATURE:
<223> OTHER INFORMATION: Recombinant protein

<400> SEQUENCE: 178

Leu Glu Tyr Ser Ser Tyr Ile Arg Thr
1               5

<210> SEQ ID NO 179
<211> LENGTH: 122
<212> TYPE: PRT
<213> ORGANISM: Artificial Sequence
<220> FEATURE:
<223> OTHER INFORMATION: Recombinant protein

<400> SEQUENCE: 179

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 180
<211> LENGTH: 5
<212> TYPE: PRT
<213> ORGANISM: Artificial Sequence
<220> FEATURE:
<223> OTHER INFORMATION: Recombinant protein
```

```
<400> SEQUENCE: 180

Asp Tyr Ala Met His
1               5

<210> SEQ ID NO 181
<211> LENGTH: 17
<212> TYPE: PRT
<213> ORGANISM: Artificial Sequence
<220> FEATURE:
<223> OTHER INFORMATION: Recombinant protein

<400> SEQUENCE: 181

Gly Ile Ser Trp Lys Gly Asp Ile Gly Gly Tyr Val Asp Ser Val Lys
1               5                   10                  15

Gly

<210> SEQ ID NO 182
<211> LENGTH: 13
<212> TYPE: PRT
<213> ORGANISM: Artificial Sequence
<220> FEATURE:
<223> OTHER INFORMATION: Recombinant protein

<400> SEQUENCE: 182

Ser Tyr Gly Ser Gly Ser Phe Tyr Asn Ala Phe Asp Ser
1               5                   10

<210> SEQ ID NO 183
<211> LENGTH: 107
<212> TYPE: PRT
<213> ORGANISM: Artificial Sequence
<220> FEATURE:
<223> OTHER INFORMATION: Recombinant protein

<400> SEQUENCE: 183

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Gln Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 184
<211> LENGTH: 11
<212> TYPE: PRT
<213> ORGANISM: Artificial Sequence
<220> FEATURE:
<223> OTHER INFORMATION: Recombinant protein

<400> SEQUENCE: 184

Arg Ala Ser Gln Ser Ile Ser Ser Trp Leu Ala
1               5                   10
```

```
<210> SEQ ID NO 185
<211> LENGTH: 7
<212> TYPE: PRT
<213> ORGANISM: Artificial Sequence
<220> FEATURE:
<223> OTHER INFORMATION: Recombinant protein

<400> SEQUENCE: 185

Lys Ala Ser Arg Leu Asp Arg
1               5

<210> SEQ ID NO 186
<211> LENGTH: 9
<212> TYPE: PRT
<213> ORGANISM: Artificial Sequence
<220> FEATURE:
<223> OTHER INFORMATION: Recombinant protein

<400> SEQUENCE: 186

Leu Glu Tyr Ser Ser Tyr Ile Arg Thr
1               5

<210> SEQ ID NO 187
<211> LENGTH: 122
<212> TYPE: PRT
<213> ORGANISM: Artificial Sequence
<220> FEATURE:
<223> OTHER INFORMATION: Recombinant protein

<400> SEQUENCE: 187

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 188
<211> LENGTH: 5
<212> TYPE: PRT
<213> ORGANISM: Artificial Sequence
<220> FEATURE:
<223> OTHER INFORMATION: Recombinant protein

<400> SEQUENCE: 188

Asp Tyr Ala Met His
1               5

<210> SEQ ID NO 189
<211> LENGTH: 17
<212> TYPE: PRT
<213> ORGANISM: Artificial Sequence
<220> FEATURE:
<223> OTHER INFORMATION: Recombinant protein
```

<400> SEQUENCE: 189

Gly Ile Ser Trp Lys Gly Asp Ile Gly Gly Tyr Val Asp Ser Val Lys
1               5                   10                  15

Gly

<210> SEQ ID NO 190
<211> LENGTH: 13
<212> TYPE: PRT
<213> ORGANISM: Artificial Sequence
<220> FEATURE:
<223> OTHER INFORMATION: Recombinant protein

<400> SEQUENCE: 190

Ser Tyr Gly Ser Gly Ser Phe Tyr Asn Ala Phe Asp Ser
1               5                   10

<210> SEQ ID NO 191
<211> LENGTH: 107
<212> TYPE: PRT
<213> ORGANISM: Artificial Sequence
<220> FEATURE:
<223> OTHER INFORMATION: Recombinant protein

<400> SEQUENCE: 191

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Ser Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 192
<211> LENGTH: 11
<212> TYPE: PRT
<213> ORGANISM: Artificial Sequence
<220> FEATURE:
<223> OTHER INFORMATION: Recombinant protein

<400> SEQUENCE: 192

Arg Ala Ser Gln Ser Ile Ser Ser Trp Leu Ala
1               5                   10

<210> SEQ ID NO 193
<211> LENGTH: 7
<212> TYPE: PRT
<213> ORGANISM: Artificial Sequence
<220> FEATURE:
<223> OTHER INFORMATION: Recombinant protein

<400> SEQUENCE: 193

Lys Ala Ser Arg Leu Asp Arg
1               5

```
<210> SEQ ID NO 194
<211> LENGTH: 9
<212> TYPE: PRT
<213> ORGANISM: Artificial Sequence
<220> FEATURE:
<223> OTHER INFORMATION: Recombinant protein

<400> SEQUENCE: 194

Leu Glu Tyr Ser Ser Tyr Ile Arg Thr
1               5

<210> SEQ ID NO 195
<211> LENGTH: 122
<212> TYPE: PRT
<213> ORGANISM: Artificial Sequence
<220> FEATURE:
<223> OTHER INFORMATION: Recombinant protein

<400> SEQUENCE: 195

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 196
<211> LENGTH: 5
<212> TYPE: PRT
<213> ORGANISM: Artificial Sequence
<220> FEATURE:
<223> OTHER INFORMATION: Recombinant protein

<400> SEQUENCE: 196

Asp Tyr Ala Met His
1               5

<210> SEQ ID NO 197
<211> LENGTH: 17
<212> TYPE: PRT
<213> ORGANISM: Artificial Sequence
<220> FEATURE:
<223> OTHER INFORMATION: Recombinant protein

<400> SEQUENCE: 197

Gly Ile Ser Trp Lys Gly Asp Ile Gly Gly Tyr Val Asp Ser Val Lys
1               5                   10                  15

Gly

<210> SEQ ID NO 198
<211> LENGTH: 13
<212> TYPE: PRT
<213> ORGANISM: Artificial Sequence
```

```
<220> FEATURE:
<223> OTHER INFORMATION: Recombinant protein

<400> SEQUENCE: 198

Ser Tyr Gly Ser Gly Ser Phe Tyr Asn Ala Phe Asp Ser
1               5                   10

<210> SEQ ID NO 199
<211> LENGTH: 107
<212> TYPE: PRT
<213> ORGANISM: Artificial Sequence
<220> FEATURE:
<223> OTHER INFORMATION: Recombinant protein

<400> SEQUENCE: 199

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 200
<211> LENGTH: 11
<212> TYPE: PRT
<213> ORGANISM: Artificial Sequence
<220> FEATURE:
<223> OTHER INFORMATION: Recombinant protein

<400> SEQUENCE: 200

Arg Ala Ser Gln Ser Ile Ser Ser Trp Leu Ala
1               5                   10

<210> SEQ ID NO 201
<211> LENGTH: 7
<212> TYPE: PRT
<213> ORGANISM: Artificial Sequence
<220> FEATURE:
<223> OTHER INFORMATION: Recombinant protein

<400> SEQUENCE: 201

Lys Ala Ser Arg Leu Asp Arg
1               5

<210> SEQ ID NO 202
<211> LENGTH: 9
<212> TYPE: PRT
<213> ORGANISM: Artificial Sequence
<220> FEATURE:
<223> OTHER INFORMATION: Recombinant protein

<400> SEQUENCE: 202

Leu Glu Tyr Ser Ser Tyr Ile Arg Thr
1               5
```

```
<210> SEQ ID NO 203
<211> LENGTH: 122
<212> TYPE: PRT
<213> ORGANISM: Artificial Sequence
<220> FEATURE:
<223> OTHER INFORMATION: Recombinant protein

<400> SEQUENCE: 203

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 204
<211> LENGTH: 5
<212> TYPE: PRT
<213> ORGANISM: Artificial Sequence
<220> FEATURE:
<223> OTHER INFORMATION: Recombinant protein

<400> SEQUENCE: 204

Asp Tyr Ala Met His
1               5

<210> SEQ ID NO 205
<211> LENGTH: 17
<212> TYPE: PRT
<213> ORGANISM: Artificial Sequence
<220> FEATURE:
<223> OTHER INFORMATION: Recombinant protein

<400> SEQUENCE: 205

Gly Ile Ser Trp Lys Gly Asp Ile Gly Gly Tyr Val Asp Ser Val Lys
1               5                   10                  15

Gly

<210> SEQ ID NO 206
<211> LENGTH: 13
<212> TYPE: PRT
<213> ORGANISM: Artificial Sequence
<220> FEATURE:
<223> OTHER INFORMATION: Recombinant protein

<400> SEQUENCE: 206

Ser Tyr Gly Ser Gly Ser Phe Tyr Asn Ala Phe Asp Ser
1               5                   10

<210> SEQ ID NO 207
<211> LENGTH: 107
<212> TYPE: PRT
<213> ORGANISM: Artificial Sequence
```

-continued

```
<220> FEATURE:
<223> OTHER INFORMATION: Recombinant protein

<400> SEQUENCE: 207

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Trp Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 208
<211> LENGTH: 11
<212> TYPE: PRT
<213> ORGANISM: Artificial Sequence
<220> FEATURE:
<223> OTHER INFORMATION: Recombinant protein

<400> SEQUENCE: 208

Arg Ala Ser Gln Ser Ile Ser Ser Trp Leu Ala
1               5                   10

<210> SEQ ID NO 209
<211> LENGTH: 7
<212> TYPE: PRT
<213> ORGANISM: Artificial Sequence
<220> FEATURE:
<223> OTHER INFORMATION: Recombinant protein

<400> SEQUENCE: 209

Lys Ala Ser Arg Leu Asp Arg
1               5

<210> SEQ ID NO 210
<211> LENGTH: 9
<212> TYPE: PRT
<213> ORGANISM: Artificial Sequence
<220> FEATURE:
<223> OTHER INFORMATION: Recombinant protein

<400> SEQUENCE: 210

Leu Glu Tyr Ser Ser Tyr Ile Arg Thr
1               5

<210> SEQ ID NO 211
<211> LENGTH: 122
<212> TYPE: PRT
<213> ORGANISM: Artificial Sequence
<220> FEATURE:
<223> OTHER INFORMATION: Recombinant protein

<400> SEQUENCE: 211

Glu Val Gln Leu Val Glu Ser Gly Gly Gly Leu Val Gln Pro Gly Arg
1               5                   10                  15

Ser Leu Arg Leu Ser Cys Ala Ala Ser Lys Phe Thr Phe His Asp Tyr
```

```
                20                  25                  30
Ala Met His Trp Val Arg Gln Ala Pro Gly Lys Gly Leu Glu Trp Val
                35                  40                  45

Ser Gly Ile Ser Trp Lys Gly Asp Ile Gly Gly Tyr Ala Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
                100                 105                 110

Gly Gln Gly Thr Leu Val Thr Val Ser Ser
                115                 120
```

<210> SEQ ID NO 212
<211> LENGTH: 5
<212> TYPE: PRT
<213> ORGANISM: Artificial Sequence
<220> FEATURE:
<223> OTHER INFORMATION: Recombinant protein

<400> SEQUENCE: 212

```
Asp Tyr Ala Met His
1               5
```

<210> SEQ ID NO 213
<211> LENGTH: 17
<212> TYPE: PRT
<213> ORGANISM: Artificial Sequence
<220> FEATURE:
<223> OTHER INFORMATION: Recombinant protein

<400> SEQUENCE: 213

```
Gly Ile Ser Trp Lys Gly Asp Ile Gly Gly Tyr Ala Asp Ser Val Lys
1               5                   10                  15

Gly
```

<210> SEQ ID NO 214
<211> LENGTH: 13
<212> TYPE: PRT
<213> ORGANISM: Artificial Sequence
<220> FEATURE:
<223> OTHER INFORMATION: Recombinant protein

<400> SEQUENCE: 214

```
Ser Tyr Gly Ser Gly Ser Phe Tyr Asn Ala Phe Asp Ser
1               5                   10
```

<210> SEQ ID NO 215
<211> LENGTH: 107
<212> TYPE: PRT
<213> ORGANISM: Artificial Sequence
<220> FEATURE:
<223> OTHER INFORMATION: Recombinant protein

<400> SEQUENCE: 215

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Phe Leu Ile
                35                  40                  45
```

```
Tyr Lys Ala Ser Lys Leu Asp Arg Gly Thr Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
                100                 105
```

<210> SEQ ID NO 216
<211> LENGTH: 11
<212> TYPE: PRT
<213> ORGANISM: Artificial Sequence
<220> FEATURE:
<223> OTHER INFORMATION: Recombinant protein

<400> SEQUENCE: 216

```
Arg Ala Ser Gln Ser Ile Ser Ser Trp Leu Ala
 1               5                  10
```

<210> SEQ ID NO 217
<211> LENGTH: 7
<212> TYPE: PRT
<213> ORGANISM: Artificial Sequence
<220> FEATURE:
<223> OTHER INFORMATION: Recombinant protein

<400> SEQUENCE: 217

```
Lys Ala Ser Lys Leu Asp Arg
 1               5
```

<210> SEQ ID NO 218
<211> LENGTH: 9
<212> TYPE: PRT
<213> ORGANISM: Artificial Sequence
<220> FEATURE:
<223> OTHER INFORMATION: Recombinant protein

<400> SEQUENCE: 218

```
Leu Glu Tyr Ser Ser Tyr Ile Arg Thr
 1               5
```

<210> SEQ ID NO 219
<211> LENGTH: 122
<212> TYPE: PRT
<213> ORGANISM: Artificial Sequence
<220> FEATURE:
<223> OTHER INFORMATION: Recombinant protein

<400> SEQUENCE: 219

```
Glu Val Gln Leu Val Glu Ser Gly Gly Gly Leu Val Gln Pro Gly Arg
 1               5                  10                  15

Ser Leu Arg Leu Ser Cys Ala Ala Ser Lys Phe Thr Phe His Asp Tyr
            20                  25                  30

Ala Met His Trp Val Arg Gln Ala Pro Gly Lys Gly Leu Glu Trp Val
         35                  40                  45

Ser Gly Ile Ser Trp Lys Gly Asp Ile Gly Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95
```

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 220
<211> LENGTH: 5
<212> TYPE: PRT
<213> ORGANISM: Artificial Sequence
<220> FEATURE:
<223> OTHER INFORMATION: Recombinant protein

<400> SEQUENCE: 220

Asp Tyr Ala Met His
1               5

<210> SEQ ID NO 221
<211> LENGTH: 17
<212> TYPE: PRT
<213> ORGANISM: Artificial Sequence
<220> FEATURE:
<223> OTHER INFORMATION: Recombinant protein

<400> SEQUENCE: 221

Gly Ile Ser Trp Lys Gly Asp Ile Gly Gly Tyr Ala Asp Ser Val Lys
1               5                   10                  15

Gly

<210> SEQ ID NO 222
<211> LENGTH: 13
<212> TYPE: PRT
<213> ORGANISM: Artificial Sequence
<220> FEATURE:
<223> OTHER INFORMATION: Recombinant protein

<400> SEQUENCE: 222

Ser Tyr Gly Ser Gly Ser Phe Tyr Asn Ala Phe Asp Ser
1               5                   10

<210> SEQ ID NO 223
<211> LENGTH: 107
<212> TYPE: PRT
<213> ORGANISM: Artificial Sequence
<220> FEATURE:
<223> OTHER INFORMATION: Recombinant protein

<400> SEQUENCE: 223

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Glu Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

```
<210> SEQ ID NO 224
<211> LENGTH: 11
<212> TYPE: PRT
<213> ORGANISM: Artificial Sequence
<220> FEATURE:
<223> OTHER INFORMATION: Recombinant protein

<400> SEQUENCE: 224

Arg Ala Ser Gln Ser Ile Ser Ser Trp Leu Ala
1               5                   10

<210> SEQ ID NO 225
<211> LENGTH: 7
<212> TYPE: PRT
<213> ORGANISM: Artificial Sequence
<220> FEATURE:
<223> OTHER INFORMATION: Recombinant protein

<400> SEQUENCE: 225

Lys Ala Ser Lys Leu Glu Arg
1               5

<210> SEQ ID NO 226
<211> LENGTH: 9
<212> TYPE: PRT
<213> ORGANISM: Artificial Sequence
<220> FEATURE:
<223> OTHER INFORMATION: Recombinant protein

<400> SEQUENCE: 226

Leu Glu Tyr Ser Ser Tyr Ile Arg Thr
1               5

<210> SEQ ID NO 227
<211> LENGTH: 122
<212> TYPE: PRT
<213> ORGANISM: Artificial Sequence
<220> FEATURE:
<223> OTHER INFORMATION: Recombinant protein

<400> SEQUENCE: 227

Glu Val Gln Leu Val Glu Ser Gly Gly Gly Leu Val Gln Pro Gly Arg
1               5                   10                  15

Ser Leu Arg Leu Ser Cys Ala Ala Ser Lys Phe Thr Phe His Asp Tyr
            20                  25                  30

Ala Met His Trp Val Arg Gln Ala Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 228
<211> LENGTH: 5
<212> TYPE: PRT
<213> ORGANISM: Artificial Sequence
<220> FEATURE:
```

```
<223> OTHER INFORMATION: Recombinant protein

<400> SEQUENCE: 228

Asp Tyr Ala Met His
1               5

<210> SEQ ID NO 229
<211> LENGTH: 17
<212> TYPE: PRT
<213> ORGANISM: Artificial Sequence
<220> FEATURE:
<223> OTHER INFORMATION: Recombinant protein

<400> SEQUENCE: 229

Gly Ile Ser Trp Lys Gly Asp Ile Gly Gly Tyr Val Asp Ser Val Lys
1               5                   10                  15

Gly

<210> SEQ ID NO 230
<211> LENGTH: 13
<212> TYPE: PRT
<213> ORGANISM: Artificial Sequence
<220> FEATURE:
<223> OTHER INFORMATION: Recombinant protein

<400> SEQUENCE: 230

Ser Tyr Gly Ser Gly Ser Phe Tyr Asn Ala Phe Asp Ser
1               5                   10

<210> SEQ ID NO 231
<211> LENGTH: 107
<212> TYPE: PRT
<213> ORGANISM: Artificial Sequence
<220> FEATURE:
<223> OTHER INFORMATION: Recombinant protein

<400> SEQUENCE: 231

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 232
<211> LENGTH: 11
<212> TYPE: PRT
<213> ORGANISM: Artificial Sequence
<220> FEATURE:
<223> OTHER INFORMATION: Recombinant protein

<400> SEQUENCE: 232

Arg Ala Ser Gln Ser Ile Ser Ser Trp Leu Ala
1               5                   10
```

<210> SEQ ID NO 233
<211> LENGTH: 7
<212> TYPE: PRT
<213> ORGANISM: Artificial Sequence
<220> FEATURE:
<223> OTHER INFORMATION: Recombinant protein

<400> SEQUENCE: 233

Lys Ala Ser Lys Leu Asp Arg
1               5

<210> SEQ ID NO 234
<211> LENGTH: 9
<212> TYPE: PRT
<213> ORGANISM: Artificial Sequence
<220> FEATURE:
<223> OTHER INFORMATION: Recombinant protein

<400> SEQUENCE: 234

Leu Glu Tyr Ser Ser Tyr Ile Arg Thr
1               5

<210> SEQ ID NO 235
<211> LENGTH: 122
<212> TYPE: PRT
<213> ORGANISM: Artificial Sequence
<220> FEATURE:
<223> OTHER INFORMATION: Recombinant protein

<400> SEQUENCE: 235

Glu Val Gln Leu Val Glu Ser Gly Gly Gly Leu Val Gln Pro Gly Arg
1               5                   10                  15

Ser Leu Arg Leu Ser Cys Ala Ala Ser Lys Phe Thr Phe His Asp Tyr
            20                  25                  30

Ala Met His Trp Val Arg Gln Ala Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 236
<211> LENGTH: 5
<212> TYPE: PRT
<213> ORGANISM: Artificial Sequence
<220> FEATURE:
<223> OTHER INFORMATION: Recombinant protein

<400> SEQUENCE: 236

Asp Tyr Ala Met His
1               5

<210> SEQ ID NO 237
<211> LENGTH: 17
<212> TYPE: PRT
<213> ORGANISM: Artificial Sequence
<220> FEATURE:

<223> OTHER INFORMATION: Recombinant protein

<400> SEQUENCE: 237

Gly Ile Ser Trp Lys Gly Asp Ile Gly Gly Tyr Val Asp Ser Val Lys
1               5                   10                  15

Gly

<210> SEQ ID NO 238
<211> LENGTH: 13
<212> TYPE: PRT
<213> ORGANISM: Artificial Sequence
<220> FEATURE:
<223> OTHER INFORMATION: Recombinant protein

<400> SEQUENCE: 238

Ser Tyr Gly Ser Gly Ser Phe Tyr Asn Ala Phe Asp Ser
1               5                   10

<210> SEQ ID NO 239
<211> LENGTH: 107
<212> TYPE: PRT
<213> ORGANISM: Artificial Sequence
<220> FEATURE:
<223> OTHER INFORMATION: Recombinant protein

<400> SEQUENCE: 239

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Glu Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 240
<211> LENGTH: 11
<212> TYPE: PRT
<213> ORGANISM: Artificial Sequence
<220> FEATURE:
<223> OTHER INFORMATION: Recombinant protein

<400> SEQUENCE: 240

Arg Ala Ser Gln Ser Ile Ser Ser Trp Leu Ala
1               5                   10

<210> SEQ ID NO 241
<211> LENGTH: 7
<212> TYPE: PRT
<213> ORGANISM: Artificial Sequence
<220> FEATURE:
<223> OTHER INFORMATION: Recombinant protein

<400> SEQUENCE: 241

Lys Ala Ser Lys Leu Glu Arg
1               5

<210> SEQ ID NO 242
<211> LENGTH: 9
<212> TYPE: PRT
<213> ORGANISM: Artificial Sequence
<220> FEATURE:
<223> OTHER INFORMATION: Recombinant protein

<400> SEQUENCE: 242

Leu Glu Tyr Ser Ser Tyr Ile Arg Thr
1               5

<210> SEQ ID NO 243
<211> LENGTH: 122
<212> TYPE: PRT
<213> ORGANISM: Artificial Sequence
<220> FEATURE:
<223> OTHER INFORMATION: Recombinant protein

<400> SEQUENCE: 243

Glu Val Gln Leu Val Glu Ser Gly Gly Gly Leu Val Gln Pro Gly Arg
1               5                   10                  15

Ser Leu Arg Leu Ser Cys Ala Ala Ser Lys Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 244
<211> LENGTH: 5
<212> TYPE: PRT
<213> ORGANISM: Artificial Sequence
<220> FEATURE:
<223> OTHER INFORMATION: Recombinant protein

<400> SEQUENCE: 244

Asp Tyr Ala Met His
1               5

<210> SEQ ID NO 245
<211> LENGTH: 17
<212> TYPE: PRT
<213> ORGANISM: Artificial Sequence
<220> FEATURE:
<223> OTHER INFORMATION: Recombinant protein

<400> SEQUENCE: 245

Gly Ile Ser Trp Lys Gly Asp Ile Gly Gly Tyr Val Asp Ser Val Lys
1               5                   10                  15

Gly

<210> SEQ ID NO 246
<211> LENGTH: 13
<212> TYPE: PRT

```
<213> ORGANISM: Artificial Sequence
<220> FEATURE:
<223> OTHER INFORMATION: Recombinant protein

<400> SEQUENCE: 246

Ser Tyr Gly Ser Gly Ser Phe Tyr Asn Ala Phe Asp Ser
1               5                   10

<210> SEQ ID NO 247
<211> LENGTH: 107
<212> TYPE: PRT
<213> ORGANISM: Artificial Sequence
<220> FEATURE:
<223> OTHER INFORMATION: Recombinant protein

<400> SEQUENCE: 247

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 248
<211> LENGTH: 11
<212> TYPE: PRT
<213> ORGANISM: Artificial Sequence
<220> FEATURE:
<223> OTHER INFORMATION: Recombinant protein

<400> SEQUENCE: 248

Arg Ala Ser Gln Ser Ile Ser Ser Trp Leu Ala
1               5                   10

<210> SEQ ID NO 249
<211> LENGTH: 7
<212> TYPE: PRT
<213> ORGANISM: Artificial Sequence
<220> FEATURE:
<223> OTHER INFORMATION: Recombinant protein

<400> SEQUENCE: 249

Lys Ala Ser Lys Leu Asp Arg
1               5

<210> SEQ ID NO 250
<211> LENGTH: 9
<212> TYPE: PRT
<213> ORGANISM: Artificial Sequence
<220> FEATURE:
<223> OTHER INFORMATION: Recombinant protein

<400> SEQUENCE: 250

Leu Glu Tyr Ser Ser Tyr Ile Arg Thr
1               5
```

```
<210> SEQ ID NO 251
<211> LENGTH: 122
<212> TYPE: PRT
<213> ORGANISM: Artificial Sequence
<220> FEATURE:
<223> OTHER INFORMATION: Recombinant protein

<400> SEQUENCE: 251

Glu Val Gln Leu Val Glu Ser Gly Gly Gly Leu Val Gln Pro Gly Arg
1               5                   10                  15

Ser Leu Arg Leu Ser Cys Ala Ala Ser Lys Phe Thr Phe His Asp Tyr
                20                  25                  30

Ala Met His Trp Val Arg Gln Val Pro Gly Lys Gly Leu Glu Trp Val
            35                  40                  45

Ser Gly Ile Ser Trp Lys Gly Asp Ile Gly Gly Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 252
<211> LENGTH: 5
<212> TYPE: PRT
<213> ORGANISM: Artificial Sequence
<220> FEATURE:
<223> OTHER INFORMATION: Recombinant protein

<400> SEQUENCE: 252

Asp Tyr Ala Met His
1               5

<210> SEQ ID NO 253
<211> LENGTH: 17
<212> TYPE: PRT
<213> ORGANISM: Artificial Sequence
<220> FEATURE:
<223> OTHER INFORMATION: Recombinant protein

<400> SEQUENCE: 253

Gly Ile Ser Trp Lys Gly Asp Ile Gly Gly Tyr Val Asp Ser Val Lys
1               5                   10                  15

Gly

<210> SEQ ID NO 254
<211> LENGTH: 13
<212> TYPE: PRT
<213> ORGANISM: Artificial Sequence
<220> FEATURE:
<223> OTHER INFORMATION: Recombinant protein

<400> SEQUENCE: 254

Ser Tyr Gly Ser Gly Ser Phe Tyr Asn Ala Phe Asp Ser
1               5                   10

<210> SEQ ID NO 255
<211> LENGTH: 107
<212> TYPE: PRT
```

-continued

```
<213> ORGANISM: Artificial Sequence
<220> FEATURE:
<223> OTHER INFORMATION: Recombinant protein

<400> SEQUENCE: 255

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Glu Arg Gly Thr Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 256
<211> LENGTH: 11
<212> TYPE: PRT
<213> ORGANISM: Artificial Sequence
<220> FEATURE:
<223> OTHER INFORMATION: Recombinant protein

<400> SEQUENCE: 256

Arg Ala Ser Gln Ser Ile Ser Ser Trp Leu Ala
1               5                   10

<210> SEQ ID NO 257
<211> LENGTH: 7
<212> TYPE: PRT
<213> ORGANISM: Artificial Sequence
<220> FEATURE:
<223> OTHER INFORMATION: Recombinant protein

<400> SEQUENCE: 257

Lys Ala Ser Lys Leu Glu Arg
1               5

<210> SEQ ID NO 258
<211> LENGTH: 9
<212> TYPE: PRT
<213> ORGANISM: Artificial Sequence
<220> FEATURE:
<223> OTHER INFORMATION: Recombinant protein

<400> SEQUENCE: 258

Leu Glu Tyr Ser Ser Tyr Ile Arg Thr
1               5

<210> SEQ ID NO 259
<211> LENGTH: 122
<212> TYPE: PRT
<213> ORGANISM: Artificial Sequence
<220> FEATURE:
<223> OTHER INFORMATION: Recombinant protein

<400> SEQUENCE: 259

Glu Val Gln Leu Val Glu Ser Gly Gly Gly Leu Val Gln Pro Gly Arg
1               5                   10                  15
```

Ser Leu Lys Leu Ser Cys Ala Ala Ser Lys Phe Thr Phe His Asp Tyr
            20                  25                  30

Ala Met His Trp Val Arg Gln Ala Pro Gly Lys Gly Leu Glu Trp Val
            35                  40                  45

Ser Gly Ile Ser Trp Lys Gly Asp Ile Gly Gly Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 260
<211> LENGTH: 5
<212> TYPE: PRT
<213> ORGANISM: Artificial Sequence
<220> FEATURE:
<223> OTHER INFORMATION: Recombinant protein

<400> SEQUENCE: 260

Asp Tyr Ala Met His
1               5

<210> SEQ ID NO 261
<211> LENGTH: 17
<212> TYPE: PRT
<213> ORGANISM: Artificial Sequence
<220> FEATURE:
<223> OTHER INFORMATION: Recombinant protein

<400> SEQUENCE: 261

Gly Ile Ser Trp Lys Gly Asp Ile Gly Gly Tyr Val Asp Ser Val Lys
1               5                   10                  15

Gly

<210> SEQ ID NO 262
<211> LENGTH: 13
<212> TYPE: PRT
<213> ORGANISM: Artificial Sequence
<220> FEATURE:
<223> OTHER INFORMATION: Recombinant protein

<400> SEQUENCE: 262

Ser Tyr Gly Ser Gly Ser Phe Tyr Asn Ala Phe Asp Ser
1               5                   10

<210> SEQ ID NO 263
<211> LENGTH: 107
<212> TYPE: PRT
<213> ORGANISM: Artificial Sequence
<220> FEATURE:
<223> OTHER INFORMATION: Recombinant protein

<400> SEQUENCE: 263

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile

```
            35                  40                  45
Tyr Lys Ala Ser Lys Leu Asp Arg Gly Thr Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
            100                 105

<210> SEQ ID NO 264
<211> LENGTH: 11
<212> TYPE: PRT
<213> ORGANISM: Artificial Sequence
<220> FEATURE:
<223> OTHER INFORMATION: Recombinant protein

<400> SEQUENCE: 264

Arg Ala Ser Gln Ser Ile Ser Ser Trp Leu Ala
 1               5                  10

<210> SEQ ID NO 265
<211> LENGTH: 7
<212> TYPE: PRT
<213> ORGANISM: Artificial Sequence
<220> FEATURE:
<223> OTHER INFORMATION: Recombinant protein

<400> SEQUENCE: 265

Lys Ala Ser Lys Leu Asp Arg
 1               5

<210> SEQ ID NO 266
<211> LENGTH: 9
<212> TYPE: PRT
<213> ORGANISM: Artificial Sequence
<220> FEATURE:
<223> OTHER INFORMATION: Recombinant protein

<400> SEQUENCE: 266

Leu Glu Tyr Ser Ser Tyr Ile Arg Thr
 1               5

<210> SEQ ID NO 267
<211> LENGTH: 122
<212> TYPE: PRT
<213> ORGANISM: Artificial Sequence
<220> FEATURE:
<223> OTHER INFORMATION: Recombinant protein

<400> SEQUENCE: 267

Glu Val Gln Leu Val Glu Ser Gly Gly Gly Leu Val Gln Pro Gly Arg
 1               5                  10                  15

Ser Leu Lys Leu Ser Cys Ala Ala Ser Lys Phe Thr Phe His Asp Tyr
                 20                  25                  30

Ala Met His Trp Val Arg Gln Ala Pro Gly Lys Gly Leu Glu Trp Val
            35                  40                  45

Ser Gly Ile Ser Trp Lys Gly Asp Ile Gly Gly Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
```

```
                    85                  90                  95
Ala Lys Ser Tyr Gly Ser Gly Ser Phe Tyr Asn Ala Phe Asp Ser Trp
                100                 105                 110

Gly Gln Gly Thr Leu Val Thr Val Ser Ser
        115                 120

<210> SEQ ID NO 268
<211> LENGTH: 5
<212> TYPE: PRT
<213> ORGANISM: Artificial Sequence
<220> FEATURE:
<223> OTHER INFORMATION: Recombinant protein

<400> SEQUENCE: 268

Asp Tyr Ala Met His
1               5

<210> SEQ ID NO 269
<211> LENGTH: 17
<212> TYPE: PRT
<213> ORGANISM: Artificial Sequence
<220> FEATURE:
<223> OTHER INFORMATION: Recombinant protein

<400> SEQUENCE: 269

Gly Ile Ser Trp Lys Gly Asp Ile Gly Gly Tyr Val Asp Ser Val Lys
1               5                   10                  15

Gly

<210> SEQ ID NO 270
<211> LENGTH: 13
<212> TYPE: PRT
<213> ORGANISM: Artificial Sequence
<220> FEATURE:
<223> OTHER INFORMATION: Recombinant protein

<400> SEQUENCE: 270

Ser Tyr Gly Ser Gly Ser Phe Tyr Asn Ala Phe Asp Ser
1               5                   10

<210> SEQ ID NO 271
<211> LENGTH: 107
<212> TYPE: PRT
<213> ORGANISM: Artificial Sequence
<220> FEATURE:
<223> OTHER INFORMATION: Recombinant protein

<400> SEQUENCE: 271

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Glu Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
                100                 105
```

<210> SEQ ID NO 272
<211> LENGTH: 11
<212> TYPE: PRT
<213> ORGANISM: Artificial Sequence
<220> FEATURE:
<223> OTHER INFORMATION: Recombinant protein

<400> SEQUENCE: 272

```
Arg Ala Ser Gln Ser Ile Ser Ser Trp Leu Ala
1               5                   10
```

<210> SEQ ID NO 273
<211> LENGTH: 7
<212> TYPE: PRT
<213> ORGANISM: Artificial Sequence
<220> FEATURE:
<223> OTHER INFORMATION: Recombinant protein

<400> SEQUENCE: 273

```
Lys Ala Ser Lys Leu Glu Arg
1               5
```

<210> SEQ ID NO 274
<211> LENGTH: 9
<212> TYPE: PRT
<213> ORGANISM: Artificial Sequence
<220> FEATURE:
<223> OTHER INFORMATION: Recombinant protein

<400> SEQUENCE: 274

```
Leu Glu Tyr Ser Ser Tyr Ile Arg Thr
1               5
```

<210> SEQ ID NO 275
<211> LENGTH: 122
<212> TYPE: PRT
<213> ORGANISM: Artificial Sequence
<220> FEATURE:
<223> OTHER INFORMATION: Recombinant protein

<400> SEQUENCE: 275

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 276
<211> LENGTH: 5
<212> TYPE: PRT
<213> ORGANISM: Artificial Sequence

```
<220> FEATURE:
<223> OTHER INFORMATION: Recombinant protein

<400> SEQUENCE: 276

Asp Tyr Ala Met His
1               5

<210> SEQ ID NO 277
<211> LENGTH: 17
<212> TYPE: PRT
<213> ORGANISM: Artificial Sequence
<220> FEATURE:
<223> OTHER INFORMATION: Recombinant protein

<400> SEQUENCE: 277

Gly Ile Ser Trp Lys Gly Asp Ile Gly Gly Tyr Val Asp Ser Val Lys
1               5                   10                  15

Gly

<210> SEQ ID NO 278
<211> LENGTH: 13
<212> TYPE: PRT
<213> ORGANISM: Artificial Sequence
<220> FEATURE:
<223> OTHER INFORMATION: Recombinant protein

<400> SEQUENCE: 278

Ser Tyr Gly Ser Gly Ser Phe Tyr Asn Ala Phe Asp Ser
1               5                   10

<210> SEQ ID NO 279
<211> LENGTH: 107
<212> TYPE: PRT
<213> ORGANISM: Artificial Sequence
<220> FEATURE:
<223> OTHER INFORMATION: Recombinant protein

<400> SEQUENCE: 279

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 280
<211> LENGTH: 11
<212> TYPE: PRT
<213> ORGANISM: Artificial Sequence
<220> FEATURE:
<223> OTHER INFORMATION: Recombinant protein

<400> SEQUENCE: 280

Arg Ala Ser Gln Ser Ile Ser Ser Trp Leu Ala
1               5                   10
```

<210> SEQ ID NO 281
<211> LENGTH: 7
<212> TYPE: PRT
<213> ORGANISM: Artificial Sequence
<220> FEATURE:
<223> OTHER INFORMATION: Recombinant protein

<400> SEQUENCE: 281

Lys Ala Ser Lys Leu Asp Arg
1               5

<210> SEQ ID NO 282
<211> LENGTH: 9
<212> TYPE: PRT
<213> ORGANISM: Artificial Sequence
<220> FEATURE:
<223> OTHER INFORMATION: Recombinant protein

<400> SEQUENCE: 282

Leu Glu Tyr Ser Ser Tyr Ile Arg Thr
1               5

<210> SEQ ID NO 283
<211> LENGTH: 122
<212> TYPE: PRT
<213> ORGANISM: Artificial Sequence
<220> FEATURE:
<223> OTHER INFORMATION: Recombinant protein

<400> SEQUENCE: 283

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 284
<211> LENGTH: 5
<212> TYPE: PRT
<213> ORGANISM: Artificial Sequence
<220> FEATURE:
<223> OTHER INFORMATION: Recombinant protein

<400> SEQUENCE: 284

Asp Tyr Ala Met His
1               5

<210> SEQ ID NO 285
<211> LENGTH: 17
<212> TYPE: PRT
<213> ORGANISM: Artificial Sequence

```
<220> FEATURE:
<223> OTHER INFORMATION: Recombinant protein

<400> SEQUENCE: 285

Gly Ile Ser Trp Lys Gly Asp Ile Gly Gly Tyr Val Asp Ser Val Lys
1               5                   10                  15

Gly

<210> SEQ ID NO 286
<211> LENGTH: 13
<212> TYPE: PRT
<213> ORGANISM: Artificial Sequence
<220> FEATURE:
<223> OTHER INFORMATION: Recombinant protein

<400> SEQUENCE: 286

Ser Tyr Gly Ser Gly Ser Phe Tyr Asn Ala Phe Asp Ser
1               5                   10

<210> SEQ ID NO 287
<211> LENGTH: 107
<212> TYPE: PRT
<213> ORGANISM: Artificial Sequence
<220> FEATURE:
<223> OTHER INFORMATION: Recombinant protein

<400> SEQUENCE: 287

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Glu Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 288
<211> LENGTH: 11
<212> TYPE: PRT
<213> ORGANISM: Artificial Sequence
<220> FEATURE:
<223> OTHER INFORMATION: Recombinant protein

<400> SEQUENCE: 288

Arg Ala Ser Gln Ser Ile Ser Ser Trp Leu Ala
1               5                   10

<210> SEQ ID NO 289
<211> LENGTH: 7
<212> TYPE: PRT
<213> ORGANISM: Artificial Sequence
<220> FEATURE:
<223> OTHER INFORMATION: Recombinant protein

<400> SEQUENCE: 289

Lys Ala Ser Lys Leu Glu Arg
1               5
```

<210> SEQ ID NO 290
<211> LENGTH: 9
<212> TYPE: PRT
<213> ORGANISM: Artificial Sequence
<220> FEATURE:
<223> OTHER INFORMATION: Recombinant protein

<400> SEQUENCE: 290

Leu Glu Tyr Ser Ser Tyr Ile Arg Thr
1               5

<210> SEQ ID NO 291
<211> LENGTH: 122
<212> TYPE: PRT
<213> ORGANISM: Artificial Sequence
<220> FEATURE:
<223> OTHER INFORMATION: Recombinant protein

<400> SEQUENCE: 291

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 292
<211> LENGTH: 5
<212> TYPE: PRT
<213> ORGANISM: Artificial Sequence
<220> FEATURE:
<223> OTHER INFORMATION: Recombinant protein

<400> SEQUENCE: 292

Asp Tyr Ala Met His
1               5

<210> SEQ ID NO 293
<211> LENGTH: 17
<212> TYPE: PRT
<213> ORGANISM: Artificial Sequence
<220> FEATURE:
<223> OTHER INFORMATION: Recombinant protein

<400> SEQUENCE: 293

Gly Ile Ser Trp Lys Gly Asp Ile Gly Tyr Val Asp Ser Val Lys
1               5                   10                  15

Gly

<210> SEQ ID NO 294
<211> LENGTH: 13

```
<212> TYPE: PRT
<213> ORGANISM: Artificial Sequence
<220> FEATURE:
<223> OTHER INFORMATION: Recombinant protein

<400> SEQUENCE: 294

Ser Tyr Gly Ser Gly Ser Phe Tyr Asn Ala Phe Asp Ser
1               5                   10

<210> SEQ ID NO 295
<211> LENGTH: 107
<212> TYPE: PRT
<213> ORGANISM: Artificial Sequence
<220> FEATURE:
<223> OTHER INFORMATION: Recombinant protein

<400> SEQUENCE: 295

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 296
<211> LENGTH: 11
<212> TYPE: PRT
<213> ORGANISM: Artificial Sequence
<220> FEATURE:
<223> OTHER INFORMATION: Recombinant protein

<400> SEQUENCE: 296

Arg Ala Ser Gln Ser Ile Ser Ser Trp Leu Ala
1               5                   10

<210> SEQ ID NO 297
<211> LENGTH: 7
<212> TYPE: PRT
<213> ORGANISM: Artificial Sequence
<220> FEATURE:
<223> OTHER INFORMATION: Recombinant protein

<400> SEQUENCE: 297

Lys Ala Ser Lys Leu Asp Arg
1               5

<210> SEQ ID NO 298
<211> LENGTH: 9
<212> TYPE: PRT
<213> ORGANISM: Artificial Sequence
<220> FEATURE:
<223> OTHER INFORMATION: Recombinant protein

<400> SEQUENCE: 298

Leu Glu Tyr Ser Ser Tyr Ile Arg Thr
1               5
```

<210> SEQ ID NO 299
<211> LENGTH: 122
<212> TYPE: PRT
<213> ORGANISM: Artificial Sequence
<220> FEATURE:
<223> OTHER INFORMATION: Recombinant protein

<400> SEQUENCE: 299

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 300
<211> LENGTH: 5
<212> TYPE: PRT
<213> ORGANISM: Artificial Sequence
<220> FEATURE:
<223> OTHER INFORMATION: Recombinant protein

<400> SEQUENCE: 300

Asp Tyr Ala Met His
1               5

<210> SEQ ID NO 301
<211> LENGTH: 17
<212> TYPE: PRT
<213> ORGANISM: Artificial Sequence
<220> FEATURE:
<223> OTHER INFORMATION: Recombinant protein

<400> SEQUENCE: 301

Gly Ile Ser Trp Lys Gly Asp Ile Gly Gly Tyr Val Asp Ser Val Lys
1               5                   10                  15

Gly

<210> SEQ ID NO 302
<211> LENGTH: 13
<212> TYPE: PRT
<213> ORGANISM: Artificial Sequence
<220> FEATURE:
<223> OTHER INFORMATION: Recombinant protein

<400> SEQUENCE: 302

Ser Tyr Gly Ser Gly Ser Phe Tyr Asn Ala Phe Asp Ser
1               5                   10

<210> SEQ ID NO 303
<211> LENGTH: 107

```
<212> TYPE: PRT
<213> ORGANISM: Artificial Sequence
<220> FEATURE:
<223> OTHER INFORMATION: Recombinant protein

<400> SEQUENCE: 303

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Glu Arg Gly Thr Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 304
<211> LENGTH: 11
<212> TYPE: PRT
<213> ORGANISM: Artificial Sequence
<220> FEATURE:
<223> OTHER INFORMATION: Recombinant protein

<400> SEQUENCE: 304

Arg Ala Ser Gln Ser Ile Ser Ser Trp Leu Ala
1               5                   10

<210> SEQ ID NO 305
<211> LENGTH: 7
<212> TYPE: PRT
<213> ORGANISM: Artificial Sequence
<220> FEATURE:
<223> OTHER INFORMATION: Recombinant protein

<400> SEQUENCE: 305

Lys Ala Ser Lys Leu Glu Arg
1               5

<210> SEQ ID NO 306
<211> LENGTH: 9
<212> TYPE: PRT
<213> ORGANISM: Artificial Sequence
<220> FEATURE:
<223> OTHER INFORMATION: Recombinant protein

<400> SEQUENCE: 306

Leu Glu Tyr Ser Ser Tyr Ile Arg Thr
1               5

<210> SEQ ID NO 307
<211> LENGTH: 122
<212> TYPE: PRT
<213> ORGANISM: Artificial Sequence
<220> FEATURE:
<223> OTHER INFORMATION: Recombinant protein

<400> SEQUENCE: 307

Glu Val Gln Leu Val Glu Ser Gly Gly Gly Leu Val Gln Pro Gly Arg
1               5                   10                  15
```

```
Ser Leu Arg Leu Ser Cys Ala Ala Ser Gly Phe Lys Phe His Asp Tyr
         20                  25                  30

Ala Met His Trp Val Arg Gln Val Pro Gly Lys Gly Leu Glu Trp Val
         35                  40                  45

Ser Gly Ile Ser Trp Lys Gly Asp Ile Gly Gly Tyr Val Asp Ser Val
 50                  55                  60

Lys Gly Arg Phe Thr Ile Ser Arg Asp Asn Glu Lys Asn Ser Leu Tyr
 65                  70                  75                  80

Leu Gln Met Asn Ser Leu Arg Ala Glu Asp Thr Ala Leu Tyr Tyr Cys
             85                  90                  95

Val Lys Ser Tyr Gly Ser Gly Ser Phe Tyr Asn Ala Phe Asp Ser Trp
             100                 105                 110

Gly Gln Gly Thr Leu Val Thr Val Ser Ser
         115                 120
```

<210> SEQ ID NO 308
<211> LENGTH: 5
<212> TYPE: PRT
<213> ORGANISM: Artificial Sequence
<220> FEATURE:
<223> OTHER INFORMATION: Recombinant protein

<400> SEQUENCE: 308

```
Asp Tyr Ala Met His
1               5
```

<210> SEQ ID NO 309
<211> LENGTH: 17
<212> TYPE: PRT
<213> ORGANISM: Artificial Sequence
<220> FEATURE:
<223> OTHER INFORMATION: Recombinant protein

<400> SEQUENCE: 309

```
Gly Ile Ser Trp Lys Gly Asp Ile Gly Gly Tyr Val Asp Ser Val Lys
1               5                   10                  15

Gly
```

<210> SEQ ID NO 310
<211> LENGTH: 13
<212> TYPE: PRT
<213> ORGANISM: Artificial Sequence
<220> FEATURE:
<223> OTHER INFORMATION: Recombinant protein

<400> SEQUENCE: 310

```
Ser Tyr Gly Ser Gly Ser Phe Tyr Asn Ala Phe Asp Ser
1               5                   10
```

<210> SEQ ID NO 311
<211> LENGTH: 107
<212> TYPE: PRT
<213> ORGANISM: Artificial Sequence
<220> FEATURE:
<223> OTHER INFORMATION: Recombinant protein

<400> SEQUENCE: 311

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
         20                  25                  30
```

-continued

```
Leu Ala Trp Tyr Gln Gln Lys Pro Gly Lys Ala Pro Lys Phe Leu Ile
             35                  40                  45

Tyr Lys Ala Ser Arg Leu Asp Arg Gly Thr Pro Ser Arg Phe Ser Gly
 50                  55                  60

Ser Gly Ser Gly Thr Glu Phe Ser Leu Thr Ile Ser Ser Leu Gln Pro
 65                  70                  75                  80

Asp Asp Phe Ala Thr Tyr Tyr Cys Leu Glu Tyr Ser Ser Tyr Ile Arg
                 85                  90                  95

Thr Phe Gly Gln Gly Thr Lys Val Glu Ile Lys
            100                 105

<210> SEQ ID NO 312
<211> LENGTH: 11
<212> TYPE: PRT
<213> ORGANISM: Artificial Sequence
<220> FEATURE:
<223> OTHER INFORMATION: Recombinant protein

<400> SEQUENCE: 312

Arg Ala Ser Gln Ser Ile Ser Ser Trp Leu Ala
 1               5                  10

<210> SEQ ID NO 313
<211> LENGTH: 7
<212> TYPE: PRT
<213> ORGANISM: Artificial Sequence
<220> FEATURE:
<223> OTHER INFORMATION: Recombinant protein

<400> SEQUENCE: 313

Lys Ala Ser Arg Leu Asp Arg
 1               5

<210> SEQ ID NO 314
<211> LENGTH: 9
<212> TYPE: PRT
<213> ORGANISM: Artificial Sequence
<220> FEATURE:
<223> OTHER INFORMATION: Recombinant protein

<400> SEQUENCE: 314

Leu Glu Tyr Ser Ser Tyr Ile Arg Thr
 1               5

<210> SEQ ID NO 315
<211> LENGTH: 122
<212> TYPE: PRT
<213> ORGANISM: Artificial Sequence
<220> FEATURE:
<223> OTHER INFORMATION: Recombinant protein

<400> SEQUENCE: 315

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe His Asp Tyr
                 20                  25                  30

Ala Met His Trp Val Arg Gln Val Pro Gly Lys Gly Leu Glu Trp Val
             35                  40                  45

Ser Gly Ile Ser Trp Lys Gly Asp Ile Gly Gly Tyr Val Asp Ser Val
         50                  55                  60

Lys Gly Arg Phe Thr Ile Ser Arg Asp Asn Asp Lys Asn Ser Leu Tyr
 65                  70                  75                  80
```

-continued

```
Leu Gln Met Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 316
<211> LENGTH: 5
<212> TYPE: PRT
<213> ORGANISM: Artificial Sequence
<220> FEATURE:
<223> OTHER INFORMATION: Recombinant protein

<400> SEQUENCE: 316

Asp Tyr Ala Met His
1               5

<210> SEQ ID NO 317
<211> LENGTH: 17
<212> TYPE: PRT
<213> ORGANISM: Artificial Sequence
<220> FEATURE:
<223> OTHER INFORMATION: Recombinant protein

<400> SEQUENCE: 317

Gly Ile Ser Trp Lys Gly Asp Ile Gly Gly Tyr Val Asp Ser Val Lys
1               5                   10                  15

Gly

<210> SEQ ID NO 318
<211> LENGTH: 13
<212> TYPE: PRT
<213> ORGANISM: Artificial Sequence
<220> FEATURE:
<223> OTHER INFORMATION: Recombinant protein

<400> SEQUENCE: 318

Ser Tyr Gly Ser Gly Ser Phe Tyr Asn Ala Phe Asp Ser
1               5                   10

<210> SEQ ID NO 319
<211> LENGTH: 107
<212> TYPE: PRT
<213> ORGANISM: Artificial Sequence
<220> FEATURE:
<223> OTHER INFORMATION: Recombinant protein

<400> SEQUENCE: 319

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
```

<210> SEQ ID NO 320
<211> LENGTH: 11
<212> TYPE: PRT
<213> ORGANISM: Artificial Sequence
<220> FEATURE:
<223> OTHER INFORMATION: Recombinant protein

<400> SEQUENCE: 320

Arg Ala Ser Gln Ser Ile Ser Ser Trp Leu Ala
1               5                   10

<210> SEQ ID NO 321
<211> LENGTH: 7
<212> TYPE: PRT
<213> ORGANISM: Artificial Sequence
<220> FEATURE:
<223> OTHER INFORMATION: Recombinant protein

<400> SEQUENCE: 321

Lys Ala Ser Arg Leu Asp Arg
1               5

<210> SEQ ID NO 322
<211> LENGTH: 9
<212> TYPE: PRT
<213> ORGANISM: Artificial Sequence
<220> FEATURE:
<223> OTHER INFORMATION: Recombinant protein

<400> SEQUENCE: 322

Leu Glu Tyr Ser Ser Tyr Ile Arg Thr
1               5

<210> SEQ ID NO 323
<211> LENGTH: 122
<212> TYPE: PRT
<213> ORGANISM: Artificial Sequence
<220> FEATURE:
<223> OTHER INFORMATION: Recombinant protein

<400> SEQUENCE: 323

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 324
<211> LENGTH: 5
<212> TYPE: PRT

```
<213> ORGANISM: Artificial Sequence
<220> FEATURE:
<223> OTHER INFORMATION: Recombinant protein

<400> SEQUENCE: 324

Asp Tyr Ala Met His
1               5

<210> SEQ ID NO 325
<211> LENGTH: 17
<212> TYPE: PRT
<213> ORGANISM: Artificial Sequence
<220> FEATURE:
<223> OTHER INFORMATION: Recombinant protein

<400> SEQUENCE: 325

Gly Ile Ser Trp Lys Gly Asp Ile Gly Gly Tyr Val Asp Ser Val Lys
1               5                   10                  15

Gly

<210> SEQ ID NO 326
<211> LENGTH: 13
<212> TYPE: PRT
<213> ORGANISM: Artificial Sequence
<220> FEATURE:
<223> OTHER INFORMATION: Recombinant protein

<400> SEQUENCE: 326

Ser Tyr Gly Ser Gly Ser Phe Tyr Asn Ala Phe Asp Ser
1               5                   10

<210> SEQ ID NO 327
<211> LENGTH: 107
<212> TYPE: PRT
<213> ORGANISM: Artificial Sequence
<220> FEATURE:
<223> OTHER INFORMATION: Recombinant protein

<400> SEQUENCE: 327

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Lys Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 328
<211> LENGTH: 11
<212> TYPE: PRT
<213> ORGANISM: Artificial Sequence
<220> FEATURE:
<223> OTHER INFORMATION: Recombinant protein

<400> SEQUENCE: 328

Arg Ala Ser Gln Lys Ile Ser Ser Trp Leu Ala
```

```
<210> SEQ ID NO 329
<211> LENGTH: 7
<212> TYPE: PRT
<213> ORGANISM: Artificial Sequence
<220> FEATURE:
<223> OTHER INFORMATION: Recombinant protein

<400> SEQUENCE: 329

Lys Ala Ser Arg Leu Asp Arg
1               5

<210> SEQ ID NO 330
<211> LENGTH: 9
<212> TYPE: PRT
<213> ORGANISM: Artificial Sequence
<220> FEATURE:
<223> OTHER INFORMATION: Recombinant protein

<400> SEQUENCE: 330

Leu Glu Tyr Ser Ser Tyr Ile Arg Thr
1               5

<210> SEQ ID NO 331
<211> LENGTH: 122
<212> TYPE: PRT
<213> ORGANISM: Artificial Sequence
<220> FEATURE:
<223> OTHER INFORMATION: Recombinant protein

<400> SEQUENCE: 331

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 332
<211> LENGTH: 5
<212> TYPE: PRT
<213> ORGANISM: Artificial Sequence
<220> FEATURE:
<223> OTHER INFORMATION: Recombinant protein

<400> SEQUENCE: 332

Asp Tyr Ala Met His
1               5

<210> SEQ ID NO 333
<211> LENGTH: 17
<212> TYPE: PRT
```

```
<213> ORGANISM: Artificial Sequence
<220> FEATURE:
<223> OTHER INFORMATION: Recombinant protein

<400> SEQUENCE: 333

Gly Ile Ser Trp Lys Gly Asp Ile Gly Gly Tyr Val Asp Ser Val Lys
1               5                   10                  15
Gly

<210> SEQ ID NO 334
<211> LENGTH: 13
<212> TYPE: PRT
<213> ORGANISM: Artificial Sequence
<220> FEATURE:
<223> OTHER INFORMATION: Recombinant protein

<400> SEQUENCE: 334

Ser Tyr Gly Ser Gly Ser Phe Tyr Asn Ala Phe Asp Ser
1               5                   10

<210> SEQ ID NO 335
<211> LENGTH: 107
<212> TYPE: PRT
<213> ORGANISM: Artificial Sequence
<220> FEATURE:
<223> OTHER INFORMATION: Recombinant protein

<400> SEQUENCE: 335

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gln Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 336
<211> LENGTH: 11
<212> TYPE: PRT
<213> ORGANISM: Artificial Sequence
<220> FEATURE:
<223> OTHER INFORMATION: Recombinant protein

<400> SEQUENCE: 336

Arg Ala Ser Gln Gln Ile Ser Ser Trp Leu Ala
1               5                   10

<210> SEQ ID NO 337
<211> LENGTH: 7
<212> TYPE: PRT
<213> ORGANISM: Artificial Sequence
<220> FEATURE:
<223> OTHER INFORMATION: Recombinant protein

<400> SEQUENCE: 337

Lys Ala Ser Arg Leu Asp Arg
```

```
<210> SEQ ID NO 338
<211> LENGTH: 9
<212> TYPE: PRT
<213> ORGANISM: Artificial Sequence
<220> FEATURE:
<223> OTHER INFORMATION: Recombinant protein

<400> SEQUENCE: 338

Leu Glu Tyr Ser Ser Tyr Ile Arg Thr
1               5

<210> SEQ ID NO 339
<211> LENGTH: 122
<212> TYPE: PRT
<213> ORGANISM: Artificial Sequence
<220> FEATURE:
<223> OTHER INFORMATION: Recombinant protein

<400> SEQUENCE: 339

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 340
<211> LENGTH: 5
<212> TYPE: PRT
<213> ORGANISM: Artificial Sequence
<220> FEATURE:
<223> OTHER INFORMATION: Recombinant protein

<400> SEQUENCE: 340

Asp Tyr Ala Met His
1               5

<210> SEQ ID NO 341
<211> LENGTH: 17
<212> TYPE: PRT
<213> ORGANISM: Artificial Sequence
<220> FEATURE:
<223> OTHER INFORMATION: Recombinant protein

<400> SEQUENCE: 341

Gly Ile Ser Trp Lys Gly Asp Ile Gly Gly Tyr Val Asp Ser Val Lys
1               5                   10                  15

Gly

<210> SEQ ID NO 342
```

```
<211> LENGTH: 13
<212> TYPE: PRT
<213> ORGANISM: Artificial Sequence
<220> FEATURE:
<223> OTHER INFORMATION: Recombinant protein

<400> SEQUENCE: 342

Ser Tyr Gly Ser Gly Ser Phe Tyr Asn Ala Phe Asp Ser
1               5                   10

<210> SEQ ID NO 343
<211> LENGTH: 107
<212> TYPE: PRT
<213> ORGANISM: Artificial Sequence
<220> FEATURE:
<223> OTHER INFORMATION: Recombinant protein

<400> SEQUENCE: 343

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gln Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 344
<211> LENGTH: 11
<212> TYPE: PRT
<213> ORGANISM: Artificial Sequence
<220> FEATURE:
<223> OTHER INFORMATION: Recombinant protein

<400> SEQUENCE: 344

Arg Ala Ser Gln Ser Ile Gln Ser Trp Leu Ala
1               5                   10

<210> SEQ ID NO 345
<211> LENGTH: 7
<212> TYPE: PRT
<213> ORGANISM: Artificial Sequence
<220> FEATURE:
<223> OTHER INFORMATION: Recombinant protein

<400> SEQUENCE: 345

Lys Ala Ser Arg Leu Asp Arg
1               5

<210> SEQ ID NO 346
<211> LENGTH: 9
<212> TYPE: PRT
<213> ORGANISM: Artificial Sequence
<220> FEATURE:
<223> OTHER INFORMATION: Recombinant protein

<400> SEQUENCE: 346

Leu Glu Tyr Ser Ser Tyr Ile Arg Thr
```

<210> SEQ ID NO 347
<211> LENGTH: 122
<212> TYPE: PRT
<213> ORGANISM: Artificial Sequence
<220> FEATURE:
<223> OTHER INFORMATION: Recombinant protein

<400> SEQUENCE: 347

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
            85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 348
<211> LENGTH: 5
<212> TYPE: PRT
<213> ORGANISM: Artificial Sequence
<220> FEATURE:
<223> OTHER INFORMATION: Recombinant protein

<400> SEQUENCE: 348

Asp Tyr Ala Met His
1               5

<210> SEQ ID NO 349
<211> LENGTH: 17
<212> TYPE: PRT
<213> ORGANISM: Artificial Sequence
<220> FEATURE:
<223> OTHER INFORMATION: Recombinant protein

<400> SEQUENCE: 349

Gly Ile Ser Trp Lys Gly Asp Ile Gly Gly Tyr Val Asp Ser Val Lys
1               5                   10                  15

Gly

<210> SEQ ID NO 350
<211> LENGTH: 13
<212> TYPE: PRT
<213> ORGANISM: Artificial Sequence
<220> FEATURE:
<223> OTHER INFORMATION: Recombinant protein

<400> SEQUENCE: 350

Ser Tyr Gly Ser Gly Ser Phe Tyr Asn Ala Phe Asp Ser
1               5                   10

<210> SEQ ID NO 351

<211> LENGTH: 107
<212> TYPE: PRT
<213> ORGANISM: Artificial Sequence
<220> FEATURE:
<223> OTHER INFORMATION: Recombinant protein

<400> SEQUENCE: 351

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Lys Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 352
<211> LENGTH: 11
<212> TYPE: PRT
<213> ORGANISM: Artificial Sequence
<220> FEATURE:
<223> OTHER INFORMATION: Recombinant protein

<400> SEQUENCE: 352

Arg Ala Ser Gln Ser Ile Ser Ser Trp Leu Ala
1               5                   10

<210> SEQ ID NO 353
<211> LENGTH: 7
<212> TYPE: PRT
<213> ORGANISM: Artificial Sequence
<220> FEATURE:
<223> OTHER INFORMATION: Recombinant protein

<400> SEQUENCE: 353

Lys Ala Ser Arg Leu Asp Lys
1               5

<210> SEQ ID NO 354
<211> LENGTH: 9
<212> TYPE: PRT
<213> ORGANISM: Artificial Sequence
<220> FEATURE:
<223> OTHER INFORMATION: Recombinant protein

<400> SEQUENCE: 354

Leu Glu Tyr Ser Ser Tyr Ile Arg Thr
1               5

<210> SEQ ID NO 355
<211> LENGTH: 122
<212> TYPE: PRT
<213> ORGANISM: Artificial Sequence
<220> FEATURE:
<223> OTHER INFORMATION: Recombinant protein

<400> SEQUENCE: 355

Glu Val Gln Leu Val Glu Ser Gly Gly Gly Leu Val Gln Pro Gly Arg

```
                1               5                   10                  15
Ser Leu Arg Leu Ser Cys Ala Ala Ser Gly Phe Thr Phe His Asp Tyr
                20                  25                  30

Ala Met His Trp Val Arg Gln Val Pro Gly Lys Gly Leu Glu Trp Val
                35                  40                  45

Ser Gly Ile Ser Trp Lys Gly Asp Ile Gly Gly Tyr Val Asp Ser Val
                50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
                115                 120

<210> SEQ ID NO 356
<211> LENGTH: 5
<212> TYPE: PRT
<213> ORGANISM: Artificial Sequence
<220> FEATURE:
<223> OTHER INFORMATION: Recombinant protein

<400> SEQUENCE: 356

Asp Tyr Ala Met His
1               5

<210> SEQ ID NO 357
<211> LENGTH: 17
<212> TYPE: PRT
<213> ORGANISM: Artificial Sequence
<220> FEATURE:
<223> OTHER INFORMATION: Recombinant protein

<400> SEQUENCE: 357

Gly Ile Ser Trp Lys Gly Asp Ile Gly Gly Tyr Val Asp Ser Val Lys
1               5                   10                  15

Gly

<210> SEQ ID NO 358
<211> LENGTH: 13
<212> TYPE: PRT
<213> ORGANISM: Artificial Sequence
<220> FEATURE:
<223> OTHER INFORMATION: Recombinant protein

<400> SEQUENCE: 358

Ser Tyr Gly Ser Gly Ser Phe Tyr Asn Ala Phe Asp Ser
1               5                   10

<210> SEQ ID NO 359
<211> LENGTH: 107
<212> TYPE: PRT
<213> ORGANISM: Artificial Sequence
<220> FEATURE:
<223> OTHER INFORMATION: Recombinant protein

<400> SEQUENCE: 359

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30
```

Leu Ala Trp Tyr Gln Gln Lys Pro Gly Lys Ala Pro Lys Phe Leu Ile
            35                  40                  45

Tyr Lys Ala Ser Arg Leu Asp Arg Gly Thr Pro Lys Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 360
<211> LENGTH: 11
<212> TYPE: PRT
<213> ORGANISM: Artificial Sequence
<220> FEATURE:
<223> OTHER INFORMATION: Recombinant protein

<400> SEQUENCE: 360

Arg Ala Ser Gln Ser Ile Ser Ser Trp Leu Ala
1               5                   10

<210> SEQ ID NO 361
<211> LENGTH: 7
<212> TYPE: PRT
<213> ORGANISM: Artificial Sequence
<220> FEATURE:
<223> OTHER INFORMATION: Recombinant protein

<400> SEQUENCE: 361

Lys Ala Ser Arg Leu Asp Arg
1               5

<210> SEQ ID NO 362
<211> LENGTH: 9
<212> TYPE: PRT
<213> ORGANISM: Artificial Sequence
<220> FEATURE:
<223> OTHER INFORMATION: Recombinant protein

<400> SEQUENCE: 362

Leu Glu Tyr Ser Ser Tyr Ile Arg Thr
1               5

<210> SEQ ID NO 363
<211> LENGTH: 122
<212> TYPE: PRT
<213> ORGANISM: Artificial Sequence
<220> FEATURE:
<223> OTHER INFORMATION: Recombinant protein

<400> SEQUENCE: 363

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
            35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

```
Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 364
<211> LENGTH: 5
<212> TYPE: PRT
<213> ORGANISM: Artificial Sequence
<220> FEATURE:
<223> OTHER INFORMATION: Recombinant protein

<400> SEQUENCE: 364

Asp Tyr Ala Met His
1               5

<210> SEQ ID NO 365
<211> LENGTH: 17
<212> TYPE: PRT
<213> ORGANISM: Artificial Sequence
<220> FEATURE:
<223> OTHER INFORMATION: Recombinant protein

<400> SEQUENCE: 365

Gly Ile Ser Trp Lys Gly Asp Ile Gly Gly Tyr Val Asp Ser Val Lys
1               5                   10                  15

Gly

<210> SEQ ID NO 366
<211> LENGTH: 13
<212> TYPE: PRT
<213> ORGANISM: Artificial Sequence
<220> FEATURE:
<223> OTHER INFORMATION: Recombinant protein

<400> SEQUENCE: 366

Ser Tyr Gly Ser Gly Ser Phe Tyr Asn Ala Phe Asp Ser
1               5                   10

<210> SEQ ID NO 367
<211> LENGTH: 107
<212> TYPE: PRT
<213> ORGANISM: Artificial Sequence
<220> FEATURE:
<223> OTHER INFORMATION: Recombinant protein

<400> SEQUENCE: 367

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Glu Leu Gln Pro
65                  70                  75                  80

Asp Asp Phe Ala Thr Tyr Tyr Cys Leu Glu Tyr Ser Ser Tyr Ile Arg
                85                  90                  95
```

```
Thr Phe Gly Gln Gly Thr Lys Val Glu Ile Lys
            100                 105
```

<210> SEQ ID NO 368
<211> LENGTH: 11
<212> TYPE: PRT
<213> ORGANISM: Artificial Sequence
<220> FEATURE:
<223> OTHER INFORMATION: Recombinant protein

<400> SEQUENCE: 368

```
Arg Ala Ser Gln Ser Ile Ser Ser Trp Leu Ala
1               5                   10
```

<210> SEQ ID NO 369
<211> LENGTH: 7
<212> TYPE: PRT
<213> ORGANISM: Artificial Sequence
<220> FEATURE:
<223> OTHER INFORMATION: Recombinant protein

<400> SEQUENCE: 369

```
Lys Ala Ser Arg Leu Asp Arg
1               5
```

<210> SEQ ID NO 370
<211> LENGTH: 9
<212> TYPE: PRT
<213> ORGANISM: Artificial Sequence
<220> FEATURE:
<223> OTHER INFORMATION: Recombinant protein

<400> SEQUENCE: 370

```
Leu Glu Tyr Ser Ser Tyr Ile Arg Thr
1               5
```

<210> SEQ ID NO 371
<211> LENGTH: 122
<212> TYPE: PRT
<213> ORGANISM: Artificial Sequence
<220> FEATURE:
<223> OTHER INFORMATION: Recombinant protein

<400> SEQUENCE: 371

```
Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe His Asp Tyr
                20                  25                  30

Ala Met His Trp Val Arg Gln Val Pro Gly Lys Gly Leu Glu Trp Val
            35                  40                  45

Ser Gly Ile Ser Trp Lys Gly Asp Ile Gly Gly Tyr Val Asp Ser Val
        50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120
```

<210> SEQ ID NO 372
<211> LENGTH: 5

```
<212> TYPE: PRT
<213> ORGANISM: Artificial Sequence
<220> FEATURE:
<223> OTHER INFORMATION: Recombinant protein

<400> SEQUENCE: 372

Asp Tyr Ala Met His
1               5

<210> SEQ ID NO 373
<211> LENGTH: 17
<212> TYPE: PRT
<213> ORGANISM: Artificial Sequence
<220> FEATURE:
<223> OTHER INFORMATION: Recombinant protein

<400> SEQUENCE: 373

Gly Ile Ser Trp Lys Gly Asp Ile Gly Gly Tyr Val Asp Ser Val Lys
1               5                   10                  15

Gly

<210> SEQ ID NO 374
<211> LENGTH: 13
<212> TYPE: PRT
<213> ORGANISM: Artificial Sequence
<220> FEATURE:
<223> OTHER INFORMATION: Recombinant protein

<400> SEQUENCE: 374

Ser Tyr Gly Ser Gly Ser Phe Tyr Asn Ala Phe Asp Ser
1               5                   10

<210> SEQ ID NO 375
<211> LENGTH: 107
<212> TYPE: PRT
<213> ORGANISM: Artificial Sequence
<220> FEATURE:
<223> OTHER INFORMATION: Recombinant protein

<400> SEQUENCE: 375

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Thr Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 376
<211> LENGTH: 11
<212> TYPE: PRT
<213> ORGANISM: Artificial Sequence
<220> FEATURE:
<223> OTHER INFORMATION: Recombinant protein

<400> SEQUENCE: 376
```

```
Arg Ala Ser Gln Ser Ile Ser Ser Trp Leu Ala
1               5                   10
```

<210> SEQ ID NO 377
<211> LENGTH: 7
<212> TYPE: PRT
<213> ORGANISM: Artificial Sequence
<220> FEATURE:
<223> OTHER INFORMATION: Recombinant protein

<400> SEQUENCE: 377

```
Lys Ala Ser Arg Leu Asp Arg
1               5
```

<210> SEQ ID NO 378
<211> LENGTH: 9
<212> TYPE: PRT
<213> ORGANISM: Artificial Sequence
<220> FEATURE:
<223> OTHER INFORMATION: Recombinant protein

<400> SEQUENCE: 378

```
Leu Glu Tyr Ser Ser Tyr Ile Arg Thr
1               5
```

<210> SEQ ID NO 379
<211> LENGTH: 122
<212> TYPE: PRT
<213> ORGANISM: Artificial Sequence
<220> FEATURE:
<223> OTHER INFORMATION: Recombinant protein

<400> SEQUENCE: 379

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 380
<211> LENGTH: 5
<212> TYPE: PRT
<213> ORGANISM: Artificial Sequence
<220> FEATURE:
<223> OTHER INFORMATION: Recombinant protein

<400> SEQUENCE: 380

```
Asp Tyr Ala Met His
1               5
```

<210> SEQ ID NO 381
<211> LENGTH: 17

-continued

```
<212> TYPE: PRT
<213> ORGANISM: Artificial Sequence
<220> FEATURE:
<223> OTHER INFORMATION: Recombinant protein

<400> SEQUENCE: 381

Gly Ile Ser Trp Lys Gly Asp Ile Gly Gly Tyr Val Asp Ser Val Lys
1               5                   10                  15

Gly

<210> SEQ ID NO 382
<211> LENGTH: 13
<212> TYPE: PRT
<213> ORGANISM: Artificial Sequence
<220> FEATURE:
<223> OTHER INFORMATION: Recombinant protein

<400> SEQUENCE: 382

Ser Tyr Gly Ser Gly Ser Phe Tyr Asn Ala Phe Asp Ser
1               5                   10

<210> SEQ ID NO 383
<211> LENGTH: 107
<212> TYPE: PRT
<213> ORGANISM: Artificial Sequence
<220> FEATURE:
<223> OTHER INFORMATION: Recombinant protein

<400> SEQUENCE: 383

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Ser Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 384
<211> LENGTH: 11
<212> TYPE: PRT
<213> ORGANISM: Artificial Sequence
<220> FEATURE:
<223> OTHER INFORMATION: Recombinant protein

<400> SEQUENCE: 384

Arg Ala Ser Gln Ser Ile Ser Ser Trp Leu Ala
1               5                   10

<210> SEQ ID NO 385
<211> LENGTH: 7
<212> TYPE: PRT
<213> ORGANISM: Artificial Sequence
<220> FEATURE:
<223> OTHER INFORMATION: Recombinant protein

<400> SEQUENCE: 385
```

Lys Ala Ser Arg Leu Asp Arg
1               5

<210> SEQ ID NO 386
<211> LENGTH: 9
<212> TYPE: PRT
<213> ORGANISM: Artificial Sequence
<220> FEATURE:
<223> OTHER INFORMATION: Recombinant protein

<400> SEQUENCE: 386

Leu Glu Tyr Ser Ser Tyr Ile Arg Thr
1               5

<210> SEQ ID NO 387
<211> LENGTH: 122
<212> TYPE: PRT
<213> ORGANISM: Artificial Sequence
<220> FEATURE:
<223> OTHER INFORMATION: Recombinant protein

<400> SEQUENCE: 387

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 388
<211> LENGTH: 5
<212> TYPE: PRT
<213> ORGANISM: Artificial Sequence
<220> FEATURE:
<223> OTHER INFORMATION: Recombinant protein

<400> SEQUENCE: 388

Asp Tyr Ala Met His
1               5

<210> SEQ ID NO 389
<211> LENGTH: 17
<212> TYPE: PRT
<213> ORGANISM: Artificial Sequence
<220> FEATURE:
<223> OTHER INFORMATION: Recombinant protein

<400> SEQUENCE: 389

Gly Ile Ser Trp Lys Gly Asp Ile Gly Gly Tyr Val Asp Ser Val Lys
1               5                   10                  15

Gly

```
<210> SEQ ID NO 390
<211> LENGTH: 13
<212> TYPE: PRT
<213> ORGANISM: Artificial Sequence
<220> FEATURE:
<223> OTHER INFORMATION: Recombinant protein

<400> SEQUENCE: 390

Ser Tyr Gly Ser Gly Ser Phe Tyr Asn Ala Phe Asp Ser
1               5                   10

<210> SEQ ID NO 391
<211> LENGTH: 107
<212> TYPE: PRT
<213> ORGANISM: Artificial Sequence
<220> FEATURE:
<223> OTHER INFORMATION: Recombinant protein

<400> SEQUENCE: 391

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Gln Ser Tyr Ile Arg
                85                  90                  95

Thr Phe Gly Gln Gly Thr Lys Val Glu Ile Lys
            100                 105

<210> SEQ ID NO 392
<211> LENGTH: 11
<212> TYPE: PRT
<213> ORGANISM: Artificial Sequence
<220> FEATURE:
<223> OTHER INFORMATION: Recombinant protein

<400> SEQUENCE: 392

Arg Ala Ser Gln Ser Ile Ser Ser Trp Leu Ala
1               5                   10

<210> SEQ ID NO 393
<211> LENGTH: 7
<212> TYPE: PRT
<213> ORGANISM: Artificial Sequence
<220> FEATURE:
<223> OTHER INFORMATION: Recombinant protein

<400> SEQUENCE: 393

Lys Ala Ser Arg Leu Asp Arg
1               5

<210> SEQ ID NO 394
<211> LENGTH: 9
<212> TYPE: PRT
<213> ORGANISM: Artificial Sequence
<220> FEATURE:
<223> OTHER INFORMATION: Recombinant protein

<400> SEQUENCE: 394
```

```
Leu Glu Tyr Gln Ser Tyr Ile Arg Thr
1               5
```

```
<210> SEQ ID NO 395
<211> LENGTH: 122
<212> TYPE: PRT
<213> ORGANISM: Artificial Sequence
<220> FEATURE:
<223> OTHER INFORMATION: Recombinant protein

<400> SEQUENCE: 395

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

```
<210> SEQ ID NO 396
<211> LENGTH: 5
<212> TYPE: PRT
<213> ORGANISM: Artificial Sequence
<220> FEATURE:
<223> OTHER INFORMATION: Recombinant protein

<400> SEQUENCE: 396

Asp Tyr Ala Met His
1               5
```

```
<210> SEQ ID NO 397
<211> LENGTH: 17
<212> TYPE: PRT
<213> ORGANISM: Artificial Sequence
<220> FEATURE:
<223> OTHER INFORMATION: Recombinant protein

<400> SEQUENCE: 397

Gly Ile Ser Trp Lys Gly Asp Ile Gly Gly Tyr Val Asp Ser Val Lys
1               5                   10                  15

Gly
```

```
<210> SEQ ID NO 398
<211> LENGTH: 13
<212> TYPE: PRT
<213> ORGANISM: Artificial Sequence
<220> FEATURE:
<223> OTHER INFORMATION: Recombinant protein

<400> SEQUENCE: 398

Ser Tyr Gly Ser Gly Ser Phe Tyr Asn Ala Phe Asp Ser
1               5                   10
```

```
<210> SEQ ID NO 399
<211> LENGTH: 107
<212> TYPE: PRT
<213> ORGANISM: Artificial Sequence
<220> FEATURE:
<223> OTHER INFORMATION: Recombinant protein

<400> SEQUENCE: 399
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Lys Ser Tyr Ile Arg
                85                  90                  95

Thr Phe Gly Gln Gly Thr Lys Val Glu Ile Lys
            100                 105

```
<210> SEQ ID NO 400
<211> LENGTH: 11
<212> TYPE: PRT
<213> ORGANISM: Artificial Sequence
<220> FEATURE:
<223> OTHER INFORMATION: Recombinant protein

<400> SEQUENCE: 400
```

Arg Ala Ser Gln Ser Ile Ser Ser Trp Leu Ala
1               5                   10

```
<210> SEQ ID NO 401
<211> LENGTH: 7
<212> TYPE: PRT
<213> ORGANISM: Artificial Sequence
<220> FEATURE:
<223> OTHER INFORMATION: Recombinant protein

<400> SEQUENCE: 401
```

Lys Ala Ser Arg Leu Asp Arg
1               5

```
<210> SEQ ID NO 402
<211> LENGTH: 9
<212> TYPE: PRT
<213> ORGANISM: Artificial Sequence
<220> FEATURE:
<223> OTHER INFORMATION: Recombinant protein

<400> SEQUENCE: 402
```

Leu Glu Tyr Lys Ser Tyr Ile Arg Thr
1               5

```
<210> SEQ ID NO 403
<211> LENGTH: 122
<212> TYPE: PRT
<213> ORGANISM: Artificial Sequence
<220> FEATURE:
<223> OTHER INFORMATION: Recombinant protein

<400> SEQUENCE: 403
```

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
            115                 120
```

<210> SEQ ID NO 404
<211> LENGTH: 5
<212> TYPE: PRT
<213> ORGANISM: Artificial Sequence
<220> FEATURE:
<223> OTHER INFORMATION: Recombinant protein

<400> SEQUENCE: 404

```
Asp Tyr Ala Met His
1               5
```

<210> SEQ ID NO 405
<211> LENGTH: 17
<212> TYPE: PRT
<213> ORGANISM: Artificial Sequence
<220> FEATURE:
<223> OTHER INFORMATION: Recombinant protein

<400> SEQUENCE: 405

```
Gly Ile Ser Trp Lys Gly Asp Ile Gly Gly Tyr Val Asp Ser Val Lys
1               5                   10                  15

Gly
```

<210> SEQ ID NO 406
<211> LENGTH: 13
<212> TYPE: PRT
<213> ORGANISM: Artificial Sequence
<220> FEATURE:
<223> OTHER INFORMATION: Recombinant protein

<400> SEQUENCE: 406

```
Ser Tyr Gly Ser Gly Ser Phe Tyr Asn Ala Phe Asp Ser
1               5                   10
```

<210> SEQ ID NO 407
<211> LENGTH: 107
<212> TYPE: PRT
<213> ORGANISM: Artificial Sequence
<220> FEATURE:
<223> OTHER INFORMATION: Recombinant protein

<400> SEQUENCE: 407

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
```

```
                20                  25                  30
Leu Ala Trp Tyr Gln Gln Lys Pro Gly Lys Ala Pro Lys Phe Leu Ile
            35                  40                  45

Tyr Lys Ala Ser Arg Leu Asp Arg Gly Thr Pro Ser Arg Phe Ser Gly
        50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Trp Ile Arg
                85                  90                  95

Thr Phe Gly Gln Gly Thr Lys Val Glu Ile Lys
            100                 105
```

<210> SEQ ID NO 408
<211> LENGTH: 11
<212> TYPE: PRT
<213> ORGANISM: Artificial Sequence
<220> FEATURE:
<223> OTHER INFORMATION: Recombinant protein

<400> SEQUENCE: 408

```
Arg Ala Ser Gln Ser Ile Ser Ser Trp Leu Ala
1               5                   10
```

<210> SEQ ID NO 409
<211> LENGTH: 7
<212> TYPE: PRT
<213> ORGANISM: Artificial Sequence
<220> FEATURE:
<223> OTHER INFORMATION: Recombinant protein

<400> SEQUENCE: 409

```
Lys Ala Ser Arg Leu Asp Arg
1               5
```

<210> SEQ ID NO 410
<211> LENGTH: 9
<212> TYPE: PRT
<213> ORGANISM: Artificial Sequence
<220> FEATURE:
<223> OTHER INFORMATION: Recombinant protein

<400> SEQUENCE: 410

```
Leu Glu Tyr Ser Ser Trp Ile Arg Thr
1               5
```

<210> SEQ ID NO 411
<211> LENGTH: 122
<212> TYPE: PRT
<213> ORGANISM: Artificial Sequence
<220> FEATURE:
<223> OTHER INFORMATION: Recombinant protein

<400> SEQUENCE: 411

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
```

```
                65                  70                  75                  80
Leu Gln Met Asn Ser Leu Arg Ala Glu Asp Thr Ala Leu Tyr Tyr Cys
                    85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
            115                 120

<210> SEQ ID NO 412
<211> LENGTH: 5
<212> TYPE: PRT
<213> ORGANISM: Artificial Sequence
<220> FEATURE:
<223> OTHER INFORMATION: Recombinant protein

<400> SEQUENCE: 412

Asp Tyr Ala Met His
1               5

<210> SEQ ID NO 413
<211> LENGTH: 17
<212> TYPE: PRT
<213> ORGANISM: Artificial Sequence
<220> FEATURE:
<223> OTHER INFORMATION: Recombinant protein

<400> SEQUENCE: 413

Gly Ile Ser Trp Lys Gly Asp Ile Gly Gly Tyr Val Asp Ser Val Lys
1               5                   10                  15

Gly

<210> SEQ ID NO 414
<211> LENGTH: 13
<212> TYPE: PRT
<213> ORGANISM: Artificial Sequence
<220> FEATURE:
<223> OTHER INFORMATION: Recombinant protein

<400> SEQUENCE: 414

Ser Tyr Gly Ser Gly Ser Phe Tyr Asn Ala Phe Asp Ser
1               5                   10

<210> SEQ ID NO 415
<211> LENGTH: 107
<212> TYPE: PRT
<213> ORGANISM: Artificial Sequence
<220> FEATURE:
<223> OTHER INFORMATION: Recombinant protein

<400> SEQUENCE: 415

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Phe Leu Ile
            35                  40                  45

Tyr Lys Ala Ser Arg Leu Asp Arg Gly Thr Pro Ser Arg Phe Ser Gly
        50                  55                  60

Ser Gly Ser Gly Thr Glu Phe Ser Leu Thr Ile Tyr Asp Leu Gln Pro
65                  70                  75                  80

Asp Asp Phe Ala Thr Tyr Tyr Cys Leu Glu Tyr Arg Ser Tyr Ile Arg
                85                  90                  95
```

```
Thr Phe Gly Gln Gly Thr Lys Val Glu Ile Lys
            100                 105

<210> SEQ ID NO 416
<211> LENGTH: 11
<212> TYPE: PRT
<213> ORGANISM: Artificial Sequence
<220> FEATURE:
<223> OTHER INFORMATION: Recombinant protein

<400> SEQUENCE: 416

Arg Ala Ser Gln Ser Ile Ser Ser Trp Leu Ala
1               5                   10

<210> SEQ ID NO 417
<211> LENGTH: 7
<212> TYPE: PRT
<213> ORGANISM: Artificial Sequence
<220> FEATURE:
<223> OTHER INFORMATION: Recombinant protein

<400> SEQUENCE: 417

Lys Ala Ser Arg Leu Asp Arg
1               5

<210> SEQ ID NO 418
<211> LENGTH: 9
<212> TYPE: PRT
<213> ORGANISM: Artificial Sequence
<220> FEATURE:
<223> OTHER INFORMATION: Recombinant protein

<400> SEQUENCE: 418

Leu Glu Tyr Arg Ser Tyr Ile Arg Thr
1               5

<210> SEQ ID NO 419
<211> LENGTH: 122
<212> TYPE: PRT
<213> ORGANISM: Artificial Sequence
<220> FEATURE:
<223> OTHER INFORMATION: Recombinant protein

<400> SEQUENCE: 419

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Glu Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 420
```

```
<211> LENGTH: 5
<212> TYPE: PRT
<213> ORGANISM: Artificial Sequence
<220> FEATURE:
<223> OTHER INFORMATION: Recombinant protein

<400> SEQUENCE: 420

Asp Tyr Ala Met His
1               5

<210> SEQ ID NO 421
<211> LENGTH: 17
<212> TYPE: PRT
<213> ORGANISM: Artificial Sequence
<220> FEATURE:
<223> OTHER INFORMATION: Recombinant protein

<400> SEQUENCE: 421

Gly Ile Ser Trp Lys Gly Asp Ile Gly Gly Tyr Val Asp Ser Val Lys
1               5                   10                  15

Gly

<210> SEQ ID NO 422
<211> LENGTH: 13
<212> TYPE: PRT
<213> ORGANISM: Artificial Sequence
<220> FEATURE:
<223> OTHER INFORMATION: Recombinant protein

<400> SEQUENCE: 422

Ser Tyr Gly Ser Gly Ser Phe Tyr Asn Ala Phe Asp Ser
1               5                   10

<210> SEQ ID NO 423
<211> LENGTH: 107
<212> TYPE: PRT
<213> ORGANISM: Artificial Sequence
<220> FEATURE:
<223> OTHER INFORMATION: Recombinant protein

<400> SEQUENCE: 423

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Gln Arg Phe Ser Gly
    50                  55                  60

Ser Gly Ser Gly Thr Glu Phe Ser Leu Thr Ile Tyr Ser Leu Gln Pro
65                  70                  75                  80

Asp Asp Phe Ala Thr Tyr Tyr Cys Leu Glu Tyr Asn Ser Tyr Ile Arg
                85                  90                  95

Thr Phe Gly Gln Gly Thr Lys Val Glu Ile Lys
            100                 105

<210> SEQ ID NO 424
<211> LENGTH: 11
<212> TYPE: PRT
<213> ORGANISM: Artificial Sequence
<220> FEATURE:
<223> OTHER INFORMATION: Recombinant protein

<400> SEQUENCE: 424
```

Arg Ala Ser Gln Ser Ile Ser Ser Trp Leu Ala
1               5                   10

<210> SEQ ID NO 425
<211> LENGTH: 7
<212> TYPE: PRT
<213> ORGANISM: Artificial Sequence
<220> FEATURE:
<223> OTHER INFORMATION: Recombinant protein

<400> SEQUENCE: 425

Lys Ala Ser Arg Leu Asp Arg
1               5

<210> SEQ ID NO 426
<211> LENGTH: 9
<212> TYPE: PRT
<213> ORGANISM: Artificial Sequence
<220> FEATURE:
<223> OTHER INFORMATION: Recombinant protein

<400> SEQUENCE: 426

Leu Glu Tyr Asn Ser Tyr Ile Arg Thr
1               5

<210> SEQ ID NO 427
<211> LENGTH: 122
<212> TYPE: PRT
<213> ORGANISM: Artificial Sequence
<220> FEATURE:
<223> OTHER INFORMATION: Recombinant protein

<400> SEQUENCE: 427

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 428
<211> LENGTH: 5
<212> TYPE: PRT
<213> ORGANISM: Artificial Sequence
<220> FEATURE:
<223> OTHER INFORMATION: Recombinant protein

<400> SEQUENCE: 428

Asp Tyr Ala Met His
1               5

<210> SEQ ID NO 429

```
<211> LENGTH: 17
<212> TYPE: PRT
<213> ORGANISM: Artificial Sequence
<220> FEATURE:
<223> OTHER INFORMATION: Recombinant protein

<400> SEQUENCE: 429

Gly Ile Ser Trp Lys Gly Asp Ile Gly Gly Tyr Val Asp Ser Val Lys
1               5                   10                  15

Gly

<210> SEQ ID NO 430
<211> LENGTH: 13
<212> TYPE: PRT
<213> ORGANISM: Artificial Sequence
<220> FEATURE:
<223> OTHER INFORMATION: Recombinant protein

<400> SEQUENCE: 430

Ser Tyr Gly Ser Gly Ser Phe Tyr Asn Ala Phe Asp Ser
1               5                   10

<210> SEQ ID NO 431
<211> LENGTH: 107
<212> TYPE: PRT
<213> ORGANISM: Artificial Sequence
<220> FEATURE:
<223> OTHER INFORMATION: Recombinant protein

<400> SEQUENCE: 431

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 432
<211> LENGTH: 11
<212> TYPE: PRT
<213> ORGANISM: Artificial Sequence
<220> FEATURE:
<223> OTHER INFORMATION: Recombinant protein

<400> SEQUENCE: 432

Arg Ala Ser Gln Ser Ile Ser Ser Trp Leu Ala
1               5                   10

<210> SEQ ID NO 433
<211> LENGTH: 7
<212> TYPE: PRT
<213> ORGANISM: Artificial Sequence
<220> FEATURE:
<223> OTHER INFORMATION: Recombinant protein

<400> SEQUENCE: 433
```

```
Lys Ala Ser Lys Leu Asp Arg
1               5

<210> SEQ ID NO 434
<211> LENGTH: 9
<212> TYPE: PRT
<213> ORGANISM: Artificial Sequence
<220> FEATURE:
<223> OTHER INFORMATION: Recombinant protein

<400> SEQUENCE: 434

Leu Glu Tyr Ser Ser Tyr Ile Arg Thr
1               5

<210> SEQ ID NO 435
<211> LENGTH: 122
<212> TYPE: PRT
<213> ORGANISM: Artificial Sequence
<220> FEATURE:
<223> OTHER INFORMATION: Recombinant protein

<400> SEQUENCE: 435

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 436
<211> LENGTH: 5
<212> TYPE: PRT
<213> ORGANISM: Artificial Sequence
<220> FEATURE:
<223> OTHER INFORMATION: Recombinant protein

<400> SEQUENCE: 436

Asp Tyr Ala Met His
1               5

<210> SEQ ID NO 437
<211> LENGTH: 17
<212> TYPE: PRT
<213> ORGANISM: Artificial Sequence
<220> FEATURE:
<223> OTHER INFORMATION: Recombinant protein

<400> SEQUENCE: 437

Gly Ile Ser Trp Arg Gly Asp Ile Gly Gly Tyr Val Asp Ser Val Lys
1               5                   10                  15

Gly
```

```
<210> SEQ ID NO 438
<211> LENGTH: 13
<212> TYPE: PRT
<213> ORGANISM: Artificial Sequence
<220> FEATURE:
<223> OTHER INFORMATION: Recombinant protein

<400> SEQUENCE: 438

Ser Tyr Gly Ser Gly Ser Phe Tyr Asn Ala Phe Asp Ser
1               5                   10

<210> SEQ ID NO 439
<211> LENGTH: 107
<212> TYPE: PRT
<213> ORGANISM: Artificial Sequence
<220> FEATURE:
<223> OTHER INFORMATION: Recombinant protein

<400> SEQUENCE: 439

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 440
<211> LENGTH: 11
<212> TYPE: PRT
<213> ORGANISM: Artificial Sequence
<220> FEATURE:
<223> OTHER INFORMATION: Recombinant protein

<400> SEQUENCE: 440

Arg Ala Ser Gln Ser Ile Ser Ser Trp Leu Ala
1               5                   10

<210> SEQ ID NO 441
<211> LENGTH: 7
<212> TYPE: PRT
<213> ORGANISM: Artificial Sequence
<220> FEATURE:
<223> OTHER INFORMATION: Recombinant protein

<400> SEQUENCE: 441

Lys Ala Ser Lys Leu Asp Arg
1               5

<210> SEQ ID NO 442
<211> LENGTH: 9
<212> TYPE: PRT
<213> ORGANISM: Artificial Sequence
<220> FEATURE:
<223> OTHER INFORMATION: Recombinant protein

<400> SEQUENCE: 442
```

```
Leu Glu Tyr Ser Ser Tyr Ile Arg Thr
1               5

<210> SEQ ID NO 443
<211> LENGTH: 122
<212> TYPE: PRT
<213> ORGANISM: Artificial Sequence
<220> FEATURE:
<223> OTHER INFORMATION: Recombinant protein

<400> SEQUENCE: 443

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 444
<211> LENGTH: 5
<212> TYPE: PRT
<213> ORGANISM: Artificial Sequence
<220> FEATURE:
<223> OTHER INFORMATION: Recombinant protein

<400> SEQUENCE: 444

Asp Tyr Ala Met His
1               5

<210> SEQ ID NO 445
<211> LENGTH: 17
<212> TYPE: PRT
<213> ORGANISM: Artificial Sequence
<220> FEATURE:
<223> OTHER INFORMATION: Recombinant protein

<400> SEQUENCE: 445

Gly Ile Ser Trp Arg Gly Asp Ile Gly Gly Tyr Val Asp Ser Val Lys
1               5                   10                  15

Gly

<210> SEQ ID NO 446
<211> LENGTH: 13
<212> TYPE: PRT
<213> ORGANISM: Artificial Sequence
<220> FEATURE:
<223> OTHER INFORMATION: Recombinant protein

<400> SEQUENCE: 446

Ser Tyr Gly Ser Gly Ser Phe Tyr Asn Ala Phe Asp Ser
1               5                   10
```

<210> SEQ ID NO 447
<211> LENGTH: 107
<212> TYPE: PRT
<213> ORGANISM: Artificial Sequence
<220> FEATURE:
<223> OTHER INFORMATION: Recombinant protein

<400> SEQUENCE: 447

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Lys Ala Ser Arg Leu Glu Arg Gly Thr Pro Ser Arg Phe Ser Gly
    50                  55                  60
Ser Gly Ser Gly Thr Glu Phe Ser Leu Thr Ile Ser Ser Leu Gln Pro
65                  70                  75                  80
Asp Asp Phe Ala Thr Tyr Tyr Cys Leu Glu Tyr Ser Ser Tyr Ile Arg
                85                  90                  95
Thr Phe Gly Gln Gly Thr Lys Val Glu Ile Lys
            100                 105
```

<210> SEQ ID NO 448
<211> LENGTH: 11
<212> TYPE: PRT
<213> ORGANISM: Artificial Sequence
<220> FEATURE:
<223> OTHER INFORMATION: Recombinant protein

<400> SEQUENCE: 448

```
Arg Ala Ser Gln Ser Ile Ser Ser Trp Leu Ala
1               5                   10
```

<210> SEQ ID NO 449
<211> LENGTH: 7
<212> TYPE: PRT
<213> ORGANISM: Artificial Sequence
<220> FEATURE:
<223> OTHER INFORMATION: Recombinant protein

<400> SEQUENCE: 449

```
Lys Ala Ser Arg Leu Glu Arg
1               5
```

<210> SEQ ID NO 450
<211> LENGTH: 9
<212> TYPE: PRT
<213> ORGANISM: Artificial Sequence
<220> FEATURE:
<223> OTHER INFORMATION: Recombinant protein

<400> SEQUENCE: 450

```
Leu Glu Tyr Ser Ser Tyr Ile Arg Thr
1               5
```

<210> SEQ ID NO 451
<211> LENGTH: 122
<212> TYPE: PRT
<213> ORGANISM: Artificial Sequence
<220> FEATURE:
<223> OTHER INFORMATION: Recombinant protein

<400> SEQUENCE: 451

-continued

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 452
<211> LENGTH: 5
<212> TYPE: PRT
<213> ORGANISM: Artificial Sequence
<220> FEATURE:
<223> OTHER INFORMATION: Recombinant protein

<400> SEQUENCE: 452

Asp Tyr Ala Met His
1               5

<210> SEQ ID NO 453
<211> LENGTH: 17
<212> TYPE: PRT
<213> ORGANISM: Artificial Sequence
<220> FEATURE:
<223> OTHER INFORMATION: Recombinant protein

<400> SEQUENCE: 453

Gly Ile Ser Trp Lys Gly Asp Ile Gly Gly Tyr Val Asp Ser Val Lys
1               5                   10                  15

Gly

<210> SEQ ID NO 454
<211> LENGTH: 13
<212> TYPE: PRT
<213> ORGANISM: Artificial Sequence
<220> FEATURE:
<223> OTHER INFORMATION: Recombinant protein

<400> SEQUENCE: 454

Ser Tyr Gly Ser Gly Ser Phe Tyr Asn Ala Phe Asp Ser
1               5                   10

<210> SEQ ID NO 455
<211> LENGTH: 107
<212> TYPE: PRT
<213> ORGANISM: Artificial Sequence
<220> FEATURE:
<223> OTHER INFORMATION: Recombinant protein

<400> SEQUENCE: 455

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Arg Leu Asp Arg Gly Thr Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 456
<211> LENGTH: 11
<212> TYPE: PRT
<213> ORGANISM: Artificial Sequence
<220> FEATURE:
<223> OTHER INFORMATION: Recombinant protein

<400> SEQUENCE: 456

Arg Ala Ser Gln Ser Ile Ser Ser Trp Leu Ala
1               5                   10

<210> SEQ ID NO 457
<211> LENGTH: 7
<212> TYPE: PRT
<213> ORGANISM: Artificial Sequence
<220> FEATURE:
<223> OTHER INFORMATION: Recombinant protein

<400> SEQUENCE: 457

Lys Ala Ser Arg Leu Asp Arg
1               5

<210> SEQ ID NO 458
<211> LENGTH: 9
<212> TYPE: PRT
<213> ORGANISM: Artificial Sequence
<220> FEATURE:
<223> OTHER INFORMATION: Recombinant protein

<400> SEQUENCE: 458

Leu Glu Tyr Ser Ser Tyr Ile Arg Thr
1               5

<210> SEQ ID NO 459
<211> LENGTH: 120
<212> TYPE: PRT
<213> ORGANISM: Artificial Sequence
<220> FEATURE:
<223> OTHER INFORMATION: Recombinant protein

<400> SEQUENCE: 459

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
50                  55                  60

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr His Ser Glu Glu Phe Asp Val Trp Gly Gln
            100                 105                 110

Gly Thr Leu Val Thr Val Ser Ser
            115                 120

<210> SEQ ID NO 460
<211> LENGTH: 5
<212> TYPE: PRT
<213> ORGANISM: Artificial Sequence
<220> FEATURE:
<223> OTHER INFORMATION: Recombinant protein

<400> SEQUENCE: 460

Thr Ser Trp Ile Val
1               5

<210> SEQ ID NO 461
<211> LENGTH: 17
<212> TYPE: PRT
<213> ORGANISM: Artificial Sequence
<220> FEATURE:
<223> OTHER INFORMATION: Recombinant protein

<400> SEQUENCE: 461

Met Ile Asp Pro Ser Asp Ser Phe Thr Ser Tyr Ser Pro Ser Phe Gln
1               5                  10                  15

Gly

<210> SEQ ID NO 462
<211> LENGTH: 11
<212> TYPE: PRT
<213> ORGANISM: Artificial Sequence
<220> FEATURE:
<223> OTHER INFORMATION: Recombinant protein

<400> SEQUENCE: 462

Leu His Tyr Tyr His Ser Glu Glu Phe Asp Val
1               5                  10

<210> SEQ ID NO 463
<211> LENGTH: 109
<212> TYPE: PRT
<213> ORGANISM: Artificial Sequence
<220> FEATURE:
<223> OTHER INFORMATION: Recombinant protein

<400> SEQUENCE: 463

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Arg
```

```
                    85                  90                  95

Leu Phe Thr Phe Gly Gln Gly Thr Lys Leu Glu Ile Lys
            100                 105

<210> SEQ ID NO 464
<211> LENGTH: 12
<212> TYPE: PRT
<213> ORGANISM: Artificial Sequence
<220> FEATURE:
<223> OTHER INFORMATION: Recombinant protein

<400> SEQUENCE: 464

Arg Ala Ser Gln Ser Val Ser Ser Ser Tyr Leu Ala
1               5                   10

<210> SEQ ID NO 465
<211> LENGTH: 7
<212> TYPE: PRT
<213> ORGANISM: Artificial Sequence
<220> FEATURE:
<223> OTHER INFORMATION: Recombinant protein

<400> SEQUENCE: 465

Gly Ala Ser Ser Arg Ala Arg
1               5

<210> SEQ ID NO 466
<211> LENGTH: 10
<212> TYPE: PRT
<213> ORGANISM: Artificial Sequence
<220> FEATURE:
<223> OTHER INFORMATION: Recombinant protein

<400> SEQUENCE: 466

Gln Gln Phe Gly Ser Ser Arg Leu Phe Thr
1               5                   10

<210> SEQ ID NO 467
<211> LENGTH: 120
<212> TYPE: PRT
<213> ORGANISM: Artificial Sequence
<220> FEATURE:
<223> OTHER INFORMATION: Recombinant protein

<400> SEQUENCE: 467

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120
```

<210> SEQ ID NO 468
<211> LENGTH: 5
<212> TYPE: PRT
<213> ORGANISM: Artificial Sequence
<220> FEATURE:
<223> OTHER INFORMATION: Recombinant protein

<400> SEQUENCE: 468

Thr Ser Trp Ile Val
1               5

<210> SEQ ID NO 469
<211> LENGTH: 17
<212> TYPE: PRT
<213> ORGANISM: Artificial Sequence
<220> FEATURE:
<223> OTHER INFORMATION: Recombinant protein

<400> SEQUENCE: 469

Met Ile Asp Pro Ser Asp Ser Phe Thr Ser Tyr Ser Pro Ser Phe Gln
1               5                   10                  15

Gly

<210> SEQ ID NO 470
<211> LENGTH: 11
<212> TYPE: PRT
<213> ORGANISM: Artificial Sequence
<220> FEATURE:
<223> OTHER INFORMATION: Recombinant protein

<400> SEQUENCE: 470

Leu His Tyr Tyr Asn Ser Glu Glu Phe Asp Val
1               5                   10

<210> SEQ ID NO 471
<211> LENGTH: 109
<212> TYPE: PRT
<213> ORGANISM: Artificial Sequence
<220> FEATURE:
<223> OTHER INFORMATION: Recombinant protein

<400> SEQUENCE: 471

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Gln
                85                  90                  95

Leu Phe Thr Phe Gly Gln Gly Thr Lys Leu Glu Ile Lys
            100                 105

<210> SEQ ID NO 472
<211> LENGTH: 12
<212> TYPE: PRT
<213> ORGANISM: Artificial Sequence
<220> FEATURE:
<223> OTHER INFORMATION: Recombinant protein -continued

```
<400> SEQUENCE: 472

Arg Ala Ser Gln Ser Val Ser Ser Ser Tyr Leu Ala
1               5                   10

<210> SEQ ID NO 473
<211> LENGTH: 7
<212> TYPE: PRT
<213> ORGANISM: Artificial Sequence
<220> FEATURE:
<223> OTHER INFORMATION: Recombinant protein

<400> SEQUENCE: 473

Gly Gln Ser Ser Arg Thr Arg
1               5

<210> SEQ ID NO 474
<211> LENGTH: 10
<212> TYPE: PRT
<213> ORGANISM: Artificial Sequence
<220> FEATURE:
<223> OTHER INFORMATION: Recombinant protein

<400> SEQUENCE: 474

Gln Gln Phe Gly Asp Ser Gln Leu Phe Thr
1               5                   10

<210> SEQ ID NO 475
<211> LENGTH: 120
<212> TYPE: PRT
<213> ORGANISM: Artificial Sequence
<220> FEATURE:
<223> OTHER INFORMATION: Recombinant protein

<400> SEQUENCE: 475

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
            35                  40                  45

Gly Met Ile Asp Pro Ser Asp Ser Phe Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 476
<211> LENGTH: 5
<212> TYPE: PRT
<213> ORGANISM: Artificial Sequence
<220> FEATURE:
<223> OTHER INFORMATION: Recombinant protein

<400> SEQUENCE: 476

Thr Ser Trp Ile Val
1               5
```

```
<210> SEQ ID NO 477
<211> LENGTH: 17
<212> TYPE: PRT
<213> ORGANISM: Artificial Sequence
<220> FEATURE:
<223> OTHER INFORMATION: Recombinant protein

<400> SEQUENCE: 477

Met Ile Asp Pro Ser Asp Ser Phe Thr Ser Tyr Ser Pro Ser Phe Gln
1               5                   10                  15

Gly

<210> SEQ ID NO 478
<211> LENGTH: 11
<212> TYPE: PRT
<213> ORGANISM: Artificial Sequence
<220> FEATURE:
<223> OTHER INFORMATION: Recombinant protein

<400> SEQUENCE: 478

Leu His Tyr Tyr Asn Ser Glu Glu Phe Asp Val
1               5                   10

<210> SEQ ID NO 479
<211> LENGTH: 109
<212> TYPE: PRT
<213> ORGANISM: Artificial Sequence
<220> FEATURE:
<223> OTHER INFORMATION: Recombinant protein

<400> SEQUENCE: 479

Glu Ile Val Leu Thr Gln Ser Pro Gly Thr Leu Ser Leu Ser Ala Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Arg
                85                  90                  95

Leu Phe Thr Phe Gly Gln Gly Thr Lys Leu Glu Ile Lys
            100                 105

<210> SEQ ID NO 480
<211> LENGTH: 12
<212> TYPE: PRT
<213> ORGANISM: Artificial Sequence
<220> FEATURE:
<223> OTHER INFORMATION: Recombinant protein

<400> SEQUENCE: 480

Arg Ala Ser Gln Ser Val Ser Ser Ser Tyr Leu Ala
1               5                   10

<210> SEQ ID NO 481
<211> LENGTH: 7
<212> TYPE: PRT
<213> ORGANISM: Artificial Sequence
<220> FEATURE:
<223> OTHER INFORMATION: Recombinant protein
```

<400> SEQUENCE: 481

Gly Ala Ser Ser Arg Ala Arg
1               5

<210> SEQ ID NO 482
<211> LENGTH: 10
<212> TYPE: PRT
<213> ORGANISM: Artificial Sequence
<220> FEATURE:
<223> OTHER INFORMATION: Recombinant protein

<400> SEQUENCE: 482

Gln Gln Phe Gly Ser Ser Arg Leu Phe Thr
1               5                   10

<210> SEQ ID NO 483
<211> LENGTH: 120
<212> TYPE: PRT
<213> ORGANISM: Artificial Sequence
<220> FEATURE:
<223> OTHER INFORMATION: Recombinant protein

<400> SEQUENCE: 483

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 484
<211> LENGTH: 5
<212> TYPE: PRT
<213> ORGANISM: Artificial Sequence
<220> FEATURE:
<223> OTHER INFORMATION: Recombinant protein

<400> SEQUENCE: 484

Thr Ser Trp Ile Ser
1               5

<210> SEQ ID NO 485
<211> LENGTH: 17
<212> TYPE: PRT
<213> ORGANISM: Artificial Sequence
<220> FEATURE:
<223> OTHER INFORMATION: Recombinant protein

<400> SEQUENCE: 485

Met Ile Asp Pro Ser Asp Ser Tyr Thr Ser Tyr Ser Pro Ser Phe Gln
1               5                   10                  15

Gly

<210> SEQ ID NO 486
<211> LENGTH: 11
<212> TYPE: PRT
<213> ORGANISM: Artificial Sequence
<220> FEATURE:
<223> OTHER INFORMATION: Recombinant protein

<400> SEQUENCE: 486

Leu His Tyr Tyr Asn Ser Glu Glu Phe Asp Val
1               5                   10

<210> SEQ ID NO 487
<211> LENGTH: 109
<212> TYPE: PRT
<213> ORGANISM: Artificial Sequence
<220> FEATURE:
<223> OTHER INFORMATION: Recombinant protein

<400> SEQUENCE: 487

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Gln
                85                  90                  95

Leu Phe Thr Phe Gly Gln Gly Thr Lys Leu Glu Ile Lys
            100                 105

<210> SEQ ID NO 488
<211> LENGTH: 12
<212> TYPE: PRT
<213> ORGANISM: Artificial Sequence
<220> FEATURE:
<223> OTHER INFORMATION: Recombinant protein

<400> SEQUENCE: 488

Arg Ala Ser Gln Ser Val Ser Ser Ser Tyr Leu Ala
1               5                   10

<210> SEQ ID NO 489
<211> LENGTH: 7
<212> TYPE: PRT
<213> ORGANISM: Artificial Sequence
<220> FEATURE:
<223> OTHER INFORMATION: Recombinant protein

<400> SEQUENCE: 489

Gly Gln Ser Ser Arg Thr Arg
1               5

<210> SEQ ID NO 490
<211> LENGTH: 10
<212> TYPE: PRT
<213> ORGANISM: Artificial Sequence
<220> FEATURE:
<223> OTHER INFORMATION: Recombinant protein

<400> SEQUENCE: 490

Gln Gln Tyr Gly Asp Ser Gln Leu Phe Thr
1               5                   10

<210> SEQ ID NO 491
<211> LENGTH: 120
<212> TYPE: PRT
<213> ORGANISM: Artificial Sequence
<220> FEATURE:
<223> OTHER INFORMATION: Recombinant protein

<400> SEQUENCE: 491

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 492
<211> LENGTH: 5
<212> TYPE: PRT
<213> ORGANISM: Artificial Sequence
<220> FEATURE:
<223> OTHER INFORMATION: Recombinant protein

<400> SEQUENCE: 492

Thr Ser Trp Ile Ser
1               5

<210> SEQ ID NO 493
<211> LENGTH: 17
<212> TYPE: PRT
<213> ORGANISM: Artificial Sequence
<220> FEATURE:
<223> OTHER INFORMATION: Recombinant protein

<400> SEQUENCE: 493

Met Ile Asp Pro Ser Asp Ser Phe Thr Ser Tyr Ser Pro Ser Phe Gln
1               5                   10                  15

Gly

<210> SEQ ID NO 494
<211> LENGTH: 11
<212> TYPE: PRT
<213> ORGANISM: Artificial Sequence
<220> FEATURE:
<223> OTHER INFORMATION: Recombinant protein

<400> SEQUENCE: 494

Leu His Tyr Tyr Asn Ser Glu Glu Phe Asp Val
1               5                   10

<210> SEQ ID NO 495
<211> LENGTH: 109
<212> TYPE: PRT
<213> ORGANISM: Artificial Sequence
<220> FEATURE:
<223> OTHER INFORMATION: Recombinant protein

<400> SEQUENCE: 495

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Gln
                85                  90                  95

Leu Phe Thr Phe Gly Gln Gly Thr Lys Leu Glu Ile Lys
                100                 105

<210> SEQ ID NO 496
<211> LENGTH: 12
<212> TYPE: PRT
<213> ORGANISM: Artificial Sequence
<220> FEATURE:
<223> OTHER INFORMATION: Recombinant protein

<400> SEQUENCE: 496

Arg Ala Ser Gln Ser Val Ser Ser Ser Tyr Leu Ala
1               5                   10

<210> SEQ ID NO 497
<211> LENGTH: 7
<212> TYPE: PRT
<213> ORGANISM: Artificial Sequence
<220> FEATURE:
<223> OTHER INFORMATION: Recombinant protein

<400> SEQUENCE: 497

Gly Gln Ser Ser Arg Thr Arg
1               5

<210> SEQ ID NO 498
<211> LENGTH: 10
<212> TYPE: PRT
<213> ORGANISM: Artificial Sequence
<220> FEATURE:
<223> OTHER INFORMATION: Recombinant protein

<400> SEQUENCE: 498

Gln Gln Tyr Gly Asp Ser Gln Leu Phe Thr
1               5                   10

<210> SEQ ID NO 499
<211> LENGTH: 120
<212> TYPE: PRT
<213> ORGANISM: Artificial Sequence
<220> FEATURE:
<223> OTHER INFORMATION: Recombinant protein

<400> SEQUENCE: 499

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 500
<211> LENGTH: 5
<212> TYPE: PRT
<213> ORGANISM: Artificial Sequence
<220> FEATURE:
<223> OTHER INFORMATION: Recombinant protein

<400> SEQUENCE: 500

Thr Ser Trp Ile Ser
1               5

<210> SEQ ID NO 501
<211> LENGTH: 17
<212> TYPE: PRT
<213> ORGANISM: Artificial Sequence
<220> FEATURE:
<223> OTHER INFORMATION: Recombinant protein

<400> SEQUENCE: 501

Met Ile Asp Pro Ser Asp Ser Tyr Thr Ser Tyr Ser Pro Ser Phe Gln
1               5                   10                  15

Gly

<210> SEQ ID NO 502
<211> LENGTH: 11
<212> TYPE: PRT
<213> ORGANISM: Artificial Sequence
<220> FEATURE:
<223> OTHER INFORMATION: Recombinant protein

<400> SEQUENCE: 502

Leu His Tyr Tyr Asn Ser Glu Glu Phe Asp Val
1               5                   10

<210> SEQ ID NO 503
<211> LENGTH: 109
<212> TYPE: PRT
<213> ORGANISM: Artificial Sequence
<220> FEATURE:
<223> OTHER INFORMATION: Recombinant protein

<400> SEQUENCE: 503

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Gln
                85                  90                  95

Leu Phe Thr Phe Gly Gln Gly Thr Lys Leu Glu Ile Lys
            100                 105

<210> SEQ ID NO 504
<211> LENGTH: 12
<212> TYPE: PRT
<213> ORGANISM: Artificial Sequence
<220> FEATURE:
<223> OTHER INFORMATION: Recombinant protein

<400> SEQUENCE: 504

Arg Ala Ser Gln Ser Val Ser Ser Ser Tyr Leu Ala
1               5                   10

<210> SEQ ID NO 505
<211> LENGTH: 7
<212> TYPE: PRT
<213> ORGANISM: Artificial Sequence
<220> FEATURE:
<223> OTHER INFORMATION: Recombinant protein

<400> SEQUENCE: 505

Gly Gln Ser Ser Arg Thr Arg
1               5

<210> SEQ ID NO 506
<211> LENGTH: 10
<212> TYPE: PRT
<213> ORGANISM: Artificial Sequence
<220> FEATURE:
<223> OTHER INFORMATION: Recombinant protein

<400> SEQUENCE: 506

Gln Gln Phe Gly Asp Ser Gln Leu Phe Thr
1               5                   10

<210> SEQ ID NO 507
<211> LENGTH: 120
<212> TYPE: PRT
<213> ORGANISM: Artificial Sequence
<220> FEATURE:
<223> OTHER INFORMATION: Recombinant protein

<400> SEQUENCE: 507

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Phe Thr Ser Tyr Ser Pro Ser Phe
 50                  55                  60
```

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 508
<211> LENGTH: 5
<212> TYPE: PRT
<213> ORGANISM: Artificial Sequence
<220> FEATURE:
<223> OTHER INFORMATION: Recombinant protein

<400> SEQUENCE: 508

Thr Ser Trp Ile Ser
1               5

<210> SEQ ID NO 509
<211> LENGTH: 17
<212> TYPE: PRT
<213> ORGANISM: Artificial Sequence
<220> FEATURE:
<223> OTHER INFORMATION: Recombinant protein

<400> SEQUENCE: 509

Met Ile Asp Pro Ser Asp Ser Phe Thr Ser Tyr Ser Pro Ser Phe Gln
1               5                  10                  15

Gly

<210> SEQ ID NO 510
<211> LENGTH: 11
<212> TYPE: PRT
<213> ORGANISM: Artificial Sequence
<220> FEATURE:
<223> OTHER INFORMATION: Recombinant protein

<400> SEQUENCE: 510

Leu His Tyr Tyr His Ser Glu Glu Phe Asp Val
1               5                  10

<210> SEQ ID NO 511
<211> LENGTH: 109
<212> TYPE: PRT
<213> ORGANISM: Artificial Sequence
<220> FEATURE:
<223> OTHER INFORMATION: Recombinant protein

<400> SEQUENCE: 511

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Phe Gly Asp Ser Gln
                85                  90                  95

Leu Phe Thr Phe Gly Gln Gly Thr Lys Leu Glu Ile Lys
            100                 105

<210> SEQ ID NO 512
<211> LENGTH: 12
<212> TYPE: PRT
<213> ORGANISM: Artificial Sequence
<220> FEATURE:
<223> OTHER INFORMATION: Recombinant protein

<400> SEQUENCE: 512

Arg Ala Ser Gln Ser Val Ser Ser Ser Tyr Leu Ala
1               5                   10

<210> SEQ ID NO 513
<211> LENGTH: 7
<212> TYPE: PRT
<213> ORGANISM: Artificial Sequence
<220> FEATURE:
<223> OTHER INFORMATION: Recombinant protein

<400> SEQUENCE: 513

Gly Gln Ser Ser Arg Thr Arg
1               5

<210> SEQ ID NO 514
<211> LENGTH: 10
<212> TYPE: PRT
<213> ORGANISM: Artificial Sequence
<220> FEATURE:
<223> OTHER INFORMATION: Recombinant protein

<400> SEQUENCE: 514

Gln Gln Phe Gly Asp Ser Gln Leu Phe Thr
1               5                   10

<210> SEQ ID NO 515
<211> LENGTH: 120
<212> TYPE: PRT
<213> ORGANISM: Artificial Sequence
<220> FEATURE:
<223> OTHER INFORMATION: Recombinant protein

<400> SEQUENCE: 515

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 516
<211> LENGTH: 5
<212> TYPE: PRT
<213> ORGANISM: Artificial Sequence
<220> FEATURE:
<223> OTHER INFORMATION: Recombinant protein

<400> SEQUENCE: 516

Thr Ser Trp Ile Ser
1               5

<210> SEQ ID NO 517
<211> LENGTH: 17
<212> TYPE: PRT
<213> ORGANISM: Artificial Sequence
<220> FEATURE:
<223> OTHER INFORMATION: Recombinant protein

<400> SEQUENCE: 517

Met Ile Asp Pro Ser Asp Ser Tyr Thr Ser Tyr Ser Pro Ser Phe Gln
1               5                   10                  15

Gly

<210> SEQ ID NO 518
<211> LENGTH: 11
<212> TYPE: PRT
<213> ORGANISM: Artificial Sequence
<220> FEATURE:
<223> OTHER INFORMATION: Recombinant protein

<400> SEQUENCE: 518

Leu His Tyr Tyr His Ser Glu Glu Phe Asp Val
1               5                   10

<210> SEQ ID NO 519
<211> LENGTH: 109
<212> TYPE: PRT
<213> ORGANISM: Artificial Sequence
<220> FEATURE:
<223> OTHER INFORMATION: Recombinant protein

<400> SEQUENCE: 519

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Gln
                85                  90                  95

Leu Phe Thr Phe Gly Gln Gly Thr Lys Leu Glu Ile Lys
            100                 105

<210> SEQ ID NO 520
<211> LENGTH: 12
<212> TYPE: PRT
<213> ORGANISM: Artificial Sequence
<220> FEATURE:
<223> OTHER INFORMATION: Recombinant protein

```
<400> SEQUENCE: 520

Arg Ala Ser Gln Ser Val Ser Ser Ser Tyr Leu Ala
1               5                   10

<210> SEQ ID NO 521
<211> LENGTH: 7
<212> TYPE: PRT
<213> ORGANISM: Artificial Sequence
<220> FEATURE:
<223> OTHER INFORMATION: Recombinant protein

<400> SEQUENCE: 521

Gly Gln Ser Ser Arg Thr Arg
1               5

<210> SEQ ID NO 522
<211> LENGTH: 10
<212> TYPE: PRT
<213> ORGANISM: Artificial Sequence
<220> FEATURE:
<223> OTHER INFORMATION: Recombinant protein

<400> SEQUENCE: 522

Gln Gln Phe Gly Asp Ser Gln Leu Phe Thr
1               5                   10

<210> SEQ ID NO 523
<211> LENGTH: 120
<212> TYPE: PRT
<213> ORGANISM: Artificial Sequence
<220> FEATURE:
<223> OTHER INFORMATION: Recombinant protein

<400> SEQUENCE: 523

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 524
<211> LENGTH: 5
<212> TYPE: PRT
<213> ORGANISM: Artificial Sequence
<220> FEATURE:
<223> OTHER INFORMATION: Recombinant protein

<400> SEQUENCE: 524

Thr Ser Trp Ile Ser
1               5
```

<210> SEQ ID NO 525
<211> LENGTH: 17
<212> TYPE: PRT
<213> ORGANISM: Artificial Sequence
<220> FEATURE:
<223> OTHER INFORMATION: Recombinant protein

<400> SEQUENCE: 525

Met Ile Asp Pro Ser Asp Ser Tyr Thr Ser Tyr Ser Pro Ser Phe Gln
1               5                   10                  15

Gly

<210> SEQ ID NO 526
<211> LENGTH: 11
<212> TYPE: PRT
<213> ORGANISM: Artificial Sequence
<220> FEATURE:
<223> OTHER INFORMATION: Recombinant protein

<400> SEQUENCE: 526

Leu His Tyr Tyr His Ser Glu Glu Phe Asp Val
1               5                   10

<210> SEQ ID NO 527
<211> LENGTH: 109
<212> TYPE: PRT
<213> ORGANISM: Artificial Sequence
<220> FEATURE:
<223> OTHER INFORMATION: Recombinant protein

<400> SEQUENCE: 527

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Gln
                85                  90                  95

Leu Phe Thr Phe Gly Gln Gly Thr Lys Leu Glu Ile Lys
            100                 105

<210> SEQ ID NO 528
<211> LENGTH: 12
<212> TYPE: PRT
<213> ORGANISM: Artificial Sequence
<220> FEATURE:
<223> OTHER INFORMATION: Recombinant protein

<400> SEQUENCE: 528

Arg Ala Ser Gln Ser Val Ser Ser Ser Tyr Leu Ala
1               5                   10

<210> SEQ ID NO 529
<211> LENGTH: 7
<212> TYPE: PRT
<213> ORGANISM: Artificial Sequence
<220> FEATURE:
<223> OTHER INFORMATION: Recombinant protein

```
<400> SEQUENCE: 529

Gly Gln Ser Ser Arg Thr Arg
1               5

<210> SEQ ID NO 530
<211> LENGTH: 10
<212> TYPE: PRT
<213> ORGANISM: Artificial Sequence
<220> FEATURE:
<223> OTHER INFORMATION: Recombinant protein

<400> SEQUENCE: 530

Gln Gln Phe Gly Asp Ser Gln Leu Phe Thr
1               5                   10

<210> SEQ ID NO 531
<211> LENGTH: 120
<212> TYPE: PRT
<213> ORGANISM: Artificial Sequence
<220> FEATURE:
<223> OTHER INFORMATION: Recombinant protein

<400> SEQUENCE: 531

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 532
<211> LENGTH: 5
<212> TYPE: PRT
<213> ORGANISM: Artificial Sequence
<220> FEATURE:
<223> OTHER INFORMATION: Recombinant protein

<400> SEQUENCE: 532

Thr Ser Trp Ile Ser
1               5

<210> SEQ ID NO 533
<211> LENGTH: 17
<212> TYPE: PRT
<213> ORGANISM: Artificial Sequence
<220> FEATURE:
<223> OTHER INFORMATION: Recombinant protein

<400> SEQUENCE: 533

Met Ile Asp Pro Ser Asp Ser Phe Thr Ser Tyr Ser Pro Ser Phe Gln
1               5                   10                  15
```

Gly

```
<210> SEQ ID NO 534
<211> LENGTH: 11
<212> TYPE: PRT
<213> ORGANISM: Artificial Sequence
<220> FEATURE:
<223> OTHER INFORMATION: Recombinant protein

<400> SEQUENCE: 534

Leu His Tyr Tyr Asn Ser Glu Glu Phe Asp Val
1               5                   10

<210> SEQ ID NO 535
<211> LENGTH: 109
<212> TYPE: PRT
<213> ORGANISM: Artificial Sequence
<220> FEATURE:
<223> OTHER INFORMATION: Recombinant protein

<400> SEQUENCE: 535

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Gln
                85                  90                  95

Leu Phe Thr Phe Gly Gln Gly Thr Lys Leu Glu Ile Lys
            100                 105

<210> SEQ ID NO 536
<211> LENGTH: 12
<212> TYPE: PRT
<213> ORGANISM: Artificial Sequence
<220> FEATURE:
<223> OTHER INFORMATION: Recombinant protein

<400> SEQUENCE: 536

Arg Ala Ser Gln Ser Val Ser Ser Ser Tyr Leu Ala
1               5                   10

<210> SEQ ID NO 537
<211> LENGTH: 7
<212> TYPE: PRT
<213> ORGANISM: Artificial Sequence
<220> FEATURE:
<223> OTHER INFORMATION: Recombinant protein

<400> SEQUENCE: 537

Gly Gln Ser Ser Arg Thr Arg
1               5

<210> SEQ ID NO 538
<211> LENGTH: 10
<212> TYPE: PRT
<213> ORGANISM: Artificial Sequence
<220> FEATURE:
<223> OTHER INFORMATION: Recombinant protein
```

```
<400> SEQUENCE: 538

Gln Gln Phe Gly Asp Ser Gln Leu Phe Thr
1               5                   10

<210> SEQ ID NO 539
<211> LENGTH: 120
<212> TYPE: PRT
<213> ORGANISM: Artificial Sequence
<220> FEATURE:
<223> OTHER INFORMATION: Recombinant protein

<400> SEQUENCE: 539

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 540
<211> LENGTH: 5
<212> TYPE: PRT
<213> ORGANISM: Artificial Sequence
<220> FEATURE:
<223> OTHER INFORMATION: Recombinant protein

<400> SEQUENCE: 540

Thr Ser Trp Ile Val
1               5

<210> SEQ ID NO 541
<211> LENGTH: 17
<212> TYPE: PRT
<213> ORGANISM: Artificial Sequence
<220> FEATURE:
<223> OTHER INFORMATION: Recombinant protein

<400> SEQUENCE: 541

Met Ile Asp Pro Ser Asp Ser Tyr Thr Ser Tyr Ser Pro Ser Phe Gln
1               5                   10                  15

Gly

<210> SEQ ID NO 542
<211> LENGTH: 11
<212> TYPE: PRT
<213> ORGANISM: Artificial Sequence
<220> FEATURE:
<223> OTHER INFORMATION: Recombinant protein

<400> SEQUENCE: 542

Leu His Tyr Tyr Asn Ser Glu Glu Phe Asp Val
```

<210> SEQ ID NO 543
<211> LENGTH: 109
<212> TYPE: PRT
<213> ORGANISM: Artificial Sequence
<220> FEATURE:
<223> OTHER INFORMATION: Recombinant protein

<400> SEQUENCE: 543

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Gln Ser Ser Arg Thr Arg Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Phe Gly Asp Ser Gln
                85                  90                  95
Leu Phe Thr Phe Gly Gln Gly Thr Lys Leu Glu Ile Lys
            100                 105

<210> SEQ ID NO 544
<211> LENGTH: 12
<212> TYPE: PRT
<213> ORGANISM: Artificial Sequence
<220> FEATURE:
<223> OTHER INFORMATION: Recombinant protein

<400> SEQUENCE: 544

Arg Ala Ser Gln Ser Val Ser Ser Ser Tyr Leu Ala
1               5                   10

<210> SEQ ID NO 545
<211> LENGTH: 7
<212> TYPE: PRT
<213> ORGANISM: Artificial Sequence
<220> FEATURE:
<223> OTHER INFORMATION: Recombinant protein

<400> SEQUENCE: 545

Gly Gln Ser Ser Arg Thr Arg
1               5

<210> SEQ ID NO 546
<211> LENGTH: 10
<212> TYPE: PRT
<213> ORGANISM: Artificial Sequence
<220> FEATURE:
<223> OTHER INFORMATION: Recombinant protein

<400> SEQUENCE: 546

Gln Gln Phe Gly Asp Ser Gln Leu Phe Thr
1               5                   10

<210> SEQ ID NO 547
<211> LENGTH: 120
<212> TYPE: PRT
<213> ORGANISM: Artificial Sequence
<220> FEATURE:
<223> OTHER INFORMATION: Recombinant protein -continued

<400> SEQUENCE: 547

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 548
<211> LENGTH: 5
<212> TYPE: PRT
<213> ORGANISM: Artificial Sequence
<220> FEATURE:
<223> OTHER INFORMATION: Recombinant protein

<400> SEQUENCE: 548

Thr Ser Trp Ile Val
1               5

<210> SEQ ID NO 549
<211> LENGTH: 17
<212> TYPE: PRT
<213> ORGANISM: Artificial Sequence
<220> FEATURE:
<223> OTHER INFORMATION: Recombinant protein

<400> SEQUENCE: 549

Met Ile Asp Pro Ser Asp Ser Tyr Thr Ser Tyr Ser Pro Ser Phe Gln
1               5                   10                  15

Gly

<210> SEQ ID NO 550
<211> LENGTH: 11
<212> TYPE: PRT
<213> ORGANISM: Artificial Sequence
<220> FEATURE:
<223> OTHER INFORMATION: Recombinant protein

<400> SEQUENCE: 550

Leu His Tyr Tyr Asn Ser Glu Glu Phe Asp Val
1               5                   10

<210> SEQ ID NO 551
<211> LENGTH: 109
<212> TYPE: PRT
<213> ORGANISM: Artificial Sequence
<220> FEATURE:
<223> OTHER INFORMATION: Recombinant protein

<400> SEQUENCE: 551

Glu Ile Val Leu Thr Gln Ser Pro Gly Thr Leu Ser Leu Ser Pro Gly

```
            1               5                  10                  15
Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Gln
                85                  90                  95

Leu Phe Thr Phe Gly Gln Gly Thr Lys Leu Glu Ile Lys
            100                 105
```

<210> SEQ ID NO 552
<211> LENGTH: 12
<212> TYPE: PRT
<213> ORGANISM: Artificial Sequence
<220> FEATURE:
<223> OTHER INFORMATION: Recombinant protein

<400> SEQUENCE: 552

```
Arg Ala Ser Gln Ser Val Ser Ser Ser Tyr Leu Ala
1               5                   10
```

<210> SEQ ID NO 553
<211> LENGTH: 7
<212> TYPE: PRT
<213> ORGANISM: Artificial Sequence
<220> FEATURE:
<223> OTHER INFORMATION: Recombinant protein

<400> SEQUENCE: 553

```
Gly Gln Ser Ser Arg Thr Arg
1               5
```

<210> SEQ ID NO 554
<211> LENGTH: 10
<212> TYPE: PRT
<213> ORGANISM: Artificial Sequence
<220> FEATURE:
<223> OTHER INFORMATION: Recombinant protein

<400> SEQUENCE: 554

```
Gln Gln Phe Gly Asp Ser Gln Leu Phe Thr
1               5                   10
```

<210> SEQ ID NO 555
<211> LENGTH: 120
<212> TYPE: PRT
<213> ORGANISM: Artificial Sequence
<220> FEATURE:
<223> OTHER INFORMATION: Recombinant protein

<400> SEQUENCE: 555

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
            35                  40                  45

Gly Met Ile Asp Pro Ser Asp Ser Phe Thr Ser Tyr Ser Pro Ser Phe
```

```
                    50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 556
<211> LENGTH: 5
<212> TYPE: PRT
<213> ORGANISM: Artificial Sequence
<220> FEATURE:
<223> OTHER INFORMATION: Recombinant protein

<400> SEQUENCE: 556

Thr Ser Trp Ile Val
1               5

<210> SEQ ID NO 557
<211> LENGTH: 17
<212> TYPE: PRT
<213> ORGANISM: Artificial Sequence
<220> FEATURE:
<223> OTHER INFORMATION: Recombinant protein

<400> SEQUENCE: 557

Met Ile Asp Pro Ser Asp Ser Phe Thr Ser Tyr Ser Pro Ser Phe Gln
1               5                   10                  15

Gly

<210> SEQ ID NO 558
<211> LENGTH: 11
<212> TYPE: PRT
<213> ORGANISM: Artificial Sequence
<220> FEATURE:
<223> OTHER INFORMATION: Recombinant protein

<400> SEQUENCE: 558

Leu His Tyr Tyr Asn Ser Glu Glu Phe Asp Val
1               5                   10

<210> SEQ ID NO 559
<211> LENGTH: 109
<212> TYPE: PRT
<213> ORGANISM: Artificial Sequence
<220> FEATURE:
<223> OTHER INFORMATION: Recombinant protein

<400> SEQUENCE: 559

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Asp Ser Gln
                85                  90                  95

Leu Phe Thr Phe Gly Gln Gly Thr Lys Leu Glu Ile Lys
            100                 105

<210> SEQ ID NO 560
<211> LENGTH: 12
<212> TYPE: PRT
<213> ORGANISM: Artificial Sequence
<220> FEATURE:
<223> OTHER INFORMATION: Recombinant protein

<400> SEQUENCE: 560

Arg Ala Ser Gln Ser Val Ser Ser Ser Tyr Leu Ala
1               5                   10

<210> SEQ ID NO 561
<211> LENGTH: 7
<212> TYPE: PRT
<213> ORGANISM: Artificial Sequence
<220> FEATURE:
<223> OTHER INFORMATION: Recombinant protein

<400> SEQUENCE: 561

Gly Gln Ser Ser Arg Thr Arg
1               5

<210> SEQ ID NO 562
<211> LENGTH: 10
<212> TYPE: PRT
<213> ORGANISM: Artificial Sequence
<220> FEATURE:
<223> OTHER INFORMATION: Recombinant protein

<400> SEQUENCE: 562

Gln Gln Tyr Gly Asp Ser Gln Leu Phe Thr
1               5                   10

<210> SEQ ID NO 563
<211> LENGTH: 120
<212> TYPE: PRT
<213> ORGANISM: Artificial Sequence
<220> FEATURE:
<223> OTHER INFORMATION: Recombinant protein

<400> SEQUENCE: 563

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120
```

```
<210> SEQ ID NO 564
<211> LENGTH: 5
<212> TYPE: PRT
<213> ORGANISM: Artificial Sequence
<220> FEATURE:
<223> OTHER INFORMATION: Recombinant protein

<400> SEQUENCE: 564

Thr Ser Trp Ile Ser
1               5

<210> SEQ ID NO 565
<211> LENGTH: 17
<212> TYPE: PRT
<213> ORGANISM: Artificial Sequence
<220> FEATURE:
<223> OTHER INFORMATION: Recombinant protein

<400> SEQUENCE: 565

Met Ile Asp Pro Ser Asp Ser Phe Thr Ser Tyr Ser Pro Ser Phe Gln
1               5                   10                  15

Gly

<210> SEQ ID NO 566
<211> LENGTH: 11
<212> TYPE: PRT
<213> ORGANISM: Artificial Sequence
<220> FEATURE:
<223> OTHER INFORMATION: Recombinant protein

<400> SEQUENCE: 566

Leu His Tyr Tyr His Ser Glu Glu Phe Asp Val
1               5                   10

<210> SEQ ID NO 567
<211> LENGTH: 109
<212> TYPE: PRT
<213> ORGANISM: Artificial Sequence
<220> FEATURE:
<223> OTHER INFORMATION: Recombinant protein

<400> SEQUENCE: 567

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Gln
                85                  90                  95

Leu Phe Thr Phe Gly Gln Gly Thr Lys Leu Glu Ile Lys
            100                 105

<210> SEQ ID NO 568
<211> LENGTH: 12
<212> TYPE: PRT
<213> ORGANISM: Artificial Sequence
<220> FEATURE:
```

<223> OTHER INFORMATION: Recombinant protein

<400> SEQUENCE: 568

Arg Ala Ser Gln Ser Val Ser Ser Tyr Leu Ala
1               5                   10

<210> SEQ ID NO 569
<211> LENGTH: 7
<212> TYPE: PRT
<213> ORGANISM: Artificial Sequence
<220> FEATURE:
<223> OTHER INFORMATION: Recombinant protein

<400> SEQUENCE: 569

Gly Gln Ser Ser Arg Thr Arg
1               5

<210> SEQ ID NO 570
<211> LENGTH: 10
<212> TYPE: PRT
<213> ORGANISM: Artificial Sequence
<220> FEATURE:
<223> OTHER INFORMATION: Recombinant protein

<400> SEQUENCE: 570

Gln Gln Tyr Gly Asp Ser Gln Leu Phe Thr
1               5                   10

<210> SEQ ID NO 571
<211> LENGTH: 120
<212> TYPE: PRT
<213> ORGANISM: Artificial Sequence
<220> FEATURE:
<223> OTHER INFORMATION: Recombinant protein

<400> SEQUENCE: 571

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
                100                 105                 110

Gly Thr Leu Val Thr Val Ser Ser
            115                 120

<210> SEQ ID NO 572
<211> LENGTH: 5
<212> TYPE: PRT
<213> ORGANISM: Artificial Sequence
<220> FEATURE:
<223> OTHER INFORMATION: Recombinant protein

<400> SEQUENCE: 572

Thr Ser Trp Ile Ser
1               5

<210> SEQ ID NO 573
<211> LENGTH: 17
<212> TYPE: PRT
<213> ORGANISM: Artificial Sequence
<220> FEATURE:
<223> OTHER INFORMATION: Recombinant protein

<400> SEQUENCE: 573

Met Ile Asp Pro Ser Asp Ser Tyr Thr Ser Tyr Ser Pro Ser Phe Gln
1               5                   10                  15

Gly

<210> SEQ ID NO 574
<211> LENGTH: 11
<212> TYPE: PRT
<213> ORGANISM: Artificial Sequence
<220> FEATURE:
<223> OTHER INFORMATION: Recombinant protein

<400> SEQUENCE: 574

Leu His Tyr Tyr His Ser Glu Glu Phe Asp Val
1               5                   10

<210> SEQ ID NO 575
<211> LENGTH: 109
<212> TYPE: PRT
<213> ORGANISM: Artificial Sequence
<220> FEATURE:
<223> OTHER INFORMATION: Recombinant protein

<400> SEQUENCE: 575

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Gln
                85                  90                  95

Leu Phe Thr Phe Gly Gln Gly Thr Lys Leu Glu Ile Lys
            100                 105

<210> SEQ ID NO 576
<211> LENGTH: 12
<212> TYPE: PRT
<213> ORGANISM: Artificial Sequence
<220> FEATURE:
<223> OTHER INFORMATION: Recombinant protein

<400> SEQUENCE: 576

Arg Ala Ser Gln Ser Val Ser Ser Ser Tyr Leu Ala
1               5                   10

<210> SEQ ID NO 577
<211> LENGTH: 7
<212> TYPE: PRT
<213> ORGANISM: Artificial Sequence
<220> FEATURE:

<223> OTHER INFORMATION: Recombinant protein

<400> SEQUENCE: 577

Gly Gln Ser Ser Arg Thr Arg
1               5

<210> SEQ ID NO 578
<211> LENGTH: 10
<212> TYPE: PRT
<213> ORGANISM: Artificial Sequence
<220> FEATURE:
<223> OTHER INFORMATION: Recombinant protein

<400> SEQUENCE: 578

Gln Gln Tyr Gly Asp Ser Gln Leu Phe Thr
1               5                   10

<210> SEQ ID NO 579
<211> LENGTH: 120
<212> TYPE: PRT
<213> ORGANISM: Artificial Sequence
<220> FEATURE:
<223> OTHER INFORMATION: Recombinant protein

<400> SEQUENCE: 579

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 580
<211> LENGTH: 5
<212> TYPE: PRT
<213> ORGANISM: Artificial Sequence
<220> FEATURE:
<223> OTHER INFORMATION: Recombinant protein

<400> SEQUENCE: 580

Thr Ser Trp Ile Ser
1               5

<210> SEQ ID NO 581
<211> LENGTH: 17
<212> TYPE: PRT
<213> ORGANISM: Artificial Sequence
<220> FEATURE:
<223> OTHER INFORMATION: Recombinant protein

<400> SEQUENCE: 581

Met Ile Asp Pro Ser Asp Ser Tyr Thr Ser Tyr Ser Pro Ser Phe Gln
1               5                   10                  15

Gly

```
<210> SEQ ID NO 582
<211> LENGTH: 11
<212> TYPE: PRT
<213> ORGANISM: Artificial Sequence
<220> FEATURE:
<223> OTHER INFORMATION: Recombinant protein

<400> SEQUENCE: 582

Leu His Tyr Tyr His Ser Glu Glu Phe Asp Val
1               5                   10

<210> SEQ ID NO 583
<211> LENGTH: 109
<212> TYPE: PRT
<213> ORGANISM: Artificial Sequence
<220> FEATURE:
<223> OTHER INFORMATION: Recombinant protein

<400> SEQUENCE: 583

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Gln
                85                  90                  95

Leu Phe Thr Phe Gly Gln Gly Thr Lys Leu Glu Ile Lys
            100                 105

<210> SEQ ID NO 584
<211> LENGTH: 12
<212> TYPE: PRT
<213> ORGANISM: Artificial Sequence
<220> FEATURE:
<223> OTHER INFORMATION: Recombinant protein

<400> SEQUENCE: 584

Arg Ala Ser Gln Ser Val Ser Ser Ser Tyr Leu Ala
1               5                   10

<210> SEQ ID NO 585
<211> LENGTH: 7
<212> TYPE: PRT
<213> ORGANISM: Artificial Sequence
<220> FEATURE:
<223> OTHER INFORMATION: Recombinant protein

<400> SEQUENCE: 585

Gly Gln Ser Ser Arg Thr Arg
1               5

<210> SEQ ID NO 586
<211> LENGTH: 10
<212> TYPE: PRT
<213> ORGANISM: Artificial Sequence
<220> FEATURE:
```

<223> OTHER INFORMATION: Recombinant protein

<400> SEQUENCE: 586

Gln Gln Tyr Gly Asp Ser Gln Leu Phe Thr
1               5                   10

<210> SEQ ID NO 587
<211> LENGTH: 120
<212> TYPE: PRT
<213> ORGANISM: Artificial Sequence
<220> FEATURE:
<223> OTHER INFORMATION: Recombinant protein

<400> SEQUENCE: 587

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 588
<211> LENGTH: 5
<212> TYPE: PRT
<213> ORGANISM: Artificial Sequence
<220> FEATURE:
<223> OTHER INFORMATION: Recombinant protein

<400> SEQUENCE: 588

Thr Ser Trp Ile Val
1               5

<210> SEQ ID NO 589
<211> LENGTH: 17
<212> TYPE: PRT
<213> ORGANISM: Artificial Sequence
<220> FEATURE:
<223> OTHER INFORMATION: Recombinant protein

<400> SEQUENCE: 589

Met Ile Asp Pro Ser Asp Ser Tyr Thr Ser Tyr Ser Pro Ser Phe Gln
1               5                   10                  15

Gly

<210> SEQ ID NO 590
<211> LENGTH: 11
<212> TYPE: PRT
<213> ORGANISM: Artificial Sequence
<220> FEATURE:
<223> OTHER INFORMATION: Recombinant protein

<400> SEQUENCE: 590

```
Leu His Tyr Tyr Asn Ser Glu Glu Phe Asp Val
 1               5                  10
```

<210> SEQ ID NO 591
<211> LENGTH: 109
<212> TYPE: PRT
<213> ORGANISM: Artificial Sequence
<220> FEATURE:
<223> OTHER INFORMATION: Recombinant protein

<400> SEQUENCE: 591

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Asp Ser Gln
                85                  90                  95

Leu Phe Thr Phe Gly Gln Gly Thr Lys Leu Glu Ile Lys
            100                 105
```

<210> SEQ ID NO 592
<211> LENGTH: 12
<212> TYPE: PRT
<213> ORGANISM: Artificial Sequence
<220> FEATURE:
<223> OTHER INFORMATION: Recombinant protein

<400> SEQUENCE: 592

```
Arg Ala Ser Gln Ser Val Ser Ser Ser Tyr Leu Ala
 1               5                  10
```

<210> SEQ ID NO 593
<211> LENGTH: 7
<212> TYPE: PRT
<213> ORGANISM: Artificial Sequence
<220> FEATURE:
<223> OTHER INFORMATION: Recombinant protein

<400> SEQUENCE: 593

```
Gly Gln Ser Ser Arg Thr Arg
 1               5
```

<210> SEQ ID NO 594
<211> LENGTH: 10
<212> TYPE: PRT
<213> ORGANISM: Artificial Sequence
<220> FEATURE:
<223> OTHER INFORMATION: Recombinant protein

<400> SEQUENCE: 594

```
Gln Gln Tyr Gly Asp Ser Gln Leu Phe Thr
 1               5                  10
```

<210> SEQ ID NO 595
<211> LENGTH: 120
<212> TYPE: PRT
<213> ORGANISM: Artificial Sequence
<220> FEATURE:

<223> OTHER INFORMATION: Recombinant protein

<400> SEQUENCE: 595

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 596
<211> LENGTH: 5
<212> TYPE: PRT
<213> ORGANISM: Artificial Sequence
<220> FEATURE:
<223> OTHER INFORMATION: Recombinant protein

<400> SEQUENCE: 596

Thr Ser Trp Ile Val
1               5

<210> SEQ ID NO 597
<211> LENGTH: 17
<212> TYPE: PRT
<213> ORGANISM: Artificial Sequence
<220> FEATURE:
<223> OTHER INFORMATION: Recombinant protein

<400> SEQUENCE: 597

Met Ile Asp Pro Ser Asp Ser Phe Thr Ser Tyr Ser Pro Ser Phe Gln
1               5                   10                  15

Gly

<210> SEQ ID NO 598
<211> LENGTH: 11
<212> TYPE: PRT
<213> ORGANISM: Artificial Sequence
<220> FEATURE:
<223> OTHER INFORMATION: Recombinant protein

<400> SEQUENCE: 598

Leu His Tyr Tyr Asn Ser Glu Glu Phe Asp Val
1               5                   10

<210> SEQ ID NO 599
<211> LENGTH: 109
<212> TYPE: PRT
<213> ORGANISM: Artificial Sequence
<220> FEATURE:
<223> OTHER INFORMATION: Recombinant protein

<400> SEQUENCE: 599

-continued

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Arg
                85                  90                  95

Leu Phe Thr Phe Gly Gln Gly Thr Lys Leu Glu Ile Lys
            100                 105

<210> SEQ ID NO 600
<211> LENGTH: 12
<212> TYPE: PRT
<213> ORGANISM: Artificial Sequence
<220> FEATURE:
<223> OTHER INFORMATION: Recombinant protein

<400> SEQUENCE: 600

Arg Ala Ser Gln Ser Val Ser Ser Ser Tyr Leu Ala
1               5                   10

<210> SEQ ID NO 601
<211> LENGTH: 7
<212> TYPE: PRT
<213> ORGANISM: Artificial Sequence
<220> FEATURE:
<223> OTHER INFORMATION: Recombinant protein

<400> SEQUENCE: 601

Gly Ala Ser Ser Arg Ala Arg
1               5

<210> SEQ ID NO 602
<211> LENGTH: 10
<212> TYPE: PRT
<213> ORGANISM: Artificial Sequence
<220> FEATURE:
<223> OTHER INFORMATION: Recombinant protein

<400> SEQUENCE: 602

Gln Gln Tyr Gly Asp Ser Arg Leu Phe Thr
1               5                   10

<210> SEQ ID NO 603
<211> LENGTH: 120
<212> TYPE: PRT
<213> ORGANISM: Artificial Sequence
<220> FEATURE:
<223> OTHER INFORMATION: Recombinant protein

<400> SEQUENCE: 603

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

```
Gly Met Ile Asp Pro Ser Asp Ser Tyr Thr Ser Tyr Ser Pro Ser Phe
    50              55                  60
Gln Gly His Val Thr Ile Ser Ala Asp Lys Ser Ile Ser Thr Ala Tyr
65              70                  75                  80
Leu Gln Trp Ser Ser Leu Lys Ala Ser Asp Thr Ala Met Tyr Tyr Cys
                85                  90                  95
Ala Arg Leu His Tyr Tyr Asn Ser Glu Glu Phe Asp Val Trp Gly Gln
                100                 105                 110
Gly Thr Met Val Thr Val Ser Ser
            115                 120

<210> SEQ ID NO 604
<211> LENGTH: 5
<212> TYPE: PRT
<213> ORGANISM: Artificial Sequence
<220> FEATURE:
<223> OTHER INFORMATION: Recombinant protein

<400> SEQUENCE: 604

Thr Ser Trp Ile Ser
1               5

<210> SEQ ID NO 605
<211> LENGTH: 17
<212> TYPE: PRT
<213> ORGANISM: Artificial Sequence
<220> FEATURE:
<223> OTHER INFORMATION: Recombinant protein

<400> SEQUENCE: 605

Met Ile Asp Pro Ser Asp Ser Tyr Thr Ser Tyr Ser Pro Ser Phe Gln
1               5                   10                  15
Gly

<210> SEQ ID NO 606
<211> LENGTH: 11
<212> TYPE: PRT
<213> ORGANISM: Artificial Sequence
<220> FEATURE:
<223> OTHER INFORMATION: Recombinant protein

<400> SEQUENCE: 606

Leu His Tyr Tyr Asn Ser Glu Glu Phe Asp Val
1               5                   10

<210> SEQ ID NO 607
<211> LENGTH: 109
<212> TYPE: PRT
<213> ORGANISM: Artificial Sequence
<220> FEATURE:
<223> OTHER INFORMATION: Recombinant protein

<400> SEQUENCE: 607

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Arg Gly Ile Pro Asp Arg Phe Ser
    50                  55                  60
Gly Ser Gly Ser Gly Thr Asp Phe Thr Leu Thr Ile Ser Arg Leu Glu
```

```
                    65                  70                  75                  80
Pro Glu Asp Phe Ala Val Tyr Tyr Cys Gln Gln Tyr Gly Asp Ser Arg
                    85                  90                  95

Leu Phe Thr Phe Gly Gln Gly Thr Lys Leu Glu Ile Lys
                100                 105
```

<210> SEQ ID NO 608
<211> LENGTH: 12
<212> TYPE: PRT
<213> ORGANISM: Artificial Sequence
<220> FEATURE:
<223> OTHER INFORMATION: Recombinant protein

<400> SEQUENCE: 608

```
Arg Ala Ser Gln Ser Val Ser Ser Ser Tyr Leu Ala
1               5                   10
```

<210> SEQ ID NO 609
<211> LENGTH: 7
<212> TYPE: PRT
<213> ORGANISM: Artificial Sequence
<220> FEATURE:
<223> OTHER INFORMATION: Recombinant protein

<400> SEQUENCE: 609

```
Gly Ala Ser Ser Arg Ala Arg
1               5
```

<210> SEQ ID NO 610
<211> LENGTH: 10
<212> TYPE: PRT
<213> ORGANISM: Artificial Sequence
<220> FEATURE:
<223> OTHER INFORMATION: Recombinant protein

<400> SEQUENCE: 610

```
Gln Gln Tyr Gly Asp Ser Arg Leu Phe Thr
1               5                   10
```

<210> SEQ ID NO 611
<211> LENGTH: 120
<212> TYPE: PRT
<213> ORGANISM: Artificial Sequence
<220> FEATURE:
<223> OTHER INFORMATION: Recombinant protein

<400> SEQUENCE: 611

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Phe Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
                100                 105                 110

Gly Thr Met Val Thr Val Ser Ser
```

```
<210> SEQ ID NO 612
<211> LENGTH: 5
<212> TYPE: PRT
<213> ORGANISM: Artificial Sequence
<220> FEATURE:
<223> OTHER INFORMATION: Recombinant protein

<400> SEQUENCE: 612

Thr Ser Trp Ile Ser
1               5

<210> SEQ ID NO 613
<211> LENGTH: 17
<212> TYPE: PRT
<213> ORGANISM: Artificial Sequence
<220> FEATURE:
<223> OTHER INFORMATION: Recombinant protein

<400> SEQUENCE: 613

Met Ile Asp Pro Ser Asp Ser Phe Thr Ser Tyr Ser Pro Ser Phe Gln
1               5                   10                  15

Gly

<210> SEQ ID NO 614
<211> LENGTH: 11
<212> TYPE: PRT
<213> ORGANISM: Artificial Sequence
<220> FEATURE:
<223> OTHER INFORMATION: Recombinant protein

<400> SEQUENCE: 614

Leu His Tyr Tyr His Ser Glu Glu Phe Asp Val
1               5                   10

<210> SEQ ID NO 615
<211> LENGTH: 109
<212> TYPE: PRT
<213> ORGANISM: Artificial Sequence
<220> FEATURE:
<223> OTHER INFORMATION: Recombinant protein

<400> SEQUENCE: 615

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Arg
                85                  90                  95

Leu Phe Thr Phe Gly Gln Gly Thr Lys Leu Glu Ile Lys
            100                 105

<210> SEQ ID NO 616
<211> LENGTH: 12
<212> TYPE: PRT
<213> ORGANISM: Artificial Sequence
```

```
<220> FEATURE:
<223> OTHER INFORMATION: Recombinant protein

<400> SEQUENCE: 616

Arg Ala Ser Gln Ser Val Ser Ser Tyr Leu Ala
1               5                   10

<210> SEQ ID NO 617
<211> LENGTH: 7
<212> TYPE: PRT
<213> ORGANISM: Artificial Sequence
<220> FEATURE:
<223> OTHER INFORMATION: Recombinant protein

<400> SEQUENCE: 617

Gly Ala Ser Ser Arg Ala Arg
1               5

<210> SEQ ID NO 618
<211> LENGTH: 10
<212> TYPE: PRT
<213> ORGANISM: Artificial Sequence
<220> FEATURE:
<223> OTHER INFORMATION: Recombinant protein

<400> SEQUENCE: 618

Gln Gln Tyr Gly Asp Ser Arg Leu Phe Thr
1               5                   10

<210> SEQ ID NO 619
<211> LENGTH: 120
<212> TYPE: PRT
<213> ORGANISM: Artificial Sequence
<220> FEATURE:
<223> OTHER INFORMATION: Recombinant protein

<400> SEQUENCE: 619

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 620
<211> LENGTH: 5
<212> TYPE: PRT
<213> ORGANISM: Artificial Sequence
<220> FEATURE:
<223> OTHER INFORMATION: Recombinant protein

<400> SEQUENCE: 620

Thr Ser Trp Ile Ser
```

```
<210> SEQ ID NO 621
<211> LENGTH: 17
<212> TYPE: PRT
<213> ORGANISM: Artificial Sequence
<220> FEATURE:
<223> OTHER INFORMATION: Recombinant protein

<400> SEQUENCE: 621

Met Ile Asp Pro Ser Asp Ser Tyr Thr Ser Tyr Ser Pro Ser Phe Gln
1               5                   10                  15
Gly

<210> SEQ ID NO 622
<211> LENGTH: 11
<212> TYPE: PRT
<213> ORGANISM: Artificial Sequence
<220> FEATURE:
<223> OTHER INFORMATION: Recombinant protein

<400> SEQUENCE: 622

Leu His Tyr Tyr His Ser Glu Glu Phe Asp Val
1               5                   10

<210> SEQ ID NO 623
<211> LENGTH: 109
<212> TYPE: PRT
<213> ORGANISM: Artificial Sequence
<220> FEATURE:
<223> OTHER INFORMATION: Recombinant protein

<400> SEQUENCE: 623

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Arg
                85                  90                  95

Leu Phe Thr Phe Gly Gln Gly Thr Lys Leu Glu Ile Lys
            100                 105

<210> SEQ ID NO 624
<211> LENGTH: 12
<212> TYPE: PRT
<213> ORGANISM: Artificial Sequence
<220> FEATURE:
<223> OTHER INFORMATION: Recombinant protein

<400> SEQUENCE: 624

Arg Ala Ser Gln Ser Val Ser Ser Ser Tyr Leu Ala
1               5                   10

<210> SEQ ID NO 625
<211> LENGTH: 7
<212> TYPE: PRT
<213> ORGANISM: Artificial Sequence
```

<220> FEATURE:
<223> OTHER INFORMATION: Recombinant protein

<400> SEQUENCE: 625

Gly Ala Ser Ser Arg Ala Arg
1               5

<210> SEQ ID NO 626
<211> LENGTH: 10
<212> TYPE: PRT
<213> ORGANISM: Artificial Sequence
<220> FEATURE:
<223> OTHER INFORMATION: Recombinant protein

<400> SEQUENCE: 626

Gln Gln Tyr Gly Asp Ser Arg Leu Phe Thr
1               5                   10

<210> SEQ ID NO 627
<211> LENGTH: 120
<212> TYPE: PRT
<213> ORGANISM: Artificial Sequence
<220> FEATURE:
<223> OTHER INFORMATION: Recombinant protein

<400> SEQUENCE: 627

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
                100                 105                 110

Gly Thr Met Val Thr Val Ser Ser
        115                 120

<210> SEQ ID NO 628
<211> LENGTH: 5
<212> TYPE: PRT
<213> ORGANISM: Artificial Sequence
<220> FEATURE:
<223> OTHER INFORMATION: Recombinant protein

<400> SEQUENCE: 628

Thr Ser Trp Ile Ser
1               5

<210> SEQ ID NO 629
<211> LENGTH: 17
<212> TYPE: PRT
<213> ORGANISM: Artificial Sequence
<220> FEATURE:
<223> OTHER INFORMATION: Recombinant protein

<400> SEQUENCE: 629

Met Ile Asp Pro Ser Asp Ser Tyr Thr Ser Tyr Ser Pro Ser Phe Gln

```
1               5                   10                  15
Gly

<210> SEQ ID NO 630
<211> LENGTH: 11
<212> TYPE: PRT
<213> ORGANISM: Artificial Sequence
<220> FEATURE:
<223> OTHER INFORMATION: Recombinant protein

<400> SEQUENCE: 630

Leu His Tyr Tyr His Ser Glu Glu Phe Asp Val
1               5                   10

<210> SEQ ID NO 631
<211> LENGTH: 109
<212> TYPE: PRT
<213> ORGANISM: Artificial Sequence
<220> FEATURE:
<223> OTHER INFORMATION: Recombinant protein

<400> SEQUENCE: 631

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Arg
                85                  90                  95

Leu Phe Thr Phe Gly Gln Gly Thr Lys Leu Glu Ile Lys
            100                 105

<210> SEQ ID NO 632
<211> LENGTH: 12
<212> TYPE: PRT
<213> ORGANISM: Artificial Sequence
<220> FEATURE:
<223> OTHER INFORMATION: Recombinant protein

<400> SEQUENCE: 632

Arg Ala Ser Gln Ser Val Ser Ser Ser Tyr Leu Ala
1               5                   10

<210> SEQ ID NO 633
<211> LENGTH: 7
<212> TYPE: PRT
<213> ORGANISM: Artificial Sequence
<220> FEATURE:
<223> OTHER INFORMATION: Recombinant protein

<400> SEQUENCE: 633

Gly Ala Ser Ser Arg Ala Arg
1               5

<210> SEQ ID NO 634
<211> LENGTH: 10
<212> TYPE: PRT
<213> ORGANISM: Artificial Sequence
```

```
<220> FEATURE:
<223> OTHER INFORMATION: Recombinant protein

<400> SEQUENCE: 634

Gln Gln Tyr Gly Asp Ser Arg Leu Phe Thr
1               5                   10

<210> SEQ ID NO 635
<211> LENGTH: 120
<212> TYPE: PRT
<213> ORGANISM: Artificial Sequence
<220> FEATURE:
<223> OTHER INFORMATION: Recombinant protein

<400> SEQUENCE: 635

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 636
<211> LENGTH: 5
<212> TYPE: PRT
<213> ORGANISM: Artificial Sequence
<220> FEATURE:
<223> OTHER INFORMATION: Recombinant protein

<400> SEQUENCE: 636

Thr Ser Trp Ile Ser
1               5

<210> SEQ ID NO 637
<211> LENGTH: 17
<212> TYPE: PRT
<213> ORGANISM: Artificial Sequence
<220> FEATURE:
<223> OTHER INFORMATION: Recombinant protein

<400> SEQUENCE: 637

Met Ile Asp Pro Ser Asp Ser Phe Thr Ser Tyr Ser Pro Ser Phe Gln
1               5                   10                  15

Gly

<210> SEQ ID NO 638
<211> LENGTH: 11
<212> TYPE: PRT
<213> ORGANISM: Artificial Sequence
<220> FEATURE:
<223> OTHER INFORMATION: Recombinant protein

<400> SEQUENCE: 638
```

Leu His Tyr Tyr Asn Ser Glu Glu Phe Asp Val
1               5                   10

<210> SEQ ID NO 639
<211> LENGTH: 109
<212> TYPE: PRT
<213> ORGANISM: Artificial Sequence
<220> FEATURE:
<223> OTHER INFORMATION: Recombinant protein

<400> SEQUENCE: 639

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Arg
                85                  90                  95

Leu Phe Thr Phe Gly Gln Gly Thr Lys Leu Glu Ile Lys
            100                 105

<210> SEQ ID NO 640
<211> LENGTH: 12
<212> TYPE: PRT
<213> ORGANISM: Artificial Sequence
<220> FEATURE:
<223> OTHER INFORMATION: Recombinant protein

<400> SEQUENCE: 640

Arg Ala Ser Gln Ser Val Ser Ser Ser Tyr Leu Ala
1               5                   10

<210> SEQ ID NO 641
<211> LENGTH: 7
<212> TYPE: PRT
<213> ORGANISM: Artificial Sequence
<220> FEATURE:
<223> OTHER INFORMATION: Recombinant protein

<400> SEQUENCE: 641

Gly Ala Ser Ser Arg Ala Arg
1               5

<210> SEQ ID NO 642
<211> LENGTH: 10
<212> TYPE: PRT
<213> ORGANISM: Artificial Sequence
<220> FEATURE:
<223> OTHER INFORMATION: Recombinant protein

<400> SEQUENCE: 642

Gln Gln Tyr Gly Asp Ser Arg Leu Phe Thr
1               5                   10

<210> SEQ ID NO 643
<211> LENGTH: 120
<212> TYPE: PRT
<213> ORGANISM: Artificial Sequence
<220> FEATURE:
<223> OTHER INFORMATION: Recombinant protein

<400> SEQUENCE: 643

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 644
<211> LENGTH: 5
<212> TYPE: PRT
<213> ORGANISM: Artificial Sequence
<220> FEATURE:
<223> OTHER INFORMATION: Recombinant protein

<400> SEQUENCE: 644

Thr Ser Trp Ile Val
1               5

<210> SEQ ID NO 645
<211> LENGTH: 17
<212> TYPE: PRT
<213> ORGANISM: Artificial Sequence
<220> FEATURE:
<223> OTHER INFORMATION: Recombinant protein

<400> SEQUENCE: 645

Met Ile Asp Pro Ser Asp Ser Tyr Thr Ser Tyr Ser Pro Ser Phe Gln
1               5                   10                  15

Gly

<210> SEQ ID NO 646
<211> LENGTH: 11
<212> TYPE: PRT
<213> ORGANISM: Artificial Sequence
<220> FEATURE:
<223> OTHER INFORMATION: Recombinant protein

<400> SEQUENCE: 646

Leu His Tyr Tyr Asn Ser Glu Glu Phe Asp Val
1               5                   10

<210> SEQ ID NO 647
<211> LENGTH: 109
<212> TYPE: PRT
<213> ORGANISM: Artificial Sequence
<220> FEATURE:
<223> OTHER INFORMATION: Recombinant protein

<400> SEQUENCE: 647

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Arg
                85                  90                  95

Leu Phe Thr Phe Gly Gln Gly Thr Lys Leu Glu Ile Lys
                100                 105
```

<210> SEQ ID NO 648
<211> LENGTH: 12
<212> TYPE: PRT
<213> ORGANISM: Artificial Sequence
<220> FEATURE:
<223> OTHER INFORMATION: Recombinant protein

<400> SEQUENCE: 648

```
Arg Ala Ser Gln Ser Val Ser Ser Ser Tyr Leu Ala
1               5                   10
```

<210> SEQ ID NO 649
<211> LENGTH: 7
<212> TYPE: PRT
<213> ORGANISM: Artificial Sequence
<220> FEATURE:
<223> OTHER INFORMATION: Recombinant protein

<400> SEQUENCE: 649

```
Gly Ala Ser Ser Arg Ala Arg
1               5
```

<210> SEQ ID NO 650
<211> LENGTH: 10
<212> TYPE: PRT
<213> ORGANISM: Artificial Sequence
<220> FEATURE:
<223> OTHER INFORMATION: Recombinant protein

<400> SEQUENCE: 650

```
Gln Gln Tyr Gly Asp Ser Arg Leu Phe Thr
1               5                   10
```

<210> SEQ ID NO 651
<211> LENGTH: 120
<212> TYPE: PRT
<213> ORGANISM: Artificial Sequence
<220> FEATURE:
<223> OTHER INFORMATION: Recombinant protein

<400> SEQUENCE: 651

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
            35                  40                  45
```

```
Gly Met Ile Asp Pro Ser Asp Ser Phe Thr Ser Tyr Ser Pro Ser Phe
        50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
            115                 120

<210> SEQ ID NO 652
<211> LENGTH: 5
<212> TYPE: PRT
<213> ORGANISM: Artificial Sequence
<220> FEATURE:
<223> OTHER INFORMATION: Recombinant protein

<400> SEQUENCE: 652

Thr Ser Trp Ile Val
1               5

<210> SEQ ID NO 653
<211> LENGTH: 17
<212> TYPE: PRT
<213> ORGANISM: Artificial Sequence
<220> FEATURE:
<223> OTHER INFORMATION: Recombinant protein

<400> SEQUENCE: 653

Met Ile Asp Pro Ser Asp Ser Phe Thr Ser Tyr Ser Pro Ser Phe Gln
1               5                   10                  15

Gly

<210> SEQ ID NO 654
<211> LENGTH: 11
<212> TYPE: PRT
<213> ORGANISM: Artificial Sequence
<220> FEATURE:
<223> OTHER INFORMATION: Recombinant protein

<400> SEQUENCE: 654

Leu His Tyr Tyr Asn Ser Glu Glu Phe Asp Val
1               5                   10

<210> SEQ ID NO 655
<211> LENGTH: 109
<212> TYPE: PRT
<213> ORGANISM: Artificial Sequence
<220> FEATURE:
<223> OTHER INFORMATION: Recombinant protein

<400> SEQUENCE: 655

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Arg
                85                  90                  95

Leu Phe Thr Phe Gly Gln Gly Thr Lys Leu Glu Ile Lys
            100                 105

<210> SEQ ID NO 656
<211> LENGTH: 12
<212> TYPE: PRT
<213> ORGANISM: Artificial Sequence
<220> FEATURE:
<223> OTHER INFORMATION: Recombinant protein

<400> SEQUENCE: 656

Arg Ala Ser Gln Ser Val Ser Ser Ser Tyr Leu Ala
1               5                   10

<210> SEQ ID NO 657
<211> LENGTH: 7
<212> TYPE: PRT
<213> ORGANISM: Artificial Sequence
<220> FEATURE:
<223> OTHER INFORMATION: Recombinant protein

<400> SEQUENCE: 657

Gly Gln Ser Ser Arg Thr Arg
1               5

<210> SEQ ID NO 658
<211> LENGTH: 10
<212> TYPE: PRT
<213> ORGANISM: Artificial Sequence
<220> FEATURE:
<223> OTHER INFORMATION: Recombinant protein

<400> SEQUENCE: 658

Gln Gln Phe Gly Asp Ser Arg Leu Phe Thr
1               5                   10

<210> SEQ ID NO 659
<211> LENGTH: 120
<212> TYPE: PRT
<213> ORGANISM: Artificial Sequence
<220> FEATURE:
<223> OTHER INFORMATION: Recombinant protein

<400> SEQUENCE: 659

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
                100                 105                 110

Gly Thr Met Val Thr Val Ser Ser
        115                 120

<210> SEQ ID NO 660
<211> LENGTH: 5
<212> TYPE: PRT
<213> ORGANISM: Artificial Sequence
<220> FEATURE:
<223> OTHER INFORMATION: Recombinant protein

<400> SEQUENCE: 660

Thr Ser Trp Ile Ser
1               5

<210> SEQ ID NO 661
<211> LENGTH: 17
<212> TYPE: PRT
<213> ORGANISM: Artificial Sequence
<220> FEATURE:
<223> OTHER INFORMATION: Recombinant protein

<400> SEQUENCE: 661

Met Ile Asp Pro Ser Asp Ser Tyr Thr Ser Tyr Ser Pro Ser Phe Gln
1               5                   10                  15

Gly

<210> SEQ ID NO 662
<211> LENGTH: 11
<212> TYPE: PRT
<213> ORGANISM: Artificial Sequence
<220> FEATURE:
<223> OTHER INFORMATION: Recombinant protein

<400> SEQUENCE: 662

Leu His Tyr Tyr Asn Ser Glu Glu Phe Asp Val
1               5                   10

<210> SEQ ID NO 663
<211> LENGTH: 109
<212> TYPE: PRT
<213> ORGANISM: Artificial Sequence
<220> FEATURE:
<223> OTHER INFORMATION: Recombinant protein

<400> SEQUENCE: 663

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Arg
                85                  90                  95

Leu Phe Thr Phe Gly Gln Gly Thr Lys Leu Glu Ile Lys
            100                 105

<210> SEQ ID NO 664
<211> LENGTH: 12
<212> TYPE: PRT

```
<213> ORGANISM: Artificial Sequence
<220> FEATURE:
<223> OTHER INFORMATION: Recombinant protein

<400> SEQUENCE: 664

Arg Ala Ser Gln Ser Val Ser Ser Tyr Leu Ala
1               5                   10

<210> SEQ ID NO 665
<211> LENGTH: 7
<212> TYPE: PRT
<213> ORGANISM: Artificial Sequence
<220> FEATURE:
<223> OTHER INFORMATION: Recombinant protein

<400> SEQUENCE: 665

Gly Gln Ser Ser Arg Thr Arg
1               5

<210> SEQ ID NO 666
<211> LENGTH: 10
<212> TYPE: PRT
<213> ORGANISM: Artificial Sequence
<220> FEATURE:
<223> OTHER INFORMATION: Recombinant protein

<400> SEQUENCE: 666

Gln Gln Phe Gly Asp Ser Arg Leu Phe Thr
1               5                   10

<210> SEQ ID NO 667
<211> LENGTH: 120
<212> TYPE: PRT
<213> ORGANISM: Artificial Sequence
<220> FEATURE:
<223> OTHER INFORMATION: Recombinant protein

<400> SEQUENCE: 667

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 668
<211> LENGTH: 5
<212> TYPE: PRT
<213> ORGANISM: Artificial Sequence
<220> FEATURE:
<223> OTHER INFORMATION: Recombinant protein

<400> SEQUENCE: 668
```

```
Thr Ser Trp Ile Ser
1               5

<210> SEQ ID NO 669
<211> LENGTH: 17
<212> TYPE: PRT
<213> ORGANISM: Artificial Sequence
<220> FEATURE:
<223> OTHER INFORMATION: Recombinant protein

<400> SEQUENCE: 669

Met Ile Asp Pro Ser Asp Ser Phe Thr Ser Tyr Ser Pro Ser Phe Gln
1               5                   10                  15

Gly

<210> SEQ ID NO 670
<211> LENGTH: 11
<212> TYPE: PRT
<213> ORGANISM: Artificial Sequence
<220> FEATURE:
<223> OTHER INFORMATION: Recombinant protein

<400> SEQUENCE: 670

Leu His Tyr Tyr His Ser Glu Glu Phe Asp Val
1               5                   10

<210> SEQ ID NO 671
<211> LENGTH: 109
<212> TYPE: PRT
<213> ORGANISM: Artificial Sequence
<220> FEATURE:
<223> OTHER INFORMATION: Recombinant protein

<400> SEQUENCE: 671

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Arg
                85                  90                  95

Leu Phe Thr Phe Gly Gln Gly Thr Lys Leu Glu Ile Lys
            100                 105

<210> SEQ ID NO 672
<211> LENGTH: 12
<212> TYPE: PRT
<213> ORGANISM: Artificial Sequence
<220> FEATURE:
<223> OTHER INFORMATION: Recombinant protein

<400> SEQUENCE: 672

Arg Ala Ser Gln Ser Val Ser Ser Ser Tyr Leu Ala
1               5                   10

<210> SEQ ID NO 673
<211> LENGTH: 7
<212> TYPE: PRT
```

<213> ORGANISM: Artificial Sequence
<220> FEATURE:
<223> OTHER INFORMATION: Recombinant protein

<400> SEQUENCE: 673

Gly Gln Ser Ser Arg Thr Arg
1               5

<210> SEQ ID NO 674
<211> LENGTH: 10
<212> TYPE: PRT
<213> ORGANISM: Artificial Sequence
<220> FEATURE:
<223> OTHER INFORMATION: Recombinant protein

<400> SEQUENCE: 674

Gln Gln Phe Gly Asp Ser Arg Leu Phe Thr
1               5                   10

<210> SEQ ID NO 675
<211> LENGTH: 120
<212> TYPE: PRT
<213> ORGANISM: Artificial Sequence
<220> FEATURE:
<223> OTHER INFORMATION: Recombinant protein

<400> SEQUENCE: 675

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 676
<211> LENGTH: 5
<212> TYPE: PRT
<213> ORGANISM: Artificial Sequence
<220> FEATURE:
<223> OTHER INFORMATION: Recombinant protein

<400> SEQUENCE: 676

Thr Ser Trp Ile Ser
1               5

<210> SEQ ID NO 677
<211> LENGTH: 17
<212> TYPE: PRT
<213> ORGANISM: Artificial Sequence
<220> FEATURE:
<223> OTHER INFORMATION: Recombinant protein

<400> SEQUENCE: 677

```
Met Ile Asp Pro Ser Asp Ser Tyr Thr Ser Tyr Ser Pro Ser Phe Gln
1               5                   10                  15

Gly
```

<210> SEQ ID NO 678
<211> LENGTH: 11
<212> TYPE: PRT
<213> ORGANISM: Artificial Sequence
<220> FEATURE:
<223> OTHER INFORMATION: Recombinant protein

<400> SEQUENCE: 678

```
Leu His Tyr Tyr His Ser Glu Glu Phe Asp Val
1               5                   10
```

<210> SEQ ID NO 679
<211> LENGTH: 109
<212> TYPE: PRT
<213> ORGANISM: Artificial Sequence
<220> FEATURE:
<223> OTHER INFORMATION: Recombinant protein

<400> SEQUENCE: 679

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Arg
                85                  90                  95

Leu Phe Thr Phe Gly Gln Gly Thr Lys Leu Glu Ile Lys
            100                 105
```

<210> SEQ ID NO 680
<211> LENGTH: 12
<212> TYPE: PRT
<213> ORGANISM: Artificial Sequence
<220> FEATURE:
<223> OTHER INFORMATION: Recombinant protein

<400> SEQUENCE: 680

```
Arg Ala Ser Gln Ser Val Ser Ser Ser Tyr Leu Ala
1               5                   10
```

<210> SEQ ID NO 681
<211> LENGTH: 7
<212> TYPE: PRT
<213> ORGANISM: Artificial Sequence
<220> FEATURE:
<223> OTHER INFORMATION: Recombinant protein

<400> SEQUENCE: 681

```
Gly Gln Ser Ser Arg Thr Arg
1               5
```

<210> SEQ ID NO 682
<211> LENGTH: 10
<212> TYPE: PRT

<213> ORGANISM: Artificial Sequence
<220> FEATURE:
<223> OTHER INFORMATION: Recombinant protein

<400> SEQUENCE: 682

Gln Gln Phe Gly Asp Ser Arg Leu Phe Thr
1               5                   10

<210> SEQ ID NO 683
<211> LENGTH: 120
<212> TYPE: PRT
<213> ORGANISM: Artificial Sequence
<220> FEATURE:
<223> OTHER INFORMATION: Recombinant protein

<400> SEQUENCE: 683

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 684
<211> LENGTH: 5
<212> TYPE: PRT
<213> ORGANISM: Artificial Sequence
<220> FEATURE:
<223> OTHER INFORMATION: Recombinant protein

<400> SEQUENCE: 684

Thr Ser Trp Ile Ser
1               5

<210> SEQ ID NO 685
<211> LENGTH: 17
<212> TYPE: PRT
<213> ORGANISM: Artificial Sequence
<220> FEATURE:
<223> OTHER INFORMATION: Recombinant protein

<400> SEQUENCE: 685

Met Ile Asp Pro Ser Asp Ser Tyr Thr Ser Tyr Ser Pro Ser Phe Gln
1               5                   10                  15

Gly

<210> SEQ ID NO 686
<211> LENGTH: 11
<212> TYPE: PRT
<213> ORGANISM: Artificial Sequence
<220> FEATURE:
<223> OTHER INFORMATION: Recombinant protein

```
<400> SEQUENCE: 686

Leu His Tyr Tyr His Ser Glu Glu Phe Asp Val
1               5                   10

<210> SEQ ID NO 687
<211> LENGTH: 109
<212> TYPE: PRT
<213> ORGANISM: Artificial Sequence
<220> FEATURE:
<223> OTHER INFORMATION: Recombinant protein

<400> SEQUENCE: 687

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Arg
                85                  90                  95

Leu Phe Thr Phe Gly Gln Gly Thr Lys Leu Glu Ile Lys
            100                 105

<210> SEQ ID NO 688
<211> LENGTH: 12
<212> TYPE: PRT
<213> ORGANISM: Artificial Sequence
<220> FEATURE:
<223> OTHER INFORMATION: Recombinant protein

<400> SEQUENCE: 688

Arg Ala Ser Gln Ser Val Ser Ser Ser Tyr Leu Ala
1               5                   10

<210> SEQ ID NO 689
<211> LENGTH: 7
<212> TYPE: PRT
<213> ORGANISM: Artificial Sequence
<220> FEATURE:
<223> OTHER INFORMATION: Recombinant protein

<400> SEQUENCE: 689

Gly Gln Ser Ser Arg Thr Arg
1               5

<210> SEQ ID NO 690
<211> LENGTH: 10
<212> TYPE: PRT
<213> ORGANISM: Artificial Sequence
<220> FEATURE:
<223> OTHER INFORMATION: Recombinant protein

<400> SEQUENCE: 690

Gln Gln Phe Gly Asp Ser Arg Leu Phe Thr
1               5                   10

<210> SEQ ID NO 691
<211> LENGTH: 120
<212> TYPE: PRT
```

<213> ORGANISM: Artificial Sequence
<220> FEATURE:
<223> OTHER INFORMATION: Recombinant protein

<400> SEQUENCE: 691

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 692
<211> LENGTH: 5
<212> TYPE: PRT
<213> ORGANISM: Artificial Sequence
<220> FEATURE:
<223> OTHER INFORMATION: Recombinant protein

<400> SEQUENCE: 692

Thr Ser Trp Ile Ser
1               5

<210> SEQ ID NO 693
<211> LENGTH: 17
<212> TYPE: PRT
<213> ORGANISM: Artificial Sequence
<220> FEATURE:
<223> OTHER INFORMATION: Recombinant protein

<400> SEQUENCE: 693

Met Ile Asp Pro Ser Asp Ser Phe Thr Ser Tyr Ser Pro Ser Phe Gln
1               5                   10                  15

Gly

<210> SEQ ID NO 694
<211> LENGTH: 11
<212> TYPE: PRT
<213> ORGANISM: Artificial Sequence
<220> FEATURE:
<223> OTHER INFORMATION: Recombinant protein

<400> SEQUENCE: 694

Leu His Tyr Tyr Asn Ser Glu Glu Phe Asp Val
1               5                   10

<210> SEQ ID NO 695
<211> LENGTH: 109
<212> TYPE: PRT
<213> ORGANISM: Artificial Sequence
<220> FEATURE:
<223> OTHER INFORMATION: Recombinant protein

<400> SEQUENCE: 695

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Arg
                85                  90                  95

Leu Phe Thr Phe Gly Gln Gly Thr Lys Leu Glu Ile Lys
            100                 105

<210> SEQ ID NO 696
<211> LENGTH: 12
<212> TYPE: PRT
<213> ORGANISM: Artificial Sequence
<220> FEATURE:
<223> OTHER INFORMATION: Recombinant protein

<400> SEQUENCE: 696

Arg Ala Ser Gln Ser Val Ser Ser Ser Tyr Leu Ala
1               5                   10

<210> SEQ ID NO 697
<211> LENGTH: 7
<212> TYPE: PRT
<213> ORGANISM: Artificial Sequence
<220> FEATURE:
<223> OTHER INFORMATION: Recombinant protein

<400> SEQUENCE: 697

Gly Gln Ser Ser Arg Thr Arg
1               5

<210> SEQ ID NO 698
<211> LENGTH: 10
<212> TYPE: PRT
<213> ORGANISM: Artificial Sequence
<220> FEATURE:
<223> OTHER INFORMATION: Recombinant protein

<400> SEQUENCE: 698

Gln Gln Phe Gly Asp Ser Arg Leu Phe Thr
1               5                   10

<210> SEQ ID NO 699
<211> LENGTH: 120
<212> TYPE: PRT
<213> ORGANISM: Artificial Sequence
<220> FEATURE:
<223> OTHER INFORMATION: Recombinant protein

<400> SEQUENCE: 699

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met

```
                  35                  40                  45
Gly Met Ile Asp Pro Ser Asp Ser Tyr Thr Ser Tyr Ser Pro Ser Phe
     50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr Asn Ser Glu Glu Phe Asp Val Trp Gly Gln
             100                 105                 110

Gly Thr Leu Val Thr Val Ser Ser
         115                 120

<210> SEQ ID NO 700
<211> LENGTH: 5
<212> TYPE: PRT
<213> ORGANISM: Artificial Sequence
<220> FEATURE:
<223> OTHER INFORMATION: Recombinant protein

<400> SEQUENCE: 700

Thr Ser Trp Ile Val
1               5

<210> SEQ ID NO 701
<211> LENGTH: 17
<212> TYPE: PRT
<213> ORGANISM: Artificial Sequence
<220> FEATURE:
<223> OTHER INFORMATION: Recombinant protein

<400> SEQUENCE: 701

Met Ile Asp Pro Ser Asp Ser Tyr Thr Ser Tyr Ser Pro Ser Phe Gln
1               5                   10                  15

Gly

<210> SEQ ID NO 702
<211> LENGTH: 11
<212> TYPE: PRT
<213> ORGANISM: Artificial Sequence
<220> FEATURE:
<223> OTHER INFORMATION: Recombinant protein

<400> SEQUENCE: 702

Leu His Tyr Tyr Asn Ser Glu Glu Phe Asp Val
1               5                   10

<210> SEQ ID NO 703
<211> LENGTH: 109
<212> TYPE: PRT
<213> ORGANISM: Artificial Sequence
<220> FEATURE:
<223> OTHER INFORMATION: Recombinant protein

<400> SEQUENCE: 703

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Gln Ser Ser Arg Thr Arg Gly Ile Pro Asp Arg Phe Ser
     50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ser Arg
                85                  90                  95

Leu Phe Thr Phe Gly Gln Gly Thr Lys Leu Glu Ile Lys
            100                 105

<210> SEQ ID NO 704
<211> LENGTH: 12
<212> TYPE: PRT
<213> ORGANISM: Artificial Sequence
<220> FEATURE:
<223> OTHER INFORMATION: Recombinant protein

<400> SEQUENCE: 704

Arg Ala Ser Gln Ser Val Ser Ser Ser Tyr Leu Ala
1               5                   10

<210> SEQ ID NO 705
<211> LENGTH: 7
<212> TYPE: PRT
<213> ORGANISM: Artificial Sequence
<220> FEATURE:
<223> OTHER INFORMATION: Recombinant protein

<400> SEQUENCE: 705

Gly Gln Ser Ser Arg Thr Arg
1               5

<210> SEQ ID NO 706
<211> LENGTH: 10
<212> TYPE: PRT
<213> ORGANISM: Artificial Sequence
<220> FEATURE:
<223> OTHER INFORMATION: Recombinant protein

<400> SEQUENCE: 706

Gln Gln Phe Gly Asp Ser Arg Leu Phe Thr
1               5                   10

<210> SEQ ID NO 707
<211> LENGTH: 120
<212> TYPE: PRT
<213> ORGANISM: Artificial Sequence
<220> FEATURE:
<223> OTHER INFORMATION: Recombinant protein

<400> SEQUENCE: 707

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
            35                  40                  45

Gly Met Ile Asp Pro Ser Asp Ser Phe Thr Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

```
Gly Thr Leu Val Thr Val Ser Ser
        115             120

<210> SEQ ID NO 708
<211> LENGTH: 5
<212> TYPE: PRT
<213> ORGANISM: Artificial Sequence
<220> FEATURE:
<223> OTHER INFORMATION: Recombinant protein

<400> SEQUENCE: 708

Thr Ser Trp Ile Val
1               5

<210> SEQ ID NO 709
<211> LENGTH: 17
<212> TYPE: PRT
<213> ORGANISM: Artificial Sequence
<220> FEATURE:
<223> OTHER INFORMATION: Recombinant protein

<400> SEQUENCE: 709

Met Ile Asp Pro Ser Asp Ser Phe Thr Ser Tyr Ser Pro Ser Phe Gln
1               5                   10                  15

Gly

<210> SEQ ID NO 710
<211> LENGTH: 11
<212> TYPE: PRT
<213> ORGANISM: Artificial Sequence
<220> FEATURE:
<223> OTHER INFORMATION: Recombinant protein

<400> SEQUENCE: 710

Leu His Tyr Tyr Asn Ser Glu Glu Phe Asp Val
1               5                   10

<210> SEQ ID NO 711
<211> LENGTH: 109
<212> TYPE: PRT
<213> ORGANISM: Artificial Sequence
<220> FEATURE:
<223> OTHER INFORMATION: Recombinant protein

<400> SEQUENCE: 711

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Gln
                85                  90                  95

Leu Phe Thr Phe Gly Gln Gly Thr Lys Leu Glu Ile Lys
            100                 105

<210> SEQ ID NO 712
<211> LENGTH: 12
```

```
<212> TYPE: PRT
<213> ORGANISM: Artificial Sequence
<220> FEATURE:
<223> OTHER INFORMATION: Recombinant protein

<400> SEQUENCE: 712

Arg Ala Ser Gln Ser Val Ser Ser Ser Tyr Leu Ala
1               5                   10

<210> SEQ ID NO 713
<211> LENGTH: 7
<212> TYPE: PRT
<213> ORGANISM: Artificial Sequence
<220> FEATURE:
<223> OTHER INFORMATION: Recombinant protein

<400> SEQUENCE: 713

Gly Gln Ser Ser Arg Thr Arg
1               5

<210> SEQ ID NO 714
<211> LENGTH: 10
<212> TYPE: PRT
<213> ORGANISM: Artificial Sequence
<220> FEATURE:
<223> OTHER INFORMATION: Recombinant protein

<400> SEQUENCE: 714

Gln Gln Phe Gly Ser Ser Gln Leu Phe Thr
1               5                   10

<210> SEQ ID NO 715
<211> LENGTH: 120
<212> TYPE: PRT
<213> ORGANISM: Artificial Sequence
<220> FEATURE:
<223> OTHER INFORMATION: Recombinant protein

<400> SEQUENCE: 715

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 716
<211> LENGTH: 5
<212> TYPE: PRT
<213> ORGANISM: Artificial Sequence
<220> FEATURE:
<223> OTHER INFORMATION: Recombinant protein

<400> SEQUENCE: 716
```

```
Thr Ser Trp Ile Val
1               5

<210> SEQ ID NO 717
<211> LENGTH: 17
<212> TYPE: PRT
<213> ORGANISM: Artificial Sequence
<220> FEATURE:
<223> OTHER INFORMATION: Recombinant protein

<400> SEQUENCE: 717

Met Ile Asp Pro Ser Asp Ser Phe Thr Ser Tyr Ser Pro Ser Phe Gln
1               5                   10                  15

Gly

<210> SEQ ID NO 718
<211> LENGTH: 11
<212> TYPE: PRT
<213> ORGANISM: Artificial Sequence
<220> FEATURE:
<223> OTHER INFORMATION: Recombinant protein

<400> SEQUENCE: 718

Leu His Tyr Tyr Asn Ser Glu Glu Phe Asp Val
1               5                   10

<210> SEQ ID NO 719
<211> LENGTH: 109
<212> TYPE: PRT
<213> ORGANISM: Artificial Sequence
<220> FEATURE:
<223> OTHER INFORMATION: Recombinant protein

<400> SEQUENCE: 719

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Glu Ser Gln
                85                  90                  95

Leu Phe Thr Phe Gly Gln Gly Thr Lys Leu Glu Ile Lys
            100                 105

<210> SEQ ID NO 720
<211> LENGTH: 12
<212> TYPE: PRT
<213> ORGANISM: Artificial Sequence
<220> FEATURE:
<223> OTHER INFORMATION: Recombinant protein

<400> SEQUENCE: 720

Arg Ala Ser Gln Ser Val Ser Ser Ser Tyr Leu Ala
1               5                   10

<210> SEQ ID NO 721
<211> LENGTH: 7
```

```
<212> TYPE: PRT
<213> ORGANISM: Artificial Sequence
<220> FEATURE:
<223> OTHER INFORMATION: Recombinant protein

<400> SEQUENCE: 721

Gly Gln Ser Ser Arg Thr Arg
1               5

<210> SEQ ID NO 722
<211> LENGTH: 10
<212> TYPE: PRT
<213> ORGANISM: Artificial Sequence
<220> FEATURE:
<223> OTHER INFORMATION: Recombinant protein

<400> SEQUENCE: 722

Gln Gln Phe Gly Glu Ser Gln Leu Phe Thr
1               5                   10

<210> SEQ ID NO 723
<211> LENGTH: 120
<212> TYPE: PRT
<213> ORGANISM: Artificial Sequence
<220> FEATURE:
<223> OTHER INFORMATION: Recombinant protein

<400> SEQUENCE: 723

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 724
<211> LENGTH: 5
<212> TYPE: PRT
<213> ORGANISM: Artificial Sequence
<220> FEATURE:
<223> OTHER INFORMATION: Recombinant protein

<400> SEQUENCE: 724

Thr Ser Trp Ile Val
1               5

<210> SEQ ID NO 725
<211> LENGTH: 17
<212> TYPE: PRT
<213> ORGANISM: Artificial Sequence
<220> FEATURE:
<223> OTHER INFORMATION: Recombinant protein

<400> SEQUENCE: 725
```

```
Met Ile Asp Pro Ser Asp Ser Phe Thr Ser Tyr Ser Pro Ser Phe Gln
1               5                   10                  15

Gly
```

<210> SEQ ID NO 726
<211> LENGTH: 11
<212> TYPE: PRT
<213> ORGANISM: Artificial Sequence
<220> FEATURE:
<223> OTHER INFORMATION: Recombinant protein

<400> SEQUENCE: 726

```
Leu His Tyr Tyr Asn Ser Glu Glu Phe Asp Val
1               5                   10
```

<210> SEQ ID NO 727
<211> LENGTH: 109
<212> TYPE: PRT
<213> ORGANISM: Artificial Sequence
<220> FEATURE:
<223> OTHER INFORMATION: Recombinant protein

<400> SEQUENCE: 727

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asn Ser Gln
                85                  90                  95

Leu Phe Thr Phe Gly Gln Gly Thr Lys Leu Glu Ile Lys
            100                 105
```

<210> SEQ ID NO 728
<211> LENGTH: 12
<212> TYPE: PRT
<213> ORGANISM: Artificial Sequence
<220> FEATURE:
<223> OTHER INFORMATION: Recombinant protein

<400> SEQUENCE: 728

```
Arg Ala Ser Gln Ser Val Ser Ser Ser Tyr Leu Ala
1               5                   10
```

<210> SEQ ID NO 729
<211> LENGTH: 7
<212> TYPE: PRT
<213> ORGANISM: Artificial Sequence
<220> FEATURE:
<223> OTHER INFORMATION: Recombinant protein

<400> SEQUENCE: 729

```
Gly Gln Ser Ser Arg Thr Arg
1               5
```

<210> SEQ ID NO 730
<211> LENGTH: 10

```
<212> TYPE: PRT
<213> ORGANISM: Artificial Sequence
<220> FEATURE:
<223> OTHER INFORMATION: Recombinant protein

<400> SEQUENCE: 730

Gln Gln Phe Gly Asn Ser Gln Leu Phe Thr
1               5                   10

<210> SEQ ID NO 731
<211> LENGTH: 120
<212> TYPE: PRT
<213> ORGANISM: Artificial Sequence
<220> FEATURE:
<223> OTHER INFORMATION: Recombinant protein

<400> SEQUENCE: 731

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 732
<211> LENGTH: 5
<212> TYPE: PRT
<213> ORGANISM: Artificial Sequence
<220> FEATURE:
<223> OTHER INFORMATION: Recombinant protein

<400> SEQUENCE: 732

Thr Ser Trp Ile Val
1               5

<210> SEQ ID NO 733
<211> LENGTH: 17
<212> TYPE: PRT
<213> ORGANISM: Artificial Sequence
<220> FEATURE:
<223> OTHER INFORMATION: Recombinant protein

<400> SEQUENCE: 733

Met Ile Asp Pro Ser Asp Ser Phe Thr Ser Tyr Ser Pro Ser Phe Gln
1               5                   10                  15

Gly

<210> SEQ ID NO 734
<211> LENGTH: 11
<212> TYPE: PRT
<213> ORGANISM: Artificial Sequence
<220> FEATURE:
<223> OTHER INFORMATION: Recombinant protein
```

-continued

<400> SEQUENCE: 734

Leu His Tyr Tyr Asn Ser Glu Glu Phe Asp Val
1               5                   10

<210> SEQ ID NO 735
<211> LENGTH: 109
<212> TYPE: PRT
<213> ORGANISM: Artificial Sequence
<220> FEATURE:
<223> OTHER INFORMATION: Recombinant protein

<400> SEQUENCE: 735

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Gln Ser Gln
                85                  90                  95

Leu Phe Thr Phe Gly Gln Gly Thr Lys Leu Glu Ile Lys
            100                 105

<210> SEQ ID NO 736
<211> LENGTH: 12
<212> TYPE: PRT
<213> ORGANISM: Artificial Sequence
<220> FEATURE:
<223> OTHER INFORMATION: Recombinant protein

<400> SEQUENCE: 736

Arg Ala Ser Gln Ser Val Ser Ser Ser Tyr Leu Ala
1               5                   10

<210> SEQ ID NO 737
<211> LENGTH: 7
<212> TYPE: PRT
<213> ORGANISM: Artificial Sequence
<220> FEATURE:
<223> OTHER INFORMATION: Recombinant protein

<400> SEQUENCE: 737

Gly Gln Ser Ser Arg Thr Arg
1               5

<210> SEQ ID NO 738
<211> LENGTH: 10
<212> TYPE: PRT
<213> ORGANISM: Artificial Sequence
<220> FEATURE:
<223> OTHER INFORMATION: Recombinant protein

<400> SEQUENCE: 738

Gln Gln Phe Gly Gln Ser Gln Leu Phe Thr
1               5                   10

<210> SEQ ID NO 739
<211> LENGTH: 120

```
<212> TYPE: PRT
<213> ORGANISM: Artificial Sequence
<220> FEATURE:
<223> OTHER INFORMATION: Recombinant protein

<400> SEQUENCE: 739

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 740
<211> LENGTH: 5
<212> TYPE: PRT
<213> ORGANISM: Artificial Sequence
<220> FEATURE:
<223> OTHER INFORMATION: Recombinant protein

<400> SEQUENCE: 740

Thr Ser Trp Ile Val
1               5

<210> SEQ ID NO 741
<211> LENGTH: 17
<212> TYPE: PRT
<213> ORGANISM: Artificial Sequence
<220> FEATURE:
<223> OTHER INFORMATION: Recombinant protein

<400> SEQUENCE: 741

Met Ile Asp Pro Ser Asp Ser Phe Thr Ser Tyr Ser Pro Ser Phe Gln
1               5                   10                  15

Gly

<210> SEQ ID NO 742
<211> LENGTH: 11
<212> TYPE: PRT
<213> ORGANISM: Artificial Sequence
<220> FEATURE:
<223> OTHER INFORMATION: Recombinant protein

<400> SEQUENCE: 742

Leu His Tyr Tyr Asn Ser Glu Glu Phe Asp Val
1               5                   10

<210> SEQ ID NO 743
<211> LENGTH: 109
<212> TYPE: PRT
<213> ORGANISM: Artificial Sequence
<220> FEATURE:
<223> OTHER INFORMATION: Recombinant protein
```

<400> SEQUENCE: 743

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ala Gln
                85                  90                  95

Leu Phe Thr Phe Gly Gln Gly Thr Lys Leu Glu Ile Lys
            100                 105

<210> SEQ ID NO 744
<211> LENGTH: 12
<212> TYPE: PRT
<213> ORGANISM: Artificial Sequence
<220> FEATURE:
<223> OTHER INFORMATION: Recombinant protein

<400> SEQUENCE: 744

Arg Ala Ser Gln Ser Val Ser Ser Ser Tyr Leu Ala
1               5                   10

<210> SEQ ID NO 745
<211> LENGTH: 7
<212> TYPE: PRT
<213> ORGANISM: Artificial Sequence
<220> FEATURE:
<223> OTHER INFORMATION: Recombinant protein

<400> SEQUENCE: 745

Gly Gln Ser Ser Arg Thr Arg
1               5

<210> SEQ ID NO 746
<211> LENGTH: 10
<212> TYPE: PRT
<213> ORGANISM: Artificial Sequence
<220> FEATURE:
<223> OTHER INFORMATION: Recombinant protein

<400> SEQUENCE: 746

Gln Gln Phe Gly Asp Ala Gln Leu Phe Thr
1               5                   10

<210> SEQ ID NO 747
<211> LENGTH: 120
<212> TYPE: PRT
<213> ORGANISM: Artificial Sequence
<220> FEATURE:
<223> OTHER INFORMATION: Recombinant protein

<400> SEQUENCE: 747

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

```
Trp Ile Val Trp Val Arg Gln Met Pro Gly Lys Gly Leu Glu Trp Met
             35                  40                  45

Gly Met Ile Asp Pro Ser Asp Ser Phe Thr Ser Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr Asn Ser Glu Glu Phe Asp Val Trp Gly Gln
                100                 105                 110

Gly Thr Leu Val Thr Val Ser Ser
            115                 120
```

<210> SEQ ID NO 748
<211> LENGTH: 5
<212> TYPE: PRT
<213> ORGANISM: Artificial Sequence
<220> FEATURE:
<223> OTHER INFORMATION: Recombinant protein

<400> SEQUENCE: 748

```
Thr Ser Trp Ile Val
 1               5
```

<210> SEQ ID NO 749
<211> LENGTH: 17
<212> TYPE: PRT
<213> ORGANISM: Artificial Sequence
<220> FEATURE:
<223> OTHER INFORMATION: Recombinant protein

<400> SEQUENCE: 749

```
Met Ile Asp Pro Ser Asp Ser Phe Thr Ser Tyr Ser Pro Ser Phe Gln
 1               5                  10                  15

Gly
```

<210> SEQ ID NO 750
<211> LENGTH: 11
<212> TYPE: PRT
<213> ORGANISM: Artificial Sequence
<220> FEATURE:
<223> OTHER INFORMATION: Recombinant protein

<400> SEQUENCE: 750

```
Leu His Tyr Tyr Asn Ser Glu Glu Phe Asp Val
 1               5                  10
```

<210> SEQ ID NO 751
<211> LENGTH: 109
<212> TYPE: PRT
<213> ORGANISM: Artificial Sequence
<220> FEATURE:
<223> OTHER INFORMATION: Recombinant protein

<400> SEQUENCE: 751

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Gln Ser Ser Arg Thr Arg Gly Ile Pro Asp Arg Phe Ser
```

```
                    50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Asp Thr Gln
                 85                  90                  95

Leu Phe Thr Phe Gly Gln Gly Thr Lys Leu Glu Ile Lys
            100                 105
```

<210> SEQ ID NO 752
<211> LENGTH: 12
<212> TYPE: PRT
<213> ORGANISM: Artificial Sequence
<220> FEATURE:
<223> OTHER INFORMATION: Recombinant protein

<400> SEQUENCE: 752

```
Arg Ala Ser Gln Ser Val Ser Ser Ser Tyr Leu Ala
 1               5                  10
```

<210> SEQ ID NO 753
<211> LENGTH: 7
<212> TYPE: PRT
<213> ORGANISM: Artificial Sequence
<220> FEATURE:
<223> OTHER INFORMATION: Recombinant protein

<400> SEQUENCE: 753

```
Gly Gln Ser Ser Arg Thr Arg
 1               5
```

<210> SEQ ID NO 754
<211> LENGTH: 10
<212> TYPE: PRT
<213> ORGANISM: Artificial Sequence
<220> FEATURE:
<223> OTHER INFORMATION: Recombinant protein

<400> SEQUENCE: 754

```
Gln Gln Phe Gly Asp Thr Gln Leu Phe Thr
 1               5                  10
```

<210> SEQ ID NO 755
<211> LENGTH: 120
<212> TYPE: PRT
<213> ORGANISM: Artificial Sequence
<220> FEATURE:
<223> OTHER INFORMATION: Recombinant protein

<400> SEQUENCE: 755

```
Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Ser Thr Ser
             20                  25                  30

Trp Ile Val Trp Val Arg Gln Met Pro Gly Lys Gly Leu Glu Trp Met
         35                  40                  45

Gly Met Ile Asp Pro Ser Asp Ser Phe Thr Ser Tyr Ser Pro Ser Phe
     50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr Asn Ser Glu Glu Phe Asp Val Trp Gly Gln
```

```
              100                 105                 110
Gly Thr Leu Val Thr Val Ser Ser
        115                 120

<210> SEQ ID NO 756
<211> LENGTH: 5
<212> TYPE: PRT
<213> ORGANISM: Artificial Sequence
<220> FEATURE:
<223> OTHER INFORMATION: Recombinant protein

<400> SEQUENCE: 756

Thr Ser Trp Ile Val
1               5

<210> SEQ ID NO 757
<211> LENGTH: 17
<212> TYPE: PRT
<213> ORGANISM: Artificial Sequence
<220> FEATURE:
<223> OTHER INFORMATION: Recombinant protein

<400> SEQUENCE: 757

Met Ile Asp Pro Ser Asp Ser Phe Thr Ser Tyr Ser Pro Ser Phe Gln
1               5                   10                  15

Gly

<210> SEQ ID NO 758
<211> LENGTH: 11
<212> TYPE: PRT
<213> ORGANISM: Artificial Sequence
<220> FEATURE:
<223> OTHER INFORMATION: Recombinant protein

<400> SEQUENCE: 758

Leu His Tyr Tyr Asn Ser Glu Glu Phe Asp Val
1               5                   10

<210> SEQ ID NO 759
<211> LENGTH: 109
<212> TYPE: PRT
<213> ORGANISM: Artificial Sequence
<220> FEATURE:
<223> OTHER INFORMATION: Recombinant protein

<400> SEQUENCE: 759

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asn Gln
                85                  90                  95

Leu Phe Thr Phe Gly Gln Gly Thr Lys Leu Glu Ile Lys
            100                 105

<210> SEQ ID NO 760
```

```
<211> LENGTH: 12
<212> TYPE: PRT
<213> ORGANISM: Artificial Sequence
<220> FEATURE:
<223> OTHER INFORMATION: Recombinant protein

<400> SEQUENCE: 760

Arg Ala Ser Gln Ser Val Ser Ser Ser Tyr Leu Ala
1               5                   10

<210> SEQ ID NO 761
<211> LENGTH: 7
<212> TYPE: PRT
<213> ORGANISM: Artificial Sequence
<220> FEATURE:
<223> OTHER INFORMATION: Recombinant protein

<400> SEQUENCE: 761

Gly Gln Ser Ser Arg Thr Arg
1               5

<210> SEQ ID NO 762
<211> LENGTH: 10
<212> TYPE: PRT
<213> ORGANISM: Artificial Sequence
<220> FEATURE:
<223> OTHER INFORMATION: Recombinant protein

<400> SEQUENCE: 762

Gln Gln Phe Gly Asp Asn Gln Leu Phe Thr
1               5                   10

<210> SEQ ID NO 763
<211> LENGTH: 120
<212> TYPE: PRT
<213> ORGANISM: Artificial Sequence
<220> FEATURE:
<223> OTHER INFORMATION: Recombinant protein

<400> SEQUENCE: 763

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 764
<211> LENGTH: 5
<212> TYPE: PRT
<213> ORGANISM: Artificial Sequence
<220> FEATURE:
<223> OTHER INFORMATION: Recombinant protein
```

```
<400> SEQUENCE: 764

Thr Ser Trp Ile Ser
1               5

<210> SEQ ID NO 765
<211> LENGTH: 17
<212> TYPE: PRT
<213> ORGANISM: Artificial Sequence
<220> FEATURE:
<223> OTHER INFORMATION: Recombinant protein

<400> SEQUENCE: 765

Met Ile Asp Pro Ser Asp Ser Tyr Thr Ser Tyr Ser Pro Ser Phe Gln
1               5                   10                  15

Gly

<210> SEQ ID NO 766
<211> LENGTH: 11
<212> TYPE: PRT
<213> ORGANISM: Artificial Sequence
<220> FEATURE:
<223> OTHER INFORMATION: Recombinant protein

<400> SEQUENCE: 766

Leu His Tyr Tyr Asn Ser Glu Glu Phe Asp Val
1               5                   10

<210> SEQ ID NO 767
<211> LENGTH: 109
<212> TYPE: PRT
<213> ORGANISM: Artificial Sequence
<220> FEATURE:
<223> OTHER INFORMATION: Recombinant protein

<400> SEQUENCE: 767

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Gln
                85                  90                  95

Leu Phe Thr Phe Gly Gln Gly Thr Lys Leu Glu Ile Lys
            100                 105

<210> SEQ ID NO 768
<211> LENGTH: 12
<212> TYPE: PRT
<213> ORGANISM: Artificial Sequence
<220> FEATURE:
<223> OTHER INFORMATION: Recombinant protein

<400> SEQUENCE: 768

Arg Ala Ser Gln Ser Val Ser Ser Ser Tyr Leu Ala
1               5                   10

<210> SEQ ID NO 769
```

<211> LENGTH: 7
<212> TYPE: PRT
<213> ORGANISM: Artificial Sequence
<220> FEATURE:
<223> OTHER INFORMATION: Recombinant protein

<400> SEQUENCE: 769

Gly Gln Ser Ser Arg Thr Arg
1               5

<210> SEQ ID NO 770
<211> LENGTH: 10
<212> TYPE: PRT
<213> ORGANISM: Artificial Sequence
<220> FEATURE:
<223> OTHER INFORMATION: Recombinant protein

<400> SEQUENCE: 770

Gln Gln Phe Gly Ser Ser Gln Leu Phe Thr
1               5                   10

<210> SEQ ID NO 771
<211> LENGTH: 120
<212> TYPE: PRT
<213> ORGANISM: Artificial Sequence
<220> FEATURE:
<223> OTHER INFORMATION: Recombinant protein

<400> SEQUENCE: 771

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 772
<211> LENGTH: 5
<212> TYPE: PRT
<213> ORGANISM: Artificial Sequence
<220> FEATURE:
<223> OTHER INFORMATION: Recombinant protein

<400> SEQUENCE: 772

Thr Ser Trp Ile Ser
1               5

<210> SEQ ID NO 773
<211> LENGTH: 17
<212> TYPE: PRT
<213> ORGANISM: Artificial Sequence
<220> FEATURE:
<223> OTHER INFORMATION: Recombinant protein

```
<400> SEQUENCE: 773

Met Ile Asp Pro Ser Asp Ser Phe Thr Ser Tyr Ser Pro Ser Phe Gln
1               5                   10                  15

Gly

<210> SEQ ID NO 774
<211> LENGTH: 11
<212> TYPE: PRT
<213> ORGANISM: Artificial Sequence
<220> FEATURE:
<223> OTHER INFORMATION: Recombinant protein

<400> SEQUENCE: 774

Leu His Tyr Tyr His Ser Glu Glu Phe Asp Val
1               5                   10

<210> SEQ ID NO 775
<211> LENGTH: 109
<212> TYPE: PRT
<213> ORGANISM: Artificial Sequence
<220> FEATURE:
<223> OTHER INFORMATION: Recombinant protein

<400> SEQUENCE: 775

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Gln
                85                  90                  95

Leu Phe Thr Phe Gly Gln Gly Thr Lys Leu Glu Ile Lys
            100                 105

<210> SEQ ID NO 776
<211> LENGTH: 12
<212> TYPE: PRT
<213> ORGANISM: Artificial Sequence
<220> FEATURE:
<223> OTHER INFORMATION: Recombinant protein

<400> SEQUENCE: 776

Arg Ala Ser Gln Ser Val Ser Ser Ser Tyr Leu Ala
1               5                   10

<210> SEQ ID NO 777
<211> LENGTH: 7
<212> TYPE: PRT
<213> ORGANISM: Artificial Sequence
<220> FEATURE:
<223> OTHER INFORMATION: Recombinant protein

<400> SEQUENCE: 777

Gly Gln Ser Ser Arg Thr Arg
1               5

<210> SEQ ID NO 778
```

```
<211> LENGTH: 10
<212> TYPE: PRT
<213> ORGANISM: Artificial Sequence
<220> FEATURE:
<223> OTHER INFORMATION: Recombinant protein

<400> SEQUENCE: 778

Gln Gln Phe Gly Ser Ser Gln Leu Phe Thr
1               5                   10

<210> SEQ ID NO 779
<211> LENGTH: 120
<212> TYPE: PRT
<213> ORGANISM: Artificial Sequence
<220> FEATURE:
<223> OTHER INFORMATION: Recombinant protein

<400> SEQUENCE: 779

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 780
<211> LENGTH: 5
<212> TYPE: PRT
<213> ORGANISM: Artificial Sequence
<220> FEATURE:
<223> OTHER INFORMATION: Recombinant protein

<400> SEQUENCE: 780

Thr Ser Trp Ile Ser
1               5

<210> SEQ ID NO 781
<211> LENGTH: 17
<212> TYPE: PRT
<213> ORGANISM: Artificial Sequence
<220> FEATURE:
<223> OTHER INFORMATION: Recombinant protein

<400> SEQUENCE: 781

Met Ile Asp Pro Ser Asp Ser Tyr Thr Ser Tyr Ser Pro Ser Phe Gln
1               5                   10                  15

Gly

<210> SEQ ID NO 782
<211> LENGTH: 11
<212> TYPE: PRT
<213> ORGANISM: Artificial Sequence
<220> FEATURE:
```

<223> OTHER INFORMATION: Recombinant protein

<400> SEQUENCE: 782

Leu His Tyr Tyr His Ser Glu Glu Phe Asp Val
1               5                   10

<210> SEQ ID NO 783
<211> LENGTH: 109
<212> TYPE: PRT
<213> ORGANISM: Artificial Sequence
<220> FEATURE:
<223> OTHER INFORMATION: Recombinant protein

<400> SEQUENCE: 783

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Gln
                85                  90                  95

Leu Phe Thr Phe Gly Gln Gly Thr Lys Leu Glu Ile Lys
            100                 105

<210> SEQ ID NO 784
<211> LENGTH: 12
<212> TYPE: PRT
<213> ORGANISM: Artificial Sequence
<220> FEATURE:
<223> OTHER INFORMATION: Recombinant protein

<400> SEQUENCE: 784

Arg Ala Ser Gln Ser Val Ser Ser Ser Tyr Leu Ala
1               5                   10

<210> SEQ ID NO 785
<211> LENGTH: 7
<212> TYPE: PRT
<213> ORGANISM: Artificial Sequence
<220> FEATURE:
<223> OTHER INFORMATION: Recombinant protein

<400> SEQUENCE: 785

Gly Gln Ser Ser Arg Thr Arg
1               5

<210> SEQ ID NO 786
<211> LENGTH: 10
<212> TYPE: PRT
<213> ORGANISM: Artificial Sequence
<220> FEATURE:
<223> OTHER INFORMATION: Recombinant protein

<400> SEQUENCE: 786

Gln Gln Phe Gly Ser Ser Gln Leu Phe Thr
1               5                   10

<210> SEQ ID NO 787

```
<211> LENGTH: 120
<212> TYPE: PRT
<213> ORGANISM: Artificial Sequence
<220> FEATURE:
<223> OTHER INFORMATION: Recombinant protein

<400> SEQUENCE: 787

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 788
<211> LENGTH: 5
<212> TYPE: PRT
<213> ORGANISM: Artificial Sequence
<220> FEATURE:
<223> OTHER INFORMATION: Recombinant protein

<400> SEQUENCE: 788

Thr Ser Trp Ile Ser
1               5

<210> SEQ ID NO 789
<211> LENGTH: 17
<212> TYPE: PRT
<213> ORGANISM: Artificial Sequence
<220> FEATURE:
<223> OTHER INFORMATION: Recombinant protein

<400> SEQUENCE: 789

Met Ile Asp Pro Ser Asp Ser Tyr Thr Ser Tyr Ser Pro Ser Phe Gln
1               5                   10                  15

Gly

<210> SEQ ID NO 790
<211> LENGTH: 11
<212> TYPE: PRT
<213> ORGANISM: Artificial Sequence
<220> FEATURE:
<223> OTHER INFORMATION: Recombinant protein

<400> SEQUENCE: 790

Leu His Tyr Tyr His Ser Glu Glu Phe Asp Val
1               5                   10

<210> SEQ ID NO 791
<211> LENGTH: 109
<212> TYPE: PRT
<213> ORGANISM: Artificial Sequence
<220> FEATURE:
```

<223> OTHER INFORMATION: Recombinant protein

<400> SEQUENCE: 791

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Gln
                85                  90                  95

Leu Phe Thr Phe Gly Gln Gly Thr Lys Leu Glu Ile Lys
            100                 105

<210> SEQ ID NO 792
<211> LENGTH: 12
<212> TYPE: PRT
<213> ORGANISM: Artificial Sequence
<220> FEATURE:
<223> OTHER INFORMATION: Recombinant protein

<400> SEQUENCE: 792

Arg Ala Ser Gln Ser Val Ser Ser Ser Tyr Leu Ala
1               5                   10

<210> SEQ ID NO 793
<211> LENGTH: 7
<212> TYPE: PRT
<213> ORGANISM: Artificial Sequence
<220> FEATURE:
<223> OTHER INFORMATION: Recombinant protein

<400> SEQUENCE: 793

Gly Gln Ser Ser Arg Thr Arg
1               5

<210> SEQ ID NO 794
<211> LENGTH: 10
<212> TYPE: PRT
<213> ORGANISM: Artificial Sequence
<220> FEATURE:
<223> OTHER INFORMATION: Recombinant protein

<400> SEQUENCE: 794

Gln Gln Phe Gly Ser Ser Gln Leu Phe Thr
1               5                   10

<210> SEQ ID NO 795
<211> LENGTH: 120
<212> TYPE: PRT
<213> ORGANISM: Artificial Sequence
<220> FEATURE:
<223> OTHER INFORMATION: Recombinant protein

<400> SEQUENCE: 795

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
          35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
              100                 105                 110

Gly Thr Leu Val Thr Val Ser Ser
          115                 120

<210> SEQ ID NO 796
<211> LENGTH: 5
<212> TYPE: PRT
<213> ORGANISM: Artificial Sequence
<220> FEATURE:
<223> OTHER INFORMATION: Recombinant protein

<400> SEQUENCE: 796

Thr Ser Trp Ile Ser
1               5

<210> SEQ ID NO 797
<211> LENGTH: 17
<212> TYPE: PRT
<213> ORGANISM: Artificial Sequence
<220> FEATURE:
<223> OTHER INFORMATION: Recombinant protein

<400> SEQUENCE: 797

Met Ile Asp Pro Ser Asp Ser Phe Thr Ser Tyr Ser Pro Ser Phe Gln
1               5                   10                  15

Gly

<210> SEQ ID NO 798
<211> LENGTH: 11
<212> TYPE: PRT
<213> ORGANISM: Artificial Sequence
<220> FEATURE:
<223> OTHER INFORMATION: Recombinant protein

<400> SEQUENCE: 798

Leu His Tyr Tyr Asn Ser Glu Glu Phe Asp Val
1               5                   10

<210> SEQ ID NO 799
<211> LENGTH: 109
<212> TYPE: PRT
<213> ORGANISM: Artificial Sequence
<220> FEATURE:
<223> OTHER INFORMATION: Recombinant protein

<400> SEQUENCE: 799

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
              20                  25                  30

Tyr Leu Ala Trp Tyr Gln Gln Lys Pro Gly Gln Ala Pro Arg Leu Leu
          35                  40                  45

```
Ile Tyr Gly Gln Ser Ser Arg Thr Arg Gly Ile Pro Asp Arg Phe Ser
    50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Phe Gly Ser Ser Gln
                 85                  90                  95
Leu Phe Thr Phe Gly Gln Gly Thr Lys Leu Glu Ile Lys
                100                 105
```

<210> SEQ ID NO 800
<211> LENGTH: 12
<212> TYPE: PRT
<213> ORGANISM: Artificial Sequence
<220> FEATURE:
<223> OTHER INFORMATION: Recombinant protein

<400> SEQUENCE: 800

```
Arg Ala Ser Gln Ser Val Ser Ser Ser Tyr Leu Ala
 1               5                  10
```

<210> SEQ ID NO 801
<211> LENGTH: 7
<212> TYPE: PRT
<213> ORGANISM: Artificial Sequence
<220> FEATURE:
<223> OTHER INFORMATION: Recombinant protein

<400> SEQUENCE: 801

```
Gly Gln Ser Ser Arg Thr Arg
 1               5
```

<210> SEQ ID NO 802
<211> LENGTH: 10
<212> TYPE: PRT
<213> ORGANISM: Artificial Sequence
<220> FEATURE:
<223> OTHER INFORMATION: Recombinant protein

<400> SEQUENCE: 802

```
Gln Gln Phe Gly Ser Ser Gln Leu Phe Thr
 1               5                  10
```

<210> SEQ ID NO 803
<211> LENGTH: 120
<212> TYPE: PRT
<213> ORGANISM: Artificial Sequence
<220> FEATURE:
<223> OTHER INFORMATION: Recombinant protein

<400> SEQUENCE: 803

```
Glu Val Gln Leu Val Gln Ser Gly Ala Glu Val Lys Lys Pro Gly Glu
 1               5                  10                  15
Ser Leu Arg Ile Ser Cys Lys Gly Ser Gly Tyr Ser Phe Ser Thr Ser
             20                  25                  30
Trp Ile Val Trp Val Arg Gln Met Pro Gly Lys Gly Leu Glu Trp Met
         35                  40                  45
Gly Met Ile Asp Pro Ser Asp Ser Tyr Thr Ser Tyr Ser Pro Ser Phe
     50                  55                  60
Gln Gly His Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
```

```
Ala Arg Leu His Tyr Tyr Asn Ser Glu Glu Phe Asp Val Trp Gly Gln
            100                 105                 110

Gly Thr Leu Val Thr Val Ser Ser
        115                 120
```

<210> SEQ ID NO 804
<211> LENGTH: 5
<212> TYPE: PRT
<213> ORGANISM: Artificial Sequence
<220> FEATURE:
<223> OTHER INFORMATION: Recombinant protein

<400> SEQUENCE: 804

```
Thr Ser Trp Ile Val
1               5
```

<210> SEQ ID NO 805
<211> LENGTH: 17
<212> TYPE: PRT
<213> ORGANISM: Artificial Sequence
<220> FEATURE:
<223> OTHER INFORMATION: Recombinant protein

<400> SEQUENCE: 805

```
Met Ile Asp Pro Ser Asp Ser Tyr Thr Ser Tyr Ser Pro Ser Phe Gln
1               5                   10                  15

Gly
```

<210> SEQ ID NO 806
<211> LENGTH: 11
<212> TYPE: PRT
<213> ORGANISM: Artificial Sequence
<220> FEATURE:
<223> OTHER INFORMATION: Recombinant protein

<400> SEQUENCE: 806

```
Leu His Tyr Tyr Asn Ser Glu Glu Phe Asp Val
1               5                   10
```

<210> SEQ ID NO 807
<211> LENGTH: 109
<212> TYPE: PRT
<213> ORGANISM: Artificial Sequence
<220> FEATURE:
<223> OTHER INFORMATION: Recombinant protein

<400> SEQUENCE: 807

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Gln
                85                  90                  95

Leu Phe Thr Phe Gly Gln Gly Thr Lys Leu Glu Ile Lys
            100                 105
```

```
<210> SEQ ID NO 808
<211> LENGTH: 12
<212> TYPE: PRT
<213> ORGANISM: Artificial Sequence
<220> FEATURE:
<223> OTHER INFORMATION: Recombinant protein

<400> SEQUENCE: 808

Arg Ala Ser Gln Ser Val Ser Ser Tyr Leu Ala
1               5                   10

<210> SEQ ID NO 809
<211> LENGTH: 7
<212> TYPE: PRT
<213> ORGANISM: Artificial Sequence
<220> FEATURE:
<223> OTHER INFORMATION: Recombinant protein

<400> SEQUENCE: 809

Gly Gln Ser Ser Arg Thr Arg
1               5

<210> SEQ ID NO 810
<211> LENGTH: 10
<212> TYPE: PRT
<213> ORGANISM: Artificial Sequence
<220> FEATURE:
<223> OTHER INFORMATION: Recombinant protein

<400> SEQUENCE: 810

Gln Gln Phe Gly Ser Ser Gln Leu Phe Thr
1               5                   10

<210> SEQ ID NO 811
<211> LENGTH: 120
<212> TYPE: PRT
<213> ORGANISM: Artificial Sequence
<220> FEATURE:
<223> OTHER INFORMATION: Recombinant protein

<400> SEQUENCE: 811

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 812
<211> LENGTH: 5
<212> TYPE: PRT
<213> ORGANISM: Artificial Sequence
<220> FEATURE:
<223> OTHER INFORMATION: Recombinant protein
```

```
<400> SEQUENCE: 812

Thr Ser Trp Ile Val
1               5

<210> SEQ ID NO 813
<211> LENGTH: 17
<212> TYPE: PRT
<213> ORGANISM: Artificial Sequence
<220> FEATURE:
<223> OTHER INFORMATION: Recombinant protein

<400> SEQUENCE: 813

Met Ile Asp Pro Ser Asp Ser Tyr Thr Ser Tyr Ser Pro Ser Phe Gln
1               5                   10                  15

Gly

<210> SEQ ID NO 814
<211> LENGTH: 11
<212> TYPE: PRT
<213> ORGANISM: Artificial Sequence
<220> FEATURE:
<223> OTHER INFORMATION: Recombinant protein

<400> SEQUENCE: 814

Leu His Tyr Tyr Asn Ser Glu Glu Phe Asp Val
1               5                   10

<210> SEQ ID NO 815
<211> LENGTH: 109
<212> TYPE: PRT
<213> ORGANISM: Artificial Sequence
<220> FEATURE:
<223> OTHER INFORMATION: Recombinant protein

<400> SEQUENCE: 815

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Gln
                85                  90                  95

Leu Phe Thr Phe Gly Gln Gly Thr Lys Leu Glu Ile Lys
            100                 105

<210> SEQ ID NO 816
<211> LENGTH: 12
<212> TYPE: PRT
<213> ORGANISM: Artificial Sequence
<220> FEATURE:
<223> OTHER INFORMATION: Recombinant protein

<400> SEQUENCE: 816

Arg Ala Ser Gln Ser Val Ser Ser Ser Tyr Leu Ala
1               5                   10
```

```
<210> SEQ ID NO 817
<211> LENGTH: 7
<212> TYPE: PRT
<213> ORGANISM: Artificial Sequence
<220> FEATURE:
<223> OTHER INFORMATION: Recombinant protein

<400> SEQUENCE: 817

Gly Gln Ser Ser Arg Thr Arg
1               5

<210> SEQ ID NO 818
<211> LENGTH: 10
<212> TYPE: PRT
<213> ORGANISM: Artificial Sequence
<220> FEATURE:
<223> OTHER INFORMATION: Recombinant protein

<400> SEQUENCE: 818

Gln Gln Phe Gly Ser Ser Gln Leu Phe Thr
1               5                   10

<210> SEQ ID NO 819
<211> LENGTH: 120
<212> TYPE: PRT
<213> ORGANISM: Artificial Sequence
<220> FEATURE:
<223> OTHER INFORMATION: Recombinant protein

<400> SEQUENCE: 819

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 820
<211> LENGTH: 5
<212> TYPE: PRT
<213> ORGANISM: Artificial Sequence
<220> FEATURE:
<223> OTHER INFORMATION: Recombinant protein

<400> SEQUENCE: 820

Thr Ser Trp Ile Ser
1               5

<210> SEQ ID NO 821
<211> LENGTH: 17
<212> TYPE: PRT
<213> ORGANISM: Artificial Sequence
<220> FEATURE:
<223> OTHER INFORMATION: Recombinant protein
```

<400> SEQUENCE: 821

Met Ile Asp Pro Ser Asp Ser Tyr Thr Ser Tyr Ser Pro Ser Phe Gln
1               5                   10                  15

Gly

<210> SEQ ID NO 822
<211> LENGTH: 11
<212> TYPE: PRT
<213> ORGANISM: Artificial Sequence
<220> FEATURE:
<223> OTHER INFORMATION: Recombinant protein

<400> SEQUENCE: 822

Leu His Tyr Tyr Asn Ser Glu Glu Phe Asp Val
1               5                   10

<210> SEQ ID NO 823
<211> LENGTH: 109
<212> TYPE: PRT
<213> ORGANISM: Artificial Sequence
<220> FEATURE:
<223> OTHER INFORMATION: Recombinant protein

<400> SEQUENCE: 823

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Glu Ser Gln
                85                  90                  95

Leu Phe Thr Phe Gly Gln Gly Thr Lys Leu Glu Ile Lys
            100                 105

<210> SEQ ID NO 824
<211> LENGTH: 12
<212> TYPE: PRT
<213> ORGANISM: Artificial Sequence
<220> FEATURE:
<223> OTHER INFORMATION: Recombinant protein

<400> SEQUENCE: 824

Arg Ala Ser Gln Ser Val Ser Ser Ser Tyr Leu Ala
1               5                   10

<210> SEQ ID NO 825
<211> LENGTH: 7
<212> TYPE: PRT
<213> ORGANISM: Artificial Sequence
<220> FEATURE:
<223> OTHER INFORMATION: Recombinant protein

<400> SEQUENCE: 825

Gly Gln Ser Ser Arg Thr Arg
1               5

```
<210> SEQ ID NO 826
<211> LENGTH: 10
<212> TYPE: PRT
<213> ORGANISM: Artificial Sequence
<220> FEATURE:
<223> OTHER INFORMATION: Recombinant protein

<400> SEQUENCE: 826

Gln Gln Phe Gly Glu Ser Gln Leu Phe Thr
1               5                   10

<210> SEQ ID NO 827
<211> LENGTH: 120
<212> TYPE: PRT
<213> ORGANISM: Artificial Sequence
<220> FEATURE:
<223> OTHER INFORMATION: Recombinant protein

<400> SEQUENCE: 827

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 828
<211> LENGTH: 5
<212> TYPE: PRT
<213> ORGANISM: Artificial Sequence
<220> FEATURE:
<223> OTHER INFORMATION: Recombinant protein

<400> SEQUENCE: 828

Thr Ser Trp Ile Ser
1               5

<210> SEQ ID NO 829
<211> LENGTH: 17
<212> TYPE: PRT
<213> ORGANISM: Artificial Sequence
<220> FEATURE:
<223> OTHER INFORMATION: Recombinant protein

<400> SEQUENCE: 829

Met Ile Asp Pro Ser Asp Ser Phe Thr Ser Tyr Ser Pro Ser Phe Gln
1               5                   10                  15

Gly

<210> SEQ ID NO 830
<211> LENGTH: 11
<212> TYPE: PRT
<213> ORGANISM: Artificial Sequence
```

```
<220> FEATURE:
<223> OTHER INFORMATION: Recombinant protein

<400> SEQUENCE: 830

Leu His Tyr Tyr His Ser Glu Glu Phe Asp Val
1               5                   10

<210> SEQ ID NO 831
<211> LENGTH: 109
<212> TYPE: PRT
<213> ORGANISM: Artificial Sequence
<220> FEATURE:
<223> OTHER INFORMATION: Recombinant protein

<400> SEQUENCE: 831

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Glu Ser Gln
                85                  90                  95

Leu Phe Thr Phe Gly Gln Gly Thr Lys Leu Glu Ile Lys
            100                 105

<210> SEQ ID NO 832
<211> LENGTH: 12
<212> TYPE: PRT
<213> ORGANISM: Artificial Sequence
<220> FEATURE:
<223> OTHER INFORMATION: Recombinant protein

<400> SEQUENCE: 832

Arg Ala Ser Gln Ser Val Ser Ser Ser Tyr Leu Ala
1               5                   10

<210> SEQ ID NO 833
<211> LENGTH: 7
<212> TYPE: PRT
<213> ORGANISM: Artificial Sequence
<220> FEATURE:
<223> OTHER INFORMATION: Recombinant protein

<400> SEQUENCE: 833

Gly Gln Ser Ser Arg Thr Arg
1               5

<210> SEQ ID NO 834
<211> LENGTH: 10
<212> TYPE: PRT
<213> ORGANISM: Artificial Sequence
<220> FEATURE:
<223> OTHER INFORMATION: Recombinant protein

<400> SEQUENCE: 834

Gln Gln Phe Gly Glu Ser Gln Leu Phe Thr
1               5                   10
```

```
<210> SEQ ID NO 835
<211> LENGTH: 120
<212> TYPE: PRT
<213> ORGANISM: Artificial Sequence
<220> FEATURE:
<223> OTHER INFORMATION: Recombinant protein

<400> SEQUENCE: 835

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 836
<211> LENGTH: 5
<212> TYPE: PRT
<213> ORGANISM: Artificial Sequence
<220> FEATURE:
<223> OTHER INFORMATION: Recombinant protein

<400> SEQUENCE: 836

Thr Ser Trp Ile Ser
1               5

<210> SEQ ID NO 837
<211> LENGTH: 17
<212> TYPE: PRT
<213> ORGANISM: Artificial Sequence
<220> FEATURE:
<223> OTHER INFORMATION: Recombinant protein

<400> SEQUENCE: 837

Met Ile Asp Pro Ser Asp Ser Tyr Thr Ser Tyr Ser Pro Ser Phe Gln
1               5                   10                  15

Gly

<210> SEQ ID NO 838
<211> LENGTH: 11
<212> TYPE: PRT
<213> ORGANISM: Artificial Sequence
<220> FEATURE:
<223> OTHER INFORMATION: Recombinant protein

<400> SEQUENCE: 838

Leu His Tyr Tyr His Ser Glu Glu Phe Asp Val
1               5                   10

<210> SEQ ID NO 839
<211> LENGTH: 109
<212> TYPE: PRT
<213> ORGANISM: Artificial Sequence
```

```
<220> FEATURE:
<223> OTHER INFORMATION: Recombinant protein

<400> SEQUENCE: 839

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Glu Ser Gln
                85                  90                  95

Leu Phe Thr Phe Gly Gln Gly Thr Lys Leu Glu Ile Lys
            100                 105

<210> SEQ ID NO 840
<211> LENGTH: 12
<212> TYPE: PRT
<213> ORGANISM: Artificial Sequence
<220> FEATURE:
<223> OTHER INFORMATION: Recombinant protein

<400> SEQUENCE: 840

Arg Ala Ser Gln Ser Val Ser Ser Ser Tyr Leu Ala
1               5                   10

<210> SEQ ID NO 841
<211> LENGTH: 7
<212> TYPE: PRT
<213> ORGANISM: Artificial Sequence
<220> FEATURE:
<223> OTHER INFORMATION: Recombinant protein

<400> SEQUENCE: 841

Gly Gln Ser Ser Arg Thr Arg
1               5

<210> SEQ ID NO 842
<211> LENGTH: 10
<212> TYPE: PRT
<213> ORGANISM: Artificial Sequence
<220> FEATURE:
<223> OTHER INFORMATION: Recombinant protein

<400> SEQUENCE: 842

Gln Gln Phe Gly Glu Ser Gln Leu Phe Thr
1               5                   10

<210> SEQ ID NO 843
<211> LENGTH: 120
<212> TYPE: PRT
<213> ORGANISM: Artificial Sequence
<220> FEATURE:
<223> OTHER INFORMATION: Recombinant protein

<400> SEQUENCE: 843

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
```

```
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
            115                 120

<210> SEQ ID NO 844
<211> LENGTH: 5
<212> TYPE: PRT
<213> ORGANISM: Artificial Sequence
<220> FEATURE:
<223> OTHER INFORMATION: Recombinant protein

<400> SEQUENCE: 844

Thr Ser Trp Ile Ser
1               5

<210> SEQ ID NO 845
<211> LENGTH: 17
<212> TYPE: PRT
<213> ORGANISM: Artificial Sequence
<220> FEATURE:
<223> OTHER INFORMATION: Recombinant protein

<400> SEQUENCE: 845

Met Ile Asp Pro Ser Asp Ser Tyr Thr Ser Tyr Ser Pro Ser Phe Gln
1               5                   10                  15

Gly

<210> SEQ ID NO 846
<211> LENGTH: 11
<212> TYPE: PRT
<213> ORGANISM: Artificial Sequence
<220> FEATURE:
<223> OTHER INFORMATION: Recombinant protein

<400> SEQUENCE: 846

Leu His Tyr Tyr His Ser Glu Glu Phe Asp Val
1               5                   10

<210> SEQ ID NO 847
<211> LENGTH: 109
<212> TYPE: PRT
<213> ORGANISM: Artificial Sequence
<220> FEATURE:
<223> OTHER INFORMATION: Recombinant protein

<400> SEQUENCE: 847

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Gln Ser Ser Arg Thr Arg Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Phe Gly Glu Ser Gln
                85                  90                  95
Leu Phe Thr Phe Gly Gln Gly Thr Lys Leu Glu Ile Lys
                100                 105

<210> SEQ ID NO 848
<211> LENGTH: 12
<212> TYPE: PRT
<213> ORGANISM: Artificial Sequence
<220> FEATURE:
<223> OTHER INFORMATION: Recombinant protein

<400> SEQUENCE: 848

Arg Ala Ser Gln Ser Val Ser Ser Ser Tyr Leu Ala
1               5                   10

<210> SEQ ID NO 849
<211> LENGTH: 7
<212> TYPE: PRT
<213> ORGANISM: Artificial Sequence
<220> FEATURE:
<223> OTHER INFORMATION: Recombinant protein

<400> SEQUENCE: 849

Gly Gln Ser Ser Arg Thr Arg
1               5

<210> SEQ ID NO 850
<211> LENGTH: 10
<212> TYPE: PRT
<213> ORGANISM: Artificial Sequence
<220> FEATURE:
<223> OTHER INFORMATION: Recombinant protein

<400> SEQUENCE: 850

Gln Gln Phe Gly Glu Ser Gln Leu Phe Thr
1               5                   10

<210> SEQ ID NO 851
<211> LENGTH: 120
<212> TYPE: PRT
<213> ORGANISM: Artificial Sequence
<220> FEATURE:
<223> OTHER INFORMATION: Recombinant protein

<400> SEQUENCE: 851

Glu Val Gln Leu Val Gln Ser Gly Ala Glu Val Lys Lys Pro Gly Glu
1               5                   10                  15
Ser Leu Arg Ile Ser Cys Lys Gly Ser Gly Tyr Ser Phe Ser Thr Ser
                20                  25                  30
Trp Ile Ser Trp Val Arg Gln Met Pro Gly Lys Gly Leu Glu Trp Met
            35                  40                  45
Gly Met Ile Asp Pro Ser Asp Ser Phe Thr Ser Tyr Ser Pro Ser Phe
        50                  55                  60
Gln Gly His Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
```

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 852
<211> LENGTH: 5
<212> TYPE: PRT
<213> ORGANISM: Artificial Sequence
<220> FEATURE:
<223> OTHER INFORMATION: Recombinant protein

<400> SEQUENCE: 852

Thr Ser Trp Ile Ser
1               5

<210> SEQ ID NO 853
<211> LENGTH: 17
<212> TYPE: PRT
<213> ORGANISM: Artificial Sequence
<220> FEATURE:
<223> OTHER INFORMATION: Recombinant protein

<400> SEQUENCE: 853

Met Ile Asp Pro Ser Asp Ser Phe Thr Ser Tyr Ser Pro Ser Phe Gln
1               5                   10                  15

Gly

<210> SEQ ID NO 854
<211> LENGTH: 11
<212> TYPE: PRT
<213> ORGANISM: Artificial Sequence
<220> FEATURE:
<223> OTHER INFORMATION: Recombinant protein

<400> SEQUENCE: 854

Leu His Tyr Tyr Asn Ser Glu Glu Phe Asp Val
1               5                   10

<210> SEQ ID NO 855
<211> LENGTH: 109
<212> TYPE: PRT
<213> ORGANISM: Artificial Sequence
<220> FEATURE:
<223> OTHER INFORMATION: Recombinant protein

<400> SEQUENCE: 855

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Glu Ser Gln
                85                  90                  95

Leu Phe Thr Phe Gly Gln Gly Thr Lys Leu Glu Ile Lys
            100                 105

```
<210> SEQ ID NO 856
<211> LENGTH: 12
<212> TYPE: PRT
<213> ORGANISM: Artificial Sequence
<220> FEATURE:
<223> OTHER INFORMATION: Recombinant protein

<400> SEQUENCE: 856

Arg Ala Ser Gln Ser Val Ser Ser Ser Tyr Leu Ala
1               5                   10

<210> SEQ ID NO 857
<211> LENGTH: 7
<212> TYPE: PRT
<213> ORGANISM: Artificial Sequence
<220> FEATURE:
<223> OTHER INFORMATION: Recombinant protein

<400> SEQUENCE: 857

Gly Gln Ser Ser Arg Thr Arg
1               5

<210> SEQ ID NO 858
<211> LENGTH: 10
<212> TYPE: PRT
<213> ORGANISM: Artificial Sequence
<220> FEATURE:
<223> OTHER INFORMATION: Recombinant protein

<400> SEQUENCE: 858

Gln Gln Phe Gly Glu Ser Gln Leu Phe Thr
1               5                   10

<210> SEQ ID NO 859
<211> LENGTH: 120
<212> TYPE: PRT
<213> ORGANISM: Artificial Sequence
<220> FEATURE:
<223> OTHER INFORMATION: Recombinant protein

<400> SEQUENCE: 859

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 860
<211> LENGTH: 5
<212> TYPE: PRT
<213> ORGANISM: Artificial Sequence
<220> FEATURE:
```

<223> OTHER INFORMATION: Recombinant protein

<400> SEQUENCE: 860

Thr Ser Trp Ile Val
1               5

<210> SEQ ID NO 861
<211> LENGTH: 17
<212> TYPE: PRT
<213> ORGANISM: Artificial Sequence
<220> FEATURE:
<223> OTHER INFORMATION: Recombinant protein

<400> SEQUENCE: 861

Met Ile Asp Pro Ser Asp Ser Tyr Thr Ser Tyr Ser Pro Ser Phe Gln
1               5                   10                  15
Gly

<210> SEQ ID NO 862
<211> LENGTH: 11
<212> TYPE: PRT
<213> ORGANISM: Artificial Sequence
<220> FEATURE:
<223> OTHER INFORMATION: Recombinant protein

<400> SEQUENCE: 862

Leu His Tyr Tyr Asn Ser Glu Glu Phe Asp Val
1               5                   10

<210> SEQ ID NO 863
<211> LENGTH: 109
<212> TYPE: PRT
<213> ORGANISM: Artificial Sequence
<220> FEATURE:
<223> OTHER INFORMATION: Recombinant protein

<400> SEQUENCE: 863

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Gln Ser Ser Arg Thr Arg Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Phe Gly Glu Ser Gln
                85                  90                  95
Leu Phe Thr Phe Gly Gln Gly Thr Lys Leu Glu Ile Lys
            100                 105

<210> SEQ ID NO 864
<211> LENGTH: 12
<212> TYPE: PRT
<213> ORGANISM: Artificial Sequence
<220> FEATURE:
<223> OTHER INFORMATION: Recombinant protein

<400> SEQUENCE: 864

Arg Ala Ser Gln Ser Val Ser Ser Ser Tyr Leu Ala
1               5                   10

```
<210> SEQ ID NO 865
<211> LENGTH: 7
<212> TYPE: PRT
<213> ORGANISM: Artificial Sequence
<220> FEATURE:
<223> OTHER INFORMATION: Recombinant protein

<400> SEQUENCE: 865

Gly Gln Ser Ser Arg Thr Arg
1               5

<210> SEQ ID NO 866
<211> LENGTH: 10
<212> TYPE: PRT
<213> ORGANISM: Artificial Sequence
<220> FEATURE:
<223> OTHER INFORMATION: Recombinant protein

<400> SEQUENCE: 866

Gln Gln Phe Gly Glu Ser Gln Leu Phe Thr
1               5                   10

<210> SEQ ID NO 867
<211> LENGTH: 120
<212> TYPE: PRT
<213> ORGANISM: Artificial Sequence
<220> FEATURE:
<223> OTHER INFORMATION: Recombinant protein

<400> SEQUENCE: 867

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 868
<211> LENGTH: 5
<212> TYPE: PRT
<213> ORGANISM: Artificial Sequence
<220> FEATURE:
<223> OTHER INFORMATION: Recombinant protein

<400> SEQUENCE: 868

Thr Ser Trp Ile Val
1               5

<210> SEQ ID NO 869
<211> LENGTH: 17
<212> TYPE: PRT
<213> ORGANISM: Artificial Sequence
<220> FEATURE:
```

<223> OTHER INFORMATION: Recombinant protein

<400> SEQUENCE: 869

Met Ile Asp Pro Ser Asp Ser Tyr Thr Ser Tyr Ser Pro Ser Phe Gln
1               5                   10                  15

Gly

<210> SEQ ID NO 870
<211> LENGTH: 11
<212> TYPE: PRT
<213> ORGANISM: Artificial Sequence
<220> FEATURE:
<223> OTHER INFORMATION: Recombinant protein

<400> SEQUENCE: 870

Leu His Tyr Tyr Asn Ser Glu Glu Phe Asp Val
1               5                   10

<210> SEQ ID NO 871
<211> LENGTH: 109
<212> TYPE: PRT
<213> ORGANISM: Artificial Sequence
<220> FEATURE:
<223> OTHER INFORMATION: Recombinant protein

<400> SEQUENCE: 871

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Glu Ser Gln
                85                  90                  95

Leu Phe Thr Phe Gly Gln Gly Thr Lys Leu Glu Ile Lys
            100                 105

<210> SEQ ID NO 872
<211> LENGTH: 12
<212> TYPE: PRT
<213> ORGANISM: Artificial Sequence
<220> FEATURE:
<223> OTHER INFORMATION: Recombinant protein

<400> SEQUENCE: 872

Arg Ala Ser Gln Ser Val Ser Ser Ser Tyr Leu Ala
1               5                   10

<210> SEQ ID NO 873
<211> LENGTH: 7
<212> TYPE: PRT
<213> ORGANISM: Artificial Sequence
<220> FEATURE:
<223> OTHER INFORMATION: Recombinant protein

<400> SEQUENCE: 873

Gly Gln Ser Ser Arg Thr Arg
1               5

<210> SEQ ID NO 874
<211> LENGTH: 10
<212> TYPE: PRT
<213> ORGANISM: Artificial Sequence
<220> FEATURE:
<223> OTHER INFORMATION: Recombinant protein

<400> SEQUENCE: 874

Gln Gln Phe Gly Glu Ser Gln Leu Phe Thr
1               5                   10

<210> SEQ ID NO 875
<211> LENGTH: 120
<212> TYPE: PRT
<213> ORGANISM: Artificial Sequence
<220> FEATURE:
<223> OTHER INFORMATION: Recombinant protein

<400> SEQUENCE: 875

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 876
<211> LENGTH: 5
<212> TYPE: PRT
<213> ORGANISM: Artificial Sequence
<220> FEATURE:
<223> OTHER INFORMATION: Recombinant protein

<400> SEQUENCE: 876

Thr Ser Trp Ile Ser
1               5

<210> SEQ ID NO 877
<211> LENGTH: 17
<212> TYPE: PRT
<213> ORGANISM: Artificial Sequence
<220> FEATURE:
<223> OTHER INFORMATION: Recombinant protein

<400> SEQUENCE: 877

Met Ile Asp Pro Ser Asp Ser Tyr Thr Ser Tyr Ser Pro Ser Phe Gln
1               5                   10                  15

Gly

<210> SEQ ID NO 878
<211> LENGTH: 11
<212> TYPE: PRT

<213> ORGANISM: Artificial Sequence
<220> FEATURE:
<223> OTHER INFORMATION: Recombinant protein

<400> SEQUENCE: 878

```
Leu His Tyr Tyr Asn Ser Glu Glu Phe Asp Val
1               5                   10
```

<210> SEQ ID NO 879
<211> LENGTH: 109
<212> TYPE: PRT
<213> ORGANISM: Artificial Sequence
<220> FEATURE:
<223> OTHER INFORMATION: Recombinant protein

<400> SEQUENCE: 879

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asn Ser Gln
                85                  90                  95

Leu Phe Thr Phe Gly Gln Gly Thr Lys Leu Glu Ile Lys
            100                 105
```

<210> SEQ ID NO 880
<211> LENGTH: 12
<212> TYPE: PRT
<213> ORGANISM: Artificial Sequence
<220> FEATURE:
<223> OTHER INFORMATION: Recombinant protein

<400> SEQUENCE: 880

```
Arg Ala Ser Gln Ser Val Ser Ser Ser Tyr Leu Ala
1               5                   10
```

<210> SEQ ID NO 881
<211> LENGTH: 7
<212> TYPE: PRT
<213> ORGANISM: Artificial Sequence
<220> FEATURE:
<223> OTHER INFORMATION: Recombinant protein

<400> SEQUENCE: 881

```
Gly Gln Ser Ser Arg Thr Arg
1               5
```

<210> SEQ ID NO 882
<211> LENGTH: 10
<212> TYPE: PRT
<213> ORGANISM: Artificial Sequence
<220> FEATURE:
<223> OTHER INFORMATION: Recombinant protein

<400> SEQUENCE: 882

```
Gln Gln Phe Gly Asn Ser Gln Leu Phe Thr
1               5                   10
```

```
<210> SEQ ID NO 883
<211> LENGTH: 120
<212> TYPE: PRT
<213> ORGANISM: Artificial Sequence
<220> FEATURE:
<223> OTHER INFORMATION: Recombinant protein

<400> SEQUENCE: 883
```

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

```
<210> SEQ ID NO 884
<211> LENGTH: 5
<212> TYPE: PRT
<213> ORGANISM: Artificial Sequence
<220> FEATURE:
<223> OTHER INFORMATION: Recombinant protein

<400> SEQUENCE: 884
```

Thr Ser Trp Ile Ser
1               5

```
<210> SEQ ID NO 885
<211> LENGTH: 17
<212> TYPE: PRT
<213> ORGANISM: Artificial Sequence
<220> FEATURE:
<223> OTHER INFORMATION: Recombinant protein

<400> SEQUENCE: 885
```

Met Ile Asp Pro Ser Asp Ser Phe Thr Ser Tyr Ser Pro Ser Phe Gln
1               5                   10                  15

Gly

```
<210> SEQ ID NO 886
<211> LENGTH: 11
<212> TYPE: PRT
<213> ORGANISM: Artificial Sequence
<220> FEATURE:
<223> OTHER INFORMATION: Recombinant protein

<400> SEQUENCE: 886
```

Leu His Tyr Tyr His Ser Glu Glu Phe Asp Val
1               5                   10

```
<210> SEQ ID NO 887
<211> LENGTH: 109
<212> TYPE: PRT
```

<213> ORGANISM: Artificial Sequence
<220> FEATURE:
<223> OTHER INFORMATION: Recombinant protein

<400> SEQUENCE: 887

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asn Ser Gln
                85                  90                  95

Leu Phe Thr Phe Gly Gln Gly Thr Lys Leu Glu Ile Lys
            100                 105

<210> SEQ ID NO 888
<211> LENGTH: 12
<212> TYPE: PRT
<213> ORGANISM: Artificial Sequence
<220> FEATURE:
<223> OTHER INFORMATION: Recombinant protein

<400> SEQUENCE: 888

Arg Ala Ser Gln Ser Val Ser Ser Ser Tyr Leu Ala
1               5                   10

<210> SEQ ID NO 889
<211> LENGTH: 7
<212> TYPE: PRT
<213> ORGANISM: Artificial Sequence
<220> FEATURE:
<223> OTHER INFORMATION: Recombinant protein

<400> SEQUENCE: 889

Gly Gln Ser Ser Arg Thr Arg
1               5

<210> SEQ ID NO 890
<211> LENGTH: 10
<212> TYPE: PRT
<213> ORGANISM: Artificial Sequence
<220> FEATURE:
<223> OTHER INFORMATION: Recombinant protein

<400> SEQUENCE: 890

Gln Gln Phe Gly Asn Ser Gln Leu Phe Thr
1               5                   10

<210> SEQ ID NO 891
<211> LENGTH: 120
<212> TYPE: PRT
<213> ORGANISM: Artificial Sequence
<220> FEATURE:
<223> OTHER INFORMATION: Recombinant protein

<400> SEQUENCE: 891

Glu Val Gln Leu Val Gln Ser Gly Ala Glu Val Lys Lys Pro Gly Glu
1               5                   10                  15

```
Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
 50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
            115                 120

<210> SEQ ID NO 892
<211> LENGTH: 5
<212> TYPE: PRT
<213> ORGANISM: Artificial Sequence
<220> FEATURE:
<223> OTHER INFORMATION: Recombinant protein

<400> SEQUENCE: 892

Thr Ser Trp Ile Ser
1               5

<210> SEQ ID NO 893
<211> LENGTH: 17
<212> TYPE: PRT
<213> ORGANISM: Artificial Sequence
<220> FEATURE:
<223> OTHER INFORMATION: Recombinant protein

<400> SEQUENCE: 893

Met Ile Asp Pro Ser Asp Ser Tyr Thr Ser Tyr Ser Pro Ser Phe Gln
1               5                   10                  15

Gly

<210> SEQ ID NO 894
<211> LENGTH: 11
<212> TYPE: PRT
<213> ORGANISM: Artificial Sequence
<220> FEATURE:
<223> OTHER INFORMATION: Recombinant protein

<400> SEQUENCE: 894

Leu His Tyr Tyr His Ser Glu Glu Phe Asp Val
1               5                   10

<210> SEQ ID NO 895
<211> LENGTH: 109
<212> TYPE: PRT
<213> ORGANISM: Artificial Sequence
<220> FEATURE:
<223> OTHER INFORMATION: Recombinant protein

<400> SEQUENCE: 895

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
                35                  40                  45
Ile Tyr Gly Gln Ser Ser Arg Thr Arg Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Phe Gly Asn Ser Gln
                 85                  90                  95
Leu Phe Thr Phe Gly Gln Gly Thr Lys Leu Glu Ile Lys
            100                 105

<210> SEQ ID NO 896
<211> LENGTH: 12
<212> TYPE: PRT
<213> ORGANISM: Artificial Sequence
<220> FEATURE:
<223> OTHER INFORMATION: Recombinant protein

<400> SEQUENCE: 896

Arg Ala Ser Gln Ser Val Ser Ser Ser Tyr Leu Ala
 1               5                  10

<210> SEQ ID NO 897
<211> LENGTH: 7
<212> TYPE: PRT
<213> ORGANISM: Artificial Sequence
<220> FEATURE:
<223> OTHER INFORMATION: Recombinant protein

<400> SEQUENCE: 897

Gly Gln Ser Ser Arg Thr Arg
 1               5

<210> SEQ ID NO 898
<211> LENGTH: 10
<212> TYPE: PRT
<213> ORGANISM: Artificial Sequence
<220> FEATURE:
<223> OTHER INFORMATION: Recombinant protein

<400> SEQUENCE: 898

Gln Gln Phe Gly Asn Ser Gln Leu Phe Thr
 1               5                  10

<210> SEQ ID NO 899
<211> LENGTH: 120
<212> TYPE: PRT
<213> ORGANISM: Artificial Sequence
<220> FEATURE:
<223> OTHER INFORMATION: Recombinant protein

<400> SEQUENCE: 899

Glu Val Gln Leu Val Gln Ser Gly Ala Glu Val Lys Lys Pro Gly Glu
 1               5                  10                  15
Ser Leu Arg Ile Ser Cys Lys Gly Ser Gly Tyr Ser Phe Thr Thr Ser
                20                  25                  30
Trp Ile Ser Trp Val Arg Gln Met Pro Gly Lys Gly Leu Glu Trp Met
            35                  40                  45
Gly Met Ile Asp Pro Ser Asp Ser Tyr Thr Ser Tyr Ser Pro Ser Phe
 50                  55                  60
Gln Gly His Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
```

85                  90                  95
Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 900
<211> LENGTH: 5
<212> TYPE: PRT
<213> ORGANISM: Artificial Sequence
<220> FEATURE:
<223> OTHER INFORMATION: Recombinant protein

<400> SEQUENCE: 900

Thr Ser Trp Ile Ser
1               5

<210> SEQ ID NO 901
<211> LENGTH: 17
<212> TYPE: PRT
<213> ORGANISM: Artificial Sequence
<220> FEATURE:
<223> OTHER INFORMATION: Recombinant protein

<400> SEQUENCE: 901

Met Ile Asp Pro Ser Asp Ser Tyr Thr Ser Tyr Ser Pro Ser Phe Gln
1               5                   10                  15

Gly

<210> SEQ ID NO 902
<211> LENGTH: 11
<212> TYPE: PRT
<213> ORGANISM: Artificial Sequence
<220> FEATURE:
<223> OTHER INFORMATION: Recombinant protein

<400> SEQUENCE: 902

Leu His Tyr Tyr His Ser Glu Glu Phe Asp Val
1               5                   10

<210> SEQ ID NO 903
<211> LENGTH: 109
<212> TYPE: PRT
<213> ORGANISM: Artificial Sequence
<220> FEATURE:
<223> OTHER INFORMATION: Recombinant protein

<400> SEQUENCE: 903

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asn Ser Gln
                85                  90                  95

Leu Phe Thr Phe Gly Gln Gly Thr Lys Leu Glu Ile Lys
            100                 105

<210> SEQ ID NO 904
<211> LENGTH: 12
<212> TYPE: PRT
<213> ORGANISM: Artificial Sequence
<220> FEATURE:
<223> OTHER INFORMATION: Recombinant protein

<400> SEQUENCE: 904

Arg Ala Ser Gln Ser Val Ser Ser Ser Tyr Leu Ala
1               5                   10

<210> SEQ ID NO 905
<211> LENGTH: 7
<212> TYPE: PRT
<213> ORGANISM: Artificial Sequence
<220> FEATURE:
<223> OTHER INFORMATION: Recombinant protein

<400> SEQUENCE: 905

Gly Gln Ser Ser Arg Thr Arg
1               5

<210> SEQ ID NO 906
<211> LENGTH: 10
<212> TYPE: PRT
<213> ORGANISM: Artificial Sequence
<220> FEATURE:
<223> OTHER INFORMATION: Recombinant protein

<400> SEQUENCE: 906

Gln Gln Phe Gly Asn Ser Gln Leu Phe Thr
1               5                   10

<210> SEQ ID NO 907
<211> LENGTH: 120
<212> TYPE: PRT
<213> ORGANISM: Artificial Sequence
<220> FEATURE:
<223> OTHER INFORMATION: Recombinant protein

<400> SEQUENCE: 907

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 908
<211> LENGTH: 5
<212> TYPE: PRT
<213> ORGANISM: Artificial Sequence

```
<220> FEATURE:
<223> OTHER INFORMATION: Recombinant protein

<400> SEQUENCE: 908

Thr Ser Trp Ile Ser
1               5

<210> SEQ ID NO 909
<211> LENGTH: 17
<212> TYPE: PRT
<213> ORGANISM: Artificial Sequence
<220> FEATURE:
<223> OTHER INFORMATION: Recombinant protein

<400> SEQUENCE: 909

Met Ile Asp Pro Ser Asp Ser Phe Thr Ser Tyr Ser Pro Ser Phe Gln
1               5                   10                  15

Gly

<210> SEQ ID NO 910
<211> LENGTH: 11
<212> TYPE: PRT
<213> ORGANISM: Artificial Sequence
<220> FEATURE:
<223> OTHER INFORMATION: Recombinant protein

<400> SEQUENCE: 910

Leu His Tyr Tyr Asn Ser Glu Glu Phe Asp Val
1               5                   10

<210> SEQ ID NO 911
<211> LENGTH: 109
<212> TYPE: PRT
<213> ORGANISM: Artificial Sequence
<220> FEATURE:
<223> OTHER INFORMATION: Recombinant protein

<400> SEQUENCE: 911

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asn Ser Gln
                85                  90                  95

Leu Phe Thr Phe Gly Gln Gly Thr Lys Leu Glu Ile Lys
            100                 105

<210> SEQ ID NO 912
<211> LENGTH: 12
<212> TYPE: PRT
<213> ORGANISM: Artificial Sequence
<220> FEATURE:
<223> OTHER INFORMATION: Recombinant protein

<400> SEQUENCE: 912

Arg Ala Ser Gln Ser Val Ser Ser Ser Tyr Leu Ala
1               5                   10
```

<210> SEQ ID NO 913
<211> LENGTH: 7
<212> TYPE: PRT
<213> ORGANISM: Artificial Sequence
<220> FEATURE:
<223> OTHER INFORMATION: Recombinant protein

<400> SEQUENCE: 913

Gly Gln Ser Ser Arg Thr Arg
1               5

<210> SEQ ID NO 914
<211> LENGTH: 10
<212> TYPE: PRT
<213> ORGANISM: Artificial Sequence
<220> FEATURE:
<223> OTHER INFORMATION: Recombinant protein

<400> SEQUENCE: 914

Gln Gln Phe Gly Asn Ser Gln Leu Phe Thr
1               5                   10

<210> SEQ ID NO 915
<211> LENGTH: 120
<212> TYPE: PRT
<213> ORGANISM: Artificial Sequence
<220> FEATURE:
<223> OTHER INFORMATION: Recombinant protein

<400> SEQUENCE: 915

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 916
<211> LENGTH: 5
<212> TYPE: PRT
<213> ORGANISM: Artificial Sequence
<220> FEATURE:
<223> OTHER INFORMATION: Recombinant protein

<400> SEQUENCE: 916

Thr Ser Trp Ile Val
1               5

<210> SEQ ID NO 917
<211> LENGTH: 17
<212> TYPE: PRT
<213> ORGANISM: Artificial Sequence
<220> FEATURE:
<223> OTHER INFORMATION: Recombinant protein

<400> SEQUENCE: 917

Met Ile Asp Pro Ser Asp Ser Tyr Thr Ser Tyr Ser Pro Ser Phe Gln
1               5                   10                  15
Gly

<210> SEQ ID NO 918
<211> LENGTH: 11
<212> TYPE: PRT
<213> ORGANISM: Artificial Sequence
<220> FEATURE:
<223> OTHER INFORMATION: Recombinant protein

<400> SEQUENCE: 918

Leu His Tyr Tyr Asn Ser Glu Glu Phe Asp Val
1               5                   10

<210> SEQ ID NO 919
<211> LENGTH: 109
<212> TYPE: PRT
<213> ORGANISM: Artificial Sequence
<220> FEATURE:
<223> OTHER INFORMATION: Recombinant protein

<400> SEQUENCE: 919

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asn Ser Gln
                85                  90                  95

Leu Phe Thr Phe Gly Gln Gly Thr Lys Leu Glu Ile Lys
            100                 105

<210> SEQ ID NO 920
<211> LENGTH: 12
<212> TYPE: PRT
<213> ORGANISM: Artificial Sequence
<220> FEATURE:
<223> OTHER INFORMATION: Recombinant protein

<400> SEQUENCE: 920

Arg Ala Ser Gln Ser Val Ser Ser Ser Tyr Leu Ala
1               5                   10

<210> SEQ ID NO 921
<211> LENGTH: 7
<212> TYPE: PRT
<213> ORGANISM: Artificial Sequence
<220> FEATURE:
<223> OTHER INFORMATION: Recombinant protein

<400> SEQUENCE: 921

Gly Gln Ser Ser Arg Thr Arg
1               5

<210> SEQ ID NO 922
<211> LENGTH: 10
<212> TYPE: PRT
<213> ORGANISM: Artificial Sequence
<220> FEATURE:
<223> OTHER INFORMATION: Recombinant protein

<400> SEQUENCE: 922

Gln Gln Phe Gly Asn Ser Gln Leu Phe Thr
1               5                   10

<210> SEQ ID NO 923
<211> LENGTH: 120
<212> TYPE: PRT
<213> ORGANISM: Artificial Sequence
<220> FEATURE:
<223> OTHER INFORMATION: Recombinant protein

<400> SEQUENCE: 923

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 924
<211> LENGTH: 5
<212> TYPE: PRT
<213> ORGANISM: Artificial Sequence
<220> FEATURE:
<223> OTHER INFORMATION: Recombinant protein

<400> SEQUENCE: 924

Thr Ser Trp Ile Val
1               5

<210> SEQ ID NO 925
<211> LENGTH: 17
<212> TYPE: PRT
<213> ORGANISM: Artificial Sequence
<220> FEATURE:
<223> OTHER INFORMATION: Recombinant protein

<400> SEQUENCE: 925

Met Ile Asp Pro Ser Asp Ser Tyr Thr Ser Tyr Ser Pro Ser Phe Gln
1               5                   10                  15

Gly

<210> SEQ ID NO 926
<211> LENGTH: 11

```
<212> TYPE: PRT
<213> ORGANISM: Artificial Sequence
<220> FEATURE:
<223> OTHER INFORMATION: Recombinant protein

<400> SEQUENCE: 926

Leu His Tyr Tyr Asn Ser Glu Glu Phe Asp Val
1               5                   10

<210> SEQ ID NO 927
<211> LENGTH: 109
<212> TYPE: PRT
<213> ORGANISM: Artificial Sequence
<220> FEATURE:
<223> OTHER INFORMATION: Recombinant protein

<400> SEQUENCE: 927

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asn Ser Gln
                85                  90                  95

Leu Phe Thr Phe Gly Gln Gly Thr Lys Leu Glu Ile Lys
            100                 105

<210> SEQ ID NO 928
<211> LENGTH: 12
<212> TYPE: PRT
<213> ORGANISM: Artificial Sequence
<220> FEATURE:
<223> OTHER INFORMATION: Recombinant protein

<400> SEQUENCE: 928

Arg Ala Ser Gln Ser Val Ser Ser Ser Tyr Leu Ala
1               5                   10

<210> SEQ ID NO 929
<211> LENGTH: 7
<212> TYPE: PRT
<213> ORGANISM: Artificial Sequence
<220> FEATURE:
<223> OTHER INFORMATION: Recombinant protein

<400> SEQUENCE: 929

Gly Gln Ser Ser Arg Thr Arg
1               5

<210> SEQ ID NO 930
<211> LENGTH: 10
<212> TYPE: PRT
<213> ORGANISM: Artificial Sequence
<220> FEATURE:
<223> OTHER INFORMATION: Recombinant protein

<400> SEQUENCE: 930

Gln Gln Phe Gly Asn Ser Gln Leu Phe Thr
1               5                   10
```

<210> SEQ ID NO 931
<211> LENGTH: 120
<212> TYPE: PRT
<213> ORGANISM: Artificial Sequence
<220> FEATURE:
<223> OTHER INFORMATION: Recombinant protein

<400> SEQUENCE: 931

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 932
<211> LENGTH: 5
<212> TYPE: PRT
<213> ORGANISM: Artificial Sequence
<220> FEATURE:
<223> OTHER INFORMATION: Recombinant protein

<400> SEQUENCE: 932

Thr Ser Trp Ile Ser
1               5

<210> SEQ ID NO 933
<211> LENGTH: 17
<212> TYPE: PRT
<213> ORGANISM: Artificial Sequence
<220> FEATURE:
<223> OTHER INFORMATION: Recombinant protein

<400> SEQUENCE: 933

Met Ile Asp Pro Ser Asp Ser Tyr Thr Ser Tyr Ser Pro Ser Phe Gln
1               5                   10                  15

Gly

<210> SEQ ID NO 934
<211> LENGTH: 11
<212> TYPE: PRT
<213> ORGANISM: Artificial Sequence
<220> FEATURE:
<223> OTHER INFORMATION: Recombinant protein

<400> SEQUENCE: 934

Leu His Tyr Tyr Asn Ser Glu Glu Phe Asp Val
1               5                   10

<210> SEQ ID NO 935
<211> LENGTH: 109

```
<212> TYPE: PRT
<213> ORGANISM: Artificial Sequence
<220> FEATURE:
<223> OTHER INFORMATION: Recombinant protein

<400> SEQUENCE: 935

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Gln Ser Gln
                85                  90                  95

Leu Phe Thr Phe Gly Gln Gly Thr Lys Leu Glu Ile Lys
            100                 105

<210> SEQ ID NO 936
<211> LENGTH: 12
<212> TYPE: PRT
<213> ORGANISM: Artificial Sequence
<220> FEATURE:
<223> OTHER INFORMATION: Recombinant protein

<400> SEQUENCE: 936

Arg Ala Ser Gln Ser Val Ser Ser Ser Tyr Leu Ala
1               5                   10

<210> SEQ ID NO 937
<211> LENGTH: 7
<212> TYPE: PRT
<213> ORGANISM: Artificial Sequence
<220> FEATURE:
<223> OTHER INFORMATION: Recombinant protein

<400> SEQUENCE: 937

Gly Gln Ser Ser Arg Thr Arg
1               5

<210> SEQ ID NO 938
<211> LENGTH: 10
<212> TYPE: PRT
<213> ORGANISM: Artificial Sequence
<220> FEATURE:
<223> OTHER INFORMATION: Recombinant protein

<400> SEQUENCE: 938

Gln Gln Phe Gly Gln Ser Gln Leu Phe Thr
1               5                   10

<210> SEQ ID NO 939
<211> LENGTH: 120
<212> TYPE: PRT
<213> ORGANISM: Artificial Sequence
<220> FEATURE:
<223> OTHER INFORMATION: Recombinant protein

<400> SEQUENCE: 939

Glu Val Gln Leu Val Gln Ser Gly Ala Glu Val Lys Lys Pro Gly Glu
1               5                   10                  15
```

```
Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
            115                 120

<210> SEQ ID NO 940
<211> LENGTH: 5
<212> TYPE: PRT
<213> ORGANISM: Artificial Sequence
<220> FEATURE:
<223> OTHER INFORMATION: Recombinant protein

<400> SEQUENCE: 940

Thr Ser Trp Ile Ser
1               5

<210> SEQ ID NO 941
<211> LENGTH: 17
<212> TYPE: PRT
<213> ORGANISM: Artificial Sequence
<220> FEATURE:
<223> OTHER INFORMATION: Recombinant protein

<400> SEQUENCE: 941

Met Ile Asp Pro Ser Asp Ser Phe Thr Ser Tyr Ser Pro Ser Phe Gln
1               5                   10                  15

Gly

<210> SEQ ID NO 942
<211> LENGTH: 11
<212> TYPE: PRT
<213> ORGANISM: Artificial Sequence
<220> FEATURE:
<223> OTHER INFORMATION: Recombinant protein

<400> SEQUENCE: 942

Leu His Tyr Tyr His Ser Glu Glu Phe Asp Val
1               5                   10

<210> SEQ ID NO 943
<211> LENGTH: 109
<212> TYPE: PRT
<213> ORGANISM: Artificial Sequence
<220> FEATURE:
<223> OTHER INFORMATION: Recombinant protein

<400> SEQUENCE: 943

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
             35                  40                  45

Ile Tyr Gly Gln Ser Ser Arg Thr Arg Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Gln Ser Gln
                 85                  90                  95

Leu Phe Thr Phe Gly Gln Gly Thr Lys Leu Glu Ile Lys
                100                 105
```

<210> SEQ ID NO 944
<211> LENGTH: 12
<212> TYPE: PRT
<213> ORGANISM: Artificial Sequence
<220> FEATURE:
<223> OTHER INFORMATION: Recombinant protein

<400> SEQUENCE: 944

```
Arg Ala Ser Gln Ser Val Ser Ser Ser Tyr Leu Ala
 1               5                  10
```

<210> SEQ ID NO 945
<211> LENGTH: 7
<212> TYPE: PRT
<213> ORGANISM: Artificial Sequence
<220> FEATURE:
<223> OTHER INFORMATION: Recombinant protein

<400> SEQUENCE: 945

```
Gly Gln Ser Ser Arg Thr Arg
 1               5
```

<210> SEQ ID NO 946
<211> LENGTH: 10
<212> TYPE: PRT
<213> ORGANISM: Artificial Sequence
<220> FEATURE:
<223> OTHER INFORMATION: Recombinant protein

<400> SEQUENCE: 946

```
Gln Gln Phe Gly Gln Ser Gln Leu Phe Thr
 1               5                  10
```

<210> SEQ ID NO 947
<211> LENGTH: 120
<212> TYPE: PRT
<213> ORGANISM: Artificial Sequence
<220> FEATURE:
<223> OTHER INFORMATION: Recombinant protein

<400> SEQUENCE: 947

```
Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Thr Ser
                 20                  25                  30

Trp Ile Ser Trp Val Arg Gln Met Pro Gly Lys Gly Leu Glu Trp Met
             35                  40                  45

Gly Met Ile Asp Pro Ser Asp Ser Tyr Thr Tyr Ser Pro Ser Phe
 50                  55                  60

Gln Gly His Val Thr Ile Ser Ala Asp Lys Ser Ile Ser Thr Ala Tyr
 65                  70                  75                  80
```

```
Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 948
<211> LENGTH: 5
<212> TYPE: PRT
<213> ORGANISM: Artificial Sequence
<220> FEATURE:
<223> OTHER INFORMATION: Recombinant protein

<400> SEQUENCE: 948

Thr Ser Trp Ile Ser
1               5

<210> SEQ ID NO 949
<211> LENGTH: 17
<212> TYPE: PRT
<213> ORGANISM: Artificial Sequence
<220> FEATURE:
<223> OTHER INFORMATION: Recombinant protein

<400> SEQUENCE: 949

Met Ile Asp Pro Ser Asp Ser Tyr Thr Ser Tyr Ser Pro Ser Phe Gln
1               5                   10                  15

Gly

<210> SEQ ID NO 950
<211> LENGTH: 11
<212> TYPE: PRT
<213> ORGANISM: Artificial Sequence
<220> FEATURE:
<223> OTHER INFORMATION: Recombinant protein

<400> SEQUENCE: 950

Leu His Tyr Tyr His Ser Glu Glu Phe Asp Val
1               5                   10

<210> SEQ ID NO 951
<211> LENGTH: 109
<212> TYPE: PRT
<213> ORGANISM: Artificial Sequence
<220> FEATURE:
<223> OTHER INFORMATION: Recombinant protein

<400> SEQUENCE: 951

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Gln Ser Gln
                85                  90                  95

Leu Phe Thr Phe Gly Gln Gly Thr Lys Leu Glu Ile Lys
```

-continued

```
                    100                 105

<210> SEQ ID NO 952
<211> LENGTH: 12
<212> TYPE: PRT
<213> ORGANISM: Artificial Sequence
<220> FEATURE:
<223> OTHER INFORMATION: Recombinant protein

<400> SEQUENCE: 952

Arg Ala Ser Gln Ser Val Ser Ser Ser Tyr Leu Ala
1               5                   10

<210> SEQ ID NO 953
<211> LENGTH: 7
<212> TYPE: PRT
<213> ORGANISM: Artificial Sequence
<220> FEATURE:
<223> OTHER INFORMATION: Recombinant protein

<400> SEQUENCE: 953

Gly Gln Ser Ser Arg Thr Arg
1               5

<210> SEQ ID NO 954
<211> LENGTH: 10
<212> TYPE: PRT
<213> ORGANISM: Artificial Sequence
<220> FEATURE:
<223> OTHER INFORMATION: Recombinant protein

<400> SEQUENCE: 954

Gln Gln Phe Gly Gln Ser Gln Leu Phe Thr
1               5                   10

<210> SEQ ID NO 955
<211> LENGTH: 120
<212> TYPE: PRT
<213> ORGANISM: Artificial Sequence
<220> FEATURE:
<223> OTHER INFORMATION: Recombinant protein

<400> SEQUENCE: 955

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Phe Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
                100                 105                 110

Gly Thr Leu Val Thr Val Ser Ser
            115                 120

<210> SEQ ID NO 956
<211> LENGTH: 5
<212> TYPE: PRT
```

```
<213> ORGANISM: Artificial Sequence
<220> FEATURE:
<223> OTHER INFORMATION: Recombinant protein

<400> SEQUENCE: 956

Thr Ser Trp Ile Ser
1               5

<210> SEQ ID NO 957
<211> LENGTH: 17
<212> TYPE: PRT
<213> ORGANISM: Artificial Sequence
<220> FEATURE:
<223> OTHER INFORMATION: Recombinant protein

<400> SEQUENCE: 957

Met Ile Asp Pro Ser Asp Ser Phe Thr Ser Tyr Ser Pro Ser Phe Gln
1               5                   10                  15

Gly

<210> SEQ ID NO 958
<211> LENGTH: 11
<212> TYPE: PRT
<213> ORGANISM: Artificial Sequence
<220> FEATURE:
<223> OTHER INFORMATION: Recombinant protein

<400> SEQUENCE: 958

Leu His Tyr Tyr Asn Ser Glu Glu Phe Asp Val
1               5                   10

<210> SEQ ID NO 959
<211> LENGTH: 109
<212> TYPE: PRT
<213> ORGANISM: Artificial Sequence
<220> FEATURE:
<223> OTHER INFORMATION: Recombinant protein

<400> SEQUENCE: 959

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Gln Ser Gln
                85                  90                  95

Leu Phe Thr Phe Gly Gln Gly Thr Lys Leu Glu Ile Lys
            100                 105

<210> SEQ ID NO 960
<211> LENGTH: 12
<212> TYPE: PRT
<213> ORGANISM: Artificial Sequence
<220> FEATURE:
<223> OTHER INFORMATION: Recombinant protein

<400> SEQUENCE: 960

Arg Ala Ser Gln Ser Val Ser Ser Ser Tyr Leu Ala
```

-continued

```
<210> SEQ ID NO 961
<211> LENGTH: 7
<212> TYPE: PRT
<213> ORGANISM: Artificial Sequence
<220> FEATURE:
<223> OTHER INFORMATION: Recombinant protein

<400> SEQUENCE: 961

Gly Gln Ser Ser Arg Thr Arg
1               5

<210> SEQ ID NO 962
<211> LENGTH: 10
<212> TYPE: PRT
<213> ORGANISM: Artificial Sequence
<220> FEATURE:
<223> OTHER INFORMATION: Recombinant protein

<400> SEQUENCE: 962

Gln Gln Phe Gly Gln Ser Gln Leu Phe Thr
1               5                   10

<210> SEQ ID NO 963
<211> LENGTH: 120
<212> TYPE: PRT
<213> ORGANISM: Artificial Sequence
<220> FEATURE:
<223> OTHER INFORMATION: Recombinant protein

<400> SEQUENCE: 963

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 964
<211> LENGTH: 5
<212> TYPE: PRT
<213> ORGANISM: Artificial Sequence
<220> FEATURE:
<223> OTHER INFORMATION: Recombinant protein

<400> SEQUENCE: 964

Thr Ser Trp Ile Val
1               5

<210> SEQ ID NO 965
<211> LENGTH: 17
<212> TYPE: PRT
```

```
<213> ORGANISM: Artificial Sequence
<220> FEATURE:
<223> OTHER INFORMATION: Recombinant protein

<400> SEQUENCE: 965

Met Ile Asp Pro Ser Asp Ser Tyr Thr Ser Tyr Ser Pro Ser Phe Gln
1               5                   10                  15

Gly

<210> SEQ ID NO 966
<211> LENGTH: 11
<212> TYPE: PRT
<213> ORGANISM: Artificial Sequence
<220> FEATURE:
<223> OTHER INFORMATION: Recombinant protein

<400> SEQUENCE: 966

Leu His Tyr Tyr Asn Ser Glu Glu Phe Asp Val
1               5                   10

<210> SEQ ID NO 967
<211> LENGTH: 109
<212> TYPE: PRT
<213> ORGANISM: Artificial Sequence
<220> FEATURE:
<223> OTHER INFORMATION: Recombinant protein

<400> SEQUENCE: 967

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Gln Ser Gln
                85                  90                  95

Leu Phe Thr Phe Gly Gln Gly Thr Lys Leu Glu Ile Lys
            100                 105

<210> SEQ ID NO 968
<211> LENGTH: 12
<212> TYPE: PRT
<213> ORGANISM: Artificial Sequence
<220> FEATURE:
<223> OTHER INFORMATION: Recombinant protein

<400> SEQUENCE: 968

Arg Ala Ser Gln Ser Val Ser Ser Ser Tyr Leu Ala
1               5                   10

<210> SEQ ID NO 969
<211> LENGTH: 7
<212> TYPE: PRT
<213> ORGANISM: Artificial Sequence
<220> FEATURE:
<223> OTHER INFORMATION: Recombinant protein

<400> SEQUENCE: 969

Gly Gln Ser Ser Arg Thr Arg
```

```
<210> SEQ ID NO 970
<211> LENGTH: 10
<212> TYPE: PRT
<213> ORGANISM: Artificial Sequence
<220> FEATURE:
<223> OTHER INFORMATION: Recombinant protein

<400> SEQUENCE: 970

Gln Gln Phe Gly Gln Ser Gln Leu Phe Thr
1               5                   10

<210> SEQ ID NO 971
<211> LENGTH: 120
<212> TYPE: PRT
<213> ORGANISM: Artificial Sequence
<220> FEATURE:
<223> OTHER INFORMATION: Recombinant protein

<400> SEQUENCE: 971

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 972
<211> LENGTH: 5
<212> TYPE: PRT
<213> ORGANISM: Artificial Sequence
<220> FEATURE:
<223> OTHER INFORMATION: Recombinant protein

<400> SEQUENCE: 972

Thr Ser Trp Ile Val
1               5

<210> SEQ ID NO 973
<211> LENGTH: 17
<212> TYPE: PRT
<213> ORGANISM: Artificial Sequence
<220> FEATURE:
<223> OTHER INFORMATION: Recombinant protein

<400> SEQUENCE: 973

Met Ile Asp Pro Ser Asp Ser Tyr Thr Ser Tyr Ser Pro Ser Phe Gln
1               5                   10                  15

Gly

<210> SEQ ID NO 974
```

-continued

```
<211> LENGTH: 11
<212> TYPE: PRT
<213> ORGANISM: Artificial Sequence
<220> FEATURE:
<223> OTHER INFORMATION: Recombinant protein

<400> SEQUENCE: 974

Leu His Tyr Tyr Asn Ser Glu Glu Phe Asp Val
1               5                   10

<210> SEQ ID NO 975
<211> LENGTH: 109
<212> TYPE: PRT
<213> ORGANISM: Artificial Sequence
<220> FEATURE:
<223> OTHER INFORMATION: Recombinant protein

<400> SEQUENCE: 975

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Gln Ser Gln
                85                  90                  95

Leu Phe Thr Phe Gly Gln Gly Thr Lys Leu Glu Ile Lys
            100                 105

<210> SEQ ID NO 976
<211> LENGTH: 12
<212> TYPE: PRT
<213> ORGANISM: Artificial Sequence
<220> FEATURE:
<223> OTHER INFORMATION: Recombinant protein

<400> SEQUENCE: 976

Arg Ala Ser Gln Ser Val Ser Ser Ser Tyr Leu Ala
1               5                   10

<210> SEQ ID NO 977
<211> LENGTH: 7
<212> TYPE: PRT
<213> ORGANISM: Artificial Sequence
<220> FEATURE:
<223> OTHER INFORMATION: Recombinant protein

<400> SEQUENCE: 977

Gly Gln Ser Ser Arg Thr Arg
1               5

<210> SEQ ID NO 978
<211> LENGTH: 10
<212> TYPE: PRT
<213> ORGANISM: Artificial Sequence
<220> FEATURE:
<223> OTHER INFORMATION: Recombinant protein

<400> SEQUENCE: 978

Gln Gln Phe Gly Gln Ser Gln Leu Phe Thr
```

```
<210> SEQ ID NO 979
<211> LENGTH: 120
<212> TYPE: PRT
<213> ORGANISM: Artificial Sequence
<220> FEATURE:
<223> OTHER INFORMATION: Recombinant protein

<400> SEQUENCE: 979

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 980
<211> LENGTH: 5
<212> TYPE: PRT
<213> ORGANISM: Artificial Sequence
<220> FEATURE:
<223> OTHER INFORMATION: Recombinant protein

<400> SEQUENCE: 980

Thr Ser Trp Ile Ser
1               5

<210> SEQ ID NO 981
<211> LENGTH: 17
<212> TYPE: PRT
<213> ORGANISM: Artificial Sequence
<220> FEATURE:
<223> OTHER INFORMATION: Recombinant protein

<400> SEQUENCE: 981

Met Ile Asp Pro Ser Asp Ser Tyr Thr Ser Tyr Ser Pro Ser Phe Gln
1               5                   10                  15

Gly

<210> SEQ ID NO 982
<211> LENGTH: 11
<212> TYPE: PRT
<213> ORGANISM: Artificial Sequence
<220> FEATURE:
<223> OTHER INFORMATION: Recombinant protein

<400> SEQUENCE: 982

Leu His Tyr Tyr Asn Ser Glu Glu Phe Asp Val
1               5                   10

<210> SEQ ID NO 983
```

```
<211> LENGTH: 109
<212> TYPE: PRT
<213> ORGANISM: Artificial Sequence
<220> FEATURE:
<223> OTHER INFORMATION: Recombinant protein

<400> SEQUENCE: 983

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ala Gln
                85                  90                  95

Leu Phe Thr Phe Gly Gln Gly Thr Lys Leu Glu Ile Lys
            100                 105

<210> SEQ ID NO 984
<211> LENGTH: 12
<212> TYPE: PRT
<213> ORGANISM: Artificial Sequence
<220> FEATURE:
<223> OTHER INFORMATION: Recombinant protein

<400> SEQUENCE: 984

Arg Ala Ser Gln Ser Val Ser Ser Ser Tyr Leu Ala
1               5                   10

<210> SEQ ID NO 985
<211> LENGTH: 7
<212> TYPE: PRT
<213> ORGANISM: Artificial Sequence
<220> FEATURE:
<223> OTHER INFORMATION: Recombinant protein

<400> SEQUENCE: 985

Gly Gln Ser Ser Arg Thr Arg
1               5

<210> SEQ ID NO 986
<211> LENGTH: 10
<212> TYPE: PRT
<213> ORGANISM: Artificial Sequence
<220> FEATURE:
<223> OTHER INFORMATION: Recombinant protein

<400> SEQUENCE: 986

Gln Gln Phe Gly Asp Ala Gln Leu Phe Thr
1               5                   10

<210> SEQ ID NO 987
<211> LENGTH: 120
<212> TYPE: PRT
<213> ORGANISM: Artificial Sequence
<220> FEATURE:
<223> OTHER INFORMATION: Recombinant protein

<400> SEQUENCE: 987

Glu Val Gln Leu Val Gln Ser Gly Ala Glu Val Lys Lys Pro Gly Glu
```

```
                1               5                  10                  15
Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Phe Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
            115                 120
```

<210> SEQ ID NO 988
<211> LENGTH: 5
<212> TYPE: PRT
<213> ORGANISM: Artificial Sequence
<220> FEATURE:
<223> OTHER INFORMATION: Recombinant protein

<400> SEQUENCE: 988

```
Thr Ser Trp Ile Ser
1               5
```

<210> SEQ ID NO 989
<211> LENGTH: 17
<212> TYPE: PRT
<213> ORGANISM: Artificial Sequence
<220> FEATURE:
<223> OTHER INFORMATION: Recombinant protein

<400> SEQUENCE: 989

```
Met Ile Asp Pro Ser Asp Ser Phe Thr Ser Tyr Ser Pro Ser Phe Gln
1               5                   10                  15

Gly
```

<210> SEQ ID NO 990
<211> LENGTH: 11
<212> TYPE: PRT
<213> ORGANISM: Artificial Sequence
<220> FEATURE:
<223> OTHER INFORMATION: Recombinant protein

<400> SEQUENCE: 990

```
Leu His Tyr Tyr His Ser Glu Glu Phe Asp Val
1               5                   10
```

<210> SEQ ID NO 991
<211> LENGTH: 109
<212> TYPE: PRT
<213> ORGANISM: Artificial Sequence
<220> FEATURE:
<223> OTHER INFORMATION: Recombinant protein

<400> SEQUENCE: 991

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Asp Ala Gln
                 85                  90                  95

Leu Phe Thr Phe Gly Gln Gly Thr Lys Leu Glu Ile Lys
            100                 105

<210> SEQ ID NO 992
<211> LENGTH: 12
<212> TYPE: PRT
<213> ORGANISM: Artificial Sequence
<220> FEATURE:
<223> OTHER INFORMATION: Recombinant protein

<400> SEQUENCE: 992

Arg Ala Ser Gln Ser Val Ser Ser Ser Tyr Leu Ala
1               5                  10

<210> SEQ ID NO 993
<211> LENGTH: 7
<212> TYPE: PRT
<213> ORGANISM: Artificial Sequence
<220> FEATURE:
<223> OTHER INFORMATION: Recombinant protein

<400> SEQUENCE: 993

Gly Gln Ser Ser Arg Thr Arg
1               5

<210> SEQ ID NO 994
<211> LENGTH: 10
<212> TYPE: PRT
<213> ORGANISM: Artificial Sequence
<220> FEATURE:
<223> OTHER INFORMATION: Recombinant protein

<400> SEQUENCE: 994

Gln Gln Phe Gly Asp Ala Gln Leu Phe Thr
1               5                  10

<210> SEQ ID NO 995
<211> LENGTH: 120
<212> TYPE: PRT
<213> ORGANISM: Artificial Sequence
<220> FEATURE:
<223> OTHER INFORMATION: Recombinant protein

<400> SEQUENCE: 995

Glu Val Gln Leu Val Gln Ser Gly Ala Glu Val Lys Lys Pro Gly Glu
1               5                  10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 996
<211> LENGTH: 5
<212> TYPE: PRT
<213> ORGANISM: Artificial Sequence
<220> FEATURE:
<223> OTHER INFORMATION: Recombinant protein

<400> SEQUENCE: 996

Thr Ser Trp Ile Ser
1               5

<210> SEQ ID NO 997
<211> LENGTH: 17
<212> TYPE: PRT
<213> ORGANISM: Artificial Sequence
<220> FEATURE:
<223> OTHER INFORMATION: Recombinant protein

<400> SEQUENCE: 997

Met Ile Asp Pro Ser Asp Ser Tyr Thr Ser Tyr Ser Pro Ser Phe Gln
1               5                   10                  15

Gly

<210> SEQ ID NO 998
<211> LENGTH: 11
<212> TYPE: PRT
<213> ORGANISM: Artificial Sequence
<220> FEATURE:
<223> OTHER INFORMATION: Recombinant protein

<400> SEQUENCE: 998

Leu His Tyr Tyr His Ser Glu Glu Phe Asp Val
1               5                   10

<210> SEQ ID NO 999
<211> LENGTH: 109
<212> TYPE: PRT
<213> ORGANISM: Artificial Sequence
<220> FEATURE:
<223> OTHER INFORMATION: Recombinant protein

<400> SEQUENCE: 999

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ala Gln
                85                  90                  95
```

Leu Phe Thr Phe Gly Gln Gly Thr Lys Leu Glu Ile Lys
            100                 105

<210> SEQ ID NO 1000
<211> LENGTH: 12
<212> TYPE: PRT
<213> ORGANISM: Artificial Sequence
<220> FEATURE:
<223> OTHER INFORMATION: Recombinant protein

<400> SEQUENCE: 1000

Arg Ala Ser Gln Ser Val Ser Ser Tyr Leu Ala
1               5                   10

<210> SEQ ID NO 1001
<211> LENGTH: 7
<212> TYPE: PRT
<213> ORGANISM: Artificial Sequence
<220> FEATURE:
<223> OTHER INFORMATION: Recombinant protein

<400> SEQUENCE: 1001

Gly Gln Ser Ser Arg Thr Arg
1               5

<210> SEQ ID NO 1002
<211> LENGTH: 10
<212> TYPE: PRT
<213> ORGANISM: Artificial Sequence
<220> FEATURE:
<223> OTHER INFORMATION: Recombinant protein

<400> SEQUENCE: 1002

Gln Gln Phe Gly Asp Ala Gln Leu Phe Thr
1               5                   10

<210> SEQ ID NO 1003
<211> LENGTH: 120
<212> TYPE: PRT
<213> ORGANISM: Artificial Sequence
<220> FEATURE:
<223> OTHER INFORMATION: Recombinant protein

<400> SEQUENCE: 1003

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1004
<211> LENGTH: 5

```
<212> TYPE: PRT
<213> ORGANISM: Artificial Sequence
<220> FEATURE:
<223> OTHER INFORMATION: Recombinant protein

<400> SEQUENCE: 1004

Thr Ser Trp Ile Ser
1               5

<210> SEQ ID NO 1005
<211> LENGTH: 17
<212> TYPE: PRT
<213> ORGANISM: Artificial Sequence
<220> FEATURE:
<223> OTHER INFORMATION: Recombinant protein

<400> SEQUENCE: 1005

Met Ile Asp Pro Ser Asp Ser Phe Thr Ser Tyr Ser Pro Ser Phe Gln
1               5                   10                  15

Gly

<210> SEQ ID NO 1006
<211> LENGTH: 11
<212> TYPE: PRT
<213> ORGANISM: Artificial Sequence
<220> FEATURE:
<223> OTHER INFORMATION: Recombinant protein

<400> SEQUENCE: 1006

Leu His Tyr Tyr Asn Ser Glu Glu Phe Asp Val
1               5                   10

<210> SEQ ID NO 1007
<211> LENGTH: 109
<212> TYPE: PRT
<213> ORGANISM: Artificial Sequence
<220> FEATURE:
<223> OTHER INFORMATION: Recombinant protein

<400> SEQUENCE: 1007

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ala Gln
                85                  90                  95

Leu Phe Thr Phe Gly Gln Gly Thr Lys Leu Glu Ile Lys
            100                 105

<210> SEQ ID NO 1008
<211> LENGTH: 12
<212> TYPE: PRT
<213> ORGANISM: Artificial Sequence
<220> FEATURE:
<223> OTHER INFORMATION: Recombinant protein

<400> SEQUENCE: 1008
```

Arg Ala Ser Gln Ser Val Ser Ser Ser Tyr Leu Ala
1               5                   10

<210> SEQ ID NO 1009
<211> LENGTH: 7
<212> TYPE: PRT
<213> ORGANISM: Artificial Sequence
<220> FEATURE:
<223> OTHER INFORMATION: Recombinant protein

<400> SEQUENCE: 1009

Gly Gln Ser Ser Arg Thr Arg
1               5

<210> SEQ ID NO 1010
<211> LENGTH: 10
<212> TYPE: PRT
<213> ORGANISM: Artificial Sequence
<220> FEATURE:
<223> OTHER INFORMATION: Recombinant protein

<400> SEQUENCE: 1010

Gln Gln Phe Gly Asp Ala Gln Leu Phe Thr
1               5                   10

<210> SEQ ID NO 1011
<211> LENGTH: 120
<212> TYPE: PRT
<213> ORGANISM: Artificial Sequence
<220> FEATURE:
<223> OTHER INFORMATION: Recombinant protein

<400> SEQUENCE: 1011

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1012
<211> LENGTH: 5
<212> TYPE: PRT
<213> ORGANISM: Artificial Sequence
<220> FEATURE:
<223> OTHER INFORMATION: Recombinant protein

<400> SEQUENCE: 1012

Thr Ser Trp Ile Val
1               5

<210> SEQ ID NO 1013
<211> LENGTH: 17

```
<212> TYPE: PRT
<213> ORGANISM: Artificial Sequence
<220> FEATURE:
<223> OTHER INFORMATION: Recombinant protein

<400> SEQUENCE: 1013

Met Ile Asp Pro Ser Asp Ser Tyr Thr Ser Tyr Ser Pro Ser Phe Gln
1               5                   10                  15

Gly

<210> SEQ ID NO 1014
<211> LENGTH: 11
<212> TYPE: PRT
<213> ORGANISM: Artificial Sequence
<220> FEATURE:
<223> OTHER INFORMATION: Recombinant protein

<400> SEQUENCE: 1014

Leu His Tyr Tyr Asn Ser Glu Glu Phe Asp Val
1               5                   10

<210> SEQ ID NO 1015
<211> LENGTH: 109
<212> TYPE: PRT
<213> ORGANISM: Artificial Sequence
<220> FEATURE:
<223> OTHER INFORMATION: Recombinant protein

<400> SEQUENCE: 1015

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ala Gln
                85                  90                  95

Leu Phe Thr Phe Gly Gln Gly Thr Lys Leu Glu Ile Lys
            100                 105

<210> SEQ ID NO 1016
<211> LENGTH: 12
<212> TYPE: PRT
<213> ORGANISM: Artificial Sequence
<220> FEATURE:
<223> OTHER INFORMATION: Recombinant protein

<400> SEQUENCE: 1016

Arg Ala Ser Gln Ser Val Ser Ser Ser Tyr Leu Ala
1               5                   10

<210> SEQ ID NO 1017
<211> LENGTH: 7
<212> TYPE: PRT
<213> ORGANISM: Artificial Sequence
<220> FEATURE:
<223> OTHER INFORMATION: Recombinant protein

<400> SEQUENCE: 1017
```

Gly Gln Ser Ser Arg Thr Arg
1               5

<210> SEQ ID NO 1018
<211> LENGTH: 10
<212> TYPE: PRT
<213> ORGANISM: Artificial Sequence
<220> FEATURE:
<223> OTHER INFORMATION: Recombinant protein

<400> SEQUENCE: 1018

Gln Gln Phe Gly Asp Ala Gln Leu Phe Thr
1               5                   10

<210> SEQ ID NO 1019
<211> LENGTH: 120
<212> TYPE: PRT
<213> ORGANISM: Artificial Sequence
<220> FEATURE:
<223> OTHER INFORMATION: Recombinant protein

<400> SEQUENCE: 1019

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
                100                 105                 110

Gly Thr Met Val Thr Val Ser Ser
        115                 120

<210> SEQ ID NO 1020
<211> LENGTH: 5
<212> TYPE: PRT
<213> ORGANISM: Artificial Sequence
<220> FEATURE:
<223> OTHER INFORMATION: Recombinant protein

<400> SEQUENCE: 1020

Thr Ser Trp Ile Val
1               5

<210> SEQ ID NO 1021
<211> LENGTH: 17
<212> TYPE: PRT
<213> ORGANISM: Artificial Sequence
<220> FEATURE:
<223> OTHER INFORMATION: Recombinant protein

<400> SEQUENCE: 1021

Met Ile Asp Pro Ser Asp Ser Tyr Thr Ser Tyr Ser Pro Ser Phe Gln
1               5                   10                  15

Gly

```
<210> SEQ ID NO 1022
<211> LENGTH: 11
<212> TYPE: PRT
<213> ORGANISM: Artificial Sequence
<220> FEATURE:
<223> OTHER INFORMATION: Recombinant protein

<400> SEQUENCE: 1022

Leu His Tyr Tyr Asn Ser Glu Glu Phe Asp Val
1               5                   10

<210> SEQ ID NO 1023
<211> LENGTH: 109
<212> TYPE: PRT
<213> ORGANISM: Artificial Sequence
<220> FEATURE:
<223> OTHER INFORMATION: Recombinant protein

<400> SEQUENCE: 1023

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Ala Gln
                85                  90                  95

Leu Phe Thr Phe Gly Gln Gly Thr Lys Leu Glu Ile Lys
            100                 105

<210> SEQ ID NO 1024
<211> LENGTH: 12
<212> TYPE: PRT
<213> ORGANISM: Artificial Sequence
<220> FEATURE:
<223> OTHER INFORMATION: Recombinant protein

<400> SEQUENCE: 1024

Arg Ala Ser Gln Ser Val Ser Ser Ser Tyr Leu Ala
1               5                   10

<210> SEQ ID NO 1025
<211> LENGTH: 7
<212> TYPE: PRT
<213> ORGANISM: Artificial Sequence
<220> FEATURE:
<223> OTHER INFORMATION: Recombinant protein

<400> SEQUENCE: 1025

Gly Gln Ser Ser Arg Thr Arg
1               5

<210> SEQ ID NO 1026
<211> LENGTH: 10
<212> TYPE: PRT
<213> ORGANISM: Artificial Sequence
<220> FEATURE:
<223> OTHER INFORMATION: Recombinant protein

<400> SEQUENCE: 1026
```

Gln Gln Phe Gly Asp Ala Gln Leu Phe Thr
1               5                  10

<210> SEQ ID NO 1027
<211> LENGTH: 120
<212> TYPE: PRT
<213> ORGANISM: Artificial Sequence
<220> FEATURE:
<223> OTHER INFORMATION: Recombinant protein

<400> SEQUENCE: 1027

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 1028
<211> LENGTH: 5
<212> TYPE: PRT
<213> ORGANISM: Artificial Sequence
<220> FEATURE:
<223> OTHER INFORMATION: Recombinant protein

<400> SEQUENCE: 1028

Thr Ser Trp Ile Ser
1               5

<210> SEQ ID NO 1029
<211> LENGTH: 17
<212> TYPE: PRT
<213> ORGANISM: Artificial Sequence
<220> FEATURE:
<223> OTHER INFORMATION: Recombinant protein

<400> SEQUENCE: 1029

Met Ile Asp Pro Ser Asp Ser Tyr Thr Ser Tyr Ser Pro Ser Phe Gln
1               5                   10                  15

Gly

<210> SEQ ID NO 1030
<211> LENGTH: 11
<212> TYPE: PRT
<213> ORGANISM: Artificial Sequence
<220> FEATURE:
<223> OTHER INFORMATION: Recombinant protein

<400> SEQUENCE: 1030

Leu His Tyr Tyr Asn Ser Glu Glu Phe Asp Val
1               5                   10

<210> SEQ ID NO 1031
<211> LENGTH: 109
<212> TYPE: PRT
<213> ORGANISM: Artificial Sequence
<220> FEATURE:
<223> OTHER INFORMATION: Recombinant protein

<400> SEQUENCE: 1031

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Thr Gln
                85                  90                  95

Leu Phe Thr Phe Gly Gln Gly Thr Lys Leu Glu Ile Lys
            100                 105

<210> SEQ ID NO 1032
<211> LENGTH: 12
<212> TYPE: PRT
<213> ORGANISM: Artificial Sequence
<220> FEATURE:
<223> OTHER INFORMATION: Recombinant protein

<400> SEQUENCE: 1032

Arg Ala Ser Gln Ser Val Ser Ser Ser Tyr Leu Ala
1               5                   10

<210> SEQ ID NO 1033
<211> LENGTH: 7
<212> TYPE: PRT
<213> ORGANISM: Artificial Sequence
<220> FEATURE:
<223> OTHER INFORMATION: Recombinant protein

<400> SEQUENCE: 1033

Gly Gln Ser Ser Arg Thr Arg
1               5

<210> SEQ ID NO 1034
<211> LENGTH: 10
<212> TYPE: PRT
<213> ORGANISM: Artificial Sequence
<220> FEATURE:
<223> OTHER INFORMATION: Recombinant protein

<400> SEQUENCE: 1034

Gln Gln Phe Gly Asp Thr Gln Leu Phe Thr
1               5                   10

<210> SEQ ID NO 1035
<211> LENGTH: 120
<212> TYPE: PRT
<213> ORGANISM: Artificial Sequence
<220> FEATURE:
<223> OTHER INFORMATION: Recombinant protein

<400> SEQUENCE: 1035

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
            115                 120

<210> SEQ ID NO 1036
<211> LENGTH: 5
<212> TYPE: PRT
<213> ORGANISM: Artificial Sequence
<220> FEATURE:
<223> OTHER INFORMATION: Recombinant protein

<400> SEQUENCE: 1036

Thr Ser Trp Ile Ser
1               5

<210> SEQ ID NO 1037
<211> LENGTH: 17
<212> TYPE: PRT
<213> ORGANISM: Artificial Sequence
<220> FEATURE:
<223> OTHER INFORMATION: Recombinant protein

<400> SEQUENCE: 1037

Met Ile Asp Pro Ser Asp Ser Phe Thr Ser Tyr Ser Pro Ser Phe Gln
1               5                   10                  15

Gly

<210> SEQ ID NO 1038
<211> LENGTH: 11
<212> TYPE: PRT
<213> ORGANISM: Artificial Sequence
<220> FEATURE:
<223> OTHER INFORMATION: Recombinant protein

<400> SEQUENCE: 1038

Leu His Tyr Tyr His Ser Glu Glu Phe Asp Val
1               5                   10

<210> SEQ ID NO 1039
<211> LENGTH: 109
<212> TYPE: PRT
<213> ORGANISM: Artificial Sequence
<220> FEATURE:
<223> OTHER INFORMATION: Recombinant protein

<400> SEQUENCE: 1039

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                    20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Thr Gln
                85                  90                  95

Leu Phe Thr Phe Gly Gln Gly Thr Lys Leu Glu Ile Lys
                100                 105
```

<210> SEQ ID NO 1040
<211> LENGTH: 12
<212> TYPE: PRT
<213> ORGANISM: Artificial Sequence
<220> FEATURE:
<223> OTHER INFORMATION: Recombinant protein

<400> SEQUENCE: 1040

```
Arg Ala Ser Gln Ser Val Ser Ser Ser Tyr Leu Ala
1               5                   10
```

<210> SEQ ID NO 1041
<211> LENGTH: 7
<212> TYPE: PRT
<213> ORGANISM: Artificial Sequence
<220> FEATURE:
<223> OTHER INFORMATION: Recombinant protein

<400> SEQUENCE: 1041

```
Gly Gln Ser Ser Arg Thr Arg
1               5
```

<210> SEQ ID NO 1042
<211> LENGTH: 10
<212> TYPE: PRT
<213> ORGANISM: Artificial Sequence
<220> FEATURE:
<223> OTHER INFORMATION: Recombinant protein

<400> SEQUENCE: 1042

```
Gln Gln Phe Gly Asp Thr Gln Leu Phe Thr
1               5                   10
```

<210> SEQ ID NO 1043
<211> LENGTH: 120
<212> TYPE: PRT
<213> ORGANISM: Artificial Sequence
<220> FEATURE:
<223> OTHER INFORMATION: Recombinant protein

<400> SEQUENCE: 1043

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
```

```
                65                  70                  75                  80
Leu Gln Trp Ser Ser Leu Lys Ala Ser Asp Thr Ala Met Tyr Tyr Cys
                    85                  90                  95

Ala Arg Leu His Tyr Tyr His Ser Glu Glu Phe Asp Val Trp Gly Gln
                100                 105                 110

Gly Thr Leu Val Thr Val Ser Ser
            115                 120

<210> SEQ ID NO 1044
<211> LENGTH: 5
<212> TYPE: PRT
<213> ORGANISM: Artificial Sequence
<220> FEATURE:
<223> OTHER INFORMATION: Recombinant protein

<400> SEQUENCE: 1044

Thr Ser Trp Ile Ser
1               5

<210> SEQ ID NO 1045
<211> LENGTH: 17
<212> TYPE: PRT
<213> ORGANISM: Artificial Sequence
<220> FEATURE:
<223> OTHER INFORMATION: Recombinant protein

<400> SEQUENCE: 1045

Met Ile Asp Pro Ser Asp Ser Tyr Thr Ser Tyr Ser Pro Ser Phe Gln
1               5                   10                  15

Gly

<210> SEQ ID NO 1046
<211> LENGTH: 11
<212> TYPE: PRT
<213> ORGANISM: Artificial Sequence
<220> FEATURE:
<223> OTHER INFORMATION: Recombinant protein

<400> SEQUENCE: 1046

Leu His Tyr Tyr His Ser Glu Glu Phe Asp Val
1               5                   10

<210> SEQ ID NO 1047
<211> LENGTH: 109
<212> TYPE: PRT
<213> ORGANISM: Artificial Sequence
<220> FEATURE:
<223> OTHER INFORMATION: Recombinant protein

<400> SEQUENCE: 1047

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Thr Gln
                85                  90                  95
```

Leu Phe Thr Phe Gly Gln Gly Thr Lys Leu Glu Ile Lys
            100                 105

<210> SEQ ID NO 1048
<211> LENGTH: 12
<212> TYPE: PRT
<213> ORGANISM: Artificial Sequence
<220> FEATURE:
<223> OTHER INFORMATION: Recombinant protein

<400> SEQUENCE: 1048

Arg Ala Ser Gln Ser Val Ser Ser Ser Tyr Leu Ala
1               5                   10

<210> SEQ ID NO 1049
<211> LENGTH: 7
<212> TYPE: PRT
<213> ORGANISM: Artificial Sequence
<220> FEATURE:
<223> OTHER INFORMATION: Recombinant protein

<400> SEQUENCE: 1049

Gly Gln Ser Ser Arg Thr Arg
1               5

<210> SEQ ID NO 1050
<211> LENGTH: 10
<212> TYPE: PRT
<213> ORGANISM: Artificial Sequence
<220> FEATURE:
<223> OTHER INFORMATION: Recombinant protein

<400> SEQUENCE: 1050

Gln Gln Phe Gly Asp Thr Gln Leu Phe Thr
1               5                   10

<210> SEQ ID NO 1051
<211> LENGTH: 120
<212> TYPE: PRT
<213> ORGANISM: Artificial Sequence
<220> FEATURE:
<223> OTHER INFORMATION: Recombinant protein

<400> SEQUENCE: 1051

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 1052

```
<211> LENGTH: 5
<212> TYPE: PRT
<213> ORGANISM: Artificial Sequence
<220> FEATURE:
<223> OTHER INFORMATION: Recombinant protein

<400> SEQUENCE: 1052

Thr Ser Trp Ile Ser
1               5

<210> SEQ ID NO 1053
<211> LENGTH: 17
<212> TYPE: PRT
<213> ORGANISM: Artificial Sequence
<220> FEATURE:
<223> OTHER INFORMATION: Recombinant protein

<400> SEQUENCE: 1053

Met Ile Asp Pro Ser Asp Ser Tyr Thr Ser Tyr Ser Pro Ser Phe Gln
1               5                   10                  15

Gly

<210> SEQ ID NO 1054
<211> LENGTH: 11
<212> TYPE: PRT
<213> ORGANISM: Artificial Sequence
<220> FEATURE:
<223> OTHER INFORMATION: Recombinant protein

<400> SEQUENCE: 1054

Leu His Tyr Tyr His Ser Glu Glu Phe Asp Val
1               5                   10

<210> SEQ ID NO 1055
<211> LENGTH: 109
<212> TYPE: PRT
<213> ORGANISM: Artificial Sequence
<220> FEATURE:
<223> OTHER INFORMATION: Recombinant protein

<400> SEQUENCE: 1055

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Thr Gln
                85                  90                  95

Leu Phe Thr Phe Gly Gln Gly Thr Lys Leu Glu Ile Lys
            100                 105

<210> SEQ ID NO 1056
<211> LENGTH: 12
<212> TYPE: PRT
<213> ORGANISM: Artificial Sequence
<220> FEATURE:
<223> OTHER INFORMATION: Recombinant protein

<400> SEQUENCE: 1056
```

Arg Ala Ser Gln Ser Val Ser Ser Tyr Leu Ala
1               5                   10

<210> SEQ ID NO 1057
<211> LENGTH: 7
<212> TYPE: PRT
<213> ORGANISM: Artificial Sequence
<220> FEATURE:
<223> OTHER INFORMATION: Recombinant protein

<400> SEQUENCE: 1057

Gly Gln Ser Ser Arg Thr Arg
1               5

<210> SEQ ID NO 1058
<211> LENGTH: 10
<212> TYPE: PRT
<213> ORGANISM: Artificial Sequence
<220> FEATURE:
<223> OTHER INFORMATION: Recombinant protein

<400> SEQUENCE: 1058

Gln Gln Phe Gly Asp Thr Gln Leu Phe Thr
1               5                   10

<210> SEQ ID NO 1059
<211> LENGTH: 120
<212> TYPE: PRT
<213> ORGANISM: Artificial Sequence
<220> FEATURE:
<223> OTHER INFORMATION: Recombinant protein

<400> SEQUENCE: 1059

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1060
<211> LENGTH: 5
<212> TYPE: PRT
<213> ORGANISM: Artificial Sequence
<220> FEATURE:
<223> OTHER INFORMATION: Recombinant protein

<400> SEQUENCE: 1060

Thr Ser Trp Ile Ser
1               5

<210> SEQ ID NO 1061

```
<211> LENGTH: 17
<212> TYPE: PRT
<213> ORGANISM: Artificial Sequence
<220> FEATURE:
<223> OTHER INFORMATION: Recombinant protein

<400> SEQUENCE: 1061

Met Ile Asp Pro Ser Asp Ser Phe Thr Ser Tyr Ser Pro Ser Phe Gln
1               5                   10                  15

Gly

<210> SEQ ID NO 1062
<211> LENGTH: 11
<212> TYPE: PRT
<213> ORGANISM: Artificial Sequence
<220> FEATURE:
<223> OTHER INFORMATION: Recombinant protein

<400> SEQUENCE: 1062

Leu His Tyr Tyr Asn Ser Glu Glu Phe Asp Val
1               5                   10

<210> SEQ ID NO 1063
<211> LENGTH: 109
<212> TYPE: PRT
<213> ORGANISM: Artificial Sequence
<220> FEATURE:
<223> OTHER INFORMATION: Recombinant protein

<400> SEQUENCE: 1063

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Thr Gln
                85                  90                  95

Leu Phe Thr Phe Gly Gln Gly Thr Lys Leu Glu Ile Lys
            100                 105

<210> SEQ ID NO 1064
<211> LENGTH: 12
<212> TYPE: PRT
<213> ORGANISM: Artificial Sequence
<220> FEATURE:
<223> OTHER INFORMATION: Recombinant protein

<400> SEQUENCE: 1064

Arg Ala Ser Gln Ser Val Ser Ser Ser Tyr Leu Ala
1               5                   10

<210> SEQ ID NO 1065
<211> LENGTH: 7
<212> TYPE: PRT
<213> ORGANISM: Artificial Sequence
<220> FEATURE:
<223> OTHER INFORMATION: Recombinant protein

<400> SEQUENCE: 1065
```

```
Gly Gln Ser Ser Arg Thr Arg
1               5

<210> SEQ ID NO 1066
<211> LENGTH: 10
<212> TYPE: PRT
<213> ORGANISM: Artificial Sequence
<220> FEATURE:
<223> OTHER INFORMATION: Recombinant protein

<400> SEQUENCE: 1066

Gln Gln Phe Gly Asp Thr Gln Leu Phe Thr
1               5                   10

<210> SEQ ID NO 1067
<211> LENGTH: 120
<212> TYPE: PRT
<213> ORGANISM: Artificial Sequence
<220> FEATURE:
<223> OTHER INFORMATION: Recombinant protein

<400> SEQUENCE: 1067

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1068
<211> LENGTH: 5
<212> TYPE: PRT
<213> ORGANISM: Artificial Sequence
<220> FEATURE:
<223> OTHER INFORMATION: Recombinant protein

<400> SEQUENCE: 1068

Thr Ser Trp Ile Val
1               5

<210> SEQ ID NO 1069
<211> LENGTH: 17
<212> TYPE: PRT
<213> ORGANISM: Artificial Sequence
<220> FEATURE:
<223> OTHER INFORMATION: Recombinant protein

<400> SEQUENCE: 1069

Met Ile Asp Pro Ser Asp Ser Tyr Thr Ser Tyr Ser Pro Ser Phe Gln
1               5                   10                  15

Gly
```

<210> SEQ ID NO 1070
<211> LENGTH: 11
<212> TYPE: PRT
<213> ORGANISM: Artificial Sequence
<220> FEATURE:
<223> OTHER INFORMATION: Recombinant protein

<400> SEQUENCE: 1070

Leu His Tyr Tyr Asn Ser Glu Glu Phe Asp Val
1               5                   10

<210> SEQ ID NO 1071
<211> LENGTH: 109
<212> TYPE: PRT
<213> ORGANISM: Artificial Sequence
<220> FEATURE:
<223> OTHER INFORMATION: Recombinant protein

<400> SEQUENCE: 1071

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Thr Gln
                85                  90                  95

Leu Phe Thr Phe Gly Gln Gly Thr Lys Leu Glu Ile Lys
            100                 105

<210> SEQ ID NO 1072
<211> LENGTH: 12
<212> TYPE: PRT
<213> ORGANISM: Artificial Sequence
<220> FEATURE:
<223> OTHER INFORMATION: Recombinant protein

<400> SEQUENCE: 1072

Arg Ala Ser Gln Ser Val Ser Ser Ser Tyr Leu Ala
1               5                   10

<210> SEQ ID NO 1073
<211> LENGTH: 7
<212> TYPE: PRT
<213> ORGANISM: Artificial Sequence
<220> FEATURE:
<223> OTHER INFORMATION: Recombinant protein

<400> SEQUENCE: 1073

Gly Gln Ser Ser Arg Thr Arg
1               5

<210> SEQ ID NO 1074
<211> LENGTH: 10
<212> TYPE: PRT
<213> ORGANISM: Artificial Sequence
<220> FEATURE:
<223> OTHER INFORMATION: Recombinant protein

<400> SEQUENCE: 1074

Gln Gln Phe Gly Asp Thr Gln Leu Phe Thr
1               5                   10

<210> SEQ ID NO 1075
<211> LENGTH: 120
<212> TYPE: PRT
<213> ORGANISM: Artificial Sequence
<220> FEATURE:
<223> OTHER INFORMATION: Recombinant protein

<400> SEQUENCE: 1075

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 1076
<211> LENGTH: 5
<212> TYPE: PRT
<213> ORGANISM: Artificial Sequence
<220> FEATURE:
<223> OTHER INFORMATION: Recombinant protein

<400> SEQUENCE: 1076

Thr Ser Trp Ile Val
1               5

<210> SEQ ID NO 1077
<211> LENGTH: 17
<212> TYPE: PRT
<213> ORGANISM: Artificial Sequence
<220> FEATURE:
<223> OTHER INFORMATION: Recombinant protein

<400> SEQUENCE: 1077

Met Ile Asp Pro Ser Asp Ser Tyr Thr Ser Tyr Ser Pro Ser Phe Gln
1               5                   10                  15

Gly

<210> SEQ ID NO 1078
<211> LENGTH: 11
<212> TYPE: PRT
<213> ORGANISM: Artificial Sequence
<220> FEATURE:
<223> OTHER INFORMATION: Recombinant protein

<400> SEQUENCE: 1078

Leu His Tyr Tyr Asn Ser Glu Glu Phe Asp Val
1               5                   10

<210> SEQ ID NO 1079
<211> LENGTH: 109
<212> TYPE: PRT
<213> ORGANISM: Artificial Sequence
<220> FEATURE:
<223> OTHER INFORMATION: Recombinant protein

<400> SEQUENCE: 1079

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Thr Gln
                85                  90                  95

Leu Phe Thr Phe Gly Gln Gly Thr Lys Leu Glu Ile Lys
            100                 105
```

<210> SEQ ID NO 1080
<211> LENGTH: 12
<212> TYPE: PRT
<213> ORGANISM: Artificial Sequence
<220> FEATURE:
<223> OTHER INFORMATION: Recombinant protein

<400> SEQUENCE: 1080

```
Arg Ala Ser Gln Ser Val Ser Ser Ser Tyr Leu Ala
1               5                   10
```

<210> SEQ ID NO 1081
<211> LENGTH: 7
<212> TYPE: PRT
<213> ORGANISM: Artificial Sequence
<220> FEATURE:
<223> OTHER INFORMATION: Recombinant protein

<400> SEQUENCE: 1081

```
Gly Gln Ser Ser Arg Thr Arg
1               5
```

<210> SEQ ID NO 1082
<211> LENGTH: 10
<212> TYPE: PRT
<213> ORGANISM: Artificial Sequence
<220> FEATURE:
<223> OTHER INFORMATION: Recombinant protein

<400> SEQUENCE: 1082

```
Gln Gln Phe Gly Asp Thr Gln Leu Phe Thr
1               5                   10
```

<210> SEQ ID NO 1083
<211> LENGTH: 120
<212> TYPE: PRT
<213> ORGANISM: Artificial Sequence
<220> FEATURE:
<223> OTHER INFORMATION: Recombinant protein

<400> SEQUENCE: 1083

Glu Val Gln Leu Val Gln Ser Gly Ala Glu Val Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65              70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 1084
<211> LENGTH: 5
<212> TYPE: PRT
<213> ORGANISM: Artificial Sequence
<220> FEATURE:
<223> OTHER INFORMATION: Recombinant protein

<400> SEQUENCE: 1084

Thr Ser Trp Ile Ser
1               5

<210> SEQ ID NO 1085
<211> LENGTH: 17
<212> TYPE: PRT
<213> ORGANISM: Artificial Sequence
<220> FEATURE:
<223> OTHER INFORMATION: Recombinant protein

<400> SEQUENCE: 1085

Met Ile Asp Pro Ser Asp Ser Tyr Thr Ser Tyr Ser Pro Ser Phe Gln
1               5                   10                  15

Gly

<210> SEQ ID NO 1086
<211> LENGTH: 11
<212> TYPE: PRT
<213> ORGANISM: Artificial Sequence
<220> FEATURE:
<223> OTHER INFORMATION: Recombinant protein

<400> SEQUENCE: 1086

Leu His Tyr Tyr Asn Ser Glu Glu Phe Asp Val
1               5                   10

<210> SEQ ID NO 1087
<211> LENGTH: 109
<212> TYPE: PRT
<213> ORGANISM: Artificial Sequence
<220> FEATURE:
<223> OTHER INFORMATION: Recombinant protein

<400> SEQUENCE: 1087

Glu Ile Val Leu Thr Gln Ser Pro Gly Thr Leu Ser Leu Ser Pro Gly
1               5                   10                  15

-continued

```
Glu Arg Ala Thr Leu Ser Cys Arg Ala Ser Gln Ser Val Ser Ser
                 20                  25                  30
Tyr Leu Ala Trp Tyr Gln Gln Lys Pro Gly Gln Ala Pro Arg Leu Leu
             35                  40                  45
Ile Tyr Gly Gln Ser Ser Arg Thr Arg Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Phe Gly Asp Asn Gln
                 85                  90                  95
Leu Phe Thr Phe Gly Gln Gly Thr Lys Leu Glu Ile Lys
            100                 105
```

<210> SEQ ID NO 1088
<211> LENGTH: 12
<212> TYPE: PRT
<213> ORGANISM: Artificial Sequence
<220> FEATURE:
<223> OTHER INFORMATION: Recombinant protein

<400> SEQUENCE: 1088

```
Arg Ala Ser Gln Ser Val Ser Ser Ser Tyr Leu Ala
 1               5                  10
```

<210> SEQ ID NO 1089
<211> LENGTH: 7
<212> TYPE: PRT
<213> ORGANISM: Artificial Sequence
<220> FEATURE:
<223> OTHER INFORMATION: Recombinant protein

<400> SEQUENCE: 1089

```
Gly Gln Ser Ser Arg Thr Arg
 1               5
```

<210> SEQ ID NO 1090
<211> LENGTH: 10
<212> TYPE: PRT
<213> ORGANISM: Artificial Sequence
<220> FEATURE:
<223> OTHER INFORMATION: Recombinant protein

<400> SEQUENCE: 1090

```
Gln Gln Phe Gly Asp Asn Gln Leu Phe Thr
 1               5                  10
```

<210> SEQ ID NO 1091
<211> LENGTH: 120
<212> TYPE: PRT
<213> ORGANISM: Artificial Sequence
<220> FEATURE:
<223> OTHER INFORMATION: Recombinant protein

<400> SEQUENCE: 1091

```
Glu Val Gln Leu Val Gln Ser Gly Ala Glu Val Lys Lys Pro Gly Glu
 1               5                  10                  15
Ser Leu Arg Ile Ser Cys Lys Gly Ser Gly Tyr Ser Phe Thr Thr Ser
                 20                  25                  30
Trp Ile Ser Trp Val Arg Gln Met Pro Gly Lys Gly Leu Glu Trp Met
             35                  40                  45
Gly Met Ile Asp Pro Ser Asp Ser Phe Thr Ser Tyr Ser Pro Ser Phe
 50                  55                  60
```

```
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr His Ser Glu Glu Phe Asp Val Trp Gly Gln
            100                 105                 110

Gly Thr Met Val Thr Val Ser Ser
            115                 120

<210> SEQ ID NO 1092
<211> LENGTH: 5
<212> TYPE: PRT
<213> ORGANISM: Artificial Sequence
<220> FEATURE:
<223> OTHER INFORMATION: Recombinant protein

<400> SEQUENCE: 1092

Thr Ser Trp Ile Ser
1               5

<210> SEQ ID NO 1093
<211> LENGTH: 17
<212> TYPE: PRT
<213> ORGANISM: Artificial Sequence
<220> FEATURE:
<223> OTHER INFORMATION: Recombinant protein

<400> SEQUENCE: 1093

Met Ile Asp Pro Ser Asp Ser Phe Thr Ser Tyr Ser Pro Ser Phe Gln
1               5                   10                  15

Gly

<210> SEQ ID NO 1094
<211> LENGTH: 11
<212> TYPE: PRT
<213> ORGANISM: Artificial Sequence
<220> FEATURE:
<223> OTHER INFORMATION: Recombinant protein

<400> SEQUENCE: 1094

Leu His Tyr Tyr His Ser Glu Glu Phe Asp Val
1               5                   10

<210> SEQ ID NO 1095
<211> LENGTH: 109
<212> TYPE: PRT
<213> ORGANISM: Artificial Sequence
<220> FEATURE:
<223> OTHER INFORMATION: Recombinant protein

<400> SEQUENCE: 1095

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asn Gln
```

```
                    85                  90                  95

Leu Phe Thr Phe Gly Gln Gly Thr Lys Leu Glu Ile Lys
                100                 105

<210> SEQ ID NO 1096
<211> LENGTH: 12
<212> TYPE: PRT
<213> ORGANISM: Artificial Sequence
<220> FEATURE:
<223> OTHER INFORMATION: Recombinant protein

<400> SEQUENCE: 1096

Arg Ala Ser Gln Ser Val Ser Ser Ser Tyr Leu Ala
1               5                   10

<210> SEQ ID NO 1097
<211> LENGTH: 7
<212> TYPE: PRT
<213> ORGANISM: Artificial Sequence
<220> FEATURE:
<223> OTHER INFORMATION: Recombinant protein

<400> SEQUENCE: 1097

Gly Gln Ser Ser Arg Thr Arg
1               5

<210> SEQ ID NO 1098
<211> LENGTH: 10
<212> TYPE: PRT
<213> ORGANISM: Artificial Sequence
<220> FEATURE:
<223> OTHER INFORMATION: Recombinant protein

<400> SEQUENCE: 1098

Gln Gln Phe Gly Asp Asn Gln Leu Phe Thr
1               5                   10

<210> SEQ ID NO 1099
<211> LENGTH: 120
<212> TYPE: PRT
<213> ORGANISM: Artificial Sequence
<220> FEATURE:
<223> OTHER INFORMATION: Recombinant protein

<400> SEQUENCE: 1099

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Tyr Thr Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
                100                 105                 110

Gly Thr Leu Val Thr Val Ser Ser
            115                 120
```

```
<210> SEQ ID NO 1100
<211> LENGTH: 5
<212> TYPE: PRT
<213> ORGANISM: Artificial Sequence
<220> FEATURE:
<223> OTHER INFORMATION: Recombinant protein

<400> SEQUENCE: 1100

Thr Ser Trp Ile Ser
1               5

<210> SEQ ID NO 1101
<211> LENGTH: 17
<212> TYPE: PRT
<213> ORGANISM: Artificial Sequence
<220> FEATURE:
<223> OTHER INFORMATION: Recombinant protein

<400> SEQUENCE: 1101

Met Ile Asp Pro Ser Asp Ser Tyr Thr Ser Tyr Ser Pro Ser Phe Gln
1               5                   10                  15

Gly

<210> SEQ ID NO 1102
<211> LENGTH: 11
<212> TYPE: PRT
<213> ORGANISM: Artificial Sequence
<220> FEATURE:
<223> OTHER INFORMATION: Recombinant protein

<400> SEQUENCE: 1102

Leu His Tyr Tyr His Ser Glu Glu Phe Asp Val
1               5                   10

<210> SEQ ID NO 1103
<211> LENGTH: 109
<212> TYPE: PRT
<213> ORGANISM: Artificial Sequence
<220> FEATURE:
<223> OTHER INFORMATION: Recombinant protein

<400> SEQUENCE: 1103

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asn Gln
                85                  90                  95

Leu Phe Thr Phe Gly Gln Gly Thr Lys Leu Glu Ile Lys
            100                 105

<210> SEQ ID NO 1104
<211> LENGTH: 12
<212> TYPE: PRT
<213> ORGANISM: Artificial Sequence
<220> FEATURE:
<223> OTHER INFORMATION: Recombinant protein
```

```
<400> SEQUENCE: 1104

Arg Ala Ser Gln Ser Val Ser Ser Ser Tyr Leu Ala
1               5                   10

<210> SEQ ID NO 1105
<211> LENGTH: 7
<212> TYPE: PRT
<213> ORGANISM: Artificial Sequence
<220> FEATURE:
<223> OTHER INFORMATION: Recombinant protein

<400> SEQUENCE: 1105

Gly Gln Ser Ser Arg Thr Arg
1               5

<210> SEQ ID NO 1106
<211> LENGTH: 10
<212> TYPE: PRT
<213> ORGANISM: Artificial Sequence
<220> FEATURE:
<223> OTHER INFORMATION: Recombinant protein

<400> SEQUENCE: 1106

Gln Gln Phe Gly Asp Asn Gln Leu Phe Thr
1               5                   10

<210> SEQ ID NO 1107
<211> LENGTH: 120
<212> TYPE: PRT
<213> ORGANISM: Artificial Sequence
<220> FEATURE:
<223> OTHER INFORMATION: Recombinant protein

<400> SEQUENCE: 1107

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Tyr Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
                100                 105                 110

Gly Thr Met Val Thr Val Ser Ser
            115                 120

<210> SEQ ID NO 1108
<211> LENGTH: 5
<212> TYPE: PRT
<213> ORGANISM: Artificial Sequence
<220> FEATURE:
<223> OTHER INFORMATION: Recombinant protein

<400> SEQUENCE: 1108

Thr Ser Trp Ile Ser
1               5
```

```
<210> SEQ ID NO 1109
<211> LENGTH: 17
<212> TYPE: PRT
<213> ORGANISM: Artificial Sequence
<220> FEATURE:
<223> OTHER INFORMATION: Recombinant protein

<400> SEQUENCE: 1109

Met Ile Asp Pro Ser Asp Ser Tyr Thr Ser Tyr Ser Pro Ser Phe Gln
1               5                   10                  15

Gly

<210> SEQ ID NO 1110
<211> LENGTH: 11
<212> TYPE: PRT
<213> ORGANISM: Artificial Sequence
<220> FEATURE:
<223> OTHER INFORMATION: Recombinant protein

<400> SEQUENCE: 1110

Leu His Tyr Tyr His Ser Glu Glu Phe Asp Val
1               5                   10

<210> SEQ ID NO 1111
<211> LENGTH: 109
<212> TYPE: PRT
<213> ORGANISM: Artificial Sequence
<220> FEATURE:
<223> OTHER INFORMATION: Recombinant protein

<400> SEQUENCE: 1111

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asn Gln
                85                  90                  95

Leu Phe Thr Phe Gly Gln Gly Thr Lys Leu Glu Ile Lys
            100                 105

<210> SEQ ID NO 1112
<211> LENGTH: 12
<212> TYPE: PRT
<213> ORGANISM: Artificial Sequence
<220> FEATURE:
<223> OTHER INFORMATION: Recombinant protein

<400> SEQUENCE: 1112

Arg Ala Ser Gln Ser Val Ser Ser Ser Tyr Leu Ala
1               5                   10

<210> SEQ ID NO 1113
<211> LENGTH: 7
<212> TYPE: PRT
<213> ORGANISM: Artificial Sequence
<220> FEATURE:
<223> OTHER INFORMATION: Recombinant protein
```

```
<400> SEQUENCE: 1113

Gly Gln Ser Ser Arg Thr Arg
1               5

<210> SEQ ID NO 1114
<211> LENGTH: 10
<212> TYPE: PRT
<213> ORGANISM: Artificial Sequence
<220> FEATURE:
<223> OTHER INFORMATION: Recombinant protein

<400> SEQUENCE: 1114

Gln Gln Phe Gly Asp Asn Gln Leu Phe Thr
1               5                  10

<210> SEQ ID NO 1115
<211> LENGTH: 120
<212> TYPE: PRT
<213> ORGANISM: Artificial Sequence
<220> FEATURE:
<223> OTHER INFORMATION: Recombinant protein

<400> SEQUENCE: 1115

Glu Val Gln Leu Val Gln Ser Gly Ala Glu Val Lys Lys Pro Gly Glu
1               5                  10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1116
<211> LENGTH: 5
<212> TYPE: PRT
<213> ORGANISM: Artificial Sequence
<220> FEATURE:
<223> OTHER INFORMATION: Recombinant protein

<400> SEQUENCE: 1116

Thr Ser Trp Ile Ser
1               5

<210> SEQ ID NO 1117
<211> LENGTH: 17
<212> TYPE: PRT
<213> ORGANISM: Artificial Sequence
<220> FEATURE:
<223> OTHER INFORMATION: Recombinant protein

<400> SEQUENCE: 1117

Met Ile Asp Pro Ser Asp Ser Phe Thr Ser Tyr Ser Pro Ser Phe Gln
1               5                  10                  15

Gly
```

<210> SEQ ID NO 1118
<211> LENGTH: 11
<212> TYPE: PRT
<213> ORGANISM: Artificial Sequence
<220> FEATURE:
<223> OTHER INFORMATION: Recombinant protein

<400> SEQUENCE: 1118

Leu His Tyr Tyr Asn Ser Glu Glu Phe Asp Val
1               5                   10

<210> SEQ ID NO 1119
<211> LENGTH: 109
<212> TYPE: PRT
<213> ORGANISM: Artificial Sequence
<220> FEATURE:
<223> OTHER INFORMATION: Recombinant protein

<400> SEQUENCE: 1119

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asn Gln
                85                  90                  95

Leu Phe Thr Phe Gly Gln Gly Thr Lys Leu Glu Ile Lys
            100                 105

<210> SEQ ID NO 1120
<211> LENGTH: 12
<212> TYPE: PRT
<213> ORGANISM: Artificial Sequence
<220> FEATURE:
<223> OTHER INFORMATION: Recombinant protein

<400> SEQUENCE: 1120

Arg Ala Ser Gln Ser Val Ser Ser Ser Tyr Leu Ala
1               5                   10

<210> SEQ ID NO 1121
<211> LENGTH: 7
<212> TYPE: PRT
<213> ORGANISM: Artificial Sequence
<220> FEATURE:
<223> OTHER INFORMATION: Recombinant protein

<400> SEQUENCE: 1121

Gly Gln Ser Ser Arg Thr Arg
1               5

<210> SEQ ID NO 1122
<211> LENGTH: 10
<212> TYPE: PRT
<213> ORGANISM: Artificial Sequence
<220> FEATURE:
<223> OTHER INFORMATION: Recombinant protein

```
<400> SEQUENCE: 1122

Gln Gln Phe Gly Asp Asn Gln Leu Phe Thr
1               5                   10

<210> SEQ ID NO 1123
<211> LENGTH: 120
<212> TYPE: PRT
<213> ORGANISM: Artificial Sequence
<220> FEATURE:
<223> OTHER INFORMATION: Recombinant protein

<400> SEQUENCE: 1123

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1124
<211> LENGTH: 5
<212> TYPE: PRT
<213> ORGANISM: Artificial Sequence
<220> FEATURE:
<223> OTHER INFORMATION: Recombinant protein

<400> SEQUENCE: 1124

Thr Ser Trp Ile Val
1               5

<210> SEQ ID NO 1125
<211> LENGTH: 17
<212> TYPE: PRT
<213> ORGANISM: Artificial Sequence
<220> FEATURE:
<223> OTHER INFORMATION: Recombinant protein

<400> SEQUENCE: 1125

Met Ile Asp Pro Ser Asp Ser Tyr Thr Ser Tyr Ser Pro Ser Phe Gln
1               5                   10                  15

Gly

<210> SEQ ID NO 1126
<211> LENGTH: 11
<212> TYPE: PRT
<213> ORGANISM: Artificial Sequence
<220> FEATURE:
<223> OTHER INFORMATION: Recombinant protein

<400> SEQUENCE: 1126

Leu His Tyr Tyr Asn Ser Glu Glu Phe Asp Val
1               5                   10
```

<210> SEQ ID NO 1127
<211> LENGTH: 109
<212> TYPE: PRT
<213> ORGANISM: Artificial Sequence
<220> FEATURE:
<223> OTHER INFORMATION: Recombinant protein

<400> SEQUENCE: 1127

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asn Gln
                85                  90                  95

Leu Phe Thr Phe Gly Gln Gly Thr Lys Leu Glu Ile Lys
            100                 105

<210> SEQ ID NO 1128
<211> LENGTH: 12
<212> TYPE: PRT
<213> ORGANISM: Artificial Sequence
<220> FEATURE:
<223> OTHER INFORMATION: Recombinant protein

<400> SEQUENCE: 1128

Arg Ala Ser Gln Ser Val Ser Ser Ser Tyr Leu Ala
1               5                   10

<210> SEQ ID NO 1129
<211> LENGTH: 7
<212> TYPE: PRT
<213> ORGANISM: Artificial Sequence
<220> FEATURE:
<223> OTHER INFORMATION: Recombinant protein

<400> SEQUENCE: 1129

Gly Gln Ser Ser Arg Thr Arg
1               5

<210> SEQ ID NO 1130
<211> LENGTH: 10
<212> TYPE: PRT
<213> ORGANISM: Artificial Sequence
<220> FEATURE:
<223> OTHER INFORMATION: Recombinant protein

<400> SEQUENCE: 1130

Gln Gln Phe Gly Asp Asn Gln Leu Phe Thr
1               5                   10

<210> SEQ ID NO 1131
<211> LENGTH: 120
<212> TYPE: PRT
<213> ORGANISM: Artificial Sequence
<220> FEATURE:
<223> OTHER INFORMATION: Recombinant protein

```
<400> SEQUENCE: 1131

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 1132
<211> LENGTH: 5
<212> TYPE: PRT
<213> ORGANISM: Artificial Sequence
<220> FEATURE:
<223> OTHER INFORMATION: Recombinant protein

<400> SEQUENCE: 1132

Thr Ser Trp Ile Val
1               5

<210> SEQ ID NO 1133
<211> LENGTH: 17
<212> TYPE: PRT
<213> ORGANISM: Artificial Sequence
<220> FEATURE:
<223> OTHER INFORMATION: Recombinant protein

<400> SEQUENCE: 1133

Met Ile Asp Pro Ser Asp Ser Tyr Thr Ser Tyr Ser Pro Ser Phe Gln
1               5                   10                  15

Gly

<210> SEQ ID NO 1134
<211> LENGTH: 11
<212> TYPE: PRT
<213> ORGANISM: Artificial Sequence
<220> FEATURE:
<223> OTHER INFORMATION: Recombinant protein

<400> SEQUENCE: 1134

Leu His Tyr Tyr Asn Ser Glu Glu Phe Asp Val
1               5                   10

<210> SEQ ID NO 1135
<211> LENGTH: 109
<212> TYPE: PRT
<213> ORGANISM: Artificial Sequence
<220> FEATURE:
<223> OTHER INFORMATION: Recombinant protein

<400> SEQUENCE: 1135

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asn Gln
                85                  90                  95

Leu Phe Thr Phe Gly Gln Gly Thr Lys Leu Glu Ile Lys
            100                 105

<210> SEQ ID NO 1136
<211> LENGTH: 12
<212> TYPE: PRT
<213> ORGANISM: Artificial Sequence
<220> FEATURE:
<223> OTHER INFORMATION: Recombinant protein

<400> SEQUENCE: 1136

Arg Ala Ser Gln Ser Val Ser Ser Ser Tyr Leu Ala
1               5                   10

<210> SEQ ID NO 1137
<211> LENGTH: 7
<212> TYPE: PRT
<213> ORGANISM: Artificial Sequence
<220> FEATURE:
<223> OTHER INFORMATION: Recombinant protein

<400> SEQUENCE: 1137

Gly Gln Ser Ser Arg Thr Arg
1               5

<210> SEQ ID NO 1138
<211> LENGTH: 10
<212> TYPE: PRT
<213> ORGANISM: Artificial Sequence
<220> FEATURE:
<223> OTHER INFORMATION: Recombinant protein

<400> SEQUENCE: 1138

Gln Gln Phe Gly Asp Asn Gln Leu Phe Thr
1               5                   10

<210> SEQ ID NO 1139
<211> LENGTH: 120
<212> TYPE: PRT
<213> ORGANISM: Artificial Sequence
<220> FEATURE:
<223> OTHER INFORMATION: Recombinant protein

<400> SEQUENCE: 1139

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120

<210> SEQ ID NO 1140
<211> LENGTH: 5
<212> TYPE: PRT
<213> ORGANISM: Artificial Sequence
<220> FEATURE:
<223> OTHER INFORMATION: Recombinant protein

<400> SEQUENCE: 1140

Thr Ser Trp Ile Ser
1               5

<210> SEQ ID NO 1141
<211> LENGTH: 17
<212> TYPE: PRT
<213> ORGANISM: Artificial Sequence
<220> FEATURE:
<223> OTHER INFORMATION: Recombinant protein

<400> SEQUENCE: 1141

Met Ile Asp Pro Ser Asp Ser Tyr Thr Ser Tyr Ser Pro Ser Phe Gln
1               5                   10                  15

Gly

<210> SEQ ID NO 1142
<211> LENGTH: 11
<212> TYPE: PRT
<213> ORGANISM: Artificial Sequence
<220> FEATURE:
<223> OTHER INFORMATION: Recombinant protein

<400> SEQUENCE: 1142

Leu His Tyr Tyr Asn Ser Glu Glu Phe Asp Val
1               5                   10

<210> SEQ ID NO 1143
<211> LENGTH: 109
<212> TYPE: PRT
<213> ORGANISM: Artificial Sequence
<220> FEATURE:
<223> OTHER INFORMATION: Recombinant protein

<400> SEQUENCE: 1143

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Phe Gly Asp Asp Gln
                85                  90                  95

Leu Phe Thr Phe Gly Gln Gly Thr Lys Leu Glu Ile Lys
            100                 105
```

<210> SEQ ID NO 1144
<211> LENGTH: 12
<212> TYPE: PRT
<213> ORGANISM: Artificial Sequence
<220> FEATURE:
<223> OTHER INFORMATION: Recombinant protein

<400> SEQUENCE: 1144

```
Arg Ala Ser Gln Ser Val Ser Ser Ser Tyr Leu Ala
1               5                   10
```

<210> SEQ ID NO 1145
<211> LENGTH: 7
<212> TYPE: PRT
<213> ORGANISM: Artificial Sequence
<220> FEATURE:
<223> OTHER INFORMATION: Recombinant protein

<400> SEQUENCE: 1145

```
Gly Gln Ser Ser Arg Thr Arg
1               5
```

<210> SEQ ID NO 1146
<211> LENGTH: 10
<212> TYPE: PRT
<213> ORGANISM: Artificial Sequence
<220> FEATURE:
<223> OTHER INFORMATION: Recombinant protein

<400> SEQUENCE: 1146

```
Gln Gln Phe Gly Asp Asp Gln Leu Phe Thr
1               5                   10
```

<210> SEQ ID NO 1147
<211> LENGTH: 120
<212> TYPE: PRT
<213> ORGANISM: Artificial Sequence
<220> FEATURE:
<223> OTHER INFORMATION: Recombinant protein

<400> SEQUENCE: 1147

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
                20                  25                  30

Trp Ile Ser Trp Val Arg Gln Met Pro Gly Lys Gly Leu Glu Trp Met
            35                  40                  45

Gly Met Ile Asp Pro Ser Asp Ser Phe Thr Ser Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
                100                 105                 110

Gly Thr Met Val Thr Val Ser Ser
            115                 120
```

<210> SEQ ID NO 1148
<211> LENGTH: 5
<212> TYPE: PRT
<213> ORGANISM: Artificial Sequence
<220> FEATURE:
<223> OTHER INFORMATION: Recombinant protein

<400> SEQUENCE: 1148

Thr Ser Trp Ile Ser
1               5

<210> SEQ ID NO 1149
<211> LENGTH: 17
<212> TYPE: PRT
<213> ORGANISM: Artificial Sequence
<220> FEATURE:
<223> OTHER INFORMATION: Recombinant protein

<400> SEQUENCE: 1149

Met Ile Asp Pro Ser Asp Ser Phe Thr Ser Tyr Ser Pro Ser Phe Gln
1               5                   10                  15

Gly

<210> SEQ ID NO 1150
<211> LENGTH: 11
<212> TYPE: PRT
<213> ORGANISM: Artificial Sequence
<220> FEATURE:
<223> OTHER INFORMATION: Recombinant protein

<400> SEQUENCE: 1150

Leu His Tyr Tyr His Ser Glu Glu Phe Asp Val
1               5                   10

<210> SEQ ID NO 1151
<211> LENGTH: 109
<212> TYPE: PRT
<213> ORGANISM: Artificial Sequence
<220> FEATURE:
<223> OTHER INFORMATION: Recombinant protein

<400> SEQUENCE: 1151

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asp Gln
                85                  90                  95

Leu Phe Thr Phe Gly Gln Gly Thr Lys Leu Glu Ile Lys
            100                 105

<210> SEQ ID NO 1152
<211> LENGTH: 12
<212> TYPE: PRT
<213> ORGANISM: Artificial Sequence
<220> FEATURE:
<223> OTHER INFORMATION: Recombinant protein -continued

<400> SEQUENCE: 1152

Arg Ala Ser Gln Ser Val Ser Ser Ser Tyr Leu Ala
1               5                   10

<210> SEQ ID NO 1153
<211> LENGTH: 7
<212> TYPE: PRT
<213> ORGANISM: Artificial Sequence
<220> FEATURE:
<223> OTHER INFORMATION: Recombinant protein

<400> SEQUENCE: 1153

Gly Gln Ser Ser Arg Thr Arg
1               5

<210> SEQ ID NO 1154
<211> LENGTH: 10
<212> TYPE: PRT
<213> ORGANISM: Artificial Sequence
<220> FEATURE:
<223> OTHER INFORMATION: Recombinant protein

<400> SEQUENCE: 1154

Gln Gln Phe Gly Asp Asp Gln Leu Phe Thr
1               5                   10

<210> SEQ ID NO 1155
<211> LENGTH: 120
<212> TYPE: PRT
<213> ORGANISM: Artificial Sequence
<220> FEATURE:
<223> OTHER INFORMATION: Recombinant protein

<400> SEQUENCE: 1155

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Leu Val Thr Val Ser Ser
        115                 120

<210> SEQ ID NO 1156
<211> LENGTH: 5
<212> TYPE: PRT
<213> ORGANISM: Artificial Sequence
<220> FEATURE:
<223> OTHER INFORMATION: Recombinant protein

<400> SEQUENCE: 1156

Thr Ser Trp Ile Ser
1               5

<210> SEQ ID NO 1157
<211> LENGTH: 17
<212> TYPE: PRT
<213> ORGANISM: Artificial Sequence
<220> FEATURE:
<223> OTHER INFORMATION: Recombinant protein

<400> SEQUENCE: 1157

```
Met Ile Asp Pro Ser Asp Ser Tyr Thr Ser Tyr Ser Pro Ser Phe Gln
1               5                   10                  15

Gly
```

<210> SEQ ID NO 1158
<211> LENGTH: 11
<212> TYPE: PRT
<213> ORGANISM: Artificial Sequence
<220> FEATURE:
<223> OTHER INFORMATION: Recombinant protein

<400> SEQUENCE: 1158

```
Leu His Tyr Tyr His Ser Glu Glu Phe Asp Val
1               5                   10
```

<210> SEQ ID NO 1159
<211> LENGTH: 109
<212> TYPE: PRT
<213> ORGANISM: Artificial Sequence
<220> FEATURE:
<223> OTHER INFORMATION: Recombinant protein

<400> SEQUENCE: 1159

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Gln Ser Ser Arg Thr Arg Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asp Gln
                85                  90                  95

Leu Phe Thr Phe Gly Gln Gly Thr Lys Leu Glu Ile Lys
            100                 105
```

<210> SEQ ID NO 1160
<211> LENGTH: 12
<212> TYPE: PRT
<213> ORGANISM: Artificial Sequence
<220> FEATURE:
<223> OTHER INFORMATION: Recombinant protein

<400> SEQUENCE: 1160

```
Arg Ala Ser Gln Ser Val Ser Ser Ser Tyr Leu Ala
1               5                   10
```

<210> SEQ ID NO 1161
<211> LENGTH: 7
<212> TYPE: PRT
<213> ORGANISM: Artificial Sequence
<220> FEATURE:
<223> OTHER INFORMATION: Recombinant protein

<400> SEQUENCE: 1161

Gly Gln Ser Ser Arg Thr Arg
1               5

<210> SEQ ID NO 1162
<211> LENGTH: 10
<212> TYPE: PRT
<213> ORGANISM: Artificial Sequence
<220> FEATURE:
<223> OTHER INFORMATION: Recombinant protein

<400> SEQUENCE: 1162

Gln Gln Phe Gly Asp Asp Gln Leu Phe Thr
1               5                   10

<210> SEQ ID NO 1163
<211> LENGTH: 120
<212> TYPE: PRT
<213> ORGANISM: Artificial Sequence
<220> FEATURE:
<223> OTHER INFORMATION: Recombinant protein

<400> SEQUENCE: 1163

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr His Ser Glu Glu Phe Asp Val Trp Gly Gln
            100                 105                 110

Gly Thr Met Val Thr Val Ser Ser
        115                 120

<210> SEQ ID NO 1164
<211> LENGTH: 5
<212> TYPE: PRT
<213> ORGANISM: Artificial Sequence
<220> FEATURE:
<223> OTHER INFORMATION: Recombinant protein

<400> SEQUENCE: 1164

Thr Ser Trp Ile Ser
1               5

<210> SEQ ID NO 1165
<211> LENGTH: 17
<212> TYPE: PRT
<213> ORGANISM: Artificial Sequence
<220> FEATURE:
<223> OTHER INFORMATION: Recombinant protein

<400> SEQUENCE: 1165

Met Ile Asp Pro Ser Asp Ser Tyr Thr Ser Tyr Ser Pro Ser Phe Gln
1               5                   10                  15

```
Gly

<210> SEQ ID NO 1166
<211> LENGTH: 11
<212> TYPE: PRT
<213> ORGANISM: Artificial Sequence
<220> FEATURE:
<223> OTHER INFORMATION: Recombinant protein

<400> SEQUENCE: 1166

Leu His Tyr Tyr His Ser Glu Glu Phe Asp Val
1               5                   10

<210> SEQ ID NO 1167
<211> LENGTH: 109
<212> TYPE: PRT
<213> ORGANISM: Artificial Sequence
<220> FEATURE:
<223> OTHER INFORMATION: Recombinant protein

<400> SEQUENCE: 1167

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asp Gln
                85                  90                  95

Leu Phe Thr Phe Gly Gln Gly Thr Lys Leu Glu Ile Lys
            100                 105

<210> SEQ ID NO 1168
<211> LENGTH: 12
<212> TYPE: PRT
<213> ORGANISM: Artificial Sequence
<220> FEATURE:
<223> OTHER INFORMATION: Recombinant protein

<400> SEQUENCE: 1168

Arg Ala Ser Gln Ser Val Ser Ser Ser Tyr Leu Ala
1               5                   10

<210> SEQ ID NO 1169
<211> LENGTH: 7
<212> TYPE: PRT
<213> ORGANISM: Artificial Sequence
<220> FEATURE:
<223> OTHER INFORMATION: Recombinant protein

<400> SEQUENCE: 1169

Gly Gln Ser Ser Arg Thr Arg
1               5

<210> SEQ ID NO 1170
<211> LENGTH: 10
<212> TYPE: PRT
<213> ORGANISM: Artificial Sequence
<220> FEATURE:
<223> OTHER INFORMATION: Recombinant protein
```

<400> SEQUENCE: 1170

Gln Gln Phe Gly Asp Asp Gln Leu Phe Thr
1               5                   10

<210> SEQ ID NO 1171
<211> LENGTH: 120
<212> TYPE: PRT
<213> ORGANISM: Artificial Sequence
<220> FEATURE:
<223> OTHER INFORMATION: Recombinant protein

<400> SEQUENCE: 1171

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Ser Trp Val Arg Gln Met Pro Gly Lys Gly Leu Glu Trp Met
        35                  40                  45

Gly Met Ile Asp Pro Ser Asp Ser Phe Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1172
<211> LENGTH: 5
<212> TYPE: PRT
<213> ORGANISM: Artificial Sequence
<220> FEATURE:
<223> OTHER INFORMATION: Recombinant protein

<400> SEQUENCE: 1172

Thr Ser Trp Ile Ser
1               5

<210> SEQ ID NO 1173
<211> LENGTH: 17
<212> TYPE: PRT
<213> ORGANISM: Artificial Sequence
<220> FEATURE:
<223> OTHER INFORMATION: Recombinant protein

<400> SEQUENCE: 1173

Met Ile Asp Pro Ser Asp Ser Phe Thr Ser Tyr Ser Pro Ser Phe Gln
1               5                   10                  15

Gly

<210> SEQ ID NO 1174
<211> LENGTH: 11
<212> TYPE: PRT
<213> ORGANISM: Artificial Sequence
<220> FEATURE:
<223> OTHER INFORMATION: Recombinant protein

<400> SEQUENCE: 1174

Leu His Tyr Tyr Asn Ser Glu Glu Phe Asp Val

-continued

```
1               5                   10

<210> SEQ ID NO 1175
<211> LENGTH: 109
<212> TYPE: PRT
<213> ORGANISM: Artificial Sequence
<220> FEATURE:
<223> OTHER INFORMATION: Recombinant protein

<400> SEQUENCE: 1175

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asp Gln
                85                  90                  95

Leu Phe Thr Phe Gly Gln Gly Thr Lys Leu Glu Ile Lys
            100                 105

<210> SEQ ID NO 1176
<211> LENGTH: 12
<212> TYPE: PRT
<213> ORGANISM: Artificial Sequence
<220> FEATURE:
<223> OTHER INFORMATION: Recombinant protein

<400> SEQUENCE: 1176

Arg Ala Ser Gln Ser Val Ser Ser Ser Tyr Leu Ala
1               5                   10

<210> SEQ ID NO 1177
<211> LENGTH: 7
<212> TYPE: PRT
<213> ORGANISM: Artificial Sequence
<220> FEATURE:
<223> OTHER INFORMATION: Recombinant protein

<400> SEQUENCE: 1177

Gly Gln Ser Ser Arg Thr Arg
1               5

<210> SEQ ID NO 1178
<211> LENGTH: 10
<212> TYPE: PRT
<213> ORGANISM: Artificial Sequence
<220> FEATURE:
<223> OTHER INFORMATION: Recombinant protein

<400> SEQUENCE: 1178

Gln Gln Phe Gly Asp Asp Gln Leu Phe Thr
1               5                   10

<210> SEQ ID NO 1179
<211> LENGTH: 120
<212> TYPE: PRT
<213> ORGANISM: Artificial Sequence
<220> FEATURE:
<223> OTHER INFORMATION: Recombinant protein
```

<400> SEQUENCE: 1179

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Leu Val Thr Val Ser Ser
        115                 120

<210> SEQ ID NO 1180
<211> LENGTH: 5
<212> TYPE: PRT
<213> ORGANISM: Artificial Sequence
<220> FEATURE:
<223> OTHER INFORMATION: Recombinant protein

<400> SEQUENCE: 1180

Thr Ser Trp Ile Val
1               5

<210> SEQ ID NO 1181
<211> LENGTH: 17
<212> TYPE: PRT
<213> ORGANISM: Artificial Sequence
<220> FEATURE:
<223> OTHER INFORMATION: Recombinant protein

<400> SEQUENCE: 1181

Met Ile Asp Pro Ser Asp Ser Tyr Thr Ser Tyr Ser Pro Ser Phe Gln
1               5                   10                  15

Gly

<210> SEQ ID NO 1182
<211> LENGTH: 11
<212> TYPE: PRT
<213> ORGANISM: Artificial Sequence
<220> FEATURE:
<223> OTHER INFORMATION: Recombinant protein

<400> SEQUENCE: 1182

Leu His Tyr Tyr Asn Ser Glu Glu Phe Asp Val
1               5                   10

<210> SEQ ID NO 1183
<211> LENGTH: 109
<212> TYPE: PRT
<213> ORGANISM: Artificial Sequence
<220> FEATURE:
<223> OTHER INFORMATION: Recombinant protein

<400> SEQUENCE: 1183

Glu Ile Val Leu Thr Gln Ser Pro Gly Thr Leu Ser Leu Ser Pro Gly

-continued

```
            1               5                   10                  15
Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
        35                  40                  45

Ile Tyr Gly Gln Ser Ser Arg Thr Arg Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Asp Asp Gln
                85                  90                  95

Leu Phe Thr Phe Gly Gln Gly Thr Lys Leu Glu Ile Lys
            100                 105
```

<210> SEQ ID NO 1184
<211> LENGTH: 12
<212> TYPE: PRT
<213> ORGANISM: Artificial Sequence
<220> FEATURE:
<223> OTHER INFORMATION: Recombinant protein

<400> SEQUENCE: 1184

```
Arg Ala Ser Gln Ser Val Ser Ser Ser Tyr Leu Ala
1               5                   10
```

<210> SEQ ID NO 1185
<211> LENGTH: 7
<212> TYPE: PRT
<213> ORGANISM: Artificial Sequence
<220> FEATURE:
<223> OTHER INFORMATION: Recombinant protein

<400> SEQUENCE: 1185

```
Gly Gln Ser Ser Arg Thr Arg
1               5
```

<210> SEQ ID NO 1186
<211> LENGTH: 10
<212> TYPE: PRT
<213> ORGANISM: Artificial Sequence
<220> FEATURE:
<223> OTHER INFORMATION: Recombinant protein

<400> SEQUENCE: 1186

```
Gln Gln Phe Gly Asp Asp Gln Leu Phe Thr
1               5                   10
```

<210> SEQ ID NO 1187
<211> LENGTH: 120
<212> TYPE: PRT
<213> ORGANISM: Artificial Sequence
<220> FEATURE:
<223> OTHER INFORMATION: Recombinant protein

<400> SEQUENCE: 1187

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
                20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
```

```
                50                  55                  60
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu His Tyr Tyr Asn Ser Glu Glu Phe Asp Val Trp Gly Gln
                100                 105                 110

Gly Thr Met Val Thr Val Ser Ser
            115                 120

<210> SEQ ID NO 1188
<211> LENGTH: 5
<212> TYPE: PRT
<213> ORGANISM: Artificial Sequence
<220> FEATURE:
<223> OTHER INFORMATION: Recombinant protein

<400> SEQUENCE: 1188

Thr Ser Trp Ile Val
 1               5

<210> SEQ ID NO 1189
<211> LENGTH: 17
<212> TYPE: PRT
<213> ORGANISM: Artificial Sequence
<220> FEATURE:
<223> OTHER INFORMATION: Recombinant protein

<400> SEQUENCE: 1189

Met Ile Asp Pro Ser Asp Ser Tyr Thr Ser Tyr Ser Pro Ser Phe Gln
 1               5                  10                  15

Gly

<210> SEQ ID NO 1190
<211> LENGTH: 11
<212> TYPE: PRT
<213> ORGANISM: Artificial Sequence
<220> FEATURE:
<223> OTHER INFORMATION: Recombinant protein

<400> SEQUENCE: 1190

Leu His Tyr Tyr Asn Ser Glu Glu Phe Asp Val
 1               5                  10

<210> SEQ ID NO 1191
<211> LENGTH: 109
<212> TYPE: PRT
<213> ORGANISM: Artificial Sequence
<220> FEATURE:
<223> OTHER INFORMATION: Recombinant protein

<400> SEQUENCE: 1191

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
             35                  40                  45

Ile Tyr Gly Gln Ser Ser Arg Thr Arg Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80
```

-continued

```
Pro Glu Asp Phe Ala Val Tyr Tyr Cys Gln Gln Phe Gly Asp Asp Gln
                85                  90                  95

Leu Phe Thr Phe Gly Gln Gly Thr Lys Leu Glu Ile Lys
            100                 105

<210> SEQ ID NO 1192
<211> LENGTH: 12
<212> TYPE: PRT
<213> ORGANISM: Artificial Sequence
<220> FEATURE:
<223> OTHER INFORMATION: Recombinant protein

<400> SEQUENCE: 1192

Arg Ala Ser Gln Ser Val Ser Ser Tyr Leu Ala
1               5                   10

<210> SEQ ID NO 1193
<211> LENGTH: 7
<212> TYPE: PRT
<213> ORGANISM: Artificial Sequence
<220> FEATURE:
<223> OTHER INFORMATION: Recombinant protein

<400> SEQUENCE: 1193

Gly Gln Ser Ser Arg Thr Arg
1               5

<210> SEQ ID NO 1194
<211> LENGTH: 10
<212> TYPE: PRT
<213> ORGANISM: Artificial Sequence
<220> FEATURE:
<223> OTHER INFORMATION: Recombinant protein

<400> SEQUENCE: 1194

Gln Gln Phe Gly Asp Asp Gln Leu Phe Thr
1               5                   10

<210> SEQ ID NO 1195
<211> LENGTH: 326
<212> TYPE: PRT
<213> ORGANISM: Artificial Sequence
<220> FEATURE:
<223> OTHER INFORMATION: Recombinant protein

<400> SEQUENCE: 1195

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 1196
<211> LENGTH: 326
<212> TYPE: PRT
<213> ORGANISM: Artificial Sequence
<220> FEATURE:
<223> OTHER INFORMATION: Recombinant protein

<400> SEQUENCE: 1196

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Leu Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 1197
<211> LENGTH: 107
<212> TYPE: PRT
<213> ORGANISM: Homo sapiens

<400> SEQUENCE: 1197

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 1198
<211> LENGTH: 329
<212> TYPE: PRT
<213> ORGANISM: Artificial Sequence
<220> FEATURE:
<223> OTHER INFORMATION: Recombinant protein

<400> SEQUENCE: 1198

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                   70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 1199
<211> LENGTH: 329
<212> TYPE: PRT
<213> ORGANISM: Artificial Sequence
<220> FEATURE:
<223> OTHER INFORMATION: Recombinant protein

<400> SEQUENCE: 1199

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 1200
<211> LENGTH: 6
<212> TYPE: PRT
<213> ORGANISM: Artificial Sequence
<220> FEATURE:
<223> OTHER INFORMATION: Recombinant peptide

<400> SEQUENCE: 1200

His His His His His His
1               5

<210> SEQ ID NO 1201
<211> LENGTH: 10
<212> TYPE: PRT
<213> ORGANISM: Artificial Sequence
<220> FEATURE:
<223> OTHER INFORMATION: Recombinant peptide

<400> SEQUENCE: 1201

Gly Gly Gly Gly Ser Gly Gly Gly Gly Ser
1               5                   10

<210> SEQ ID NO 1202
```

<211> LENGTH: 122
<212> TYPE: PRT
<213> ORGANISM: Artificial Sequence
<220> FEATURE:
<223> OTHER INFORMATION: Recombinant Protein

<400> SEQUENCE: 1202

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Gly Ile Ser Trp Lys Gly Asp Ile Gly Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 1203
<211> LENGTH: 5
<212> TYPE: PRT
<213> ORGANISM: Artificial Sequence
<220> FEATURE:
<223> OTHER INFORMATION: Recombinant Protein

<400> SEQUENCE: 1203

Asp Tyr Ala Met His
1               5

<210> SEQ ID NO 1204
<211> LENGTH: 17
<212> TYPE: PRT
<213> ORGANISM: Artificial Sequence
<220> FEATURE:
<223> OTHER INFORMATION: Recombinant Protein

<400> SEQUENCE: 1204

Gly Ile Ser Trp Lys Gly Asp Ile Gly Gly Tyr Val Asp Ser Val Lys
1               5                   10                  15

Gly

<210> SEQ ID NO 1205
<211> LENGTH: 13
<212> TYPE: PRT
<213> ORGANISM: Artificial Sequence
<220> FEATURE:
<223> OTHER INFORMATION: Recombinant Protein

<400> SEQUENCE: 1205

Ser Tyr Gly Ser Gly Ser Phe Tyr Asn Ala Phe Asp Ser
1               5                   10

<210> SEQ ID NO 1206
<211> LENGTH: 107
<212> TYPE: PRT
<213> ORGANISM: Homo sapiens

<400> SEQUENCE: 1206

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 1207
<211> LENGTH: 11
<212> TYPE: PRT
<213> ORGANISM: Homo sapiens

<400> SEQUENCE: 1207

Arg Ala Ser Gln Ser Ile Ser Ser Trp Leu Ala
1               5                   10

<210> SEQ ID NO 1208
<211> LENGTH: 7
<212> TYPE: PRT
<213> ORGANISM: Artificial Sequence
<220> FEATURE:
<223> OTHER INFORMATION: Recombinant Protein

<400> SEQUENCE: 1208

Lys Ala Ser Lys Leu Asp Arg
1               5

<210> SEQ ID NO 1209
<211> LENGTH: 9
<212> TYPE: PRT
<213> ORGANISM: Artificial Sequence
<220> FEATURE:
<223> OTHER INFORMATION: Recombinant Sequence

<400> SEQUENCE: 1209

Leu Glu Tyr Ser Ser Tyr Ile Arg Thr
1               5

<210> SEQ ID NO 1210
<211> LENGTH: 122
<212> TYPE: PRT
<213> ORGANISM: Artificial Sequence
<220> FEATURE:
<223> OTHER INFORMATION: Recombinant Protein

<400> SEQUENCE: 1210

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Val Lys Ser Tyr Gly Ser Gly Ser Phe Tyr Asn Ala Phe Asp Ser Trp
             100                 105                 110

Gly Gln Gly Thr Leu Val Thr Val Ser Ser
         115                 120

<210> SEQ ID NO 1211
<211> LENGTH: 5
<212> TYPE: PRT
<213> ORGANISM: Artificial Sequence
<220> FEATURE:
<223> OTHER INFORMATION: Recombinant Protein

<400> SEQUENCE: 1211

Asp Tyr Ala Met His
 1               5

<210> SEQ ID NO 1212
<211> LENGTH: 17
<212> TYPE: PRT
<213> ORGANISM: Artificial Sequence
<220> FEATURE:
<223> OTHER INFORMATION: Recombinant Protein

<400> SEQUENCE: 1212

Gly Ile Ser Trp Arg Gly Asp Ile Gly Gly Tyr Val Lys Ser Val Lys
 1               5                  10                  15

Gly

<210> SEQ ID NO 1213
<211> LENGTH: 13
<212> TYPE: PRT
<213> ORGANISM: Artificial Sequence
<220> FEATURE:
<223> OTHER INFORMATION: Recombinant Protein

<400> SEQUENCE: 1213

Ser Tyr Gly Ser Gly Ser Phe Tyr Asn Ala Phe Asp Ser
 1               5                  10

<210> SEQ ID NO 1214
<211> LENGTH: 107
<212> TYPE: PRT
<213> ORGANISM: Artificial Sequence
<220> FEATURE:
<223> OTHER INFORMATION: Recombinant Protein

<400> SEQUENCE: 1214

Asp Ile Gln Met Thr Gln Ser Pro Ser Thr Leu Ser Ala Ser Val Gly
 1               5                  10                  15

Asp Glu Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Phe Leu Ile
             35                  40                  45

Tyr Lys Ala Ser Lys Leu Glu Arg Gly Thr Pro Ser Arg Phe Ser Gly
         50                  55                  60

Ser Gly Ser Gly Thr Glu Phe Ser Leu Thr Ile Ser Ser Leu Gln Pro

```
                65                  70                  75                  80
Asp Asp Phe Ala Thr Tyr Tyr Cys Leu Glu Tyr Ser Ser Tyr Ile Arg
                    85                  90                  95

Thr Phe Gly Gln Gly Thr Lys Val Glu Ile Lys
                100                 105
```

<210> SEQ ID NO 1215
<211> LENGTH: 11
<212> TYPE: PRT
<213> ORGANISM: Artificial Sequence
<220> FEATURE:
<223> OTHER INFORMATION: Recombinant Protein

<400> SEQUENCE: 1215

```
Arg Ala Ser Gln Ser Ile Ser Ser Trp Leu Ala
1               5                   10
```

<210> SEQ ID NO 1216
<211> LENGTH: 7
<212> TYPE: PRT
<213> ORGANISM: Artificial Sequence
<220> FEATURE:
<223> OTHER INFORMATION: Recombinant Protein

<400> SEQUENCE: 1216

```
Lys Ala Ser Lys Leu Glu Arg
1               5
```

<210> SEQ ID NO 1217
<211> LENGTH: 9
<212> TYPE: PRT
<213> ORGANISM: Artificial Sequence
<220> FEATURE:
<223> OTHER INFORMATION: Recombinant Protein

<400> SEQUENCE: 1217

```
Leu Glu Tyr Ser Ser Tyr Ile Arg Thr
1               5
```

<210> SEQ ID NO 1218
<211> LENGTH: 122
<212> TYPE: PRT
<213> ORGANISM: Artificial Sequence
<220> FEATURE:
<223> OTHER INFORMATION: Recombinant Protein

<400> SEQUENCE: 1218

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
                20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Ala Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
```

<210> SEQ ID NO 1219
<211> LENGTH: 5
<212> TYPE: PRT
<213> ORGANISM: Artificial Sequence
<220> FEATURE:
<223> OTHER INFORMATION: Recombinant Protein

<400> SEQUENCE: 1219

Asp Tyr Ala Met His
1               5

<210> SEQ ID NO 1220
<211> LENGTH: 17
<212> TYPE: PRT
<213> ORGANISM: Artificial Sequence
<220> FEATURE:
<223> OTHER INFORMATION: Recombinant Protein

<400> SEQUENCE: 1220

Gly Ile Ser Trp Arg Gly Asp Ile Gly Gly Tyr Ala Lys Ser Val Lys
1               5                   10                  15

Gly

<210> SEQ ID NO 1221
<211> LENGTH: 13
<212> TYPE: PRT
<213> ORGANISM: Artificial Sequence
<220> FEATURE:
<223> OTHER INFORMATION: Recombinant Protein

<400> SEQUENCE: 1221

Ser Tyr Gly Ser Gly Ser Phe Tyr Asn Ala Phe Asp Ser
1               5                   10

<210> SEQ ID NO 1222
<211> LENGTH: 107
<212> TYPE: PRT
<213> ORGANISM: Artificial Sequence
<220> FEATURE:
<223> OTHER INFORMATION: Recombinant Protein

<400> SEQUENCE: 1222

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 1223
<211> LENGTH: 11
<212> TYPE: PRT
<213> ORGANISM: Homo sapiens

<400> SEQUENCE: 1223

Arg Ala Ser Gln Ser Ile Ser Ser Trp Leu Ala
1               5                   10

<210> SEQ ID NO 1224
<211> LENGTH: 7
<212> TYPE: PRT
<213> ORGANISM: Homo sapiens

<400> SEQUENCE: 1224

Lys Ala Ser Lys Leu Asp Arg
1               5

<210> SEQ ID NO 1225
<211> LENGTH: 9
<212> TYPE: PRT
<213> ORGANISM: Artificial Sequence
<220> FEATURE:
<223> OTHER INFORMATION: Recombinant Protein

<400> SEQUENCE: 1225

Leu Glu Tyr Ser Ser Tyr Ile Arg Thr
1               5

<210> SEQ ID NO 1226
<211> LENGTH: 122
<212> TYPE: PRT
<213> ORGANISM: Artificial Sequence
<220> FEATURE:
<223> OTHER INFORMATION: Recombinant Protein

<400> SEQUENCE: 1226

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Arg Gly Asp Ile Gly Gly Tyr Val Lys Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
                100                 105                 110

Gly Gln Gly Thr Leu Val Thr Val Ser Ser
            115                 120

<210> SEQ ID NO 1227
<211> LENGTH: 5
<212> TYPE: PRT
<213> ORGANISM: Artificial Sequence
<220> FEATURE:
<223> OTHER INFORMATION: Recombinant Protein

<400> SEQUENCE: 1227

Asp Tyr Ala Met His
1               5

<210> SEQ ID NO 1228

```
<211> LENGTH: 17
<212> TYPE: PRT
<213> ORGANISM: Artificial Sequence
<220> FEATURE:
<223> OTHER INFORMATION: Recombinant Protein

<400> SEQUENCE: 1228

Gly Ile Ser Trp Arg Gly Asp Ile Gly Gly Tyr Val Lys Ser Val Lys
1               5                   10                  15

Gly

<210> SEQ ID NO 1229
<211> LENGTH: 13
<212> TYPE: PRT
<213> ORGANISM: Artificial Sequence
<220> FEATURE:
<223> OTHER INFORMATION: Recombinant Protein

<400> SEQUENCE: 1229

Ser Tyr Gly Ser Gly Ser Phe Tyr Asn Ala Phe Asp Ser
1               5                   10

<210> SEQ ID NO 1230
<211> LENGTH: 107
<212> TYPE: PRT
<213> ORGANISM: Artificial Sequence
<220> FEATURE:
<223> OTHER INFORMATION: Recombinant Protein

<400> SEQUENCE: 1230

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 1231
<211> LENGTH: 11
<212> TYPE: PRT
<213> ORGANISM: Artificial Sequence
<220> FEATURE:
<223> OTHER INFORMATION: Recombinant Protein

<400> SEQUENCE: 1231

Arg Ala Ser Gln Ser Ile Ser Ser Trp Leu Ala
1               5                   10

<210> SEQ ID NO 1232
<211> LENGTH: 7
<212> TYPE: PRT
<213> ORGANISM: Artificial Sequence
<220> FEATURE:
<223> OTHER INFORMATION: Recombinant Protein

<400> SEQUENCE: 1232
```

Lys Ala Ser Lys Leu Asp Arg
1               5

<210> SEQ ID NO 1233
<211> LENGTH: 9
<212> TYPE: PRT
<213> ORGANISM: Artificial Sequence
<220> FEATURE:
<223> OTHER INFORMATION: Recombinant Protein

<400> SEQUENCE: 1233

Leu Glu Tyr Ser Ser Tyr Ile Arg Thr
1               5

<210> SEQ ID NO 1234
<211> LENGTH: 122
<212> TYPE: PRT
<213> ORGANISM: Artificial Sequence
<220> FEATURE:
<223> OTHER INFORMATION: Recombinant Protein

<400> SEQUENCE: 1234

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 1235
<211> LENGTH: 5
<212> TYPE: PRT
<213> ORGANISM: Artificial Sequence
<220> FEATURE:
<223> OTHER INFORMATION: Recombinant Protein

<400> SEQUENCE: 1235

Asp Tyr Ala Met His
1               5

<210> SEQ ID NO 1236
<211> LENGTH: 17
<212> TYPE: PRT
<213> ORGANISM: Artificial Sequence
<220> FEATURE:
<223> OTHER INFORMATION: Recombinant Protein

<400> SEQUENCE: 1236

Gly Ile Ser Trp Arg Gly Asp Ile Gly Gly Tyr Val Lys Ser Val Lys
1               5                   10                  15

Gly

<210> SEQ ID NO 1237
<211> LENGTH: 13
<212> TYPE: PRT
<213> ORGANISM: Artificial Sequence
<220> FEATURE:
<223> OTHER INFORMATION: Recombinant Protein

<400> SEQUENCE: 1237

Ser Tyr Gly Ser Gly Ser Phe Tyr Asn Ala Phe Asp Ser
1               5                   10

<210> SEQ ID NO 1238
<211> LENGTH: 107
<212> TYPE: PRT
<213> ORGANISM: Artificial Sequence
<220> FEATURE:
<223> OTHER INFORMATION: Recombinant Protein

<400> SEQUENCE: 1238

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 1239
<211> LENGTH: 11
<212> TYPE: PRT
<213> ORGANISM: Artificial Sequence
<220> FEATURE:
<223> OTHER INFORMATION: Recombinant Protein

<400> SEQUENCE: 1239

Arg Ala Ser Gln Ser Ile Ser Ser Trp Leu Ala
1               5                   10

<210> SEQ ID NO 1240
<211> LENGTH: 7
<212> TYPE: PRT
<213> ORGANISM: Artificial Sequence
<220> FEATURE:
<223> OTHER INFORMATION: Recombinant Protein

<400> SEQUENCE: 1240

Lys Ala Ser Lys Leu Asp Arg
1               5

<210> SEQ ID NO 1241
<211> LENGTH: 9
<212> TYPE: PRT
<213> ORGANISM: Artificial Sequence
<220> FEATURE:
<223> OTHER INFORMATION: Recombinant Protein

<400> SEQUENCE: 1241

```
Leu Glu Tyr Ser Ser Tyr Ile Arg Thr
1               5
```

<210> SEQ ID NO 1242
<211> LENGTH: 122
<212> TYPE: PRT
<213> ORGANISM: Artificial Sequence
<220> FEATURE:
<223> OTHER INFORMATION: Recombinant Protein

<400> SEQUENCE: 1242

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 1243
<211> LENGTH: 5
<212> TYPE: PRT
<213> ORGANISM: Artificial Sequence
<220> FEATURE:
<223> OTHER INFORMATION: Recombinant Protein

<400> SEQUENCE: 1243

```
Asp Tyr Ala Met His
1               5
```

<210> SEQ ID NO 1244
<211> LENGTH: 17
<212> TYPE: PRT
<213> ORGANISM: Artificial Sequence
<220> FEATURE:
<223> OTHER INFORMATION: Recombinant Protein

<400> SEQUENCE: 1244

```
Gly Ile Ser Trp Arg Gly Asp Ile Gly Gly Tyr Val Lys Ser Val Lys
1               5                   10                  15

Gly
```

<210> SEQ ID NO 1245
<211> LENGTH: 13
<212> TYPE: PRT
<213> ORGANISM: Artificial Sequence
<220> FEATURE:
<223> OTHER INFORMATION: Recombinant Protein

<400> SEQUENCE: 1245

```
Ser Tyr Gly Ser Gly Ser Phe Tyr Asn Ala Phe Asp Ser
1               5                   10
```

```
<210> SEQ ID NO 1246
<211> LENGTH: 107
<212> TYPE: PRT
<213> ORGANISM: Artificial Sequence
<220> FEATURE:
<223> OTHER INFORMATION: Recombinant Protein

<400> SEQUENCE: 1246

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105

<210> SEQ ID NO 1247
<211> LENGTH: 11
<212> TYPE: PRT
<213> ORGANISM: Artificial Sequence
<220> FEATURE:
<223> OTHER INFORMATION: Recombinant Protein

<400> SEQUENCE: 1247

Arg Ala Ser Gln Ser Ile Ser Ser Trp Leu Ala
1               5                   10

<210> SEQ ID NO 1248
<211> LENGTH: 7
<212> TYPE: PRT
<213> ORGANISM: Artificial Sequence
<220> FEATURE:
<223> OTHER INFORMATION: Recombinant Protein

<400> SEQUENCE: 1248

Lys Ala Ser Lys Leu Asp Arg
1               5

<210> SEQ ID NO 1249
<211> LENGTH: 9
<212> TYPE: PRT
<213> ORGANISM: Artificial Sequence
<220> FEATURE:
<223> OTHER INFORMATION: Recombinant Protein

<400> SEQUENCE: 1249

Leu Glu Tyr Ser Ser Tyr Ile Arg Thr
1               5
```

PROCOAGULANT ANTIBODIES

CROSS-REFERENCE TO RELATED APPLICATIONS

This application is a continuation of an International Application No. PCT/EP2019/070628 (WO 2020/025672), filed Jul. 31, 2019, which claims priority to European Patent Application No. 18193191.6, filed Sep. 7, 2018, International Application No. PCT/CN2018/099339, filed Aug. 8, 2018, and International Application No. PCT/CN2018/097834, filed Aug. 1, 2018; the contents all of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 27, 2021, is named 180021 US01_SeqList.txt and is 541 kilobytes in size.

BACKGROUND

In patients with a coagulopathy, such as in human beings with haemophilia A and B, various steps of the coagulation cascade are rendered dysfunctional due to, for example, the absence or insufficient presence of a functional coagulation factor. Such dysfunction of one part of the coagulation cascade results in insufficient blood coagulation and poten- Coagulation Factor VIII (FVIII) deficiency, commonly referred to as haemophilia A, is a congenital bleeding disorder affecting approximately 420,000 people worldwide, of which around 105,000 are currently diagnosed.

Patients with haemophilia A may receive coagulation factor replacement therapy such as exogenous FVIII. Conventional treatment consists of replacement therapy, provided as prophylaxis or on demand treatment of bleeding episodes. Until recently prophylactic treatment for a patient with severe haemophilia A was up to three intravenous injections/week with either plasma derived FVIII or recombinant FVIII or long-acting variants thereof.

However, such patients are at risk of developing neutralizing antibodies, so-called inhibitors, to such exogenous factors, rendering formerly efficient therapy ineffective. Haemophilia A patients with inhibitors is a non-limiting example of a coagulopathy that is partly congenital and partly acquired. Patients that have developed inhibitors to FVIII cannot be treated with conventional replacement therapy. Exogenous coagulation factors may only be administered intravenously, which is of considerable inconvenience and discomfort to patients. For example, infants and toddlers may have to have intravenous catheters surgically inserted into a chest vein, in order for venous access to be guaranteed. This leaves them at great risk of developing bacterial infections.

In a bleeding individual, coagulation is initiated by formation of the Tissue Factor/Factor VIIa (TF/FVIIa) complex when extravascular TF is exposed to activated FVII (FVIIa) in the blood. TF/FVIIa complex formation leads to the activation of coagulation Factor X (FX) to activated coagulation Factor Xa (FXa) which, together with activated coagulation Factor V (FVa), generates a limited amount of thrombin, which in turn activates blood platelets. Activated platelets support the assembly of the tenase complex composed of activated Factor VIII (FVIIIa) and activated coagulation Factor IX (FIXa). The tenase complex is a very efficient catalyst of FX activation and FXa generated in this second step serves as the active protease in the FVa/FXa pro-thrombinase complex which is responsible for the final thrombin burst. Thrombin cleaves fibrinogen to generate fibrin monomers, which polymerise to form a fibrin network which seals the leaking vessel and stops the bleeding. The rapid and extensive thrombin burst is a prerequisite for the formation of a solid and stable fibrin clot.

An inadequate FXa formation and decreased thrombin generation caused by reduced or absent FVIII activity is the reason underlying the bleeding diathesis in haemophilia A patients.

As mentioned, proteolytic conversion of FX into its enzymatically active form FXa can be achieved by the intrinsic FX-activating complex comprising FIXa and its cofactor FVIIIa. Cofactor binding increases the enzymatic activity of FIXa by about five orders of magnitude and is believed to result through multiple mechanisms as outlined by Scheiflinger et al. (2008) *J Thromb Haemost,* 6:315-322. Notably, FVIIIa has been found to stabilize a conformation of FIXa that has increased proteolytic activity towards FX (Kolkman J A, Mertens K (2000) Biochemistry, 39:7398-7405, Zögg T, Brandstetter H (2009) *Biol Chem,* 390:391-400). Based on this observation and realizing that antibodies are versatile binding proteins capable of mimicking a variety of protein-protein interactions, Scheiflinger et al. performed a screen for agonistic anti-FIXa antibodies characterized by an ability to enhance FX activation by FIXa in the presence of a phospholipid surface and calcium, but in the absence of the natural cofactor FVIIIa. From a screen of 5280 hybridoma supernatants, 88 were found to produce antibodies exhibiting various degrees of FIXa agonistic activity, cf. EP1220923 B1 and EP1660536 B1. With respect to the kinetics of FX activation and ability to stimulate thrombin generation in FVIII-deficient human plasma, EP1660536 B1 consistently points to the anti-FIXa antibody 224F3 as the most efficient antibody.

Recently, a new drug, emicizumab (HEMLIBRA®) also known as ACE910, has been approved for subcutaneous prophylactic treatment of Haemophilia A with or without inhibitors against conventional replacement therapy factors. Emicizumab is a humanized, bispecific anti-FIX(a)/anti-FX(a) monoclonal antibody developed by Chugai Pharmaceuticals/Roche Pharmaceuticals for the treatment of haemophilia A. Emicizumab is designed to mimic FVIII cofactor function (see Sampei et al.: (2013) *PLoS One,* 8, e57479 and WO2012067176), however, some patients have developed inhibitors against emicizumab rendering treatment with this compound ineffective.

There are still many unmet medical needs in the haemophilia community, in particular, and in subjects with coagulopathies, in general and the present invention relates to improved compounds capable of substituting for FVIII and thus being useful for the treatment of a coagulopathy such as haemophilia A.

SUMMARY

The present invention relates to compounds, which serve as a substitute for coagulation Factor VIII (FVIII) in patients suffering from a coagulopathy and in particular patients lacking functional FVIII, such as haemophilia A patients including haemophilia A patients with inhibitors.

Hence, one aspect of the present invention relates to compounds capable of enhancing the generation of FXa and thus partially or completely restoring coagulation in patients lacking functional FVIII.

In one aspect, the compound is an antibody or antigen-binding fragment thereof. In one such aspect, the compound is a multispecific antibody or antigen-binding fragment thereof such as a bispecific antibody or antigen-binding fragment thereof.

In one particular aspect, the invention relates to procoagulant antibodies or antigen-binding fragment thereof which serve as a substitute for FVIII in patients lacking functional FVIII, such as haemophilia A patients.

In one such aspect, the antibody or antigen-binding fragment thereof is capable of binding FIX(a) and increases the enzymatic activity of FIXa towards FX, optionally also being capable of binding FX.

In one aspect, the invention relates to a procoagulant antibody or antigen-binding fragment thereof that is capable of binding FIX(a) and FX(a), including bispecific procoagulant antibodies or antigen-binding fragment thereof which increase the enzymatic activity of FIXa towards FX. In one aspect, the invention relates to a procoagulant bispecific antibody or antigen-binding fragment thereof that is capable of binding to FIX(a) and FX(a).

A further aspect of the invention relates to the individual component (intermediate) antibodies or antigen-binding fragment thereof that are part of a procoagulant antibody, such as a particular anti-FIX(a) antibody or antigen-binding fragment thereof or a particular anti-FX(a) antibody or antigen-binding fragment thereof.

A further aspect of the invention relates to the manufacture of the antibodies or antigen-binding fragment thereof—and components (intermediates) thereof—as disclosed herein.

A further aspect of the invention relates to an antibody that competes with a procoagulant antibody or antigen-binding fragment thereof, as disclosed herein, for binding to FIX(a) and/or FX(a).

A further aspect of the invention relates to an antibody or antigen-binding fragment thereof which shares epitope residues or epitope hot-spot residues on FIX(a) and/or FX(a) with a procoagulant antibody or antigen-binding fragment hereof, as disclosed herein.

A further aspect of the invention is directed to the procoagulant antibodies or antigen-binding fragment thereof disclosed herein for prevention and/or treatment of a coagulopathy, a disease accompanying coagulopathy, or a disease caused by coagulopathy. In one aspect the coagulopathy is haemophilia A with or without inhibitors.

A still further aspect of the invention relates to a pharmaceutical composition comprising a procoagulant antibody or antigen-binding fragment thereof as disclosed herein formulated for the delivery of said antibody for the prevention and/or treatment of a coagulopathy, such as haemophilia A with or without inhibitors, as well as an injection device with content thereof.

A further aspect of the invention is directed to a kit comprising (i) an antibody or antigen-binding fragment thereof as disclosed herein such as a bispecific antibody and (ii) instructions for use.

The invention may also solve further problems that will be apparent from the disclosure of the exemplary embodiments.

BRIEF DESCRIPTION OF THE FIGURES

FIG. 1A-1D shows alignments of sequences representing heavy- and light chain variable domains of the anti-FIX(a) (FIGS. 1A and 1B) and anti-FX(a) (FIGS. 1C and 1D) IgG antibodies as disclosed herein. CDR1, 2 and 3 sequences are highlighted in bold and underlined in uppermost sequence and is representative for the remaining sequences.

FIG. 4A-4B shows results from antibody binning experiments on an Octet Fortebio system using a modified in-tandem setup. Briefly, biotinylated human FIXa was captured on streptavidin tips. Captured FIXa was then saturated by initial exposure to a first (1st) bivalent anti-FIXa antibody, which was followed by a second exposure to an equimolar mixture of the first (1st) antibody and a second (2nd) bivalent anti-FIXa antibody. Binding responses for each of the three phases as well as the identity of the antibodies used are shown. In FIG. 4A, top diagram (labelled as C), the $1^{st}$ bivalent anti-FIXa antibody is mAb01-2434 and the $2^{nd}$ bivalent anti-FIXa antibodies are mAb01-2434 (shown in dash line) or mAb01-1767 (shown in solid line), respectively. In FIG. 4A, bottom diagram (labelled as D), the $1^{st}$ bivalent anti-FIXa antibody is mAb01-2434 and the $2^{nd}$ bivalent anti-FIXa antibodies are IgG4 (shown in dash line) or mAb01-9985 (shown in solid line), respectively. In FIG. 4B, top diagram (labelled as E), the $1^{st}$ bivalent anti-FIXa antibody is mAb01-1582 and the $2^{nd}$ bivalent anti-FIXa antibodies are mAb01-1582 (shown in dash line) or mAb01-1767 (shown in solid line), respectively. In FIG. 4B, bottom diagram (labelled as F), the $1^{st}$ bivalent anti-FIXa antibody is mAb01-1582 and the $2^{nd}$ bivalent anti-FIXa antibodies are IgG4 (shown in dash line) or mAb01-9985 (shown in solid line), respectively.

FIG. 5 shows results from antibody binning experiments on an Octet Fortebio system using a modified in-tandem setup. Briefly, biotinylated human FXa was captured on streptavidin tips. Captured FXa was then saturated by initial exposure to a first (1st) bivalent anti-FXa antibody, which was followed by a second exposure to an equimolar mixture of the first (1st) antibody and a second (2nd) bivalent anti-FXa antibody. Binding responses for each of the three phases as well as the identity of the antibodies used are shown. In top diagram (labelled as A), the $1^{st}$ bivalent anti-FIXa antibody is mAb01-2435 and the $2^{nd}$ bivalent anti-FIXa antibodies are mAb01-2435 (shown in dash line) or mAb01-6723 (shown in solid line), respectively. In bottom diagram (labelled as B), the $1^{st}$ bivalent anti-FIXa antibody is mAb01-2435 and the $2^{nd}$ bivalent anti-FIXa antibodies are IgG4 (shown in dash line) or mAb01-8174 (shown in solid line), respectively.

BRIEF DESCRIPTION OF THE SEQUENCES

Figure 2:
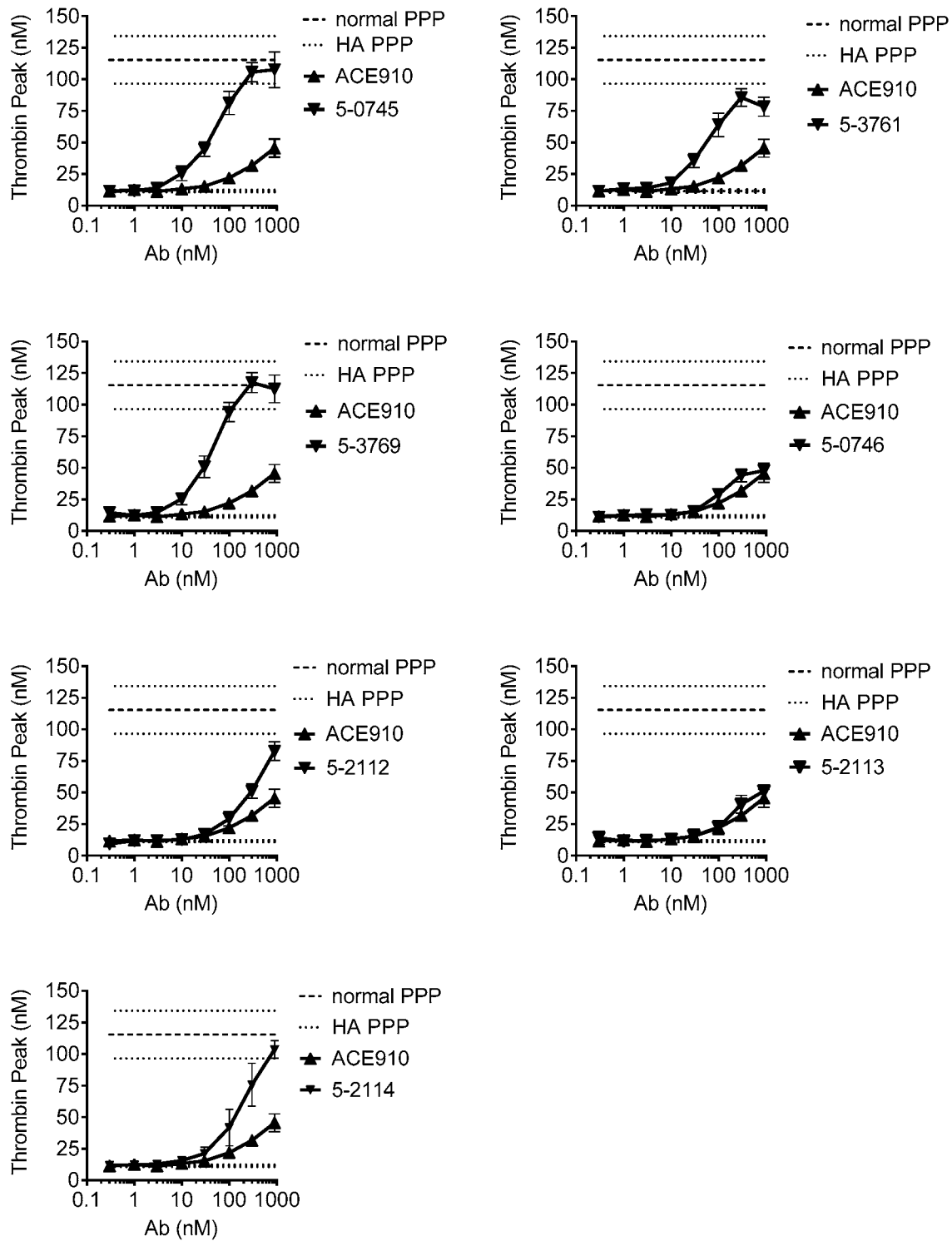
FIG. 2 shows thrombin generation test (TGT) results from the bispecific antibodies bimAb05-0745, bimAb05-3761, bimAb05-3769, bimAb05-0746, bimAb05-2112, bimAb05-2113, bimAb05-2114 and ACE910 in human tissue factor activated haemophilia A platelet-poor plasma (PPP). The experiment was performed as described in Example 16. Dotted and stippled lines indicate the peak thrombin level (nM) observed in the absence of antibody in HA-PPP and normal PPP, respectively, and with their standard deviation indicated by dotted lines. The profiles of bimAb05-0745, bimAb05-3761, bimAb05-3769, bimAb05-0746, bimAb05-2112, bimAb05-2113 and bimAb05-2114 are indicated by down-pointing triangles, whereas that of ACE910 is indicated by up-pointing triangles. Results are shown as mean±standard deviation from at least three independent experiments.

SEQ ID NO:1 represents the amino acid sequence of human coagulation Factor IX.

SEQ ID NO:2 represents the amino acid sequence of human coagulation Factor X.

SEQ ID NOs:3-1194 and 1202-1249 represent the sequences of the heavy chain variable domains (VH) and light chain variable domains (VL) and Complementarity Determining Regions (CDRs) of anti-FIX(a) and anti-FX(a) monoclonal antibodies (mAbs) described herein.

SEQ ID NO:1195 represents the human IgG4 heavy chain constant region with S228P and C-terminal lysine truncation.

SEQ ID NO:1196 represents the human IgG4 heavy chain constant region with S228P, F405L, R409K and C-terminal lysine truncation.

SEQ ID NO:1197 represents the human kappa light chain constant region.

SEQ ID NO:1198 represents the human IgG1 heavy chain constant region with F405L and C-terminal lysine truncation.

SEQ ID NO:1199 represents the human IgG1 heavy chain constant region with K405R and C-terminal lysine truncation.

SEQ ID NO:1200 represents a N-terminal His-tag.
SEQ ID NO:1201 represents a GS-linker.
The tables in Example 6 link the SEQ ID NOs to individual (component) anti-FIX(a) and anti-FX(a) antibodies and bispecific antibodies of the invention.

DESCRIPTION

In subjects with a coagulopathy, such as in human beings with haemophilia A, the coagulation cascade is rendered dysfunctional due to the absence or insufficient presence of functional FVIII. Such dysfunction of one part of the coagulation cascade results in insufficient blood coagulation and potentially life-threatening bleeding, or damage to internal organs, such as the joints. The present invention relates to compounds, which serve as a substitute for coagulation Factor VIII (FVIII) in patients suffering from a coagulopathy and in particular patients lacking functional FVIII, such as haemophilia A patients including haemophilia A patients with inhibitors. In one aspect, such compound is an antibody.

In particular the inventors of the present invention have surprisingly identified antibodies which mimic FVIII cofactor activity with high potency and efficacy. In one particular aspect, the invention relates to procoagulant antibodies which serve as a substitute for FVIII in patients lacking functional FVIII, such as haemophilia A patients. In one such aspect, the procoagulant antibodies bind to and increase the enzymatic activity of coagulation Factor IXa (FIXa) towards coagulation Factor X (FX), optionally also binding FX. In one such aspect the antibodies of the invention are bispecific antibodies capable of binding to FIX/FIXa and FX.

A further aspect of the invention relates to the individual component (intermediate) antibodies or antigen-binding fragment thereof that are part of a multispecific procoagulant antibody, such as a particular anti-FIX(a) antibody or antigen-binding fragment thereof or a particular anti-FX(a) antibody or antigen-binding fragment thereof.

A further aspect of the invention relates to the manufacture of the antibodies or antigen-binding fragment thereof—and components (intermediates) thereof—as disclosed herein.

A further aspect of the invention relates to an antibody that competes with a procoagulant antibody or antigen-binding fragment thereof, as disclosed herein, for binding to FIX(a) and/or FX(a).

A further aspect of the invention relates to an antibody or antigen-binding fragment thereof which shares epitope residues or epitope hot-spot residues on FIX(a) and/or FX(a) with a procoagulant antibody or antigen-binding fragment hereof, as disclosed herein.

In one aspect, the antibody is a human or humanised antibody, such as a human or humanised bispecific antibody.

A further aspect of the invention is directed to the procoagulant antibodies or antigen-binding fragment thereof disclosed herein for prevention and/or treatment of a coagulopathy, a disease accompanying coagulopathy, or a disease caused by coagulopathy. In one aspect the coagulopathy is haemophilia A with or without inhibitors.

A still further aspect of the invention relates to a pharmaceutical composition comprising a procoagulant antibody or antigen-binding fragment thereof as disclosed herein formulated for the delivery of said antibody for the prevention and/or treatment of a coagulopathy, such as haemophilia A with or without inhibitors, as well as an injection device with content thereof.

A further aspect of the invention is directed to a kit comprising (i) an antibody or antigen-binding fragment thereof as disclosed herein such as a bispecific antibody and (ii) instructions for use.

Coagulation Factor IX

Coagulation Factor IX (FIX) is a vitamin K-dependent coagulation factor with structural similarities to Factor VII, prothrombin, Factor X, and Protein C. FIX circulates in plasma as a single-chain zymogen (SEQ ID NO:1). The circulating zymogen form consists of 415 amino acids divided into four distinct domains comprising an N-terminal γ-carboxyglutamic acid-rich (Gla) domain, two EGF domains and a C-terminal trypsin-like serine protease domain. Activation of FIX occurs by limited proteolysis at Arg145 and Arg180 to release the activation peptide (residues 146 to 180 of SEQ ID NO:1). Thus, activated FIX (FIXa) is composed of residues 1-145 of SEQ ID NO:1 (light chain) and residues 181-415 of SEQ ID NO:1 (heavy chain). Circulating FIX molecules thus comprise the FIX zymogen and the activated form of FIX which are herein generally referred to as FIX and FIXa with reference to SEQ ID NO:1.

Activated Factor IX is referred to as Factor IXa or FIXa. The term "FIX (SEQ ID NO:1) and/or the activated form thereof (FIXa)" may also be referred to as "FIX/FIXa" or simply "FIX(a)".

FIXa is a trypsin-like serine protease that serves a key role in haemostasis by generating, as part of the tenase complex, most of the Factor Xa required to support proper thrombin formation during coagulation.

FIX is herein represented by SEQ ID NO:1 corresponding to the Ala148 allelic form of human FIX (Anson et al. EMBO J. 1984 3:1053-1060; McGraw et al., Proc Natl Acad Sci USA. 1985 82:2847-2851; Graham et al. Am. J. Hum. Genet. 1988 42:573-580). In the present invention FIX is intended to cover all natural variants of FIX, such as the T148 variant (Uniprot ID P00740).

Coagulation Factor X

FX is a vitamin K-dependent coagulation factor with structural similarities to Factor VII, prothrombin, FIX, and protein C. FX circulates in plasma as a two-chain zymogen including residues 1-139 of SEQ ID NO:2 (light chain) and residues 143-448 of SEQ ID NO:2 (heavy chain). Human FX zymogen comprises four distinct domains comprising an N-terminal gamma-carboxyglutamic acid rich (Gla) domain (residues 1-45), two EGF domains, EGF1 (residues 46-82) and EGF2 (residues 85-125), respectively, and a C-terminal trypsin-like serine protease domain (residues 195-448). Activation of FX occurs by limited proteolysis at Arg194, which results in the release of the activation peptide (residues 143-194). Thus, activated FX (FXa) is composed of residues 1-139 of SEQ ID NO:2 (light chain) and residues 195-448 of SEQ ID NO:2 (activated heavy chain). Circulating Factor X molecules thus comprises the FX zymogen and the activated form of FX which are herein referred to as FX and FXa, respectively, with reference to SEQ ID NO:2. In the present invention FX is intended to cover all natural variants of FX. The term "FX (SEQ ID NO:2) and/or the activated form thereof (FXa)" may also be referred to as "FX/FXa" or "FX(a)".

Antibodies

The term "antibody" herein refers to a protein, derived from an immunoglobulin sequence, which is capable of binding to an antigen or a portion thereof. The term antibody includes, but is not limited to, full length antibodies of any class (or isotype), that is, IgA, IgD, IgE, IgG, IgM and/or IgY. The term antibody includes—but is not limited to—antibodies that are bivalent, such as bispecific antibodies.

Natural full-length antibodies comprise at least four polypeptide chains: two heavy chains (HC) and two light chains (LC) that are connected by disulfide bonds. In some cases, natural antibodies comprise less than four chains, as in the case of the IgNARs found in Chondrichthyes. One class of immunoglobulins of particular pharmaceutical interest is the IgGs. In humans, the IgG class may be divided into four sub-classes IgG1, IgG2, IgG3 and IgG4, based on the sequence of their heavy chain constant regions. The light chains can be divided into two types, kappa and lambda chains, based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable domain ($V_H$) and up to three heavy chain constant ($C_H$) domains: $C_H1$, $C_H2$ and $C_H3$. A light chain may comprise a light chain variable domain ($V_L$) and a light chain constant domain ($C_L$). $V_H$ and $V_L$ regions can be further subdivided into regions of hypervariability, termed complementarity determining regions (CDRs) or hypervariable regions (HvRs), interspersed with regions that are more conserved, termed framework regions (FR). $V_H$ and $V_L$ domains are typically composed of three CDRs and four FRs, arranged from amino-terminus to carboxy-terminus in the following order: FR1, CDR1, FR2, CDR2, FR3, CDR3, FR4. The heavy and light chain variable domains containing the hypervariable regions (CDRs) form a structure that is capable of interacting with an antigen, whilst the constant region of an antibody may mediate binding of the immunoglobulin to host tissues or factors, including, but not limited to various cells of the immune system (effector cells), Fc receptors and the first component, C1q, of the C1 complex of the classical complement system.

Antibodies of the invention may be monoclonal antibodies (mAbs), in the sense that they represent a set of unique heavy and light chain variable domain sequences as expressed from a single B-cell or by a clonal population of B cells. Antibodies of the invention may be produced and purified using various methods that are known to a person skilled in the art. For example, antibodies may be produced from hybridoma cells. Antibodies may be produced by B-cell expansion. Antibodies or fragment thereof may be recombinantly expressed in mammalian or microbial expression systems, or by in vitro translation. Antibodies or fragment thereof may also be recombinantly expressed as cell surface bound molecules, by means of e.g. phage display, bacterial display, yeast display, mammalian cell display or ribosome or mRNA display. Antibodies of the current invention may be isolated. The term "isolated antibody" refers to an antibody that has been separated and/or recovered from (an)other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain(s) the ability to specifically bind to or recognise an antigen, such as FIX/FIXa, FX/FXa or another target molecule, as described herein. Examples of antigen-binding fragments include (but is not limited to) Fab, Fab', Fab$_2$, Fab'$_2$, Fv (typically the combination of $V_L$ and $V_H$ domains of a single arm of an antibody), single-chain Fv (scFv); see e.g. Bird et al. Science 1988; 242:423-426; and Huston et al. PNAS 1988; 85:5879-5883), dsFv, Fd (typically the $V_H$ and $C_H1$ domain), monovalent molecules comprising both a single $V_H$ and a single $V_L$ domain; minibodies, diabodies, triabodies, tetrabodies, and kappa bodies (see, e.g. III et al (1997) Protein Eng 10: 949-57); as well as one or more isolated CDRs or a functional paratope, where the isolated CDRs or antigen-binding residues or polypeptides can be associated or linked together so as to form a functional antibody fragment. These antibody fragments may be obtained using conventional techniques known to those skilled in the art, and the fragments may be screened for utility in the same manner as intact antibodies.

"Fab fragments" of an antibody, including "Fab" and "Fab'2" fragments, can be derived from an antibody by cleavage of the heavy chain in the hinge region on the N-terminal or C-terminal side, respectively, of the hinge cysteine residues connecting the heavy chains of the antibody. A "Fab" fragment includes the variable and constant domains of the light chain and the variable domain and $C_H1$ domain of the heavy chain. "Fab'$_2$" fragments comprise a pair of "Fab" fragments that are generally covalently linked by their hinge cysteines. A Fab' is formally derived from a Fab'$_2$ fragment by cleavage of the hinge disulfide bonds connecting the heavy chains in the Fab'$_2$. Other chemical couplings than disulfide linkages of antibody fragments are also known in the art. A Fab fragment retains the ability of the parent antibody to bind to its antigen, potentially with a lower affinity. Fab'$_2$ fragments are capable of bivalent binding, whereas Fab and Fab' fragments can only bind monovalently. Generally, Fab fragments lack the constant $C_H2$ and $C_H3$ domains, i.e. the Fc part, where interaction with the Fc receptors and C1q would occur. Thus, Fab fragments are in general devoid of effector functions. Fab fragments may be produced by methods known in the art, either by enzymatic cleavage of an antibody, e.g. using papain to obtain the Fab or pepsin to obtain the Fab'$_2$, Fab fragments including Fab, Fab', Fab'$_2$ may be produced recombinantly using techniques that are well known to the person skilled in the art. An "Fv" (fragment variable) fragment is an antibody fragment that contains a complete antigen recognition and binding site, and generally comprises one heavy and one light chain variable domain in association that can be covalent in nature, for example in a single chain variable domain fragment (scFv). It is in this configuration that the three hypervariable regions of each variable domain interact to define an antigen-binding site on the surface of the $V_H$-$V_L$ dimer.

Collectively, the six hypervariable regions or a subset thereof confer antigen binding specificity to the antibody.

"Single-chain Fv" or "scFv" antibody comprise the $V_H$ and $V_L$ domains of antibody, where these domains are present in a single polypeptide chain. Generally, the Fv polypeptide further comprises a polypeptide linker between the $V_H$ and $V_L$ domains that enables the scFv to form the desired structure for antigen binding. For a review of scFv, see Pluckthun, 1994, In: The *Pharmacology of Monoclonal Antibodies*, Vol. 113, Rosenburg and Moore eds. Springer-Verlag, New York, pp. 269-315.

"Single-chain Fab" or "scFab" antibody comprise the $V_H$, $C_H1$, $V_L$ and $C_L$ domains of an antibody, where these domains are present in a single polypeptide chain. Generally, the Fab polypeptide further comprises a polypeptide linker between either $V_H$ and $C_L$ or $V_L$ and $C_H1$ domains that enables the scFab to form the desired structure for antigen binding (Koerber et al. (2015) J Mol Biol. 427:576-86).

The term "diabodies" refers to small antibody fragments with two antigen-binding sites, in which fragments comprise a heavy chain variable domain ($V_H$) connected to a light chain variable domain ($V_L$) in the same polypeptide chain ($V_H$ and $V_L$). By using a linker that is too short to allow pairing between the two variable domains on the same chain, the variable domains are forced to pair with complementary domains of another chain, creating two antigen-binding sites.

The expression "linear antibodies" refers to antibodies as described in Zapata et al. (1995) Protein Eng. 8: 1057-1062. Briefly, these antibodies contain a pair of tandem Fd segments ($V_H$-$C_H1$-$V_H$-$C_H1$) that, together with complementary light chain polypeptides, form a pair of antigen binding regions. Linear antibodies can be bispecific or monospecific.

Antibody fragments may be obtained using conventional recombinant or protein engineering techniques and the fragments can be screened for binding to FIX and the activated form thereof, FX or another function, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of the antibody, or a variant of any one of the antibodies disclosed herein. An antibody of the invention may be, or may comprise, an antigen binding portion of one of these antibodies, or variants thereof. For example, an antibody of the invention may be a Fab fragment of one of these antibodies or variants thereof, or it may be a single chain antibody derived from one of these antibodies, or a variant thereof. Also, an antibody of the invention may be a combination of a full length antibody and fragment thereof.

The term "one-armed" as used herein, refers to a particular type of monovalent antibody constituted by an antibody heavy chain, a truncated heavy chain lacking the Fab region, and a single light chain.

The term "monospecific" antibody as used herein, refers to an antibody which is capable of binding to one particular epitope (including but not limited to bivalent antibodies).

The term "bispecific" antibody as used herein, refers to an antibody which is capable of binding to two different antigens or two different epitopes on the same antigen.

The term "trispecific" antibody as used herein, refers to an antibody which is capable of binding to three different antigens or three different epitopes on the same antigen or three different epitopes present on two different antigens.

The term "multispecific" antibody as used herein, refers to an antibody which is capable of binding to two or more different antigens or two or more different epitopes on the same antigen. Multispecific antibodies thus comprise bi- and trispecific antibodies.

Bispecific antibodies in full length IgG format can be generated by fusion of two individual hybridomas to form a hybrid quadroma which produces a mixture of antibodies including a fraction of bispecific heterodimerising antibodies (Chelius D. et al.; *MAbs.* 2010 May-June; 2(3): 309-319). Bispecific heterodimerising antibodies may alternatively be produced by using recombinant technologies. Heterodimerisation can also be achieved by engineering the dimerisation interface of the Fc region to promote heterodimerisation. One example hereof is the so-called knob-in-hole mutations where sterically bulky side chains (knobs) are introduced in one Fc matched by sterically small side chains (holes) on the opposite Fc thereby creating steric complementarity promoting heterodimerisation. Other methods for engineered heterodimerisation Fc interfaces are electrostatic complementarity, fusion to non-IgG heterodimerisation domains or utilising the natural Fab-arm exchange phenomenon of human IgG4 to control heterodimerisation. Examples of heterodimerised bispecific antibodies are well described in the literature, e.g. (Klein C, et al.; *MAbs.* 2012 November-December; 4(6): 653-663). Special attention has to be paid to the light chains in heterodimeric antibodies. Correct pairing of LCs and HCs can be accomplished by the use of a common light chain. Again engineering of the LC/HC interface can be used to promote heterodimerisation or light chain cross-over engineering as in CrossMabs. In vitro re-assembly under mildly reducing conditions of antibodies from two individual IgGs containing appropriate mutations can also be used to generate bispecific antibodies (e.g. Labrijn et al., *PNAS,* 110, 5145-5150 (2013)). Also the natural Fab-arm exchange method is reported to ensure correct light chains paring.

Multispecific antibody-based molecules may also be expressed recombinantly as fusion proteins combining the natural modules of IgGs to form multispecific and multivalent antibody derivatives as described in the literature. Examples of fusion antibodies are DVD-Igs, IgG-scFV, Diabodies, DARTs etc. Specific detection or purification tags, half-life extension moieties or other components can be incorporated in the fusion proteins. Additional non-IgG modalities may also be incorporated in the fusion proteins. Bispecific full length antibodies based on Fc heterodimerisation are commonly referred to as asymmetric IgGs, irrespective of the LC paring methodology.

Generally, bispecific antibodies may be produced in a variety of molecular formats as reviewed by Brinkmann et al. (Brinkmann et al. The making of bispecific antibodies. *Mabs* 9, 182-212 (2017)).

Multispecific antibody-based molecules may also be produced by chemical conjugation or coupling of individual full length IgGs or coupling of fragments of IgGs to form multispecific and multivalent antibody derivatives as described in the literature. Examples are chemically coupled Fab fragments, IgG-dimer etc. Specific detection or purification tags, half-life extension molecules or other components can be incorporated in the conjugate proteins. Additional non-IgG polypeptide may also be incorporated in the fusion proteins. Multispecific molecules may also be produced by combining recombinant and chemical methods including those described above.

In one aspect, an antibody of the invention is a chimeric antibody, a human antibody or a humanised antibody. Such antibody can be generated by using, for example, suitable antibody display or immunization platforms or other suitable platforms or methods known in the field. The term "human antibody", as used herein, is intended to include antibodies having variable domains in which at least a portion of a framework region and/or at least a portion of a CDR region are derived from human germline immunoglobulin sequences. For example, a human antibody may have variable domains in which both the framework and CDR regions are derived from human germline immunoglobulin sequences. Furthermore, if the antibody contains a constant region, the constant region or a portion thereof is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Such a human antibody may be a human monoclonal antibody. Such a human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalised cell. Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

Human antibodies may be produced by recombinant methods known in the art.

The term "human antibody derivative" refers to any modified form of the human antibody, such as a conjugate of the antibody and another agent or antibody.

The term "humanised antibody", as used herein, refers to a human/non-human antibody that contains a sequence (CDR regions or parts thereof) derived from a non-human immunoglobulin. A humanised antibody is, thus, a human immunoglobulin (recipient antibody) in which residues from at least a hypervariable region of the recipient are replaced by residues from a hypervariable region of an antibody from a non-human species (donor antibody) such as from a mouse, rat, rabbit or non-human primate, which have the desired specificity, affinity, sequence composition and functionality. In some instances, framework (FR) residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (back-mutation) of the amino acid residue from the donor antibody has beneficial impact on the properties of the humanised antibody. In addition to donor antibody derived back-mutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and a chemical agent or a conjugate of the antibody with another antibody.

The term "chimeric antibody", as used herein, refers to an antibody comprising portions of antibodies derived from two or more species. For example, the genes encoding such antibody comprise genes encoding variable domains and genes encoding constant domains originated from two different species. For example, the genes encoding variable domains of a mouse monoclonal antibody may be joined to the genes encoding the constant domains of an antibody of human origin.

The fragment crystallisable region ("Fc region"/"Fc domain") of an antibody is the C-terminal region of an antibody, which comprises the hinge and the constant $C_H2$ and $C_H3$ domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprising one or more, and perhaps all of the following mutations that will result in decreased affinity to certain Fc-gamma receptors (L234A, L235E, and G237A) and in reduced C1q-mediated complement fixation (A330S and P331S), respectively (residue numbering according to the EU index). Alternatively, other amino acid substitutions, and combinations thereof and combinations with the above mentioned, known in the art to lead to altered (reduced or increased) Fc-gamma receptor binding may be used.

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment the hinge region of the antibody is modified such that the number of cysteine residues in the hinge region is altered, e.g., increased or decreased. This approach is described further for instance in U.S. Pat. No. 5,677,425 by Bodmer et al.

The constant region may be modified to stabilise the antibody, e.g., to reduce the risk of a bivalent antibody separating into half antibodies. For example, in an IgG4 constant region, residue S228 (according to the EU numbering index and S241 according to Kabat) may be mutated to a proline (P) residue to stabilise inter heavy chain disulphide bridge formation at the hinge (see, e.g., Angal et al. Mol Immunol. 1993; 30:105-8).

Antibodies or fragment thereof may be defined in terms of their complementarity-determining regions (CDRs). The term "complementarity-determining region" or "hypervariable region", when used herein, refers to the regions of an antibody in which amino acid residues involved in antigen-binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al. 1991; Sequences of Proteins of Immunological Interest, Fifth Edition, U.S. Department of Health and Human Services, NIH Publication No. 91-3242). Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol. 1987; 196:901-917). Typically, the numbering of amino acid residues in this region is performed by the method described in Kabat et al. supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those $V_H$ or $V_L$ amino acid residues that are not within the CDRs, as defined herein.

An antibody of the invention may comprise a CDR region from one or more of the specific antibodies disclosed herein.

The term "procoagulant antibody" refers to an antibody which potentiates blood coagulation for example by accelerating the process of blood coagulation and/or increasing the enzymatic activity of one or more coagulation factors.

The term "procoagulant activity" refers to the ability of a compound, such as an antibody, to potentiate blood coagulation for example by accelerating the process of blood coagulation and/or increasing the enzymatic activity of one or more coagulation factors.

The term "antigen" (Ag) refers to the molecular entity used for immunisation of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunisation process, or other process, e.g. phage display, used for generating the Ab. The present invention encompasses variants of the antibodies, or antigen-binding fragments thereof of the invention, which may comprise 1, 2, 3, 4 or 5 amino acid substitutions and/or deletions and/or insertions in the individual sequences disclosed herein.

"Substitution" variants preferably involve the replacement of one or more amino acid(s) with the same number of amino acid(s). Substitutions may be, but are not limited to, conservative substitutions. For example, an amino acid may be substituted to an amino acid with similar biochemical properties, for example, a basic amino acid may be substituted to another basic amino acid (e.g. lysine to arginine), an acidic amino acid may be substituted to another acidic amino acid (e.g glutamate to aspartate), a neutral amino acid may be substituted to another neutral amino acid (e.g threonine to serine), a charged amino acid may be substituted to another charged amino acid (e.g. glutamate to aspartate), a hydrophilic amino acid may be substituted to another hydrophilic amino acid (e.g. asparagine to glutamine), a hydrophobic amino acid may be substituted to another hydrophobic amino acid (e.g. alanine to valine), a polar amino acid may be substituted to another polar amino acid (e.g. serine to threonine), an aromatic amino acid may be substituted to another aromatic amino acid (e.g. phenylalanine to tryptophan) and an aliphatic amino acid may be substituted to another aliphatic amino acid (e.g. leucine to isoleucine).

Preferred variants include those in which instead of the amino acid which appears in the sequence comprises a structural analog of the amino acid.

Epitope and Paratope

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab binds, i.e. the area or region in physical contact with the Ab. Physical contact may be defined using various criteria (e.g. a distance cut-off of 2-6 Å, such as 3 Å, such as 3.5 Å such as 4 Å, such as 4.5 Å, such as 5 Å; or solvent accessibility) for atoms in the Ab and Ag molecules.

FIX/FIXa and FX/FXa may comprise a number of different epitopes, which may include, without limitation, (1) linear peptide epitopes (2) conformational epitopes which consist of one or more non-contiguous amino acids located near each other in the mature FIX/FIXa or FX/FXa conformation; and (3) epitopes which consist, either in whole or part, of molecular structures covalently attached to FIX/FIXa or FX/FXa, such as carbohydrate groups.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen Deuterium eXchange Mass Spectrometry (HDX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

In the context of an X-ray derived crystal structure defined by spatial coordinates of a complex between an Ab, e.g. a Fab fragment, and its Ag, the term epitope is herein, unless otherwise specified or contradicted by context, specifically defined as FIX/FIXa or FX/FXa residues characterized by having a heavy atom (i.e. a non-hydrogen atom) within a distance of 3.5 Å, from a heavy atom in the Ab.

Epitopes described at the amino acid level, e.g. determined from an X-ray structure, are said to be identical if they contain the same set of amino acid residues. Epitopes are said to overlap if at least one amino acid residue is shared by the epitopes. Epitopes are said to be separate (unique) if no amino acid residue is shared by the epitopes.

The definition of the term "paratope" is derived from the above definition of "epitope" by reversing the perspective. Thus, the term "paratope" refers to the area or region on the antibody, or fragment thereof to which an antigen binds, i.e. to which it makes physical contact to the antigen.

In the context of an X-ray derived crystal structure, defined by spatial coordinates of a complex between an Ab, such as a Fab fragment, and its Ag, the term paratope is herein, unless otherwise specified or contradicted by context, specifically defined as Ab residues characterized by having a heavy atom (i.e. a non-hydrogen atom) within a distance of 3.5 Å from a heavy atom in FIX/FIXa or FX/FXa.

The epitope and paratope for a given antibody (Ab)/antigen (Ag) pair may be identified by routine methods. For example, the general location of an epitope may be determined by assessing the ability of an antibody to bind to different fragments or variants of FIX/FIXa or FX/FXa. The specific amino acids within FIX/FIXa or FX/FXa that make contact with an antibody (epitope) and the specific amino acids in an antibody that make contact with FIX/FIXa or FX/FXa (paratope) may also be determined using routine methods. For example, the antibody and target molecule may be combined and the Ab:Ag complex may be crystallised. The crystal structure of the complex may be determined and used to identify specific sites of interaction between the antibody and its target.

Epitopes on an antigen may comprise one or more hot-spot residues, i.e. residues which are particularly important for the interaction with the cognate antibody, and where interactions mediated by the side chain of said hot-spot residue contribute significantly to the binding energy for the antibody/antigen interaction (Peng et al. (2014) PNAS 111, E2656-E2665). Hot-spot residues can be identified by testing variants of the antigen (here FIX/FIXa and FX), where single epitope residues have been substituted by e.g. alanine, for binding to the cognate antibody. If substitution of an epitope residue with alanine has a strong impact on binding to the antibody, said epitope residue is considered a hot-spot residue, and therefore of particular importance for binding of the antibody to the antigen.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope.

Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes. Thus, in some embodiments antibodies of the invention will bind to the same epitope as at least one of the antibodies specifically disclosed herein.

Competition assays for determining whether an antibody competes for binding with, an anti-FIX/FIXa or anti-FX/FXa antibody disclosed herein are known in the art. Exemplary competition assays include immunoassays (e.g., ELISA assays, RIA assays), surface plasmon resonance analysis (e.g. using a BIAcore™ instrument), biolayer interferometry (ForteBio®) and flow cytometry.

Typically, a competition assay involves the use of an antigen bound to a solid surface or expressed on a cell surface, a test FIX- or FIXa binding antibody and a reference antibody. The reference antibody is labelled and the test antibody is unlabelled. Competitive inhibition is measured by determining the amount of labelled reference antibody bound to the solid surface or cells in the presence of the test antibody. Usually the test antibody is present in excess (e.g., 1, 5, 10, 20, 100, 1000, 10000 or 100000 fold). Antibodies identified as being competitive in the competition assay (i.e., competing antibodies) include antibodies binding to the same epitope, or overlapping epitopes, as the reference antibody, and antibodies binding to an adjacent epitope sufficiently proximal to the epitope bound by the reference antibody for steric hindrance to occur. In an exemplary competition assay, a reference anti-FIX or anti-FIXa antibody is biotinylated using commercially available reagents.

The biotinylated reference antibody is mixed with serial dilutions of the test antibody or unlabelled reference antibody (self-competition control) resulting in a mixture of various molar ratios (e.g., 1, 5, 10, 20, 100, 1000, 10000 or 100000 fold) of test antibody (or unlabelled reference antibody) to labelled reference antibody. The antibody mixture is added to a FIX or FIXa polypeptide coated-ELISA plate. The plate is then washed, and horseradish peroxidase (HRP)-strepavidin is added to the plate as the detection reagent. The amount of labelled reference antibody bound to the target antigen is detected following addition of a chromogenic substrate (e.g., TMB (3,3',5,5'-tetramethylbenzidine) or ABTS (2,2''-azino-di-(3-ethylbenzthiazoline-6-sulfonate)), which are known in the art. Optical density readings (OD units) are made using a spectrometer (e.g. SpectraMax® M2 spectrometer (Molecular Devices)). The response (OD units) corresponding to zero percent inhibition is determined from wells without any competing antibody. The response (OD units) corresponding to 100% inhibition, i.e. the assay background, is determined from wells without any labelled reference antibody or test antibody. Percent inhibition of labelled reference antibody to FIX or FIXa by the test antibody (or the unlabelled reference antibody) at each concentration is calculated as follows: % inhibition= (1−(OD units−100% inhibition)/(0% inhibition−100% inhibition))*100.

The person skilled in the art will understand that similar assays may be performed to determine if two or more anti-FX/FXa antibodies shares a binding region, a bin and/or competitively binds the antigen. Persons skilled in the art will also appreciate that the competition assay can be performed using various detection systems known in the art.

A test antibody competes with the reference antibody for binding to the antigen if an excess of one antibody (e.g., 1, 5, 10, 20, 100, 1000, 10000 or 100000 fold) inhibits binding of the other antibody, e.g., by at least 50%, 75%, 90%, 95% or 99%, as measured in a competitive binding assay.

Unless otherwise indicated competition is determined using a competitive ELISA assay as described above.

The term "binding affinity" is herein used as a measure of the strength of a non-covalent interaction between two molecules, e.g. an antibody, or fragment thereof, and an antigen. The term "binding affinity" is used to describe monovalent interactions.

Binding affinity between two molecules, e.g. an antibody, or fragment thereof, and an antigen, through a monovalent interaction may be quantified by determining the equilibrium dissociation constant ($K_D$). $K_D$ can be determined by measurement of the kinetics of complex formation and dissociation, e.g. by the Surface Plasmon Resonance (SPR) method or the Isothermal Titration calorimetry (ITC) method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

The value of the dissociation constant can be determined directly by well-known methods. Standard assays to evaluate the binding ability of ligands such as antibodies towards targets are known in the art and include, for example, ELISAs, Western blots, RIAs, and flow cytometry analysis. The binding kinetics and binding affinity of the antibody also can be assessed by standard assays known in the art, such as SPR. Preferably, however, isothermal titration calorimetry (ITC) may be used to measure affinities for an antibody/target interaction as well as to derive thermodynamic parameters for the interaction.

A competitive binding assay can be conducted in which the binding of the antibody to the target is compared to the binding of the target by another ligand of that target, such as another antibody.

The $K_D$ of an antibody of the invention for its target may be less than 100 µM such as less than 10 µM, such as less than 9 µM, such as less than 8 µM, such as less than 7 µM, such as less than 6 µM, such as less than 5 µM, such as less than 4 µM, such as less than 3 µM, such as less than 2 µM, such as less than 1 µM, such as less than 0.9 µM, such as less than 0.8 µM, such as less than 0.7 µM, such as less than 0.6 µM, such as less than 0.5 µM, such as less than 0.4 µM, such as less than 0.3 µM, such as less than 0.2 µM, such as less than 0.1 µM.

In one such embodiment the antibody is a bispecific antibody comprising an anti-FX arm with a $K_D$ towards FX of less than 100 µM such as less than 10 µM, such as less than 9 µM, such as less than 8 µM, such as less than 7 µM, such as less than 6 µM, such as less than 5 µM, such as less than 4 µM, such as less than 3 µM, such as less than 2 µM, such as less than 1 µM, such as less than 0.9 µM, such as less than 0.8 µM, such as less than 0.7 µM, such as less than 0.6 µM, such as less than 0.5 µM, such as less than 0.4 µM, such as less than 0.3 µM, such as less than 0.2 µM, such as less than 0.1 µM, such as less than 0.09 µM, such as less than 0.08 µM, such as less than 0.07 µM, such as less than 0.06 µM, such as less than 0.05 µM, such as less than 0.04 µM, such as less than 0.03 µM, such as less than 0.02 µM, such as less than 0.01 µM, such as less than 9 nM, such as less than 8 nM, such as less than 7 nM, such as less than 6 nM, such as less than 5 nM, such as less than 4 nM, such as less than 3 nM, such as less than 2 nM, such as less than 1 nM such as less than 0.5 nM.

The antibodies and antibody fragment thereof as described herein may be combined with other antibodies and antibody fragments known in the art creating bispecific, trispecific or multispecific antibody molecules. Compounds mimicking FVIII cofactor function have previously been created using other FIX(a) and FX(a) binding domains, which may potentially each substitute for the FIX(a) and/or FX(a) binding domains described herein. It is thus clear that the FIX(a) and FX(a) binding domains of the invention are of separate interest as individual component (intermediate) molecules, as part of a bi-, tri- or multispecific antibody comprising at least one FIX(a) and/or FX(a) binding domain.

The activity of procoagulant antibodies including bi-, tri and multispecific antibodies may be determined by methods known in the art. Standard assays include whole blood-Thrombin-Generation Test (TGT), measuring of clotting time by thrombelastography (TEG) and FXa generation assays.

Identity

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods.

In the present invention similarity and identity were determined using Needleman (Needleman et al. J. Mol. Biol. 1970; 48:443-453) from EMBOSS-6.6.0 using the parameters 10 and 0.5 for gaps opening and extensions, respectively (gapopen=10, gapextend=0.5).

Pharmaceutical Formulations

In another aspect, the present invention provides compositions and formulations comprising compounds of the invention, such as the antibodies described herein. For example, the invention provides a pharmaceutical composition that comprises one or more antibodies of the invention, formulated together with a pharmaceutically acceptable carrier.

Accordingly, one object of the invention is to provide a pharmaceutical formulation comprising such an antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabilizer, or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19$^{th}$ edition, 1995.

In one embodiment the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, to which a solvent and/or a diluent is added prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In one embodiment the present invention relates to an injection device with content of said composition. In some embodiments the pharmaceutical composition of the invention is intended for use and/or contained in an injection device. In some embodiments, the injection device is a disposable, pre-filled, multi-dose pen of the FlexTouch® type (supplier Novo Nordisk A/S, Denmark). In some embodiments the injection device is a single shot device.

In some embodiments the injection device is a fixed dose device, such as one configured to deliver multiple predetermined doses of drug, sometimes referred to as a multiple fixed dose device or a fixed dose, multi-shot device.

In one embodiment the pharmaceutical composition of the invention is administered using an injection device comprising a tube having a needle gauge of 20 or greater.

In one embodiment a bispecific antibody according to table 1 herein is administered using a an injection device comprising a tube having a needle gauge of 20 or greater.

In one embodiment a bispecific antibody according to table 1 herein is administered using a an injection device comprising a tube having a needle gauge of 20 to 36. In one such embodiment the bispecific antibody is selected from a list consisting of bimAb05-0745, bimAb05-3761, bimAb05-3761, bimAb05-2112, bimAb05-2113, bimAb05-2114, bimAb05-3769, bimAb05-4271, bimAb05-4756, bimAb05-0396, bimAb05-0417 and bimAb05-0438, Administration and Dosages A compound of the invention, such as an antibody, may be administered parenterally, such as intravenously, such as intramuscularly, such as subcutaneously. Alternatively, an antibody of the invention may be administered via a non-parenteral route, such as periorally or topically. An antibody of the invention may be administered prophylactically. An antibody of the invention may be administered therapeutically (on demand).

The dose of the compounds to be delivered may be from about 0.01 mg to 500 mg of the compound per day, preferably from about 0.1 mg to 250 mg per day, and more preferably from about 0.5 mg to about 250 mg per day, per week, per second week or per month as loading and maintenance doses, depending on the severity of the condition. A suitable dose may also be adjusted for a particular compound based on the properties of that compound, including its in vivo half-life or mean residence time and its biological activity. For example, compounds to be delivered could in one embodiment be administered once weekly, or in another embodiment once every second week or in another embodiment once monthly and in either of said embodiments in a dose of for example 0.025, 0.05, 0.075, 0.1, 0.125, 0.15, 0.175, 0.2, 0.25, 0.3, 0.35, 0.4, 0.45, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10 mg per kg body weight.

The compositions containing the compounds as disclosed herein can be administered for prophylactic and/or in some embodiments therapeutic treatments. In therapeutic applications, compositions are administered to a subject already suffering from a disease, such as any bleeding disorder as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject.

Embodiments

The invention is further described by the following embodiments:

1. An antibody or antigen-binding fragment thereof capable of binding to Factor IX (FIX) according to SEQ ID NO:1 and/or the activated form thereof (FIXa).
2. The antibody or antigen-binding fragment thereof according to embodiment 1, wherein the antibody or antigen-binding fragment thereof is part of "BinB" as described herein.
3. The antibody or antigen-binding fragment thereof according to embodiment 1, wherein the antibody or antigen-binding fragment thereof competes with a reference antibody wherein the reference antibody comprises
   a. a heavy chain variable domain identified by SEQ ID NO:35 and a light chain variable domain identified by SEQ ID NO:39,
   b. a heavy chain variable domain identified by SEQ ID NO:43 and a light chain variable domain identified by SEQ ID NO:47, or c. a heavy chain variable domain identified by SEQ ID NO:51 and a light chain variable domain identified by SEQ ID NO:55, or
d. a heavy chain variable domain identified by SEQ ID NO:67 and a light chain variable domain identified by SEQ ID NO:71, or
e. a heavy chain variable domain identified by SEQ ID NO:1202 and a light chain variable domain identified by SEQ ID NO:1206, or
f. a heavy chain variable domain identified by SEQ ID NO:1210 and a light chain variable domain identified by SEQ ID NO:1214, or
g. a heavy chain variable domain identified by SEQ ID NO:1218 and a light chain variable domain identified by SEQ ID NO:1222, or
h. a heavy chain variable domain identified by SEQ ID NO:1226 and a light chain variable domain identified by SEQ ID NO:1230, or
i. a heavy chain variable domain identified by SEQ ID NO:1234 and a light chain variable domain identified by SEQ ID NO:1238, or
j. a heavy chain variable domain identified by SEQ ID NO:1242 and a light chain variable domain identified by SEQ ID NO:1246.

4. The antibody or antigen-binding fragment thereof according to the previous embodiment, wherein the reference antibody is a Fab.

5. The antibody or antigen-binding fragment thereof according to any of the previous embodiments, wherein the antibody or antigen-binding fragment thereof comprises
   a. a heavy chain variable domain at least 90% identical to the sequence identified by SEQ ID NO:35 and a light chain variable domain at least 90% identical to the sequence identified by SEQ ID NO:39; or
   b. a heavy chain variable domain at least 90% identical to the sequence identified by SEQ ID NO:43 and a light chain variable domain at least 90% identical to the sequence identified by SEQ ID NO:47; or
   c. a heavy chain variable domain at least 90% identical to the sequence identified by SEQ ID NO:51 and a light chain variable domain at least 90% identical to the sequence identified by SEQ ID NO:55; or
   d. a heavy chain variable domain at least 90% identical to the sequence identified by SEQ ID NO:67 and a light chain variable domain at least 90% identical to the sequence identified by SEQ ID NO:71, or
   e. a heavy chain variable domain at least 90% identical to the sequence identified by SEQ ID NO:1202 and a light chain variable domain at least 90% identical to the sequence identified by SEQ ID NO:1206, or
   f. a heavy chain variable domain at least 90% identical to the sequence identified by SEQ ID NO:1210 and a light chain variable domain at least 90% identical to the sequence identified by SEQ ID NO:1214, or
   g. a heavy chain variable domain at least 90% identical to the sequence identified by SEQ ID NO:1218 and a light chain variable domain at least 90% identical to the sequence identified by SEQ ID NO:1222, or
   h. a heavy chain variable domain at least 90% identical to the sequence identified by SEQ ID NO:1226 and a light chain variable domain at least 90% identical to the sequence identified by SEQ ID NO:1230, or
   i. a heavy chain variable domain at least 90% identical to the sequence identified by SEQ ID NO:1234 and a light chain variable domain at least 90% identical to the sequence identified by SEQ ID NO:1238, or
   j. a heavy chain variable domain at least 90% identical to the sequence identified by SEQ ID NO:1242 and a light chain variable domain at least 90% identical to the sequence identified by SEQ ID NO:1246.

6. The antibody or antigen-binding fragment thereof according to embodiment 5, wherein the heavy chain variable domain is at least 92, 94, 96, 97, 98, 99, 99.1 or 99.2% identical to the sequence identified by SEQ ID NO:35, 43, 51, 67, 1202, 1210, 1218, 1226, 1234 or 1242 respectively.

7. The antibody or antigen-binding fragment thereof according to embodiment 5, wherein the light chain variable domain is at least 92, 94, 96, 97, 98, 99, 99.1 or 99.2% identical to the sequence identified by SEQ ID NO: 39, 47, 55, 71, 1206, 1214, 1222, 1230, 1238 or 1246 respectively.

8. The antibody or antigen-binding fragment thereof according to embodiment 6 and 7, wherein both the heavy chain variable domain and the light chain variable domain are at least 92, 94, 96, 97, 98, 99, 99.1 or 99.2% identical to the identified SEQ IDs.

9. The antibody or antigen-binding fragment thereof according to any of the previous embodiments, wherein the antibody or antigen-binding fragment thereof is capable of binding an epitope comprising one or more of the amino acid residues L337, R338, S339, T340, K341 and T343 of SEQ ID NO:1.

10. The antibody or antigen-binding fragment thereof according to any of the previous embodiments, wherein the antibody or antigen-binding fragment thereof is capable of binding an epitope comprising amino acid residue R338 of SEQ ID NO:1.

11. The antibody or antigen-binding fragment thereof according to any of the previous embodiments, wherein the antibody or antigen-binding fragment thereof is capable of binding an epitope comprising amino acid residues R338 and K341 of SEQ ID NO:1.

12. The antibody or antigen-binding fragment thereof according to any of the previous embodiments, wherein the antibody or antigen-binding fragment thereof is capable of binding an epitope comprising two or three of the amino acid residues L337, R338, S339, T340, K341 and T343 of SEQ ID NO:1.

13. The antibody or antigen-binding fragment thereof according to any of the previous embodiments, wherein the antibody or antigen-binding fragment thereof is capable of binding an epitope comprising four or five of the amino acid residues L337, R338, S339, T340, K341 and T343 of SEQ ID NO:1.

14. The antibody or antigen-binding fragment thereof according to any of the previous embodiments, wherein the antibody or antigen-binding fragment thereof is capable of binding an epitope comprising
   a. R338, S339, T340, K341 and T343,
   b. L337, S339, T340, K341 and T343,
   c. L337, R338, T340, K341 and T343,
   d. L337, R338, S339, K341 and T343,
   e. L337, R338, S339, T340 and T343
   f. L337, R338, S339, T340 and K341,
   g. L337, R338, S339 and T340, or
   h. R338, T340 and K341 of SEQ ID NO:1.

15. The antibody or antigen-binding fragment thereof according to any of embodiments 1-11, wherein the antibody or antigen-binding fragment thereof is capable of binding an epitope comprising amino acid residues
   a. R338, T340 and K341 of SEQ ID NO:1, or
   b. L337, R338, S339, T340 and K341 of SEQ ID NO:1.

16. The antibody or antigen-binding fragment thereof according to any of the previous embodiments, comprising a paratope having the following amino acid residues
    a. H30, D31, W53, D56, S102, S104, Y106 and N107 in the heavy chain variable domain (SEQ ID NO:67) and Y91 and S92 in the light chain variable domain (SEQ ID NO:71), optionally comprising one, two or three amino acid substitutions in the ten recited paratope amino acid residues, or
    b. H30, D31, W53, S102, S104, Y106 and N107 in the heavy chain variable domain (SEQ ID NO:51) and residues Y91 and S92 in the light chain variable domain (SEQ ID NO:55), optionally comprising one, two or three amino acid substitutions in the nine recited paratope amino acid residues.
17. The antibody or antigen-binding fragment thereof according to any of embodiments 1-16, comprising a paratope having the following amino acid residues D30, D31, W53, S102, S104 and N107 in the heavy chain variable domain (SEQ ID NO:35) and Y91 and S92 in the light chain variable domain (SEQ ID NO:39), optionally comprising one, two or three amino acid substitutions in the eight recited paratope amino acid residues.
18. The antibody or antigen-binding fragment thereof according to embodiment 16 or 17 wherein said substitution(s) is/are a conservative substitution(s).
19. The antibody or antigen-binding fragment thereof according to any of the previous embodiments, wherein the antibody or antigen-binding fragment thereof comprises
    a.
        i. three heavy chain CDR sequences with at most 10 amino acid changes compared to the CDR sequences of the heavy chain variable domain identified by SEQ ID NO:35 and
        ii. three light chain CDR sequences with at most 10 amino acid changes compared to the CDR sequences of the light chain variable domain identified by SEQ ID NO:39, or
    b.
        i. three heavy chain CDR sequences with at most 10 amino acid changes compared to the CDR sequences of the heavy chain variable domain identified by SEQ ID NO:43 and
        ii. three light chain CDR sequences with at most 10 amino acid changes compared to the CDR sequences of the light chain variable domain identified by SEQ ID NO:47, or
    c.
        i. three heavy chain CDR sequences with at most 10 amino acid changes compared to the CDR sequences of the heavy chain variable domain identified by SEQ ID NO:51 and
        ii. three light chain CDR sequences with at most 10 amino acid changes compared to the CDR sequences of the light chain variable domain identified by SEQ ID NO:55, or
    d.
        i. three heavy chain CDR sequences with at most 10 amino acid changes compared to the CDR sequences of the heavy chain variable domain identified by SEQ ID NO:67 and
        ii. three light chain CDR sequences with at most 10 amino acid changes compared to the CDR sequences of the light chain variable domain identified by SEQ ID NO:71, or
    e.
        i. three heavy chain CDR sequences with at most 10 amino acid changes compared to the CDR sequences of the heavy chain variable domain identified by SEQ ID NO:1202 and
        ii. three light chain CDR sequences with at most 10 amino acid changes compared to the CDR sequences of the light chain variable domain identified by SEQ ID NO:1206, or
    f.
        i. three heavy chain CDR sequences with at most 10 amino acid changes compared to the CDR sequences of the heavy chain variable domain identified by SEQ ID NO:1210 and
        ii. three light chain CDR sequences with at most 10 amino acid changes compared to the CDR sequences of the light chain variable domain identified by SEQ ID NO:1214, or
    g.
        i. three heavy chain CDR sequences with at most 10 amino acid changes compared to the CDR sequences of the heavy chain variable domain identified by SEQ ID NO:1218 and
        ii. three light chain CDR sequences with at most 10 amino acid changes compared to the CDR sequences of the light chain variable domain identified by SEQ ID NO:1222, or
    h.
        i. three heavy chain CDR sequences with at most 10 amino acid changes compared to the CDR sequences of the heavy chain variable domain identified by SEQ ID NO:1226 and
        ii. three light chain CDR sequences with at most 10 amino acid changes compared to the CDR sequences of the light chain variable domain identified by SEQ ID NO:1230, or
    i.
        i. three heavy chain CDR sequences with at most 10 amino acid changes compared to the CDR sequences of the heavy chain variable domain identified by SEQ ID NO:1234 and
        ii. three light chain CDR sequences with at most 10 amino acid changes compared to the CDR sequences of the light chain variable domain identified by SEQ ID NO:1238, or
    j.
        i. three heavy chain CDR sequences with at most 10 amino acid changes compared to the CDR sequences of the heavy chain variable domain identified by SEQ ID NO:1242 and
        ii. three light chain CDR sequences with at most 10 amino acid changes compared to the CDR sequences of the light chain variable domain identified by SEQ ID NO:1246.
20. The antibody or antigen-binding fragment thereof according to embodiment 19, wherein the three heavy chain CDR sequences have at most 9, such as 8, such as 7 or such as 6 amino acid changes compared to the CDRs of the identified SEQ ID NOs.
21. The antibody or antigen-binding fragment thereof according to embodiment 19, wherein the three heavy chain CDR sequences have at most 5, such as 4, such as 3, such as 2 or at most 1 amino acid changes compared to the CDRs of the identified SEQ ID NOs.

22. The antibody or antigen-binding fragment thereof according to embodiment 19, wherein the three light chain CDR sequences have at most 9, such as 8, such as 7 or such as 6 amino acid changes compared to the CDRs of the identified SEQ ID NOs.
23. The antibody or antigen-binding fragment thereof according to embodiment 19, wherein the three light chain CDR sequences have at most 5, such as 4, such as 3, such as 2 or at most 1 amino acid changes compared to the CDRs of the identified SEQ IDs.
24. The antibody or antigen-binding fragment thereof according to any of the previous embodiments, wherein the antibody or antigen-binding fragment thereof comprises
    a. the CDR sequences of the heavy chain variable domain identified by SEQ ID NO:35 and the CDR sequences of the light chain variable domain identified by SEQ ID NO:39, or
    b. the CDR sequences of the heavy chain variable domain identified by SEQ ID NO:43 and the CDR sequences of the light chain variable domain identified by SEQ ID NO:47, or
    c. the CDR sequences of the heavy chain variable domain identified by SEQ ID NO:51 and the CDR sequences of the light chain variable domain identified by SEQ ID NO:55, or
    d. the CDR sequences of the heavy chain variable domain identified by SEQ ID NO:67 and the CDR sequences of the light chain variable domain identified by SEQ ID NO:71, or
    e. the CDR sequences of the heavy chain variable domain identified by SEQ ID NO:1202 and the CDR sequences of the light chain variable domain identified by SEQ ID NO:1206, or
    f. the CDR sequences of the heavy chain variable domain identified by SEQ ID NO:1210 and the CDR sequences of the light chain variable domain identified by SEQ ID NO:1214, or
    g. the CDR sequences of the heavy chain variable domain identified by SEQ ID NO:1218 and the CDR sequences of the light chain variable domain identified by SEQ ID NO:1222, or
    h. the CDR sequences of the heavy chain variable domain identified by SEQ ID NO:1226 and the CDR sequences of the light chain variable domain identified by SEQ ID NO:1230, or
    i. the CDR sequences of the heavy chain variable domain identified by SEQ ID NO:1234 and the CDR sequences of the light chain variable domain identified by SEQ ID NO:1238, or
    j. the CDR sequences of the heavy chain variable domain identified by SEQ ID NO:1242 and the CDR sequences of the light chain variable domain identified by SEQ ID NO:1246.
25. The antibody or antigen-binding fragment thereof according to any of the previous embodiments, wherein the antibody or antigen-binding fragment thereof comprises
    a. a heavy chain variable domain identified by SEQ ID NO:35 and a light chain variable domain identified by SEQ ID NO:39, or
    b. a heavy chain variable domain identified by SEQ ID NO:43 and a light chain variable domain identified by SEQ ID NO:47, or
    c. a heavy chain variable domain identified by SEQ ID NO:51 and a light chain variable domain identified by SEQ ID NO:55, or
    d. a heavy chain variable domain identified by SEQ ID NO:67 and a light chain variable domain identified by SEQ ID NO:71, or
    e. a heavy chain variable domain identified by SEQ ID NO:1202 and a light chain variable domain identified by SEQ ID NO:1206, or
    f. a heavy chain variable domain identified by SEQ ID NO:1210 and a light chain variable domain identified by SEQ ID NO:1214, or
    g. a heavy chain variable domain identified by SEQ ID NO:1218 and a light chain variable domain identified by SEQ ID NO:1222, or
    h. a heavy chain variable domain identified by SEQ ID NO:1226 and a light chain variable domain identified by SEQ ID NO:1230, or
    i. a heavy chain variable domain identified by SEQ ID NO:1234 and a light chain variable domain identified by SEQ ID NO:1238, or
    j. a heavy chain variable domain identified by SEQ ID NO:1242 and a light chain variable domain identified by SEQ ID NO:1246.
26. An antibody or antigen-binding fragment thereof capable of binding to FX (SEQ ID NO:2) and/or the activated form thereof (FXa).
27. The antibody or antigen-binding fragment thereof according to embodiment 26, wherein the antibody or antigen-binding fragment thereof is part of "Bin2".
28. The antibody or antigen-binding fragment thereof according to embodiment 26, wherein the antibody or antigen-binding fragment thereof competes with a reference antibody wherein the reference antibody comprises
    a. a heavy chain variable domain identified by SEQ ID NO:467 and a light chain variable domain identified by SEQ ID NO:471, or
    b. a heavy chain variable domain identified by SEQ ID NO:483 and a light chain variable domain identified by SEQ ID NO:487, or
    c. a heavy chain variable domain identified by SEQ ID NO:707 and a light chain variable domain identified by SEQ ID NO:711, or
    d. a heavy chain variable domain identified by SEQ ID NO:731 and a light chain variable domain identified by SEQ ID NO:735, or
    e. a heavy chain variable domain identified by SEQ ID NO:907 and a light chain variable domain identified by SEQ ID NO:911, or
    f. a heavy chain variable domain identified by SEQ ID NO:1075 and a light chain variable domain identified by SEQ ID NO:1079.
29. The antibody according to any of the previous embodiments, wherein the reference antibody is a Fab.
30. The antibody or antigen-binding fragment thereof according to any of the previous embodiments, wherein the antibody or antigen-binding fragment thereof comprises a heavy chain variable domain at least 90% identical to the sequence identified by SEQ ID NO:467, 483, 707, 731, 907 or 1075 and a light chain variable domain at least 90% identical to the sequence identified by SEQ ID NO:471, 487, 711, 735, 911 or 1079.
31. The antibody or antigen-binding fragment thereof according to embodiment 30, wherein the heavy chain variable domain is at least 92, 94, 96, 97, 98, 99, 99.1 or 99.2% identical to the sequence identified by SEQ ID NO: 467, 483, 707, 731, 907 or 1075.
32. The antibody or antigen-binding fragment thereof according to embodiment 30, wherein the light chain variable domain is at least 92, 94, 96, 97, 98, 99, 99.1 or 99.2% identical to the sequence identified by SEQ ID NO:471, 487, 711, 735, 911 or 1079.

33. The antibody or antigen-binding fragment thereof according to embodiment 31 and 32, wherein both the heavy chain variable domain and the light chain variable domain are at least 92, 94, 96, 97, 98, 99 or 99.1% identical to the identified SEQ IDs.

34. The antibody or antigen-binding fragment thereof according to any of the previous embodiments, wherein the antibody or antigen-binding fragment thereof is capable of binding an epitope comprising one or more of the amino acid residues E103, Q104, V108, R113, T116, L117, D119, I125, T127, E228, F229, Y230, E266, R287, P291, I292, P304, L419, K420, D423, R424, M426, K427 and T428 of FX(a).

35. The antibody or antigen-binding fragment thereof according to any of the previous embodiments, wherein the antibody or antigen-binding fragment thereof is capable of binding an epitope comprising 15, 16, 17, 18, 19, 20, 21, 22, 23 or 24 of the amino acid residues E103, Q104, V108, R113, T116, L117, D119, I125, T127, E228, F229, Y230, E266, R287, P291, I292, P304, L419, K420, D423, R424, M426, K427 and T428 of FX(a)

36. The antibody or antigen-binding fragment thereof according to any of the previous embodiments, wherein the antibody or antigen-binding fragment thereof is capable of binding an epitope comprising the amino acid residues Y230, D423, R424 and K427 of FX(a).

37. The antibody or antigen-binding fragment thereof according to any of the previous embodiments, wherein the antibody or antigen-binding fragment thereof is capable of binding an epitope comprising the amino acid residues E103, Q104, V108, R113, T116, L117, D119, I125, T127, E228, F229, Y230, E266, R287, P291, I292, P304, L419, K420, D423, R424, M426, K427 and T428 of FX(a).

38. The antibody or antigen-binding fragment thereof according to any of the previous embodiments, comprising a paratope comprising the following amino acid residues K23, S25, G26, Y27, F29, W33, D52, S54, D55, F57, S77, H100, Y101, Y102, N103, S104 in the heavy chain variable domain (SEQ ID NO:467) and residues V29, S30, S31, Y33, Y50, Q52, S54, R55, R57 and D94 in the light chain variable domain (SEQ ID NO:471), optionally comprising one, two, three, four or five amino acid substitutions, deletions or insertions in the 26 recited paratope amino acid residues.

39. The antibody or antigen-binding fragment thereof according to any of the previous embodiments, wherein the antibody or antigen-binding fragment thereof is capable of binding an epitope comprising one or more of the amino acid residues E103, Q104, V108, R113, T116, L117, A118, D119, I125, T127, S227, E228, Y230, R287, I292, L303, P304, L419, K420, D423, R424, M426, K427 and T428 of FX(a).

40. The antibody or antigen-binding fragment thereof according to any of the previous embodiments, wherein the antibody or antigen-binding fragment thereof is capable of binding an epitope comprising 15, 16, 17, 18, 19, 20, 21, 22, 23 or 24 of the amino acid residues E103, Q104, V108, R113, T116, L117, A118, D119, I125, T127, S227, E228, Y230, R287, I292, L303, P304, L419, K420, D423, R424, M426, K427 and T428 of FX(a).

41. The antibody or antigen-binding fragment thereof according to any of the previous embodiments, wherein the antibody or antigen-binding fragment thereof is capable of binding an epitope comprising the amino acid residues E103, Q104, V108, R113, T116, L117, D119, I125, T127, E228, F229, Y230, E266, R287, P291, I292, P304, L419, K420, D423, R424, M426, K427 and T428 of FX(a).

42. The antibody or antigen-binding fragment thereof according to any of the previous embodiments, comprising a paratope comprising the following amino acid residues K23, G24, S25, G26, Y27, W33, D52, S54, D55, Y57, S77, L99, H100, Y101, Y102, N103 and S104 in the variable heavy chain domain (SEQ ID NO:483) and residues S30, S31, Y33, Y50, Q52, S54, R55, R57, Y92 and D94 in the light chain variable domain (SEQ ID NO:487), optionally comprising one, two, three, four or five amino acid substitutions, deletions or insertions in the 27 recited paratope amino acid residues.

43. The antibody or antigen-binding fragment thereof according to embodiment 38 or 42 wherein said substitution(s) is/are a conservative substitution(s).

44. The antibody or antigen-binding fragment thereof according to any of embodiments 26-43, wherein the antibody or antigen-binding fragment thereof comprises
   a. three heavy chain CDR sequences with at most 10 amino acid changes compared to the CDR sequences of the heavy chain variable domain identified by SEQ ID NO:467 and
      three light chain CDR sequences with at most 10 amino acid changes compared to the CDR sequences of the light chain variable domain identified by SEQ ID NO:471; or
   b. three heavy chain CDR sequences with at most 10 amino acid changes compared to the CDR sequences of the heavy chain variable domain identified by SEQ ID NO:483, and
      three light chain CDR sequences with at most 10 amino acid changes compared to the CDR sequences of the light chain variable domain identified by SEQ ID NO:487.

45. The antibody or antigen-binding fragment thereof according to embodiment 44, wherein the three heavy chain CDR sequences have at most 9, such as 8, such as 7 or such as 6 amino acid changes compared to the CDRs of the identified SEQ IDs.

46. The antibody or antigen-binding fragment thereof according to embodiment 44, wherein the three heavy chain CDR sequences have at most 5, such as 4, such as 3, such as 2 or at most 1 amino acid changes compared to the CDRs of the identified SEQ IDs.

47. The antibody or antigen-binding fragment thereof according to embodiment 44, wherein the three light chain CDR sequences have at most 9, such as 8, such as 7 or such as 6 amino acid changes compared to the CDRs of the identified SEQ IDs.

48. The antibody or antigen-binding fragment thereof according to embodiment 44, wherein the three light chain CDR sequences have at most 5, such as 4, such as 3, such as 2 or at most 1 amino acid changes compared to the CDRs of the identified SEQ IDs.

49. The antibody or antigen-binding fragment thereof according to any of the previous embodiments, wherein the antibody or antigen-binding fragment thereof comprises the CDR sequences of a. the heavy chain variable domain identified by SEQ ID NO:467 and the CDR sequences of the light chain variable domain identified by SEQ ID NO:471; or
b. the heavy chain variable domain identified by SEQ ID NO:483 and the CDR sequences of the light chain variable domain identified by SEQ ID NO:487; or
c. the heavy chain variable domain identified by SEQ ID NO:555 and the CDR sequences of the light chain variable domain identified by SEQ ID NO:559; or
d. the heavy chain variable domain identified by SEQ ID NO:587 and the CDR sequences of the light chain variable domain identified by SEQ ID NO:591; or
e. the heavy chain variable domain identified by SEQ ID NO:707 and the CDR sequences of the light chain variable domain identified by SEQ ID NO:711; or
f. the heavy chain variable domain identified by SEQ ID NO:731 and the CDR sequences of the light chain variable domain identified by SEQ ID NO:735; or
g. the heavy chain variable domain identified by SEQ ID NO:907 and the CDR sequences of the light chain variable domain identified by SEQ ID NO:911; or
h. the heavy chain variable domain identified by SEQ ID NO:1075 and the CDR sequences of the light chain variable domain identified by SEQ ID NO:1079.

50. The antibody or antigen-binding fragment thereof according to any of the previous embodiments, wherein the antibody or antigen-binding fragment thereof comprises
a. a heavy chain variable domain identified by SEQ ID NO:467 and a light chain variable domain identified by SEQ ID NO:471; or
b. a heavy chain variable domain identified by SEQ ID NO:483 and a light chain variable domain identified by SEQ ID NO:487; or
c. a heavy chain variable domain identified by SEQ ID NO:555 and a light chain variable domain identified by SEQ ID NO:559; or
d. a heavy chain variable domain identified by SEQ ID NO:587 and a light chain variable domain identified by SEQ ID NO:591; or
e. a heavy chain variable domain identified by SEQ ID NO:707 and a light chain variable domain identified by SEQ ID NO:711; or
f. a heavy chain variable domain identified by SEQ ID NO:731 and a light chain variable domain identified by SEQ ID NO:735; or
g. a heavy chain variable domain identified by SEQ ID NO:907 and a light chain variable domain identified by SEQ ID NO:911; or
h. a heavy chain variable domain identified by SEQ ID NO:1075 and a light chain variable domain identified by SEQ ID NO:1079.

51. A multispecific antibody or antigen-binding fragment thereof capable of binding to FIX according to SEQ ID NO:1 or the activated form thereof (FIXa), and FX (SEQ ID NO:2) or the activated form thereof (FXa).

52. The multispecific antibody or antigen-binding fragment thereof according to embodiment 51, wherein the antibody comprises an antibody or antigen-binding fragment thereof according to any of the previous embodiments 1-50.

53. The multispecific antibody or antigen-binding fragment thereof according to embodiment 51, wherein the antibody comprises an antibody or antigen-binding fragment thereof according to any of the previous embodiments 2-25.

54. The multispecific antibody or antigen-binding fragment thereof according to embodiment 51, wherein the antibody comprises an antibody or antigen-binding fragment thereof according to any of the previous embodiments 26-50.

55. The multispecific antibody or antigen-binding fragment thereof according to embodiment 51, wherein the antibody comprises an antibody or antigen-binding fragment thereof according to any of the previous embodiments 27-50.

56. The multispecific antibody or antigen-binding fragment thereof according to embodiment 51, wherein the antibody comprises an antibody or antigen-binding fragment thereof according to any of the previous embodiments 1-25 and an antigen-binding fragment according to any of the previous embodiments 26-50.

57. The multispecific antibody or antigen-binding fragment thereof according to embodiment 51, wherein the antibody comprises an antibody or antigen-binding fragment thereof according to any of the previous embodiments 2-25 and an antibody or antigen-binding fragment thereof according to any of the previous embodiments 27-50.

58. The multispecific antibody or antigen-binding fragment thereof according to any of embodiments 51-57 comprising
a. the anti-FIX(a) antibody heavy chain CDR3 sequence identified by SEQ ID NO:38, optionally comprising 1, 2 or 3 amino acid substitutions and/or deletions and/or insertions; and
the anti-FIX(a) antibody light chain CDR3 sequence identified by SEQ ID NO:42, optionally comprising 1, 2 or 3 amino acid substitutions and/or deletions and/or insertions; and
the anti-FX(a) antibody heavy chain CDR3 sequence identified by SEQ ID NO:470, optionally comprising 1, 2 or 3 amino acid substitutions and/or deletions and/or insertions; and
the anti-FX(a) antibody light chain CDR3 sequence identified by SEQ ID NO:474, optionally comprising 1, 2 or 3 amino acid substitutions and/or deletions and/or insertions; or
b. the anti-FIX(a) antibody heavy chain CDR3 sequence identified by SEQ ID NO:38, optionally comprising 1, 2 or 3 amino acid substitutions and/or deletions and/or insertions; and
the anti-FIX(a) antibody light chain CDR3 sequence identified by SEQ ID NO:42, optionally comprising 1, 2 or 3 amino acid substitutions and/or deletions and/or insertions; and
the anti-FX(a) antibody heavy chain CDR3 sequence identified by SEQ ID NO: 486, optionally comprising 1, 2 or 3 amino acid substitutions and/or deletions and/or insertions; and
the anti-FX(a) antibody light chain CDR3 sequence identified by SEQ ID NO: 490, optionally comprising 1, 2 or 3 amino acid substitutions and/or deletions and/or insertions; or
c. the anti-FIX(a) antibody heavy chain CDR3 sequence identified by SEQ ID NO:46, optionally comprising 1, 2 or 3 amino acid substitutions and/or deletions and/or insertions; and
the anti-FIX(a) antibody light chain CDR3 sequence identified by SEQ ID NO:50, optionally comprising 1, 2 or 3 amino acid substitutions and/or deletions and/or insertions; and the anti-FX(a) antibody heavy chain CDR3 sequence identified by SEQ ID NO:470, optionally comprising 1, 2 or 3 amino acid substitutions and/or deletions and/or insertions; and the anti-FX(a) antibody light chain CDR3 sequence identified by SEQ ID NO:474, optionally comprising 1, 2 or 3 amino acid substitutions and/or deletions and/or insertions; or d. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:470, optionally comprising 1, 2 or 3 amino acid substitutions and/or deletions and/or insertions; and the anti-FX(a) antibody light chain CDR3 sequence identified by SEQ ID NO:474, optionally comprising 1, 2 or 3 amino acid substitutions and/or deletions and/or insertions; or e. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:486, optionally comprising 1, 2 or 3 amino acid substitutions and/or deletions and/or insertions; and the anti-FX(a) antibody light chain CDR3 sequence identified by SEQ ID NO:490, optionally comprising 1, 2 or 3 amino acid substitutions and/or deletions and/or insertions; or f. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:558, optionally comprising 1, 2 or 3 amino acid substitutions and/or deletions and/or insertions; and the anti-FX(a) antibody light chain CDR3 sequence identified by SEQ ID NO:562, optionally comprising 1, 2 or 3 amino acid substitutions and/or deletions and/or insertions; or g. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:590, optionally comprising 1, 2 or 3 amino acid substitutions and/or deletions and/or insertions; and the anti-FX(a) antibody light chain CDR3 sequence identified by SEQ ID NO:594, optionally comprising 1, 2 or 3 amino acid substitutions and/or deletions and/or insertions; or h. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:710, optionally comprising 1, 2 or 3 amino acid substitutions and/or deletions and/or insertions; and the anti-FX(a) antibody light chain CDR3 sequence identified by SEQ ID NO:714, optionally comprising 1, 2 or 3 amino acid substitutions and/or deletions and/or insertions; or i. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:734, optionally comprising 1, 2 or 3 amino acid substitutions and/or deletions and/or insertions; and the anti-FX(a) antibody light chain CDR3 sequence identified by SEQ ID NO:738, optionally comprising 1, 2 or 3 amino acid substitutions and/or deletions and/or insertions; or j. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:910, optionally comprising 1, 2 or 3 amino acid substitutions and/or deletions and/or insertions; and the anti-FX(a) antibody light chain CDR3 sequence identified by SEQ ID NO:914, optionally comprising 1, 2 or 3 amino acid substitutions and/or deletions and/or insertions; or k. the anti-FIX(a) antibody heavy chain CDR3 sequence identified by SEQ ID NO:54, optionally comprising 1, 2 or 3 amino acid substitutions and/or deletions and/or insertions; and the anti-FIX(a) antibody light chain CDR3 sequence identified by SEQ ID NO:58, optionally comprising 1, 2 or 3 amino acid substitutions and/or deletions and/or insertions; and the anti-FX(a) antibody heavy chain CDR3 sequence identified by SEQ ID NO:1078, optionally comprising 1, 2 or 3 amino acid substitutions and/or deletions and/or insertions; and the anti-FX(a) antibody light chain CDR3 sequence identified by SEQ ID NO:1082, optionally comprising 1, 2 or 3 amino acid substitutions and/or deletions and/or insertions; or
l. the anti-FIX(a) antibody heavy chain CDR3 sequence identified by SEQ ID NO:70, optionally comprising 1, 2 or 3 amino acid substitutions and/or deletions and/or insertions; and
　the anti-FIX(a) antibody light chain CDR3 sequence identified by SEQ ID NO:74, optionally comprising 1, 2 or 3 amino acid substitutions and/or deletions and/or insertions; and
　the anti-FX(a) antibody heavy chain CDR3 sequence identified by SEQ ID NO:470, optionally comprising 1, 2 or 3 amino acid substitutions and/or deletions and/or insertions; and
　the anti-FX(a) antibody light chain CDR3 sequence identified by SEQ ID NO:474, optionally comprising 1, 2 or 3 amino acid substitutions and/or deletions and/or insertions; or
m. the anti-FIX(a) antibody heavy chain CDR3 sequence identified by SEQ ID NO:70, optionally comprising 1, 2 or 3 amino acid substitutions and/or deletions and/or insertions; and
　the anti-FIX(a) antibody light chain CDR3 sequence identified by SEQ ID NO:74, optionally comprising 1, 2 or 3 amino acid substitutions and/or deletions and/or insertions; and
　the anti-FX(a) antibody heavy chain CDR3 sequence identified by SEQ ID NO:486, optionally comprising 1, 2 or 3 amino acid substitutions and/or deletions and/or insertions; and
　the anti-FX(a) antibody light chain CDR3 sequence identified by SEQ ID NO:490, optionally comprising 1, 2 or 3 amino acid substitutions and/or deletions and/or insertions; or
n. the anti-FIX(a) antibody heavy chain CDR3 sequence identified by SEQ ID NO:1205, optionally comprising 1, 2 or 3 amino acid substitutions and/or deletions and/or insertions; and
　the anti-FIX(a) antibody light chain CDR3 sequence identified by SEQ ID NO:1209, optionally comprising 1, 2 or 3 amino acid substitutions and/or deletions and/or insertions; and
　the anti-FX(a) antibody heavy chain CDR3 sequence identified by SEQ ID NO:1213, optionally comprising 1, 2 or 3 amino acid substitutions and/or deletions and/or insertions; and
　the anti-FX(a) antibody light chain CDR3 sequence identified by SEQ ID NO:1217, optionally comprising 1, 2 or 3 amino acid substitutions and/or deletions and/or insertions; or
o. the anti-FIX(a) antibody heavy chain CDR3 sequence identified by SEQ ID NO:1221, optionally comprising 1, 2 or 3 amino acid substitutions and/or deletions and/or insertions; and
　the anti-FIX(a) antibody light chain CDR3 sequence identified by SEQ ID NO:1225, optionally comprising 1, 2 or 3 amino acid substitutions and/or deletions and/or insertions; and
　the anti-FX(a) antibody heavy chain CDR3 sequence identified by SEQ ID NO:470, optionally comprising 1, 2 or 3 amino acid substitutions and/or deletions and/or insertions; and
　the anti-FX(a) antibody light chain CDR3 sequence identified by SEQ ID NO:474, optionally comprising 1, 2 or 3 amino acid substitutions and/or deletions and/or insertions; or
p. the anti-FIX(a) antibody heavy chain CDR3 sequence identified by SEQ ID NO:1229, optionally comprising 1, 2 or 3 amino acid substitutions and/or deletions and/or insertions; and
　the anti-FIX(a) antibody light chain CDR3 sequence identified by SEQ ID NO:1233, optionally comprising 1, 2 or 3 amino acid substitutions and/or deletions and/or insertions; and
　the anti-FX(a) antibody heavy chain CDR3 sequence identified by SEQ ID NO:470, optionally comprising 1, 2 or 3 amino acid substitutions and/or deletions and/or insertions; and
　the anti-FX(a) antibody light chain CDR3 sequence identified by SEQ ID NO:474, optionally comprising 1, 2 or 3 amino acid substitutions and/or deletions and/or insertions; or
q. the anti-FIX(a) antibody heavy chain CDR3 sequence identified by SEQ ID NO:1237, optionally comprising 1, 2 or 3 amino acid substitutions and/or deletions and/or insertions; and
　the anti-FIX(a) antibody light chain CDR3 sequence identified by SEQ ID NO:1241, optionally comprising 1, 2 or 3 amino acid substitutions and/or deletions and/or insertions; and
　the anti-FX(a) antibody heavy chain CDR3 sequence identified by SEQ ID NO:470, optionally comprising 1, 2 or 3 amino acid substitutions and/or deletions and/or insertions; and
　the anti-FX(a) antibody light chain CDR3 sequence identified by SEQ ID NO:474, optionally comprising 1, 2 or 3 amino acid substitutions and/or deletions and/or insertions; or
r. the anti-FIX(a) antibody heavy chain CDR3 sequence identified by SEQ ID NO:1245, optionally comprising 1, 2 or 3 amino acid substitutions and/or deletions and/or insertions; and
　the anti-FIX(a) antibody light chain CDR3 sequence identified by SEQ ID NO:1249, optionally comprising 1, 2 or 3 amino acid substitutions and/or deletions and/or insertions; and
　the anti-FX(a) antibody heavy chain CDR3 sequence identified by SEQ ID NO:470, optionally comprising 1, 2 or 3 amino acid substitutions and/or deletions and/or insertions; and
　the anti-FX(a) antibody light chain CDR3 sequence identified by SEQ ID NO:474, optionally comprising 1, 2 or 3 amino acid substitutions and/or deletions and/or insertions; or
59. The multispecific antibody or antigen-binding fragment thereof according to any of embodiments 51-57 comprising
a. the anti-FIX(a) antibody heavy chain CDR1-3 sequences identified by SEQ ID NOs:36, 37 and 38, respectively, optionally comprising 1, 2 or 3 amino acid substitutions and/or deletions and/or insertions; and
　the anti-FIX(a) antibody light chain CDR1-3 sequences identified by SEQ ID NOs:40, 41 and 42, respectively, optionally comprising 1, 2 or 3 amino acid substitutions and/or deletions and/or insertions; and
　the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or b. the anti-FIX(a) antibody heavy chain CDR1-3 sequences identified by SEQ ID NOs:36, 37 and 38, respectively, optionally comprising 1, 2 or 3 amino acid substitutions and/or deletions and/or insertions; and the anti-FIX(a) antibody light chain CDR1-3 sequences identified by SEQ ID NOs:40, 41 and 42, respectively, optionally comprising 1, 2 or 3 amino acid substitutions and/or deletions and/or insertions; and the anti-FX(a) antibody heavy chain CDR1-3 sequences identified by SEQ ID NOs:484, 485 and 486, respectively, optionally comprising 1, 2 or 3 amino acid substitutions and/or deletions and/or insertions; and the anti-FX(a) antibody light chain CDR1-3 sequences identified by SEQ ID NOs:488, 489 and 490, respectively, optionally comprising 1, 2 or 3 amino acid substitutions and/or deletions and/or insertions; or c. the anti-FIX(a) antibody heavy chain CDR1-3 sequences identified by SEQ ID NOs:44, 45 and 46, respectively, optionally comprising 1, 2 or 3 amino acid substitutions and/or deletions and/or insertions; and the anti-FIX(a) antibody light chain CDR1-3 sequences identified by SEQ ID NOs:48, 49 and 50, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or d. the anti-FIX(a) antibody heavy chain CDR1-3 sequences identified by SEQ ID NOs:52, 53 and 54, respectively, optionally comprising 1, 2 or 3 amino acid substitutions and/or deletions and/or insertions; and the anti-FIX(a) antibody light chain CDR1-3 sequences identified by SEQ ID NOs:56, 57 and 58, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or e. the anti-FIX(a) antibody heavy chain CDR1-3 sequences identified by SEQ ID NOs:52, 53 and 54, respectively, optionally comprising 1, 2 or 3 amino acid substitutions and/or deletions and/or insertions; and the anti-FIX(a) antibody light chain CDR1-3 sequences identified by SEQ ID NOs:56, 57 and 58, respectively, optionally comprising 1, 2 or 3 amino acid substitutions and/or deletions and/or insertions; and the anti-FX(a) antibody heavy chain CDR1-3 sequences identified by SEQ ID NOs:708, 709 and 710, respectively, optionally comprising 1, 2 or 3 amino acid substitutions and/or deletions and/or insertions; and the anti-FX(a) antibody light chain CDR1-3 sequences identified by SEQ ID NOs:712, 713 and 714, respectively, optionally comprising 1, 2 or 3 amino acid substitutions and/or deletions and/or insertions; or f. the anti-FIX(a) antibody heavy chain CDR1-3 sequences identified by SEQ ID NOs:52, 53 and 54, respectively, optionally comprising 1, 2 or 3 amino acid substitutions and/or deletions and/or insertions; and the anti-FIX(a) antibody light chain CDR1-3 sequences identified by SEQ ID NOs:56, 57 and 58, respectively, optionally comprising 1, 2 or 3 amino acid substitutions and/or deletions and/or insertions; and the anti-FX(a) antibody heavy chain CDR1-3 sequences identified by SEQ ID NOs:732, 733 and 734, respectively, optionally comprising 1, 2 or 3 amino acid substitutions and/or deletions and/or insertions; and the anti-FX(a) antibody light chain CDR1-3 sequences identified by SEQ ID NOs:736, 737 and 738, respectively, optionally comprising 1, 2 or 3 amino acid substitutions and/or deletions and/or insertions; or g. the anti-FIX(a) antibody heavy chain CDR1-3 sequences identified by SEQ ID NOs:52, 53 and 54, respectively, optionally comprising 1, 2 or 3 amino acid substitutions and/or deletions and/or insertions; and the anti-FIX(a) antibody light chain CDR1-3 sequences identified by SEQ ID NOs:56, 57 and 58, respectively, optionally comprising 1, 2 or 3 amino acid substitutions and/or deletions and/or insertions; and the anti-FX(a) antibody heavy chain CDR1-3 sequences identified by SEQ ID NOs:908, 909 and 910, respectively, optionally comprising 1, 2 or 3 amino acid substitutions and/or deletions and/or insertions; and the anti-FX(a) antibody light chain CDR1-3 sequences identified by SEQ ID NOs:912, 913 and 914, respectively, optionally comprising 1, 2 or 3 amino acid substitutions and/or deletions and/or insertions; or h. the anti-FIX(a) antibody heavy chain CDR1-3 sequences identified by SEQ ID NOs:52, 53 and 54, respectively, optionally comprising 1, 2 or 3 amino acid substitutions and/or deletions and/or insertions; and the anti-FIX(a) antibody light chain CDR1-3 sequences identified by SEQ ID NOs:56, 57 and 58, respectively, optionally comprising 1, 2 or 3 amino acid substitutions and/or deletions and/or insertions; and the anti-FX(a) antibody heavy chain CDR1-3 sequences identified by SEQ ID NOs:1076, 1077 and 1078, respectively, optionally comprising 1, 2 or 3 amino acid substitutions and/or deletions and/or insertions; and the anti-FX(a) antibody light chain CDR1-3 sequences identified by SEQ ID NOs:1080, 1081 and 1082, respectively, optionally comprising 1, 2 or 3 amino acid substitutions and/or deletions and/or insertions; or i. the anti-FIX(a) antibody heavy chain CDR1-3 sequences identified by SEQ ID NOs:52, 53 and 54, respectively, optionally comprising 1, 2 or 3 amino acid substitutions and/or deletions and/or insertions; and the anti-FIX(a) antibody light chain CDR1-3 sequences identified by SEQ ID NOs:56, 57 and 58, respectively, optionally comprising 1, 2 or 3 amino acid substitutions and/or deletions and/or insertions; and the anti-FX(a) antibody heavy chain CDR1-3 sequences identified by SEQ ID NOs: 484, 485 and 486, respectively, optionally comprising 1, 2 or 3 amino acid substitutions and/or deletions and/or insertions; and the anti-FX(a) antibody light chain CDR1-3 sequences identified by SEQ ID NOs:488, 489 and 490, respectively, optionally comprising 1, 2 or 3 amino acid substitutions and/or deletions and/or insertions; or j. the anti-FIX(a) antibody heavy chain CDR1-3 sequences identified by SEQ ID NOs:68, 69 and 70, respectively, optionally comprising 1, 2 or 3 amino acid substitutions and/or deletions and/or insertions; and the anti-FIX(a) antibody light chain CDR1-3 sequences identified by SEQ ID NOs: 72, 73 and 74, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or k. the anti-FIX(a) antibody heavy chain CDR1-3 sequences identified by SEQ ID NOs:68, 69 and 70, respectively, optionally comprising 1, 2 or 3 amino acid substitutions and/or deletions and/or insertions; and the anti-FIX(a) antibody light chain CDR1-3 sequences identified by SEQ ID NOs:72, 73 and 74, respectively, optionally comprising 1, 2 or 3 amino acid substitutions and/or deletions and/or insertions; and the anti-FX(a) antibody heavy chain CDR1-3 sequences identified by SEQ ID NOs:484, 485 and 486, respectively, optionally comprising 1, 2 or 3 amino acid substitutions and/or deletions and/or insertions; and the anti-FX(a) antibody light chain CDR1-3 sequences identified by SEQ ID NOs:488, 489 and 490, respectively, optionally comprising 1, 2 or 3 amino acid substitutions and/or deletions and/or insertions; or l. the anti-FIX(a) antibody heavy chain CDR1-3 sequences identified by SEQ ID NOs:1203, 1204 and 1205, respectively, optionally comprising 1, 2 or 3 amino acid substitutions and/or deletions and/or insertions; and the anti-FIX(a) antibody light chain CDR1-3 sequences identified by SEQ ID NOs:1207, 1208 and 1209, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or m. the anti-FIX(a) antibody heavy chain CDR1-3 sequences identified by SEQ ID NOs:1211, 1212 and 1213, respectively, optionally comprising 1, 2 or 3 amino acid substitutions and/or deletions and/or insertions; and the anti-FIX(a) antibody light chain CDR1-3 sequences identified by SEQ ID NOs:1215, 1216 and 1217, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or n. the anti-FIX(a) antibody heavy chain CDR1-3 sequences identified by SEQ ID NOs:1219, 1220 and 1221, respectively, optionally comprising 1, 2 or 3 amino acid substitutions and/or deletions and/or insertions; and the anti-FIX(a) antibody light chain CDR1-3 sequences identified by SEQ ID NOs:1223, 1224 and 1225, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or o. the anti-FIX(a) antibody heavy chain CDR1-3 sequences identified by SEQ ID NOs:1227, 1228 and 1229, respectively, optionally comprising 1, 2 or 3 amino acid substitutions and/or deletions and/or insertions; and the anti-FIX(a) antibody light chain CDR1-3 sequences identified by SEQ ID NOs:1231, 1232 and 1233, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or p. the anti-FIX(a) antibody heavy chain CDR1-3 sequences identified by SEQ ID NOs:1235, 1236 and 1237, respectively, optionally comprising 1, 2 or 3 amino acid substitutions and/or deletions and/or insertions; and the anti-FIX(a) antibody light chain CDR1-3 sequences identified by SEQ ID NOs:1239, 1240 and 1241, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions; or q. the anti-FIX(a) antibody heavy chain CDR1-3 sequences identified by SEQ ID NOs:1243, 1244 and 1245, respectively, optionally comprising 1, 2 or 3 amino acid substitutions and/or deletions and/or insertions; and the anti-FIX(a) antibody light chain CDR1-3 sequences identified by SEQ ID NOs:1247, 1248 and 1249, respectively, optionally comprising 1, 2 or 3 amino acid substitutions and/or deletions and/or insertions; and the anti-FX(a) antibody heavy chain CDR1-3 sequences identified by SEQ ID NOs:468, 469 and 470, respectively, optionally comprising 1, 2 or 3 amino acid substitutions and/or deletions and/or insertions; and the anti-FX(a) antibody light chain CDR1-3 sequences identified by SEQ ID NOs:472, 473 and 474, respectively, optionally comprising 1, 2 or 3 amino acid substitutions and/or deletions and/or insertions.

60. The multispecific antibody or antigen-binding fragment thereof according to embodiment 51 wherein the antibody is a bispecific antibody capable of specifically binding FIX(a) and FX(a) wherein the binding domains are those of the mAb pairs consisting of: mAb01-9933/mAb01-8174, mAb01-9933/mAb01-9772, mAb01-9978/mAb01-8174, mAb01-9978/mAb01-9772, mAb01-9985/mAb01-8174, mAb01-9985/mAb01-9772, mAb01-9994/mAb01-8174, mAb01-9994/mAb01-9772, mAb01-9985/mAb11-1431, mAb01-9985/mAb11-1434, mAb01-9985/mAb11-1457, mAb01-9985/mAb11-1480, mAb01-9985/mAb11-1121, mAb01-9985/mAb11-1125, mAb11-0173/mAb01-8174, mAb11-1204/mAb01-8174, mAb11-1495/mAb01-8174, mAb11-1501/mAb01-8174 or mAb11-1502/mAb01-8174.

61. The multispecific antibody or antigen-binding fragment thereof according to any of embodiments 51-60 wherein the antibody or antigen-binding fragment thereof is a procoagulant antibody.

62. The multispecific antibody or antigen-binding fragment thereof according to any of embodiments 51-60 wherein the antibody or antigen-binding fragment thereof is capable of increasing the procoagulant activity of FIXa.

63. The multispecific antibody or antigen-binding fragment thereof according to any of embodiments 51-60 wherein the antibody or antigen-binding fragment thereof is capable of increasing the enzymatic activity of FIXa towards FX.

64. The multispecific antibody or antigen-binding fragment thereof according to any of embodiments 51-60 wherein the antibody or antigen-binding fragment thereof is capable of functionally substituting for FVIII and/or FVIIIa.

65. The multispecific antibody or antigen-binding fragment thereof according to any of embodiments 51-64 wherein the antibody or antigen-binding fragment thereof is a bispecific antibody.

66. The multispecific antibody or antigen-binding fragment thereof according to any of embodiments 63-65 wherein the increase of the enzymatic activity of FIXa towards FX is determined in a FXa generation assay as described herein using a monovalent one-armed anti-FIX/FIXa antibody where in the stimulation index is at least 1300, 1400, 1500, 1600, 1700, 1800, 1900, 2000, 2100, 2200, 2300, 2400, 2500, 3000, 3500, 4000, 4500, 5000, 5500, 6000, 6500, 7000, 7500, 8000, 8500, 9000, 9500, 10000, 10500, 11000, 11500, 12000, 12500, 13000, 13500, 13730, 14000, 14500, 15000, 15500, 16000, 16500, 17000, 17500, 18000, 18500, 19000 or 19500 fold when measured using an one-armed antibody concentration resulting in at least 80% saturation of FIXa.

67. The multispecific antibody or antigen-binding fragment thereof according to any of embodiments 51-65 wherein said antibody or antigen-binding fragment thereof is capable of providing a mean peak thrombin (in nM) of at least 47, 48, 49, 50, 55, 60, 65, 70, 75, 80, 85, 90, 95, 100, 105 or 107 at a compound concentration of 900 nM in a TGT assay (in HA-PRP) according to example 16 herein.

68. The antibody according to any of the previous embodiments wherein the antibody isotype is IgG1, IgG2, IgG3 or IgG4 or a combination thereof.
69. A pharmaceutical composition comprising an antibody or antigen-binding fragment thereof according to any of the previous embodiments and optionally one or more pharmaceutically acceptable carrier(s).
70. The pharmaceutical composition comprising an antibody or antigen-binding fragment thereof according to embodiment 69 for the treatment of a coagulopathy or blood coagulation disorder, such as haemophilia A with or without inhibitors.
71. The antibody or antigen-binding fragment thereof or composition according to any of the previous embodiments for use in a method of treatment of a coagulopathy or blood coagulation disorder.
72. The antibody or antigen-binding fragment thereof or composition according to any of the previous embodiments for use in the treatment of haemophilia A with or without inhibitors.
73. A method of treating a subject suffering from a coagulopathy or blood coagulation disorder, comprising administering to said subject an antibody or antigen-binding fragment thereof or composition according to any of the previous embodiments.
74. A method according to embodiment 73 wherein the coagulopathy or blood coagulation disorder is haemophilia A or haemophilia A with inhibitors.
75. Use of an antibody or antigen-binding fragment thereof or composition according to any of embodiments 1-69 for the manufacture of a medicament for the treatment of a subject in need thereof.
76. Use of an antibody or antigen-binding fragment thereof or composition according to any of embodiments 1-69 for the manufacture of a medicament for the treatment of haemophilia A with or without inhibitors.
77. A eukaryotic cell which expresses the antibody or antigen-binding fragment thereof, according to any one of embodiments 1-68.
78. A kit comprising the antibody or antigen-binding fragment thereof or composition according to any of embodiments 1-69 and instructions for use.
79. The antibody or antigen-binding fragment thereof according to any of embodiments 1-25 wherein the antibody or antigen-binding fragment thereof is a component (intermediate) for use in a procoagulant multispecific antibody.
80. The antibody or antigen-binding fragment thereof according to any of embodiments 26-50 wherein the antibody or antigen-binding fragment thereof is a component (intermediate) for use in a procoagulant multispecific antibody.
81. The antibody or antigen-binding fragment thereof according to any of embodiments 1-25 wherein the antibody or antigen-binding fragment thereof is a component (intermediate) for use in the manufacture of a procoagulant multispecific antibody.
82. The antibody or antigen-binding fragment thereof according to any of embodiments 26-50 wherein the antibody or antigen-binding fragment thereof is an a component (intermediate) for use in the manufacture of a procoagulant multispecific antibody.
83. The multispecific antibody or antigen-binding fragment thereof according to any of embodiments 61-68 wherein the procoagulant activity of said antibody is improved over the multispecific antibodies disclosed in WO2018/141863.
84. The multispecific antibody or antigen-binding fragment thereof according to embodiment 83 wherein said improvement is determined using an assay as disclosed herein, such as in a FXa generation assay using monovalent one-armed (OA) anti-FIXa antibodies (as described in example 12 herein), a haemophilia A (HA) plasma TGT assay (as described in example 15 herein), in a HA-PPP TGT assay or in a HA-PRP TGT assay (as described in example 16 herein) or in a murine Tail Vein Transsection (TVT) model (as described in example 17 herein).
85. The multispecific antibody or antigen-binding fragment thereof according to embodiment 51, wherein the antibody or antigen binding fragment thereof is a bispecific antibody comprising an antibody or antigen-binding fragment thereof according to embodiment 14 and an antibody or antigen-binding fragment thereof according to embodiment 36 or 37.
86. The multispecific antibody or antigen-binding fragment thereof according to embodiment 85 wherein the stimulation of the enzymatic activity of FIXa towards FX is determined in a FXa generation assay as described in example 12 herein using a monovalent one-armed anti-FIX/FIXa antibody where in the stimulation index is at least 1300, 1400, 1500, 1600, 1700, 1800, 1900, 2000, 2100, 2200, 2300, 2400, 2500, 3000, 3500, 4000, 4500, 5000, 5500, 6000, 6500, 7000, 7500, 8000, 8500, 9000, 9500, 10000, 10500, 11000, 11500, 12000, 12500, 13000, 13500, 13730, 14000, 14500, 15000, 15500, 16000, 16500, 17000, 17500, 18000, 18500, 19000 or 19500 fold when measured using an one-armed antibody concentration resulting in at least 80% saturation of FIXa.
87. The multispecific antibody or antigen-binding fragment thereof according to any of embodiment 85 wherein said antibody or antigen-binding fragment thereof is capable of providing a mean peak thrombin (in nM) of at least 47, 48, 49, 50, 55, 60, 65, 70, 75, 80, 85, 90, 95, 100, 105 or 107 at a compound concentration of 900 nM in a TGT assay (in HA-PRP) according to example 16 herein.
88. The antibody according to any of embodiments 85-87 wherein the antibody isotype is IgG1 or IgG4.
89. A pharmaceutical composition comprising an antibody or antigen-binding fragment thereof according to any of embodiments 85-88 and optionally one or more pharmaceutically acceptable carrier(s).
90. The pharmaceutical composition comprising an antibody or antigen-binding fragment thereof according to embodiment 89 for the treatment of a coagulopathy or blood coagulation disorder, such as haemophilia A with or without inhibitors.
91. The antibody or antigen-binding fragment thereof or composition according to any of embodiments 83-90 for use in a method of treatment of a coagulopathy or blood coagulation disorder.
92. The antibody or antigen-binding fragment thereof or composition according to any of embodiments 91 for use in the treatment of haemophilia A with or without inhibitors.
93. A method of treating a subject suffering from a coagulopathy or blood coagulation disorder, comprising administering to said subject an antibody or antigen-binding fragment thereof or composition according to any of embodiments 83-90.

94. A method according to embodiment 93 wherein the coagulopathy or blood coagulation disorder is haemophilia A or haemophilia A with inhibitors.
95. Use of an antibody or antigen-binding fragment thereof or composition according to any of embodiments 83-89 for the manufacture of a medicament for the treatment of a subject in need thereof.
96. Use of an antibody or antigen-binding fragment thereof or composition according to any of embodiments 83-89 for the manufacture of a medicament for the treatment of haemophilia A with or without inhibitors.
97. A eukaryotic cell which expresses the antibody or antigen-binding fragment thereof, according to any one of embodiments 83-88.
98. A kit comprising the antibody or antigen-binding fragment thereof or composition according to any of embodiments 83-89 and instructions for use.
99. The antibody or antigen-binding fragment thereof according to any of embodiments 83-88 wherein the antibody or antigen-binding fragment capable of binding to FIX(a) is a component (intermediate) for use in a procoagulant multispecific antibody.
100. The antibody or antigen-binding fragment thereof according to any of embodiments 83-88 wherein the antibody or antigen-binding fragment thereof capable of binding to FIX(a) is a component (intermediate) for use in the manufacture of a procoagulant multispecific antibody.
101. The antibody or antigen-binding fragment thereof according to any of embodiments 83-88 wherein the antibody or antigen-binding fragment thereof is a component (intermediate) for use in the manufacture of a procoagulant multispecific antibody.
102. An injection device comprising an antibody or antigen-binding fragment thereof or composition according to any of embodiments 51-69.
103. An injection device comprising an antibody or antigen-binding fragment thereof or composition according to any of embodiments 83-90.
104. The injection device according to embodiment 102 wherein said device is a disposable and/or pre-filled and/or multi-dose device, such as a pen.
105. The injection device according to embodiment 104 wherein said device is a pre-filled pen.
106. The injection device according to embodiment 104 wherein said device is a multi-dose pen.
107. The injection device according to any of embodiments 102, 104, 105 or 106 wherein said injection device comprises a tube having a needle gauge of 20 to 36.
108. The injection device according to embodiment 103 wherein said device is a disposable and/or pre-filled and/or multi-dose device, such as a pen.
109. The injection device according to embodiment 103 wherein said device is a pre-filled pen.
110. The injection device according to embodiment 108 wherein said device is a multi-dose pen.
111. The injection device according to any of embodiments 103, 108, 109 or 110 wherein said injection device comprises a tube having a needle gauge of 20 to 36.

In some embodiments the antibodies or antigen-binding fragments thereof of the invention are procoagulant bispecific antibodies capable of binding to FIX (SEQ ID NO:1) and/or the activated form thereof (FIXa) and to FX (SEQ ID NO:2) and/or the activated form thereof (FXa).

In one embodiment the bispecific antibody (bimAb) is bimAb05-0745 wherein the anti-FIX(a) arm comprises the following CDR-sequences:

```
VH CDR1 (SEQ ID NO: 68):
DYAMH

VH CDR2 (SEQ ID NO: 69):
GISWKGDIGGYVDSVKG

VH CDR3 (SEQ ID NO: 70):
SYGSGSFYNAFDS

VL CDR1 (SEQ ID NO: 72):
RASQSISSWLA

VL CDR2 (SEQ ID NO: 73):
KASRLDR

VL CDR3 (SEQ ID NO: 74):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-0746 wherein the anti-FIX(a) arm comprises the following CDR-sequences:

```
VH CDR1 (SEQ ID NO: 44):
DYAMH

VH CDR2 (SEQ ID NO: 45):
GISWKGDIGGYVDSVKG

VH CDR3 (SEQ ID NO: 46):
SYGSGSFYNAFDS

VL CDR1 (SEQ ID NO: 48):
RASQSISSWLA

VL CDR2 (SEQ ID NO: 49):
KASRLER

VL CDR3 (SEQ ID NO: 50):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG
```

```
VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-1229 wherein the anti-FIX(a) arm comprises the following CDR-sequences:

```
VH CDR1 (SEQ ID NO: 4):
DYAMH

VH CDR2 (SEQ ID NO: 5):
GISWRGDIGGYVDSVKG

VH CDR3 (SEQ ID NO: 6):
SYGSGSFYNAFDS

VL CDR1 (SEQ ID NO: 8):
RASQSISSWLA

VL CDR2 (SEQ ID NO: 9):
KASRLER

VL CDR3 (SEQ ID NO: 10):
LEYSSYIRT
``` and wherein the anti-FX(a) arm comprises the following CDR-sequences:

```
VH CDR1 (SEQ ID NO: 460):
TSWIV

VH CDR2 (SEQ ID NO: 461):
MIDPSDSFTSYSPSFQG

VH CDR3 (SEQ ID NO: 462):
LHYYHSEEFDV

VL CDR1 (SEQ ID NO: 464):
RASQSVSSSYLA

VL CDR2 (SEQ ID NO: 465):
GASSRAR

VL CDR3 (SEQ ID NO: 466):
QQFGSSRLFT
```

In one embodiment the bispecific antibody is bimAb05-2112 wherein the anti-FIX(a) arm comprises the following CDR-sequences:

```
VH CDR1 (SEQ ID NO: 68):
DYAMH

VH CDR2 (SEQ ID NO: 69):
GISWKGDIGGYVDSVKG

VH CDR3 (SEQ ID NO: 70):
SYGSGSFYNAFDS

VL CDR1 (SEQ ID NO: 72):
RASQSISSWLA

VL CDR2 (SEQ ID NO: 73):
KASRLDR

VL CDR3 (SEQ ID NO: 74):
LEYSSYIRT
``` and wherein the anti-FX(a) arm comprises the following CDR-sequences:

```
VH CDR1 (SEQ ID NO: 484):
TSWIS

VH CDR2 (SEQ ID NO: 485):
MIDPSDSYTSYSPSFQG

VH CDR3 (SEQ ID NO: 486):
LHYYNSEEFDV

VL CDR1 (SEQ ID NO: 488):
RASQSVSSSYLA

VL CDR2 (SEQ ID NO: 489):
GQSSRTR

VL CDR3 (SEQ ID NO: 490):
QQYGDSQLFT
```

In one embodiment the bispecific antibody is bimAb05-2113 wherein the anti-FIX(a) arm comprises the following CDR-sequences:

```
VH CDR1 (SEQ ID NO: 36):
DYAMH

VH CDR2 (SEQ ID NO: 37):
GISWKGDIGGYVDSVKG

VH CDR3 (SEQ ID NO: 38):
SYGSGSFYNAFDS

VL CDR1 (SEQ ID NO: 40):
RASQSISSWLA

VL CDR2 (SEQ ID NO: 41):
KASKLDR

VL CDR3 (SEQ ID NO: 42):
LEYSSYIRT
``` and wherein the anti-FX(a) arm comprises the following CDR-sequences:

```
VH CDR1 (SEQ ID NO: 484):
TSWIS

VH CDR2 (SEQ ID NO: 485):
MIDPSDSYTSYSPSFQG

VH CDR3 (SEQ ID NO: 486):
LHYYNSEEFDV

VL CDR1 (SEQ ID NO: 488):
RASQSVSSSYLA

VL CDR2 (SEQ ID NO: 489):
GQSSRTR

VL CDR3 (SEQ ID NO: 490):
QQYGDSQLFT
```

In one embodiment the bispecific antibody is bimAb05-2114 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 484):
TSWIS

VH CDR2 (SEQ ID NO: 485):
MIDPSDSYTSYSPSFQG

VH CDR3 (SEQ ID NO: 486):
LHYYNSEEFDV

VL CDR1 (SEQ ID NO: 488):
RASQSVSSSYLA

VL CDR2 (SEQ ID NO: 489):
GQSSRTR

VL CDR3 (SEQ ID NO: 490):
QQYGDSQLFT

In one embodiment the bispecific antibody is bimAb05-2115 wherein the anti-FIX(a) arm comprises the following CDR-sequences:

VH CDR1 (SEQ ID NO: 44):
DYAMH

VH CDR2 (SEQ ID NO: 45):
GISWKGDIGGYVDSVKG

VH CDR3 (SEQ ID NO: 46):
SYGSGSFYNAFDS

VL CDR1 (SEQ ID NO: 48):
RASQSISSWLA

VL CDR2 (SEQ ID NO: 49):
KASRLER

VL CDR3 (SEQ ID NO: 50):
LEYSSYIRT and wherein the anti-FX(a) arm comprises the following CDR-sequences:

VH CDR1 (SEQ ID NO: 484):
TSWIS

VH CDR2 (SEQ ID NO: 485):
MIDPSDSYTSYSPSFQG

VH CDR3 (SEQ ID NO: 486):
LHYYNSEEFDV

VL CDR1 (SEQ ID NO: 488):
RASQSVSSSYLA

VL CDR2 (SEQ ID NO: 489):
GQSSRTR

VL CDR3 (SEQ ID NO: 490):
QQYGDSQLFT

In one embodiment the bispecific antibody is bimAb05-2375 wherein the anti-FIX(a) arm comprises the following CDR-sequences:

VH CDR1 (SEQ ID NO: 4):
DYAMH

VH CDR2 (SEQ ID NO: 5):
GISWRGDIGGYVDSVKG

VH CDR3 (SEQ ID NO: 6):
SYGSGSFYNAFDS

VL CDR1 (SEQ ID NO: 8):
RASQSISSWLA

VL CDR2 (SEQ ID NO: 9):
KASRLER

VL CDR3 (SEQ ID NO: 10):
LEYSSYIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT

In one embodiment the bispecific antibody is bimAb05-2379 wherein the anti-FIX(a) arm comprises the following CDR-sequences:

VH CDR1 (SEQ ID NO: 4):
DYAMH

VH CDR2 (SEQ ID NO: 5):
GISWRGDIGGYVDSVKG

VH CDR3 (SEQ ID NO: 6):
SYGSGSFYNAFDS

VL CDR1 (SEQ ID NO: 8):
RASQSISSWLA

VL CDR2 (SEQ ID NO: 9):
KASRLER

VL CDR3 (SEQ ID NO: 10):
LEYSSYIRT and wherein the anti-FX(a) arm comprises the following CDR-sequences:

VH CDR1 (SEQ ID NO: 476):
TSWIV

VH CDR2 (SEQ ID NO: 477):
MIDPSDSFTSYSPSFQG

VH CDR3 (SEQ ID NO: 478):
LHYYNSEEFDV

VL CDR1 (SEQ ID NO: 480):
RASQSVSSSYLA

VL CDR2 (SEQ ID NO: 481):
GASSRAR

VL CDR3 (SEQ ID NO: 482):
QQFGSSRLFT

In one embodiment the bispecific antibody is bimAb05-2532 wherein the anti-FIX(a) arm comprises the following CDR-sequences:

VH CDR1 (SEQ ID NO: 12):
DYAMH

VH CDR2 (SEQ ID NO: 13):
GISWRGDIIGYVDSVKG

VH CDR3 (SEQ ID NO: 14):
SYGSGSFYNAFDS

VL CDR1 (SEQ ID NO: 16):
RASKSISSWLA

VL CDR2 (SEQ ID NO: 17):
KASRLDR

VL CDR3 (SEQ ID NO: 18):
LEYSSYIRT and wherein the anti-FX(a) arm comprises the following CDR-sequences:

VH CDR1 (SEQ ID NO: 460):
TSWIV

VH CDR2 (SEQ ID NO: 461):
MIDPSDSFTSYSPSFQG

VH CDR3 (SEQ ID NO: 462):
LHYYHSEEFDV

VL CDR1 (SEQ ID NO: 464):
RASQSVSSSYLA

VL CDR2 (SEQ ID NO: 465):
GASSRAR

VL CDR3 (SEQ ID NO: 466):
QQFGSSRLFT

In one embodiment the bispecific antibody is bimAb05-3279 wherein the anti-FIX(a) arm comprises the following CDR-sequences:

VH CDR1 (SEQ ID NO: 36):
DYAMH

VH CDR2 (SEQ ID NO: 37):
GISWKGDIGGYVDSVKG

VH CDR3 (SEQ ID NO: 38):
SYGSGSFYNAFDS

VL CDR1 (SEQ ID NO: 40):
RASQSISSWLA

VL CDR2 (SEQ ID NO: 41):
KASKLDR

VL CDR3 (SEQ ID NO: 42):
LEYSSYIRT and wherein the anti-FX(a) arm comprises the following CDR-sequences:

VH CDR1 (SEQ ID NO: 460):
TSWIV

VH CDR2 (SEQ ID NO: 461):
MIDPSDSFTSYSPSFQG

VH CDR3 (SEQ ID NO: 462):
LHYYHSEEFDV

VL CDR1 (SEQ ID NO: 464):
RASQSVSSSYLA

VL CDR2 (SEQ ID NO: 465):
GASSRAR

VL CDR3 (SEQ ID NO: 466):
QQFGSSRLFT

In one embodiment the bispecific antibody is bimAb05-3409 wherein the anti-FIX(a) arm comprises the following CDR-sequences:

VH CDR1 (SEQ ID NO: 44):
DYAMH

VH CDR2 (SEQ ID NO: 45):
GISWKGDIGGYVDSVKG

VH CDR3 (SEQ ID NO: 46):
SYGSGSFYNAFDS

VL CDR1 (SEQ ID NO: 48):
RASQSISSWLA

VL CDR2 (SEQ ID NO: 49):
KASRLER

VL CDR3 (SEQ ID NO: 501):
LEYSSYIRT and wherein the anti-FX(a) arm comprises the following CDR-sequences:

VH CDR1 (SEQ ID NO: 460):
TSWIV

VH CDR2 (SEQ ID NO: 461):
MIDPSDSFTSYSPSFQG

VH CDR3 (SEQ ID NO: 462):
LHYYHSEEFDV

VL CDR1 (SEQ ID NO: 464):
RASQSVSSSYLA

VL CDR2 (SEQ ID NO: 465):
GASSRAR

VL CDR3 (SEQ ID NO: 466):
QQFGSSRLFT

In one embodiment the bispecific antibody is bimAb05-3416 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 460):
TSWIV

VH CDR2 (SEQ ID NO: 461):
MIDPSDSFTSYSPSFQG

VH CDR3 (SEQ ID NO: 462):
LHYYHSEEFDV

VL CDR1 (SEQ ID NO: 464):
RASQSVSSSYLA

VL CDR2 (SEQ ID NO: 465):
GASSRAR

VL CDR3 (SEQ ID NO: 466):
QQFGSSRLFT
```

In one embodiment the bispecific antibody is bimAb05-3755 wherein the anti-FIX(a) arm comprises the following CDR-sequences:

```
VH CDR1 (SEQ ID NO: 68):
DYAMH

VH CDR2 (SEQ ID NO: 69):
GISWKGDIGGYVDSVKG

VH CDR3 (SEQ ID NO: 70):
SYGSGSFYNAFDS

VL CDR1 (SEQ ID NO: 72):
RASQSISSWLA

VL CDR2 (SEQ ID NO: 73):
KASRLDR

VL CDR3 (SEQ ID NO: 74):
LEYSSYIRT
``` and wherein the anti-FX(a) arm comprises the following CDR-sequences:

```
VH CDR1 (SEQ ID NO: 460):
TSWIV

VH CDR2 (SEQ ID NO: 461):
MIDPSDSFTSYSPSFQG

VH CDR3 (SEQ ID NO: 462):
LHYYHSEEFDV

VL CDR1 (SEQ ID NO: 464):
RASQSVSSSYLA

VL CDR2 (SEQ ID NO: 465):
GASSRAR

VL CDR3 (SEQ ID NO: 466):
QQFGSSRLFT
```

In one embodiment the bispecific antibody is bimAb05-3761 wherein the anti-FIX(a) arm comprises the following CDR-sequences:

```
VH CDR1 (SEQ ID NO: 36):
DYAMH

VH CDR2 (SEQ ID NO: 37):
GISWKGDIGGYVDSVKG

VH CDR3 (SEQ ID NO: 38):
SYGSGSFYNAFDS

VL CDR1 (SEQ ID NO: 40):
RASQSISSWLA

VL CDR2 (SEQ ID NO: 41):
KASKLDR

VL CDR3 (SEQ ID NO: 42):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-3769 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-3770 wherein the anti-FIX(a) arm comprises the following CDR-sequences:

```
VH CDR1 (SEQ ID NO: 60):
DYAMH

VH CDR2 (SEQ ID NO: 61):
GISWRGDIGGYVKSVKG

VH CDR3 (SEQ ID NO: 62):
SYGSGSFYNAFDS

VL CDR1 (SEQ ID NO: 64):
RASQSISSWLA

VL CDR2 (SEQ ID NO: 65):
KASRLER

VL CDR3 (SEQ ID NO: 66):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-3862 wherein the anti-FIX(a) arm comprises the following CDR-sequences:

```
VH CDR1 (SEQ ID NO: 20):
DYAMH

VH CDR2 (SEQ ID NO: 21):
GISWRGDIGGYVDSVKG

VH CDR3 (SEQ ID NO: 22):
SYGSGSFYNAFDS

VL CDR1 (SEQ ID NO: 24):
RASQSISSWLA

VL CDR2 (SEQ ID NO: 25):
KASRLDR

VL CDR3 (SEQ ID NO: 26):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-3863 wherein the anti-FIX(a) arm comprises the following CDR-sequences:

```
VH CDR1 (SEQ ID NO: 28):
DYAMH

VH CDR2 (SEQ ID NO: 29):
GISWRGDIGGYVDSVKG

VH CDR3 (SEQ ID NO: 30):
SYGSGSFYNAFDS

VL CDR1 (SEQ ID NO: 32):
RASQSISSWLA

VL CDR2 (SEQ ID NO: 33):
KASRLER

VL CDR3 (SEQ ID NO: 34):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-3880 wherein the anti-FIX(a) arm comprises the following CDR-sequences:

VH CDR1 (SEQ ID NO: 76):
DYAMH

VH CDR2 (SEQ ID NO: 77):
GISWRGDIKGYVDSVKG

VH CDR3 (SEQ ID NO: 78):
SYGSGSFYNAFDS

VL CDR1 (SEQ ID NO: 80):
RASKSISSWLA

VL CDR2 (SEQ ID NO: 81):
KASRLDR

VL CDR3 (SEQ ID NO: 82):
LEYSSYIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT

In one embodiment the bispecific antibody is bimAb05-3886 wherein the anti-FIX(a) arm comprises the following CDR-sequences:

VH CDR1 (SEQ ID NO: 84):
DYAMH

VH CDR2 (SEQ ID NO: 85):
GISWRGDIKGYVDSVKG

VH CDR3 (SEQ ID NO: 86):
SYGSGSFYNAFDS

VL CDR1 (SEQ ID NO: 88):
RASQSISSWLA

VL CDR2 (SEQ ID NO: 89):
KASRLDR

VL CDR3 (SEQ ID NO: 901:
LEYNSYIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT

In one embodiment the bispecific antibody is bimAb05-3955 wherein the anti-FIX(a) arm comprises the following CDR-sequences:

VH CDR1 (SEQ ID NO: 92):
DYAMH

VH CDR2 (SEQ ID NO: 93):
GISWRGDIGGYVKSVKG

VH CDR3 (SEQ ID NO: 94):
SYGSGSFYNAFDS

VL CDR1 (SEQ ID NO: 96):
RASQSISSWLA

VL CDR2 (SEQ ID NO: 97):
KAQRLDR

VL CDR3 (SEQ ID NO: 98):
LEYSSYIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT

In one embodiment the bispecific antibody is bimAb05-4100 wherein the anti-FIX(a) arm comprises the following CDR-sequences:

VH CDR1 (SEQ ID NO: 100):
DYAMH

VH CDR2 (SEQ ID NO: 101):
GISWKGDIGGYVDSVKG

VH CDR3 (SEQ ID NO: 102):
SYGSGSFYNAFDS

VL CDR1 (SEQ ID NO: 104):
RASQSIKSWLA

VL CDR2 (SEQ ID NO: 105):
KASRLDR

VL CDR3 (SEQ ID NO: 106):
LEYSSYIRT and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4114 wherein the anti-FIX(a) arm comprises the following CDR-sequences:

```
VH CDR1 (SEQ ID NO: 108):
DYAMH

VH CDR2 (SEQ ID NO: 109):
GISWKGDIGGYADSVKG

VH CDR3 (SEQ ID NO: 110):
SYGSGSFYNAFDS

VL CDR1 (SEQ ID NO: 112):
RASKSISSWLA

VL CDR2 (SEQ ID NO: 113):
KASRLER

VL CDR3 (SEQ ID NO: 114):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4121 wherein the anti-FIX(a) arm comprises the following CDR-sequences:

```
VH CDR1 (SEQ ID NO: 116):
DYAMH

VH CDR2 (SEQ ID NO: 117):
GISWKGDIGGYADSVKG

VH CDR3 (SEQ ID NO: 118):
SYGSGSFYNAFDS

VL CDR1 (SEQ ID NO: 120):
RASQSISSWLA

VL CDR2 (SEQ ID NO: 121):
KASRLER

VL CDR3 (SEQ ID NO: 122):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4220 wherein the anti-FIX(a) arm comprises the following CDR-sequences:

```
VH CDR1 (SEQ ID NO: 212):
DYAMH

VH CDR2 (SEQ ID NO: 213):
GISWKGDIGGYADSVKG

VH CDR3 (SEQ ID NO: 214):
SYGSGSFYNAFDS

VL CDR1 (SEQ ID NO: 216):
RASQSISSWLA

VL CDR2 (SEQ ID NO: 217):
KASKLDR

VL CDR3 (SEQ ID NO: 218):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4226 wherein the anti-FIX(a) arm comprises the following CDR-sequences:

```
VH CDR1 (SEQ ID NO: 220):
DYAMH

VH CDR2 (SEQ ID NO: 221):
GISWKGDIGGYADSVKG

VH CDR3 (SEQ ID NO: 222):
SYGSGSFYNAFDS

VL CDR1 (SEQ ID NO: 224):
RASQSISSWLA

VL CDR2 (SEQ ID NO: 225):
KASKLER

VL CDR3 (SEQ ID NO: 226):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4283 wherein the anti-FIX(a) arm comprises the following CDR-sequences:

```
VH CDR1 (SEQ ID NO: 228):
DYAMH

VH CDR2 (SEQ ID NO: 229):
GISWKGDIGGYVDSVKG

VH CDR3 (SEQ ID NO: 230):
SYGSGSFYNAFDS

VL CDR1 (SEQ ID NO: 232):
RASQSISSWLA

VL CDR2 (SEQ ID NO: 233):
KASKLDR

VL CDR3 (SEQ ID NO: 234):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4289 wherein the anti-FIX(a) arm comprises the following CDR-sequences:

```
VH CDR1 (SEQ ID NO: 236):
DYAMH

VH CDR2 (SEQ ID NO: 237):
GISWKGDIGGYVDSVKG

VH CDR3 (SEQ ID NO: 238):
SYGSGSFYNAFDS

VL CDR1 (SEQ ID NO: 240):
RASQSISSWLA

VL CDR2 (SEQ ID NO: 241):
KASKLER

VL CDR3 (SEQ ID NO: 242):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4292 wherein the anti-FIX(a) arm comprises the following CDR-sequences:

```
VH CDR1 (SEQ ID NO: 252):
DYAMH

VH CDR2 (SEQ ID NO: 253):
GISWKGDIGGYVDSVKG

VH CDR3 (SEQ ID NO: 254):
SYGSGSFYNAFDS

VL CDR1 (SEQ ID NO: 256):
RASQSISSWLA

VL CDR2 (SEQ ID NO: 257):
KASKLER

VL CDR3 (SEQ ID NO: 258):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4293 wherein the anti-FIX(a) arm comprises the following CDR-sequences:

```
VH CDR1 (SEQ ID NO: 244):
DYAMH

VH CDR2 (SEQ ID NO: 245):
GISWKGDIGGYVDSVKG

VH CDR3 (SEQ ID NO: 246):
SYGSGSFYNAFDS

VL CDR1 (SEQ ID NO: 248):
RASQSISSWLA

VL CDR2 (SEQ ID NO: 249):
KASKLDR

VL CDR3 (SEQ ID NO: 250):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4387 wherein the anti-FIX(a) arm comprises the following CDR-sequences:

```
VH CDR1 (SEQ ID NO: 260):
DYAMH

VH CDR2 (SEQ ID NO: 261):
GISWKGDIGGYVDSVKG

VH CDR3 (SEQ ID NO: 262):
SYGSGSFYNAFDS

VL CDR1 (SEQ ID NO: 264):
RASQSISSWLA

VL CDR2 (SEQ ID NO: 265):
KASKLDR

VL CDR3 (SEQ ID NO: 266):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4392 wherein the anti-FIX(a) arm comprises the following CDR-sequences:

```
VH CDR1 (SEQ ID NO: 268):
DYAMH

VH CDR2 (SEQ ID NO: 269):
GISWKGDIGGYVDSVKG

VH CDR3 (SEQ ID NO: 270):
SYGSGSFYNAFDS

VL CDR1 (SEQ ID NO: 272):
RASQSISSWLA

VL CDR2 (SEQ ID NO: 273):
KASKLER

VL CDR3 (SEQ ID NO: 274):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4419 wherein the anti-FIX(a) arm comprises the following CDR-sequences:

```
VH CDR1 (SEQ ID NO: 124):
DYAMH

VH CDR2 (SEQ ID NO: 125):
GISWKGDIGGYVDSVKG

VH CDR3 (SEQ ID NO: 126):
SYGSGSFYNAFDS

VL CDR1 (SEQ ID NO: 128):
RASQSISSWLA

VL CDR2 (SEQ ID NO: 129):
KASKLDR

VL CDR3 (SEQ ID NO: 130):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4422 wherein the anti-FIX(a) arm comprises the following CDR-sequences:

```
VH CDR1 (SEQ ID NO: 276):
DYAMH

VH CDR2 (SEQ ID NO: 277):
GISWKGDIGGYVDSVKG

VH CDR3 (SEQ ID NO: 278):
SYGSGSFYNAFDS

VL CDR1 (SEQ ID NO: 280):
RASQSISSWLA

VL CDR2 (SEQ ID NO: 281):
KASKLDR

VL CDR3 (SEQ ID NO: 282):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4428 wherein the anti-FIX(a) arm comprises the following CDR-sequences:

```
VH CDR1 (SEQ ID NO: 284):
DYAMH

VH CDR2 (SEQ ID NO: 285):
GISWKGDIGGYVDSVKG

VH CDR3 (SEQ ID NO: 286):
SYGSGSFYNAFDS

VL CDR1 (SEQ ID NO: 288):
RASQSISSWLA

VL CDR2 (SEQ ID NO: 289):
KASKLER

VL CDR3 (SEQ ID NO: 290):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4443 wherein the anti-FIX(a) arm comprises the following CDR-sequences:

```
VH CDR1 (SEQ ID NO: 300):
DYAMH

VH CDR2 (SEQ ID NO: 301):
GISWKGDIGGYVDSVKG

VH CDR3 (SEQ ID NO: 302):
SYGSGSFYNAFDS

VL CDR1 (SEQ ID NO: 304):
RASQSISSWLA

VL CDR2 (SEQ ID NO: 305):
KASKLER

VL CDR3 (SEQ ID NO: 306):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4444 wherein the anti-FIX(a) arm comprises the following CDR-sequences:

```
VH CDR1 (SEQ ID NO: 292):
DYAMH

VH CDR2 (SEQ ID NO: 293):
GISWKGDIGGYVDSVKG

VH CDR3 (SEQ ID NO: 294):
SYGSGSFYNAFDS

VL CDR1 (SEQ ID NO: 296):
RASQSISSWLA

VL CDR2 (SEQ ID NO: 297):
KASKLDR

VL CDR3 (SEQ ID NO: 298):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4601 wherein the anti-FIX(a) arm comprises the following CDR-sequences:

```
VH CDR1 (SEQ ID NO: 188):
DYAMH

VH CDR2 (SEQ ID NO: 189):
GISWKGDIGGYVDSVKG

VH CDR3 (SEQ ID NO: 190):
SYGSGSFYNAFDS

VL CDR1 (SEQ ID NO: 192):
RASQSISSWLA

VL CDR2 (SEQ ID NO: 193):
KASRLDR

VL CDR3 (SEQ ID NO: 194):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4604 wherein the anti-FIX(a) arm comprises the following CDR-sequences:

```
VH CDR1 (SEQ ID NO: 140):
DYAMH

VH CDR2 (SEQ ID NO: 141):
GISWKGDIGGYVDSVKG

VH CDR3 (SEQ ID NO: 142):
SYGSGSFYNAFDS

VL CDR1 (SEQ ID NO: 144):
RASQSISSWLA

VL CDR2 (SEQ ID NO: 145):
KASRLDR

VL CDR3 (SEQ ID NO: 146):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4608 wherein the anti-FIX(a) arm comprises the following CDR-sequences:

```
VH CDR1 (SEQ ID NO: 204):
DYAMH

VH CDR2 (SEQ ID NO: 205):
GISWKGDIGGYVDSVKG

VH CDR3 (SEQ ID NO: 206):
SYGSGSFYNAFDS

VL CDR1 (SEQ ID NO: 208):
RASQSISSWLA

VL CDR2 (SEQ ID NO: 209):
KASRLDR

VL CDR3 (SEQ ID NO: 210):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4611 wherein the anti-FIX(a) arm comprises the following CDR-sequences:

```
VH CDR1 (SEQ ID NO: 180):
DYAMH

VH CDR2 (SEQ ID NO: 181):
GISWKGDIGGYVDSVKG

VH CDR3 (SEQ ID NO: 182):
SYGSGSFYNAFDS

VL CDR1 (SEQ ID NO: 184):
RASQSISSWLA

VL CDR2 (SEQ ID NO: 185):
KASRLDR

VL CDR3 (SEQ ID NO: 186):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4612 wherein the anti-FIX(a) arm comprises the following CDR-sequences:

```
VH CDR1 (SEQ ID NO: 196):
DYAMH

VH CDR2 (SEQ ID NO: 197):
GISWKGDIGGYVDSVKG

VH CDR3 (SEQ ID NO: 198):
SYGSGSFYNAFDS

VL CDR1 (SEQ ID NO: 200):
RASQSISSWLA

VL CDR2 (SEQ ID NO: 201):
KASRLDR

VL CDR3 (SEQ ID NO: 202):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4613 wherein the anti-FIX(a) arm comprises the following CDR-sequences:

```
VH CDR1 (SEQ ID NO: 172):
DYAMH

VH CDR2 (SEQ ID NO: 173):
GISWKGDIGGYVDSVKG

VH CDR3 (SEQ ID NO: 174):
SYGSGSFYNAFDS

VL CDR1 (SEQ ID NO: 176):
RASQSISSWLA

VL CDR2 (SEQ ID NO: 177):
KASRLDR

VL CDR3 (SEQ ID NO: 178):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4615 wherein the anti-FIX(a) arm comprises the following CDR-sequences:

```
VH CDR1 (SEQ ID NO: 164):
DYAMH

VH CDR2 (SEQ ID NO: 165):
GISWKGDIGGYVDSVKG

VH CDR3 (SEQ ID NO: 166):
SYGSGSFYNAFDS

VL CDR1 (SEQ ID NO: 168):
RASQSISSWLA

VL CDR2 (SEQ ID NO: 169):
KASRLDR

VL CDR3 (SEQ ID NO: 170):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4617 wherein the anti-FIX(a) arm comprises the following CDR-sequences:

```
VH CDR1 (SEQ ID NO: 148):
DYAMH

VH CDR2 (SEQ ID NO: 149):
GISWKGDIGGYVDSVKG

VH CDR3 (SEQ ID NO: 150):
SYGSGSFYNAFDS

VL CDR1 (SEQ ID NO: 152):
RASQSISSWLA

VL CDR2 (SEQ ID NO: 153):
KASRLDR

VL CDR3 (SEQ ID NO: 154):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4618 wherein the anti-FIX(a) arm comprises the following CDR-sequences:

```
VH CDR1 (SEQ ID NO: 156):
DYAMH

VH CDR2 (SEQ ID NO: 157):
GISWKGDIGGYVDSVKG

VH CDR3 (SEQ ID NO: 158):
SYGSGSFYNAFDS

VL CDR1 (SEQ ID NO: 160):
RASQSISSWLA

VL CDR2 (SEQ ID NO: 161):
KASRLDR

VL CDR3 (SEQ ID NO: 162):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4684 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 500):
TSWIS

VH CDR2 (SEQ ID NO: 501):
MIDPSDSYTSYSPSFQG

VH CDR3 (SEQ ID NO: 502):
LHYYNSEEFDV

VL CDR1 (SEQ ID NO: 504):
RASQSVSSSYLA

VL CDR2 (SEQ ID NO: 505):
GQSSRTR

VL CDR3 (SEQ ID NO: 506):
QQFGDSQLFT
```

In one embodiment the bispecific antibody is bimAb05-4685 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 508):
TSWIS

VH CDR2 (SEQ ID NO: 509):
MIDPSDSFTSYSPSFQG

VH CDR3 (SEQ ID NO: 510):
LHYYHSEEFDV

VL CDR1 (SEQ ID NO: 512):
RASQSVSSSYLA

VL CDR2 (SEQ ID NO: 513):
GQSSRTR

VL CDR3 (SEQ ID NO: 514):
QQFGDSQLFT
```

In one embodiment the bispecific antibody is bimAb05-4686 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 516):
TSWIS

VH CDR2 (SEQ ID NO: 517):
MIDPSDSYTSYSPSFQG

VH CDR3 (SEQ ID NO: 518):
LHYYHSEEFDV

VL CDR1 (SEQ ID NO: 520):
RASQSVSSSYLA

VL CDR2 (SEQ ID NO: 521):
GQSSRTR

VL CDR3 (SEQ ID NO: 522):
QQFGDSQLFT
```

In one embodiment the bispecific antibody is bimAb05-4687 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 524):
TSWIS

VH CDR2 (SEQ ID NO: 525):
MIDPSDSYTSYSPSFQG

VH CDR3 (SEQ ID NO: 526):
LHYYHSEEFDV

VL CDR1 (SEQ ID NO: 528):
RASQSVSSSYLA

VL CDR2 (SEQ ID NO: 529):
GQSSRTR

VL CDR3 (SEQ ID NO: 530):
QQFGDSQLFT
```

In one embodiment the bispecific antibody is bimAb05-4688 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 532):
TSWIS

VH CDR2 (SEQ ID NO: 533):
MIDPSDSFTSYSPSFQG

VH CDR3 (SEQ ID NO: 534):
LHYYNSEEFDV

VL CDR1 (SEQ ID NO: 536):
RASQSVSSSYLA

VL CDR2 (SEQ ID NO: 537):
GQSSRTR

VL CDR3 (SEQ ID NO: 538):
QQFGDSQLFT
```

In one embodiment the bispecific antibody is bimAb05-4689 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 540):
TSWIV

VH CDR2 (SEQ ID NO: 541):
MIDPSDSYTSYSPSFQG

VH CDR3 (SEQ ID NO: 542):
LHYYNSEEFDV

VL CDR1 (SEQ ID NO: 544):
RASQSVSSSYLA

VL CDR2 (SEQ ID NO: 545):
GQSSRTR

VL CDR3 (SEQ ID NO: 546):
QQFGDSQLFT
```

In one embodiment the bispecific antibody is bimAb05-4690 wherein the anti-FIX(a) arm comprises the following CDR-sequences:

```
VH CDR1
(SEQ ID NO: 52):
DYAMH

VH CDR2
(SEQ ID NO: 53):
GISWRGDIGGYVKSVKG

VH CDR3
(SEQ ID NO: 54):
SYGSGSFYNAFDS

VL CDR1
(SEQ ID NO: 56):
RASQSISSWLA

VL CDR2
(SEQ ID NO: 57):
KASKLER

VL CDR3
(SEQ ID NO: 58):
LEYSSYIRT
``` and wherein the anti-FX(a) arm comprises the following CDR-sequences:

```
VH CDR1
(SEQ ID NO: 556):
TSWIV

VH CDR2
(SEQ ID NO: 557):
MIDPSDSFTSYSPSFQG

VH CDR3
(SEQ ID NO: 558):
LHYYNSEEFDV
```

-continued

VL CDR1
(SEQ ID NO: 560):
RASQSVSSSYLA

VL CDR2
(SEQ ID NO: 561):
GQSSRTR

VL CDR3
(SEQ ID NO: 562):
QQYGDSQLFT

In one embodiment the bispecific antibody is bimAb05-4692 wherein the anti-FIX(a) arm comprises the following CDR-sequences:

VH CDR1
(SEQ ID NO: 52):
DYAMH

VH CDR2
(SEQ ID NO: 53):
GISWRGDIGGYVKSVKG

VH CDR3
(SEQ ID NO: 54):
SYGSGSFYNAFDS

VL CDR1
(SEQ ID NO: 56):
RASQSISSWLA

VL CDR2
(SEQ ID NO: 57):
KASKLER

VL CDR3
(SEQ ID NO: 58):
LEYSSYIRT and wherein the anti-FX(a) arm comprises the following CDR-sequences:

VH CDR1
(SEQ ID NO: 564):
TSWIS

VH CDR2
(SEQ ID NO: 565):
MIDPSDSFTSYSPSFQG

VH CDR3
(SEQ ID NO: 566):
LHYYHSEEFDV

VL CDR1
(SEQ ID NO: 568):
RASQSVSSSYLA

VL CDR2
(SEQ ID NO: 569):
GQSSRTR

VL CDR3
(SEQ ID NO: 570):
QQYGDSQLFT

In one embodiment the bispecific antibody is bimAb05-4693 wherein the anti-FIX(a) arm comprises the following CDR-sequences:

VH CDR1
(SEQ ID NO: 52):
DYAMH

-continued

VH CDR2
(SEQ ID NO: 53):
GISWRGDIGGYVKSVKG

VH CDR3
(SEQ ID NO: 54):
SYGSGSFYNAFDS

VL CDR1
(SEQ ID NO: 56):
RASQSISSWLA

VL CDR2
(SEQ ID NO: 57):
KASKLER

VL CDR3
(SEQ ID NO: 58):
LEYSSYIRT and wherein the anti-FX(a) arm comprises the following CDR-sequences:

VH CDR1
(SEQ ID NO: 572):
TSWIS

VH CDR2
(SEQ ID NO: 573):
MIDPSDSYTSYSPSFQG

VH CDR3
(SEQ ID NO: 574):
LHYYHSEEFDV

VL CDR1
(SEQ ID NO: 576):
RASQSVSSSYLA

VL CDR2
(SEQ ID NO: 577):
GQSSRTR

VL CDR3
(SEQ ID NO: 578):
QQYGDSQLFT

In one embodiment the bispecific antibody is bimAb05-4694 wherein the anti-FIX(a) arm comprises the following CDR-sequences:

VH CDR1
(SEQ ID NO: 52):
DYAMH

VH CDR2
(SEQ ID NO: 53):
GISWRGDIGGYVKSVKG

VH CDR3
(SEQ ID NO: 54):
SYGSGSFYNAFDS

VL CDR1
(SEQ ID NO: 56):
RASQSISSWLA

VL CDR2
(SEQ ID NO: 57):
KASKLER

VL CDR3
(SEQ ID NO: 58):
LEYSSYIRT and wherein the anti-FX(a) arm comprises the following CDR-sequences:

```
VH CDR1
(SEQ ID NO: 580):
TSWIS

VH CDR2
(SEQ ID NO: 581):
MIDPSDSYTSYSPSFQG

VH CDR3
(SEQ ID NO: 582):
LHYYHSEEFDV

VL CDR1
(SEQ ID NO: 584):
RASQSVSSSYLA

VL CDR2
(SEQ ID NO: 585):
GQSSRTR

VL CDR3
(SEQ ID NO: 586):
QQYGDSQLFT
```

In one embodiment the bispecific antibody is bimAb05-4695 wherein the anti-FIX(a) arm comprises the following CDR-sequences:

```
VH CDR1
(SEQ ID NO: 52):
DYAMH

VH CDR2
(SEQ ID NO: 53):
GISWRGDIGGYVKSVKG

VH CDR3
(SEQ ID NO: 54):
SYGSGSFYNAFDS

VL CDR1
(SEQ ID NO: 56):
RASQSISSWLA

VL CDR2
(SEQ ID NO: 57):
KASKLER

VL CDR3
(SEQ ID NO: 58):
LEYSSYIRT
``` and wherein the anti-FX(a) arm comprises the following CDR-sequences:

```
VH CDR1
(SEQ ID NO: 492):
TSWIS

VH CDR2
(SEQ ID NO: 493):
MIDPSDSFTSYSPSFQG

VH CDR3
(SEQ ID NO: 494):
LHYYNSEEFDV

VL CDR1
(SEQ ID NO: 496):
RASQSVSSSYLA

VL CDR2
(SEQ ID NO: 497):
GQSSRTR

VL CDR3
(SEQ ID NO: 498):
QQYGDSQLFT
```

In one embodiment the bispecific antibody is bimAb05-4696 wherein the anti-FIX(a) arm comprises the following CDR-sequences:

```
VH CDR1
(SEQ ID NO: 52):
DYAMH

VH CDR2
(SEQ ID NO: 53):
GISWRGDIGGYVKSVKG

VH CDR3
(SEQ ID NO: 54):
SYGSGSFYNAFDS

VL CDR1
(SEQ ID NO: 56):
RASQSISSWLA

VL CDR2
(SEQ ID NO: 57):
KASKLER

VL CDR3
(SEQ ID NO: 58):
LEYSSYIRT
``` and wherein the anti-FX(a) arm comprises the following CDR-sequences:

```
VH CDR1
(SEQ ID NO: 588):
TSWIV

VH CDR2
(SEQ ID NO: 589):
MIDPSDSYTSYSPSFQG

VH CDR3
(SEQ ID NO: 590):
LHYYNSEEFDV

VL CDR1
(SEQ ID NO: 592):
RASQSVSSSYLA

VL CDR2
(SEQ ID NO: 593):
GQSSRTR

VL CDR3
(SEQ ID NO: 594):
QQYGDSQLFT
```

In one embodiment the bispecific antibody is bimAb05-4697 wherein the anti-FIX(a) arm comprises the following CDR-sequences:

```
VH CDR1
(SEQ ID NO: 52):
DYAMH

VH CDR2
(SEQ ID NO: 53):
GISWRGDIGGYVKSVKG

VH CDR3
(SEQ ID NO: 54):
SYGSGSFYNAFDS
```

```
VL CDR1
(SEQ ID NO: 56):
RASQSISSWLA

VL CDR2
(SEQ ID NO: 57):
KASKLER

VL CDR3
(SEQ ID NO: 58):
LEYSSYIRT
``` and wherein the anti-FX(a) arm comprises the following CDR-sequences:

```
VH CDR1
(SEQ ID NO: 596):
TSWIV

VH CDR2
(SEQ ID NO: 597):
MIDPSDSFTSYSPSFQG

VH CDR3
(SEQ ID NO: 598):
LHYYNSEEFDV

VL CDR1
(SEQ ID NO: 600):
RASQSVSSSYLA

VL CDR2
(SEQ ID NO: 601):
GASSRAR

VL CDR3
(SEQ ID NO: 602):
QQYGDSRLFT
```

In one embodiment the bispecific antibody is bimAb05-4698 wherein the anti-FIX(a) arm comprises the following CDR-sequences:

```
VH CDR1
(SEQ ID NO: 52):
DYAMH

VH CDR2
(SEQ ID NO: 53):
GISWRGDIGGYVKSVKG

VH CDR3
(SEQ ID NO: 54):
SYGSGSFYNAFDS

VL CDR1
(SEQ ID NO: 56):
RASQSISSWLA

VL CDR2
(SEQ ID NO: 57):
KASKLER

VL CDR3
(SEQ ID NO: 58):
LEYSSYIRT
``` and wherein the anti-FX(a) arm comprises the following CDR-sequences:

```
VH CDR1 (SEQ ID NO: 604):
TSWIS

VH CDR2 (SEQ ID NO: 605):
MIDPSDSYTSYSPSFQG

VH CDR3 (SEQ ID NO: 606):
LHYYNSEEFDV

VL CDR1 (SEQ ID NO: 608):
RASQSVSSSYLA

VL CDR2 (SEQ ID NO: 609):
GASSRAR

VL CDR3 (SEQ ID NO: 610):
QQYGDSRLFT
```

In one embodiment the bispecific antibody is bimAb05-4699 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 612):
TSWIS

VH CDR2 (SEQ ID NO: 613):
MIDPSDSFTSYSPSFQG

VH CDR3 (SEQ ID NO: 614):
LHYYHSEEFDV

VL CDR1 (SEQ ID NO: 616):
RASQSVSSSYLA

VL CDR2 (SEQ ID NO: 617):
GASSRAR

VL CDR3 (SEQ ID NO: 618):
QQYGDSRLFT
```

In one embodiment the bispecific antibody is bimAb05-4700 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER
```

-continued
```
VL CDR3 (SEQ ID NO: 58):
LEYSSYIRT
``` and wherein the anti-FX(a) arm comprises the following CDR-sequences:

```
VH CDR1 (SEQ ID NO: 620):
TSWIS

VH CDR2 (SEQ ID NO: 621):
MIDPSDSYTSYSPSFQG

VH CDR3 (SEQ ID NO: 622):
LHYYHSEEFDV

VL CDR1 (SEQ ID NO: 624):
RASQSVSSSYLA

VL CDR2 (SEQ ID NO: 625):
GASSRAR

VL CDR3 (SEQ ID NO: 626):
QQYGDSRLFT
```

In one embodiment the bispecific antibody is bimAb05-4701 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 628):
TSWIS

VH CDR2 (SEQ ID NO: 629):
MIDPSDSYTSYSPSFQG

VH CDR3 (SEQ ID NO: 630):
LHYYHSEEFDV

VL CDR1 (SEQ ID NO: 632):
RASQSVSSSYLA

VL CDR2 (SEQ ID NO: 633):
GASSRAR

VL CDR3 (SEQ ID NO: 634):
QQYGDSRLFT
```

In one embodiment the bispecific antibody is bimAb05-4702 wherein the anti-FIX(a) arm comprises the following CDR-sequences:

```
VH CDR1 (SEQ ID NO: 52):
DYAMH
```

-continued
```
VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 636):
TSWIS

VH CDR2 (SEQ ID NO: 637):
MIDPSDSFTSYSPSFQG

VH CDR3 (SEQ ID NO: 638):
LHYYNSEEFDV

VL CDR1 (SEQ ID NO: 640):
RASQSVSSSYLA

VL CDR2 (SEQ ID NO: 641):
GASSRAR

VL CDR3 (SEQ ID NO: 642):
QQYGDSRLFT
```

In one embodiment the bispecific antibody is bimAb05-4703 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 644):
TSWIV

VH CDR2 (SEQ ID NO: 645):
MIDPSDSYTSYSPSFQG

VH CDR3 (SEQ ID NO: 646):
LHYYNSEEFDV

VL CDR1 (SEQ ID NO: 648):
RASQSVSSSYLA

VL CDR2 (SEQ ID NO: 649):
GASSRAR
```

```
VL CDR3 (SEQ ID NO: 650):
QQYGDSRLFT
```

In one embodiment the bispecific antibody is bimAb05-4704 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 652):
TSWIV

VH CDR2 (SEQ ID NO: 653):
MIDPSDSFTSYSPSFQG

VH CDR3 (SEQ ID NO: 654):
LHYYNSEEFDV

VL CDR1 (SEQ ID NO: 656):
RASQSVSSSYLA

VL CDR2 (SEQ ID NO: 657):
GQSSRTR

VL CDR3 (SEQ ID NO: 658):
QQFGDSRLFT
```

In one embodiment the bispecific antibody is bimAb05-4705 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 660):
TSWIS

VH CDR2 (SEQ ID NO: 661):
MIDPSDSYTSYSPSFQG

VH CDR3 (SEQ ID NO: 662):
LHYYNSEEFDV

VL CDR1 (SEQ ID NO: 664):
RASQSVSSSYLA

VL CDR2 (SEQ ID NO: 665):
GQSSRTR

VL CDR3 (SEQ ID NO: 666):
QQFGDSRLFT
```

In one embodiment the bispecific antibody is bimAb05-4706 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 668):
TSWIS

VH CDR2 (SEQ ID NO: 669):
MIDPSDSFTSYSPSFQG

VH CDR3 (SEQ ID NO: 670):
LHYYHSEEFDV

VL CDR1 (SEQ ID NO: 672):
RASQSVSSSYLA

VL CDR2 (SEQ ID NO: 673):
GQSSRTR

VL CDR3 (SEQ ID NO: 674):
QQFGDSRLFT
```

In one embodiment the bispecific antibody is bimAb05-4707 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS
```

```
VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 676):
TSWIS

VH CDR2 (SEQ ID NO: 677):
MIDPSDSYTSYSPSFQG

VH CDR3 (SEQ ID NO: 678):
LHYYHSEEFDV

VL CDR1 (SEQ ID NO: 680):
RASQSVSSSYLA

VL CDR2 (SEQ ID NO: 681):
GQSSRTR

VL CDR3 (SEQ ID NO: 682):
QQFGDSRLFT
```

In one embodiment the bispecific antibody is bimAb05-4708 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 684):
TSWIS

VH CDR2 (SEQ ID NO: 685):
MIDPSDSYTSYSPSFQG

VH CDR3 (SEQ ID NO: 686):
LHYYHSEEFDV

VL CDR1 (SEQ ID NO: 688):
RASQSVSSSYLA

VL CDR2 (SEQ ID NO: 689):
GQSSRTR

VL CDR3 (SEQ ID NO: 690):
QQFGDSRLFT
```

In one embodiment the bispecific antibody is bimAb05-4709 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 692):
TSWIS

VH CDR2 (SEQ ID NO: 693):
MIDPSDSFTSYSPSFQG

VH CDR3 (SEQ ID NO: 694):
LHYYNSEEFDV

VL CDR1 (SEQ ID NO: 696):
RASQSVSSSYLA

VL CDR2 (SEQ ID NO: 697):
GQSSRTR

VL CDR3 (SEQ ID NO: 698):
QQFGDSRLFT
```

In one embodiment the bispecific antibody is bimAb05-4710 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 700):
TSWIV

VH CDR2 (SEQ ID NO: 701):
MIDPSDSYTSYSPSFQG

VH CDR3 (SEQ ID NO: 702):
LHYYNSEEFDV

VL CDR1 (SEQ ID NO: 704):
RASQSVSSSYLA
```

-continued
```
VL CDR2 (SEQ ID NO: 705):
GQSSRTR

VL CDR3 (SEQ ID NO: 706):
QQFGDSRLFT
```

In one embodiment the bispecific antibody is bimAb05-4788 wherein the anti-FIX(a) arm comprises the following CDR-sequences:

```
VH CDR1 (SEQ ID NO: 308):
DYAMH

VH CDR2 (SEQ ID NO: 309):
GISWKGDIGGYVDSVKG

VH CDR3 (SEQ ID NO: 310):
SYGSGSFYNAFDS

VL CDR1 (SEQ ID NO: 312):
RASQSISSWLA

VL CDR2 (SEQ ID NO: 313):
KASRLDR

VL CDR3 (SEQ ID NO: 314):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4884 wherein the anti-FIX(a) arm comprises the following CDR-sequences:

```
VH CDR1 (SEQ ID NO: 316):
DYAMH

VH CDR2 (SEQ ID NO: 317):
GISWKGDIGGYVDSVKG

VH CDR3 (SEQ ID NO: 318):
SYGSGSFYNAFDS

VL CDR1 (SEQ ID NO: 320):
RASQSISSWLA

VL CDR2 (SEQ ID NO: 321):
KASRLDR

VL CDR3 (SEQ ID NO: 322):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4895 wherein the anti-FIX(a) arm comprises the following CDR-sequences:

```
VH CDR1 (SEQ ID NO: 340):
DYAMH

VH CDR2 (SEQ ID NO: 341):
GISWKGDIGGYVDSVKG

VH CDR3 (SEQ ID NO: 342):
SYGSGSFYNAFDS

VL CDR1 (SEQ ID NO: 344):
RASQSIQSWLA

VL CDR2 (SEQ ID NO: 345):
KASRLDR

VL CDR3 (SEQ ID NO: 346):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4896 wherein the anti-FIX(a) arm comprises the following CDR-sequences:

```
VH CDR1 (SEQ ID NO: 324):
DYAMH

VH CDR2 (SEQ ID NO: 325):
GISWKGDIGGYVDSVKG

VH CDR3 (SEQ ID NO: 326):
SYGSGSFYNAFDS
```

-continued

```
VL CDR1 (SEQ ID NO: 328):
RASQKISSWLA

VL CDR2 (SEQ ID NO: 329):
KASRLDR

VL CDR3 (SEQ ID NO: 330):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4898 wherein the anti-FIX(a) arm comprises the following CDR-sequences:

```
VH CDR1 (SEQ ID NO: 332):
DYAMH

VH CDR2 (SEQ ID NO: 333):
GISWKGDIGGYVDSVKG

VH CDR3 (SEQ ID NO: 334):
SYGSGSFYNAFDS

VL CDR1 (SEQ ID NO: 336):
RASQQISSWLA

VL CDR2 (SEQ ID NO: 337):
KASRLDR

VL CDR2 (SEQ ID NO: 338):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4903 wherein the anti-FIX(a) arm comprises the following CDR-sequences:

```
VH CDR1 (SEQ ID NO: 356):
DYAMH

VH CDR2 (SEQ ID NO: 357):
GISWKGDIGGYVDSVKG

VH CDR3 (SEQ ID NO: 358):
SYGSGSFYNAFDS

VL CDR1 (SEQ ID NO: 360):
RASQSISSWLA

VL CDR2 (SEQ ID NO: 361):
KASRLDR

VL CDR3 (SEQ ID NO: 362):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4906 wherein the anti-FIX(a) arm comprises the following CDR-sequences:

```
VH CDR1 (SEQ ID NO: 348):
DYAMH

VH CDR2 (SEQ ID NO: 349):
GISWKGDIGGYVDSVKG

VH CDR3 (SEQ ID NO: 350):
SYGSGSFYNAFDS

VL CDR1 (SEQ ID NO: 352):
RASQSISSWLA

VL CDR2 (SEQ ID NO: 353):
KASRLDK

VL CDR3 (SEQ ID NO: 354):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA
```

```
VL CDR2 (SEQ ID NO: 473):
GQSSRTR

VL CDR3 (SEQ ID NO: 474):
QQFGDSQLFT
```

In one embodiment the bispecific antibody is bimAb05-4910 wherein the anti-FIX(a) arm comprises the following CDR-sequences:

```
VH CDR1 (SEQ ID NO: 364):
DYAMH

VH CDR2 (SEQ ID NO: 365):
GISWKGDIGGYVDSVKG

VH CDR3 (SEQ ID NO: 366):
SYGSGSFYNAFDS

VL CDR1 (SEQ ID NO: 368):
RASQSISSWLA

VL CDR2 (SEQ ID NO: 369):
KASRLDR

VL CDR3 (SEQ ID NO: 370):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4914 wherein the anti-FIX(a) arm comprises the following CDR-sequences:

```
VH CDR1 (SEQ ID NO: 372):
DYAMH

VH CDR2 (SEQ ID NO: 373):
GISWKGDIGGYVDSVKG

VH CDR3 (SEQ ID NO: 374):
SYGSGSFYNAFDS

VL CDR1 (SEQ ID NO: 376):
RASQSISSWLA

VL CDR2 (SEQ ID NO: 377):
KASRLDR

VL CDR3 (SEQ ID NO: 378):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4915 wherein the anti-FIX(a) arm comprises the following CDR-sequences:

```
VH CDR1 (SEQ ID NO: 380):
DYAMH

VH CDR2 (SEQ ID NO: 381):
GISWKGDIGGYVDSVKG

VH CDR3 (SEQ ID NO: 382):
SYGSGSFYNAFDS

VL CDR1 (SEQ ID NO: 384):
RASQSISSWLA

VL CDR2 (SEQ ID NO: 385):
KASRLDR

VL CDR3 (SEQ ID NO: 386):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4919 wherein the anti-FIX(a) arm comprises the following CDR-sequences:

```
VH CDR1 (SEQ ID NO: 388):
DYAMH

VH CDR2 (SEQ ID NO: 389):
GISWKGDIGGYVDSVKG

VH CDR3 (SEQ ID NO: 390):
SYGSGSFYNAFDS
```

VL CDR1 (SEQ ID NO: 392):
RASQSISSWLA

VL CDR2 (SEQ ID NO: 393):
KASRLDR

VL CDR3 (SEQ ID NO: 394):
LEYQSYIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT

In one embodiment the bispecific antibody is bimAb05-4920 wherein the anti-FIX(a) arm comprises the following CDR-sequences:

VH CDR1 (SEQ ID NO: 404):
DYAMH

VH CDR2 (SEQ ID NO: 405):
GISWKGDIGGYVDSVKG

VH CDR3 (SEQ ID NO: 406):
SYGSGSFYNAFDS

VL CDR1 (SEQ ID NO: 408):
RASQSISSWLA

VL CDR2 (SEQ ID NO: 409):
KASRLDR

VL CDR3 (SEQ ID NO: 410):
LEYSSWIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT

In one embodiment the bispecific antibody is bimAb05-4921 wherein the anti-FIX(a) arm comprises the following CDR-sequences:

VH CDR1 (SEQ ID NO: 396):
DYAMH

VH CDR2 (SEQ ID NO: 397):
GISWKGDIGGYVDSVKG

VH CDR3 (SEQ ID NO: 398):
SYGSGSFYNAFDS

VL CDR1 (SEQ ID NO: 400):
RASQSISSWLA

VL CDR2 (SEQ ID NO: 401):
KASRLDR

VL CDR3 (SEQ ID NO: 402):
LEYKSYIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT

In one embodiment the bispecific antibody is bimAb05-4924 wherein the anti-FIX(a) arm comprises the following CDR-sequences:

VH CDR1 (SEQ ID NO: 420):
DYAMH

VH CDR2 (SEQ ID NO: 421):
GISWKGDIGGYVDSVKG

VH CDR3 (SEQ ID NO: 422):
SYGSGSFYNAFDS

VL CDR1 (SEQ ID NO: 424):
RASQSISSWLA

VL CDR2 (SEQ ID NO: 425):
KASRLDR

VL CDR3 (SEQ ID NO: 426):
LEYNSYIRT and wherein the anti-FX(a) arm comprises the following CDR-sequences:

VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

-continued
```
VL CDR2 (SEQ ID NO: 473):
GQSSRTR

VL CDR3 (SEQ ID NO: 474):
QQFGDSQLFT
```

In one embodiment the bispecific antibody is bimAb05-4927 wherein the anti-FIX(a) arm comprises the following CDR-sequences:

```
VH CDR1 (SEQ ID NO: 412):
DYAMH

VH CDR2 (SEQ ID NO: 413):
GISWKGDIGGYVDSVKG

VH CDR3 (SEQ ID NO: 414):
SYGSGSFYNAFDS

VL CDR1 (SEQ ID NO: 416):
RASQSISSWLA

VL CDR2 (SEQ ID NO: 417):
KASRLDR

VL CDR3 (SEQ ID NO: 418):
LEYRSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-5092 wherein the anti-FIX(a) arm comprises the following CDR-sequences:

```
VH CDR1 (SEQ ID NO: 428):
DYAMH

VH CDR2 (SEQ ID NO: 429):
GISWKGDIGGYVDSVKG

VH CDR3 (SEQ ID NO: 430):
SYGSGSFYNAFDS

VL CDR1 (SEQ ID NO: 432):
RASQSISSWLA

VL CDR2 (SEQ ID NO: 433):
KASKLDR

VL CDR3 (SEQ ID NO: 434):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-5095 wherein the anti-FIX(a) arm comprises the following CDR-sequences:

```
VH CDR1 (SEQ ID NO: 132):
DYAMH

VH CDR2 (SEQ ID NO: 133):
GISWKGDIGGYVDSVKG

VH CDR3 (SEQ ID NO: 134):
SYGSGSFYNAFDS

VL CDR1 (SEQ ID NO: 136):
RASQSISSWLA

VL CDR2 (SEQ ID NO: 137):
KASRLDR

VL CDR3 (SEQ ID NO: 138):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-5204 wherein the anti-FIX(a) arm comprises the following CDR-sequences:

```
VH CDR1 (SEQ ID NO: 436):
DYAMH

VH CDR2 (SEQ ID NO: 437):
GISWRGDIGGYVDSVKG
```

-continued

```
VH CDR3 (SEQ ID NO: 438):
SYGSGSFYNAFDS

VL CDR1 (SEQ ID NO: 440):
RASQSISSWLA

VL CDR2 (SEQ ID NO: 441):
KASKLDR

VL CDR3 (SEQ ID NO: 442):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-5205 wherein the anti-FIX(a) arm comprises the following CDR-sequences:

```
VH CDR1 (SEQ ID NO: 444):
DYAMH

VH CDR2 (SEQ ID NO: 445):
GISWRGDIGGYVDSVKG

VH CDR3 (SEQ ID NO: 446):
SYGSGSFYNAFDS

VL CDR1 (SEQ ID NO: 448):
RASQSISSWLA

VL CDR2 (SEQ ID NO: 449):
KASRLER

VL CDR3 (SEQ ID NO: 450):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb5-5240 wherein the anti-FIX(a) arm comprises the following CDR-sequences:

```
VH CDR1 (SEQ ID NO: 452):
DYAMH

VH CDR2 (SEQ ID NO: 453):
GISWKGDIGGYVDSVKG

VH CDR3 (SEQ ID NO: 454):
SYGSGSFYNAFDS

VL CDR1 (SEQ ID NO: 456):
RASQSISSWLA

VL CDR2 (SEQ ID NO: 457):
KASRLDR

VL CDR3 (SEQ ID NO: 458):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-5339 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 581:
LEYSSYIRT
``` and wherein the anti-FX(a) arm comprises the following CDR-sequences:

```
VH CDR1 (SEQ ID NO: 772):
TSWIS

VH CDR2 (SEQ ID NO: 773):
MIDPSDSFTSYSPSFQG
```

```
VH CDR3 (SEQ ID NO: 774):
LHYYHSEEFDV

VL CDR1 (SEQ ID NO: 776):
RASQSVSSSYLA

VL CDR2 (SEQ ID NO: 777):
GQSSRTR

VL CDR3 (SEQ ID NO: 778):
QQFGSSQLFT
```

In one embodiment the bispecific antibody is bimAb05-5340 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 708):
TSWIV

VH CDR2 (SEQ ID NO: 709):
MIDPSDSFTSYSPSFQG

VH CDR3 (SEQ ID NO: 710):
LHYYNSEEFDV

VL CDR1 (SEQ ID NO: 712):
RASQSVSSSYLA

VL CDR2 (SEQ ID NO: 713):
GQSSRTR

VL CDR3 (SEQ ID NO: 714):
QQFGSSQLFT
```

In one embodiment the bispecific antibody is bimAb05-5341 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 780):
TSWIS

VH CDR2 (SEQ ID NO: 781):
MIDPSDSYTSYSPSFQG

VH CDR3 (SEQ ID NO: 782):
LHYYHSEEFDV

VL CDR1 (SEQ ID NO: 784):
RASQSVSSSYLA

VL CDR2 (SEQ ID NO: 785):
GQSSRTR

VL CDR3 (SEQ ID NO: 786):
QQFGSSQLFT
```

In one embodiment the bispecific antibody is bimAb05-5342 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 764):
TSWIS

VH CDR2 (SEQ ID NO: 765):
MIDPSDSYTSYSPSFQG

VH CDR3 (SEQ ID NO: 766):
LHYYNSEEFDV

VL CDR1 (SEQ ID NO: 768):
RASQSVSSSYLA

VL CDR2 (SEQ ID NO: 769):
GQSSRTR

VL CDR3 (SEQ ID NO: 770):
QQFGSSQLFT
```

In one embodiment the bispecific antibody is bimAb05-5343 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 788):
TSWIS

VH CDR2 (SEQ ID NO: 789):
MIDPSDSYTSYSPSFQG

VH CDR3 (SEQ ID NO: 790):
LHYYHSEEFDV

VL CDR1 (SEQ ID NO: 792):
RASQSVSSSYLA

VL CDR2 (SEQ ID NO: 793):
GQSSRTR

VL CDR3 (SEQ ID NO: 794):
QQFGSSQLFT
```

In one embodiment the bispecific antibody is bimAb05-5344 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 796):
TSWIS

VH CDR2 (SEQ ID NO: 797):
MIDPSDSFTSYSPSFQG

VH CDR3 (SEQ ID NO: 798):
LHYYNSEEFDV

VL CDR1 (SEQ ID NO: 800):
RASQSVSSSYLA
```

-continued
```
VL CDR2 (SEQ ID NO: 801):
GQSSRTR

VL CDR3 (SEQ ID NO: 802):
QQFGSSQLFT
```

In one embodiment the bispecific antibody is bimAb05-5345 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 820):
TSWIS

VH CDR2 (SEQ ID NO: 821):
MIDPSDSYTSYSPSFQG

VH CDR3 (SEQ ID NO: 822):
LHYYNSEEFDV

VL CDR1 (SEQ ID NO: 824):
RASQSVSSSYLA

VL CDR2 (SEQ ID NO: 825):
GQSSRTR

VL CDR3 (SEQ ID NO: 826):
QQFGESQLFT
```

In one embodiment the bispecific antibody is bimAb05-5346 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

VH CDR1 (SEQ ID NO: 804):
TSWIV

VH CDR2 (SEQ ID NO: 805):
MIDPSDSYTSYSPSFQG

VH CDR3 (SEQ ID NO: 806):
LHYYNSEEFDV

VL CDR1 (SEQ ID NO: 808):
RASQSVSSSYLA

VL CDR2 (SEQ ID NO: 809):
GQSSRTR

VL CDR3 (SEQ ID NO: 810):
QQFGSSQLFT

In one embodiment the bispecific antibody is bimAb05-5347 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 828):
TSWIS

VH CDR2 (SEQ ID NO: 829):
MIDPSDSFTSYSPSFQG

VH CDR3 (SEQ ID NO: 830):
LHYYHSEEFDV

VL CDR1 (SEQ ID NO: 832):
RASQSVSSSYLA

VL CDR2 (SEQ ID NO: 833):
GQSSRTR

VL CDR3 (SEQ ID NO: 834):
QQFGESQLFT

In one embodiment the bispecific antibody is bimAb05-5348 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 812):
TSWIV

VH CDR2 (SEQ ID NO: 813):
MIDPSDSYTSYSPSFQG

VH CDR3 (SEQ ID NO: 814):
LHYYNSEEFDV

VL CDR1 (SEQ ID NO: 816):
RASQSVSSSYLA

VL CDR2 (SEQ ID NO: 817):
GQSSRTR

VL CDR3 (SEQ ID NO: 818):
QQFGSSQLFT

In one embodiment the bispecific antibody is bimAb05-5349 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 836):
TSWIS

VH CDR2 (SEQ ID NO: 837):
MIDPSDSYTSYSPSFQG

VH CDR3 (SEQ ID NO: 838):
LHYYHSEEFDV

VL CDR1 (SEQ ID NO: 840):
RASQSVSSSYLA

VL CDR2 (SEQ ID NO: 841):
GQSSRTR

VL CDR3 (SEQ ID NO: 842):
QQFGESQLFT

In one embodiment the bispecific antibody is bimAb05-5350 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 716):
TSWIV

VH CDR2 (SEQ ID NO: 717):
MIDPSDSFTSYSPSFQG

VH CDR3 (SEQ ID NO: 718):
LHYYNSEEFDV

VL CDR1 (SEQ ID NO: 720):
RASQSVSSSYLA

VL CDR2 (SEQ ID NO: 721):
GQSSRTR

VL CDR3 (SEQ ID NO: 722):
QQFGESQLFT
```

In one embodiment the bispecific antibody is bimAb05-5351 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 844):
TSWIS

VH CDR2 (SEQ ID NO: 845):
MIDPSDSYTSYSPSFQG

VH CDR3 (SEQ ID NO: 846):
LHYYHSEEFDV

VL CDR1 (SEQ ID NO: 848):
RASQSVSSSYLA

VL CDR2 (SEQ ID NO: 849):
GQSSRTR

VL CDR3 (SEQ ID NO: 850):
QQFGESQLFT
```

In one embodiment the bispecific antibody is bimAb05-5352 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 852):
TSWIS

VH CDR2 (SEQ ID NO: 853):
MIDPSDSFTSYSPSFQG

VH CDR3 (SEQ ID NO: 854):
LHYYNSEEFDV

VL CDR1 (SEQ ID NO: 856):
RASQSVSSSYLA

VL CDR2 (SEQ ID NO: 857):
GQSSRTR

VL CDR3 (SEQ ID NO: 858):
QQFGESQLFT
```

In one embodiment the bispecific antibody is bimAb05-5353 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

VH CDR1 (SEQ ID NO: 876):
TSWIS

VH CDR2 (SEQ ID NO: 877):
MIDPSDSYTSYSPSFQG

VH CDR3 (SEQ ID NO: 878):
LHYYNSEEFDV

VL CDR1 (SEQ ID NO: 880):
RASQSVSSSYLA

VL CDR2 (SEQ ID NO: 881):
GQSSRTR

VL CDR3 (SEQ ID NO: 882):
QQFGNSQLFT

In one embodiment the bispecific antibody is bimAb05-5354 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 860):
TSWIV

VH CDR2 (SEQ ID NO: 861):
MIDPSDSYTSYSPSFQG

VH CDR3 (SEQ ID NO: 862):
LHYYNSEEFDV

VL CDR1 (SEQ ID NO: 864):
RASQSVSSSYLA

VL CDR2 (SEQ ID NO: 865):
GQSSRTR

VL CDR3 (SEQ ID NO: 866):
QQFGESQLFT

In one embodiment the bispecific antibody is bimAb05-5355 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 884):
TSWIS

VH CDR2 (SEQ ID NO: 885):
MIDPSDSFTSYSPSFQG

VH CDR3 (SEQ ID NO: 886):
LHYYHSEEFDV

VL CDR1 (SEQ ID NO: 888):
RASQSVSSSYLA

VL CDR2 (SEQ ID NO: 889):
GQSSRTR

VL CDR3 (SEQ ID NO: 890):
QQFGNSQLFT

In one embodiment the bispecific antibody is bimAb05-5356 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 868):
TSWIV

VH CDR2 (SEQ ID NO: 869):
MIDPSDSYTSYSPSFQG

VH CDR3 (SEQ ID NO: 870):
LHYYNSEEFDV

VL CDR1 (SEQ ID NO: 872):
RASQSVSSSYLA

VL CDR2 (SEQ ID NO: 873):
GQSSRTR

VL CDR3 (SEQ ID NO: 874):
QQFGESQLFT

In one embodiment the bispecific antibody is bimAb05-5357 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 892):
TSWIS

VH CDR2 (SEQ ID NO: 893):
MIDPSDSYTSYSPSFQG

VH CDR3 (SEQ ID NO: 894):
LHYYHSEEFDV

VL CDR1 (SEQ ID NO: 896):
RASQSVSSSYLA

VL CDR2 (SEQ ID NO: 897):
GQSSRTR

VL CDR3 (SEQ ID NO: 898):
QQFGNSQLFT

In one embodiment the bispecific antibody is bimAb05-5358 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 724):
TSWIV

VH CDR2 (SEQ ID NO: 725):
MIDPSDSFTSYSPSFQG

VH CDR3 (SEQ ID NO: 726):
LHYYNSEEFDV

VL CDR1 (SEQ ID NO: 728):
RASQSVSSSYLA

VL CDR2 (SEQ ID NO: 729):
GQSSRTR

VL CDR3 (SEQ ID NO: 730):
QQFGNSQLFT

In one embodiment the bispecific antibody is bimAb05-5359 wherein the anti-FIX(a) arm comprises the following CDR-sequences:

VH CDR1 (SEQ ID NO: 52): DYAMH

VH CDR2 (SEQ ID NO: 53): GISWRGDIGGYVKSVKG

VH CDR3 (SEQ ID NO: 54): SYGSGSFYNAFDS

VL CDR1 (SEQ ID NO: 56): RASQSISSWLA

VL CDR2 (SEQ ID NO: 57): KASKLER

VL CDR3 (SEQ ID NO: 58): LEYSSYIRT and wherein the anti-FX(a) arm comprises the following CDR-sequences:

VH CDR1 (SEQ ID NO: 900): TSWIS

VH CDR2 (SEQ ID NO: 901): MIDPSDSYTSYSPSFQG

VH CDR3 (SEQ ID NO: 902): LHYYHSEEFDV

VL CDR1 (SEQ ID NO: 904): RASQSVSSSYLA

VL CDR2 (SEQ ID NO: 905): GQSSRTR

VL CDR3 (SEQ ID NO: 906): QQFGNSQLFT

In one embodiment the bispecific antibody is bimAb05-5361 wherein the anti-FIX(a) arm comprises the following CDR-sequences:

VH CDR1 (SEQ ID NO: 52): DYAMH

VH CDR2 (SEQ ID NO: 53): GISWRGDIGGYVKSVKG

VH CDR3 (SEQ ID NO: 54): SYGSGSFYNAFDS

VL CDR1 (SEQ ID NO: 56): RASQSISSWLA

VL CDR2 (SEQ ID NO: 57): KASKLER

VL CDR3 (SEQ ID NO: 58): LEYSSYIRT and wherein the anti-FX(a) arm comprises the following CDR-sequences:

VH CDR1 (SEQ ID NO: 924): TSWIV

VH CDR2 (SEQ ID NO: 925): MIDPSDSYTSYSPSFQG

VH CDR3 (SEQ ID NO: 926): LHYYNSEEFDV

VL CDR1 (SEQ ID NO: 928): RASQSVSSSYLA

VL CDR2 (SEQ ID NO: 929): GQSSRTR

VL CDR     (SEQ ID NO: 930): QQFGNSQLFT

In one embodiment the bispecific antibody is bimAb05-5362 wherein the anti-FIX(a) arm comprises the following CDR-sequences:

```
VH CDR1 (SEQ ID NO: 52): DYAMH
VH CDR2 (SEQ ID NO: 53): GISWRGDIGGYVKSVKG
VH CDR3 (SEQ ID NO: 54): SYGSGSFYNAFDS
VL CDR1 (SEQ ID NO: 56): RASQSISSWLA
VL CDR2 (SEQ ID NO: 57): KASKLER
VL CDR3 (SEQ ID NO: 58): LEYSSYIRT
``` and wherein the anti-FX(a) arm comprises the following CDR-sequences:

```
VH CDR1 (SEQ ID NO: 908): TSWIS
VH CDR2 (SEQ ID NO: 909): MIDPSDSFTSYSPSFQG
VH CDR3 (SEQ ID NO: 910): LHYYNSEEFDV
VL CDR1 (SEQ ID NO: 912): RASQSVSSSYLA
VL CDR2 (SEQ ID NO: 913): GQSSRTR
VL CDR3 (SEQ ID NO: 914): QQFGNSQLFT
```

In one embodiment the bispecific antibody is bimAb05-5363 wherein the anti-FIX(a) arm comprises the following CDR-sequences:

```
VH CDR1 (SEQ ID NO: 52): DYAMH
VH CDR2 (SEQ ID NO: 53): GISWRGDIGGYVKSVKG
VH CDR3 (SEQ ID NO: 54): SYGSGSFYNAFDS
VL CDR1 (SEQ ID NO: 56): RASQSISSWLA
VL CDR2 (SEQ ID NO: 57): KASKLER
VL CDR3 (SEQ ID NO: 58): LEYSSYIRT
``` and wherein the anti-FX(a) arm comprises the following CDR-sequences:

```
VH CDR1 (SEQ ID NO: 732): TSWIV
VH CDR2 (SEQ ID NO: 733): MIDPSDSFTSYSPSFQG
VH CDR3 (SEQ ID NO: 734): LHYYNSEEFDV
VL CDR1 (SEQ ID NO: 736): RASQSVSSSYLA
VL CDR2 (SEQ ID NO: 737): GQSSRTR
VL CDR3 (SEQ ID NO: 738): QQFGQSQLFT
```

In one embodiment the bispecific antibody is bimAb05-5364 wherein the anti-FIX(a) arm comprises the following CDR-sequences:

```
VH CDR1 (SEQ ID NO: 52): DYAMH
VH CDR2 (SEQ ID NO: 53): GISWRGDIGGYVKSVKG
VH CDR3 (SEQ ID NO: 54): SYGSGSFYNAFDS
VL CDR1 (SEQ ID NO: 56): RASQSISSWLA
VL CDR2 (SEQ ID NO: 57): KASKLER
VL CDR3 (SEQ ID NO: 58): LEYSSYIRT
``` and wherein the anti-FX(a) arm comprises the following CDR-sequences:

```
VH CDR1 (SEQ ID NO: 916): TSWIV
VH CDR2 (SEQ ID NO: 917): MIDPSDSYTSYSPSFQG
VH CDR3 (SEQ ID NO: 918): LHYYNSEEFDV
VL CDR1 (SEQ ID NO: 920): RASQSVSSSYLA
VL CDR2 (SEQ ID NO: 921): GQSSRTR
VL CDR3 (SEQ ID NO: 922): QQFGNSQLFT
```

In one embodiment the bispecific antibody is bimAb05-5365 wherein the anti-FIX(a) arm comprises the following CDR-sequences:

```
VH CDR1 (SEQ ID NO: 52): DYAMH
VH CDR2 (SEQ ID NO: 53): GISWRGDIGGYVKSVKG
VH CDR3 (SEQ ID NO: 54): SYGSGSFYNAFDS
VL CDR1 (SEQ ID NO: 56): RASQSISSWLA
VL CDR2 (SEQ ID NO: 57): KASKLER
VL CDR3 (SEQ ID NO: 58): LEYSSYIRT
``` and wherein the anti-FX(a) arm comprises the following CDR-sequences:

```
VH CDR1 (SEQ ID NO: 932): TSWIS
VH CDR2 (SEQ ID NO: 933): MIDPSDSYTSYSPSFQG
VH CDR3 (SEQ ID NO: 934): LHYYNSEEFDV
VL CDR1 (SEQ ID NO: 936): RASQSVSSSYLA
VL CDR2 (SEQ ID NO: 937): GQSSRTR
VL CDR3 (SEQ ID NO: 938): QQFGQSQLFT
```

In one embodiment the bispecific antibody is bimAb05-5366 wherein the anti-FIX(a) arm comprises the following CDR-sequences:

```
VH CDR1 (SEQ ID NO: 52): DYAMH
VH CDR2 (SEQ ID NO: 53): GISWRGDIGGYVKSVKG
VH CDR3 (SEQ ID NO: 54): SYGSGSFYNAFDS
VL CDR1 (SEQ ID NO: 56): RASQSISSWLA
VL CDR2 (SEQ ID NO: 57): KASKLER
VL CDR3 (SEQ ID NO: 58): LEYSSYIRT
``` and wherein the anti-FX(a) arm comprises the following CDR-sequences:

```
VH CDR1 (SEQ ID NO: 940): TSWIS
VH CDR2 (SEQ ID NO: 941): MIDPSDSFTSYSPSFQG
VH CDR3 (SEQ ID NO: 942): LHYYHSEEFDV
VL CDR1 (SEQ ID NO: 944): RASQSVSSSYLA
```

```
VL CDR2 (SEQ ID NO: 945): GQSSRTR

VL CDR3 (SEQ ID NO: 946): QQFGQSQLFT
```

In one embodiment the bispecific antibody is bimAb05-5367 wherein the anti-FIX(a) arm comprises the following CDR-sequences:

```
VH CDR1 (SEQ ID NO: 52): DYAMH

VH CDR2 (SEQ ID NO: 53): GISWRGDIGGYVKSVKG

VH CDR3 (SEQ ID NO: 54): SYGSGSFYNAFDS

VL CDR1 (SEQ ID NO: 56): RASQSISSWLA

VL CDR2 (SEQ ID NO: 57): KASKLER

VL CDR3 (SEQ ID NO: 58): LEYSSYIRT
``` and wherein the anti-FX(a) arm comprises the following CDR-sequences:

```
VH CDR1 (SEQ ID NO: 964):
TSWIV

VH CDR2 (SEQ ID NO: 965):
MIDPSDSYTSYSPSFQG

VH CDR3 (SEQ ID NO: 966):
LHYYNSEEFDV

VL CDR1 (SEQ ID NO: 968):
RASQSVSSSYLA

VL CDR2 (SEQ ID NO: 969):
GQSSRTR

VL CDR3 (SEQ ID NO: 970):
QQFGQSQLFT
```

In one embodiment the bispecific antibody is bimAb05-5369 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 972):
TSWIV

VH CDR2 (SEQ ID NO: 973):
MIDPSDSYTSYSPSFQG

VH CDR3 (SEQ ID NO: 974):
LHYYNSEEFDV

VL CDR1 (SEQ ID NO: 976):
RASQSVSSSYLA

VL CDR2 (SEQ ID NO: 977):
GQSSRTR

VL CDR3 (SEQ ID NO: 978):
QQFGQSQLFT
```

In one embodiment the bispecific antibody is bimAb05-5370 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 948):
TSWIS

VH CDR2 (SEQ ID NO: 949):
MIDPSDSYTSYSPSFQG

VH CDR3 (SEQ ID NO: 950):
LHYYHSEEFDV

VL CDR1 (SEQ ID NO: 952):
RASQSVSSSYLA

VL CDR2 (SEQ ID NO: 953):
GQSSRTR

VL CDR3 (SEQ ID NO: 954):
QQFGQSQLFT
```

In one embodiment the bispecific antibody is bimAb05-5371 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

VH CDR1 (SEQ ID NO: 740):
TSWIV

VH CDR2 (SEQ ID NO: 741):
MIDPSDSFTSYSPSFQG

VH CDR3 (SEQ ID NO: 742):
LHYYNSEEFDV

VL CDR1 (SEQ ID NO: 744):
RASQSVSSSYLA

VL CDR2 (SEQ ID NO: 745):
GQSSRTR

VL CDR3 (SEQ ID NO: 746):
QQFGDAQLFT

In one embodiment the bispecific antibody is bimAb05-5372 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 956):
TSWIS

VH CDR2 (SEQ ID NO: 957):
MIDPSDSFTSYSPSFQG

VH CDR3 (SEQ ID NO: 958):
LHYYNSEEFDV

VL CDR1 (SEQ ID NO: 960):
RASQSVSSSYLA

VL CDR2 (SEQ ID NO: 961):
GQSSRTR

VL CDR3 (SEQ ID NO: 962):
QQFGQSQLFT

In one embodiment the bispecific antibody is bimAb05-5373 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 980):
TSWIS

VH CDR2 (SEQ ID NO: 981):
MIDPSDSYTSYSPSFQG

VH CDR3 (SEQ ID NO: 982):
LHYYNSEEFDV

VL CDR1 (SEQ ID NO: 984):
RASQSVSSSYLA

VL CDR2 (SEQ ID NO: 985):
GQSSRTR

VL CDR3 (SEQ ID NO: 986):
QQFGDAQLFT

In one embodiment the bispecific antibody is bimAb05-5374 wherein the anti-FIX(a) arm comprises the following CDR-sequences:

VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT and wherein the anti-FX(a) arm comprises the following CDR-sequences:

VH CDR1 (SEQ ID NO: 988):
TSWIS

VH CDR2 (SEQ ID NO: 989):
MIDPSDSFTSYSPSFQG

VH CDR3 (SEQ ID NO: 990):
LHYYHSEEFDV

VL CDR1 (SEQ ID NO: 992):
RASQSVSSSYLA

VL CDR2 (SEQ ID NO: 993):
GQSSRTR

VL CDR3 (SEQ ID NO: 994):
QQFGDAQLFT

In one embodiment the bispecific antibody is bimAb05-5375 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1012):
TSWIV

VH CDR2 (SEQ ID NO: 1013):
MIDPSDSYTSYSPSFQG

VH CDR3 (SEQ ID NO: 1014):
LHYYNSEEFDV

VL CDR1 (SEQ ID NO: 1016):
RASQSVSSSYLA

VL CDR2 (SEQ ID NO: 1017):
GQSSRTR

VL CDR3 (SEQ ID NO: 1018):
QQFGDAQLFT
```

In one embodiment the bispecific antibody is bimAb05-5377 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1020):
TSWIV

VH CDR2 (SEQ ID NO: 1021):
MIDPSDSYTSYSPSFQG

VH CDR3 (SEQ ID NO: 1022):
LHYYNSEEFDV

VL CDR1 (SEQ ID NO: 1024):
RASQSVSSSYLA

VL CDR2 (SEQ ID NO: 1025):
GQSSRTR

VL CDR3 (SEQ ID NO: 1026):
QQFGDAQLFT
```

In one embodiment the bispecific antibody is bimAb05-5378 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 996):
TSWIS

VH CDR2 (SEQ ID NO: 997):
MIDPSDSYTSYSPSFQG

VH CDR3 (SEQ ID NO: 998):
LHYYHSEEFDV

VL CDR1 (SEQ ID NO: 1000):
RASQSVSSSYLA

VL CDR2 (SEQ ID NO: 1001):
GQSSRTR

VL CDR3 (SEQ ID NO: 1002):
QQFGDAQLFT
```

In one embodiment the bispecific antibody is bimAb05-5379 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 748):
TSWIV

VH CDR2 (SEQ ID NO: 749):
MIDPSDSFTSYSPSFQG

VH CDR3 (SEQ ID NO: 750):
LHYYNSEEFDV

VL CDR1 (SEQ ID NO: 752):
RASQSVSSSYLA

VL CDR2 (SEQ ID NO: 753):
GQSSRTR

VL CDR3 (SEQ ID NO: 754):
QQFGDTQLFT
```

In one embodiment the bispecific antibody is bimAb05-5380 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1004):
TSWIS

VH CDR2 (SEQ ID NO: 1005):
MIDPSDSFTSYSPSFQG

VH CDR3 (SEQ ID NO: 1006):
LHYYNSEEFDV

VL CDR1 (SEQ ID NO: 1008):
RASQSVSSSYLA

VL CDR2 (SEQ ID NO: 1009):
GQSSRTR

VL CDR3 (SEQ ID NO: 1010):
QQFGDAQLFT
```

In one embodiment the bispecific antibody is bimAb05-5381 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1028):
TSWIS

VH CDR2 (SEQ ID NO: 1029):
MIDPSDSYTSYSPSFQG

VH CDR3 (SEQ ID NO: 1030):
LHYYNSEEFDV

VL CDR1 (SEQ ID NO: 1032):
RASQSVSSSYLA

VL CDR2 (SEQ ID NO: 1033):
GQSSRTR

VL CDR3 (SEQ ID NO: 1034):
QQFGDTQLFT
```

In one embodiment the bispecific antibody is bimAb05-5383 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1052):
TSWIS

VH CDR2 (SEQ ID NO: 1053):
MIDPSDSYTSYSPSFQG

VH CDR3 (SEQ ID NO: 1054):
LHYYHSEEFDV

VL CDR1 (SEQ ID NO: 1056):
RASQSVSSSYLA

VL CDR2 (SEQ ID NO: 1057):
GQSSRTR

VL CDR3 (SEQ ID NO: 1058):
QQFGDTQLFT
```

In one embodiment the bispecific antibody is bimAb05-5384 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1036):
TSWIS

VH CDR2 (SEQ ID NO: 1037):
MIDPSDSFTSYSPSFQG

VH CDR3 (SEQ ID NO: 1038):
LHYYHSEEFDV

VL CDR1 (SEQ ID NO: 1040):
RASQSVSSSYLA

VL CDR2 (SEQ ID NO: 1041):
GQSSRTR

VL CDR3 (SEQ ID NO: 1042):
QQFGDTQLFT
```

In one embodiment the bispecific antibody is bimAb05-5385 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1060):
TSWIS

VH CDR2 (SEQ ID NO: 1061):
MIDPSDSFTSYSPSFQG

VH CDR3 (SEQ ID NO: 1062):
LHYYNSEEFDV

VL CDR1 (SEQ ID NO: 1064):
RASQSVSSSYLA

VL CDR2 (SEQ ID NO: 1065):
GQSSRTR

VL CDR3 (SEQ ID NO: 1066):
QQFGDTQLFT
```

In one embodiment the bispecific antibody is bimAb05-5386 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1044):
TSWIS

VH CDR2 (SEQ ID NO: 1045):
MIDPSDSYTSYSPSFQG

VH CDR3 (SEQ ID NO: 1046):
LHYYHSEEFDV

VL CDR1 (SEQ ID NO: 1048):
RASQSVSSSYLA

VL CDR2 (SEQ ID NO: 1049):
GQSSRTR

VL CDR3 (SEQ ID NO: 1050):
QQFGDTQLFT
```

In one embodiment the bispecific antibody is bimAb05-5387 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1068):
TSWIV

VH CDR2 (SEQ ID NO: 1069):
MIDPSDSYTSYSPSFQG

VH CDR3 (SEQ ID NO: 1070):
LHYYNSEEFDV

VL CDR1 (SEQ ID NO: 1072):
RASQSVSSSYLA

VL CDR2 (SEQ ID NO: 1073):
GQSSRTR

VL CDR3 (SEQ ID NO: 1074):
QQFGDTQLFT
```

In one embodiment the bispecific antibody is bimAb05-5388 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1076):
TSWIV

VH CDR2 (SEQ ID NO: 1077):
MIDPSDSYTSYSPSFQG

VH CDR3 (SEQ ID NO: 1078):
LHYYNSEEFDV

VL CDR1 (SEQ ID NO: 1080):
RASQSVSSSYLA

VL CDR2 (SEQ ID NO: 1081):
GQSSRTR

VL CDR3 (SEQ ID NO: 1082):
QQFGDTQLFT
```

In one embodiment the bispecific antibody is bimAb05-5389 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1100):
TSWIS

VH CDR2 (SEQ ID NO: 1101):
MIDPSDSYTSYSPSFQG

VH CDR3 (SEQ ID NO: 1102):
LHYYHSEEFDV

VL CDR1 (SEQ ID NO: 1104):
RASQSVSSSYLA

VL CDR2 (SEQ ID NO: 1105):
GQSSRTR

VL CDR3 (SEQ ID NO: 1106):
QQFGDNQLFT
```

In one embodiment the bispecific antibody is bimAb05-5390 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 756):
TSWIV

VH CDR2 (SEQ ID NO: 757):
MIDPSDSFTSYSPSFQG

VH CDR3 (SEQ ID NO: 758):
LHYYNSEEFDV

VL CDR1 (SEQ ID NO: 760):
RASQSVSSSYLA

VL CDR2 (SEQ ID NO: 761):
GQSSRTR

VL CDR3 (SEQ ID NO: 762):
QQFGDNQLFT
```

In one embodiment the bispecific antibody is bimAb05-5391 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1108):
TSWIS

VH CDR2 (SEQ ID NO: 1109):
MIDPSDSYTSYSPSFQG

VH CDR3 (SEQ ID NO: 1110):
LHYYHSEEFDV

VL CDR1 (SEQ ID NO: 1112):
RASQSVSSSYLA

VL CDR2 (SEQ ID NO: 1113):
GQSSRTR

VL CDR3 (SEQ ID NO: 1114):
QQFGDNQLFT
```

In one embodiment the bispecific antibody is bimAb05-5392 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1084):
TSWIS

VH CDR2 (SEQ ID NO: 1085):
MIDPSDSYTSYSPSFQG

VH CDR3 (SEQ ID NO: 1086):
LHYYNSEEFDV

VL CDR1 (SEQ ID NO: 1088):
RASQSVSSSYLA

VL CDR2 (SEQ ID NO: 1089):
GQSSRTR

VL CDR3 (SEQ ID NO: 1090):
QQFGDNQLFT
```

In one embodiment the bispecific antibody is bimAb05-5393 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1116):
TSWIS

VH CDR2 (SEQ ID NO: 1117):
MIDPSDSFTSYSPSFQG

VH CDR3 (SEQ ID NO: 1118):
LHYYNSEEFDV

VL CDR1 (SEQ ID NO: 1120):
RASQSVSSSYLA

VL CDR2 (SEQ ID NO: 1121):
GQSSRTR

VL CDR3 (SEQ ID NO: 1122):
QQFGDNQLFT
```

In one embodiment the bispecific antibody is bimAb05-5394 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1092):
TSWIS

VH CDR2 (SEQ ID NO: 1093):
MIDPSDSFTSYSPSFQG

VH CDR3 (SEQ ID NO: 1094):
LHYYHSEEFDV

VL CDR1 (SEQ ID NO: 1096):
RASQSVSSSYLA

VL CDR2 (SEQ ID NO: 1097):
GQSSRTR

VL CDR3 (SEQ ID NO: 1098):
QQFGDNQLFT
```

In one embodiment the bispecific antibody is bimAb05-5395 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1124):
TSWIV

VH CDR2 (SEQ ID NO: 1125):
MIDPSDSYTSYSPSFQG

VH CDR3 (SEQ ID NO: 1126):
LHYYNSEEFDV

VL CDR1 (SEQ ID NO: 1128):
RASQSVSSSYLA

VL CDR2 (SEQ ID NO: 1129):
GQSSRTR

VL CDR3 (SEQ ID NO: 1130):
QQFGDNQLFT
```

In one embodiment the bispecific antibody is bimAb05-5396 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1132):
TSWIV

VH CDR2 (SEQ ID NO: 1133):
MIDPSDSYTSYSPSFQG

VH CDR3 (SEQ ID NO: 1134):
LHYYNSEEFDV

VL CDR1 (SEQ ID NO: 1136):
RASQSVSSSYLA

VL CDR2 (SEQ ID NO: 1137):
GQSSRTR

VL CDR3 (SEQ ID NO: 1138):
QQFGDNQLFT
```

In one embodiment the bispecific antibody is bimAb05-5397 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1156):
TSWIS

VH CDR2 (SEQ ID NO: 1157):
MIDPSDSYTSYSPSFQG

VH CDR3 (SEQ ID NO: 1158):
LHYYHSEEFDV

VL CDR1 (SEQ ID NO: 1160):
RASQSVSSSYLA

VL CDR2 (SEQ ID NO: 1161):
GQSSRTR

VL CDR3 (SEQ ID NO: 1162):
QQFGDDQLFT
```

In one embodiment the bispecific antibody is bimAb05-5399 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1164):
TSWIS

VH CDR2 (SEQ ID NO: 1165):
MIDPSDSYTSYSPSFQG

VH CDR3 (SEQ ID NO: 1166):
LHYYHSEEFDV

VL CDR1 (SEQ ID NO: 1168):
RASQSVSSSYLA

VL CDR2 (SEQ ID NO: 1169):
GQSSRTR

VL CDR3 (SEQ ID NO: 1170):
QQFGDDQLFT
```

In one embodiment the bispecific antibody is bimAb05-5400 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1140):
TSWIS

VH CDR2 (SEQ ID NO: 1141):
MIDPSDSYTSYSPSFQG

VH CDR3 (SEQ ID NO: 1142):
LHYYNSEEFDV

VL CDR1 (SEQ ID NO: 1144):
RASQSVSSSYLA

VL CDR2 (SEQ ID NO: 1145):
GQSSRTR

VL CDR3 (SEQ ID NO: 1146):
QQFGDDQLFT
```

In one embodiment the bispecific antibody is bimAb05-5401 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1172):
TSWIS

VH CDR2 (SEQ ID NO: 1173):
MIDPSDSFTSYSPSFQG

VH CDR3 (SEQ ID NO: 1174):
LHYYNSEEFDV

VL CDR1 (SEQ ID NO: 1176):
RASQSVSSSYLA

VL CDR2 (SEQ ID NO: 1177):
GQSSRTR

VL CDR3 (SEQ ID NO: 1178):
QQFGDDQLFT
```

In one embodiment the bispecific antibody is bimAb05-5402 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1148):
TSWIS

VH CDR2 (SEQ ID NO: 1149):
MIDPSDSFTSYSPSFQG

VH CDR3 (SEQ ID NO: 1150):
LHYYHSEEFDV

VL CDR1 (SEQ ID NO: 1152):
RASQSVSSSYLA

VL CDR2 (SEQ ID NO: 1153):
GQSSRTR

VL CDR3 (SEQ ID NO: 1154):
QQFGDDQLFT
```

In one embodiment the bispecific antibody is bimAb05-5403 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1180):
TSWIV

VH CDR2 (SEQ ID NO: 1181):
MIDPSDSYTSYSPSFQG

VH CDR3 (SEQ ID NO: 1182):
LHYYNSEEFDV

VL CDR1 (SEQ ID NO: 1184):
RASQSVSSSYLA

VL CDR2 (SEQ ID NO: 1185):
GQSSRTR

VL CDR3 (SEQ ID NO: 1186):
QQFGDDQLFT
```

In one embodiment the bispecific antibody is bimAb05-5406 wherein the anti-FIX(a) arm comprises the following CDR sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 1188):
TSWIV

VH CDR2 (SEQ ID NO: 1189):
MIDPSDSYTSYSPSFQG

VH CDR3 (SEQ ID NO: 1190):
LHYYNSEEFDV

VL CDR1 (SEQ ID NO: 1192):
RASQSVSSSYLA

VL CDR2 (SEQ ID NO: 1193):
GQSSRTR

VL CDR3 (SEQ ID NO: 1194):
QQFGDDQLFT
```

In one embodiment the bispecific antibody is bimAb05-5413 wherein the anti-FIX(a) arm comprises the following CDR-sequences:

```
VH CDR1 (SEQ ID NO: 52):
DYAMH

VH CDR2 (SEQ ID NO: 53):
GISWRGDIGGYVKSVKG

VH CDR3 (SEQ ID NO: 54):
SYGSGSFYNAFDS

VL CDR1 (SEQ ID NO: 56):
RASQSISSWLA

VL CDR2 (SEQ ID NO: 57):
KASKLER

VL CDR3 (SEQ ID NO: 58):
LEYSSYIRT
``` and wherein the anti-FX(a) arm comprises the following CDR-sequences:

```
VH CDR1 (SEQ ID NO: 548):
TSWIV

VH CDR2 (SEQ ID NO: 549):
MIDPSDSYTSYSPSFQG

VH CDR3 (SEQ ID NO: 550):
LHYYNSEEFDV

VL CDR1 (SEQ ID NO: 552):
RASQSVSSSYLA

VL CDR2 (SEQ ID NO: 553):
GQSSRTR

VL CDR3 (SEQ ID NO: 554):
QQFGDSQLFT
```

In one embodiment the bispecific antibody is bimAb05-4271 wherein the anti-FIX(a) arm comprises the following CDR-sequences:

```
VH CDR1 (SEQ ID NO: 1203):
DYAMH

VH CDR2 (SEQ ID NO: 1204):
GISWKGDIGGYVDSVKG

VH CDR3 (SEQ ID NO: 1205):
SYGSGSFYNAFDS

VL CDR1 (SEQ ID NO: 1207):
RASQSISSWLA

VL CDR2 (SEQ ID NO: 1208):
KASKLDR

VL CDR3 (SEQ ID NO: 1209):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-4756 wherein the anti-FIX(a) arm comprises the following CDR-sequences:

```
VH CDR1 (SEQ ID NO: 1211):
DYAMH

VH CDR2 (SEQ ID NO: 1212):
GISWRGDIGGYVKSVKG

VH CDR3 (SEQ ID NO: 1213):
SYGSGSFYNAFDS

VL CDR1 (SEQ ID NO: 1215):
RASQSISSWLA

VL CDR2 (SEQ ID NO: 1216):
KASKLER

VL CDR3 (SEQ ID NO: 1217):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-0396 wherein the anti-FIX(a) arm comprises the following CDR-sequences:

```
VH CDR1 (SEQ ID NO: 1219):
DYAMH

VH CDR2 (SEQ ID NO: 1220):
GISWRGDIGGYAKSVKG

VH CDR3 (SEQ ID NO: 1221):
SYGSGSFYNAFDS

VL CDR1 (SEQ ID NO: 1223):
RASQSISSWLA

VL CDR2 (SEQ ID NO: 1224):
KASKLDR

VL CDR3 (SEQ ID NO: 1225):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 4741:
QQFGDSQLFT
```

In one embodiment the bispecific antibody is bimAb05-0417 wherein the anti-FIX(a) arm comprises the following CDR-sequences:

```
VH CDR1 (SEQ ID NO: 1227):
DYAMH

VH CDR2 (SEQ ID NO: 1228):
GISWRGDIGGYVKSVKG

VH CDR3 (SEQ ID NO: 1229):
SYGSGSFYNAFDS

VL CDR1 (SEQ ID NO: 1231):
RASQSISSWLA

VL CDR2 (SEQ ID NO: 1232):
KASKLDR

VL CDR3 (SEQ ID NO: 1233):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody is bimAb05-0438 wherein the anti-FIX(a) arm comprises the following CDR-sequences:

```
VH CDR1 (SEQ ID NO: 1235):
DYAMH

VH CDR2 (SEQ ID NO: 1236):
GISWRGDIGGYVKSVKG

VH CDR3 (SEQ ID NO: 1237):
SYGSGSFYNAFDS

VL CDR1 (SEQ ID NO: 1239):
RASQSISSWLA

VL CDR2 (SEQ ID NO: 1240):
KASKLDR

VL CDR3 (SEQ ID NO: 1241):
LEYSSYIRT
``` and wherein the anti-FX(a) arm comprises the following CDR-sequences:

```
VH CDR1 (SEQ ID NO: 468):
TSWIV

VH CDR2 (SEQ ID NO: 469):
MIDPSDSFTSYSPSFQG

VH CDR3 (SEQ ID NO: 470):
LHYYNSEEFDV

VL CDR1 (SEQ ID NO: 472):
RASQSVSSSYLA

VL CDR2 (SEQ ID NO: 473):
GQSSRTR

VL CDR3 (SEQ ID NO: 474):
QQFGDSQLFT
```

In one embodiment the bispecific antibody comprises anti-FIX(a) arm VH and VL domains corresponding to SEQ ID NO:67 and SEQ ID NO:71, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:43 and SEQ ID NO:47, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:3 and SEQ ID NO:7, respectively, and anti-FX(a) arm VH and VL domains corresponding to SEQ ID NO:459 and SEQ ID NO:463, respectively.

In one embodiment the bispecific antibody comprises anti-FIX(a) arm VH and VL domains corresponding to SEQ ID NO:67 and SEQ ID NO:71, respectively, and anti-FX(a) arm VH and VL domains corresponding to SEQ ID NO:483 and SEQ ID NO:487, respectively.

In one embodiment the bispecific antibody comprises anti-FIX(a) arm VH and VL domains corresponding to SEQ ID NO:35 and SEQ ID NO:39, respectively, and anti-FX(a) arm VH and VL domains corresponding to SEQ ID NO:483 and SEQ ID NO:487, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:483 and SEQ ID NO:487, respectively.

In one embodiment the bispecific antibody comprises anti-FIX(a) arm VH and VL domains corresponding to SEQ ID NO:43 and SEQ ID NO:47, respectively, and anti-FX(a) arm VH and VL domains corresponding to SEQ ID NO:483 and SEQ ID NO:487, respectively.

In one embodiment the bispecific antibody comprises anti-FIX(a) arm VH and VL domains corresponding to SEQ ID NO:3 and SEQ ID NO:7, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:3 and SEQ ID NO:7, respectively, and anti-FX(a) arm VH and VL domains corresponding to SEQ ID NO:475 and SEQ ID NO:479, respectively.

In one embodiment the bispecific antibody comprises anti-FIX(a) arm VH and VL domains corresponding to SEQ ID NO:11 and SEQ ID NO:15, respectively, and anti-FX(a) arm VH and VL domains corresponding to SEQ ID NO:459 and SEQ ID NO:463, respectively.

In one embodiment the bispecific antibody comprises anti-FIX(a) arm VH and VL domains corresponding to SEQ ID NO:35 and SEQ ID NO:39, respectively, and anti-FX(a) arm VH and VL domains corresponding to SEQ ID NO:459 and SEQ ID NO:463, respectively.

In one embodiment the bispecific antibody comprises anti-FIX(a) arm VH and VL domains corresponding to SEQ ID NO:43 and SEQ ID NO:47, respectively, and anti-FX(a) arm VH and VL domains corresponding to SEQ ID NO:459 and SEQ ID NO:463, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:459 and SEQ ID NO:463, respectively.

In one embodiment the bispecific antibody comprises anti-FIX(a) arm VH and VL domains corresponding to SEQ ID NO:67 and SEQ ID NO:71, respectively, and anti-FX(a) arm VH and VL domains corresponding to SEQ ID NO:459 and SEQ ID NO:463, respectively.

In one embodiment the bispecific antibody comprises anti-FIX(a) arm VH and VL domains corresponding to SEQ ID NO:35 and SEQ ID NO:39, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:59 and SEQ ID NO:63, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:19 and SEQ ID NO:23, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:27 and SEQ ID NO:31, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:75 and SEQ ID NO:79, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:83 and SEQ ID NO:87, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:91 and SEQ ID NO:95, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:99 and SEQ ID NO:103, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:107 and SEQ ID NO:111, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:115 and SEQ ID NO:119, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:211 and SEQ ID NO:215, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:219 and SEQ ID NO:223, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:227 and SEQ ID NO:231, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:235 and SEQ ID NO:239, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:251 and SEQ ID NO:255, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:243 and SEQ ID NO:247, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:259 and SEQ ID NO:263, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:267 and SEQ ID NO:271, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:123 and SEQ ID NO:127, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:275 and SEQ ID NO:279, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:283 and SEQ ID NO:287, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:299 and SEQ ID NO:303, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:291 and SEQ ID NO:295, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:187 and SEQ ID NO:191, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:139 and SEQ ID NO:143, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:203 and SEQ ID NO:207, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:179 and SEQ ID NO:183, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:195 and SEQ ID NO:199, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:171 and SEQ ID NO:175, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:163 and SEQ ID NO:167, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:147 and SEQ ID NO:151, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:155 and SEQ ID NO:159, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:499 and SEQ ID NO:503, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:507 and SEQ ID NO:511, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:515 and SEQ ID NO:519, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:523 and SEQ ID NO:527, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:531 and SEQ ID NO:535, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:539 and SEQ ID NO:543, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:555 and SEQ ID NO:559, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:563 and SEQ ID NO:567, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:571 and SEQ ID NO:575, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:579 and SEQ ID NO:583, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:491 and SEQ ID NO:495, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:587 and SEQ ID NO:591, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:595 and SEQ ID NO:599, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:603 and SEQ ID NO:607, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:611 and SEQ ID NO:615, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:619 and SEQ ID NO:623, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:627 and SEQ ID NO:631, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:635 and SEQ ID NO:639, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:643 and SEQ ID NO:647, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:651 and SEQ ID NO:655, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:659 and SEQ ID NO:663, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:667 and SEQ ID NO:671, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:675 and SEQ ID NO:679, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:683 and SEQ ID NO:687, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:691 and SEQ ID NO:695, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:699 and SEQ ID NO:703, respectively.

In one embodiment the bispecific antibody comprises anti-FIX(a) arm VH and VL domains corresponding to SEQ ID NO:307 and SEQ ID NO:311, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:315 and SEQ ID NO:319, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:339 and SEQ ID NO:343, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:323 and SEQ ID NO:327, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:331 and SEQ ID NO:335, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:355 and SEQ ID NO:359, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:347 and SEQ ID NO:351, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:363 and SEQ ID NO:367, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:371 and SEQ ID NO:375, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:379 and SEQ ID NO:383, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:387 and SEQ ID NO:391, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:403 and SEQ ID NO:407, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:395 and SEQ ID NO:399, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:419 and SEQ ID NO:423, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:411 and SEQ ID NO:415, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:427 and SEQ ID NO:431, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:131 and SEQ ID NO:135, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:435 and SEQ ID NO:439, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:443 and SEQ ID NO:447, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:451 and SEQ ID NO:455, respectively, and
anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:771 and SEQ ID NO:775, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:707 and SEQ ID NO:711, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:779 and SEQ ID NO:783, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:763 and SEQ ID NO:767, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:787 and SEQ ID NO:791, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:795 and SEQ ID NO:799, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:819 and SEQ ID NO:823, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:803 and SEQ ID NO:807, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:827 and SEQ ID NO:831, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:811 and SEQ ID NO:815, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:835 and SEQ ID NO:839, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:715 and SEQ ID NO:719, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:843 and SEQ ID NO:847, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:851 and SEQ ID NO:855, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:875 and SEQ ID NO:879, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:859 and SEQ ID NO:863, respectively. In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:883 and SEQ ID NO:887, respectively. In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:867 and SEQ ID NO:871, respectively. In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:891 and SEQ ID NO:895, respectively. In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:723 and SEQ ID NO:727, respectively. In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:899 and SEQ ID NO:903, respectively. In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:923 and SEQ ID NO:927, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:907 and SEQ ID NO:911, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:731 and SEQ ID NO:735, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:915 and SEQ ID NO:919, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:931 and SEQ ID NO:935, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:939 and SEQ ID NO:943, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:963 and SEQ ID NO:967, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:971 and SEQ ID NO:975, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:947 and SEQ ID NO:951, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:739 and SEQ ID NO:743, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:955 and SEQ ID NO:959, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:979 and SEQ ID NO:983, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:987 and SEQ ID NO:991, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1011 and SEQ ID NO:1015, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1019 and SEQ ID NO:1023, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:995 and SEQ ID NO:999, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:747 and SEQ ID NO:751, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1003 and SEQ ID NO:1007, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1027 and SEQ ID NO:1031, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1051 and SEQ ID NO:1055, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1035 and SEQ ID NO:1039, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1059 and SEQ ID NO:1063, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1043 and SEQ ID NO:1047, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1067 and SEQ ID NO:1071, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1075 and SEQ ID NO:1079, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1099 and SEQ ID NO:1103, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:755 and SEQ ID NO:759, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1107 and SEQ ID NO:1111, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1083 and SEQ ID NO:1087, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1115 and SEQ ID NO:1119, respectively.

In one embodiment the bispecific antibody comprises anti-FIX(a) arm VH and VL domains corresponding to SEQ ID NO:51 and SEQ ID NO:55, respectively, and
anti-FX(a) arm VH and VL domains corresponding to SEQ ID NO:1091 and SEQ ID NO:1095, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1123 and SEQ ID NO:1127, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1131 and SEQ ID NO:1135, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1155 and SEQ ID NO:1159, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1163 and SEQ ID NO:1167, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1139 and SEQ ID NO:1143, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1171 and SEQ ID NO:1175, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1147 and SEQ ID NO:1151, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1179 and SEQ ID NO:1183, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:1187 and SEQ ID NO:1191, respectively.

In one embodiment the bispecific antibody comprises anti-FIX(a) arm VH and VL domains corresponding to SEQ ID NO:51 and SEQ ID NO:55, respectively, and anti-FX(a) arm VH and VL domains corresponding to SEQ ID NO:547 and SEQ ID NO:551, respectively.

In one embodiment the bispecific antibody comprises anti-FIX(a) arm VH and VL domains corresponding to SEQ ID NO:1202 and SEQ ID NO:1206, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:1210 and SEQ ID NO:1214, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:1218 and SEQ ID NO:1222, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:1226 and SEQ ID NO:1230, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:1234 and SEQ ID NO:1238, respectively, and anti-FX(a) arm VH and VL domains corresponding to SEQ ID NO:467 and SEQ ID NO:471, respectively.

In one embodiment the bispecific antibody comprises anti-FIX(a) arm VH and VL domains corresponding to SEQ ID NO:1242 and SEQ ID NO:1246, respectively, and anti-FX(a) arm VH and VL domains corresponding to SEQ ID NO:467 and SEQ ID NO:471, respectively.

In one embodiment the paratope of an anti-FIX(a) antibody or antigen-binding fragment thereof of the invention comprises amino acid residues H30, D31, W53, D56, S102, S104, Y106 and N107 in the heavy chain variable domain (SEQ ID NO:67) and residues Y91 and S92 in the light chain variable domain (SEQ ID NO:71).

In one embodiment an anti-FIX(a) antibody or antigen-binding fragment thereof of the invention comprises one, two or three amino acid substitutions or deletions within the group of paratope amino acid residues H30, D31, W53, D56, S102, S104, Y106 and N107 in the heavy chain variable domain (SEQ ID NO:67) and residues Y91 and S92 in the light chain variable domain (SEQ ID NO:71).

In another embodiment the paratope of an anti-FIX(a) antibody or antigen-binding fragment thereof of the invention comprises amino acid residues D30, D31, W53, S102, S104 and N107 in the heavy chain variable domain (SEQ ID NO:35) and residues Y91 and S92 in the light chain variable domain (SEQ ID NO:39).

In another embodiment an anti-FIX(a) antibody of the invention comprises one, two or three amino acid substitutions or deletions within the group of paratope amino acid residues: D30, D31, W53, S102, S104 and N107 in the heavy chain variable domain (SEQ ID NO:35) and residues Y91 and S92 in the light chain variable domain (SEQ ID NO:39).

In one embodiment the CDR sequences of an antibody or antigen-binding fragment thereof of the invention may be described by anti-FIX(a) paratope amino acid residues being part of the CDRs.

In one such embodiment the anti-FIX(a) paratope CDRs are

VH CDR1 (based on SEQ ID NO: 68):
DXXXX

VH CDR2 (based on SEQ ID NO: 69):
XXXWXXDXXXXXXXXXX

VH CDR3 (based on SEQ ID NO: 70):
XXXSXSXYNXXXX

VL CDR1 (based on SEQ ID NO: 72):
XXXXXXXXXXX

VL CDR2 (based on SEQ ID NO: 73):
XXXXXXX

VL CDR3 (based on SEQ ID NO: 74):
XXYSXXXXX wherein paratope amino acid residues are in bold, and X represents a naturally occurring amino acid residue.

In another such embodiment the anti-FIX(a) paratope CDRs are

```
VH CDR1 (based on SEQ ID NO: 36):
DXXXX

VH CDR2 (based on SEQ ID NO: 37):
XXXWXXXXXXXXXXXX

VH CDR3 (based on SEQ ID NO: 38):
XXXSXSXXNXXXX

VL CDR1 (based on SEQ ID NO: 40):
XXXXXXXXXXX

VL CDR2 (based on SEQ ID NO: 41):
XXXXXXX

VL CDR3 (based on SEQ ID NO: 42):
XXYSXXXXX
``` wherein paratope amino acid residues are in bold, and X represents a naturally occurring amino acid residue.

In another such embodiment the anti-FIX(a) paratope CDRs are

```
VH CDR1 (based on SEQ ID NO: 52):
DXXXX

VH CDR2 (based on SEQ ID NO: 53):
XXXWXXXXXXXXXXXX

VH CDR3 (based on SEQ ID NO: 54):
XXXSXSXYNXXXX

VL CDR1 (based on SEQ ID NO: 56):
XXXXXXXXXXX

VL CDR2 (based on SEQ ID NO: 57):
XXXXXXX

VL CDR3 (based on SEQ ID NO: 58):
XXYSXXXXX
``` wherein paratope amino acid residues are in bold, and X represents a naturally occurring amino acid residue.

In one embodiment the paratope of an anti-FX(a) antibody of the invention comprises residues K23, S25, G26, Y27, F29, W33, D52, S54, D55, F57, S77, H100, Y101, Y102, N103 and S104 in the heavy chain variable domain (SEQ ID NO:467) and residues V29, S30, S31, Y33, Y50, Q52, S54, R55, R57 and D94 in the light chain variable domain (SEQ ID NO:471).

In another embodiment an anti-FX(a) antibody of the invention comprises one, two or three amino acid substitutions or deletions within the group of paratope residues K23, S25, G26, Y27, F29, W33, D52, S54, D55, F57, S77, H100, Y101, Y102, N103 and S104 in the heavy chain variable domain (SEQ ID NO:467) and residues V29, S30, S31, Y33, Y50, Q52, S54, R55, R57 and D94 in the light chain variable domain (SEQ ID NO:471).

In another embodiment the paratope of an anti-FX(a) antibody of the invention comprises residues K23, G24, S25, G26, Y27, W33, D52, S54, D55, Y57, S77, L99, H100, Y101, Y102, N103 and S104 in the variable heavy chain domain (SEQ ID NO:483) and residues S30, S31, Y33, Y50, Q52, S54, R55, R57, Y92 and D94 in the light chain variable domain (SEQ ID NO:487).

In another embodiment an anti-FX(a) antibody of the invention comprises one, two or three amino acid substitutions or deletions within the group of paratope residues K23, G24, S25, G26, Y27, W33, D52, S54, D55, Y57, S77, L99, H100, Y101, Y102, N103 and S104 in the variable heavy chain domain (SEQ ID NO:483) and residues S30, S31, Y33, Y50, Q52, S54, R55, R57, Y92 and D94 in the light chain variable domain (SEQ ID NO:487).

In one embodiment the CDR sequences of such an antibody may be described by anti-FX(a) paratope amino acid residues being part of the CDRs.

In one such embodiment the anti-FX(a) paratope CDRs are

```
VH CDR1 (based on SEQ ID NO: 468):
XXWXX

VH CDR2 (based on SEQ ID NO: 469):
XXDXSDXFXXXXXXXXX

VH CDR3 (based on SEQ ID NO: 470):
XHYYNSXXXXX

VL CDR1 (based on SEQ ID NO: 472):
XXXXXXVSSXYXX

VL CDR2 (based on SEQ ID NO: 473):
XQXSRXR

VL CDR3 (based on SEQ ID NO: 474):
XXXXDXXXXX
``` wherein paratope amino acid residues are in bold, and X represents a naturally occurring amino acid residue.

In another such embodiment the anti-FX(a) paratope CDRs are

```
VH CDR1 (based on SEQ ID NO: 484):
XXWXX

VH CDR2 (based on SEQ ID NO: 485):
XXDXSDXYXXXXXXXXX

VH CDR3 (based on SEQ ID NO: 486):
LHYYNSXXXXX

VL CDR1 (based on SEQ ID NO: 488):
XXXXXXXSSXYXX

VL CDR2 (based on SEQ ID NO: 489):
XQXSRXR

VL CDR3 (based on SEQ ID NO: 490):
XXYXDXXXXX
``` wherein paratope amino acid residues are in bold, and X represents a naturally occurring amino acid residue.

In one embodiment an antibody of the invention is a multispecific antibody or antigen-binding fragment thereof capable of stimulating the enzymatic activity of FIXa towards FX comprising a first antigen-binding site capable of binding to FIX (SEQ ID NO:1) and/or the activated form thereof (FIXa), and a second antigen-binding site capable of binding to FX (SEQ ID NO:2) and/or the activated form thereof (FXa).

In one such embodiment the first antigen-binding site comprises a paratope comprising amino acid residues D30, D31, W53, S102, S104 and N107 in the heavy chain variable domain (SEQ ID NO:35) and amino acid residues Y91 and S92 in the light chain variable domain (SEQ ID NO:39), and the second antigen-binding site comprises a paratope comprising amino acid residues K23, G24, S25, G26, Y27, W33, D52, S54, D55, Y57, S77, L99, H100, Y101, Y102, N103 and S104 in the variable heavy chain domain (SEQ ID NO:483) and amino acid residues S30, S31, Y33, Y50, Q52, S54, R55, R57, Y92 and D94 in the light chain variable domain (SEQ ID NO:487).

In one such embodiment the first antigen-binding site comprises a paratope comprising amino acid residues H30, D31, W53, D56, S102, S104, Y106 and N107 in the heavy chain variable domain (SEQ ID NO:67) and amino acid residues Y91 and S92 in the light chain variable domain (SEQ ID NO:71), and the second antigen-binding site comprises a paratope comprising amino acid residues K23, G24, S25, G26, Y27, W33, D52, S54, D55, Y57, S77, L99, H100, Y101, Y102, N103 and S104 in the variable heavy chain domain (SEQ ID NO:483) and amino acid residues S30, S31, Y33, Y50, Q52, S54, R55, R57, Y92 and D94 in the light chain variable domain (SEQ ID NO:487).

In one such embodiment the first antigen-binding site comprises a paratope comprising amino acid residues H30, D31, W53, D56, S102, S104, Y106 and N107 in the heavy chain variable domain (SEQ ID NO:67) and amino acid residues Y91 and S92 in the light chain variable domain (SEQ ID NO:71), and the second antigen-binding site comprises a paratope comprising amino acid residues K23, S25, G26, Y27, F29, W33, D52, S54, D55, F57, S77, H100, Y101, Y102, N103 and S104 in the heavy chain variable domain (SEQ ID NO:467) and amino acid residues V29, S30, S31, Y33, Y50, Q52, S54, R55, R57 and D94 in the light chain variable domain (SEQ ID NO:471).

In one such embodiment the first antigen-binding site comprises a paratope comprising amino acid residues D30, D31, W53, S102, S104 and N107 in the heavy chain variable domain (SEQ ID NO:35) and amino acid residues Y91 and S92 in the light chain variable domain (SEQ ID NO:39), and the second antigen-binding site comprises a paratope comprising amino acid residues K23, S25, G26, Y27, F29, W33, D52, S54, D55, F57, S77, H100, Y101, Y102, N103 and S104 in the heavy chain variable domain (SEQ ID NO:467) and amino acid residues V29, S30, S31, Y33, Y50, Q52, S54, R55, R57 and D94 in the light chain variable domain (SEQ ID NO:471).

In one such embodiment the first antigen-binding site comprises a paratope comprising amino acid residues H30, D31, W53, S102, S104, Y106 and N107 in the heavy chain variable domain (SEQ ID NO:51) and amino acid residues Y91 and S92 in the light chain variable domain (SEQ ID NO:55), and the second antigen-binding site comprises a paratope comprising amino acid residues K23, S25, G26, Y27, F29, W33, D52, S54, D55, F57, S77, H100, Y101, Y102, N103 and S104 in the heavy chain variable domain (SEQ ID NO:467) and amino acid residues V29, S30, S31, Y33, Y50, Q52, S54, R55, R57 and D94 in the light chain variable domain (SEQ ID NO:471).

In one embodiment the antibody is a bispecific antibody capable of binding to FIX(a) and FX(a).

In one embodiment an antibody of the invention is capable of binding FIXa with a higher affinity than that with which it binds FIX.

In one embodiment an antibody of the invention is capable of increasing the enzymatic activity of FIXa towards FX.

In one such embodiment an antibody of the invention is capable of increasing the enzymatic activity of FIXa towards FX as measured in a FXa generation assay using monovalent one-armed antibodies as described herein.

In one embodiment an antibody of the invention is capable of increasing the enzymatic activity of FIXa towards FX as measured in a FXa generation assay using bivalent antibodies as described herein.

In one embodiment the multispecific antibodies, such as bispecific antibodies, of the invention do not interfere with the effect of FVIII, such as recombinant FVIII administered to a patient suffering from haemophilia A, when said antibodies are used in clinically relevant dosages in the treatment of haemophilia A.

In one embodiment an antibody of the invention is not the anti-FIX antibody CLB-FIX 13 as described in Rohlena et al. (2003) J. Biol. Chem. 278(11):9394-9401. In one embodiment an antibody of the invention is not the anti-FIX antibody HIX-1 (IgG1 murine) (Merck KGaA, SigmaAldrich). In one embodiment an antibody or antigen-binding fragment thereof of the invention is not the anti-FIX antibody AHIX-5041 (IgG1) (Haematologic Technologies, Inc.).

In one embodiment an antibody or antigen-binding fragment thereof of the invention has reduced immunogenicity as compared to procoagulant antibodies of the art.

In a preferred embodiment antibodies of the invention were—unless otherwise stated or contradicted by context—expressed in the IgG4/kappa format.

The heavy chain constant domain regions ($C_H1$-$C_H2$-$C_H3$) were for the anti-FIX(a) arm human IgG4 with a S228P (EU-numbering) substitution and with truncation of the C-terminal lysine:

```
                                        (SEQ ID NO: 1195)
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLG.
```

In one embodiment the heavy chain constant domain regions ($C_H1$-$C_H2$-$C_H3$) were for the anti-FX(a) arm human IgG4 with the S228P substitution and with two additional substitutions, F405L and R409K (EU numbering), in the $C_H3$ domain to facilitate hetero-dimerization of the heavy chains (described in example 4) and with truncation of the C-terminal lysine:

```
                                        (SEQ ID NO: 1196)
ASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDK

RVESKYGPPCPPCPAPEFLGGPSVFLFPPKPKDTLMISRTPEVTCVVV

DVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTK

NQVSLTCLVKGFYPSDIAVEWESNGQPENNYKTIPPVLDSDGSFLLYS

KLTVDKSRWQEGNVFSCSVMHEALHNHYTQKSLSLSLG.
``` and, the light chain constant region (CL) was human kappa:

```
                                        (SEQ ID NO: 1197)
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGEC.
```

In another embodiment antibodies can also be expressed in the IgG4 format with heavy chain constant domain regions ($C_H1$-$C_H2$-$C_H3$) for the anti-FIX(a) arm carrying S228P, F405L and R409K substitutions and with heavy chain constant domain regions for the anti-FX(a) arm carrying the S228P substitution, with or without C-terminal lysine deletion.

In one embodiment antibodies can also be expressed in the IgG1/kappa format. In that case the heavy chain constant domain regions of the anti-FIX(a) arm is human IgG1 F405L with truncation of the C-terminal lysine:

```
                                          (SEQ ID NO: 1198)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFL

LYSKLTVDKSRWQQGNVFSCSVMHEALHNHYTQKSLSLSPG.
``` and the heavy chain constant domain regions of the anti-FX(a) arm is human IgG1 K409R with truncation of the C-terminal lysine:

```
                                          (SEQ ID NO: 1199)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSRLTVDKSRWQQGNVFSCSVMHEALHNHYTQKSLSLSPG.
```

Antibodies can also be expressed in the IgG1 format with heavy chain constant domain regions ($C_H1$-$C_H2$-$C_H3$) for the anti-FIX(a) arm carrying the K409R substitution and with heavy chain constant domain regions for the anti-FX(a) arm carrying the F405L substitution, with or without C-terminal lysine deletion.

The constant domain regions may further comprise additional substitutions or other modifications e.g. to modulate effector functions, half-life or other properties.

The present disclosure also provides kits that comprise antibodies or antigen-binding fragments thereof as disclosed herein suitable for treatment as described herein. In some embodiments, a kit comprises (i) an antibody, such as a bispecific antibody or antigen-binding fragment thereof, pharmaceutical composition, nucleic acid, vector, or cell (e.g., a host cell) as disclosed herein, or a combination thereof, and (ii) instructions for use. A skilled person will readily recognize that the antibodies, bispecific molecules (e.g., bispecific antibodies), pharmaceutical compositions, nucleic acids, vectors, or cells (e.g., a host cell) disclosed herein, or combinations thereof can be readily incorporated into one of the established kit formats which are well known in the art.

EXAMPLES

List of Abbreviations

ACN: Acetonitrile
bimAb: Bispecific monoclonal Antibody
CDR: Complementarity Determining Region
EGR-CK: EGR-chloromethylketone
LC-MS Liquid chromatography-mass spectrometry
FACS: Fluorescence-activated cell sorting
FIX: Coagulation Factor IX
FIXa: Coagulation Factor IXa
FX: Coagulation Factor X
FXa: Coagulation Factor Xa
HA: Haemophilia A
HA-PPP: HA-induced human platelet-poor plasma
HA-PRP: HA-induced human platelet-rich plasma
hFIXa: human Coagulation Factor IXa
ITC: Isothermal Titration calorimetry
MACS: Magnetic-activated cell sorting
OA: One-armed
PCR: Polymerase Chain Reaction
SPR: Surface Plasmon Resonance
References to ACE910 should be understood as referring to an antibody having an amino acid sequence which is identical to that of ACE910.

Example 1: Development of Anti-FIX(a) and Anti-FX(a) Antibodies

FIX(a) and FX(a) binding antibodies as disclosed herein were identified using various antibody development methods. In order to generate a diverse set of antibodies, immunisations of mice and rabbits were performed and phage display and Adimab yeast antibody expression platforms were also utilized.

Adimab Yeast Antibody Platform

The Adimab platform is a yeast antibody expression system encompassing a fully human naïve IgG1/kappa library with a diversity of $10^{10}$. The antibody selection process was directed using MACS and FACS based methods which allowed monitoring of applied selection criteria in real time. Since selections were based on MACS and FACS, labelled antigens (e.g. biotin) were needed. Selection campaigns were performed using biotin-labelled active-site inhibited hFIXa (FIXa-EGR-biotin), or antibody mediated immobilization of hFIXa. Hits were evaluated for binding using Bio-layer interferometry (Octet fortebio systems).

Phage Display

The utilized antibody phage display platform is a proprietary fully human Fab display library. The library has a size of $10^{10}$ and was constructed by a combinational approach utilizing chemical synthesis of the light chain, as well as the heavy chain CDR1 and CDR2, complemented with PCR amplification of the heavy chain CDR3 from human peripheral blood mononuclear cells. To maximise epitope diversity, different panning strategies were explored, including panning using biotinylated FIXa-EGR, FX, active-site inhibited FXa, or antigen capture using anti-FIXa antibodies. Initial hits were identified by phage ELISA. After sequence analysis, unique hits were cloned and recombinantly expressed as IgG1 antibodies, and ranked using SPR (Biacore) or Bio-layer interferometry (Octet fortebio systems).

In Vivo Platforms

Mice and rabbits were used for the generation of antibodies using in vivo platforms. For the generation of anti- FIX/FIXa antibodies, mice or rabbits were immunized with human FIXa, FIXa-EGR or FIX using standard protocols. The spleen cells from mice were fused with myeloma cells using standard techniques and the resulting antibody containing hybridoma supernatants were screened for binding to FIXa using ELISA. FIXa binding rabbit B-cells were single cell sorted using FACS by gating on cells binding randomly biotinylated FIXa-EGR (detected by streptavidin conjugated fluorophore). Sorted rabbit B cells were cultured for seven days in 384w plates using feeder cells and conditioned medium from splenocytes, prior to screening against FIXa in ELISA. Rabbit B-cells and mouse hybridoma clones, expressing FIXa binding antibody hits, were either used for VH/VL sequencing followed by recombinant expression (for rabbit or hybridoma mAbs) or further propagated for mAb production (mouse hybridomas).

For the generation of anti-FX antibodies, mice and rabbits were immunised with FX using standard protocols. Rabbit B-cells were isolated by FACS based single-cell sorting and using randomly biotinylated FX (detected by streptavidin conjugated flourophore) while spleen cells from immunized mice were used for standard hybridoma development. Resulting antibody producing B-cell or mouse hybridoma clones were screened for FX binding using ELISA and Octet fortebio systems. Rabbit B-cell or mouse hybridoma clones expressing antibody hits were either used for VH/VL sequencing followed by recombinant expression (for rabbit or hybridoma mAbs) or further propagated for mAb production (mouse hybridomas)

Sequencing of Hybridoma-Derived Antibodies

Anti-FIXa and anti-FX antibody producing hybridomas were sequenced and expressed in HEK293 cells using standard techniques. Expressed antibodies were evaluated for antigen binding using Octet fortebio systems.

Total RNA was extracted from antibody producing clones and the variable domain ($V_H$ and $V_L$) encoding DNA sequences were amplified using RT-PCR. $V_H$ and $V_L$ sequences were determined and inserted into a pTT-based mammalian expression vector (Durocher et al (2002) Nucleic Acid Res. 30: E9) or into a pcDNA3.4 mammalian expression vector (Invitrogen) containing antibody constant region encoding DNA sequences. For pTT/pcDNA3.4 mAb expression vectors, the $V_H$ and $V_L$ DNA sequences were inserted in-frame with human IgG1 or IgG4 S228P ($C_H1C_H2C_H3$), optionally with additional amino acid substitutions and deletions, e.g. substitutions in the $C_H3$ domain and deletion of the C-terminal lysine) or human $C_L$ kappa constant region encoding DNA sequences, respectively. For the corresponding pTT/pcDNA3.4 Fab expression vectors the $V_H$ DNA sequences were inserted in-frame with human IgG4 $C_H1$ encoding DNA sequences.

Example 2: Recombinant Expression of Antibodies and Antibody Fab Fragments

Antibodies and antibody Fab fragments were expressed using transient transfection of HEK293 suspension cells (293Expi, Invitrogen) essentially following manufacturer's instructions. 293Expi cells were typically subcultivated every 3-4 days in Expi293F expression medium (Invitrogen, catalogue number A1435104) supplemented with 1% P/S (GIBCO catalogue number 15140-122). Expi293F cells were transfected at a cell density of 2.5-3 mill/mL using Expifectamine. For each litre of Expi293F cells, the transfection was performed by diluting a total of 1 mg of plasmid DNA ($V_H$-$C_H1$ (for Fab) or $V_H$-$C_H1$-$C_H2$-$C_H3$ (for mAb) and LC plasmids in 1:1 ratio) into 50 mL Optimem (GIBCO, cat. no. 51985-026, dilution A) and by diluting 2.7 mL Expifectamine into 50 mL Optimem (dilution B). For Fab and mAb producing co-transfections, $V_H$-$C_H1$ and LC plasmids (Fab) and $V_H$-$C_H1$-$C_H2$-$C_H3$ and LC plasmids (mAb), respectively, were used in a 1:1 ratio. Dilution A and B were mixed and incubated at room temperature for 10-20 minutes. The transfection mix was hereafter added to the Expi293F cells and cells were incubated at 37° C. in a humidified incubator with orbital rotation (85-125 rpm). One day post-transfection, transfected cells were supplemented with 5 ml of ExpiFectamine 293 Transfection Enhancer 1 and 50 ml of ExpiFectamine 293 Transfection Enhancer 2. Cell culture supernatants were typically harvested 4-5 days post-transfection by centrifugation followed by filtration.

Example 3: Fab and Antibody Purification and Characterization

All purification steps were carried out at 4° C. For lab scale, Milli-Q water was used for buffer preparation. The HPLC system used for SE-HPLC analysis was Aglient 1100. Aggregation and LC/MS were assessed for QC.

Capturing of Fab was performed with HiTrap Protein G HP affinity chromatography with binding buffer in 1×PBS (10 mM Na2HPO4, 1.8 mM KH2PO4, 137 mM NaCl, 2.7 mM KCl), pH 7.4. One step elution was performed with 0.1M Glycine, pH 2.8. The final product was desalted via 52 mL GE Hiprep 16 desalting column into formulation buffer (25 mM HEPES, 150 mM NaCl) with pH 7.4 and concentrated by centrifugal ultrafilter (30 KD C.O.) for storage at −80° C.

To assess the quality of the purified Fab, SDS-PAGE and high-performance size-exclusion chromatography (SE-HPLC) analysis were performed. Batches that did not meet the quality standards (e.g., <95% monomeric by SE-HPLC) were further purified by size-exclusion chromatography. LC/MS was carried out to verify identity of Fab protein. Molecular weights (MWs) of all Fab's were shown to be consistent with theoretical MW of heavy chain and light chain, respectively.

Antibody Purification and Characterization

Purification of the antibodies was conducted by affinity chromatography using a Protein A MabSelect SuRe resins (GE Healthcare, cat. no. 17-5438-01). For small-scale antibody productions, protein A based purification was performed in 96 well plates while for larger productions, the ÄktaExplorer chromatography system (GE Healthcare, cat. no. 18-1112-41) was used. The buffer systems used for the affinity purification step were 1) an equilibration buffer composed of 20 mM NaPhosphate pH 7.2, 150 mM NaCl and 2) an elution buffer composed of 10 mM Formic acid pH 3.5 and 3) a pH-adjustment buffer composed of 0.4 M NaPhosphate pH 9.0. Cell supernatants were applied directly without any adjustments onto a pre-equilibrated MabSelect SuRe column. The column was washed with approximately 10 column volumes of equilibration buffer and the antibodies were eluted isocratically in approx. 2-5 column volume of elution buffer. The pH of the pooled fractions was adjusted to neutral using the described pH-adjustment buffer immediately after elution.

The purified antibodies were characterized using different methods such as SDS-PAGE/Coomassie, size-exclusion high-pressure liquid-chromatography (SE-HPLC) and liquid-chromatography mass spectrometry (LC-MS) analyses. The SDS-PAGE/Coomassie analysis was performed using NuPage 4-12% Bis-Tris gels (Invitrogen, cat. no. NP0321 BOX). Here, all antibodies displayed expected light chain and heavy chain components. Intact molecular mass determinations were performed using a Liquid Chromatography Electrospray Ionisation Time-of-Flight Mass Spectrometry method setup on an Agilent 6210 instrument and a desalting column MassPREP (Waters, cat. no. USRM10008656). The buffer system used was an equilibration buffer composed of 0.1% Formic acid in LC-MS graded-$H_2O$ and an elution buffer composed of 0.1% formic acid in LC-MS graded-ACN. Analyses were performed with and without N-Glycosidase F (Roche Diagnostics, cat. no. 11365177001) and reducing agent (i.e. mercaptoethanol or DTT). All antibodies displayed expected intact molecular masses in accordance with sequence and one heavy chain N-glycan. Purity was determined based on SE-HPLC. The final protein purity was analysed based on SE-HPLC method setup on an Agilent LC 1100/1200 system and using a BIOSep-SEC-S3000 300×7.8 mm column (Phenomenex, cat. no. OOH-2146-KO) and a running buffer composed of 200 mM NaPhosphate pH 6.9, 300 mM NaCl and 10% isopropanol. UV280 and fluorescence (Ex 280 nm/Em 354 nm) detectors was used for detection. The antibodies eluted as single symmetric peaks with retention times reflecting the size of the antibodies. Purity estimates were all between 95-99% for the different antibodies. To measure the final protein concentrations, a NanoDrop spectrophotometer (Thermo Scientific) was used together with specific extinction coefficients for each of the antibodies.

Example 4: Bispecific Antibodies Prepared by In Vitro Assembly

Bispecific antibodies were generated by in vitro assembly of a first and a second antibody by the Duobody® method (Genmab) described (Labrijn et al. PNAS 2013, vol. 110, pp. 5145-5150) for bispecific human IgG1 antibodies and using a slightly modified variant for bispecific human IgG4 antibodies as detailed in the following.

For IgG1 the heavy chain constant region of the first antibody is human IgG1 K409R (anti-FIX/FIXa) and the heavy chain constant region of the second antibody is human IgG1 F405L (anti-FX/FXa). The IgG1 may be a IgG1 variant with reduced effector functions, as referred to earlier.

For human IgG4, the heavy chain constant region of the first antibody is IgG4 S228P (anti-FIX/FIXa) and the heavy chain constant region of the second antibody is IgG4 S228P F405L+R409K (anti-FX). The two parental antibodies are produced as described in Examples 1-3. The Fab arm exchange reaction is carried out in HEPES buffer (pH 7.4) under reducing conditions using 75 mM 2-mercaptoethylamine (2-MEA) and incubation at 30° C. for 4 hours.

Example 5: Preparation of Monovalent (One-Armed) Antibodies

To avoid any potential avidity effects associated with conventional monospecific and bivalent antibodies, e.g. in FXa generation assays (Example 12) and in certain SPR-based experiments (Examples 10 and 11), a monovalent one-armed (OA) antibody format was used, as described by Martens et al.: A Novel One-Armed Anti-c-Met Antibody Inhibits Glioblastoma Growth In vivo. Clin. Cancer Res. 12, 6144-6152 (2006), where a full heavy chain, a truncated heavy chain (lacking the Fab region) and a light chain are co-expressed. Instead of co-expression of the three chains described by Martens et al. monovalent antibodies of the present invention were prepared using the Duobody® principle as described for bispecific antibodies (Example 4). Thus, monovalent antibodies were prepared by mixing a full monospecific and bivalent antibody and a truncated heavy chain dimer (formally derived from a full antibody by removing the Fab region) and allow exchange of chains to proceed under the same experimental conditions as described in Example 4. Formation of the monovalent antibody requires that the antibody and truncated heavy chain dimer carry appropriate complementary mutations to promote hetero-dimerization, i.e. F405L/K409R for human IgG1 and F405L+R409K/WT for human IgG4, as described in Example 4.

In case of monovalent antibodies of the IgG1 subtype the truncation of the heavy chain can be from the N-terminus to a position in-between Cys 220 and the upper hinge Cys 226 (EU numbering). A specific example of a truncated human IgG1 heavy chain is one where residues 1-220 are truncated.

In case of monovalent antibodies of the human IgG4 subtype the truncation of the heavy chain can be from the N-terminus to a position in-between Cys 200 and the upper hinge Cys 226 (EU numbering). A specific example of a truncated human IgG4 heavy chain is one where residues 1-214 are truncated.

Example 6: Overview of Bispecific Antibody (Component) IDs and SEQ ID NOs

TABLE 1

Overview of bispecific antibody components and corresponding VH/VL SEQ ID NOs

| BimAb ID | Component anti-FIX antibody ID | # VH\|VL | Component anti-FX antibody ID | # VH\|VL |
|---|---|---|---|---|
| bimAb05-0745 | mAb01-9994 | 67\|71 | mAb01-8174 | 467\|471 |
| bimAb05-0746 | mAb01-9978 | 43\|47 | mAb01-8174 | 467\|471 |
| bimAb05-1229 | mAb01-9016 | 3\|7 | mAb01-6723 | 459\|463 |
| bimAb05-2112 | mAb01-9994 | 67\|71 | mAb01-9772 | 483\|487 |
| bimAb05-2113 | mAb01-9933 | 35\|39 | mAb01-9772 | 483\|487 |
| bimAb05-2114 | mAb01-9985 | 51\|55 | mAb01-9772 | 483\|487 |
| bimAb05-2115 | mAb01-9978 | 43\|47 | mAb01-9772 | 483\|487 |
| bimAb05-2375 | mAb01-9016 | 3\|7 | mAb01-8174 | 467\|471 |
| bimAb05-2379 | mAb01-9016 | 3\|7 | mAb01-8913 | 475\|479 |
| bimAb05-2532 | mAb01-9373 | 11\|15 | mAb01-6723 | 459\|463 |
| bimAb05-3279 | mAb01-9933 | 35\|39 | mAb01-6723 | 459\|463 |
| bimAb05-3409 | mAb01-9978 | 43\|47 | mAb01-6723 | 459\|463 |
| bimAb05-3416 | mAb01-9985 | 51\|55 | mAb01-6723 | 459\|463 |
| bimAb05-3755 | mAb01-9994 | 67\|71 | mAb01-6723 | 459\|463 |
| bimAb05-3761 | mAb01-9933 | 35\|39 | mAb01-8174 | 467\|471 |
| bimAb05-3769 | mAb01-9985 | 51\|55 | mAb01-8174 | 467\|471 |
| bimAb05-3770 | mAb01-9986 | 59\|63 | mAb01-8174 | 467\|471 |
| bimAb05-3862 | mAb01-9696 | 19\|23 | mAb01-8174 | 467\|471 |
| bimAb05-3863 | mAb01-9697 | 27\|31 | mAb01-8174 | 467\|471 |
| bimAb05-3880 | mAb11-0047 | 75\|79 | mAb01-8174 | 467\|471 |
| bimAb05-3886 | mAb11-0049 | 83\|87 | mAb01-8174 | 467\|471 |
| bimAb05-3955 | mAb11-0107 | 91\|95 | mAb01-8174 | 467\|471 |
| bimAb05-4100 | mAb11-0149 | 99\|103 | mAb01-8174 | 467\|471 |
| bimAb05-4114 | mAb11-0160 | 107\|111 | mAb01-8174 | 467\|471 |
| bimAb05-4121 | mAb11-0164 | 115\|119 | mAb01-8174 | 467\|471 |
| bimAb05-4220 | mAb11-0962 | 211\|215 | mAb01-8174 | 467\|471 |
| bimAb05-4226 | mAb11-0965 | 219\|223 | mAb01-8174 | 467\|471 |
| bimAb05-4283 | mAb11-1021 | 227\|231 | mAb01-8174 | 467\|471 |
| bimAb05-4289 | mAb11-1024 | 235\|239 | mAb01-8174 | 467\|471 |
| bimAb05-4292 | mAb11-1033 | 251\|255 | mAb01-8174 | 467\|471 |
| bimAb05-4293 | mAb11-1030 | 243\|247 | mAb01-8174 | 467\|471 |
| bimAb05-4387 | mAb11-1039 | 259\|263 | mAb01-8174 | 467\|471 |
| bimAb05-4392 | mAb11-1042 | 267\|271 | mAb01-8174 | 467\|471 |
| bimAb05-4419 | mAb11-0174 | 123\|127 | mAb01-8174 | 467\|471 |
| bimAb05-4422 | mAb11-1073 | 275\|279 | mAb01-8174 | 467\|471 |
| bimAb05-4428 | mAb11-1076 | 283\|287 | mAb01-8174 | 467\|471 |
| bimAb05-4443 | mAb11-1094 | 299\|303 | mAb01-8174 | 467\|471 |
| bimAb05-4444 | mAb11-1091 | 291\|295 | mAb01-8174 | 467\|471 |

TABLE 1-continued

Overview of bispecific antibody components and corresponding VH/VL SEQ ID NOs

| BimAb ID | Component anti-FIX antibody ID | # VH\|VL | Component anti-FX antibody ID | # VH\|VL |
|---|---|---|---|---|
| bimAb05-4601 | mAb11-0937 | 187\|191 | mAb01-8174 | 467\|471 |
| bimAb05-4604 | mAb11-0923 | 139\|143 | mAb01-8174 | 467\|471 |
| bimAb05-4608 | mAb11-0939 | 203\|207 | mAb01-8174 | 467\|471 |
| bimAb05-4611 | mAb11-0935 | 179\|183 | mAb01-8174 | 467\|471 |
| bimAb05-4612 | mAb11-0938 | 195\|199 | mAb01-8174 | 467\|471 |
| bimAb05-4613 | mAb11-0933 | 171\|175 | mAb01-8174 | 467\|471 |
| bimAb05-4615 | mAb11-0932 | 163\|167 | mAb01-8174 | 467\|471 |
| bimAb05-4617 | mAb11-0929 | 147\|151 | mAb01-8174 | 467\|471 |
| bimAb05-4618 | mAb11-0931 | 155\|159 | mAb01-8174 | 467\|471 |
| bimAb05-4684 | mAb01-9985 | 51\|55 | mAb11-1114 | 499\|503 |
| bimAb05-4685 | mAb01-9985 | 51\|55 | mAb11-1115 | 507\|511 |
| bimAb05-4686 | mAb01-9985 | 51\|55 | mAb11-1116 | 515\|519 |
| bimAb05-4687 | mAb01-9985 | 51\|55 | mAb11-1117 | 523\|527 |
| bimAb05-4688 | mAb01-9985 | 51\|55 | mAb11-1118 | 531\|535 |
| bimAb05-4689 | mAb01-9985 | 51\|55 | mAb11-1119 | 539\|543 |
| bimAb05-4690 | mAb01-9985 | 51\|55 | mAb11-1121 | 555\|559 |
| bimAb05-4692 | mAb01-9985 | 51\|55 | mAb11-1122 | 563\|567 |
| bimAb05-4693 | mAb01-9985 | 51\|55 | mAb11-1123 | 571\|575 |
| bimAb05-4694 | mAb01-9985 | 51\|55 | mAb11-1124 | 579\|583 |
| bimAb05-4695 | mAb01-9985 | 51\|55 | mAb01-9778 | 491\|495 |
| bimAb05-4696 | mAb01-9985 | 51\|55 | mAb11-1125 | 587\|591 |
| bimAb05-4697 | mAb01-9985 | 51\|55 | mAb11-1127 | 595\|599 |
| bimAb05-4698 | mAb01-9985 | 51\|55 | mAb11-1128 | 603\|607 |
| bimAb05-4699 | mAb01-9985 | 51\|55 | mAb11-1129 | 611\|615 |
| bimAb05-4700 | mAb01-9985 | 51\|55 | mAb11-1130 | 619\|623 |
| bimAb05-4701 | mAb01-9985 | 51\|55 | mAb11-1131 | 627\|631 |
| bimAb05-4702 | mAb01-9985 | 51\|55 | mAb11-1132 | 635\|639 |
| bimAb05-4703 | mAb01-9985 | 51\|55 | mAb11-1133 | 643\|647 |
| bimAb05-4704 | mAb01-9985 | 51\|55 | mAb11-1416 | 651\|655 |
| bimAb05-4705 | mAb01-9985 | 51\|55 | mAb11-1417 | 659\|663 |
| bimAb05-4706 | mAb01-9985 | 51\|55 | mAb11-1418 | 667\|671 |
| bimAb05-4707 | mAb01-9985 | 51\|55 | mAb11-1419 | 675\|679 |
| bimAb05-4708 | mAb01-9985 | 51\|55 | mAb11-1420 | 683\|687 |
| bimAb05-4709 | mAb01-9985 | 51\|55 | mAb11-1421 | 691\|695 |
| bimAb05-4710 | mAb01-9985 | 51\|55 | mAb11-1422 | 699\|703 |
| bimAb05-4788 | mAb11-1233 | 307\|311 | mAb01-8174 | 467\|471 |
| bimAb05-4884 | mAb11-1254 | 315\|319 | mAb01-8174 | 467\|471 |
| bimAb05-4895 | mAb11-1262 | 339\|343 | mAb01-8174 | 467\|471 |
| bimAb05-4896 | mAb11-1259 | 323\|327 | mAb01-8174 | 467\|471 |
| bimAb05-4898 | mAb11-1260 | 331\|335 | mAb01-8174 | 467\|471 |
| bimAb05-4903 | mAb11-1268 | 355\|359 | mAb01-8174 | 467\|471 |
| bimAb05-4906 | mAb11-1266 | 347\|351 | mAb01-8174 | 467\|471 |
| bimAb05-4910 | mAb11-1273 | 363\|367 | mAb01-8174 | 467\|471 |
| bimAb05-4914 | mAb11-1275 | 371\|375 | mAb01-8174 | 467\|471 |
| bimAb05-4915 | mAb11-1276 | 379\|383 | mAb01-8174 | 467\|471 |
| bimAb05-4919 | mAb11-1278 | 387\|391 | mAb01-8174 | 467\|471 |
| bimAb05-4920 | mAb11-1282 | 403\|407 | mAb01-8174 | 467\|471 |
| bimAb05-4921 | mAb11-1279 | 395\|399 | mAb01-8174 | 467\|471 |
| bimAb05-4924 | mAb11-1288 | 419\|423 | mAb01-8174 | 467\|471 |
| bimAb05-4927 | mAb11-1286 | 411\|415 | mAb01-8174 | 467\|471 |
| bimAb05-5092 | mAb11-1344 | 427\|431 | mAb01-8174 | 467\|471 |
| bimAb05-5095 | mAb11-0723 | 131\|135 | mAb01-8174 | 467\|471 |
| bimAb05-5204 | mAb11-1358 | 435\|439 | mAb01-8174 | 467\|471 |
| bimAb05-5205 | mAb11-1360 | 443\|447 | mAb01-8174 | 467\|471 |
| bimAb05-5240 | mAb11-1389 | 451\|455 | mAb01-8174 | 467\|471 |
| bimAb05-5339 | mAb01-9985 | 51\|55 | mAb11-1440 | 771\|775 |
| bimAb05-5340 | mAb01-9985 | 51\|55 | mAb11-1431 | 707\|711 |
| bimAb05-5341 | mAb01-9985 | 51\|55 | mAb11-1441 | 779\|783 |
| bimAb05-5342 | mAb01-9985 | 51\|55 | mAb11-1439 | 763\|767 |
| bimAb05-5343 | mAb01-9985 | 51\|55 | mAb11-1442 | 787\|791 |
| bimAb05-5344 | mAb01-9985 | 51\|55 | mAb11-1443 | 795\|799 |
| bimAb05-5345 | mAb01-9985 | 51\|55 | mAb11-1446 | 819\|823 |
| bimAb05-5346 | mAb01-9985 | 51\|55 | mAb11-1444 | 803\|807 |
| bimAb05-5347 | mAb01-9985 | 51\|55 | mAb11-1447 | 827\|831 |
| bimAb05-5348 | mAb01-9985 | 51\|55 | mAb11-1445 | 811\|815 |
| bimAb05-5349 | mAb01-9985 | 51\|55 | mAb11-1448 | 835\|839 |
| bimAb05-5350 | mAb01-9985 | 51\|55 | mAb11-1432 | 715\|719 |
| bimAb05-5351 | mAb01-9985 | 51\|55 | mAb11-1449 | 843\|847 |
| bimAb05-5352 | mAb01-9985 | 51\|55 | mAb11-1450 | 851\|855 |
| bimAb05-5353 | mAb01-9985 | 51\|55 | mAb11-1453 | 875\|879 |
| bimAb05-5354 | mAb01-9985 | 51\|55 | mAb11-1451 | 859\|863 |
| bimAb05-5355 | mAb01-9985 | 51\|55 | mAb11-1454 | 883\|887 |
| bimAb05-5356 | mAb01-9985 | 51\|55 | mAb11-1452 | 867\|871 |
| bimAb05-5357 | mAb01-9985 | 51\|55 | mAb11-1455 | 891\|895 |
| bimAb05-5358 | mAb01-9985 | 51\|55 | mAb11-1433 | 723\|727 |
| bimAb05-5359 | mAb01-9985 | 51\|55 | mAb11-1456 | 899\|903 |
| bimAb05-5361 | mAb01-9985 | 51\|55 | mAb11-1459 | 923\|927 |
| bimAb05-5362 | mAb01-9985 | 51\|55 | mAb11-1457 | 907\|911 |
| bimAb05-5363 | mAb01-9985 | 51\|55 | mAb11-1434 | 731\|735 |
| bimAb05-5364 | mAb01-9985 | 51\|55 | mAb11-1458 | 915\|919 |
| bimAb05-5365 | mAb01-9985 | 51\|55 | mAb11-1460 | 931\|935 |
| bimAb05-5366 | mAb01-9985 | 51\|55 | mAb11-1461 | 939\|943 |
| bimAb05-5367 | mAb01-9985 | 51\|55 | mAb11-1465 | 963\|967 |
| bimAb05-5369 | mAb01-9985 | 51\|55 | mAb11-1466 | 971\|975 |
| bimAb05-5370 | mAb01-9985 | 51\|55 | mAb11-1463 | 947\|951 |
| bimAb05-5371 | mAb01-9985 | 51\|55 | mAb11-1435 | 739\|743 |
| bimAb05-5372 | mAb01-9985 | 51\|55 | mAb11-1464 | 955\|959 |
| bimAb05-5373 | mAb01-9985 | 51\|55 | mAb11-1467 | 979\|983 |
| bimAb05-5374 | mAb01-9985 | 51\|55 | mAb11-1468 | 987\|991 |
| bimAb05-5375 | mAb01-9985 | 51\|55 | mAb11-1472 | 1011\|1015 |
| bimAb05-5377 | mAb01-9985 | 51\|55 | mAb11-1473 | 1019\|1023 |
| bimAb05-5378 | mAb01-9985 | 51\|55 | mAb11-1470 | 995\|999 |
| bimAb05-5379 | mAb01-9985 | 51\|55 | mAb11-1436 | 747\|751 |
| bimAb05-5380 | mAb01-9985 | 51\|55 | mAb11-1471 | 1003\|1007 |
| bimAb05-5381 | mAb01-9985 | 51\|55 | mAb11-1474 | 1027\|1031 |
| bimAb05-5383 | mAb01-9985 | 51\|55 | mAb11-1477 | 1051\|1055 |
| bimAb05-5384 | mAb01-9985 | 51\|55 | mAb11-1475 | 1035\|1039 |
| bimAb05-5385 | mAb01-9985 | 51\|55 | mAb11-1478 | 1059\|1063 |
| bimAb05-5386 | mAb01-9985 | 51\|55 | mAb11-1476 | 1043\|1047 |
| bimAb05-5387 | mAb01-9985 | 51\|55 | mAb11-1479 | 1067\|1071 |
| bimAb05-5388 | mAb01-9985 | 51\|55 | mAb11-1480 | 1075\|1079 |
| bimAb05-5389 | mAb01-9985 | 51\|55 | mAb11-1483 | 1099\|1103 |
| bimAb05-5390 | mAb01-9985 | 51\|55 | mAb11-1437 | 755\|759 |
| bimAb05-5391 | mAb01-9985 | 51\|55 | mAb11-1484 | 1107\|1111 |
| bimAb05-5392 | mAb01-9985 | 51\|55 | mAb11-1481 | 1083\|1087 |
| bimAb05-5393 | mAb01-9985 | 51\|55 | mAb11-1485 | 1115\|1119 |
| bimAb05-5394 | mAb01-9985 | 51\|55 | mAb11-1482 | 1091\|1095 |
| bimAb05-5395 | mAb01-9985 | 51\|55 | mAb11-1486 | 1123\|1127 |
| bimAb05-5396 | mAb01-9985 | 51\|55 | mAb11-1487 | 1131\|1135 |
| bimAb05-5397 | mAb01-9985 | 51\|55 | mAb11-1490 | 1155\|1159 |
| bimAb05-5399 | mAb01-9985 | 51\|55 | mAb11-1491 | 1163\|1167 |
| bimAb05-5400 | mAb01-9985 | 51\|55 | mAb11-1488 | 1139\|1143 |
| bimAb05-5401 | mAb01-9985 | 51\|55 | mAb11-1492 | 1171\|1175 |
| bimAb05-5402 | mAb01-9985 | 51\|55 | mAb11-1489 | 1147\|1151 |
| bimAb05-5403 | mAb01-9985 | 51\|55 | mAb11-1493 | 1179\|1183 |
| bimAb05-5406 | mAb01-9985 | 51\|55 | mAb11-1494 | 1187\|1191 |
| bimAb05-5413 | mAb01-9985 | 51\|55 | mAb11-1120 | 547\|551 |
| bimAb05-4271 | mAb11-0173 | 1202\|1206 | mAb01-8174 | 467\|471 |
| bimAb05-4756 | mAb11-1204 | 1210\|1214 | mAb01-8174 | 467\|471 |
| bimAb05-0396 | mAb11-1495 | 1218\|1222 | mAb01-8174 | 467\|471 |
| bimAb05-0417 | mAb11-1501 | 1226\|1230 | mAb01-8174 | 467\|471 |
| bimAb05-0438 | mAb11-1502 | 1234\|1238 | mAb01-8174 | 467\|471 |

TABLE 2

Overview of anti-FIX(a) antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| mAb01-9016 | VH | EVQLVESGGGLVQPGRSLKLSCAASGFTFDDYAMHWVRQVPGKGLEWVSGISWRGDIGGYVDSVKGRFTISRDNAKNSLYLQLNSLRAEDTALYYCVKSYGSGSFYNAFDSWGQGTLVTVSS | 3 | DYAMH | 4 | GISWRGDIGGYVDSVKG | 5 | SYGSGSFYNAFDS | 6 |
| mAb01-9016 | VL | DIQMTQSPSTLSASAGDRVTITCRASQSISSWLAWYQQKPGKAPKFLIYKASRLERGVPSRFSGSGSGTEFSLTISSLQPDDFATYYCLEYSSYIRTFGQGTKVEIK | 7 | RASQSISSWLA | 8 | KASRLER | 9 | LEYSSYIRT | 10 |
| mAb01-9373 | VH | EVQLVESGGGLVQPGRSLKLSCAASGFTFHDYAMHWVRQVPGKGLEWVSGISWRGDIIGYVDSVKGRFTISRDNAKNSLYLQLNSLRAEDTALYYCVKSYGSGSFYNAFDSWGQGTLVTVSS | 11 | DYAMH | 12 | GISWRGDIIGYVDSVKG | 13 | SYGSGSFYNAFDS | 14 |
| mAb01-9373 | VL | DIQMTQSPSTLSASAGDEVTITCRASKSISSWLAWYQQKPGKAPRFLIYKASRLDRGTPSRFSGSGSGTEFTLTISHLQPDDFATYYCLEYSSYIRTFGQGTKVEIK | 15 | RASKSISSWLA | 16 | KASRLDR | 17 | LEYSSYIRT | 18 |
| mAb01-9696 | VH | EVQLVESGGGLVQPGRSLKLSCAASGFTFDDYAMHWVRQVPGKGLEWVSGISWRGDIGGYVDSVKGRFTISRDNAKNSLYLQLNSLRAEDTALYYCVKSYGSGSFYNAFDSWGQGTLVTVSS | 19 | DYAMH | 20 | GISWRGDIGGYVDSVKG | 21 | SYGSGSFYNAFDS | 22 |
| mAb01-9696 | VL | DIQMTQSPSTLSASAGDRVTITCRASQSISSWLAWYQQKPGKAPKFLIYKASRLDRGTPSRFSGSGSGTEFSLTISSLQPDDFATYYCLEYSSYIRTFGQGTKVEIK | 23 | RASQSISSWLA | 24 | KASRLDR | 25 | LEYSSYIRT | 26 |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb01-9697 | VH | EVQLVESGGGLVQPGRSLKLSCAASGFTFDDYAMHWRQVPGKGLEWVSGISWRGDIGGYVDSVKGRFTISRDNAKNSLYLQLNSLRAEDTALYYCVKSYGSGSFYNAFDSWGQGTLVTVSS | 27 | DYAMH | 28 | GISWRGDIGGYVDSVKG | 29 | SYGSGSFYNAFDS |
| mAb01-9697 | VL | DIQMTQSPSTLSASVGDRVTITCRASQSISSWLAWYQQKPGKAPKFLIYKASRLERGTPSRFSGSGSGTEFSLTISSLQPDDFATYYCLEYSSYIRTFGQGTKVEIK | 31 | RASQSISSWLA | 32 | KASRLER | 33 | LEYSSYIRT |
| mAb01-9933 | VH | EVQLVESGGGLVQPGRSLKLSCAASGFTFDDYAMHWRQVPGKGLEWVSGISWKGDIGGYVDSVKGRFTISRDNAKNSLYLQLNSLRAEDTALYYCAKSYGSGSFYNAFDSWGQGTLVTVSS | 35 | DYAMH | 36 | GISWKGDIGGYVDSVKG | 37 | SYGSGSFYNAFDS |
| mAb01-9933 | VL | DIQMTQSPSTLSASAGDEVTITCRASQSISSWLAWYQQKPGKAPKLLIYKASKLDRGVPSRFSGSGSGTEFSLTISDLQPDDFATYYCLEYSSYIRTFGQGTKVEIK | 39 | RASQSISSWLA | 40 | KASKLDR | 41 | LEYSSYIRT |
| mAb01-9978 | VH | EVQLVESGGGLVQPGRSLRLSCAASGFTFHDYAMHWRQVPGKGLEWVSGISWKGDIGGYVDSVKGRFTISRDNEKNSLYLQMNSLRAEDTALYYCVKSYGSGSFYNAFDSWGQGTLVTVSS | 43 | DYAMH | 44 | GISWKGDIGGYVDSVKG | 45 | SYGSGSFYNAFDS |
| mAb01-9978 | VL | DIQMTQSPSTLSASVGDRVTITCRASQSISSWLAWYQQKPGKAPKLLIYKASRLERGTPSRFSGSGSGTEFSLTISSLQPDDFATYYCLEYSSYIRTFGQGTKVEIK | 47 | RASQSISSWLA | 48 | KASRLER | 49 | LEYSSYIRT |
| mAb01-9985 | VH | EVQLVESGGGLVQPGRSLRLSCAASGFTFHDYAMH | 51 | DYAMH | 52 | GISWRGDIGGYVKSVKG | 53 | SYGSGSFYNAFDS |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WVRQVPGKGLEWVSGIS WRGDIGGYVKSVKGRFTI SRDNAKNSLYLQMNSLR AEDTALYYCVKSYGSGSF YNAFDSWGQGTLVTVSS | | | | | | |
| mAb01-9985 | VL | DIQMTQSPSTLSASVGDR VTITCRASQSISSWLAWY QQKPGKAPKFLIYKASKL ERGTPSRFSGSGSGTEF SLTISSLQPDDFATYYCLE YSSYIRTFGQGTKVEIK | 55 | RASQSISSW LA | 56 | KASKLER | 57 | LEYSSYIRT | 58 |
| mAb01-9986 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 59 | DYAMH | 60 | GISWRGDIGGYV KSVKG | 61 | SYGSGSFYNAFDS | 62 |
| mAb01-9986 | VL | DIQMTQSPSTLSASVGDR VTITCRASQSISSWLAWY QQKPGKAPKFLIYKASRL ERGTPSRFSGSGSGTEF SLTISSLQPDDFATYYCLE YSSYIRTFGQGTKVEIK | 63 | RASQSISSW LA | 64 | KASRLER | 65 | LEYSSYIRT | 66 |
| mAb01-9994 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 67 | DYAMH | 68 | GISWKGDIGGYV DSVKG | 69 | SYGSGSFYNAFDS | 70 |
| mAb01-9994 | VL | DIQMTQSPSTLSASVGDR VTITCRASQSISSWLAWY QQKPGKAPKFLIYKASRL DRGTPSRFSGSGSGTEF SLTISSLQPDDFATYYCLE YSSYIRTFGQGTKVEIK | 71 | RASQSISSW LA | 72 | KASRLDR | 73 | LEYSSYIRT | 74 |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-0047 | VH | EVQLVESGGGLVQPGRS LRLSCAASGFTFHDYAMH WVRQAPGKGLEWVSGIS WRGDIKGYVDSVKGRFTI SRDNAKNSLYLQLNSLRA EDTALYYCAKSYGSGSFY NAFDSWGQGTLVTVSS | 75 | DYAMH | 76 | GISWRGDIKGYVD SVKG | 77 | SYGSGSFYNAFDS |
| mAb11-0047 | VL | DIQMTQSPSTLSASAGDR VTITCRASKSISSWLAWY QQKPGKAPKFLIYKASRL DRGTPQRFSGSGSGTEF SLTISSLQPDDFATYYCLE YSSYIRTFGQGTKVEIK | 79 | RASKSISSW LA | 80 | KASRLDR | 81 | LEYSSYIRT |
| mAb11-0049 | VH | EVQLVESGGGLVQPGRS LRLSCAASGFTFHDYAMH WVRQAPGKGLEWVSGIS WRGDIKGYVDSVKGRFTI SRDNAKNSLYLQLNSLRA EDTALYYCAKSYGSGSFY NAFDSWGQGTLVTVSS | 83 | DYAMH | 84 | GISWRGDIKGYVD SVKG | 85 | SYGSGSFYNAFDS |
| mAb11-0049 | VL | DIQMTQSPSTLSASAGDR VTISCRASQSISSWLAWY QQKPGKAPKLLIYKASRL DRGTPSRFSGSGSGTEF TLTISSLQPDDFATYYCLE YNSYIRTFGQGTKVEIK | 87 | RASQSISSW LA | 88 | KASRLDR | 89 | LEYNSYIRT |
| mAb11-0107 | VH | EVQLVESGGGLVQPGRS LKLSCAASGFTFHDYAMH WVRQVPGKGLEWVSGIS WRGDIGGYVKSVKGRFTI SRDNAKNSLYLQLNSLRA EDTALYYCVKSYGSGSFY NAFDSWGQGTLVTVSS | 91 | DYAMH | 92 | GISWRGDIGGYV KSVKG | 93 | SYGSGSFYNAFDS |
| mAb11-0107 | VL | DIQMTQSPSTLSASVGDE VTITCRASQSISSWLAWY QQKPGKAPKFLIYKAQRL DRGTPQRFSGSGSGTEF TLTISSLQPDDFATYYCLE YSSYIRTFGQGTKVEIK | 95 | RASQSISSW LA | 96 | KAQRLDR | 97 | LEYSSYIRT |
| mAb11-0149 | VH | EVQLVESGGGLVQPGRS LKLSCAASGFTFDDYAMH | 99 | DYAMH | 100 | GISWKGDIGGYV DSVKG | 101 | SYGSGSFYNAFDS |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| | | WVRQAPGKGLEWVSGIS WKGDIGGYVDSVKGRFTI SRDNAKNSLYLQMNSLR AEDTALYYCVKSYGSGSF YNAFDSWGQGTLVTVSS | | | | | | | |
| mAb11-0149 | VL | DIQMTQSPSTLSASAGDE VTITCRASQSIKSWLAWY QQKPGKAPKFLIYKASRL DRGTPQRFSGSGSGTEF SLTISRLQPDDFATYYCLE YSSYIRTFGQGTKVEIK | | RASQSIKSW LA | 103 | KASRLDR | 104 | LEYSSYIRT | 105 | | 106 |
| mAb11-0160 | VH | EVQLVESGGGLVQPGRS LKLSCAASGFRFDDYAMH WVRQVPGKGLEWVSGIS WKGDIGGYADSVKGRFTI SRDNAKNSLYLQLNSLRA EDTALYYCVKSYGSGSFY NAFDSWGQGTLVTVSS | | DYAMH | 107 | GISWKGDIGGYA DSVKG | 108 | SYGSGSFYNAFDS | 109 | | 110 |
| mAb11-0160 | VL | DIQMTQSPSTLSASVGDE VTITCRASKSISSWLAWY QQKPGKAPRFLIYKASRL ERGTPQRFSGSGSGTEF TLITYSLQPDDFATYYCLE YSSYIRTFGQGTKVEIK | | RASKSISSW LA | 111 | KASRLER | 112 | LEYSSYIRT | 113 | | 114 |
| mAb11-0164 | VH | EVQLVESGGGLVQPGRS LKLSCAASGFRFDDYAMH WVRQVPGKGLEWVSGIS WKGDIGGYADSVKGRFTI SRDNAKNSLYLQLNSLRA EDTALYYCVKSYGSGSFY NAFDSWGQGTLVTVSS | | DYAMH | 115 | GISWKGDIGGYA DSVKG | 116 | SYGSGSFYNAFDS | 117 | | 118 |
| mAb11-0164 | VL | DIQMTQSPSTLSASVGDR VTITCRASQSISSWLAWY QQKPGKAPKFLIYKASRL ERGTPSRFSGSGSGTEF SLTISSLQPDDFATYYCLE YSSYIRTFGQGTKVEIK | | RASQSISSW LA | 119 | KASRLER | 120 | LEYSSYIRT | 121 | | 122 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence |
|---|---|---|---|---|---|---|---|---|
| mAb11-0174 | VH | EVQLVESGGGLVQPGRSLKLSCAASGFTFHDYAMHWVRQAPGKGLEWVSGISWKGDIGGYVDSVKGRFTISRDNAKNSLYLQMNSLRAEDTALYYCAKSYGSGSFYNAFDSWGQGTLVTVSS | 123 | DYAMH | 124 | GISWKGDIGGYVDSVKG | 125 | SYGSGSFYNAFDS | 126 |
| mAb11-0174 | VL | DIQMTQSPSTLSASVGDRVTITCRASQSISSWLAWYQQKPGKAPKFLIYKASKLDRGTPSRFSGSGSGTEFTLTISSLQPDDFATYYCLEYSSYIRTFGQGTKVEIK | 127 | RASQSISSWLA | 128 | KASKLDR | 129 | LEYSSYIRT | 130 |
| mAb11-0723 | VH | EVQLVESGGGLVQPGRSLKLSCAASGFTFDDYAMHWVRQVPGKGLEWVSGISWKGDIGGYVDSVKGRFTISRDNAKNSLYLQLNSLRAEDTALYYCAKSYGSGSFYNAFDSWGQGTLVTVSS | 131 | DYAMH | 132 | GISWKGDIGGYVDSVKG | 133 | SYGSGSFYNAFDS | 134 |
| mAb11-0723 | VL | DIQMTQSPSTLSASAGDRVTITCRASQSISSWLAWYQQKPGKAPKFLIYKASRLDRGTPSRFSGSGSGTEFSLTISSLQPDDFATYYCLEYSSYIRTFGQGTKVEIK | 135 | RASQSISSWLA | 136 | KASRLDR | 137 | LEYSSYIRT | 138 |
| mAb11-0923 | VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS | 139 | DYAMH | 140 | GISWKGDIGGYVDSVKG | 141 | SYGSGSFYNAFDS | 142 |
| mAb11-0923 | VL | DIQMTQSPSTLSASVGDRVTITCRASQSISSWLAWYQQKPGKAPKFLIYKASRLDRGCPSRFSGSGSGTEFSLTISSLQPDDFATYYCLEYSSYIRTFGQGTKVEIK | 143 | RASQSISSWLA | 144 | KASRLDR | 145 | LEYSSYIRT | 146 |
| mAb11-0929 | VH | EVQLVESGGGLVQPGRSLRLSCAASGFTFHDYAMH | 147 | DYAMH | 148 | GISWKGDIGGYVDSVKG | 149 | SYGSGSFYNAFDS | 150 |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WVRQVPGKGLEWVSGIS WKGDIGGYVDSVKGRFTI SRDNEKNSLYLQMNSLR AEDTALYYCVKSYGSGSF YNAFDSWGQGTLVTVSS | | | | | | |
| mAb11-0929 | VL | DIQMTQSPSTLSASVGDR VTITCRASQSISSWLAWY QQKPGKAPKFLIYKASRL DRGIPSRFSGSGSGTEFS LTISSLQPDDFATYYCLEY SSYIRTFGQGTKVEIK | 151 | RASQSISSW LA | 152 | KASRLDR | 153 | LEYSSYIRT | 154 |
| mAb11-0931 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 155 | DYAMH | 156 | GISWKGDIGGYV DSVKG | 157 | SYGSGSFYNAFDS | 158 |
| mAb11-0931 | VL | DIQMTQSPSTLSASVGDR VTITCRASQSISSWLAWY QQKPGKAPKFLIYKASRL DRGLPSRFSGSGSGTEF SLITSSLQPDDFATYYCLE YSSYIRTFGQGTKVEIK | 159 | RASQSISSW LA | 160 | KASRLDR | 161 | LEYSSYIRT | 162 |
| mAb11-0932 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 163 | DYAMH | 164 | GISWKGDIGGYV DSVKG | 165 | SYGSGSFYNAFDS | 166 |
| mAb11-0932 | VL | DIQMTQSPSTLSASVGDR VTITCRASQSISSWLAWY QQKPGKAPKFLIYKASRL DRGMPSRFSGSGSGTEF SLITSSLQPDDFATYYCLE YSSYIRTFGQGTKVEIK | 167 | RASQSISSW LA | 168 | KASRLDR | 169 | LEYSSYIRT | 170 |
| mAb11-0933 | VH | EVQLVESGGGLVQPGRS LRLSCAASGFTFHDYAMH WRQVPGKGLEWVSGIS WKGDIGGYVDSVKGRFTI | 171 | DYAMH | 172 | GISWKGDIGGYV DSVKG | 173 | SYGSGSFYNAFDS | 174 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence |
|---|---|---|---|---|---|---|---|---|
| mAb11-0933 | | SRDNEKNSLYLQMNSLR AEDTALYYCVKSYGSGSF YNAFDSWGQGTLVTVSS | | | | | | |
| mAb11-0935 | VL | DIQMTQSPSTLSASVGDR VTITCRASQSISSWLAWY QQKPGKAPKFLIYKASRL DRGNPSRFSGSGSGTEF SLTISSLQPDDFATYYCLE YSSYIRTFGQGTKVEIK | 175 | RASQSISSW LA | 176 | KASRLDR | 177 | LEYSSYIRT | 178 |
| mAb11-0935 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 179 | DYAMH | 180 | GISWKGDIGGYV DSVKG | 181 | SYGGSFYNAFDS | 182 |
| mAb11-0937 | VL | DIQMTQSPSTLSASVGDR VTITCRASQSISSWLAWY QQKPGKAPKFLIYKASRL DRGQPSRFSGSGSGTEF SLTISSLQPDDFATYYCLE YSSYIRTFGQGTKVEIK | 183 | RASQSISSW LA | 184 | KASRLDR | 185 | LEYSSYIRT | 186 |
| mAb11-0937 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 187 | DYAMH | 188 | GISWKGDIGGYV DSVKG | 189 | SYGGSFYNAFDS | 190 |
| mAb11-0937 | VL | DIQMTQSPSTLSASVGDR VTITCRASQSISSWLAWY QQKPGKAPKFLIYKASRL DRGSPSRFSGSGSGTEF SLTISSLQPDDFATYYCLE YSSYIRTFGQGTKVEIK | 191 | RASQSISSW LA | 192 | KASRLDR | 193 | LEYSSYIRT | 194 |
| mAb11-0938 | VH | EVQLVESGGGLVQPGRS LRLSCAASGFTFHDYAMH WVRQVPGKGLEWVSGIS WKGDIGGYVDSVKGRFTI | 195 | DYAMH | 196 | GISWKGDIGGYV DSVKG | 197 | SYGGSFYNAFDS | 198 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| | | SRDNEKNSLYLQMNSLR AEDTALYYCVKSYGSGSF YNAFDSWGQGTLVTVSS | | | | | | | |
| mAb11-0938 | VL | DIQMTQSPSTLSASVGDR VTITCRASQSISSWLAWY QQKPGKAPKFLIYKASRL DRGVPSRFSGSGSGTEF SLTISSLQPDDFATYYCLE YSSYIRTFGQGTKVEIK | 199 | RASQSISSW LA | 200 | KASRLDR | 201 | LEYSSYIRT | 202 |
| mAb11-0939 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 203 | DYAMH | 204 | GISWKGDIGGYV DSVKG | 205 | SYGSGSFYNAFDS | 206 |
| mAb11-0939 | VL | DIQMTQSPSTLSASVGDR VTITCRASQSISSWLAWY QQKPGKAPKFLIYKASRL DRGWPSRFSGSGSGTEF SLTISSLQPDDFATYYCLE YSSYIRTFGQGTKVEIK | 207 | RASQSISSW LA | 208 | KASRLDR | 209 | LEYSSYIRT | 210 |
| mAb11-0962 | VH | EVQLVESGGGLVQPGRS LRLSCAASKFTFHDYAMH WVRQAPGKGLEWVSGIS WKGDIGGYADSVKGRFTI SRDNAKNSLYLQMNSLR AEDTALYYCAKSYGSGSF YNAFDSWGQGTLVTVSS | 211 | DYAMH | 212 | GISWKGDIGGYA DSVKG | 213 | SYGSGSFYNAFDS | 214 |
| mAb11-0962 | VL | DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 215 | RASQSISSW LA | 216 | KASKLDR | 217 | LEYSSYIRT | 218 |
| mAb11-0965 | VH | EVQLVESGGGLVQPGRS LRLSCAASKFTFHDYAMH WVRQAPGKGLEWVSGIS WKGDIGGYADSVKGRFTI | 219 | DYAMH | 220 | GISWKGDIGGYA DSVKG | 221 | SYGSGSFYNAFDS | 222 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| | | SRDNAKNSLYLQMNSLR AEDTALYYCAKSYGSGSF YNAFDSWGQGTLVTVSS | | | | | | | |
| mAb11-0965 | VL | DIQMTQSPSTLSASVGDR VTITCRASQSISSWLAWY QQKPGKAPKFLIYKASKL ERGTPSRFSGSGSGTEF TLTISSLQPDDFATYYCLE YSSYIRTFGQGTKVEIK | 223 | RASQSISSW LA | 224 | KASKLER | 225 | LEYSSYIRT | 226 |
| mAb11-1021 | VH | EVQLVESGGGLVQPGRS LRLSCAASKFTFHDYAMH WVRQAPGKGLEWVSGIS WKGDIGGYVDSVKGRFTI SRDNAKNSLYLQMNSLR AEDTALYYCAKSYGSGSF YNAFDSWGQGTLVTVSS | 227 | DYAMH | 228 | GISWKGDIGGYV DSVKG | 229 | SYGSGSFYNAFDS | 230 |
| mAb11-1021 | VL | DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 231 | RASQSISSW LA | 232 | KASKLDR | 233 | LEYSSYIRT | 234 |
| mAb11-1024 | VH | EVQLVESGGGLVQPGRS LRLSCAASKFTFHDYAMH WVRQAPGKGLEWVSGIS WKGDIGGYVDSVKGRFTI SRDNAKNSLYLQMNSLR AEDTALYYCAKSYGSGSF YNAFDSWGQGTLVTVSS | 235 | DYAMH | 236 | GISWKGDIGGYV DSVKG | 237 | SYGSGSFYNAFDS | 238 |
| mAb11-1024 | VL | DIQMTQSPSTLSASVGDR VTITCRASQSISSWLAWY QQKPGKAPKFLIYKASKL ERGTPSRFSGSGSGTEF TLTISSLQPDDFATYYCLE YSSYIRTFGQGTKVEIK | 239 | RASQSISSW LA | 240 | KASKLER | 241 | LEYSSYIRT | 242 |
| mAb11-1030 | VH | EVQLVESGGGLVQPGRS LRLSCAASKFTFHDYAMH WVRQVPGKGLEWVSGIS WKGDIGGYVDSVKGRFTI SRDNAKNSLYLQMNSLR | 243 | DYAMH | 244 | GISWKGDIGGYV DSVKG | 245 | SYGSGSFYNAFDS | 246 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| mAb11-1030 | VL | AEDTALYYCAKSYGSGSF YNAFDSWGQGTLVTVSS DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 247 | RASQSISSW LA | 248 | KASKLDR | 249 | LEYSSYIRT | 250 |
| mAb11-1033 | VH | EVQLVESGGGLVQPGRS LRLSCAASKFTFHDYAMH WVRQVPGKGLEWVSGIS WKGDIGGYVDSVKGRFTI SRDNAKNSLYLQMNSLR AEDTALYYCAKSYGSGSF YNAFDSWGQGTLVTVSS | 251 | DYAMH | 252 | GISWKGDIGGYV DSVKG | 253 | SYGSGSFYNAFDS | 254 |
| mAb11-1033 | VL | DIQMTQSPSTLSASVGDR VTITCRASQSISSWLAWY QQKPGKAPKFLIYKASKL ERGTPSRFSGSGSGTEF TLTISSLQPDDFATYYCLE YSSYIRTFGQGTKVEIK | 255 | RASQSISSW LA | 256 | KASKLER | 257 | LEYSSYIRT | 258 |
| mAb11-1039 | VH | EVQLVESGGGLVQPGRS LKLSCAASKFTFHDYAMH WVRQAPGKGLEWVSGIS WKGDIGGYVDSVKGRFTI SRDNAKNSLYLQMNSLR AEDTALYYCAKSYGSGSF YNAFDSWGQGTLVTVSS | 259 | DYAMH | 260 | GISWKGDIGGYV DSVKG | 261 | SYGSGSFYNAFDS | 262 |
| mAb11-1039 | VL | DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 263 | RASQSISSW LA | 264 | KASKLDR | 265 | LEYSSYIRT | 266 |
| mAb11-1042 | VH | EVQLVESGGGLVQPGRS LKLSCAASKFTFHDYAMH WVRQAPGKGLEWVSGIS WKGDIGGYVDSVKGRFTI SRDNAKNSLYLQMNSLR AEDTALYYCAKSYGSGSF YNAFDSWGQGTLVTVSS | 267 | DYAMH | 268 | GISWKGDIGGYV DSVKG | 269 | SYGSGSFYNAFDS | 270 |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1042 | VL | DIQMTQSPSTLSASVGDR VTITCRASQSISSWLAWY QQKPGKAPKFLIYKASKL ERGTPSRFSGSGSGTEF TLTISSLQPDDFATYYCLE YSSYIRTFGQGTKVEIK | 271 | RASQSISSW LA | 272 | KASKLER | 273 | LEYSSYIRT | 274 |
| mAb11-1073 | VH | EVQLVESGGGLVQPGRS LRLSCAASGFTFHDYAMH WVRQVPGKGLEWVSGIS WKGDIGGYVDSVKGRFTI SRDNAKNSLYLQMNSLR AEDTALYYCAKSYGSGSF YNAFDSWGQGTLVTVSS | 275 | DYAMH | 276 | GISWKGDIGGYV DSVKG | 277 | SYGSGSFYNAFDS | 278 |
| mAb11-1073 | VL | DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 279 | RASQSISSW LA | 280 | KASKLDR | 281 | LEYSSYIRT | 282 |
| mAb11-1076 | VH | EVQLVESGGGLVQPGRS LRLSCAASGFTFHDYAMH WVRQVPGKGLEWVSGIS WKGDIGGYVDSVKGRFTI SRDNAKNSLYLQMNSLR AEDTALYYCAKSYGSGSF YNAFDSWGQGTLVTVSS | 283 | DYAMH | 284 | GISWKGDIGGYV DSVKG | 285 | SYGSGSFYNAFDS | 286 |
| mAb11-1076 | VL | DIQMTQSPSTLSASVGDR VTITCRASQSISSWLAWY QQKPGKAPKFLIYKASKL ERGTPSRFSGSGSGTEF TLTISSLQPDDFATYYCLE YSSYIRTFGQGTKVEIK | 287 | RASQSISSW LA | 288 | KASKLER | 289 | LEYSSYIRT | 290 |
| mAb11-1091 | VH | EVQLVESGGGLVQPGRS LKLSCAASGFTFHDYAMH WVRQVPGKGLEWVSGIS WKGDIGGYVDSVKGRFTI SRDNAKNSLYLQMNSLR AEDTALYYCAKSYGSGSF YNAFDSWGQGTLVTVSS | 291 | DYAMH | 292 | GISWKGDIGGYV DSVKG | 293 | SYGSGSFYNAFDS | 294 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| mAb11-1091 | VL | DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 295 | RASQSISSW LA | 296 | KASKLDR | 297 | LEYSSYIRT | 298 |
| mAb11-1094 | VH | EVQLVESGGGLVQPGRS LKLSCAASGFTFHDYAMH WVRQVPGKGLEWVSGIS WKGDIGGYVDSVKGRFTI SRDNAKNSLYLQMNSLR AEDTALYYCAKSYGSGSF YNAFDSWGQGTLVTVSS | 299 | DYAMH | 300 | GISWKGDIGGYV DSVKG | 301 | SYGSGSFYNAFDS | 302 |
| mAb11-1094 | VL | DIQMTQSPSTLSASVGDR VTITCRASQSISSWLAWY QQKPGKAPKFLIYKASKL ERGTPSRFSGSGSGTEF TLTISSLQPDDFATYYCLE YSSYIRTFGQGTKVEIK | 303 | RASQSISSW LA | 304 | KASKLER | 305 | LEYSSYIRT | 306 |
| mAb11-1233 | VH | EVQLVESGGGLVQPGRS LRLSCAASGFKFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 307 | DYAMH | 308 | GISWKGDIGGYV DSVKG | 309 | SYGSGSFYNAFDS | 310 |
| mAb11-1233 | VL | DIQMTQSPSTLSASVGDR VTITCRASQSISSWLAWY QQKPGKAPKFLIYKASRL DRGTPSRFSGSGSGTEF SLTISSLQPDDFATYYCLE YSSYIRTFGQGTKVEIK | 311 | RASQSISSW LA | 312 | KASRLDR | 313 | LEYSSYIRT | 314 |
| mAb11-1254 | VH | EVQLVESGGGLVQPGRS LRLSCAASGFTFHDYAMH WVRQVPGKGLEWVSGIS WKGDIGGYVDSVKGRFTI SRDNDKNSLYLQMNSLR AEDTALYYCVKSYGSGSF YNAFDSWGQGTLVTVSS | 315 | DYAMH | 316 | GISWKGDIGGYV DSVKG | 317 | SYGSGSFYNAFDS | 318 |
| mAb11-1254 | VL | DIQMTQSPSTLSASVGDR VTITCRASQSISSWLAWY | 319 | RASQSISSW LA | 320 | KASRLDR | 321 | LEYSSYIRT | 322 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence |
|---|---|---|---|---|---|---|---|---|
| | | QQKPGKAPKFLIYKASRL DRGTPSRFSGSGSGTEF SLTISSLQPDDFATYYCLE YSSYIRTFGQGTKVEIK | | | | | | |
| mAb1-1259 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 323 | DYAMH | 324 | GISWKGDIGGYV DSVKG | 325 | SYGSGSFYNAFDS | 326 |
| mAb1-1259 | VL | DIQMTQSPSTLSASVGDR VTITCRASQKISSWLAWY QQKPGKAPKFLIYKASRL DRGTPSRFSGSGSGTEF SLTISSLQPDDFATYYCLE YSSYIRTFGQGTKVEIK | 327 | RASQKISSW LA | 328 | KASRLDR | 329 | LEYSSYIRT | 330 |
| mAb1-1260 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 331 | DYAMH | 332 | GISWKGDIGGYV DSVKG | 333 | SYGSGSFYNAFDS | 334 |
| mAb1-1260 | VL | DIQMTQSPSTLSASVGDR VTITCRASQQISSWLAWY QQKPGKAPKFLIYKASRL DRGTPSRFSGSGSGTEF SLTISSLQPDDFATYYCLE YSSYIRTFGQGTKVEIK | 335 | RASQQISS WLA | 336 | KASRLDR | 337 | LEYSSYIRT | 338 |
| mAb1-1262 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 339 | DYAMH | 340 | GISWKGDIGGYV DSVKG | 341 | SYGSGSFYNAFDS | 342 |
| mAb1-1262 | VL | DIQMTQSPSTLSASVGDR VTITCRASQSIQSWLAWY QQKPGKAPKFLIYKASRL DRGTPSRFSGSGSGTEF | 343 | RASQSIQS WLA | 344 | KASRLDR | 345 | LEYSSYIRT | 346 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence |
|---|---|---|---|---|---|---|---|---|
| | | SLITSSLQPDDFATYYCLE YSSYIRTFGQGTKVEIK | | | | | | |
| mAb11-1266 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 347 | DYAMH | 348 | GISWKGDIGGYV DSVKG | 349 | SYGSGSFYNAFDS 350 |
| mAb11-1266 | VL | DIQMTQSPSTLSASVGDR VTITCRASQSISSWLAWY QQKPGKAPKFLIYKASRL DKGTPSRFSGSGSGTEF SLITSSLQPDDFATYYCLE YSSYIRTFGQGTKVEIK | 351 | RASQSISSW LA | 352 | KASRLDK | 353 | LEYSSYIRT 354 |
| mAb11-1268 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 355 | DYAMH | 356 | GISWKGDIGGYV DSVKG | 357 | SYGSGSFYNAFDS 358 |
| mAb11-1268 | VL | DIQMTQSPSTLSASVGDR VTITCRASQSISSWLAWY QQKPGKAPKFLIYKASRL DRGTPKRFSGSGSGTEF SLITSSLQPDDFATYYCLE YSSYIRTFGQGTKVEIK | 359 | RASQSISSW LA | 360 | KASRLDR | 361 | LEYSSYIRT 362 |
| mAb11-1273 | VH | EVQLVESGGGLVQPGRS LRLSCAASGFTFHDYAMH WVRQVPGKGLEWVSGIS WKGDIGGYVDSVKGRFTI SRDNEKNSLYLQMNSLR AEDTALYYCVKSYGSGSF YNAFDSWGQGTLVTVSS | 363 | DYAMH | 364 | GISWKGDIGGYV DSVKG | 365 | SYGSGSFYNAFDS 366 |
| mAb11-1273 | VL | DIQMTQSPSTLSASVGDR VTITCRASQSISSWLAWY QQKPGKAPKFLIYKASRL DRGTPSRFSGSGSGTEF SLITSELQPDDFATYYCLE YSSYIRTFGQGTKVEIK | 367 | RASQSISSW LA | 368 | KASRLDR | 369 | LEYSSYIRT 370 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence |
|---|---|---|---|---|---|---|---|---|
| mAb11-1275 | VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS | 371 | DYAMH | 372 | GISWKGDIGGYVDSVKG | 373 | SYGSGSFYNAFDS | 374 |
| mAb11-1275 | VL | DIQMTQSPSTLSASVGDRVTITCRASQSISSWLAWYQQKPGKAPKFLIYKASRLDRGTPSRFSGSGSGTEFSLTISSLTPDDFATYYCLEYSSYIRTFGQGTKVEIK | 375 | RASQSISSWLA | 376 | KASRLDR | 377 | LEYSSYIRT | 378 |
| mAb11-1276 | VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS | 379 | DYAMH | 380 | GISWKGDIGGYVDSVKG | 381 | SYGSGSFYNAFDS | 382 |
| mAb11-1276 | VL | DIQMTQSPSTLSASVGDRVTITCRASQSISSWLAWYQQKPGKAPKFLIYKASRLDRGTPSRFSGSGSGTEFSLTISSLSPDDFATYYCLEYSSYIRTFGQGTKVEIK | 383 | RASQSISSWLA | 384 | KASRLDR | 385 | LEYSSYIRT | 386 |
| mAb11-1278 | VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS | 387 | DYAMH | 388 | GISWKGDIGGYVDSVKG | 389 | SYGSGSFYNAFDS | 390 |
| mAb11-1278 | VL | DIQMTQSPSTLSASVGDRVTITCRASQSISSWLAWYQQKPGKAPKFLIYKASRLDRGTPSRFSGSGSGTEFSLTISSLQPDDFATYYCLEYQSYIRTFGQGTKVEIK | 391 | RASQSISSWLA | 392 | KASRLDR | 393 | LEYQSYIRT | 394 |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1279 | VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS | 395 | DYAMH | 396 | GISWKGDIGGYVDSVKG | 397 | SYGSGSFYNAFDS |
| mAb11-1279 | VL | DIQMTQSPSTLSASVGDRVTITCRASQSISSWLAWYQQKPGKAPKFLIYKASRLDRGTPSRFSGSGSGTEFSLTISSLQPDDFATYYCLEYKSYIRTFGQGTKVEIK | 399 | RASQSISSWLA | 400 | KASRLDR | 401 | LEYKSYIRT |
| mAb11-1282 | VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS | 403 | DYAMH | 404 | GISWKGDIGGYVDSVKG | 405 | SYGSGSFYNAFDS |
| mAb11-1282 | VL | DIQMTQSPSTLSASVGDRVTITCRASQSISSWLAWYQQKPGKAPKFLIYKASRLDRGTPSRFSGSGSGTEFSLTISSLQPDDFATYYCLEYSSWIRTFGQGTKVEIK | 407 | RASQSISSWLA | 408 | KASRLDR | 409 | LEYSSWIRT |
| mAb11-1286 | VH | EVQLVESGGGLVQPGRSLRLSCAASGFTFHDYAMHWVRQVPGKGLEWVSGISWKGDIGGYVDSVKGRFTISRDNEKNSLYLQMNSLRAEDTALYYCVKSYGSGSFYNAFDSWGQGTLVTVSS | 411 | DYAMH | 412 | GISWKGDIGGYVDSVKG | 413 | SYGSGSFYNAFDS |
| mAb11-1286 | VL | DIQMTQSPSTLSASVGDRVTITCRASQSISSWLAWYQQKPGKAPKFLIYKASRLDRGTPSRFSGSGSGTEFSLTIYDLQPDDFATYYCLEYRSYIRTFGQGTKVEIK | 415 | RASQSISSWLA | 416 | KASRLDR | 417 | LEYRSYIRT |
| mAb11-1288 | VH | EVQLVESGGGLVQPGRSLRLSCAASGFTFHDYAMH | 419 | DYAMH | 420 | GISWKGDIGGYVDSVKG | 421 | SYGSGSFYNAFDS |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| | | WVRQVPGKGLEWVSGIS WKGDIGGYVDSVKGRFTI SRDNEKNSLYLQMNSLR AEDTALYYCVKSYGSGSF YNAFDSWGQGTLVTVSS | | | | | | | |
| mAb11-1288 | VL | DIQMTQSPSTLSASVGDR VTITCRASQSISSWLAWY QQKPGKAPKFLIYKASRL DRGTPQRFSGSGSGTEF SLTIYSLQPDDFATYYCLE YNSYIRTFGQGTKVEIK | 423 | RASQSISSW LA | 424 | KASRLDR | 425 | LEYNSYIRT | 426 |
| mAb11-1344 | VH | EVQLVESGGGLVQPGRS LKLSCAASGFTFDDYAMH WVRQVPGKGLEWVSGIS WKGDIGGYVDSVKGRFTI SRDNAKNSLYLQLNSLRA EDTALYYCAKSYGSGSFY NAFDSWGQGTLVTVSS | 427 | DYAMH | 428 | GISWKGDIGGYV DSVKG | 429 | SYGSGSFYNAFDS | 430 |
| mAb11-1344 | VL | DIQMTQSPSTLSASAGDR VTITCRASQSISSWLAWY QQKPGKAPKFLIYKASKL DRGTPSRFSGSGSGTEF SLITSSLQPDDFATYYCLE YSSYIRTFGQGTKVEIK | 431 | RASQSISSW LA | 432 | KASKLDR | 433 | LEYSSYIRT | 434 |
| mAb11-1358 | VH | EVQLVESGGGLVQPGRS LKLSCAASGFTFDDYAMH WVRQVPGKGLEWVSGIS WRGDIGGYVDSVKGRFTI SRDNAKNSLYLQLNSLRA EDTALYYCVKSYGSGSFY NAFDSWGQGTLVTVSS | 435 | DYAMH | 436 | GISWRGDIGGYV DSVKG | 437 | SYGSGSFYNAFDS | 438 |
| mAb11-1358 | VL | DIQMTQSPSTLSASAGDR VTITCRASQSISSWLAWY QQKPGKAPKFLIYKASKL DRGTPSRFSGSGSGTEF SLITSSLQPDDFATYYCLE YSSYIRTFGQGTKVEIK | 439 | RASQSISSW LA | 440 | KASKLDR | 441 | LEYSSYIRT | 442 |
| mAb11-1360 | VH | EVQLVESGGGLVQPGRS LKLSCAASGFTFDDYAMH WVRQVPGKGLEWVSGIS WRGDIGGYVDSVKGRFTI | 443 | DYAMH | 444 | GISWRGDIGGYV DSVKG | 445 | SYGSGSFYNAFDS | 446 |

TABLE 2-continued

Overview of anti-FIX(a) antibody VH, VL and CDR sequences

| mAb ID | Domain | VH/VL Sequence | # | CDR1 Sequence | # | CDR2 Sequence | # | CDR3 Sequence |
|---|---|---|---|---|---|---|---|---|
| mAb11-1360 | | SRDNAKNSLYLQLNSLRA EDTALYYCVKSYGSGSFY NAFDSWGQGTLVTVSS | | | | | | |
| | VL | DIQMTQSPSTLSASVGDR VTITCRASQSISSWLAWY QQKPGKAPKLLIYKASRL ERGTPSRFSGSGSGTEF SLTISSLQPDDFATYYCLE YSSYIRTFGQGTKVEIK | 447 | RASQSISSW LA | 448 | KASRLER | 449 | LEYSSYIRT | 450 |
| mAb11-1389 | VH | EVQLVESGGGLVQPGRS LKLSCAASGFTFHDYAMH WVRQAPGKGLEWVSGIS WKGDIGGYVDSVKGRFTI SRDNAKNSLYLQMNSLR AEDTALYYCAKSYGSGSF YNAFDSWGQGTLVTVSS | 451 | DYAMH | 452 | GISWKGDIGGYV DSVKG | 453 | SYGSGSFYNAFDS | 454 |
| mAb11-1389 | VL | DIQMTQSPSTLSASAGDR VTITCRASQSISSWLAWY QQKPGKAPKFLIYKASRL DRGTPSRFSGSGSGTEF SLTISSLQPDDFATYYCLE YSSYIRTFGQGTKVEIK | 455 | RASQSISSW LA | 456 | KASRLDR | 457 | LEYSSYIRT | 458 |
| mAb11-0173 | VH | EVQLVESGGGLVQPGRS LRLSCAASGFTFHDYAMH WVRQAPGKGLEWVSGIS WKGDIGGYVDSVKGRFTI SRDNAKNSLYLQMNSLR AEDTALYYCAKSYGSGSF YNAFDSWGQGTLVTVSS | 1202 | DYAMH | 1203 | GISWKGDIGGYV DSVKG | 1204 | SYGSGSFYNAFDS | 1205 |
| mAb11-0173 | VL | DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 1206 | RASQSISSW LA | 1207 | KASKLDR | 1208 | LEYSSYIRT | 1209 |
| mAb11-1204 | VH | EVQLVESGGGLVQPGRS LRLSCAASGFTFHDYAMH WVRQVPGKGLEWVSGIS WRGDIGGYVKSVKGRFTI | 1210 | DYAMH | 1211 | GISWRGDIGGYV KSVKG | 1212 | SYGSGSFYNAFDS | 1213 |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | SRDNAKNSLYLQMNSLR AEDTALYYCVKSYGSGSF YNAFDSWGQGTLVTVSS | | | | | | |
| mAb11-1204 | VL | DIQMTQSPSTLSASVGDE VIITCRASQSISSWLAWY QQKPGKAPKFLIYKASKL ERGTPSRFSGSGSGTEF SLTISSLQPDDFATYYCLE YSSYIRTFGQGTKVEIK | 1214 | RASQSISSW LA | 1215 | KASKLER | 1216 | LEYSSYIRT | 1217 |
| mAb11-1495 | VH | EVQLVESGGGLVQPGRS LRLSCAASGFTFHDYAMH WVRQVPGKGLEWVSGIS WRGDIGGYAKSVKGRFTI SRDNAKNSLYLQMNSLR AEDTALYYCVKSYGSGSF YNAFDSWGQGTLVTVSS | 1218 | DYAMH | 1219 | GISWRGDIGGYA KSVKG | 1220 | SYGSGSFYNAFDS | 1221 |
| mAb11-1495 | VL | DIQMTQSPSTLSASVGDR VIITCRASQSISSWLAWY QQKPGKAPKFLIYKASKL DRGTPSRFSGSGSGTEF TLTISSLQPDDFATYYCLE YSSYIRTFGQGTKVEIK | 1222 | RASQSISSW LA | 1223 | KASKLDR | 1224 | LEYSSYIRT | 1225 |
| mAb11-1501 | VH | EVQLVESGGGLVQPGRS LRLSCAASGFTFDDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 1226 | DYAMH | 1227 | GISWRGDIGGYV KSVKG | 1228 | SYGSGSFYNAFDS | 1229 |
| mAb11-1501 | VL | DIQMTQSPSTLSASVGDR VIITCRASQSISSWLAWY QQKPGKAPKFLIYKASKL DRGTPSRFSGSGSGTEF TLTISSLQPDDFATYYCLE YSSYIRTFGQGTKVEIK | 1230 | RASQSISSW LA | 1231 | KASKLDR | 1232 | LEYSSYIRT | 1233 |
| mAb11-1502 | VH | EVQLVESGGGLVQPGRS LRLSCAASGFTFDDYAMH WVRQVPGKGLEWVSGIS WRGDIGGYVKSVKGRFTI | 1234 | DYAMH | 1235 | GISWRGDIGGYV KSVKG | 1236 | SYGSGSFYNAFDS | 1237 |

TABLE 2-continued

Overview of anti-FIX(a) antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | SRDNAKNSLYLQMNSLR AEDTALYYCVKSYGSGSF YNAFDSWGQGTLVTVSS | | | | | | |
| mAb11-1502 | VL | DIQMTQSPSTLSASVGDR VTITCRASQSISSWLAWY QQKPGKAPKLLIYKASKL DRGTPSRFSGSGSGTEF TLTISSLQPDDFATYYCLE YSSYIRTFGQGTKVEIK | 1238 | RASQSISSW LA | 1239 | KASKLDR | 1240 | LEYSSYIRT | 1241 |
| mAb11-1499 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 1242 | DYAMH | 1243 | GISWRGDIGGYV KSVKG | 1244 | SYGSGSFYNAFDS | 1245 |
| mAb11-1499 | VL | DIQMTQSPSTLSASVGDR VTITCRASQSISSWLAWY QQKPGKAPKFLIYKASKL DRGTPSRFSGSGSGTEF TLTISSLQPDDFATYYCLE YSSYIRTFGQGTKVEIK | 1246 | RASQSISSW LA | 1247 | KASKLDR | 1248 | LEYSSYIRT | 1249 |

TABLE 3

Overview of anti-FX antibody VH, VL and CDR sequences

| mAb ID | VH/VL Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb01-6723 | VH | EVQLVQSGAEVKKPGESLRISCKGSGYSFTTSWIVWRQMPGKGLEWMGMIDPSDSFTSYSPSFQGHVTISADKSISTAYLQWSSLKASDTAMYYCARLHYYHSEEFDVWGQGTLVTVSS | 459 | TSWIV | 460 | MIDPSDSFTSYSPSFQG | 461 | LHYYHSEEFDV | 462 |
| mAb01-6723 | VL | EIVLTQSPGTLSLSPGERATLSCRASQSVSSSYLAWYQQKPGQAPRLLIYGASSRARGIPDRFSGSGSGTDFTLTISRLEPEDFAVYYCQQFGSSRLFTFGQGTKLEIK | 463 | RASQSVSSSYLA | 464 | GASSRAR | 465 | QQFGSSRLFT | 466 |
| mAb01-8174 | VH | EVQLVQSGAEVKKPGESLRISCKGSGYSFSTSWIVWRQMPGKGLEWMGMIDPSDSFTSYSPSFQGHVTISADKSISTAYLQWSSLKASDTAMYYCARLHYYNSEEFDVWGQGTLVTVSS | 467 | TSWIV | 468 | MIDPSDSFTSYSPSFQG | 469 | LHYYNSEEFDV | 470 |
| mAb01-8174 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSQLFTFGQGTKLEIK | 471 | RASQSVSSSYLA | 472 | GQSSRTR | 473 | QQFGDSQLFT | 474 |
| mAb01-8913 | VH | EVQLVQSGAEVKKPGESLRISCKGSGYSFSTSWIVWRQMPGKGLEWMGMIDPSDSFTSYSPSFQGHVTISADKSISTAYLQWSSLKASDTAMYYCARLHYYNSEEFDVWGQGTLVTVSS | 475 | TSWIV | 476 | MIDPSDSFTSYSPSFQG | 477 | LHYYNSEEFDV | 478 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb01-8913 | VL | EIVLTQSPGTLSLSAGE RATLSCRASQSVSSSYL AWYQQKPGQAPRLLIY GASSRARGIPDRFSGS GSGTDFTLTISRLEPED FAVYYCQQFGSSRLFTF GQGTKLEIK | 479 | RASQSVSSS YLA | 480 | GASSRAR | 481 | QQFGSSRLFT | 482 |
| mAb01-9772 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 483 | TSWIS | 484 | MIDPSDSYTSYSPSFQ G | 485 | LHYYNSEEFDV | 486 |
| mAb01-9772 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQYGDSQLFT FGQGTKLEIK | 487 | RASQSVSSS YLA | 488 | GQSSRTR | 489 | QQYGDSQLFT | 490 |
| mAb01-9778 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYYNSEEFDVWGQGT LVTVSS | 491 | TSWIS | 492 | MIDPSDSFTSYSPSFQ G | 493 | LHYYNSEEFDV | 494 |
| mAb01-9778 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQYGDSQLFT FGQGTKLEIK | 495 | RASQSVSSS YLA | 496 | GQSSRTR | 497 | QQYGDSQLFT | 498 |
| mAb11-1114 | VH | EVQLVQSGAEVKKPGE SLRISCKGSGYSFSTSW ISWVRQMPGKGLEWM GMIDPSDSYTSYSPSFQ GHVTISADKSISTAYLQ | 499 | TSWIS | 500 | MIDPSDSYTSYSPSFQ G | 501 | LHYYNSEEFDV | 502 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYNSEEFDVWGQGT MVTVSS | | | | | | |
| mAb11-1114 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSQLFT FGQGTKLEIK | 503 | RASQSVSSS YLA | 504 | GQSSRTR | 505 | QQFGDSQLFT | 506 |
| mAb11-1115 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 507 | TSWIS | 508 | MIDPSDSFTSYSPSFQ G | 509 | LHYYHSEEFDV | 510 |
| mAb11-1115 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSQLFT FGQGTKLEIK | 511 | RASQSVSSS YLA | 512 | GQSSRTR | 513 | QQFGDSQLFT | 514 |
| mAb11-1116 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 515 | TSWIS | 516 | MIDPSDSYTSYSPSFQ G | 517 | LHYYHSEEFDV | 518 |
| mAb11-1116 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSQLFT FGQGTKLEIK | 519 | RASQSVSSS YLA | 520 | GQSSRTR | 521 | QQFGDSQLFT | 522 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1117 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 523 | TSWIS | 524 | MIDPSDSYTSYSPSFQG | 525 | LHYYHSEEFDV | 526 |
| mAb11-1117 | VL | EIVLTQSPGTLSLSPGE RATLSCRASQSVSSSYL AWYQQKPGQAPRLLIY GQSSRTGIPDRFSGS GSGTDFTLTISRLEPED FAVYYCQQFGDSQLFT FGQGTKLEIK | 527 | RASQSVSSS YLA | 528 | GQSSRTR | 529 | QQFGDSQLFT | 530 |
| mAb11-1118 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYYNSEEFDVWGQGT LVTVSS | 531 | TSWIS | 532 | MIDPSDSFTSYSPSFQG | 533 | LHYYNSEEFDV | 534 |
| mAb11-1118 | VL | EIVLTQSPGTLSLSPGE RATLSCRASQSVSSSYL AWYQQKPGQAPRLLIY GQSSRTGIPDRFSGS GSGTDFTLTISRLEPED FAVYYCQQFGDSQLFT FGQGTKLEIK | 535 | RASQSVSSS YLA | 536 | GQSSRTR | 537 | QQFGDSQLFT | 538 |
| mAb11-1119 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 539 | TSWIV | 540 | MIDPSDSYTSYSPSFQG | 541 | LHYYNSEEFDV | 542 |
| mAb11-1119 | VL | EIVLTQSPGTLSLSPGE RATLSCRASQSVSSSYL AWYQQKPGQAPRLLIY GQSSRTGIPDRFSGS | 543 | RASQSVSSS YLA | 544 | GQSSRTR | 545 | QQFGDSQLFT | 546 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQFGDSQLFT FGQGTKLEIK | | | | | | |
| mAb11-1120 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT MVTVSS | 547 | TSWIV | 548 | MIDPSDSYTSYSPSFQG | 549 | LHYYNSEEFDV |
| mAb11-1120 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSQLFT FGQGTKLEIK | 551 | RASQSVSSS YLA | 552 | GQSSRTR | 553 | QQFGDSQLFT |
| mAb11-1121 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 555 | TSWIV | 556 | MIDPSDSFTSYSPSFQG | 557 | LHYYNSEEFDV |
| mAb11-1121 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQYGDSQLFT FGQGTKLEIK | 559 | RASQSVSSS YLA | 560 | GQSSRTR | 561 | QQYGDSQLFT |
| mAb11-1122 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 563 | TSWIS | 564 | MIDPSDSFTSYSPSFQG | 565 | LHYYHSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1122 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK | 567 | RASQSVSSSYLA | 568 | GQSSRTR | 570 | QQYGDSQLFT |
| mAb11-1123 | VH | EVQLVQSGAEVKKPGESLRISCKGSGYSFTTSWISWVRQMPGKGLEWMGMIDPSDSYTSYSPSFQGHVTISADKSISTAYLQWSSLKASDTAMYYCARLHYHSEEFDVWGQGTLVTVSS | 571 | TSWIS | 572 | MIDPSDSYTSYSPSFQG | 574 | LHYYHSEEFDV |
| mAb11-1123 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK | 575 | RASQSVSSSYLA | 576 | GQSSRTR | 578 | QQYGDSQLFT |
| mAb11-1124 | VH | EVQLVQSGAEVKKPGESLRISCKGSGYSFTTSWISWVRQMPGKGLEWMGMIDPSDSYTSYSPSFQGHVTISADKSISTAYLQWSSLKASDTAMYYCARLHYHSEEFDVWGQGTMVTVSS | 579 | TSWIS | 580 | MIDPSDSYTSYSPSFQG | 582 | LHYYHSEEFDV |
| mAb11-1124 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQYGDSQLFTFGQGTKLEIK | 583 | RASQSVSSSYLA | 584 | GQSSRTR | 586 | QQYGDSQLFT |
| mAb11-1125 | VH | EVQLVQSGAEVKKPGESLRISCKGSGYSFSTSWIVWVRQMPGKGLEWMGMIDPSDSYTSYSPSFQGHVTISADKSISTAYLQ | 587 | TSWIV | 588 | MIDPSDSYTSYSPSFQG | 590 | LHYYNSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYNSEEFDVWGQGT LVTVSS | | | | | | |
| mAb11-1125 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQYGDSQLFT FGQGTKLEIK | 591 | RASQSVSSS YLA | 592 | GQSSRTR | 593 | QQYGDSQLFT |
| mAb11-1127 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 595 | TSWIV | 596 | MIDPSDSFTSYSPSFQ G | 597 | LHYYNSEEFDV |
| mAb11-1127 | VL | EIVLTQSPGTLSLSPGE RATLSCRASQSVSSSYL AWYQQKPGQAPRLLIY GASSRARGIPDRFSGS GSGTDFTLTISRLEPED FAVYYCQQYGDSRLFT FGQGTKLEIK | 599 | RASQSVSSS YLA | 600 | GASSRAR | 601 | QQYGDSRLFT |
| mAb11-1128 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 603 | TSWIS | 604 | MIDPSDSYTSYSPSFQ G | 605 | LHYYNSEEFDV |
| mAb11-1128 | VL | EIVLTQSPGTLSLSPGE RATLSCRASQSVSSSYL AWYQQKPGQAPRLLIY GASSRARGIPDRFSGS GSGTDFTLTISRLEPED FAVYYCQQYGDRLFT FGQGTKLEIK | 607 | RASQSVSSS YLA | 608 | GASSRAR | 609 | QQYGDRLFT |

TABLE 3-continued

Overview of anti-FX antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| mAb11-1129 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 611 | TSWIS | 612 | MIDPSDSFTSYSPSFQG | 613 | LHYYHSEEFDV | 614 |
| mAb11-1129 | VL | EIVLTQSPGTLSLSPGE RATLSCRASQSVSSSYL AWYQQKPGQAPRLLIY GASSRARGIPDRFSGS GSGTDFTLTISRLEPED FAVYYCQQYGDSRLFT FGQGTKLEIK | 615 | RASQSVSSS YLA | 616 | GASSRAR | 617 | QQYGDSRLFT | 618 |
| mAb11-1130 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 619 | TSWIS | 620 | MIDPSDSYTSYSPSFQG | 621 | LHYYHSEEFDV | 622 |
| mAb11-1130 | VL | EIVLTQSPGTLSLSPGE RATLSCRASQSVSSSYL AWYQQKPGQAPRLLIY GASSRARGIPDRFSGS GSGTDFTLTISRLEPED FAVYYCQQYGDSRLFT FGQGTKLEIK | 623 | RASQSVSSS YLA | 624 | GASSRAR | 625 | QQYGDSRLFT | 626 |
| mAb11-1131 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 627 | TSWIS | 628 | MIDPSDSYTSYSPSFQG | 629 | LHYYHSEEFDV | 630 |
| mAb11-1131 | VL | EIVLTQSPGTLSLSPGE RATLSCRASQSVSSSYL AWYQQKPGQAPRLLIY GASSRARGIPDRFSGS | 631 | RASQSVSSS YLA | 632 | GASSRAR | 633 | QQYGDSRLFT | 634 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQYGDSRLFT FGQGTKLEIK | | | | | | |
| mAb11-1132 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYYNSEEFDVWGQGT LVTVSS | 635 | TSWIS | 636 | MIDPSDSFTSYSPSFQG | 637 | LHYYNSEEFDV |
| mAb11-1132 | VL | EIVLTQSPGTLSLSPGE RATLSCRASQSVSSSYL AWYQQKPGQAPRLLIY GASSRARGIPDRFSGS GSGTDFTLTISRLEPED FAVYYCQQYGDSRLFT FGQGTKLEIK | 639 | RASQSVSSS YLA | 640 | GASSRAR | 641 | QQYGDSRLFT |
| mAb11-1133 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 643 | TSWIV | 644 | MIDPSDSYTSYSPSFQG | 645 | LHYYNSEEFDV |
| mAb11-1133 | VL | EIVLTQSPGTLSLSPGE RATLSCRASQSVSSSYL AWYQQKPGQAPRLLIY GASSRARGIPDRFSGS GSGTDFTLTISRLEPED FAVYYCQQYGDSRLFT FGQGTKLEIK | 647 | RASQSVSSS YLA | 648 | GASSRAR | 649 | QQYGDSRLFT |
| mAb11-1416 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 651 | TSWIV | 652 | MIDPSDSFTSYSPSFQG | 653 | LHYYNSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1416 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSRLFTFGQGTKLEIK | 655 | RASQSVSSSYLA | 656 | GQSSRTR | 657 | QQFGDSRLFT |
| mAb11-1417 | VH | EVQLVQSGAEVKKPGESLRISCKGSGYSFSTSWISWVRQMPGKGLEWMGMIDPSDSYTSYSPSFQGHVTISADKSISTAYLQWSSLKASDTAMYYCARLHYYNSEEFDVWGQGTMVTVSS | 659 | TSWIS | 660 | MIDPSDSYTSYSPSFQG | 661 | LHYYNSEEFDV |
| mAb11-1417 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSRLFTFGQGTKLEIK | 663 | RASQSVSSSYLA | 664 | GQSSRTR | 665 | QQFGDSRLFT |
| mAb11-1418 | VH | EVQLVQSGAEVKKPGESLRISCKGSGYSFTTSWISWVRQMPGKGLEWMGMIDPSDSFTSYSPSFQGHVTISADKSISTAYLQWSSLKASDTAMYYCARLHYYHSEEFDVWGQGTMVTVSS | 667 | TSWIS | 668 | MIDPSDSFTSYSPSFQG | 669 | LHYYHSEEFDV |
| mAb11-1418 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDSRLFTFGQGTKLEIK | 671 | RASQSVSSSYLA | 672 | GQSSRTR | 673 | QQFGDSRLFT |
| mAb11-1419 | VH | EVQLVQSGAEVKKPGESLRISCKGSGYSFTTSWISWVRQMPGKGLEWMGMIDPSDSYTSYSPSFQGHVTISADKSISTAYLQ | 675 | TSWIS | 676 | MIDPSDSYTSYSPSFQG | 677 | LHYYHSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYHSEEFDVWGQGT LVTVSS | | | | | | |
| mAb11-1419 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSRLFT FGQGTKLEIK | 679 | RASQSVSSS YLA | 680 | GQSSRTR | 681 | QQFGDSRLFT | 682 |
| mAb11-1420 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 683 | TSWIS | 684 | MIDPSDSYTSYSPSFQ G | 685 | LHYYHSEEFDV | 686 |
| mAb11-1420 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSRLFT FGQGTKLEIK | 687 | RASQSVSSS YLA | 688 | GQSSRTR | 689 | QQFGDSRLFT | 690 |
| mAb11-1421 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYNSEEFDVWGQGT LVTVSS | 691 | TSWIS | 692 | MIDPSDSFTSYSPSFQ G | 693 | LHYYNSEEFDV | 694 |
| mAb11-1421 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSRLFT FGQGTKLEIK | 695 | RASQSVSSS YLA | 696 | GQSSRTR | 697 | QQFGDSRLFT | 698 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1422 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 699 | TSWIV | 700 | MIDPSDSYTSYSPSFQG | 701 | LHYYNSEEFDV | 702 |
| mAb11-1422 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDSRLFT FGQGTKLEIK | 703 | RASQSVSSS YLA | 704 | GQSSRTR | 705 | QQFGDSRLFT | 706 |
| mAb11-1431 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 707 | TSWIV | 708 | MIDPSDSFTSYSPSFQG | 709 | LHYYNSEEFDV | 710 |
| mAb11-1431 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGSQLFT FGQGTKLEIK | 711 | RASQSVSSS YLA | 712 | GQSSRTR | 713 | QQFGSQLFT | 714 |
| mAb11-1432 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 715 | TSWIV | 716 | MIDPSDSFTSYSPSFQG | 717 | LHYYNSEEFDV | 718 |
| mAb11-1432 | VL | EIVLTQSPGTLSLSPGE RATLSCRASQSVSSSYL AWYQQKPGQAPRLLIY GQSSRTRGIPDRFSGS | 719 | RASQSVSSS YLA | 720 | GQSSRTR | 721 | QQFGESQLFT | 722 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQFGESQLFT FGQGTKLEIK | | | | | | |
| mAb11-1433 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 723 | TSWIV | 724 | MIDPSDSFTSYSPSFQG | 725 | LHYYNSEEFDV |
| mAb11-1433 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGNSQLFT FGQGTKLEIK | 727 | RASQSVSSS YLA | 728 | GQSSRTR | 729 | QQFGNSQLFT |
| mAb11-1434 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 731 | TSWIV | 732 | MIDPSDSFTSYSPSFQG | 733 | LHYYNSEEFDV |
| mAb11-1434 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGQSQLFT FGQGTKLEIK | 735 | RASQSVSSS YLA | 736 | GQSSRTR | 737 | QQFGQSQLFT |
| mAb11-1435 | VH | EVQLVQSGAEVKKPGE SLRISCKGSGYSFSTSW IVWVRQMPGKGLEWM GMIDPSDSFTSYSPSFQ GHVTISADKSISTAYLQ WSSLKASDTAMYYCAR LHYYNSEEFDVWGQGT LVTVSS | 739 | TSWIV | 740 | MIDPSDSFTSYSPSFQG | 741 | LHYYNSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1435 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDAQLFTFGQGTKLEIK | 743 | RASQSVSSSYLA | 744 | GQSSRTR | 745 | QQFGDAQLFT |
| mAb11-1436 | VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYNSEEFDVWGQGTLVTVSS | 747 | TSWIV | 748 | MIDPSDSFTSYSPSFQG | 749 | LHYYNSEEFDV |
| mAb11-1436 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDTQLFTFGQGTKLEIK | 751 | RASQSVSSSYLA | 752 | GQSSRTR | 753 | QQFGDTQLFT |
| mAb11-1437 | VH | EVQLVQSGAEVKKPGESLRISCKGSGYSFSTSWIVWVRQMPGKGLEWMGMIDPSDSFTSYSPSFQGHVTISADKSISTAYLQWSSLKASDTAMYYCARLHYYNSEEFDVWGQGTLVTVSS | 755 | TSWIV | 756 | MIDPSDSFTSYSPSFQG | 757 | LHYYNSEEFDV |
| mAb11-1437 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDNQLFTFGQGTKLEIK | 759 | RASQSVSSSYLA | 760 | GQSSRTR | 761 | QQFGDNQLFT |
| mAb11-1439 | VH | EVQLVQSGAEVKKPGESLRISCKGSGYSFSTSWISWVRQMPGKGLEWMGMIDPSDSYTSYSPSFQGHVTISADKSISTAYLQ | 763 | TSWIS | 764 | MIDPSDSYTSYSPSFQG | 765 | LHYYNSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYNSEEFDVWGQGT MVTVSS | | | | | | |
| mAb11-1439 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGSSQLFT FGQGTKLEIK | 767 | RASQSVSSS YLA | 768 | GQSSRTR | 769 | QQFGSSQLFT | 770 |
| mAb11-1440 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 771 | TSWIS | 772 | MIDPSDSFTSYSPSFQ G | 773 | LHYYHSEEFDV | 774 |
| mAb11-1440 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGSSQLFT FGQGTKLEIK | 775 | RASQSVSSS YLA | 776 | GQSSRTR | 777 | QQFGSSQLFT | 778 |
| mAb11-1441 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 779 | TSWIS | 780 | MIDPSDSYTSYSPSFQ G | 781 | LHYYHSEEFDV | 782 |
| mAb11-1441 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGSSQLFT FGQGTKLEIK | 783 | RASQSVSSS YLA | 784 | GQSSRTR | 785 | QQFGSSQLFT | 786 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1442 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 787 | TSWIS | 788 | MIDPSDSYTSYSPSFQG | 789 | LHYYHSEEFDV | 790 |
| mAb11-1442 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGSSQLFT FGQGTKLEIK | 791 | RASQSVSSS YLA | 792 | GQSSRTR | 793 | QQFGSSQLFT | 794 |
| mAb11-1443 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYYNSEEFDVWGQGT LVTVSS | 795 | TSWIS | 796 | MIDPSDSFTSYSPSFQG | 797 | LHYYNSEEFDV | 798 |
| mAb11-1443 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGSSQLFT FGQGTKLEIK | 799 | RASQSVSSS YLA | 800 | GQSSRTR | 801 | QQFGSSQLFT | 802 |
| mAb11-1444 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 803 | TSWIV | 804 | MIDPSDSYTSYSPSFQG | 805 | LHYYNSEEFDV | 806 |
| mAb11-1444 | VL | EIVLTQSPGTLSLSPGE RATLSCRASQSVSSSYL AWYQQKPGQAPRLLIY GQSSRTRGIPDRFSGS | 807 | RASQSVSSS YLA | 808 | GQSSRTR | 809 | QQFGSSQLFT | 810 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQFGSSQLFT FGQGTKLEIK | | | | | | |
| mAb11-1445 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT MVTVSS | 811 | TSWIV | 812 | MIDPSDSYTSYSPSFQG | 813 | LHYYNSEEFDV |
| mAb11-1445 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGSSQLFT FGQGTKLEIK | 815 | RASQSVSSS YLA | 816 | GQSSRTR | 817 | QQFGSSQLFT |
| mAb11-1446 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 819 | TSWIS | 820 | MIDPSDSYTSYSPSFQG | 821 | LHYYNSEEFDV |
| mAb11-1446 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGESQLFT FGQGTKLEIK | 823 | RASQSVSSS YLA | 824 | GQSSRTR | 825 | QQFGESQLFT |
| mAb11-1447 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 827 | TSWIS | 828 | MIDPSDSFTSYSPSFQG | 829 | LHYYHSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1447 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGESQLFT FGQGTKLEIK | 831 | RASQSVSSS YLA | 832 | GQSSRTR | 833 | QQFGESQLFT | 834 |
| mAb11-1448 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 835 | TSWIS | 836 | MIDPSDSYTSYSPSFQ G | 837 | LHYYHSEEFDV | 838 |
| mAb11-1448 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGESQLFT FGQGTKLEIK | 839 | RASQSVSSS YLA | 840 | GQSSRTR | 841 | QQFGESQLFT | 842 |
| mAb11-1449 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 843 | TSWIS | 844 | MIDPSDSYTSYSPSFQ G | 845 | LHYYHSEEFDV | 846 |
| mAb11-1449 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGESQLFT FGQGTKLEIK | 847 | RASQSVSSS YLA | 848 | GQSSRTR | 849 | QQFGESQLFT | 850 |
| mAb11-1450 | VH | EVQLVQSGAEVKKPGE SLRISCKGSGYSFSTSW ISWVRQMPGKGLEWM GMIDPSDSFTSYSPSFQ GHVTISADKSISTAYLQ | 851 | TSWIS | 852 | MIDPSDSFTSYSPSFQ G | 853 | LHYYNSEEFDV | 854 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYNSEEFDVWGQGT LVTVSS | | | | | | |
| mAb11-1450 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGESQLFT FGQGTKLEIK | 855 | RASQSVSSS YLA | 856 | GQSSRTR | 857 | QQFGESQLFT |
| mAb11-1451 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 859 | TSWIV | 860 | MIDPSDSYTSYSPSFQG | 861 | LHYYNSEEFDV |
| mAb11-1451 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGESQLFT FGQGTKLEIK | 863 | RASQSVSSS YLA | 864 | GQSSRTR | 865 | QQFGESQLFT |
| mAb11-1452 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT MVTVSS | 867 | TSWIV | 868 | MIDPSDSYTSYSPSFQG | 869 | LHYYNSEEFDV |
| mAb11-1452 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGESQLFT FGQGTKLEIK | 871 | RASQSVSSS YLA | 872 | GQSSRTR | 873 | QQFGESQLFT |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence | # |
|---|---|---|---|---|---|---|---|---|---|
| mAb11-1453 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 875 | TSWIS | 876 | MIDPSDSYTSYSPSFQG | 877 | LHYYNSEEFDV | 878 |
| mAb11-1453 | VL | EIVLTQSPGTLSLPGE RATLSCRASQSVSSSYL AWYQQKPGQAPRLLIY GQSSRTRGIPDRFSGS GSGTDFTLTISRLEPED FAVYYCQQFGNSQLFT FGQGTKLEIK | 879 | RASQSVSSS YLA | 880 | GQSSRTR | 881 | QQFGNSQLFT | 882 |
| mAb11-1454 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 883 | TSWIS | 884 | MIDPSDSFTSYSPSFQG | 885 | LHYYHSEEFDV | 886 |
| mAb11-1454 | VL | EIVLTQSPGTLSLPGE RATLSCRASQSVSSSYL AWYQQKPGQAPRLLIY GQSSRTRGIPDRFSGS GSGTDFTLTISRLEPED FAVYYCQQFGNSQLFT FGQGTKLEIK | 887 | RASQSVSSS YLA | 888 | GQSSRTR | 889 | QQFGNSQLFT | 890 |
| mAb11-1455 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 891 | TSWIS | 892 | MIDPSDSYTSYSPSFQG | 893 | LHYYHSEEFDV | 894 |
| mAb11-1455 | VL | EIVLTQSPGTLSLPGE RATLSCRASQSVSSSYL AWYQQKPGQAPRLLIY GQSSRTRGIPDRFSGS | 895 | RASQSVSSS YLA | 896 | GQSSRTR | 897 | QQFGNSQLFT | 898 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQFGNSQLFT FGQGTKLEIK | | | | | | |
| mAb11-1456 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 899 | TSWIS | 900 | MIDPSDSYTSYSPSFQG | 901 | LHYYHSEEFDV | 902 |
| mAb11-1456 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGNSQLFT FGQGTKLEIK | 903 | RASQSVSSS YLA | 904 | GQSSRTR | 905 | QQFGNSQLFT | 906 |
| mAb11-1457 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYYNSEEFDVWGQGT LVTVSS | 907 | TSWIS | 908 | MIDPSDSFTSYSPSFQG | 909 | LHYYNSEEFDV | 910 |
| mAb11-1457 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGNSQLFT FGQGTKLEIK | 911 | RASQSVSSS YLA | 912 | GQSSRTR | 913 | QQFGNSQLFT | 914 |
| mAb11-1458 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 915 | TSWIV | 916 | MIDPSDSYTSYSPSFQG | 917 | LHYYNSEEFDV | 918 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1458 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGNSQLFT FGQGTKLEIK | 919 | RASQSVSSS YLA | 920 | GQSSRTR | 921 | QQFGNSQLFT | 922 |
| mAb11-1459 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT MVTVSS | 923 | TSWIV | 924 | MIDPSDSYTSYSPSFQ G | 925 | LHYYNSEEFDV | 926 |
| mAb11-1459 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGNSQLFT FGQGTKLEIK | 927 | RASQSVSSS YLA | 928 | GQSSRTR | 929 | QQFGNSQLFT | 930 |
| mAb11-1460 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 931 | TSWIS | 932 | MIDPSDSYTSYSPSFQ G | 933 | LHYYNSEEFDV | 934 |
| mAb11-1460 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGQSQLFT FGQGTKLEIK | 935 | RASQSVSSS YLA | 936 | GQSSRTR | 937 | QQFGQSQLFT | 938 |
| mAb11-1461 | VH | EVQLVQSGAEVKKPGE SLRISCKGSGYSFTTSW ISWVRQMPGKGLEWM GMIDPSDSFTSYSPSFQ GHVTISADKSISTAYLQ | 939 | TSWIS | 940 | MIDPSDSFTSYSPSFQ G | 941 | LHYYHSEEFDV | 942 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYHSEEFDVWGQGT MVTVSS | | | | | | |
| mAb11-1461 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGQSQLFT FGQGTKLEIK | 943 | RASQSVSSS YLA | 944 | GQSSRTR | 945 | QQFGQSQLFT | 946 |
| mAb11-1463 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 947 | TSWIS | 948 | MIDPSDSYTSYSPSFQ G | 949 | LHYYHSEEFDV | 950 |
| mAb11-1463 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGQSQLFT FGQGTKLEIK | 951 | RASQSVSSS YLA | 952 | GQSSRTR | 953 | QQFGQSQLFT | 954 |
| mAb11-1464 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYNSEEFDVWGQGT LVTVSS | 955 | TSWIS | 956 | MIDPSDSFTSYSPSFQ G | 957 | LHYYNSEEFDV | 958 |
| mAb11-1464 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGQSQLFT FGQGTKLEIK | 959 | RASQSVSSS YLA | 960 | GQSSRTR | 961 | QQFGQSQLFT | 962 |

TABLE 3-continued

Overview of anti-FX antibody VH, VL and CDR sequences

| mAb ID | Domain | VH/VL Sequence | # | CDR1 Sequence | # | CDR2 Sequence | # | CDR3 Sequence | # |
|---|---|---|---|---|---|---|---|---|---|
| mAb11-1465 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 963 | TSWIV | 964 | MIDPSDSYTSYSPSFQG | 965 | LHYYNSEEFDV | 966 |
| mAb11-1465 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGQSQLFT FGQGTKLEIK | 967 | RASQSVSSS YLA | 968 | GQSSRTR | 969 | QQFGQSQLFT | 970 |
| mAb11-1466 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT MVTVSS | 971 | TSWIV | 972 | MIDPSDSYTSYSPSFQG | 973 | LHYYNSEEFDV | 974 |
| mAb11-1466 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGQSQLFT FGQGTKLEIK | 975 | RASQSVSSS YLA | 976 | GQSSRTR | 977 | QQFGQSQLFT | 978 |
| mAb11-1467 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 979 | TSWIS | 980 | MIDPSDSYTSYSPSFQG | 981 | LHYYNSEEFDV | 982 |
| mAb11-1467 | VL | EIVLTQSPGTLSLSPGE RATLSCRASQSVSSSYL AWYQQKPGQAPRLLIY GQSSRTRGIPDRFSGS | 983 | RASQSVSSS YLA | 984 | GQSSRTR | 985 | QQFGDAQLFT | 986 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQFGDAQLFT FGQGTKLEIK | | | | | | |
| mAb11-1468 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 987 | TSWIS | 988 | MIDPSDSFTSYSPSFQG | 989 | LHYYHSEEFDV |
| mAb11-1468 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDAQLFT FGQGTKLEIK | 991 | RASQSVSSS YLA | 992 | GQSSRTR | 993 | QQFGDAQLFT |
| mAb11-1470 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 995 | TSWIS | 996 | MIDPSDSYTSYSPSFQG | 997 | LHYYHSEEFDV |
| mAb11-1470 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDAQLFT FGQGTKLEIK | 999 | RASQSVSSS YLA | 1000 | GQSSRTR | 1001 | QQFGDAQLFT |
| mAb11-1471 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYYNSEEFDVWGQGT LVTVSS | 1003 | TSWIS | 1004 | MIDPSDSFTSYSPSFQG | 1005 | LHYYNSEEFDV |

TABLE 3-continued

Overview of anti-FX antibody VH, VL and CDR sequences

| | VH/VL | | | CDR1 | | CDR2 | | CDR3 | |
|---|---|---|---|---|---|---|---|---|---|
| mAb ID | Domain | Sequence | # | Sequence | # | Sequence | # | Sequence | # |
| mAb11-1471 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDAQLFTFGQGTKLEIK | 1007 | RASQSVSSSYLA | 1008 | GQSSRTR | 1009 | QQFGDAQLFT | 1010 |
| mAb11-1472 | VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTLVTVSS | 1011 | TSWIV | 1012 | MIDPSDSYTSYSPSFQG | 1013 | LHYYNSEEFDV | 1014 |
| mAb11-1472 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDAQLFTFGQGTKLEIK | 1015 | RASQSVSSSYLA | 1016 | GQSSRTR | 1017 | QQFGDAQLFT | 1018 |
| mAb11-1473 | VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS | 1019 | TSWIV | 1020 | MIDPSDSYTSYSPSFQG | 1021 | LHYYNSEEFDV | 1022 |
| mAb11-1473 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDAQLFTFGQGTKLEIK | 1023 | RASQSVSSSYLA | 1024 | GQSSRTR | 1025 | QQFGDAQLFT | 1026 |
| mAb11-1474 | VH | EVQLVQSGAEVKKPGESLRISCKGSGYSFSTSWISWVRQMPGKGLEWMGMIDPSDSYTSYSPSFQGHVTISADKSISTAYLQ | 1027 | TSWIS | 1028 | MIDPSDSYTSYSPSFQG | 1029 | LHYYNSEEFDV | 1030 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYNSEEFDVWGQGT MVTVSS | | | | | | |
| mAb11-1474 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDTQLFT FGQGTKLEIK | 1031 | RASQSVSSS YLA | 1032 | GQSSRTR | 1033 | QQFGDTQLFT | 1034 |
| mAb11-1475 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 1035 | TSWIS | 1036 | MIDPSDSFTSYSPSFQ G | 1037 | LHYYHSEEFDV | 1038 |
| mAb11-1475 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDTQLFT FGQGTKLEIK | 1039 | RASQSVSSS YLA | 1040 | GQSSRTR | 1041 | QQFGDTQLFT | 1042 |
| mAb11-1476 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 1043 | TSWIS | 1044 | MIDPSDSYTSYSPSFQ G | 1045 | LHYYHSEEFDV | 1046 |
| mAb11-1476 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDTQLFT FGQGTKLEIK | 1047 | RASQSVSSS YLA | 1048 | GQSSRTR | 1049 | QQFGDTQLFT | 1050 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1477 | VH | EVQLVQSGAEVKKPGESLRISCKGSGYSFTTSWISWVRQMPGKGLEWMGMIDPSDSYTSYSPSFQGHVTISADKSISTAYLQWSSLKASDTAMYYCARLHYYHSEEFDVWGQGTMVTVSS | 1051 | TSWIS | 1052 | MIDPSDSYTSYSPSFQG | 1053 | LHYYHSEEFDV | 1054 |
| mAb11-1477 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDTQLFTFGQGTKLEIK | 1055 | RASQSVSSSYLA | 1056 | GQSSRTR | 1057 | QQFGDTQLFT | 1058 |
| mAb11-1478 | VH | EVQLVQSGAEVKKPGESLRISCKGSGYSFSTSWISWVRQMPGKGLEWMGMIDPSDSFTSYSPSFQGHVTISADKSISTAYLQWSSLKASDTAMYYCARLHYYNSEEFDVWGQGTLVTVSS | 1059 | TSWIS | 1060 | MIDPSDSFTSYSPSFQG | 1061 | LHYYNSEEFDV | 1062 |
| mAb11-1478 | VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGDTQLFTFGQGTKLEIK | 1063 | RASQSVSSSYLA | 1064 | GQSSRTR | 1065 | QQFGDTQLFT | 1066 |
| mAb11-1479 | VH | EVQLVQSGAEVKKPGESLRISCKGSGYSFSTSWIVWRQMPGKGLEWMGMIDPSDSYTSYSPSFQGHVTISADKSISTAYLQWSSLKASDTAMYYCARLHYYNSEEFDVWGQGTLVTVSS | 1067 | TSWIV | 1068 | MIDPSDSYTSYSPSFQG | 1069 | LHYYNSEEFDV | 1070 |
| mAb11-1479 | VL | EIVLTQSPGTLSLSPGERATLSCRASQSVSSSYLAWYQQKPGQAPRLLIYGQSSRTRGIPDRFSGS | 1071 | RASQSVSSSYLA | 1072 | GQSSRTR | 1073 | QQFGDTQLFT | 1074 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQFGDTQLFT FGQGTKLEIK | | | | | | |
| mAb11-1480 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT MVTVSS | 1075 | TSWIV | 1076 | MIDPSDSYTSYSPSFQG | 1077 | LHYYNSEEFDV |
| mAb11-1480 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDTQLFT FGQGTKLEIK | 1079 | RASQSVSSS YLA | 1080 | GQSSRTR | 1081 | QQFGDTQLFT |
| mAb11-1481 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 1083 | TSWIS | 1084 | MIDPSDSYTSYSPSFQG | 1085 | LHYYNSEEFDV |
| mAb11-1481 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDNQLFT FGQGTKLEIK | 1087 | RASQSVSSS YLA | 1088 | GQSSRTR | 1089 | QQFGDNQLFT |
| mAb11-1482 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 1091 | TSWIS | 1092 | MIDPSDSFTSYSPSFQG | 1093 | LHYYHSEEFDV |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1482 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDNQLFT FGQGTKLEIK | 1095 | RASQSVSSS YLA | 1096 | GQSSRTR | 1097 | QQFGDNQLFT | 1098 |
| mAb11-1483 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 1099 | TSWIS | 1100 | MIDPSDSYTSYSPSFQ G | 1101 | LHYYHSEEFDV | 1102 |
| mAb11-1483 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDNQLFT FGQGTKLEIK | 1103 | RASQSVSSS YLA | 1104 | GQSSRTR | 1105 | QQFGDNQLFT | 1106 |
| mAb11-1484 | VH | EVQLVQSGAEVKKPGE SLISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 1107 | TSWIS | 1108 | MIDPSDSYTSYSPSFQ G | 1109 | LHYYHSEEFDV | 1110 |
| mAb11-1484 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDNQLFT FGQGTKLEIK | 1111 | RASQSVSSS YLA | 1112 | GQSSRTR | 1113 | QQFGDNQLFT | 1114 |
| mAb11-1485 | VH | EVQLVQSGAEVKKPGE SLRISCKGSGYSFSTSW ISWVRQMPGKGLEWM GMIDPSDSFTSYSPSFQ GHVTISADKSISTAYLQ | 1115 | TSWIS | 1116 | MIDPSDSFTSYSPSFQ G | 1117 | LHYYNSEEFDV | 1118 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | WSSLKASDTAMYYCAR LHYYNSEEFDVWGQGT LVTVSS | | | | | | |
| mAb11-1485 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDNQLFT FGQGTKLEIK | 1119 | RASQSVSSS YLA | 1120 | GQSSRTR | 1121 | QQFGDNQLFT | 1122 |
| mAb11-1486 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 1123 | TSWIV | 1124 | MIDPSDSYTSYSPSFQ G | 1125 | LHYYNSEEFDV | 1126 |
| mAb11-1486 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDNQLFT FGQGTKLEIK | 1127 | RASQSVSSS YLA | 1128 | GQSSRTR | 1129 | QQFGDNQLFT | 1130 |
| mAb11-1487 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT MVTVSS | 1131 | TSWIV | 1132 | MIDPSDSYTSYSPSFQ G | 1133 | LHYYNSEEFDV | 1134 |
| mAb11-1487 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDNQLFT FGQGTKLEIK | 1135 | RASQSVSSS YLA | 1136 | GQSSRTR | 1137 | QQFGDNQLFT | 1138 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1488 | VH | EVQLVQSGAEVKKPGE SLRISCKGSGYSFSTSW ISWVRQMPGKGLEWM GMIDPSDSYTSYSPSFQ GHVTISADKSISTAYLQ WSSLKASDTAMYYCAR LHYYNSEEFDVWGQGT MVTVSS | 1139 | TSWIS | 1140 | MIDPSDSYTSYSPSFQG | 1141 | LHYYNSEEFDV | 1142 |
| mAb11-1488 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDDQLFT FGQGTKLEIK | 1143 | RASQSVSSS YLA | 1144 | GQSSRTR | 1145 | QQFGDDQLFT | 1146 |
| mAb11-1489 | VH | EVQLVQSGAEVKKPGE SLRISCKGSGYSFTTSW ISWVRQMPGKGLEWM GMIDPSDSFTSYSPSFQ GHVTISADKSISTAYLQ WSSLKASDTAMYYCAR LHYYHSEEFDVWGQGT MVTVSS | 1147 | TSWIS | 1148 | MIDPSDSFTSYSPSFQG | 1149 | LHYYHSEEFDV | 1150 |
| mAb11-1489 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDDQLFT FGQGTKLEIK | 1151 | RASQSVSSS YLA | 1152 | GQSSRTR | 1153 | QQFGDDQLFT | 1154 |
| mAb11-1490 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT LVTVSS | 1155 | TSWIS | 1156 | MIDPSDSYTSYSPSFQG | 1157 | LHYYHSEEFDV | 1158 |
| mAb11-1490 | VL | EIVLTQSPGTLSLSPGE RATLSCRASQSVSSSYL AWYQQKPGQAPRLLIY GQSSRTRGIPDRFSGS | 1159 | RASQSVSSS YLA | 1160 | GQSSRTR | 1161 | QQFGDDQLFT | 1162 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| | | GSGTDFTLTISRLEPED FAVYYCQQFGDDQLFT FGQGTKLEIK | | | | | | |
| mAb11-1491 | VH | EVQLVQSGAEVKKPGE SLRISCKGSGYSFTTSW ISWVRQMPGKGLEWM GMIDPSDSYTSYSPSFQ GHVTISADKSISTAYLQ WSSLKASDTAMYYCAR LHYYHSEEFDVWGQGT MVTVSS | 1163 | TSWIS | 1164 | MIDPSDSYTSYSPSFQG | 1165 | LHYYHSEEFDV | 1166 |
| mAb11-1491 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDDQLFT FGQGTKLEIK | 1167 | RASQSVSSS YLA | 1168 | GQSSRTR | 1169 | QQFGDDQLFT | 1170 |
| mAb11-1492 | VH | EVQLVQSGAEVKKPGE SLRISCKGSGYSFSTSW ISWVRQMPGKGLEWM GMIDPSDSFTSYSPSFQ GHVTISADKSISTAYLQ WSSLKASDTAMYYCAR LHYYNSEEFDVWGQGT LVTVSS | 1171 | TSWIS | 1172 | MIDPSDSFTSYSPSFQG | 1173 | LHYYNSEEFDV | 1174 |
| mAb11-1492 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDDQLFT FGQGTKLEIK | 1175 | RASQSVSSS YLA | 1176 | GQSSRTR | 1177 | QQFGDDQLFT | 1178 |
| mAb11-1493 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYYNSEEFDVWGQGT LVTVSS | 1179 | TSWIV | 1180 | MIDPSDSYTSYSPSFQG | 1181 | LHYYNSEEFDV | 1182 |

TABLE 3-continued

Overview of anti-FX antibody VH, VL and CDR sequences

| mAb ID | Domain | VH/VL Sequence | CDR1 # | CDR1 Sequence | CDR2 # | CDR2 Sequence | CDR3 # | CDR3 Sequence |
|---|---|---|---|---|---|---|---|---|
| mAb11-1493 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDDQLFT FGQGTKLEIK | 1183 | RASQSVSSS YLA | 1184 | GQSSRTR | 1185 | QQFGDDQLFT 1186 |
| mAb11-1494 | VH | EVQLVQSGAEVKKPGE SLRISCKGSGYSFSTSW IVWVRQMPGKGLEWM GMIDPSDSYTSYSPSFQ GHVTISADKSISTAYLQ WSSLKASDTAMYYCAR LHYNSEEFDVWGQGT MVTVSS | 1187 | TSWIV | 1188 | MIDPSDSYTSYSPSFQ G | 1189 | LHYYNSEEFDV 1190 |
| mAb11-1494 | VL | EIVLTQSPGTLSLSPGE RATLSCRASQSVSSSYL AWYQQKPGQAPRLLIY GQSSRTRGIPDRFSGS GSGTDFTLTISRLEPED FAVYYCQQFGDDQLFT FGQGTKLEIK | 1191 | RASQSVSSS YLA | 1192 | GQSSRTR | 1193 | QQFGDDQLFT 1194 |

Example 7a: Binning of Anti-FIX/FIXa Stimulating Antibodies

Antibodies capable of stimulating the enzymatic activity of FIXa towards FX were analysed in binning experiments to determine the binding characteristics for the identified antibodies using the method described below. Both parent antibodies and engineered variants were analysed, and compared to other known antibodies.

Method for Binning of Antibodies

Binning experiments were performed using Octet fortebio systems (HTX, Red384), based on the principle of Bio-Layer Interferometry, and equipped with streptavidin sensors (Pall Life Sciences, Menlo Park, Calif.), and using 8-channel mode. The binning assays were performed using a modified in-tandem setup. Briefly, (1) 370 nM randomly biotinylated human FIXa (biotinylated using NHS-d-biotin from Sigma H1759 and human FIXa obtained from Haematologic Technologies, Essex Junction, Vt.) was captured by streptavidin tips (dip and read biosensors Part NO:18-5019, Pall Life Sciences, Menlo Park, Calif.) for 5 minutes, (2) 330 nM of a first bivalent anti-FIXa antibody was then offered to the streptavidin tips, and incubated for 10 minutes until the biotinylated FIXa were fully saturated and (3) the tips were then offered to an equimolar solution of 330 nM of the first antibody and 330 nM of a second bivalent anti-FIXa antibody for 5 minutes. This modified in-tandem set-up, with inclusion of an equimolar concentration of the first antibody in the second antibody incubation step, were preferred due to the very low affinity (and fast koff rates) of some of the used antibodies. Unspecific binding were evaluated by including an unrelated human IgG4 bivalent antibody as first and second antibody control. As seen in Table 4, where the response values from step (3) are reported, the analysis identified three different bins, represented by the bivalent anti-FIXa antibodies 224F3 (mAb01-1582), mAb01-1767 and mAb01-2434 (ACE910 anti-FIX(a) arms). From Table 4 it is also clear, that the engineered antibodies mAb01-9933, mAb01-9978, mAb01-9985, and mAb01-9994 show the same binning pattern as their parent antibody mAb01-1767 and consequently belong to BinB (as indicated in Table 4).

TABLE 4

Interferometry response values

| | 1st antibody | | | |
|---|---|---|---|---|
| 2nd antibody | 224F3 (BinA) | mAb01-1767 (BinB) | mAb01-2434 (BinC) | hIgG4 (control) |
| 224F3 | 0.11 | 1.60 | 1.69 | 2.11 |
| mAb01-1767 | 0.95 | 0.02 | 1.11 | 1.41 |
| mAb01-2434 | 0.41 | 0.49 | 0.14 | 0.85 |
| mAb01-9933 | 0.34 | 0.02 | 0.46 | 0.59 |
| mAb01-9978 | 0.24 | 0.01 | 0.34 | 0.40 |
| mAb01-9985 | 0.44 | 0.02 | 0.60 | 0.83 |
| mAb01-9994 | 0.40 | 0.01 | 0.56 | 0.75 |
| hIgG4 (control) | 0.08 | −0.02 | −0.04 | −0.03 |

As seen from Table 4, the control antibody human IgG4 was not able to bind to FIXa when used as second antibody (Table 4 last row) and did not prevent binding of the second antibody to FIXa when used as first antibody (Table 4 last column). 224F3 and mAb01-2434 had self-competition response values higher that zero, namely 0.11 and 0.14, respectively, still well beyond the lowest response values among the second antibodies belonging to a different bin, e.g. 0.24 for mAb01-9978 ($2^{nd}$ antibody)/224F3 ($1^{st}$ antibody) and 0.34 for the mAb01-9978 ($2^{nd}$ antibody)/mAb01-2434 ($1^{st}$ antibody). Some examples of the full binding curves are shown in FIGS. 4A and 4B (C, D, E and F)

Example 7b: Binning of Anti-FX/FXa Stimulating Antibodies

Anti-FX(a) antibodies were analysed in binning experiments to determine the binding characteristics for the identified antibodies using the method described below. Both parent antibodies and engineered variants were analysed, and compared to other known antibodies.

Method for Binning of Antibodies

Binning experiments were performed using Octet fortebio systems (HTX, Red384) equipped with streptavidin sensors (Pall Life Sciences, Menlo Park, Calif.), and using 8-channel mode (Red384 and HTX). The binning assays were performed using a modified in-tandem setup. Briefly, (1) 363 nM randomly biotinylated human FXa (obtained from Haematologic technologies and biotinylated using NHS-d-biotin) was captured by streptavidin tips for 5 minutes (dip and read biosensors Part NO:18-5019, Pall Life Sciences, Menlo Park, Calif.), (2) 330 nM of a first bivalent anti-FX(a) antibody was then offered to the streptavidin tips, and incubated for 10 minutes until the biotinylated FXa were fully saturated and (3) the tips were then offered to an equimolar solution of 330 nM of the first antibody and 330 nM of a second bivalent anti-FX(a) antibody for 5 minutes. The set-up with inclusion of an equimolar concentration of the first antibody in the second antibody incubation step, were preferred due to the very low affinity (and fast koff rates) of some of the used antibodies. Unspecific binding were evaluated by including an unrelated human IgG4 bivalent antibody as first and second antibody control. As seen in Table 5, where the response values from step (3) are reported, the analysis identified two different bins, represented by the bivalent anti-FX(a) antibodies mAb01-2435 (ACE910 anti-FX(a) arms) and mAb01-6723. From Table 5 it is also clear, that the engineered antibodies mAb01-8174 and mAb01-9772 show the same binning pattern as their parent antibody mAb01-6723 and consequently belong to Bin2 (as indicated in Table 5). Some examples of the full binding curves are shown in FIG. 5 (A and B).

TABLE 5

Interferometry response values

| | 1st antibody | | |
|---|---|---|---|
| 2nd antibody | mAb01-2435 (Bin1) | mAb01-6723 (Bin2) | hIgG4 (control) |
| mAb01-2435 | −0.05 | 0.85 | 2.63 |
| mAb01-6723 | 0.79 | −0.02 | 2.59 |
| mAb01-8174 | 0.62 | 0.05 | 2.29 |
| mAb01-9772 | 0.22 | −0.01 | 1.49 |
| hIgG4 (control) | −0.08 | −0.03 | −0.09 |

Example 8: Crystallization and Epitope/Paratope Mapping of Anti-FIX(a) Antibodies Using X-Ray Crystallography Crystallization and Epitope/Paratope Mapping of Anti-FIX(a) Antibody mAb01-9994

Crystallization

Fab fragment corresponding to mAb01-9994 was mixed in a 1:1 molar ratio with human EGR-CK-inhibited Factor IXa Gla-domainless (wild-type) bacterial expression, Lot #hGDFIXAWTEGR_05 (purchased from Cambridge ProteinWorks) and crystals of the Fab/FIXa complex were grown using the sitting drop vapour diffusion technique at 18° C. A protein solution of 100 nl 5.5 mg/ml complex in 20 mM Tris-HCl, pH 7.4, 50 mM NaCl, and 2.5 mM $CaCl_2$) was mixed with 100 nl of 0.1M Bicine, pH 9.0, 2% (v/v) 1,4-dioxane, 10% PEG 20000 as precipitant and incubated over 60 µl precipitant.

Diffraction Data Collection

The crystal was cryo protected by addition of 1 µl of precipitant added 20% of ethylene glycol to the crystallization drop prior to flash cooling in liquid nitrogen. Diffraction data were collected at 100K at the Diamond Light Source beamline i03 (0.9763 Å wavelength) using a Pilatus3 6M pixel detector from Dectris. Autoindexing, integration and scaling of the data were performed with programmes from the XDS package (diffracting data statistics are summarised in Table 6).

Structure Determination and Refinement

The asymmetric unit contains one Fab:FIXa complex as judged from Matthews coefficient analysis. The structure was determined by molecular replacement using Phaser as implemented in the programme suite Phenix using a structure of a predetermined Fab:FIXa complex as search model. The correct amino acid sequence was model built using COOT and thereafter the structure was refined using steps of Phenix refinement and manual rebuilding in COOT. The refinement statistics are found in Table 6.

TABLE 6

| Data collection and refinement statistics | |
| --- | --- |
| Wavelength (Å) | 0.9763 |
| Resolution range (Å) | 43.06-2.7 (2.797-2.7) |
| Space group | $P4_32_12$ |
| Unit cell (Å, deg) | 87.65 87.65 231.8 90 90 90 |
| Total reflections | 327518 (33655) |
| Unique reflections | 25718 (2511) |
| Multiplicity | 12.7 (13.4) |
| Completeness (%) | 99.94 (100.00) |
| Mean I/sigma(I) | 13.21 (1.28) |
| Wilson B-factor (Å$^2$) | 77.47 |
| R-merge | 0.15 (2.05) |
| R-meas | 0.1565 (2.13) |
| R-pim | 0.04391 (0.5757) |
| CC1/2 | 0.998 (0.447) |
| CC* | 1 (0.786) |
| Reflections used in refinement | 25715 (2511) |
| Reflections used for R-free | 968 (93) |
| R-work | 0.1978 (0.3407) |
| R-free | 0.2494 (0.4171) |
| CC(work) | 0.933 (0.554) |
| CC(free) | 0.988 (0.575) |
| Number of non-hydrogen atoms | 5597 |
| macromolecules | 5540 |
| ligands | 25 |
| solvent | 32 |
| Protein residues | 719 |
| RMS(bonds) (Å) | 0.012 |
| RMS(angles) (deg) | 1.92 |
| Ramachandran favored (%) | 90.24 |

TABLE 6-continued

| Data collection and refinement statistics | |
| --- | --- |
| Ramachandran allowed (%) | 7.92 |
| Ramachandran outliers (%) | 1.84 |
| Rotamer outliers (%) | 0.00 |
| Clashscore | 12.93 |
| Average B-factor (Å$^2$) | 82.66 |
| Macromolecules | 82.77 |
| Ligands | 85.42 |
| Solvent | 61.00 |

Statistics for the highest-resolution shell are shown in parentheses.

Determination of the Epitope of mAb01-9994

The epitope of mAb01-9994, defined as FIX(a) residues characterized by having a heavy atom (i.e. a non-hydrogen atom) within a distance of 3.5 Å from a heavy atom in the Fab, comprises the following residues L337, R338, T340, K341 and T343, according to SEQ ID NO:1.

Determination of the Paratope of mAb01-9994

The paratope for mAb01-9994 defined as Fab residues characterized by having a heavy atom (i.e. a non-hydrogen atom) within a distance of 3.5 Å from a heavy atom in FIXa, comprises the residues (consecutive numbering): H30, D31, W53, D56, S102, S104, Y106 and N107 in the heavy chain variable domain (SEQ ID NO:67) and residues Y91 and S92 in the light chain variable domain (SEQ ID NO:71).

Residues in bold are located in the CDR sequences, as defined using the Kabat definition, while the remaining paratope residues H30 (in the heavy chain variable domain) is a framework residue.

Crystallization and Epitope/Paratope Mapping of Anti-FIX/FIXa Antibody mAb01-9933

Crystallization

Fab fragment corresponding to mAb01-9933 was mixed in a 1:1 molar ratio with human EGR-CK-inhibited Factor IXa Gla-domainless (wild-type) bacterial expression, Lot #hGDFIXAWTEGR_05 (purchased from Cambridge ProteinWorks) and crystals of the Fab/FIXa complex were grown using the sitting drop vapour diffusion technique at 18° C. A protein solution of 150 nl 8.1 mg/ml complex in 20 mM Tris-HCl, pH 7.4, 50 mM NaCl, and 2.5 mM $CaCl_2$) was mixed with 50 nl of 0.1 M Bis-Tris, pH 6.5, 20% (w/v) PEG 5000 MME as precipitant and incubated over 60 µl precipitant.

Diffraction Data Collection

The crystal was cryo protected by addition of 1 µl of precipitant added 20% of ethylene glycol to the crystallization drop prior to flash cooling in liquid nitrogen. Diffraction data were collected at 100K at the Diamond Light Source beamline i03 (0.9763 Å wavelength) using a Pilatus3 6M pixel detector from Dectris. Autoindexing, integration and scaling of the data were performed with programmes from the XDS package (diffracting data statistics are summarised in Table 7).

Structure Determination and Refinement

The asymmetric unit contains one Fab:FIXa complex as judged from Matthews coefficient analysis. The structure was determined by molecular replacement using Phaser as implemented in the programme suite Phenix using a structure of a predetermined Fab:FIXa complex as search model. The correct amino acid sequence was model built using COOT and thereafter the structure was refined using steps of Phenix refinement and manual rebuilding in COOT. The refinement statistics are found in Table 7.

TABLE 7

Data collection and refinement statistics

| | |
|---|---|
| Wavelength (Å) | 0.9763 |
| Resolution range (Å) | 47.16-2.4 (2.486-2.4) |
| Space group | P $4_3 2_1 2$ |
| Unit cell (Å, deg) | 85.7 85.7 225.95 90 90 90 |
| Total reflections | 433016 (39929) |
| Unique reflections | 33886 (3317) |
| Multiplicity | 12.8 (12.0) |
| Completeness (%) | 99.95 (99.97) |
| Mean I/sigma(I) | 13.85 (1.41) |
| Wilson B-factor | 53.78 |
| R-merge | 0.1353 (1.658) |
| R-meas | 0.1412 (1.732) |
| R-pim | 0.03956 (0.4966) |
| CC1/2 | 0.999 (0.591) |
| CC* | 1 (0.862) |
| Reflections used in refinement | 33879 (3317) |
| Reflections used for R-free | 1279 (128) |
| R-work | 0.2171 (0.2721) |
| R-free | 0.2623 (0.3245) |
| CC(work) | 0.957 (0.764) |
| CC(free) | 0.991 (0.670) |
| Number of non-hydrogen atoms | 5624 |
| macromolecules | 5497 |
| Ligands | 25 |
| Solvent | 102 |
| Protein residues | 715 |
| RMS(bonds) (Å) | 0.011 |
| RMS(angles) (deg) | 1.36 |
| Ramachandran favored (%) | 90.70 |
| Ramachandran allowed (%) | 7.58 |
| Ramachandran outliers (%) | 1.72 |
| Rotamer outliers (%) | 0.49 |
| Clashscore | 9.45 |
| Average B-factor (Å$^2$) | 64.71 |
| Macromolecules | 64.92 |
| Ligands | 60.38 |
| Solvent | 54.67 |

Statistics for the highest-resolution shell are shown in parentheses.

Determination of the Epitope of mAb01-9933

The epitope of mAb01-9933, defined as FIX(a) residues characterized by having a heavy atom (i.e. a non-hydrogen atom) within a distance of 3.5 Å from a heavy atom in the Fab, comprises the following residues L337, R338, T340, and K341, according to SEQ ID NO:1.

Determination of the Paratope of mAb01-9933

Additionally, the paratope for mAb01-9933 defined as Fab residues characterized by having a heavy atom (i.e. a non-hydrogen atom) within a distance of 3.5 Å from a heavy atom in FIXa, comprises the residues (consecutive numbering): D30, D31, W53, S102, S104, N107 in the heavy chain variable domain (SEQ ID NO:35) and residues: Y91 and S92 in the light chain variable domain (SEQ ID NO:39).

Residues in bold are located in the CDR sequences, as defined using the Kabat definition, while the remaining paratope residues D30 (in the heavy chain variable domain) is a framework residue.

Example 8a: Crystallization and Epitope/Paratope Mapping of Anti-FIX(a) Antibody mAb01-9985

Crystallization

Fab fragment corresponding to mAb01-9985 was mixed in a 1:1 molar ratio with human EGR-CK-inhibited Factor IXa Gla-domainless (wild-type) bacterial expression, Lot #hGDFIXAWTEGR_11 (purchased from Cambridge ProteinWorks). The complex was subjected to size exclusion chromatography on a HiLoad 16/60 Superdex 200 pg column (GE Healthcare) run with 20 mM Hepes, pH 7.5, 140 mM NaCl, 1 mM CaCl$_2$) buffer. The fractions containing the Fab/FIXa complex were pooled and concentrated to 10.1 mg/ml. Crystals of the Fab/FIXa complex were grown using the microseed matrix screening technique as described in D'Arcy et al. (2014) *Acta Crystallographica Section F* 70, 1117-1126 using sitting drop vapour diffusion at 18° C. The crystal used was grown using a protein solution of 200 nl 10.1 mg/ml complex in 20 mM Hepes, pH 7.4, 140 mM NaCl, 1 mM CaCl$_2$) mixed with 100 nl seed stock and 300 nl of 2 M ammonium sulphate, 0.1 M Hepes, pH 7.5 as precipitant and incubated over 80 µl precipitant. The seed stock was prepared from crystals of the Fab fragment corresponding to mAb01-9933 in complex with human EGR-CK-inhibited Factor IXa Gla-domainless (wild-type).

Diffraction Data Collection

The crystal was cryo protected by addition of 1.5 µl of precipitant added 20% of ethylene glycol to the crystallization drop prior to flash cooling in liquid nitrogen. Diffraction data were collected at 100K at the Swiss Light Source beamline X10SA (1.00 Å wavelength) using a Pilatus3 6M pixel detector from Dectris. Autoindexing, integration and scaling of the data were performed with programmes from the XDS package (diffracting data statistics are summarised in Table 7a).

Structure Determination and Refinement

The asymmetric unit contains one Fab:FIXa complex as judged from Matthews coefficient analysis. The structure was determined by molecular replacement using Phaser as implemented in the programme suite Phenix using a structure of a predetermined Fab:FIXa complex as search model. The correct amino acid sequence was model built using COOT and thereafter the structure was refined using steps of Phenix refinement and manual rebuilding in COOT. The refinement statistics are found in Table 7a.

TABLE 7a

Data collection and refinement statistics

| | |
|---|---|
| Wavelength (Å) | 1.00 |
| Resolution range (Å) | 48.51-3.105 (3.216-3.105) |
| Space group | P $4_1 22$ |
| Unit cell (Å, deg) | 97.03 97.03 254.51 90 90 90 |
| Total reflections | 295893 (28675) |
| Unique reflections | 22811 (2201) |
| Multiplicity | 13.0 (13.0) |
| Completeness (%) | 99.80 (99.19) |
| Mean I/sigma(I) | 4.30 (0.95) |
| Wilson B-factor (Å$^2$) | 50.79 |
| R-merge | 0.692 (2.568) |
| R-meas | 0.7205 (2.672) |
| R-pim | 0.1985 (0.7295) |
| CC1/2 | 0.957 (0.476) |
| CC* | 0.989 (0.803) |
| Reflections used in refinement | 22786 (2193) |
| Reflections used for R-free | 548 (53) |
| R-work | 0.2240 (0.3283) |
| R-free | 0.2794 (0.3814) |
| CC(work) | 0.940 (0.725) |
| CC(free) | 0.928 (0.614) |
| Number of non-hydrogen atoms | 5690 |
| macromolecules | 5595 |
| ligands | 95 |
| Protein residues | 726 |
| RMS(bonds) (Å) | 0.012 |
| RMS(angles) (deg) | 1.70 |
| Ramachandran favored (%) | 97.21 |
| Ramachandran allowed (%) | 2.65 |

TABLE 7a-continued

Data collection and refinement statistics

| | |
|---|---|
| Ramachandran outliers (%) | 0.14 |
| Rotamer outliers (%) | 0.16 |
| Clashscore | 3.58 |
| Average B-factor (Å$^2$) | 43.84 |
| Macromolecules | 43.53 |
| Ligands | 61.76 |

Statistics for the highest-resolution shell are shown in parentheses.

Determination of the Epitope of mAb01-9985

The epitope of mAb01-9985, defined as FIX(a) residues characterized by having a heavy atom (i.e. a non-hydrogen atom) within a distance of 3.5 Å from a heavy atom in the Fab, comprises the following residues L337, R338, S339, T340, and K341, according to SEQ ID NO:1.

Determination of the Paratope of mAb01-9985

The paratope for mAb01-9985 defined as Fab residues characterized by having a heavy atom (i.e. a non-hydrogen atom) within a distance of 3.5 Å from a heavy atom in FIXa, comprises the residues (consecutive numbering): H30, D31, W53, S102, S104, Y106 and N107 in the heavy chain variable domain (SEQ ID NO:51) and residues Y91 and S92 in the light chain variable domain (SEQ ID NO:55). Residues in bold are located in the CDR sequences, as defined using the Kabat definition, while the remaining paratope residue H30 (in the heavy chain variable domain) is a framework residue.

Example 9: Crystallization and Epitope/Paratope Mapping of Anti-FX Antibodies Using X-Ray Crystallography Crystallization and Epitope/Paratope Mapping of Anti-FXa Antibody mAb01-8174

Crystallization

Fab fragment corresponding to mAb01-8174 was mixed in a 1:1 molar ratio with human EGR-CK-inhibited Factor Xa Gla-domainless (wild-type) bacterial expression, Lot #hGDFXAEGR_026 (purchased from Cambridge ProteinWorks) and crystals of the Fab/FXa complex were grown using the sitting drop vapour diffusion technique at 18° C. A protein solution of 150 nl 4.7 mg/ml complex in 20 mM Tris-HCl, pH 7.4, 50 mM NaCl, and 2.5 mM CaCl$_2$) was mixed with 50 nl of 0.2 M sodium acetate, 0.1 M sodium cacodylate, pH 6.5, 18% (w/v) PEG 8000 as precipitant and incubated over 60 µl precipitant.

Diffraction Data Collection

The crystal was cryo protected by addition of 1 µl of precipitant added 20% of ethylene glycol to the crystallization drop prior to flash cooling in liquid nitrogen. Diffraction data were collected at 100K at the Swiss Light Source beamline X06DA (1.00 Å wavelength) using a Pilatus2M pixel detector from Dectris. Autoindexing, integration and scaling of the data were performed with programmes from the XDS package (diffracting data statistics are summarised in Table 8).

Structure Determination and Refinement

The asymmetric unit contains two Fab:FXa complexes as judged from Matthews coefficient analysis. The structure was determined by molecular replacement with Molrep as implemented in the programme suite CCP4 using structures of predetermined Fab:FXa complexes as search models. The correct amino acid sequence for the Fab was model built using COOT and thereafter the structure was refined using steps of Phenix refinement and manual rebuilding in COOT. The refinement statistics are found in Table 8.

TABLE 8

Data collection and refinement statistics

| | |
|---|---|
| Wavelength (Å) | 1.000 |
| Resolution range (Å) | 44.12-2.6 (2.693-2.6) |
| Space group | P2$_1$ |
| Unit cell (Å, deg) | 63.13 105.25 145.78 90 89.995 90 |
| Total reflections | 302807 (30703) |
| Unique reflections | 58767 (5896) |
| Multiplicity | 5.2 (5.2) |
| Completeness (%) | 99.90 (99.97) |
| Mean I/sigma(I) | 12.31 (1.56) |
| Wilson B-factor (Å$^2$) | 50.13 |
| R-merge | 0.1209 (1.024) |
| R-meas | 0.1346 (1.138) |
| R-pim | 0.05869 (0.4933) |
| CC1/2 | 0.996 (0.523) |
| CC* | 0.999 (0.829) |
| Reflections used in refinement | 58761 (5896) |
| Reflections used for R-free | 1999 (202) |
| R-work | 0.2033 (0.3027) |
| R-free | 0.2623 (0.3140) |
| CC(work) | 0.857 (0.463) |
| CC(free) | 0.788 (0.347) |
| Number of non-hydrogen atoms | 11641 |
| macromolecules | 11145 |
| ligands | 52 |
| solvent | 444 |
| Protein residues | 1447 |
| RMS(bonds) | 0.011 |
| RMS(angles) | 1.70 |
| Ramachandran favored (%) | 95.74 |
| Ramachandran allowed (%) | 3.70 |
| Ramachandran outliers (%) | 0.56 |
| Rotamer outliers (%) | 0.32 |
| Clashscore | 22.55 |
| Average B-factor | 46.64 |
| macromolecules | 46.94 |
| ligands | 46.66 |
| solvent | 39.14 |
| Twin refinement | h, −k, −l |

Statistics for the highest-resolution shell are shown in parentheses.

Determination of Epitope of mAb01-8174

The epitope of mAb01-8174, defined as FXa residues characterized by having a heavy atom (i.e. a non-hydrogen atom) within a distance of 3.5 Å from a heavy atom in the Fab in one or both of the complexes in the asymmetric unit, comprises the following residues: E103, Q104, V108, R113, T116, L117, D119, I125, T127, E228, F229, Y230, E266, R287, P291, I292, P304, L419, K420, D423, R424, M426, K427 and T428 according to SEQ ID NO:2.

Determination of Paratope of mAb01-8174

The paratope for mAb01-8174 defined as Fab residues characterized by having a heavy atom (i.e. a non-hydrogen atom) within a distance of 3.5 Å from a heavy atom in FXa in one or both of the complexes in the asymmetric unit, comprises the residues (consecutive numbering): K23, S25, G26, Y27, F29, W33, D52, S54, D55, F57, S77, H100, Y101, Y102, N103, S104 in the heavy chain variable domain (SEQ ID NO:467) and residues V29, S30, S31, Y33, Y50, Q52, S54, R55, R57 and D94 in the light chain variable domain (SEQ ID NO:471).

Residues in bold are located in the CDR sequences, as defined using the Kabat definition, while the remaining paratope residues K23, S25, G26, Y27, F29 and S77 (in the heavy chain variable domain) and Y50 (in light chain variable domain) are framework residues.

Crystallization and Epitope/Paratope Mapping of Anti-FXa Antibody mAb01-9772

Fab fragment corresponding to mAb01-9772 was mixed in a 1:1 molar ratio with human EGR-CK-inhibited Factor Xa Gla-domainless (wild-type) bacterial expression, Lot #hGDFXAEGR_026 (purchased from Cambridge ProteinWorks) and crystals of the Fab/FXa complex were grown using the sitting drop vapour diffusion technique at 18° C. A protein solution of 150 nl 3.7 mg/ml complex in 20 mM Tris-HCl, pH 7.4, 50 mM NaCl, and 2.5 mM $CaCl_2$) was mixed with 50 nl of 0.2 M sodium formate, 20% (w/v) PEG 3350 as precipitant and incubated over 60 µl precipitant.

Diffraction Data Collection

The crystal was cryo protected by addition of 1 µl of precipitant added 20% of ethylene glycol to the crystallisation drop prior to flash cooling in liquid nitrogen. Diffraction data were collected at 100K at the Swiss Light Source beamline X06DA (1.00 Å wavelength) using a Pilatus2M pixel detector from Dectris. Autoindexing, integration and scaling of the data were performed with programmes from the XDS package (diffracting data statistics are summarised in Table 9).

Structure Determination and Refinement

The asymmetric unit contains two Fab:FXa complexes as judged from Matthews coefficient analysis. The structure was determined by molecular replacement with Molrep as implemented in the programme suite CCP4 using structures of predetermined Fab:FXa complexes as search models. The correct amino acid sequence for the Fab was model built using COOT and thereafter the structure was refined using steps of Phenix refinement and manual rebuilding in COOT. The refinement statistics are found in Table 9.

TABLE 9

Data collection and refinement statistics

| | |
|---|---|
| Wavelength (Å) | 1.000 |
| Resolution range | 48.33-3.15 (3.263-3.15) |
| Space group | P 2₁ |
| Unit cell (Å, deg) | 62.34 104.72 144.98 90 90.048 90 |
| Total reflections | 102910 (10275) |
| Unique reflections | 31847 (3182) |
| Multiplicity | 3.2 (3.2) |
| Completeness (%) | 98.16 (98.45) |
| Mean I/sigma(I) | 8.51 (1.45) |
| Wilson B-factor (Å²) | 74.36 |
| R-merge | 0.126 (0.7224) |
| R-meas | 0.1512 (0.8628) |
| R-pim | 0.08262 (0.4665) |
| CC1/2 | 0.994 (0.571) |
| CC* | 0.998 (0.853) |
| Reflections used in refinement | 31824 (3182) |
| Reflections used for R-free | 1083 (113) |
| R-work | 0.2163 (0.2810) |
| R-free | 0.2929 (0.2997) |
| CC(work) | 0.849 (0.374) |
| CC(free) | 0.736 (0.325) |
| Number of non-hydrogen atoms | 11190 |
| macromolecules | 11138 |
| ligands | 52 |
| Protein residues | 1446 |
| RMS(bonds) | 0.013 |
| RMS(angles) | 1.98 |
| Ramachandran favored (%) | 95.03 |
| Ramachandran allowed (%) | 4.20 |
| Ramachandran outliers (%) | 0.77 |
| Rotamer outliers (%) | 0.00 |
| Clashscore | 26.08 |
| Average B-factor (Å²) | 73.74 |

TABLE 9-continued

Data collection and refinement statistics

| | |
|---|---|
| macromolecules | 73.78 |
| ligands | 65.77 |
| Twin refinement | h, −k, −l |

Statistics for the highest-resolution shell are shown in parentheses.

Determination of Epitope of mAb01-9772

The epitope of mAb01-9772, defined as FXa residues characterized by having a heavy atom (i.e. a non-hydrogen atom) within a distance of 3.5 Å from a heavy atom in the Fab in one or both of the complexes in the asymmetric unit, comprises the following residues: E103, Q104, V108, R113, T116, L117, A118, D119, I125, T127, S227, E228, Y230, R287, I292, L303, P304, L419, K420, D423, R424, M426, K427 and T428 according to SEQ ID NO:2.

Determination of Paratope of mAb01-9772

The paratope for mAb01-9772 defined as Fab residues characterized by having a heavy atom (i.e. a non-hydrogen atom) within a distance of 3.5 Å from a heavy atom in FXa in one or both of the complexes in the asymmetric unit, comprises the residues (consecutive numbering): K23, G24, S25, G26, Y27, W33, D52, S54, D55, Y57, S77, L99, H100, Y101, Y102, N103 and S104 in the variable heavy chain domain (SEQ ID NO:483) and residues S30, S31, Y33, Y50, Q52, S54, R55, R57, Y92 and D94 in the light chain variable domain (SEQ ID NO:487).

Residues in bold are located in the CDR sequences, as defined using the Kabat definition, while the remaining paratope residues K23, G24, S25, G26, Y27 and S77 (in the heavy chain variable domain) and Y50 (in light chain variable domain) are framework residues.

Example 10: Identification of Hot-Spot Residues on FIX

In order to determine residues critical for the interaction (referred to as hot-spot) between the anti-FIX/FIXa mAb01-9994 and mAb01-9985 and FIX, a set of FIX variants was selected based on Fab/FIXa structure of the Fab fragment of mAb01-9994 and FIXa. As detailed below the selected FIX variants were transiently expressed in mammalian cells, purified and characterized with respect to their binding to monovalent variants of mAb01-9994 and mAb01-9985 using Surface Plasmon Resonance (SPR).

Generation of FIX Mutants

A DNA plasmid, suitable for transient mammalian expression, was constructed with an expression cassette encoding amino acids residues 1-461 of human FIX (uniprot P00740, except for a T194A mutation according to the UNIPROT numbering, corresponding to T148A of SEQ ID NO:1) directly followed by six Histidines (6× His-tag, for affinity purification). The secreted, mature FIX protein chain produced using this construct is identical to the A148 allelic form of human FIX (Anson et al. EMBO J. 1984 3:1053-1060, McGraw et al., Proc Natl Acad Sci USA. 1985 82:2847-2851) except for the addition of the C-terminal His-tag. Using the construct as template, selected mutations were introduced by PCR. For each single-point mutation listed in Table 10, a forward primer containing the desired amino acid change and a reverse primer without amino acid mutations were designed. These primers were used in a standard PCR reaction with the vector described above as template to amplify the entire vector sequence. Ligation-free cloning was used to join the ends of the resulting amplified DNA fragment into a circular expression plasmid using overlap sequences introduced by the forward and the reverse primers.

The circularized plasmids were transformed into E. coli cells, grown on selective agar plates to form colonies, and the colonies used to start liquid E. coli cultures. After overnight growth of the E. coli cultures, plasmid preparations were performed and the mutants identified by DNA sequencing.

Recombinant protein production was performed by transfecting expi293F cells growing in suspension culture in Expi293 Expression™ medium (ThermoFisher Scientific, cat #A1435101) using the ExpiFectamine™ 293 Transfection Kit (ThermoFisher Scientific, cat #A14525) and plasmid DNA encoding each of the desired variants as well as wild-type FIX (corresponding to SEQ ID NO:1 with C-terminal His-tag). Vitamin K was added to a final concentration of 5 mg/mL at the time of transfection. Transfection Enhancers 1 and 2 from the ExpiFectamine™ 293 Transfection Kit were added the day after transfection. The cell cultures were harvested 5 days after transfection by centrifugation.

The C-terminal His-tag on each FIX variant was used for batch protein purification in a multi-well, robotic setup. Briefly, the harvested cell culture supernatants were adjusted to binding conditions, mixed with Ni Sepharose 6 Fast Flow affinity purification resin (GE Healthcare, cat #17-5318-02, 50 µl sedimented resin/ml cell culture medium) and incubated while shaking for 20 minutes. The resin/supernatant mixes were then transferred to a filter plate and the liquid drawn through the filter plate by application of vacuum. The resin remaining in the filter plate was washed three times before elution in a high-imidazole buffer.

Concentration determination of the purified protein solutions was performed by ELISA, using an anti-FIX antibody for detection and high-purity recombinant wild-type FIX for standard curves.

The FIX variants were characterized with respect to their binding to mAb01-9994 and mAb01-9985 using surface plasmon resonance (SPR) by capturing the FIX variant via the C-terminal His-tag. To avoid avidity effects, i.e. ensure a 1:1 interaction, one-armed (OA) variants of mAb01-9994 and mAb01-9985 (prepared as described in Example 5), were used as analytes.

SPR analyses were carried out on Biacore T200 instruments (Biacore AB, Uppsala, Sweden). For the experiments on the T200 instrument the following conditions were applied: measurements were conducted at a temperature of 25° C. Anti-His antibody at 25 µg/ml (R&D Systems, catalogue #MAB050) was immobilized on a CM5 sensor chip using standard amine coupling chemistry. Anti-FIX variants at 25 nM were injected at a flow rate of 10 µl/min for 1 min and were captured via their His-tag by the immobilized anti-His antibody. Subsequently, 20 µM (with 2.5 fold dilution) of OA mAb01-9994 and OA mAb01-9985 were injected at a flow rate of 50 µl/min for 3 min to allow for binding to captured FIX variant followed by a 3 min buffer injection allowing for dissociation of the monovalent anti-FIX antibodies. The running buffer used was 20 mM Tris, 150 mM NaCl, 5 mM $CaCl_2$), 0.05 Tween-20, 10 mg/ml BSA, pH 7.4. This was also used for dilution of anti-FIX antibody and FIX samples. Regeneration of the chip was achieved using 10 mM Glycine pH 2.0. Binding data were analysed according to a 1:1 model using BiaEvaluation 4.1 supplied by the manufacturer (Biacore AB, Uppsala, Sweden).

Binding data are reported as % binding of the antibody to the FIX variant relative to binding of the antibody to wild-type FIX calculated according to the formula:

$$\text{Binding } (\%) = 100\% \times [(R_{max\_Ab,FIX\_var})/(R_{max\_FIXvar})] / [(R_{max\_Ab,FIX\_wt})/(R_{max\_FIXwt})]$$

where $R_{max\_FIXvar}$ and $R_{max\_FIXwt}$ represent capture level (RU) of FIX variant and wild-type FIX, respectively, and where $R_{max\_Ab,FIX\_var}$ and $R_{max\_Ab,FIX\_wt}$ represent Rmax (RU) of the 20 OA antibody to captured FIX variant and wild-type FIX, respectively. Results are shown in Tables 10 and 11.

TABLE 10

Results from SPR analysis (mAb01-9994)
Results from hot-spot analysis of OA variant of mAb01-9994

| Residue# | FIX variant | Binding (%) |
|---|---|---|
| 301 | K301A | 89 |
| 332 | D332S | 41 |
| 332 | D332A | 41 |
| 333 | R333A | 55 |
| 334 | A334L | 38 |
| 335 | T335A | 43 |
| 337 | L337A | 38 |
| 338 | R338A | 0 |
| 339 | S339L | 46 |
| 340 | T340A | 16 |
| 341 | K341E | 3 |
| 341 | K341A | 18 |
| 343 | T343I | 62 |
| 343 | T343A | 58 |
| 346 | N346Q | 101 |
| 346 | N346A | 92 |
| NA | WT | 100 |

TABLE 11

Results from SPR analysis (mAb01-9985)
Results from hot-spot analysis of OA variant of mAb01-9985

| Residue# | FIX variant | Binding (%) |
|---|---|---|
| 301 | K301A | 94 |
| 332 | D332S | 59 |
| 332 | D332A | 59 |
| 333 | R333A | 73 |
| 334 | A334L | 60 |
| 335 | T335A | 64 |
| 337 | L337A | 61 |
| 338 | R338A | 8 |
| 339 | S339L | 66 |
| 340 | T340A | 29 |
| 341 | K341E | 10 |
| 341 | K341A | 30 |
| 343 | T343I | 84 |
| 343 | T343A | 86 |
| 346 | N346Q | 93 |
| 346 | N346A | 100 |
| NA | WT | 100 |

Hot-Spot Residues for mAb01-9994 and mAb01-9985

Hot-spot residues for mAb01-9994 and mAb01-9985 are defined as positions were substitution of the wild-type residue with alanine reduces the binding of the antibody to 30% or less relative to binding of the antibody to wild-type FIX.

Hot-Spot Residues for mAb01-9994:

R338, T340 and K341

Hot-Spot Residues for mAb01-9985:

R338, T340 and K341

For both mAb01-9994 and mAb01-9985 the residue contributing most to binding is R338; substitution of R338 with alanine (R338A) in FIX exhibited the largest impact on antibody binding, which was greatly reduced to no observable binding and 8% for mAb01-9994 and mAb01-9985, respectively, relative to antibody binding to wild-type FIX.

Example 11: Identification of Hot-Spot Residues on FX

The data provided in the present example determines the hot-spot epitope residues on FX for mAb01-8174. The FX variants used were single-site alanine variants (except for position 118, which is alanine in the wild-type, where an alanine to serine substitution was introduced) of desGla-desEGF1-FX, corresponding to residues 86-448 of SEQ ID NO:2, with a N-terminal His-tag (HHHHHH) (SEQ ID NO:1200), for affinity purification) attached via a short GS-linker (GGGGSGGGGS) (SEQ ID NO:1201). The FX variants tested are listed in Table 12.

TABLE 12

List of generated desGla-desEGF1-FX mutants

| Position[1)] | Variant | Domain[2)] |
|---|---|---|
| 101 | H101A | EGF2 |
| 103 | E103A | EGF2 |
| 113 | R113A | EGF2 |
| 116 | T116A | EGF2 |
| 118 | A118S | EGF2 |
| 127 | T127A | EGF2 |
| 227 | S227A | PD |
| 228 | E228A | PD |
| 229 | F229A | PD |
| 230 | Y230A | PD |
| 266 | E266A | PD |
| 287 | R287A | PD |
| 305 | E305A | PD |
| 419 | L419A | PD |
| 420 | K420A | PD |
| 423 | D423A | PD |
| 424 | R424A | PD |
| 427 | K427A | PD |
| 428 | T428A | PD |

[1)]According to SEQ ID NO: 2

[2)]EGF2 and PD refer to second epidermal growth factor-like and protease domains, respectively The wild-type desGla-desEGF1-FX and variants listed in Table 12 were expressed in the HEK293 system and purified via affinity chromatography. Identification of hot-spot epitope residues was done using a Biacore 4000 instrument at 25° C. The wild-type desGla-desEGF1-FX and variants were immobilized on a Series-S Sensor Chip CM5 (GE Healthcare, Catalogue #BR100530) using standard amine coupling chemistry. 10 μM (with 2 fold serial dilutions) of the one-armed variant of mAb01-8174 was injected at the flow rate of 10 μL/min for 300 sec to allow for binding to the immobilized wild-type desGla-desEGF1-FX and variants followed by a 600 sec buffer injection to allow for dissociation of the monovalent antibody. The running buffer (also used for diluting the monovalent antibody and desGLA-desEGF1-hFX variants) contained 10 mM HEPES, 150 mM NaCl, 1 mg/mL BSA and 5 mM $CaCl_2$) (pH 7.4). No regeneration buffer was used because near complete dissociation of the antibody from the sensor chip was observed during the 600 sec dissociation stage. Binding data were analyzed according to the 1:1 model and the affinity (i.e. dissociation equilibrium constant) for each binding was derived from steady-state fitting of the binding curves in the Biacore 4000 Evaluation Software 1.0 supplied by GE Healthcare. Binding data are reported as fold of affinity of all the FX variants for the antibody with reference to that of the wild-type FX. Relative affinities measured for the FX variants are shown in table 13.

TABLE 13

Relative affinities ($K_D$(variant)/$K_D$(wild-type)) for binding of one-armed mAb01-8174 to FX variants

| Variant | Relative affinity |
|---|---|
| Wild Type | 1.0 |
| H101A | 3.6 |
| E103A | 3.5 |
| R113A | 2.3 |
| T116A | 0.55 |
| A118S | 1.5 |
| T127A | 0.85 |
| S227A | 2.8 |
| E228A | 0.85 |
| F229A | 0.95 |
| Y230A | No Binding |
| E266A | 0.65 |
| R287A | >5 |
| E305A | 2.1 |
| L419A | 4.5 |
| K420A | >5 |
| D423A | No Binding |
| R424A | No Binding |
| K427A | No Binding |
| T428A | 1.0 |

"No binding" means that binding was too weak to be detected

Hot-Spot Residues for mAb01-8174

As shown in Table 13 alanine-substitutions at positions 230, 423, 424 and 427 in FX completely abrogated binding to one-armed mAb01-8174. Thus, hot-spot residues on FX for binding to mAb01-8174 are:

Y230, D423, R424 and K427

Example 12: Activity of Monovalent Anti-FIX/FIXa Antibodies in a FXa Generation Assay To avoid any potential avidity effects arising as a consequence of the bivalency of the conventional IgG antibody format, the stimulatory activity of anti-FIX(a) antibodies on FIXa enzymatic activity towards FX was determined following reformatting into a monovalent one-armed (OA) antibody format (see Example 5). Tested antibodies are listed in Table 14 below. The monovalent OA versions of the anti-FIXa antibodies 224F3 and ACE910 were included for comparison.

The stimulatory activity of OA antibodies was measured in assay buffer (50 mM HEPES, 100 mM NaCl, 5 mM $CaCl_2$), 0.1% (w/v) PEG8000, pH 7.3+1 mg/ml BSA) at fixed concentrations of phosphatidyl serine (PS):phosphatidyl choline (PC) phospholipid vesicles (final concentration of 500 μM; Haematologic Technologies Inc, USA) and plasma-derived FIXa (final concentrations of 0.04, 0.1, 0.17, 0.2, 0.3, 0.5 or 1 nM; Haematologic Technologies Inc, USA). The concentration of FIXa was chosen to ensure that less than 15% of the substrate FX was converted into FXa. Following pre-incubation in the presence of monovalent OA antibody (final concentrations listed in Table 14), 100 nM plasma-derived FX (Haematologic Technologies Inc, USA) was added to give a final reaction volume of 50 μl, and activation was allowed to proceed for 20 min at room temperature. The reaction was then quenched by addition of 25 μl quench buffer (50 mM HEPES, 100 mM NaCl, 60 mM EDTA, 0.1% PEG8000, pH 7.3+1 mg/ml BSA) and the amount of FXa generated was determined by further addition of 25 μl 2 mM S-2765 chromogenic substrate (Chromogenix, Sweden) and measurement of chromogenic substrate conversion by absorbance measurement at 405 nm (ΔOD/min) in a microplate reader. The measured activity was corrected for background activity by subtraction of the signal measured in the same assay but with FIXa and antibody replaced by assay buffer, and then normalized according to the concentration of FIXa present in the assay ([FIXa]$_{total}$). Dividing this number by the similarly normalized rate of FXa generation in the absence of antibody ($A_{FIXa,norm}$), an antibody stimulation index was calculated providing the fold stimulation of FIXa activity by the antibody at the concentration used. Due to slow rate of FXa generation by free FIXa, activation reactions in the absence of antibody were carried out as described above but with 5, 10, or 20 nM FIXa present. Measured activities were then background subtracted and normalized according to the FIXa concentration in the assay. For the calculation of the stimulation index, the average of the three normalized activities of free FIXa was used.

Determination of Stimulation Index

In summary, calculation of the stimulation index can be described as follows

Stimulation index=(($A_{FIXa+OA}-A_{bckg}$)/[FIXa]$_{total}$)/$A_{FIXa,norm}$ where $A_{FIXa+OA}$ is the activity measured in the presence of OA antibody, $A_{bckg}$ is the background activity measured in the absence of FIXa and OA antibody, [FIXa]$_{total}$ is the FIXa concentration in the assay, and $A_{FIXa,norm}$ is average normalized activity of free FIXa.

Determination of FIXa Saturation

The fraction of FIXa saturated with OA antibody in the assay is determined by the concentrations of FIXa and OA antibody, and the equilibrium dissociation constant ($K_d$) governing their interaction. The latter can be measured by techniques known in the art, such as isothermal titration calorimetry (ITC).

Since the stimulation index will increase as the concentration of OA antibody is increased until saturation of FIXa is reached, the concentration of OA antibody in the assay should be chosen to ensure at least 80% saturation of FIXa in the assay to provide a proper determination of the stimulation index at full FIXa saturation.

The fraction of FIXa bound to OA antibody at equilibrium ($f_{FIXa+OA}$), can be calculated from the total concentrations of FIXa ([FIXa]$_{total}$) and OA antibody ([OA]$_{total}$) in the assay and the equilibrium dissociation constant ($K_d$) for their interaction using the quadractic binding equation as described by Krishnaswamy et al. (1992) J. Biol. Chem., 267:23696-23706 and detailed in Eq. 1 and 2 below, wherein

[FIXa+OA]$_{assay}$ represents the calculated concentration of FIXa-OA antibody complex at equilibrium in the assay $f_{FIXa+OA}$ represents the calculated fraction (in percent) of FIXa, which is bound to OA antibody at equilibrium in the assay The stimulation index for each OA antibody is provided in Table 14. With a concentration of OA 224F3 antibody of 3260 nM in the assay and a $K_d$ for the interaction with FIXa of 0.477 nM as reported by Kerschbaumer et al. (U.S. Pat. No. 7,297,336B2), more than 95% of FIXa was bound to the OA 224F3 antibody in the assay. In the case of the OA ACE910 antibody, FIXa stimulation was determined at eight different antibody concentrations which allowed for the estimation of the stimulation index at full FIXa saturation using the quadratic binding equation as outlined above. This also provided an estimated equilibrium dissociation constant ($K_d$) for the interaction of ACE910 with FIXa of 1.1 μM, which is in good agreement with the value of 1.52 OA reported by Kitazawa et al. (2017) Thromb Haemost, 117: 1348-1357 and the value of 1.97 OA determined by ITC in Example 13. For the remaining antibodies, the degree of FIXa saturation was not known and the listed stimulation indices therefore represent conservative estimates of the stimulation that would be obtained at a degree of FIXa saturation of 80% or greater. For the tested antibodies the measured stimulation index was found to be higher than that measured for the OA 224F3 and OA ACE910 antibodies.

TABLE 14

Stimulation of FIXa activity by monovalent one-armed (OA) anti-FIXa antibodies

| anti-FIX mAb ID | OA antibody concentration (nM) | Stimulation Index |
| --- | --- | --- |
| ACE910 | saturation | 1372 |
| 224F3 | 3260 | <10 |
| 01-9016 | 1600 | 5905 |
| 01-9373 | 1600 | 1392 |
| 01-9696 | 1600 | 5166 |
| 01-9697 | 3200 | 6539 |
| 01-9933 | 3600 | 6444 |
| 01-9978 | 3600 | 3667 |
| 01-9985 | 2400 | 13730 |
| 01-9986 | 800 | 5822 |
| 01-9994 | 3600 | 10593 |
| 11-0047 | 800 | 2856 |
| 11-0049 | 800 | 1509 |
| 11-0107 | 800 | 3264 |
| 11-0149 | 800 | 3315 |
| 11-0160 | 800 | 4549 |
| 11-0164 | 800 | 3269 |
| 11-0173 | 1600 | 8480 |
| 11-0174 | 800 | 3690 |
| 11-0723 | 800 | 3772 |
| 11-0923 | 800 | 2823 |
| 11-0929 | 800 | 1559 |
| 11-0931 | 800 | 1882 |
| 11-0932 | 800 | 1688 |
| 11-0933 | 800 | 1614 |
| 11-0935 | 800 | 1572 |
| 11-0937 | 800 | 2684 |
| 11-0938 | 800 | 1818 |
| 11-0939 | 800 | 2011 |
| 11-0962 | 800 | 3372 |
| 11-0965 | 800 | 2857 |
| 11-1021 | 800 | 4646 |

$$[FIXa + OA]_{assay} = \frac{([FIXa]_{total} + [OA]_{total} + K_d) - \sqrt{([Fixa]_{total} + [OA]_{total} + K_d)^2 - 4 \times [FIXa]_{total} \times [OA]_{total}}}{(2)} \quad \text{Eq. 1}$$

$$f_{FIXa+OA} = 100\% \times \frac{[FIXa + OA]_{assay}}{[FIXa]_{total}} \quad \text{Eq. 2}$$

TABLE 14-continued

Stimulation of FIXa activity by monovalent one-armed (OA) anti-FIXa antibodies

| anti-FIX mAb ID | OA antibody concentration (nM) | Stimulation Index |
|---|---|---|
| 11-1024 | 800 | 3654 |
| 11-1030 | 800 | 5751 |
| 11-1033 | 800 | 5126 |
| 11-1039 | 800 | 3960 |
| 11-1042 | 800 | 4316 |
| 11-1073 | 800 | 6146 |
| 11-1076 | 800 | 3587 |
| 11-1091 | 800 | 5402 |
| 11-1094 | 800 | 4083 |
| 11-1204 | 1600 | 9099 |
| 11-1233 | 800 | 1700 |
| 11-1254 | 760 | 1890 |
| 11-1259 | 800 | 2005 |
| 11-1260 | 800 | 1757 |
| 11-1262 | 800 | 1952 |
| 11-1266 | 800 | 1696 |
| 11-1268 | 800 | 1796 |
| 11-1273 | 800 | 1540 |
| 11-1275 | 800 | 1835 |
| 11-1276 | 800 | 1739 |
| 11-1278 | 800 | 1694 |
| 11-1279 | 800 | 1562 |
| 11-1282 | 800 | 1461 |
| 11-1286 | 800 | 1816 |
| 11-1288 | 800 | 2534 |
| 11-1344 | 800 | 4662 |
| 11-1358 | 800 | 2831 |
| 11-1360 | 800 | 1114 |
| 11-1389 | 800 | 5786 |
| 11-1495 | 1600 | 7694 |
| 11-1499 | 1600 | 9013 |
| 11-1501 | 1600 | 10277 |
| 11-1502 | 1600 | 5853 |

The anti-FIX mAb ID refers to the ID of the antibody used for reformatting into the OA format. Columns labelled 'OA antibody concentration (nM)' and 'Stimulation index' list the concentration of OA antibody (nM) used in the assay and the corresponding stimulation of FIXa activity measured relative to free FIXa. In the case of ACE910, the estimated stimulation index at full FIXa saturation is provided.

Example 13: Binding Affinities Determined by Isothermal Titration Calorimetry (ITC)

Binding affinities for anti-FIX(a) and anti-FX(a) antibodies were measured by isothermal titration calorimetry (ITC) by using a PEAQ-ITC calorimeter (Malvern, UK). The experiments were conducted at 37° C. and pH 7.4 using 25 mM Tris, 150 mM NaCl, 5 mM $CaCl_2$) (Tris-buffer). The sample cell (200 µl) contained either FIX, FIXa, or FX (macromolecule) and anti-FIX(a) and anti-FX(a) antibodies (ligand) were injected via a syringe (40 µl). All proteins were extensively dialyzed in Tris-buffer prior to measurements to secure matched buffer conditions. A thermal equilibration step was followed by a 60 s delay and subsequently an initial 0.2 µl injection of antibody, followed by 12-16 injections of 1.5-3 µl of antibody at an interval of 120 s. The stirring speed was maintained at 750 rpm, and the reference power is kept constant at 5-10 µcal/s. The heat associated with each injection of antibody is integrated and plotted against the molar ratio of ligand to macromolecule. The resulting isotherm is fitted to a one-site binding model to obtain the affinity ($K_D$), stoichiometry (n), and enthalpy of interaction (ΔH) using the software provided by the manufacturer. Experiments were performed in at least duplicates. $K_D$ values in µM units are reported in Table 15.

TABLE 15

Dissociation constant ($K_D$) values using ITC

| | $K_D$, µM | | |
|---|---|---|---|
| | FIX | FIXa | FX |
| mAb01-9994 | 2.48 ± 0.23 | 1.8 ± 0.13 | NA |
| mAb01-9933 | 2.39 ± 0.33 | 1.3 ± 0.12 | NA |
| mAb01-9985 | 1.92 ± 0.18 | 1.26 ± 0.08 | NA |
| mAb01-9978 | 5.6 ± 0.93 | 3.57 ± 0.52 | NA |
| mAb01-8913 | NA | NA | 0.35 ± 0.19 |
| mAb01-8174 | NA | NA | 0.75 ± 0.66 |
| mAb01-9772 | NA | NA | 1.37 ± 0.39 |
| ACE910 | 2.77 ± 1.44 | 1.97 ± 0.42 | 2.42 ± 0.2 |

NA: Not applicable since antibody is directed to different macromolecule

Example 14: Activity of Anti-FIX(a)/FX(a) Bispecific Antibodies in a FXa Generation Assay The procoagulant activity of anti-FIXa/FX bispecific antibodies was determined based on their ability to promote FX activation by FIXa in the presence of a procoagulant phospholipid membrane. The bispecific antibodies (BiAb) tested are listed in Table 16 and ACE910 was included for comparison.

The procoagulant activity of each bispecific antibody is reported as fold stimulation relative to FX activation by free FIXa at a given antibody concentration. Bispecific antibodies were tested at 8 concentrations (made by serial three fold dilutions in assay buffer) by pre-incubation with 35 or 125 pM human plasma-derived FIXa (Haematologic Technologies Inc, USA) and 500 µM 25:75 phosphatidyl serine: phosphatidyl choline phospholipid vesicles (Haematologic Technologies Inc, USA) in assay buffer (50 mM HEPES, 100 mM NaCl, 5 mM $CaCl_2$), 0.1% (w/v) PEG8000, pH 7.3+1 mg/ml BSA) for 10 min. Activation was then initiated by addition of human plasma-derived FX (Haematologic Technologies Inc, USA) to a concentration of 25 nM. Following 15 min activation at room temperature, the reaction (50 µl) was quenched by addition of 25 µl quench buffer (50 mM HEPES, 100 mM NaCl, 60 mM EDTA, 0.1% PEG8000, pH 7.3+1 mg/ml BSA). The amount of FXa generated was determined by addition of 25 µl 2 mM S-2765 chromogenic substrate (Chromogenix, Sweden) and measurement of chromogenic substrate conversion by absorbance measurement at 405 nm (ΔOD/min) in a microplate reader. Similarly, FX activation by free FIXa was determined at a FIXa concentration of 25 nM and a reaction time of 60 min. The measured activity was normalized according to the concentration of FIXa present in the assay and the reaction time. By dividing this number by the similarly normalized rate of FXa generation in the absence of antibody, fold stimulation by the antibody at a given concentration was calculated.

In summary, calculation of biAb stimulation can be described as follows $$\text{BiAb stimulation} = (A_{FIXa+biAb}/([\text{FIXa}]_{assay} \times t_{reaction}))/A_{FIXa,norm}$$

where $A_{FIXa+biAb}$ is the activity measured in the presence of bispecific antibody, $[\text{FIXa}]_{assay}$ is the FIXa concentration in the assay, $t_{reaction}$ is the reaction time, and $A_{FIXa,norm}$ is the normalized activity of free FIXa.

Table 16 lists the maximum stimulation determined for each bispecific antibody among the 8 antibody concentrations tested as well as the concentration at which maximum stimulation (fold) was observed. For all tested bispecific antibodies the maximum stimulation was found to be higher than that measured for ACE910, which was tested at a concentration interval from 0 to 15300 nM.

TABLE 16

Maximum stimulation by bispecific anti-FIXa/FX antibodies

| BiAb antibody ID | Concentration span tested (nM) | BiAb conc at maximum stimulation (nM) | Maximum stimulation (fold) |
|---|---|---|---|
| ACE910 | 14.38-31440 | 10480 | 891 |
| bimAb05-0745 | 3.65-7980 | 7980 | 21143 |
| bimAb05-3761 | 3.69-8070 | 2690 | 16332 |
| bimAb05-3769 | 3.735-8170 | 8170 | 27417 |
| bimAb05-0746 | 5.1-11150 | 3717 | 14595 |
| bimAb05-2112 | 3.575-7820 | 7820 | 30426 |
| bimAb05-2113 | 3.475-7600 | 7600 | 26321 |
| bimAb05-2114 | 3.465-7580 | 7580 | 35222 |
| bimAb05-2115 | 3.56-7790 | 7790 | 14921 |
| bimAb05-3755 | 1.93-4212 | 156 | 7573 |

Example 15: TGT of Anti-FIX(a)/FX(a) Bispecific Antibodies in Haemophilia A (HA) Plasma Thrombin generation tests (TGT) were conducted in an automated HTP 384-well setup triggering with tissue factor. In brief, 10 μl antibodies were added to 30 μl haemophilia A (HA) plasma (George King). Then, 10 μl TissueFactor trigger (Thrombinoscope, #TS31.00) mixed with phospholipids was added, followed by addition of 10 μl thrombin substrate (FluCa, Thrombinoscope, #TS50.00) to a final assay volume of 60 μl. Fluorescence time series were measured at room temperature on a Perkin Elmer EnVision multi-label plate reader at 1-minute intervals for 2 hours. Thrombograms were calculated as the smoothed first derivative of the fluorescence time series. Peak height was calculated as the maximum value observed in the thrombogram, and normalized (peak ratio) to the peak height observed for the ACE910 reference at the highest concentration (333 nM). The test results for the bispecific antibodies (bimAb) are shown in Table 17. Peak ratio (fold) is the maximum value observed for the bimAb in the thrombogram relative to the value for ACE910 at 333 nM. The concentration (nM) at which the peak is observed is also listed.

TABLE 17

TGT activity of anti-FIX/FX bimAbs relative to ACE910

| bimAb ID | anti-FIX mAb ID | anti-FX mAb ID | Concentration (nM) | Peak ratio (fold) |
|---|---|---|---|---|
| bimAb05-0396 | mAb11-1495 | mAb01-8174 | 111 | 1.18 |
| bimAb05-0417 | mAb11-1501 | mAb01-8174 | 111 | 1.25 |
| bimAb05-0438 | mAb11-1502 | mAb01-8174 | 333 | 1.10 |
| bimAb05-0745 | mAb01-9994 | mAb01-8174 | 111 | 1.24 |
| bimAb05-2114 | mAb01-9985 | mAb01-9772 | 333 | 1.07 |
| bimAb05-2375 | mAb01-9016 | mAb01-8174 | 111 | 1.14 |
| bimAb05-2379 | mAb01-9016 | mAb01-8913 | 666 | 1.26 |
| bimAb05-2532 | mAb01-9373 | mAb01-6723 | 333 | 1.24 |
| bimAb05-3416 | mAb01-9985 | mAb01-6723 | 111 | 1.13 |
| bimAb05-3769 | mAb01-9985 | mAb01-8174 | 111 | 1.27 |
| bimAb05-3770 | mAb01-9986 | mAb01-8174 | 333 | 1.23 |
| bimAb05-3862 | mAb01-9696 | mAb01-8174 | 333 | 1.52 |
| bimAb05-3880 | mAb11-0047 | mAb01-8174 | 333 | 1.4 |
| bimAb05-3886 | mAb11-0049 | mAb01-8174 | 333 | 1.16 |
| bimAb05-3955 | mAb11-0107 | mAb01-8174 | 333 | 1.34 |
| bimAb05-4100 | mAb11-0149 | mAb01-8174 | 333 | 1.25 |
| bimAb05-4114 | mAb11-0160 | mAb01-8174 | 333 | 1.26 |
| bimAb05-4121 | mAb11-0164 | mAb01-8174 | 333 | 1.34 |
| bimAb05-4220 | mAb11-0962 | mAb01-8174 | 333 | 1.39 |
| bimAb05-4226 | mAb11-0965 | mAb01-8174 | 333 | 1.31 |
| bimAb05-4271 | mAb11-0173 | mAb01-8174 | 111 | 1.32 |
| bimAb05-4283 | mAb11-1021 | mAb01-8174 | 333 | 1.19 |
| bimAb05-4289 | mAb11-1024 | mAb01-8174 | 333 | 1.06 |
| bimAb05-4292 | mAb11-1033 | mAb01-8174 | 111 | 1.19 |
| bimAb05-4293 | mAb11-1030 | mAb01-8174 | 111 | 1.35 |
| bimAb05-4387 | mAb11-1039 | mAb01-8174 | 333 | 1.28 |
| bimAb05-4392 | mAb11-1042 | mAb01-8174 | 111 | 1.24 |
| bimAb05-4419 | mAb11-0174 | mAb01-8174 | 111 | 1.21 |
| bimAb05-4422 | mAb11-1073 | mAb01-8174 | 333 | 1.2 |
| bimAb05-4428 | mAb11-1076 | mAb01-8174 | 111 | 1.12 |
| bimAb05-4443 | mAb11-1094 | mAb01-8174 | 333 | 1.14 |
| bimAb05-4444 | mAb11-1091 | mAb01-8174 | 333 | 1.19 |
| bimAb05-4601 | mAb11-0937 | mAb01-8174 | 111 | 1.17 |
| bimAb05-4604 | mAb11-0923 | mAb01-8174 | 333 | 1.02 |
| bimAb05-4611 | mAb11-0935 | mAb01-8174 | 333 | 1.02 |
| bimAb05-4612 | mAb11-0938 | mAb01-8174 | 111 | 1.23 |
| bimAb05-4613 | mAb11-0933 | mAb01-8174 | 333 | 1.03 |
| bimAb05-4684 | mAb01-9985 | mAb11-1114 | 333 | 1.05 |
| bimAb05-4685 | mAb01-9985 | mAb11-1115 | 111 | 1.12 |
| bimAb05-4686 | mAb01-9985 | mAb11-1116 | 333 | 1.16 |
| bimAb05-4687 | mAb01-9985 | mAb11-1117 | 333 | 1.12 |
| bimAb05-4688 | mAb01-9985 | mAb11-1118 | 111 | 1.16 |
| bimAb05-4689 | mAb01-9985 | mAb11-1119 | 333 | 1.26 |
| bimAb05-4690 | mAb01-9985 | mAb11-1121 | 333 | 1.36 |
| bimAb05-4693 | mAb01-9985 | mAb11-1123 | 333 | 1.02 |
| bimAb05-4696 | mAb01-9985 | mAb11-1125 | 333 | 1.3 |
| bimAb05-4704 | mAb01-9985 | mAb11-1416 | 333 | 1.17 |
| bimAb05-4708 | mAb01-9985 | mAb11-1420 | 111 | 1.02 |
| bimAb05-4710 | mAb01-9985 | mAb11-1422 | 333 | 1.1 |
| bimAb05-4756 | mAb11-1204 | mAb01-8174 | 111 | 1.20 |
| bimAb05-4788 | mAb11-1233 | mAb01-8174 | 333 | 1.13 |
| bimAb05-4884 | mAb11-1254 | mAb01-8174 | 316 | 1.16 |
| bimAb05-4895 | mAb11-1262 | mAb01-8174 | 111 | 1.28 |
| bimAb05-4896 | mAb11-1259 | mAb01-8174 | 333 | 1.13 |
| bimAb05-4898 | mAb11-1260 | mAb01-8174 | 333 | 1.17 |
| bimAb05-4903 | mAb11-1268 | mAb01-8174 | 333 | 1.1 |
| bimAb05-4906 | mAb11-1266 | mAb01-8174 | 111 | 1.38 |
| bimAb05-4910 | mAb11-1273 | mAb01-8174 | 333 | 1.12 |
| bimAb05-4914 | mAb11-1275 | mAb01-8174 | 333 | 1.16 |
| bimAb05-4915 | mAb11-1276 | mAb01-8174 | 111 | 1.23 |
| bimAb05-4919 | mAb11-1278 | mAb01-8174 | 333 | 1.17 |
| bimAb05-4920 | mAb11-1282 | mAb01-8174 | 111 | 1.22 |
| bimAb05-4921 | mAb11-1279 | mAb01-8174 | 333 | 1.14 |
| bimAb05-4924 | mAb11-1288 | mAb01-8174 | 333 | 1.22 |
| bimAb05-4927 | mAb11-1286 | mAb01-8174 | 333 | 1.22 |
| bimAb05-5092 | mAb11-1344 | mAb01-8174 | 111 | 1.23 |
| bimAb05-5095 | mAb11-0723 | mAb01-8174 | 111 | 1.31 |
| bimAb05-5204 | mAb11-1358 | mAb01-8174 | 333 | 1.5 |
| bimAb05-5205 | mAb11-1360 | mAb01-8174 | 111 | 1.38 |
| bimAb05-5240 | mAb11-1389 | mAb01-8174 | 111 | 1.29 |
| bimAb05-5340 | mAb01-9985 | mAb11-1431 | 111 | 1.28 |
| bimAb05-5341 | mAb01-9985 | mAb11-1441 | 111 | 1.05 |
| bimAb05-5342 | mAb01-9985 | mAb11-1439 | 333 | 1.14 |
| bimAb05-5344 | mAb01-9985 | mAb11-1443 | 333 | 1.03 |
| bimAb05-5346 | mAb01-9985 | mAb11-1444 | 158 | 1.17 |
| bimAb05-5348 | mAb01-9985 | mAb11-1445 | 111 | 1.19 |
| bimAb05-5353 | mAb01-9985 | mAb11-1453 | 333 | 1.15 |
| bimAb05-5354 | mAb01-9985 | mAb11-1451 | 116 | 1.01 |
| bimAb05-5356 | mAb01-9985 | mAb11-1452 | 111 | 1.16 |
| bimAb05-5357 | mAb01-9985 | mAb11-1455 | 333 | 1.11 |
| bimAb05-5358 | mAb01-9985 | mAb11-1433 | 111 | 1.22 |
| bimAb05-5359 | mAb01-9985 | mAb11-1456 | 333 | 1.07 |
| bimAb05-5361 | mAb01-9985 | mAb11-1459 | 111 | 1.21 |
| bimAb05-5362 | mAb01-9985 | mAb11-1457 | 111 | 1.39 |
| bimAb05-5363 | mAb01-9985 | mAb11-1434 | 333 | 1.56 |
| bimAb05-5364 | mAb01-9985 | mAb11-1458 | 111 | 1.18 |
| bimAb05-5365 | mAb01-9985 | mAb11-1460 | 333 | 1.04 |
| bimAb05-5366 | mAb01-9985 | mAb11-1461 | 333 | 1.12 |
| bimAb05-5367 | mAb01-9985 | mAb11-1465 | 333 | 1.15 |
| bimAb05-5369 | mAb01-9985 | mAb11-1466 | 333 | 1.17 |
| bimAb05-5370 | mAb01-9985 | mAb11-1463 | 333 | 1.06 |
| bimAb05-5371 | mAb01-9985 | mAb11-1435 | 208 | 1.19 |
| bimAb05-5372 | mAb01-9985 | mAb11-1464 | 333 | 1.05 |
| bimAb05-5373 | mAb01-9985 | mAb11-1467 | 333 | 1.15 |

TABLE 17-continued

TGT activity of anti-FIX/FX bimAbs relative to ACE910

| bimAb ID | anti-FIX mAb ID | anti-FX mAb ID | Concentration (nM) | Peak ratio (fold) |
|---|---|---|---|---|
| bimAb05-5374 | mAb01-9985 | mAb11-1468 | 333 | 1.07 |
| bimAb05-5375 | mAb01-9985 | mAb11-1472 | 308 | 1.27 |
| bimAb05-5377 | mAb01-9985 | mAb11-1473 | 111 | 1.27 |
| bimAb05-5378 | mAb01-9985 | mAb11-1470 | 333 | 1.16 |
| bimAb05-5379 | mAb01-9985 | mAb11-1436 | 111 | 1.07 |
| bimAb05-5380 | mAb01-9985 | mAb11-1471 | 333 | 1.09 |
| bimAb05-5381 | mAb01-9985 | mAb11-1474 | 333 | 1.15 |
| bimAb05-5383 | mAb01-9985 | mAb11-1477 | 111 | 1.05 |
| bimAb05-5385 | mAb01-9985 | mAb11-1478 | 333 | 1.03 |
| bimAb05-5386 | mAb01-9985 | mAb11-1476 | 333 | 1.08 |
| bimAb05-5387 | mAb01-9985 | mAb11-1479 | 333 | 1.27 |
| bimAb05-5388 | mAb01-9985 | mAb11-1480 | 111 | 1.36 |
| bimAb05-5389 | mAb01-9985 | mAb11-1483 | 111 | 1.19 |
| bimAb05-5390 | mAb01-9985 | mAb11-1437 | 133 | 1.06 |
| bimAb05-5396 | mAb01-9985 | mAb11-1487 | 111 | 1.07 |
| bimAb05-5406 | mAb01-9985 | mAb11-1494 | 333 | 1.19 |

Example 16: Activity of Bispecific Anti-FIX(a)/FX(a) Antibodies in a Thrombin Generation Test (TGT) in Human Haemophilia a Platelet-Poor and Platelet-Rich Mimic Plasma The procoagulant activity of the bispecific antibodies bimAb05-0745, bimAb05-3761, bimAb05-3769, bimAb05-0746, bimAb05-2112, bimAb05-2113 and bimAb005-2114 was determined based on their ability to promote thrombin generation in the presence of either a procoagulant synthetic phospholipid membrane or platelets according to the principles described by Hemker et al. (Pathophysiol Haemost Thromb, 2002; 32:249-253). ACE910 was included for comparison. Each antibody (test compound) was tested in a thrombin generation test (TGT) using commercially available Haemophilia A (HA) patient pooled platelet-poor plasma (HA-PPP) and HA-induced human platelet-rich plasma (HA-PRP) freshly prepared from healthy consenting donors.

Materials and Methods:
Preparation of Haemophilia A-Induced Human Platelet-Rich Plasma (HA-PRP)

Blood was obtained from healthy consenting donors by venipuncture. Six volumes of blood was collected into 1 volume acid citrate dextrose (ACD; 85 mM sodium citrate, 110 mM dextrose, and 62.3 mM citric acid, pH 4.9), final pH 6.5, and centrifuged for 20 min at 220 g at room temperature (RT). Platelet-rich plasma (PRP) was collected and platelet concentrations were determined with a Medonic CA 620 hematology analyzer (Boule Diagnostics AB, Spånga, Sweden).

The red blood cell-containing plasma part was centrifuged for another 10 min at 600 g at RT. Platelet-poor plasma (PPP) was collected and used to dilute the PRP to 300,000 platelets/µl. HA conditions were induced by addition of a FVIII-neutralising anti-human FVIII antibody (Sheep anti-Human Factor VIII—5 mg, Haematologic Technologies, VT, USA) to a final concentration of 0.1 mg/ml and rotated gently at 2 rpm for 30 minutes at RT.

Thrombin Generation Test

Thrombin generation tests (TGT) in both HA-PPP (George King Bio-Medical Inc, KS, USA) (Exp. A) and HA-PRP (Exp. B) were performed by standard calibrated automated thrombography using a 96-well plate fluorometer (Fluoroscan Ascent FL, Thermolabsystems, Helsinki, Finland). Reaction mixtures contained 70 µl HA-PRP (~300,000 platelets/µl) or HA-PPP, 10 µl test compound dilution (diluted in 20 mM HEPES, 140 mM NaCl, pH 7.4, 2% BSA), 20 µl CAT reagents containing tissue factor (TF) (PRP reagent; TF without synthetic phospholipids, PPP-reagent LOW; TF with synthetic phospholipids, 1 pM TF final, Thrombinoscope BV, Maastricht, the Netherlands) or Thrombin Calibrator (Thrombinoscope BV), and 20 µl of a mixture containing the fluorescently labelled thrombin substrate z-Gly-Gly-Arg-AMC (3 mM) and $CaCl_2$) (90 mM) (Thrombinoscope BV). TGT was performed at up to eight concentrations of test compound (0.3, 1.0, 3, 10, 30, 100, 300, and 900 nM, final plasma concentration) or added buffer (20 mM HEPES, 140 mM NaCl, pH 7.4, 2% BSA) only (representing HA control). The concentration ranges were tested in at least three independent experiments in HA-PPP from the same stock or in blood from four different donors. Normal control levels in TGT were measured using untreated human PRP or CRYOcheck™ pooled normal human PPP plasma (Precision Biologic Inc., Dartmouth, Canada) added buffer (20 mM HEPES, 140 mM NaCl, pH 7.4, 2% BSA) only. The TGT was allowed to proceed for a total of 90 minutes and the TGT parameter Peak Thrombin Height (nM) was analysed by Thrombinoscope software (Thrombinoscope BV).

Results and Discussion

Exp. A: FIG. 2 and Table 18 shows the measured peak thrombin generation rates for each bispecific antibody at the concentrations tested in HA-PPP. The data show that all test compounds increase the peak thrombin formation above the level observed in the absence of antibody, i.e. exhibit procoagulant activity. In addition, thrombin generation levels between 10 and 300 nM for bimAb05-0745, bimAb05-3761, bimAb05-3769, bimAb05-0746, bimAb05-2112, bimAb05-2113, and bimAb05-2114 are higher than that observed for ACE910, demonstrating superior potency. Moreover, thrombin generation levels at 300 to 900 nM of bimAb05-0745, bimAb05-3761, bimAb05-3769, bimAb05-2112, and bimAb05-2114 are higher than that observed with 900 nM ACE910, demonstrating higher potencies and efficacies of these compounds compared to ACE910.

Figure 3:
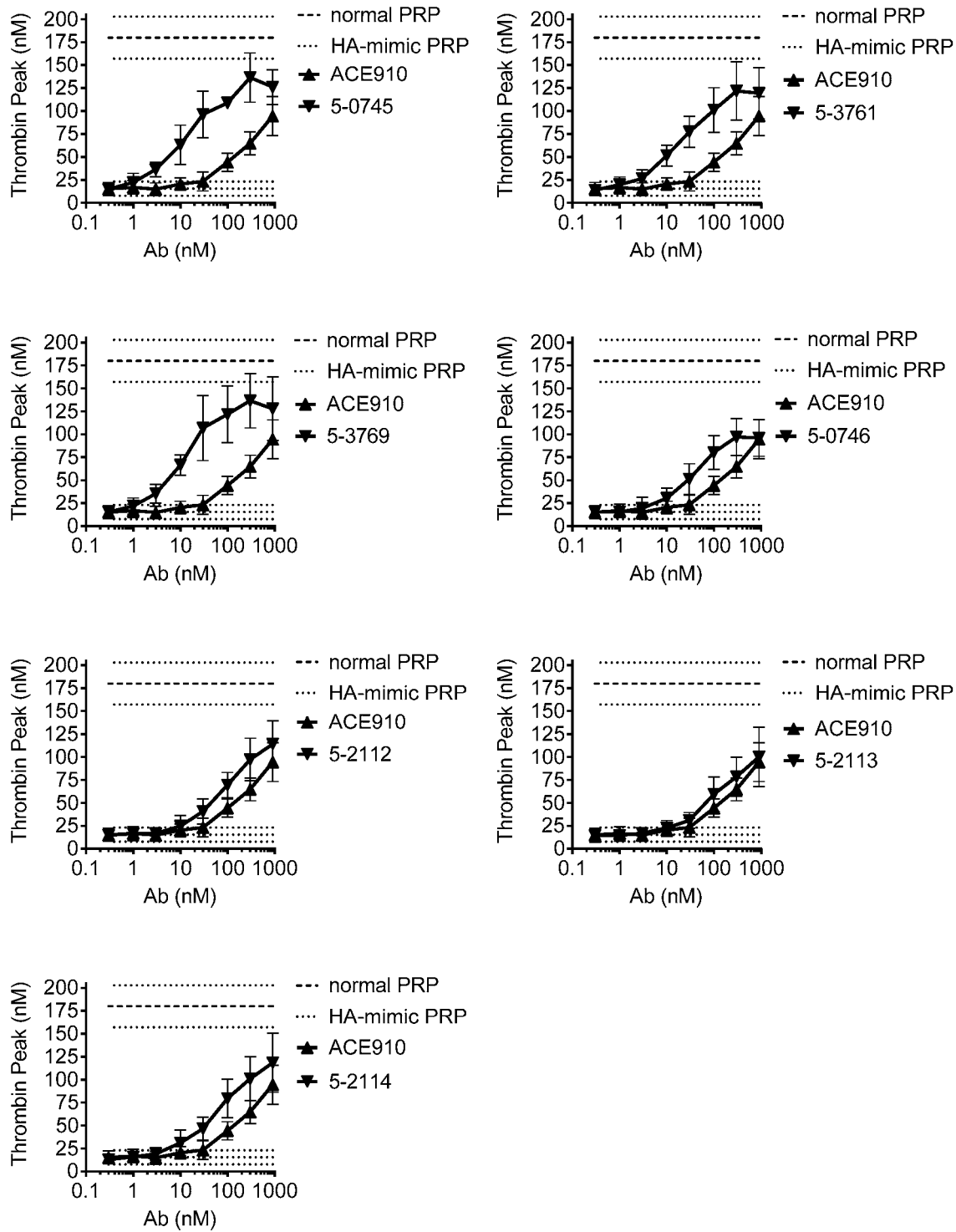
FIG. 3 shows thrombin generation test (TGT) results from the bispecific antibodies bimAb05-0745, bimAb05-3761, bimAb05-3769, bimAb05-0746, bimAb05-2112, bimAb05-2113, bimAb05-2114 and ACE910 in human tissue factor activated haemophilia A platelet-rich plasma (PRP). The experiment was performed as described in Example 16. Dotted and stippled lines indicate the peak thrombin level (nM) observed in the absence of antibody in HA-PRP and normal PRP, respectively, and with their standard deviation indicated by the dotted lines. The profiles of bimAb05-0745, bimAb05-3761, bimAb05-3769, bimAb05-0746, bimAb05-2112, bimAb05-2113 and bimAb05-2114 are indicated by down-pointing triangles, whereas that of ACE910 is indicated by up-pointing triangles. Results are shown as mean±standard deviation from at least three independent experiments.

Exp. B: FIG. 3 and Table 19 shows the measured peak thrombin generation for each bispecific antibody at the concentrations tested in HA-PRP. Under these conditions, bimAb05-0745, bimAb05-3761, bimAb05-3769, bimAb05-0746, bimAb05-2112, bimAb05-2113, and bimAb05-2114 also display better potencies and efficacies compared to ACE910.

TABLE 18

| Thrombin generation test (TGT) in HA-PPP (Exp. A) | | | |
|---|---|---|---|
| Exp. A Compound concentration (nM) | Peak thrombin (mean ± SD in nM) for ACE910 | Peak thrombin (mean ± SD in nM) for bimAb05-0745 | Peak thrombin (mean ± SD in nM) for bimAb05-3761 |
| 0 | 15.5 ± 7.8 | 11.6 ± 0.9 | 11.6 ± 0.9 |
| 0.3 | 11.5 ± 1.1 | 11.6 ± 1.9 | 11.4 ± 0.7 |

TABLE 18-continued

| Thrombin generation test (TGT) in HA-PPP (Exp. A) | | | |
|---|---|---|---|
| 1 | 12.6 ± 0.1 | 11.8 ± 1.2 | 13.5 ± 1.6 |
| 3 | 11.2 ± 2.5 | 14.0 ± 3.6 | 13.8 ± 2.7 |
| 10 | 13.3 ± 0.0 | 25.5 ± 5.8 | 18.1 ± 3.8 |
| 30 | 15.3 ± 4.3 | 44.8 ± 5.8 | 35.7 ± 5.4 |
| 100 | 22.0 ± 4.1 | 81.4 ± 9.2 | 64.1 ± 9.2 |
| 300 | 31.6 ± 4.0 | 105.7 ± 7.7 | 85.7 ± 7.0 |
| 900 | 45.6 ± 7.2 | 107.7 ± 14.1 | 78.4 ± 7.5 |

| Exp. A Compound concentration (nM) | Peak thrombin (mean ± SD in nM) for bimAb05-3769 | Peak thrombin (mean ± SD in nM) for bimAb05-0746 | Peak thrombin (mean ± SD in nM) for bimAb05-2112 |
|---|---|---|---|
| 0 | 11.6 ± 0.9 | 11.6 ± 0.9 | 11.6 ± 0.9 |
| 0.3 | 14.6 ± 3.8 | 11.1 ± 1.2 | 9.4 ± 2.5 |
| 1 | 12.3 ± 0.8 | 12.4 ± 2.5 | 11.8 ± 1.0 |
| 3 | 14.7 ± 3.2 | 13.1 ± 3.2 | 12.0 ± 1.1 |
| 10 | 25.4 ± 4.8 | 12.6 ± 1.3 | 12.7 ± 1.2 |
| 30 | 50.8 ± 8.7 | 15.3 ± 0.9 | 17.0 ± 4.0 |
| 100 | 94.1 ± 7.5 | 29.0 ± 3.6 | 29.1 ± 5.7 |
| 300 | 117.5 ± 8.1 | 44.2 ± 5.2 | 51.2 ± 5.7 |
| 900 | 112.5 ± 11.0 | 47.8 ± 6.0 | 82.8 ± 7.5 |

| Exp. A Compound concentration (nM) | Peak thrombin (mean ± SD in nM) for bimAb05-2113 | Peak thrombin (mean ± SD in nM) for bimAb05-2114 |
|---|---|---|
| 0 | 11.6 ± 0.9 | 11.6 ± 0.9 |
| 0.3 | 14.2 ± 5.2 | 11.9 ± 0.5 |
| 1 | 11.5 ± 1.2 | 12.3 ± 0.8 |
| 3 | 11.8 ± 0.7 | 12.9 ± 1.2 |
| 10 | 13.0 ± 2.7 | 15.7 ± 2.8 |
| 30 | 15.7 ± 5.4 | 21.3 ± 5.1 |
| 100 | 22.4 ± 5.5 | 41.9 ± 14.5 |
| 300 | 40.7 ± 7.2 | 75.8 ± 17.0 |
| 900 | 51.1 ± 4.0 | 103.7 ± 7.1 |

Thrombin generation test (TGT) of the bispecific antibodies bimAb05-0745, bimAb05-3761, bimAb05-3769, bimAb05-0746, bimAb05-2112, bimAb05-2113, bimAb05-2114, and ACE910 in human tissue factor activated haemophilia A platelet-poor plasma (PPP). Mean peak thrombin generation levels±standard deviation measured at each of the tested compound concentrations in at least three independent experiments in HA-PPP (Exp. A).

TABLE 19

| Thrombin generation test (TGT) in HA-PRP (Exp. B) | | | |
|---|---|---|---|
| Exp. B Compound concentration (nM) | Peak thrombin (mean ± SD in nM) for ACE910 | Peak thrombin (mean ± SD in nM) for bimAb05-0745 | Peak thrombin (mean ± SD in nM) for bimAb05-3761 |
| 0 | 15.5 ± 7.8 | 15.5 ± 7.8 | 15.5 ± 7.8 |
| 0.3 | 15.2 ± 7.1 | 12.0 ± 2.1 | 11.6 ± 0.7 |
| 1 | 16.9 ± 7.5 | 11.9 ± 1.4 | 14.0 ± 1.6 |
| 3 | 15.0 ± 6.9 | 14.5 ± 4.2 | 14.3 ± 3.0 |
| 10 | 20.3 ± 7.0 | 23.5 ± 5.2 | 18.8 ± 4.2 |
| 30 | 23.3 ± 10.3 | 45.0 ± 7.1 | 36.1 ± 6.5 |
| 100 | 44.3 ± 10.0 | 79.9 ± 10.6 | 65.8 ± 10.4 |
| 300 | 64.9 ± 12.6 | 106.0 ± 9.4 | 86.0 ± 8.6 |
| 900 | 94.5 ± 21.3 | 108.9 ± 17.0 | 80.8 ± 7.2 |
| Exp. B Compound concentration (nM) | Peak thrombin (mean ± SD in nM) for bimAb05-3769 | Peak thrombin (mean ± SD in nM) for bimAb05-0746 | Peak thrombin (mean ± SD in nM) for bimAb05-2112 |
| 0 | 15.5 ± 7.8 | 15.5 ± 7.8 | 15.5 ± 7.8 |
| 0.3 | 13.0 ± 2.6 | 11.3 ± 1.4 | 9.0 ± 2.9 |
| 1 | 12.6 ± 0.8 | 13.0 ± 2.7 | 12.0 ± 1.2 |
| 3 | 15.7 ± 3.1 | 13.7 ± 3.7 | 12.3 ± 1.1 |
| 10 | 24.8 ± 5.7 | 13.0 ± 1.2 | 12.9 ± 1.4 |
| 30 | 49.8 ± 10.4 | 15.5 ± 1.0 | 17.1 ± 4.8 |
| 100 | 95.6 ± 8.5 | 30.4 ± 2.8 | 30.8 ± 5.8 |

TABLE 19-continued

Thrombin generation test (TGT) in HA-PRP (Exp. B)

| | | | |
|---|---|---|---|
| 300 | 118.6 ± 9.6 | 45.3 ± 5.8 | 51.3 ± 6.9 |
| 900 | 114.4 ± 12.6 | 49.5 ± 5.9 | 83.3 ± 9.1 |

| Exp. B Compound concentration (nM) | Peak thrombin (mean ± SD in nM) for bimAb05-2113 | Peak thrombin (mean ± SD in nM) for bimAb05-2114 |
|---|---|---|
| 0 | 15.5 ± 7.8 | 15.5 ± 7.8 |
| 0.3 | 11.7 ± 1.1 | 11.9 ± 0.5 |
| 1 | 11.6 ± 1.4 | 12.3 ± 0.8 |
| 3 | 11.7 ± 0.9 | 12.9 ± 1.2 |
| 10 | 13.6 ± 2.9 | 15.7 ± 2.8 |
| 30 | 16.8 ± 6.1 | 21.3 ± 5.1 |
| 100 | 24.2 ± 5.2 | 41.9 ± 14.5 |
| 300 | 43.3 ± 6.2 | 75.8 ± 17.0 |
| 900 | 52.3 ± 4.1 | 103.7 ± 7.1 |

Thrombin generation test (TGT) of the bispecific antibodies bimAb05-0745, bimAb05-3761, bimAb05-3769, bimAb05-0746, bimAb05-2112, bimAb05-2113, bimAb05-2114 and ACE910 in human tissue factor activated haemophilia A platelet-rich plasma (PRP). Mean peak thrombin generation±standard deviation at each of the tested compound concentrations from four independent experiments in HA-PRP (Exp. B).

Example 17: In Vivo Efficacy of Bispecific Anti-FIX(a)/FX(a) Antibodies in a Tail Vein Transection (TVT) Model In vivo efficacy was determined using a Tail Vein Transection (TVT) model in FVIII knockout-mice. The efficacy of a high dose (8 mg/kg) of antibody test compounds and ACE910 was investigated in a Tail Vein Transection (TVT) study in FVIII knockout mice (B6; 129S-F8tm1 Kaz/J, The Jackson Laboratory, Bar Harbor, Me., US) co-treated with human FIX (2 mg/kg) (Benefix, Pfizer, New York City, N.Y., US) and FX (1.5 mg/kg) (Haematologic Technologies, INC, Essex Junction, Vt., US). In short, the mice were anaesthetized with isoflurane and placed on a heating pad, set to keep animal body temperature at 37° C., with their tails immersed in saline (37° C.). Dosing was performed in the right lateral tail vein 5 minutes prior to the injury. In the present TVT model (Johansen et al., Haemophilia, 2016, 625-31) the lateral vein was transected. If the bleeding stopped at 10, 20, or 30 min, the tail was taken up from the saline, and wound was gently wiped with a saline wetted gauze swab. Total blood loss was determined after 40 min by quantifying the amount of haemoglobin in the saline (see Table 20). The efficacy of the antibody test compound was compared with a One-way ANOVA followed by a Tukey multiple comparison test. A p-value<0.05 was considered significant.

TABLE 20

Comparison of the efficacy in the bleeding models in F8 knockout mice

| Bispecific antibody ID | Blood loss mean (nmol haemoglobin) |
|---|---|
| Vehicle (control) | 4441 |
| bimAb05-0745 | 1072* |
| bimAb05-0746 | 925* |
| bimAb05-3761 | 566* |
| bimAb05-3769 | 860* |
| bimAb05-2112 | 1301* |
| bimAb05-2113 | 450* |
| bimAb05-2114 | 1222* |
| ACE910 | 1462* |

*Significantly different from vehicle treated FVIII knockout mice

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A multispecific antibody or antigen-binding fragment thereof comprising an anti-FIX(a) antibody or antigen-binding fragment thereof capable of binding to FIX (SEQ ID NO:1) and/or the activated form thereof (FIXa), comprising a heavy chain and a light chain, and an anti-FX(a) antibody or antigen-binding fragment thereof capable of binding to FX (SEQ ID NO:2) and/or the activated form thereof (FXa), comprising a heavy chain and a light chain, wherein a. the heavy chain of the anti-FIX(a) antibody or antigen-binding fragment thereof comprises CDR1-3 sequences identified by SEQ ID NOs:36, 37 and 38, respectively, and the light chain of the anti-FIX(a) antibody or antigen-binding fragment thereof comprises CDR1-3 sequences identified by SEQ ID NOs:40, 41 and 42, respectively, and the heavy chain of the anti-FX(a) antibody or antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences are identified by SEQ ID NOs:472, 473 and 474, respectively, or b. the heavy chain of the anti-FIX(a) antibody or antigen-binding fragment thereof comprises CDR1-3 sequences identified by SEQ ID NOs:36, 37 and 38, respectively, and the light chain of the anti-FIX(a) antibody or antigen-binding fragment thereof comprises CDR1-3 sequences identified by SEQ ID NOs:40, 41 and 42, respectively, and the heavy chain of the anti-FX(a) antibody or antigen-binding fragment thereof comprises CDR1-3 sequences identified by SEQ ID NOs:484, 485 and 486, respectively, and the light chain of the anti-FX(a) antibody or antigen-binding fragment thereof comprises CDR1-3 sequences identified by SEQ ID NOs:488, 489 and 490, respectively, or c. the heavy chain of the anti-FIX(a) antibody or antigen-binding fragment thereof comprises CDR1-3 sequences identified by SEQ ID NOs:44, 45 and 46, respectively, and the light chain of the anti-FIX(a) antibody or antigen-binding fragment thereof comprises CDR1-3 sequences identified by SEQ ID NOs:48, 49 and 50, respectively, and the heavy chain of the anti-FX(a) antibody or antigen-binding fragment thereof comprises CDR1-3 sequences identified by SEQ ID NOs: 468, 469 and 470, respectively, and the light chain of the anti-FX(a) antibody or antigen-binding fragment thereof comprises CDR1-3 sequences identified by SEQ ID NOs: 472, 473 and 474, respectively, or d. the heavy chain of the anti-FIX(a) antibody or antigen-binding fragment thereof comprises CDR1-3 sequences identified by SEQ ID NOs:52, 53 and 54, respectively, and the light chain of the anti-FIX(a) antibody or antigen-binding fragment thereof comprises CDR1-3 sequences identified by SEQ ID NOs: 56, 57 and 58, respectively, and the heavy chain of the anti-FX(a) antibody or antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences identified by SEQ ID NOs:472, 473 and 474, respectively, or e. the heavy chain of the anti-FIX(a) antibody or antigen-binding fragment thereof comprises CDR1-3 sequences identified by SEQ ID NOs: 52, 53 and 54, respectively, and the light chain of anti-FIX(a) antibody or antigen-binding fragment thereof comprises CDR1-3 sequences identified by SEQ ID NOs:56, 57 and 58, respectively, and the heavy chain of the anti-FX(a) antibody or antigen-binding fragment thereof comprises CDR1-3 sequences identified by SEQ ID NOs: 484, 485 and 486, respectively, and the light chain of the anti-FX(a) antibody or antigen-binding fragment thereof comprises CDR1-3 sequences identified by SEQ ID NOs:488, 489 and 490, respectively, or f. the heavy chain of the anti-FIX(a) antibody or antigen-binding fragment thereof comprises CDR1-3 sequences identified by SEQ ID NOs:68, 69 and 70, respectively, and the light chain of anti-FIX(a) antibody or antigen-binding fragment thereof comprises CDR1-3 sequences identified by SEQ ID NOs:72, 73 and 74, respectively, and the heavy chain of the anti-FX(a) antibody or antigen-binding fragment thereof comprises CDR1-3 sequences identified by SEQ ID NOs: 468, 469 and 470, respectively, and the light chain of the anti-FX(a) antibody or antigen-binding fragment thereof comprises CDR1-3 sequences identified by SEQ ID NOs:472, 473 and 474, respectively, or g. the heavy chain of the anti-FIX(a) antibody or antigen-binding fragment thereof comprises CDR1-3 sequences identified by SEQ ID NOs:68, 69 and 70, respectively, and the light chain of the anti-FIX(a) antibody or antigen-binding fragment thereof comprises CDR1-3 sequences identified by SEQ ID NOs:72, 73 and 74, respectively, and the heavy chain of the anti-FX(a) antibody or antigen-binding fragment thereof comprises CDR1-3 sequences identified by SEQ ID NOs:484, 485 and 486, respectively, and the light chain of the anti-FX(a) antibody or antigen-binding fragment thereof comprises CDR1-3 sequences identified by SEQ ID NOs: 488, 489 and 490, respectively, or h. the heavy chain of the anti-FIX(a) antibody or antigen-binding fragment thereof comprises CDR1-3 sequences identified by SEQ ID NOs:1203, 1204 and 1205, respectively, and the light chain of the anti-FIX(a) antibody or antigen-binding fragment thereof comprises CDR1-3 sequences identified by SEQ ID NOs:1207, 1208 and 1209, respectively, and the heavy chain of the anti-FX(a) antibody or antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences identified by SEQ ID NOs:472, 473, and 474, respectively, or i. the heavy chain of the anti-FIX(a) antibody or antigen-binding fragment thereof comprises CDR1-3 sequences identified by SEQ ID NOs:1211, 1212 and 1213, respectively, and the light chain of anti-FIX(a) antibody or antigen-binding fragment thereof comprises CDR1-3 sequences identified by SEQ ID NOs:1215, 1216 and 1217, respectively, and the heavy chain of the anti-FX(a) antibody or antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences identified by SEQ ID NOs:472, 473, and 474, respectively, or j. the heavy chain of the anti-FIX(a) antibody or antigen-binding fragment thereof comprises CDR1-3 sequences identified by SEQ ID NOs:1219, 1220 and 1221, respectively, and the light chain of anti-FIX(a) antibody or antigen-binding fragment thereof comprises CDR1-3 sequences identified by SEQ ID NOs:1223, 1224 and 1225, respectively, and the heavy chain of the anti-FX(a) antibody or antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences identified by SEQ ID NOs:472, 473, and 474, respectively, or k. the heavy chain of the anti-FIX(a) antibody or antigen-binding fragment thereof comprises CDR1-3 sequences identified by SEQ ID NOs:1227, 1228 and 1229, respectively, and the light chain of anti-FIX(a) antibody or antigen-binding fragment thereof comprises CDR1-3 sequences identified by SEQ ID NOs:1231, 1232 and 1233, respectively, and the heavy chain of the anti-FX(a) antibody or antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences identified by SEQ ID NOs:472, 473, and 474, respectively, or l. the heavy chain of the anti-FIX(a) antibody or antigen-binding fragment thereof comprises CDR1-3 sequences identified by SEQ ID NOs:1235, 1236 and 1237, respectively, and the light chain of the anti-FX(a) antibody or antigen-binding fragment thereof comprises CDR1-3 sequences identified by SEQ ID NOs:1239, 1240 and 1241, respectively, and the heavy chain of the anti-FX(a) antibody or antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences identified by SEQ ID NOs:472, 473, and 474, respectively, or m. the heavy chain of the anti-FIX(a) antibody or antigen-binding fragment thereof comprises CDR1-3 sequences identified by SEQ ID NOs:1243, 1244 and 1245, respectively, and the light chain of anti-FIX(a) antibody or antigen-binding fragment thereof comprises CDR1-3 sequences identified by SEQ ID NOs:1247, 1248 and 1249, respectively, and the heavy chain of the anti-FX(a) antibody or the antigen-binding fragment thereof comprises CDR1-3 sequences identified by SEQ ID NOs:468, 469 and 470, respectively, and the light chain of the anti-FX(a) antibody or antigen-binding fragment thereof comprises CDR1-3 sequences identified by SEQ ID NOs:472, 473, and 474, respectively.

2. The multispecific antibody or antigen-binding fragment thereof according to claim 1, wherein the anti-FIX(a) antibody or antigen-binding fragment thereof comprises
   a. a heavy chain variable domain identified by SEQ ID NO:35 and a light chain variable domain identified by SEQ ID NO:39, or
   b. a heavy chain variable domain identified by SEQ ID NO:43 and a light chain variable domain identified by SEQ ID NO:47, or
   c. a heavy chain variable domain identified by SEQ ID NO:51 and a light chain variable domain identified by SEQ ID NO:55, or
   d. a heavy chain variable domain identified by SEQ ID NO:67 and a light chain variable domain identified by SEQ ID NO:71,
   e. a heavy chain variable domain identified by SEQ ID NO:1202 and a light chain variable domain identified by SEQ ID NO:1206,
   f. a heavy chain variable domain identified by SEQ ID NO:1210 and a light chain variable domain identified by SEQ ID NO:1214,
   g. a heavy chain variable domain identified by SEQ ID NO:1218 and a light chain variable domain identified by SEQ ID NO:1222,
   h. a heavy chain variable domain identified by SEQ ID NO:1226 and a light chain variable domain identified by SEQ ID NO:1230,
   i. a heavy chain variable domain identified by SEQ ID NO:1234 and a light chain variable domain identified by SEQ ID NO:1238, or
   j. a heavy chain variable domain identified by SEQ ID NO:1242 and a light chain variable domain identified by SEQ ID NO:1246, and wherein the anti-FX(a) antibody or antigen-binding fragment thereof comprises
   k. a heavy chain variable domain identified by SEQ ID NO:467 and a light chain variable domain identified by SEQ ID NO:471, or
   l. a heavy chain variable domain identified by SEQ ID NO:483 and a light chain variable domain identified by SEQ ID NO:487.

3. The multispecific antibody or antigen-binding fragment thereof according to claim 1, wherein said multispecific antibody or antigen-binding fragment thereof is a bispecific antibody or antigen-binding fragment thereof.

4. The multispecific antibody or antigen-binding fragment thereof according to claim 2, wherein said multispecific antibody or antigen-binding fragment thereof is a bispecific antibody or antigen-binding fragment thereof.

5. The bispecific antibody or antigen-binding fragment thereof according to claim 3, wherein
   the heavy chain of the anti-FIX(a) antibody or antigen-binding fragment thereof comprises CDR1-3 sequences identified by SEQ ID NOs:52, 53 and 54, respectively, and
   the light chain of the anti-FIX(a) antibody or antigen-binding fragment thereof comprises CDR1-3 sequences identified by SEQ ID NOs:56, 57 and 58, respectively, and
   the heavy chain of the anti-FX(a) antibody or antigen-binding fragment thereof comprises CDR1-3 sequences identified by SEQ ID NOs: 468, 469 and 470, respectively, and the light chain of the anti-FX(a) antibody or antigen-binding fragment thereof comprises CDR1-3 sequences identified by SEQ ID NOs: 472, 473 and 474, respectively.

6. The bispecific antibody or antigen-binding fragment thereof according to claim 4, wherein the anti-FIX(a) antibody or antigen-binding fragment thereof comprises
a heavy chain variable domain identified by SEQ ID NO:51 and a light chain variable domain identified by SEQ ID NO:55, and
the anti-FX(a) antibody or antigen-binding fragment thereof comprises a heavy chain variable domain identified by SEQ ID NO:467 and a light chain variable domain identified by SEQ ID NO:471.

7. The multispecific antibody or antigen-binding fragment thereof according to claim 1, wherein the isotype of the bispecific antibody is IgG4.

8. The multispecific antibody or antigen-binding fragment thereof according to claim 2, wherein the isotype of the bispecific antibody is IgG4.

9. The bispecific antibody or antigen-binding fragment thereof according to claim 5, wherein the isotype of the bispecific antibody is IgG4.

10. The bispecific antibody or antigen-binding fragment thereof according to claim 6, wherein the isotype of the bispecific antibody is IgG4.

11. A pharmaceutical composition comprising the antibody or antigen-binding fragment thereof according to claim 1 and a pharmaceutically acceptable carrier.

12. A pharmaceutical composition comprising the antibody or antigen-binding fragment thereof according to claim 2 and a pharmaceutically acceptable carrier.

13. A pharmaceutical composition comprising the antibody or antigen-binding fragment thereof according to claim 5 and a pharmaceutically acceptable carrier.

14. A pharmaceutical composition comprising the antibody or antigen-binding fragment thereof according to claim 6 and a pharmaceutically acceptable carrier.

15. A method of treating haemophilia A with or without inhibitors, comprising administering the pharmaceutical composition according to claim 11 to a subject in need thereof.

16. A method of treating haemophilia A with or without inhibitors, comprising administering the pharmaceutical composition according to claim 12 to a subject in need thereof.

17. A method of treating haemophilia A with or without inhibitors, comprising administering the pharmaceutical composition according to claim 13 to a subject in need thereof.

18. A method of treating haemophilia A with or without inhibitors, comprising administering the pharmaceutical composition according to claim 14 to a subject in need thereof.

19. An antibody or antigen-binding fragment thereof which is capable of binding to FIX (SEQ ID NO:1) and/or the activated form thereof (FIXa) comprising a heavy chain and a light chain wherein
a. the heavy chain comprises CDR1-3 sequences identified by SEQ ID NOs:36, 37 and 38, respectively, and the light chain comprises CDR1-3 sequences identified by SEQ ID NOs:40, 41 and 42, respectively, or
b. the heavy chain comprises CDR1-3 sequences identified by SEQ ID NOs:44, 45 and 46, respectively, and the light chain comprises CDR1-3 sequences identified by SEQ ID NOs:48, 49 and 50, respectively, or
c. the heavy chain comprises CDR1-3 sequences identified by SEQ ID NOs:52, 53 and 54, respectively, and the light chain comprises CDR1-3 sequences identified by SEQ ID NOs: 56, 57 and 58, respectively, or
d. the heavy chain comprises CDR1-3 sequences identified by SEQ ID NOs:68, 69 and 70, respectively, and the light chain comprises CDR1-3 sequences identified by SEQ ID NOs:72, 73 and 74, respectively, or
e. the heavy chain comprises CDR1-3 sequences identified by SEQ ID NOs:1203, 1204 and 1205, respectively, and
the light chain comprises CDR1-3 sequences identified by SEQ ID NOs:1207, 1208 and 1209, respectively, or
f. the heavy chain comprises CDR1-3 sequences identified by SEQ ID NOs:1211, 1212 and 1213, respectively, and
the light chain comprises CDR1-3 sequences identified by SEQ ID NOs:1215, 1216 and 1217, respectively, or
g. the heavy chain comprises CDR1-3 sequences identified by SEQ ID NOs:1219, 1220 and 1221, respectively, and
the light chain comprises CDR1-3 sequences identified by SEQ ID NOs:1223, 1224 and 1225, respectively, or
h. the heavy chain comprises CDR1-3 sequences identified by SEQ ID NOs:1227, 1228 and 1229, respectively, and
the light chain comprises CDR1-3 sequences identified by SEQ ID NOs:1231, 1232 and 1233, respectively, or
i. the heavy chain comprises CDR1-3 sequences identified by SEQ ID NOs:1235, 1236 and 1237, respectively, and
the light chain comprises CDR1-3 sequences identified by SEQ ID NOs:1239, 1240 and 1241, respectively, or
j. the heavy chain comprises CDR1-3 sequences identified by SEQ ID NOs:1243, 1244 and 1245, respectively, and
the light chain comprises CDR1-3 sequences identified by SEQ ID NOs:1247, 1248 and 1249, respectively.

20. The antibody or antigen-binding fragment thereof according to claim 19, which is capable of stimulating the enzymatic activity of FIXa towards FX.

21. The antibody or antigen-binding fragment thereof according to claim 19 wherein the heavy chain comprises CDR1-3 sequences identified by SEQ ID NOs:52, 53 and 54, respectively, and
the light chain comprises CDR1-3 sequences identified by SEQ ID NOs:56, 57 and 58, respectively.

22. The antibody or antigen-binding fragment thereof according to claim 21, comprising a heavy chain variable domain identified by SEQ ID NO:51 and a light chain variable domain identified by SEQ ID NO:55.

23. A pharmaceutical composition comprising the antibody or antigen-binding fragment thereof according to claim 21 and a pharmaceutically acceptable carrier.

24. A pharmaceutical composition comprising the antibody or antigen-binding fragment thereof according to claim 22 and a pharmaceutically acceptable carrier.

25. A method of treating haemophilia A with or without inhibitors, comprising administering the pharmaceutical composition according to claim 23 to a subject in need thereof.

26. A method of treating haemophilia A with or without inhibitors, comprising administering the pharmaceutical composition according to claim 24 to a subject in need thereof.

* * * * *

UNITED STATES PATENT AND TRADEMARK OFFICE
CERTIFICATE OF CORRECTION

| | |
|---|---|
| PATENT NO. | : 11,220,554 B2 |
| APPLICATION NO. | : 17/161741 |
| DATED | : January 11, 2022 |
| INVENTOR(S) | : Karina Thorn et al. |

It is certified that error appears in the above-identified patent and that said Letters Patent is hereby corrected as shown below:

On the Title Page

At Column 1, Under Item (63) Related U.S. Application Data please replace Line 27 with the following:
"PCT/EP2019/070628, filed on Jul. 31, 2019"

Signed and Sealed this
Thirteenth Day of September, 2022

Katherine Kelly Vidal
*Director of the United States Patent and Trademark Office*